US009051383B2

(12) United States Patent
Hayashi et al.

(10) Patent No.: US 9,051,383 B2

(45) Date of Patent: Jun. 9, 2015

(54) SPIDER SILK DRAGLINE POLYNUCLEOTIDES, POLYPEPTIDES AND METHODS OF USE THEREOF

(75) Inventors: Cheryl Y. Hayashi, Riverside, CA (US); Jessica E. Garb, Arlington, MA (US); Nadia A. Ayoub, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 259 days.

(21) Appl. No.: 12/664,309

(22) PCT Filed: Jun. 10, 2008

(86) PCT No.: PCT/US2008/066448

§ 371 (c)(1), (2), (4) Date: Dec. 11, 2009

(87) PCT Pub. No.: WO2008/154547

PCT Pub. Date: Dec. 18, 2008

(65) Prior Publication Data

US 2010/0222553 A1 Sep. 2, 2010

Related U.S. Application Data

(60) Provisional application No. 60/943,107, filed on Jun. 11, 2007.

(51) Int. Cl.

*D01B 7/06* (2006.01)
*C07K 14/435* (2006.01)
*A61K 38/00* (2006.01)

(52) U.S. Cl.

CPC ................................ *C07K 14/43518* (2013.01)

(58) Field of Classification Search

CPC ................................................ C07K 14/43518
See application file for complete search history.

(56) References Cited

U.S. PATENT DOCUMENTS

| | | | | |
|---|---|---|---|---|
| 5,733,771 | A * | 3/1998 | Lewis et al. | 435/252.3 |
| 5,756,677 | A * | 5/1998 | Lewis et al. | 530/353 |
| 5,994,099 | A * | 11/1999 | Lewis et al. | 435/69.1 |
| 7,288,391 | B2 * | 10/2007 | Roth et al. | 435/69.1 |
| 7,521,228 | B2 * | 4/2009 | Lewis et al. | 435/320.1 |
| 2003/0077730 | A1 * | 4/2003 | Peelle | 435/69.1 |
| 2004/0210956 | A1 * | 10/2004 | Roth et al. | 800/278 |
| 2004/0228913 | A1 * | 11/2004 | Kumar et al. | 424/468 |
| 2005/0010035 | A1 * | 1/2005 | Lewis et al. | 530/353 |
| 2006/0241074 | A1 * | 10/2006 | Woolf et al. | 514/44 |
| 2009/0226969 | A1 * | 9/2009 | Johansson et al. | 435/69.7 |

FOREIGN PATENT DOCUMENTS

WO 2008/154547 A2 12/2008

OTHER PUBLICATIONS

Ayoub et al. (Nov. 2007) Multiple Recombining Loci Encode MaSp1, the Primary Constituent of Dragline Silk, in Widow Spiders (*Latrodectus*: Theridiidae), Mol. Biol. Evol., vol. 25, No. 2, pp. 277-286.*

Garb et al. (2005) Modular evolution of egg case silk genes across orb-weaving spider superfamilies, Proc. Natl. Acad. Sci. USA, vol. 102, No. 32, pp. 11379-11384.*

Garb et al. (20070 Expansion and Intragenic Homogenization of Spider Silk Genes since the Triassic: Evidence from Mygalomorphae (Tarantulas and Their Kin) Spidroins, Mol. Biol. Evol., vol. 24, No. 111, pp. 2454-2464.*

NCBI (2012, updated) "*Latrodectus hesperus* isolate LT51 major ampullate spidroin 1 mRNA", http://www.ncbi. nlm.nih.gov/nuccore/AY953074, pp. 1-2.*

NCBI (2006) "*Latrodectus hesperus* major ampullate spidroin 1 (MaSp1) mRNA",www.ncbi.nlm.nih.gov/nuccore/DQ409057.1, pp. 11-3).*

Nickitas-Etienne, Athina, International Preliminary Report on Patentability and Written Opinion, Date of Issuance of Report: Dec. 11, 2009, International Application No. PCT/US2008/66448.

Ayoub, Nadia A. et al., "Blueprint for a High-Performance Biomaterial: Full-Length Spider Dragline Silk Genes". PLoS one, Jun. 2007, Issue 6, e514, pp. 1-13.

Lawrence, Barbara A. et al., "Molecular and Mechanical Properties of Major Ampullate Silk of the Black Widow Spider, *Latrodectus hesperus*", Biomacromolecules, 2004, pp. 689-695.

* cited by examiner

*Primary Examiner* — Maryam Monshipouri
*Assistant Examiner* — Samuel Liu
(74) *Attorney, Agent, or Firm* — Joseph R. Baker, Jr.; Gavrilovich, Dodd & Lindsey LLP

(57) ABSTRACT

The disclosure provides spider silk dragline polypeptides and polynucleotides encoding the same. Methods of using such polypeptides and polynucleotides and designing novel biomaterials using repeat units of the polypeptides and polynucleotides.

2 Claims, 24 Drawing Sheets

Figure 1A(i)-(ii)

>46B18 [organism=*Latrodectus hesperus*] [molecule=DNA] [moltype=Genomic DNA] [location=genomic] [clone=46B18] *Latrodectus hesperus* major ampullate spidroin 2 (MaSp2) gene, complete cds is shown in Bold-underline ACTTCGAAACATTCACGCATTTCGGTACCATTCAGTACCACTACAAAGAGCCAACTCGAAGCAAAAATAAGAAA
TTCATAATTATTCATACTATTTTCAATTCCATTTGTATCACTTATCTTTACAGGTGTTACATCGTACACGTGAT
TTTACTGCTGTTACCTTAGTATTTGTGAAAAGCAACAGCTATTCAAATACACAGTATGTAAAAACGTCTCTTTG
AATAATTTCTCTGCACGAAATCATATAATATTTCAGAAAAAGAAGTATTTTTAGAAAATATAATCATATAGAGC
AAACTTGAAAGGTATATGGTGTTTGAGAAACCTCGTGGCAGATTCCCCACAAATGATAAAGCAAACAGTGTCTG
CATGAACTAAAATTTTTAGAAAACAAAATTATTGTTTCAGCCAATATCACACGGAATTAAGATTTTAAGACGTA
GATACCAACAGCATCATTTCTAACTTTAACGTAAATTGTGACCTAAATTCAAATAATCCATTTTACTTGAAATA
TCTTGCACGCGATAGATAATTTCTGAATTAACACTTGTTGTCTTAATGAATGTCATTTGATAATAATTATTAAT
TCCGAAATTCGCGAATTTAAACAAACATTAATTCAGGCATGCATACACAAATCAAATGCCACGAAATTAATTGA
CATAAACTTTAAAGCTTAATCTTATTTTGCAAATCTTTAAAAAAAGTATTTGGACTTAATTATATATAAGCGAA
TCCATGATTTGACAGTACTTTACATATTTAAAGGAGAATAATCCGTCCAACGTGTCTAGTGGTCAGTGTGTCTG
ACTGCGGATAGTGAGGTCCTGGGTTCGAATCCCGGTTCGGGCATGGATGATCTTTCTCTATCTATCATGTTTTT
GTTCTTTTTTTGTATGAATGTGGAATGAATGCTTGCCTACCCTGTAAGCGGGTACCTATGGCATTTGTGTACTG
AGGAAGTCGGACTCCACACCAAAATATGTTTCAGTTGGAAAAGTGGAGCAGAGCACCCCATATTGTGCCAGCCT
GGCTGGCATACGACAACAACAACAACAAAGGAGAATAAAATTGTGGAAATTTTTAACACCAATGAAGTGGGACA
AAAATGTATCGTGTTTAAGACGTTGCTCCTTTTAATTATAAACTTCGCAATTATTGGTTAAATATTAATTTGCC
ATTGAATTGAACAGTTTAAATTCTTTAATGTATTATCTAGCTTGTAAATGTCAGTAACTCATTCAAATAACTTA
TAAAAATGTTTTGAAACTGCATATTATCTATAGTTTATTATATCCAATTAAAAGTATCTCAAAGTTTTATACTT
AGTGTATTTCACTATTGAGATTTAGTAATTTGGAGAGTAAAGTGTTGCTAAGATACAGTGAGCGCGATATCTTA
ATAATCAAATGGCATCGAGGGCTTTTCCCCACAAAAAGATTCCATAGGGTCCTGTGTCCCTCACATGATGGGAT
GTGATGTTGAGAAAAATATACAATATTAGATGTCGAATTGAGGTTCAAAATTTAGTGACAGGGCTGTTTCATCG
ATTTGTCTCGGCAGAAATAAGCAGTTTGAATTGTATCTTAAATACCTAACCTTAACTTCGTTTGTTTCAAATTT
CACTTTAATAAAGGTAAGCTTTTAAAATTAAGAATAGTTATTTTTATAGTAAATTTAAACCCATTGAAGATGAA
AATCTATGACAAATGCATCGTGATTTTACGCCGTTTATTATCCGGTCATTTTAGAATCTTAAAATTAATTTCAA
ATCAGTCAAACAATTGACTCTAGATCTTGTTTGGTCATCCAATGATTACAATCTAAGTCCATGCTAGATCGATA
GTGTTTTCAAGCAGAATCGAAGAGTAATTTCGGTAGTATTATCATCCACGCGCGTTTTACAAGCAATGGCAAAA
ATATAACTGCAACAACTATACCAAGGTTCAGACACTTTAATAAACTATATACATGAGTATCACACGCTTCAATT
CTACACCACTGACCATTAAAATTGCAAGAAGGAATGCAAATAACAGAACGATATTTATTGGACACATACGTTAT
AGTGGAAAGAGCAAGTGATTAGATTTACAGGAAATTAGGATGTATAGATCTTGAGAAATCAGTACCCAGAGCAG
CCCCCTCTGGCTGCAATAACAGCATTTATCCGCCTAGGCATGGAGTCAAACAGAGATTGTATGGCATGTACGGG
GATCTCAGTCCATGCAGCTTCAATACTATGCCACAGTTCATCGACAGTAGTGGATGGTGAGTGATGGCGTGCCA
ATCGTTCGGCAACCATTGACCAAACGTTCTCAATTGGTGACAGATCAGGAGAACGTGCTAGCCAGGGTAACAGT
GGAACCTGTTCTGTATCAAGGGAGTTAAGAACAGTACGGGCAACATGCGGAGGTGCATTATCCTGTTGAAACAA
AGCATTAGGGTGGCCTCGAAGATAGGGCAGAGCCATGGGCCTTAATACATCGGAAATGTAACGGTTGCTGTTCA
AAGTGCCGGTAATGCGAACAAGAGGTGATCGAGACGTGTATCCAATGGCACCCCATACCATCACTCCAGCCGAT
GGGCCAGTATGGCGATGTCCAATGCAAGCTGGCAATGCGCGTTCTCCACGATGCCTCCAAACACGGATGCGGCC
CTCATGGTCCTGTATACAGGACCATGAGGTATAAACCGAGATTCATCTGTAAAGATGACATGACGCCAATCCCG
CGTCCAGGTTCGTCGCGGATCACACCATTGAAGGCGCTCCTGTCTGTGACGCAGCGTCAATGGTAGCCGAAGCC
ATGGTCGCCGTGCAGACAATCCATGCTGCTGGAAACGTCGTCGAACGGAGCAGAAACTTGTTGCCTTGCAAATG
ACTCCATTTATCGACTCAGGGTTCGTGACGTGGCTGTACGATCCCTTGTGACCATGCGATAAGACGTCTGTCTT
CTCTGCTGTTAGTGATGGGGGGTCGCTGAGATCCTGCATGACGTTCCGTATGATTGTCCTGAACCCATCGATTC
CATATTCTGCTAACAGTCATGGAGTCTCGACCAACGCGAGCAGCAATATTGCGGTACGATAAACCGCAATCCCG
GTAGGCTATAATCCTTCTTCGATCAAAGTCAGACTCGTGCTGATAGGCATTTCTTCTTCTTACATGAGGCATTA
CAACAACTTTCTTTGCCGAAAACAACGCTGAAAACGGAAATTGAGTATGAGAAAACTGCTGTCAAATCTCTGGT
GGTTTTATACACATTGTAGATGTCGCTACTGTCGCCTGCTTTGTATGAATGCGCTGAAAATCTAATCATTTGCA
TATCACAGCAAGTTCTACTTGTCATGCAATTTTCACGTGTGTGGTGTGACGCTTTCCTTTAGTAGCGTTTTTAA
TGGCCAGTAGTGGATATTGTAATTATTTTTAAGGAACACGATTGTAGCAGTTCAGCAGATATTTAAATTGTAC
GATCTCCGATAGAGTGACAAAGTTTAAATAATGAATGAGTTGATATTTACTCAACAATATTATGACATGCGTTG
CATTTAATATGTGCTGGAGAATTGAAGATATACTACGTGACATTAAAAATGCAACACCAAGAATCAGTGACCAG
AAAATTATACAAATTTAAGGTTAGACGTACCATACATAGTTATGAAAATGATCTGAAATATGGAAACTCTTCTG
CATACGTAGGATAAGATAAAAGGTGAGGAACTGGCAGAATGGGAAATATTCACCCCGTTATTGCTGCTTCAAAA
ATAATCCTTGAAAATTTGTTCCTGTCTTAAAGTACGCCTGCAATTCCCGAGAATAATAGGCCATCCTCGTCGGA
GTCAGGTGCAGCAGACTGACGTGTTTACAAGGGACATGGTGATCGAACTGAGAAAAGCAAGTTGGTCCTTACTA
CAAACCACAGCTAACAGACACCTGTGCGCTTCCAGTGCATCGGCTGTGCAGAAGATGTTTACAACAAGGAACTG
TGGAACGTTGGCGGGGTACCGGTACAGACAGAGTGACGTCAGTACGCTTGGATCCACGTATCCAATGGGAAGTG

FIGURE 7

GTAGCAATTCCGTAAAGCAAGTCTACCAAAATTCTGCAGCATGTGTAAGACACCTAGGATGATACCGTATCGAG
CAGAACACTTTGCCAACGATTGGTTGCTAGTGTCCTGTGGTCATAGAGTCTGTTAAGAAGATTGGCATTGACTT
AACATCTTAGACACCAACGTCGGAAATGGTGCCGAATTAGATAGACATGTGGACGACGGAGCGGCAAAGGATCG
TCTTCTCAGATGAGTCACGCTTCTGTTTTTTCAGTGATAGTCGCCGCGTACAAGTGTGGCGTCGACATAGAGAC
AGGTCCAATCTTGAAGCAATTACAGAACTCCCCACAGCGTGACAACGTGGCATCATGGATAGGAGCACCATTGC
GTTTGATTACAGGTAACCTCTAATTCGTATTTACGGCCATGTGAAAGCACAACATTATGTGGATAATATGGTGC
GGCCAGTGGCACTTCCCAATCTTCAAGGGGTGTCCAATGTATTTTATCAGCAGGATGATGCCCGACCGCACATT
TCTCGGATCACCCAACATGCTTTTAAAGGTGTAAAGCTGTTTCCCTGACCACCGTGCTCGCCAGATCTCTCACC
AATCAAGCACGTTTGGGATGTTATTGGATGCTATTAACAGACCCTGCCACTGCCTCCTTTAGAAGAAGCACTTT
AGCAAATGGTTGACATTCCTCAGGACGGCATCCGTATTTTCATTGATTCTGTGCCTAGACGTGTTGCTTCATGT
ATCGCCGTCCACGGTGGTCCTACTACCTACTGATCCGACCCTGCTTTCGATATGTAGTATGCTTATCATTTCGA
AATACAGATCACTAATTTTCCGTTGCTGTCTCTCTGTGGTCGCGGAGTTTCGTCACTTTCTGGCAACTCCTTCT
TGGTGTTGCATTTTCAATATCGAGCAGTGTATATACAACTTAGAGAACATCATACAATCAGAAGTGAGTTTAAA
ACACATCGGGACAACATCTAAGCAAGATATGGATTGCGTGTTTCTTATAACATTTCCTTATTTAAATTCTGGAG
CCATACACAATAGGTGGAGAATTGATTGTATTTTCGGTAAAAAAAAATTTCTTAACCAATTGTGAACGGTTGAT
AATTCATTAATTATATAATATCGGTGATATGCTTCACCTGATACCGCATCCTATTTACTCCACTAATAGTAAGG
TATCGATTAAAGTTTTTAGATCTAACTGACATGAAATGCACCGTGTAGGCACAAACAAGCTTTTCACATTATAA
AAAGGATTTTACTGAATAATAATGCAGCACAAATAATTGACGAAATGGCTCAATCCGTAGCAATTTCTTTATAT
GAATACTTAAAAAGTCTGAATTTTCTATAAATAATCTTTGATATAAAAGTCCACTTTACAAAAAAAAAACAAGT
TTTATTTTTAACTTGTACAAGAGGGAAAATTTTCCAAATATTGTTAGTTACTAAAAGTTTTGAAATCATTAATT
AAAGTGAAATGTTATTAACGAATTAAAATATTTTTCTATATACAATATATACCTATTCCCAGTAACATTTCTTT
TGATACTGTCCGCCTCAAGGGATTAACCTTTTTTAGGTAAACACGGGTGTCACAATCCCGAGGTACCAAGTGAT
CTGTCCTCTTCTTTAATTTCTTCTCATCTCTACTCTTCTGCTTTTTCTTCCTTTTCCTCCTCGTTGTGGTTGCC
TCATAAGAAGTTGGGAGCTACCCTTGAGTAGAGATTTCGCCGCTATGTTGCAATTAGCTCCTCATGGGGACTAA
ATCACACGCGTGTTTGCAGTGCGTGGATACCCGTGTCCCTGGAAAGGAGGGTCCTGGTAATTGAGGACACCAGA
GACCAACACATTACTTTGACTTCTGCTTCAGGTAAACGGGAAATGTATTGTGGTCAGCAGCACATCAATCGGCT
TTATGGATCAAGCAATCGGTACATCTATAGGATGACTCGTTAAGGGTGGAGACCATCTCAGGGATGTACTGTGA
GCGTATAGGACCTAGCAAGTACTGGTGCAGCTGGTCTGCATCCCCTTGTTGGATTCAGTAGTGGGTGGTGCGGT
CAGGTCCCAAAATTTAAAAAATATTATAATGGCGAATAAACATTTTAAATTTCTCCCACGAGAGCAACAGTTTG
AAAACTTAAATCCTAAATTTTTCATAATCAAAAGAAAAGAGAGAAACTTTACAACTAAAACTCCTTTCCTCAAT
TTCAAAGGAATATCGGGTATTGTTGGAGAAGTTAAGAAGGTTCAGAAGATGCGCTCAGGTGACCTGCTTGTTGA
GGCCAGCATCTGACTCTCAAGCAGAAATTCTGGCAAGCATGAAATCTCTGGCAAATATTGAAGTGACTGTCTCT
CCTCATAGCAACCTGAACTTTCCTTGTGGTGTAATCTCAGCAAGGGATTTATTATATTCGCCGACGCAAGAGAT
TTACAGAATCAGAAGGTCTGTGGCGTTAGACGCATTACAGTCAGACGAGATGGTAATGTTTTCGATACTAAGTC
CTGACTTTTGCGACACCATTATGTAAAATCTGCGTACATGAATTTACCCGACAGGCCTTACATCCCAAATCCTT
TGTGATGTTTCCAATGTCAGCGCTTTGGACACTCGAGAAATGCTTGCAGAGGCAAAACTACTTGCGCCCGCTGC
GCGGTGGTTGGCCACGATAGTTCGAACTGTACAGCTAAGGAGAGGTGTGTCAACTGTCATAGTGATCACCGCTC
TCATTCTCGAAGTTGTTGTCCGTATATATTGGAGAAAGAGATAACCACGGTTAAGTTCAATCAAAAATGTTCTT
ATCCTGAGGTGAGACGATTGCTCGCTGCTTGCAATATTCAGTCAGGAGTCAGTTATACCACTGCTGCCAGAAAA
GTCACCAAATCAAGCAGCTCTTAAACTGAATCATTTTCGTTTTCCCCAATAAGATTATCCCAAACATCTGAAAA
GCCAAATTTCAAAAAATCTCTTACATTTGCTAGAAAAGCTCCTTTTGCTAAATCAAAAGCGGAGAAAGCTTTAA
AATTAAAAAAACTAAACAGTTTTCCATTTTCAACCAAAATATTTTCTCTTGCTTGGAGACTGACACGACTTCTT
TACTTCCCTCGGATGATGATACGTCACTCGAGGATATGACAGAAAACCCACCTTCCAATCCCGAGAAAGGAGCT
TTTCAATTTAAAAAATGACTTCCTTTATTTCTTGGAACTGCCATGGTTTGCGATCACATCTTGATGGCATCAAG
TTTCTAATAACAGATTATAATCCCCCATGTGTTGCACTTCAGGAGACATTCCTGAAGTCTAATAAAAACTTTAC
CATGCGTGGGTTAACATGTTTTAGAAAAGACTGTGGTGATGATGGTGCAGTGTCTGGTGGTGTTACTGTATTAA
CATCCACTAATTTTCCCAGTACTGTCCACCATTTGGATACTACTCTAAAAGCTGTAGCTGTGAAAATACACACT
ACATGCTTGATTACAGTCTGTTGTTTATATTTTCCATCACACAATCCACCAAGAGGAACTCGATGCTTTAGTTG
ATCAGCTGCCCACACCATTTTTGTTCATCGGTGACTTTAACGGACATCATTCTTTGTGGAGAAGTGATGATATC
AATTCTCGTGGACGACAGATAGAACAGTTTATTTCTGATAATTGTCTCTGTCTGCTTAATACCGACGAGAAGAC
ATATTTCCATGTACCCACAAGAATATTTCATTCCCTCGATTTAGCCATCTGTTCCCCATCTCTTCTGCCATTAT
TAAATTTAACTGTAGGAAATGATCTGCGTAATAGCTATCATTTTCCTCTCGTCATCTCCCAGACTGGAAGTAGT
AGTATAAGACAACGCTTACCTACTTACGTGTACAGTTGGGCAGATTGGACATTATTTACACAAATGGCAGTTGT
TGATTATGAAATGGTTTCAATCGATAATATTGATATCGCAGTTTGTAAAGTCAAAAAAACAATTGACAATATAG
CTTATACATCAATTCGAAGAGTTCGCCTATACCAAACAGGCGTAGCAAACCTTAGTGGAATAAAGAATATCAAG
AAACAATTAAAAAACAGAGGAAGTTATGGGGGTTATTTAGGAGGTACCCCACAACAGAGAATCTTATCGCCTTT
AAGAGAGCAAAAGCATTAGCTCGCAGAGCTCTTCGTCGAAGTCAGAAGGAATCTTGGTCTCGCTATGTATCTTC
AATTACATCTTCCATATCCAGTAAGCAGCTGTGGAGAAAAGTGAAAGCAGCCAATGGAATATATAAGGAATTCT

FIGURE 7 (cont'd)

TTATTCCTATTTTAAAATCCGGAGCTGCTATATACTCTTCTCCTAAGGAGATTGCTAACGTCCTTCGTGAAACC
TTTGCTAGCGTCTCAAGCATCGACTCTTATAGTCCTTCGTTCTTAAGGACAAAGAGTCTGGCTGAGCAAACAGC
AATTCGTTTCAAACATGGATAAGCTTTGCTTTACAACTGTGAATTTCCGATGTTGGAATTGAAGAGAGCATTAC
AGCAGACCAATAATACCAGTCCAGAATCTTATGGAATCAGATATCAAATGCTTCGTCATTTATGTCCAGATTCC
TTATCGAACGAATTGTTTTTGTTCAATAGGATATGGATTGAAAAGAAATTTCCATCACTTTGGATTGAAGCAAC
AGTGATTCCGGTCCTGAAGGCTGATAAAGATCCTTCATATACTTCACATTATCAACCAATCGCTCTGAAGAGTT
GCTGATGTAAGTAAGATTCTCGAACGTATTGCCAACGCACGTCTCGTATATGTCCTAGAAAAAAATTAATGTAT
ACATATTAATCAGAGTGGCTTCCGAAAGATCCACTTTTGATAATATCACTTAATTGGAAACCCAGATACGAAAC
GCCTTTGTGCGAAGGAATCATCTGGTTTCTGTTTTTTTCGACATAGAGAAGGCATACGACCGTACATGGCGATA
TGGAATTCTTCGTTCATTATATAATTTTGGCTTTCGGGGTAATCTTCCAATATTCCTATAAAAATTTTTAAGCT
CCCGTGTTTTTAAAGTCCGTGTTGGAACAGTTTTTTCCAATACTTTTATTCAAGCTAAGGGTGTTCCCCAAGGC
TCCATTTTAAGTGTCACTATTTTTAATCTTTTCATCATTAACATCCTTCATCAATTACCGCCTTCAATAAATGG
TACACTATATGTTGACGACCTGTAAATATCATGTCAGGGGTCTAATATGCGATTGACAGACAACTGCAAACAGC
AGTTAACAAACTTCCTGCATGGTGTGTAGAAATGGCCATACCTTATCACCAAGCAAGAGTAAATGTGTCCACTT
TCGTTGAAAGACTAGCTTACATAATGATCCAATTATTTATATCAACAACACTCCAATACAAGTAGTCAATGAAA
TAAAATTTTTGGGAATTATCTTTGACCGAAAATTAACCTTTCTTCCGCATGTTTTATATTTGCGGAAGAAGTGT
GAGCAATCGCTTAATATCCTCAAAGTGTTGTCAAATACATCTTGGGGTGCAGATCACACATCACTTCTTCAAGT
TTATCAGTCTTTGATTTTATCCCGCATTGATTACGAATGAGTTGTTTATGGATTGGCTAGATCTTCTGTTTTAC
GAAGACTGGACACAGTACATCACTCTGCTTTAAGGATATGTTCTGGAGCATTCCACACATCCCCTATCCTGAGT
CTATACGTGATTTGTCAATAATTACTTTTAAACCGGAGACGAATGCAGCAAACTCTCAATTATTTCGCAAAGAT
AATATCGACCCCACATCACCCATTACGTTCCATGATTCCTAGTGCGTTTCTTATTAGACTGTTTGATGCTCGCC
CATTGAGCATTTCACCTTTTCTCACAAGAGCCAAATCACATCTGCGGCTCATAGATCTATGTGATGTTCGGACA
AAATCTGTTGACAAATTTGCTTATCTACCTTGGTATGACCCAACAAATACTTTCATTAATATCTTTGCTCAGTA
TAGAAAATCGGATACAACACCTATTGTTTTTCAACAGTAATACTCTTCTCATCGCTGTCAGTATCAATCATATA
AACCTGTATTCATAGATGGTTCTAAAACAGCAGGACATGTTGCCTGTGGAGTTTTTATCAATAATACAGATTTT
AATTACAGCCTACATCCATCCTGCTCCATCTTTACTGCTGACGCAACCACCTTATACTGCGAGCTTCAGCATGT
GAACACAGATAACTATCATCAATATTGTGTTTATACTGACAACATGAGTATTTTAGAAGCCTTAAGAAGCAATA
GTTTCACCTGTCACCCTGTTGTCTCCAAACTTTTTAGAGCACTGAATTCCCTTGCTGACAAAGGAAATGAAATT
GTATTTTCTTGGATACCAAGCCACGTAGGTCTTGTTGGAAATGAGAGAGCGGATACAGCTGCAAAGACTGCATC
AGGTACAGTTTTACCATCAGTTCCTCTCTCAGATGTGAGAAAATGTGTTAAAATATTTATACATTCTCTATGGC
AGGAATCATGGAACTTACAGGTCGGCAACAAACTACATACCATTTTTTCATCCCTCATCCCATTATCAGTTTTA
TCGTTACGAAGTGCTGATGTTAGATAGACTCGCCATGATATCGGACACGCACGTTTTACACACCGACATTTATT
CTTACATGAATTAATTCCTTGGTGTGATACGTGTGAAGAACCATATACTGTGTTTCAAATTTTAATCTCATGTC
CTACTTTTAACGTTTACCGTTTTAAATTTTTCAAAATAAACATTTTAACCATGTCTGATTTGCTGGGCAACCC
CCCCACAGAAATCTATTTGCTTATTTGAGAGCAACAGGTATTTTAAATTTTATATAATTTAAATTTTAAATTTG
AAAATTATATTTATGTTTGATTTATCTTATTTTATATCCTATAATTAGGGAGCCAGTCCCAAGAGATTTGAAAG
ATTAGATTTATATTGTAATTCCCGGAACAATGGCCTAGAGTCTATTCCGGGAAATAGCTATATTGAGTGATAGT
TGATTAATATTGTAATTCAAATCTCTTCTCACTCCGGCCTGCACCTCTACGTTGGTGGCTCCTAGTAACACCAA
TAACATCGGTGGCTAACGTAGGCGGAGGGGACACCGCTTTTGTTCTAATTTTTCATAATTTGCTTAATTTTTTT
TGGTTGCGTGTGCCAAATTTCTTGACTTATTTTCGTTTAAGTTAATTTTGTCAGGTGTGCTAAGGCTTAGCACA
AGACACCATTATGACGGAAGTACCGTTGAACCAAGGTGGAGATGCCACAGTTTTAAGTTTGGACTTAAACGAAA
GACTCAATGCTGTCTTCTATCTCGAAAAAGATATTCAGACTATTTTAGCTAACAGTAAGATATCATTAACATCT
CAAGCTAAAATACGAGATGGAGTGAGCGACTTGATGAAGATAGTTATGAATCAAATGCAAGAGATATCTTATTT
AAAAGCACAGATAAAGACAACTAAGTCATATGCAGAAGTAGTACAGAAGGTGACGGGGATTGAACATAACTTGC
AAACGCAATTAAGGGCTAAGGAAACTAGAGATAGGTCTCGTCAGAGGAAAAATAACATACTAATAGTTTATCCC
AATCAAGAAGGGAATACATCTGATGATACTAGGAATGTAGTTAAGAGAATTATAGATCCATCAAAAGTGAAAGT
AAACAAAACTAGATCTATTAGAAAGGGAGGCATAATAATAGAAATGAATACAGTTGAGGACATAGACATTCTGC
TGGGTGAAATTAAAAACCAAGATAAAGATAATGAGTTGGTGGCTACCAAACCAAACAGGAGAAAACCAAGAATT
ATAATATACGATGTAGACAAGGAAATAGATAAAGATGAAATAGTACATAAACTTAGGCAACAAAACGATTTAGA
TGAAGACTTCGGTCTAGAAAAACTATATAAATTTAGCGGAAAATATGGAAATAATTGGATATTGAGTGTAGAGT
CTAAAATTTGAAACTATTAAAAGAAATATAGAACCACGATTGAATTTCAAAACAGTTGATCAGTCAAAATTCAG
ACAAAAAATAGCAACTCTAATAGAAGAAATTAATGACGAAATCATAGAAGAATTGGAAACAAATGAATTAGTAG
AACTGATTGAAAACAGTATACATAGGATCTGTATAGAAAGCAATAAGAAATCTAATAAACAAATAAGAAGTACT
AACTATTGGTGGACAAAAGAACTAACTACTCAAAGATCAAAAATCAGAGCATTAAGAAGGAGATATCAGAAAGA
ACCAGACGCAGATAACAGATTGAAATTTATGAAGACATATAAAAAAGCAGCTGCAATCTATAGGAAGAACATAG
TTCATACCAAACAAAAAGCATTTAAAGATTATCTAAGCTCAATTACCAATGAAAGTGCATTTGGAAATTACTAT
AAATCCATTAAACAAGAAAGATCCAGTAATAATCTATCTAATATGATTTTGAAAGAAGATGGAAACCTTACCAC
AAATTTCATGGAGGCAACAAACGAAATTTTAAACTATAACTTTCCCTATGAAGATCAAGTACAAGTTGTTGAGA

FIGURE 7 (cont'd)

ACTACGTCGATTTAGAAGATAAGAACATTACTGAATATGAAATCGAAGAAGCTATTAATGAAATGAAATTGGGT
AAAGCCCCTGGTTTTAACAATATCGAACTTGAAATCTATAAAGAAATATTTTACATTCATAAAGCATGGTTTGC
CAAAATATTAAACAAATGTTGGAGGAATTATACCTTTTCAAAGACGTGGAAAACTACTAAAGTGGTCTTAATAC
CGAAAGAAGGCAAAGATTTAACAATGGCAGATTCTTACAGGCCAATTTGCCTATTACCAATATTTGGGAAAATC
TTAGATAAAATTATTACAGACTAAACTATATATTGAACCAGGAGAACTTTATAAGCAGTAAACAGTATGGATTT
ATCCGTGGTAAAAGTACAAATGACGCAATACACGAAATAGTCAAACAAATAAATGAAAATAAGAGAAATAAACA
ATATACATGTATAATCTCATTGGATATCAAGAACGCATTTAATTCTGTAAGAACAGCTAACATTCTGGAAATCT
TGAATAAATGTAAATTGAATAAAAATTTATACAAGATAATTAAATCGTTCTTAACTGACAGAACATATTTGGAT
TATGACAAAAAAGCCAAAAGATATAATATTGGGGTTCCACAGGGTTCCTCCTTAGGTCCAATTTTTTGGAACTT
GGTCGTAAATGAGTTACTAGTAGAGAATATAAATGATAATGTTTATCTGCAGGCTTATGCGGACGACATAATAA
TACTATTAAAGGACAAAACATATTATAAATTTACTAATCTATCAAGTGAACCTTTGAAAATTATAGAAAAATGG
ATTATTAATTATAGAGAAATGGAAAGAAGTATTAATAAGAGCTGTTACTCAATATTCCCCATTAAAAAAGATAT
TACAAGAAGACCAAAAATACAGATTATGGGGCAGAATATTAAATATACATCTCATATTAAATATCTTGGAGTTA
TTATGGATACCAAATTAAGTTGGGCAGATCACCTAAATAACCTACAGGAGAAGGTATACAAGTTCATGAATAAA
ATACATAGGATCTCTAGAGTGACTTGGGGCATTAAACCCGAAGTCACTAAGACCATTTACAAAGCAGTCATAGA
AAAAATGATTCTATATGCAGCTCCAATATGGTACAAGAATACAGTTAAGATAAATAATAAGTTAAATCAGATAC
AAAGAATACCACTATTGAAAATATCTAAAGCCTATAAAACCGTTTCAACGGACGCTCTTCAAGTATTAACGGGT
TGCCCACCCATAGATTTATTGGCCTACATTGAAAAACAAAAATACTTAATATTGAATCAAGGCATTAAAGTCAG
AATAGGCAATATAGATTTTGACAATAATAATTCTTGGCATAGATGGAAATCATATATCCATCCTCCATGGGACA
AGAAAGAAATTAATTGGCCTCGAACTATAAATACTCAATATCACTTTGCATTTATAGATGGGTCCAAAATAAAT
AATAAAGTAGGAGCAGCCATAATAATTGGGTATAATAATAAAATAGAAGACATTAAAAGGATAAGACTCAACGA
TCAGGCCACGGTCTACGAGGCAGAGGCCAAAGCAATATTAAAAACATTGGAATACATAATTAACAAAAATATCA
ATAGCTGTAATATTCACACAGATTCCAGATCCGTCCTAGAAACTTTAAAGAGCTATAAACAAGGTAATAAAACA
ATAGATAGCATATTAAGCCTCATACATCAAAATGATAAAAGATTTACTTTTCATTGGGTCAAAGCCCATCAAGG
AATTGAATTTAACGAATTAGCGGATTTGAACGCAAAACATGCTACTAACGAACCAATCATATCGCATATTGCAC
CATATTCGAAACAACAAATTAAAACAATAGCCAATAAACACATACTGAGTCTTTGGCAGGACAGATGGAAAACA
TCAACTAAAACTAGAAGACTATGAAATTTATCCTGCAGTAATAACTAAGAGACTCTCAGCGGATTTCCTTCTTA
ATCAAGTCAAGACAGGCCATGGGGCCTTTGGCTCATATCAGAACAGATTTTTCAATAAGACTGAAATTTGTAAA
TACGACAATAAATTACAAGATGTTGAACACATTATTTATGACTGTACAAATTTTAAAGAAATAAGGAATAAAAC
ATTCCCTAAAAATTATAAATTATTGGAAATAAAACAATTGTTAAGTAGTATTAAAACTAGAAAAGGAATAGTCG
AAATGATGTATATTCTCTTCATAGACTCCTTACCATGTACATATTAACCGTTAATTTATTGTATTTTATAAGTT
TGTAGACAAGATCAGGTCTACTCATGTTAAACTTAAGTTTTTGATTTGCTAAACGGGTTGTTTAATTGTTGTTA
ACCTTTTGTTAGATTCTTTAGTTTTGAATTTTAATAAAGGCAAGTTGCCCATTCTTCCGTCAGAGCGAGTCTGG
GTGGACCGCAGGGTGGTGGTCACCGGTCTGCGTGTGAGGCCCAGACCGTAACATGGTGTTATGGACCTTTTGGA
CTGCGCCGATGTTGTTGCAGTCTTGGATCGGAAGCTGGTGTACCGGCTACCGATCGGCCATGGGCCGGGTGCTC
TCCTGGCGGATTACTGTCCGCGAACAGTCATTTTCGCTGCCGTATACCTTAGGGTGGGTCGGCCTTAACATCTA
GCGTTATATCCTATAATTATATATATAGATTTTAAAATAATATATACACTGATTTTTTTAAAGTTTTACTGTTC
CTTGGGTTTCCAAAAAAAAAGTAATAAATAAATAAATAAAATATCTTCTTCAAAAACTTTATTCTTGGCGCAGC
ATGTCCATTTTGGACCTTTTGCCATAAAATCCAACCAACCAATCTTTTGATACTGACGGTGAATAATAAAACAA
GACTTTCTGATATATTTAAAACAAGCTGTACCGAATAAATTATCAGTCGGTTATAGATAAAATTTAGTGACAAA
AAATATTAGCGAGCGCTTGCATGAATGATTAGATTTTTTCTTAAAGCTTTTATAGAAATCAAGAGTAAGTAATC
TATGAGAGATAATTTGCTCAATCTTATTTGTACAAAATGGTGAAGAATAGCTTTAATCGTCATTTTAAAATGAT
TTTATAGGCTCTTCAATGTAGAGTTGGAATTTATAAAAAAAGAAAATAACATGAGACAAAATTTTATTAAATAA
AAATAATACAGACTATAAATTTGATTTATTTGCCAAACTTAGCAAAACTATACTCAGAGGCTCCTGACTACTTT
TCCATCTTTCTGTCTGGTAGAGCGAGGATTCAGAGTAATTTTGAATCTTATGACACGAAAAAAACCGATTAGAA
ATTGGTTTCGGAGGGAAGGAGAGTTTCGGTTCGGCTGCTGCTCAAAAGTATTGAGCCGGGCATACACCCATAAC
ATCTTAAGTGCGACTAAGTCTCATTAATTTAATTTAATTGTACTTAAAACAAATTCTTCTTTAAGAAAATCCAA
CTCATTTGTTATTTTCATAGTATGCATTTCCACTAAAGATTCCATGGGTCATAAGGTTTGGAAACCACTGTTCT
TTGTGGTTTGAAGTTGAATCTTTACAGATATTTTATATATAAAGAATTATGTGTGTGAGAGTGATATATTTCTT
ATTCAACAAAATTTCAGTCTGTAAACCAAATATTTAGCACTTATTACTTATTTATATTCCTAAATATAGAAATA
TTTATAAATACAGTTGTAAAGAAATATAAACATATTTACAGATTATAATAAATTTATTTCAAACAAATTCTGCG
TATTACGGTTTCAATTTGACCAATAAAAACGATAAAAGCATAAATCTTCTCAAACATGTTTCTCAATTTATTAA
CTTTTCGAAATTTCGAATTAAAGACTCAAATCCTTATAACATTTTCGATGTATTTAAAGAACTCCATTTAAAAA
TATGCTGAAAAAGTTTCCGAAAATGTGTTACATACTATAATGTTAAAAAGATTATATATTTGAGAACTAAAATA
TATATAACTATGTTGAACATGAAATATTTTTAAAAAAAACACTACAAAAATATACATAATAATTTTAAATTAAA
ACTGACTTAAATTATAACTGACTTATAGTGTATTTCTATACACTATAAGTCAATTTAAATAACAAAATAAATTT
TATCATTTTAAGGAAATTTATCATTTTAGTATACTAAAAAATAATTAATAGAAATTTTCAAACAGTACATCATT

FIGURE 7 (cont'd)

TTGAGAAAGCTAAGCATTGATTTTTATGCAGAAAGTTTTTAAACTTATTAAAGAATTTTAGTAAAATTTCAATA
AGTAAAATAAATAATATAATCAAAATAAGGTTAGACGTCTGAATTAAATTTTTGACAAAAAATTACTACGCATT
TCATTTCGCCACCAACAGCTGAATTTGCCACGCAGCCAGATTTAGAGCGTCACAAAATAACGTCGCGATGATAT
CATTACTTGCACATTTCCAGGTGGATTTGCCAACCTGCTTTTTATCACGAAAACACATATAGTATAAAAAGGAT
ACGCATTTTTGGAACAATATTCAGTAGGGATTTCCCAATGACTACAATGAATTGGTCTACTCGACTTGTGTTGT
CAATACTCGTAGTGCTTTGCACTCAGAGCCTCTGTGCTCTGGGACAAGCAAACACTCCGTGGTCCAGTAAAGAA
AACGCTGACGCTTTTATAGGCGCATTTATGAATGCTGCTTCACAAAGTGGAGCATTTTCATCGGATCAGATAGA
TGATATGTCAGTTATTAGTAATACATTGATGGCTGCAATGGACAACATGGGTGGAAGAATCACACAATCAAAAT
TACAGGCTTTAGATATGGCTTTTGCATCATCCGTGGCAGAAATAGCTGTAGCTGATGGCCAAAACGTTGGAGCC
GCTACGAATGCCATATCAGACGCATTACGGTCAGCCTTCTATCAAACTACCGGAGTGGTAAACAATCAATTTAT
TACTGGGATAAGTAGCCTAATTGGCATGTTTGCCCAAGTATCAGGCAATGAAGTTTCTTATTCATCAGCTGGGT
CATCCAGCGCCGCAGCTTCAGAAGCAGTCTCAGCAGGACAAGGACCAGCAGCACAACCAGTTTACGCACCAAGC
GGAGCAAGTGCAGCTGCAGCAGCGGCTAGTGGAGCAGCACCTGCAATACAACAAGCATATGAACGAGGAGGTTC
AGGATCAGCAGCTGCAGCAGCAGGCTCAGGACCAAGTGGATACGGACAAGGAGCAGGAGGACCAGGAGGAGCAG
GTGCTGCAGCAGGAGCGGCTGCCGCAGGAGGATCTGGCCCTGGAGGATACGGACAAGGACCAGCTGCTTATGGC
CCATCAGGACCTAGTGGACAACAAGGTTACGGACCAGGTGGATCAGGAGCAGCAGCTGCCGCAGCCGCAGCAGC
AGGCTCAGGACCTAGTGGATACGGACCAGGAGCAGGTGGACCAGGAGGAGCAGGTGCTGCAGCAGCAGCGGCTG
CCGCAGGAGGATCTGGCCCTGGAGGATACGGACAAGGACAAGCTAGTTATGGCCCGTCAGGACCTAGTGGACAA
CAAGGTTACGGACCAGGTGGATCAGGAGCAGCAGCTGCCGCAGCCGCAGCAGCAGGATCAGGACCTAGTGGATA
CGGACCAGGAGCAGCTGCAGCAGCTGCGGCAGGCAGCGCTGGACCTGGAACACAACAAGGATATGGACCAGGAG
GATCAGGTGCAGCCGCTGCCGCAGGTTCAGGACCTAGAGGATACGGACCAAGAGGACCAGGAGGAGCAGGTGCA
GCAGCAACTGCCGCAAGAGGATCTGGCCCTGGAGGATACGGACAAGGACCAGCTGGTTATGGTACATCAGGACC
TAGTAGACAACAAGGTTACGGACCAGGAGGATCTGGAGCAGCAGCCGCAGCAGCTGCGGCAGCAGGTGGAGCAG
GACCTGGTAGACAACAAGGATATGGACCAGGAGGTTCTGGAGCAGCAGCTGCAACAGCAGCTGGTGGACCAGGA
TATGTAGGTCAACAAAGGTACGGACCAGGAGGAGCAGGTGCAGCAGCAGCGGCAGCAGCTGGTAGTGCAGGACC
TAGTAGACAACAAGCATATGGACCAGGAGGATCAGGTCCAGCAGCTGCAACAGCAGCAGCAGGCTCAGGACCTA
GTGGATACGGTCCAGGAGCAAGTGGACCAGTAGGAGCAGATGCAGCTGCAGCAGCTGCGACAGGCAGCGCTGGA
CCTGGAAGACAACAAGCATATGGACCAGGAGAATCTGGAGCAGCAGCCGCGGCAGCAAGTGGAGCAGGACCTGG
TAGACAACTAGGATATGGACCAGGAGGTTCTGGAGCAGCAGCGGCAGCAGCAGCTGGTGGACCAGGATATGGAG
GTCAACAAGGTTACGGTCCAGGAGGAGCAGGTGCAGCAGCAGCGGCGGCAGCTGGTGGTGCAGGACCTGGTAGA
CAACAAACATATGGACCAGGAGGATCCGGTGCAGCAGCAACTGCCGCAGGAGGATCTGGACCTGGAGGTTACGG
ACAAGGACCATCAGGTTACGGCCCATCAGGACCTGGTGGACAACAAGGTTACGGACCAGGAGGATCTGGAGCAG
CAGCAGCCGCGGCAGCAGGTGAAGCAGGACCTGGTAGACAACAAGGATATGGACCAAGAGGTTCTGGAGCAGCA
GCGGCAGCAGCAGCTGGTGGACCAGGATATGGAGGTCAATCAGGTTACGGACCTGGAGGAGCAGGTGCAGCAGC
AGCGGCGGCAGCTGGTGGTGCAGGACCTGGTAGACAACAAGAATATGGACCAGGAGGATCAGGTGCAGCAGCTG
CAGCAGCCGCTGCCGCAGGGTCAGGACCTAGTGGATACGGACCAGGAGCAGCAGGACCAATTGGACCAGGAGGA
GCAGGTGCAGCTGCCGCAGGAGGATCTGGACCTGTAGGTTACGGACAAGGACCATCAGGTTACGGCGCATCAGG
AACTGGTGGAGAACAAGATTATGGACCAGGAGGATCTGGAGCAGCAGCCGCAGCAGCTGCGGCAGCAGGTGGAG
CAGGACCTGGTAGACAACAAGGATATGGACCAGGAGGTTCTGGAGCAGCAGCGGCAGCAGCAGCTGGTGGACCA
GGATATGGAGGTCAACAAGGTTACGGACCAGGAGGAGCAGGTGCAGCAGCAGCGGCGGCAGCTGGTGGTGCAGG
ACCTGGTAGACAACAACCATATGGACCAGGAGGAGCAGGTGCAGCAGCAGCTGCCGCAGGAGGATCTGGACCTG
GAGGTTACGGACAAGGACCATCAGGTTACGGCGCATCAGGACCTGGTGGACAACAAGGTTTCGGACCAGGAGGA
TCTGGAGCAGCAGCAGCCGCGGCAGCAGGTGGAGCAGGACCTGGTAGACAACAAGGATATGGACCAGGAGGTTC
TGGAGCAGCAGCAGCAGCTGGTGGAACAGGATATGGAGGTCAACAAGGTTACGGACCAGGAGGAGCAGGTGCAG
CAGCAGCGGCGGCAGCTGCTGGTGCAGGACCTGGTAGACAACAAGAATATGGACCAGGAGGAACAGGTGCAGCA
GCTGCAGCAGCCGCTGCCGCAGGGTCAGGACCTAGTGGATACGGACAAGGAGCAGCCGGACCAAGTGGACCAGG
AGGAGAAGGTACAGCAGCAGCAGCAGCTGCTGCAGGAGGATCTGGACCTGGAGGTTACGGACAAGGACCATCAG
GTTACAGCGCATCAGGACCTGGTGGACAACAAGGATACGGACCAGGGGGATCTGGACTAGCAGCCGCAGCAGCT
GCGGCAGCAGGTGGAGCAGGAACTGGTAGACAACAAGGATATGGACCTGGTGGTTCTGGAGCAGCAGCGGCAGC
AGCAGCTGTTGGACCAGGATATGGAGGTCAACAAGGTTACGGACCAGGAGGAGCAGGTGCAGCAGCAGCTGCGG
CAGCTGGTGGTGCAGGTCCTGGTAGACAACAGGCATATGGACCAGGAGGATCAGGTGCAACAGCCGCTGCAGCA
GTAGCAGGGTCAGGACCTAGTGGATACGGACCAGGAGGAGCAGGTGCAGCAGCAGCAGCTGCGGCAGGCGGCGC
TGGTCCTGGAAGACAACAAGCATATGGACCAGGAGGATCTGGAGCAGCAGCCGCGGCAGCAAGTGGAGCAGGAC
CTGGTAGACAACAAGTATATGGACCAGGTGGTTCTGGAGCAGCAGCGGCAGCAGCAGCTGGTGGACCAGGATAT
GGAGGTCAACAAGGTTACGGACCAGGAGGAGCAGGTGCAGCAGCTGCGGCGGCAGCTGGTGGTGCAGGACAAGG
TACAAGACAAGCATATGGACCAGGAGGATCAGGTGCAGCAGCCGCTGCCGCAGGGCCAGGACCTAGTGGATACG
GACCAGGAGCAGCAGGACCAAGTGGACCAGGATTAGCAGGTGCAGCAGCAGCAGCTGCCGCAGGAGGATCTGGA

FIGURE 7 (cont'd)

CCTGGAGGTAATGGACAAAGACCATCAGGTTACGGCCAATCAGGAACTGGTGGACAACAAGGTTATGGACCAGG
AGGATCTGGAGCAGCCGCTGCAGCAGCCGCGGCAGCAGGTGGAGCCGGACCTGGTAGACAACAAGGATATGGAC
CAGGAAGTTCTGGAGCAGCAGCGGCAGCAGCAGCTGGTGGACCAGGATATGGAGGTCAACAAGGTTACGGACCA
GGAGGAGCAGGTGCAGCAGCTGCGGCGGCAGCTGGTGGTGCAGGACCTGGTACACAACAAGCATATGGACCAGG
AGGATCTGGAGCAGCAGCTGCAGCAGCCGCGGCAGCAGGTGGAGCCGGACCTGGTAGACAACAAGGATATGGAC
CAGGAAGTTCTGGAGCAGCAGCGGCAGCAGCAGCTGGTGGACCAGGATATGGAGGTCAACAAGGTTACGGACCA
GGAGGAGCAGGTGCAGCAGCAGCGGCGGCAGCTGGAGGTGCAGGAGCTGGTAGACAACAAGCATATGGACCAGG
AGGATCAGGTGCAGCAGCAGCAGGCTCAGGACCTAGTGGATACGAACCAGGAGCAGCTGGACCAGGAGGAGCAG
GTGCAGCTGCAGCAGCTGCGGCTGTCGGCGCTGGACCTGGAAGACAACAAGCATATGGACAAGGTGGTTCTGGA
GCAGTAGCGGCAGCAGCAGCTGGTGGACCAGGATATGGAGGTCAACAAGGTTACGAACAAGGAGGAGCAGGTGC
AGCATCAGCGGCGGCAGCTGGAGGTGAAGGACCTGCTAGACAACAAGCATATGGACCAGGAGGATCAGGTGCAG
CAGCTGCAGCAGCAGGTGGAGCAGGACCTGGTAGACAACAAGGATATGGACCAGGAAGTTCTGGAGCAGCAGCG
GCAGCAGCAGCTGGTGGACCAGGATATGGAGGTCAACAAGGTTACGGACCAGGAGGAGCAGGTGCAGCAGCAGC
GGCGGCAGCTGGTGGTGCAGGACCAGGTAGACAACAAGCATATGGACCAGGAGGATCAGGTGCAGCAGCTGCAG
CAGCAGCAGGCACAGGACCTAGTGGATACGGACCAGGAGCAGCTGGACCGGGAGGAGCAGGTGCAGCTGCAGCA
GCTGCGGCAGGCAGCGCTGGACCTGGAAGACAACAAGCATATGGACCAGGTGGTTCTGGAGCAGCAGCGGCAGC
AGCTGCTGGTGGACCAGGTTATGGAGGTCAACAAGGTTACGGACCAGGAGGAGCAGGTGCAGCAGCTGCGGCGG
CAGCTGGTGGTGCAGGACCTGGTACACAACAAGCATATGGACCAGGAGGATCTGGAGCAGCAGCTGCAGCAGCC
GCGGCAGCAGGTGGAGCAGGACCTGATAGACAACAAGGATATGGACCAGGAAGTTCTGGAGCAGCAGCGGCAGC
AGCAGCTGGTGGACCAGGATATGGAGGTCAACAAGGTTATGGACCAGGAGGAGCAGGTGCAGCAGCTGCTGCAG
CCGCTGCCGCAGGGCCAGGACCTAGTGGATACGGACCAGGAGGAGCAGGTGCAGCAGCAGCAGCAGCTGCTGCA
GGAGGATCTGGACCTGGAGGTTACGGACAAGGACCATCAGGTTACAGCGCATCAGGACCTGGTGGACAACAAGG
ATACGGACCAGGGGGATCTGGACTAGCAGCCGCAGCAGCTGCGGCAGCAGGTGGAGCAGGAACTGGTAGACAAC
AAGGATATGGACCTGGTGGTTCTGGAGCAGCAGCGGCAGCAGCAGCTGTTGGACCAGGATATGGAGGTCAACAA
GGTTACGGACCAGGAGGAGCAGGTGCAGCAGCAGCTGCGGCAGCTGGTGGTGCAGGTCCTGGTAGACAACAGGC
ATATGGACCAGGAGGATCAGGTGCAACAGCCGCTGCAGCAGCAGCAGGGTCAGGACCTAGTGGATACGGACCAG
GAGGAGCAGGTGCAGCAGCAGCAGCTGCGGCAGGCGGCGCTGGTCCTGGAAGACAACAAGCATATGGACCAGGA
GGATCTGGAGCAGCAGCCGCGGCAGCAAGTGGAGCAGGACCTGGTAGACAACAAGTATATGGACCAGTTGGTTC
TGGAGCAGCAGCGGCAGCAGCAGCTGGTGGACCAGGATATGGAGGTCAACAAGGTTACGGACCAGGAGGAGCAG
GTGCAGCAGCTGCGGCGGCAGCTGGTGGTGCAGGACAAGGTACAAGACAAGCATATGGACCAGGAGGATCAGGT
GCAGCAGCCGCTGCCGCAGGGCCAGGACCTAGTGGATACGGACCAGGAGCAGCAGGACCAAGTGGACCAGGATT
AGCAGGTGCAGCAGCAGCAGCTGCCGCAGGAGGATCTGGACCTGGAGGTAATGGACAAAGACCATCAGGTTACG
GCCAATCAGGACCTGGTGGACAACAAGGTTATGGACCAGGAGGATCTGGAGCAGCCGCTGCAGCAGCCGCGGCA
GCAGGTGGAGCCGGACCTGGTAGACAACAAGGATATGGACCAGGAAGTTCTGGAGCAGCAGCGGCAGCAGCAGC
TGGTGGACCAGGATATGGAGGTCAACAAGGTTACGGACCAGGAGGAGCAGGTGCAGCAGCTGCGGCGGCAGCTG
GTGGTGCAGGACCTGGTACACAACAAGCATATGGACCAGGAGGATCTGGAGCAGCAGCTGCAGCAGCCGCGGCA
GCAGGTGGAGCCGGACCTGGTAGACAACAAGGATATGGACCAGGAAGTTCTGGAGCAGCAGCGGCAGCAGCAGC
TGGTGGACCAGGATATGGAGGTCAACAAGGTTACGGACCAGGAGGAGCAGGTGCAGCAGCAGCGGCGGCAGCTG
GAGGTGCAGGAGCTGGTAGACAACAAGCATATGGACCAGGAGGATCAGGTGCAGCAGCAGCAGGCTCAGGACCT
AGTGGATACGAATCAGGAGCAGCTGGACCAGGAGGAGCAGGTGCAGCTGCAGCAGCTGCGGCTGTCGGCGCTGG
ACCTGGAAGACAACAAGCATATGGACAAGGTGGTTCTGGAGCAGTAGCGGCAGCAGCAGCTGGTGGACCAGGAT
ATGGAGGTCAACAAGGTTACGAACAAGGAGGAGCAGGTGCAGCATCAGCGGCGGCAGCTGGAGGTGAAGGACCT
GCTAGACAACAAGCATATGGACCAGGAGGATCAGGTGCAGCAGCTGCAGCAGCAGGTGGAGCAGGACCTGGTAG
ACAACAAGGATATGGACCAGGAAGTTCTGGAGCAGCAGCGGCAGCAGCAGCTGGTGGACCAGGATATGGAGGTC
AACAAGGTTACGGACCAGGAGGAGCAGGTGCAGCAGCAGCGGCGGCAGCTGGTGGTGCAGGACCAGGTAGACAA
CAAGCATATGGACCAGGAGGATCAGGTGCAGCAGCTGCAGCAGCAGCAGGCACAGGACCTAGTGGATACGGACC
AGGAGCAGCTGGACCGGGAGGAGCAGGTGCAGCTGCAGCAGCTGCGGCAGGCGGCGCTGGACCTGGAAGACAAC
AAGCATATGGACCAGGTGGTTCTGGAGCAGCAGCGGCAGCAGCTGCTGGTGGACCAGGTTATGGAGGTCAACAA
GGTTACGGACCAGGAGGAGCAGGTGCAGCAGCTGCGGCGGCAGCTGGTGGTGCAGGACCTGGTACACAACAAGC
ATATGGACCAGGAGGATCTGGAGCAGCAGCTGCAGCAGCCGCGGCAGCAGGTGGAGCAGGACCTGATAGACAAC
AAGGATATGGACCAGGAAGTTCTGGAGCAGCAGCGGCAGCAGCAGCTGGTGGACCAGGATATGGAGGTCAACAA
GGTTATGGACCAGGAGGAGCAGGTGCAGCAGCTGCTGCAGCCGCTGCCGCAGGGCCAGGACCTAGTGGATACGG
ACCAGGAGGAGCAGGTGCAGCAGCAGCAGCAGCTGCCGCAGGAGGATCTGGACCTGGAGGTTACGGACAAGGAC
CATCAGGTTACGGCCCATCAGGACCTGGTGGACAACAAGGTAACGGACCAGGAGGATCTGGAGCAGCAGCTGCA
GCAGCCGCGGCAGCAGGTGGAGCAGGACCTGGTAGACAACAAGGATATGGACCAGGAGGAGCAGCAGCGGCAGC
CGCAGCTGGTGGACCAGGATATGGAGGTCAACAAGGTTACGGACCAGGAGGAGCAGGTGCAGCAGCAGCGGCGG
CAGCTGGTGGTGCAGGACCAGGTAGACAACAAGCATATGGACCAGGAGGAGCAGGTGCAGCAGCTGCTGCAGCC
GCTGCCGCAGGTCCAGGACCTAGTGGATACGGACCAGGAGCATCAGGACCAAGTGGAACAGGAGGAGCAGGTGC

FIGURE 7 (cont'd)

AGCAGCAGCAGCAGCTGCCGCAGGAGGATCTGGACCTGGAGGTTACGGACAAGGAGCATCAGGTTACGGCCCAT
CTGGACCTGGTGGACAACAAGGTTATGGACCAGGAGGATCTGGAGCAGCAGCTGCAGCAGCCGCGGCAGCAGGT
GGAGCAGGACCTGGTAGACAACAAGGATATGGACCAGGAAGTTCTGGAGCCGCAGCGGCAGCAGCAGCTGGTGG
ACCAGGATATGGAGGTCCACAAGGATACGGACCAGGAGGAGCAGGTGCAGCAGCAGCGGCGGCAGCTGGTGGTG
CAGGACCTGGTAGACAACAAGCATATGGACCAGGAGGATCAGGTGCAGCAGCTGCAGCAGCAGGCTCAGGACCT
AGTGGATACGGACCAGGAGCAGCTGGACCAGGAGGAACAGGTGCAGCAGCAGTAGCTGCGGCAGGTGGTGCTGG
TCCTGGAAGACAACAAGCATATGGACCAGGTGGTTCTGGAGCAGCAGCGGCAGCAGCAGCTGGTGGACCAGGAT
ATGGAGGTCAACAAGGTTACGGACCAGGAGGAGCAGGTGCAGCAGCTGCGGCGGCAGCTGGTGGTGCAGGACCT
GGTACACAACAATTATATGGACCAGGAGGATCTGGTGCAGCAGCTGCAGCAGCCGCTGCCGCAGGGTCAGGACC
TAGTGGATACGGACCAGGAGCAGCAGGACCAAGTGGACCAGGAGGAGCAGGTGCAGCAGCAGCAGCAGCTTCCG
CAGGAGGATCTGGACCTGGAGGTTACGGACAAGGACCATCAGGTTACGGCCCAACAGGACCTGTTGGACAACAA
GGTTATGGACCAGGAGGATCTGGAGCAGCAGCTGCAGCAGCCGCGGCAGCAGGTGGAGCAGGACCTGGTAGACA
ACAAGGATATGGACCAGGAAGTTCTGGAGCAGCAGCGGCAGCAGCAGCTGGTGGACCAGGATATGGAGGTCAAC
AAGGTTACGGACCAGGAGGAGCAGGTGCAGCAGCAGCGGTGGCAGCTGGTGGTGCAGGACCTGGTAGACAACAA
GGATATGGACCAGGAAGTTCTGGAGCAGCAGCGGCAGCAGCAGCTGGTGGACCAGGATATGGAGGTCAACAAGG
TTACGGACCAGGAGGAGCAGGTGCAGCAGCAGCGGTGGCAGCTGGTGGTGCAGGACCTGGTAGACAACAAGGAT
ATGGACCAGGAAGTTCTGGAGCAGCAGCGGCAGCAGCAGCTGGTGGACCAGGATATGGAGGTCAACAAGGTTAC
GGATTAGGAGTAGCAGGTGCAGCAGCAGCGGTGGCAGCTGGTGGTGCAGGACCTGGTAGACAACAAGCATATGG
ACCAGGAGGATCAGGTGCAGCAGCTGCCGCAGCAGCAGGCTCAGGACGTAGTGGATACGGACCAGGAGCAGCTG
GAACAGGAGGAGCAGGTGCAGCAGCAGCAGCTGCGGCAGGTGGCGCTGGTTCTGGAAGACAACAAGCATATGGA
CCAGGTGGTTCTGGAGCAGCAGCGGCATCAGCAGCTGGTGGACCAGGATATGGAGGTCAACAAGGTTACGGACC
AGGAGGAGCAGGTGCAGCAGCTGCGGCGGCAGCTGGTGGTGCAGGACCTGGTACACAACAAGCATATGGACCAG
GAGGATCAGGTGCAGCAGCTGCAGCAGCCGCTGCCTCAGGGCCAGGACCTAGTGGATACGAACCAGGAGCAGCA
GGACCAAGTGGACCAGCAGGAGCAGGTGCAGCAGCAGCAGCAGCTGCCGCAGGAGGATCTGGACCTGGAGGTTA
CGGACAAGGACCATCAGGTTACGGCCCATCAGGACCTGGTGGACAACAAGGTTACGGACCAGGAGGATCTGGAG
CAGCAGCTGCAGCAGCCGCGGCAGCAGGTGGAGCAGGACCTGGTAGACAACAAGGATATGGACAAGGAAGTTCT
GGAGCAGCAGCGGCCGCAGCAGCTGGTGGACCAGGATATGGAGGTCAACAAGTTTACGGACCAGGAGGAGCAGG
TGCAGCAGCAGCGGTGGCAGCTGGTGGTGCAGGACCTGGTAGACAACAAGCATATGGACCAGGAGGATCAGGTG
CAGCAGCAGGCTCAGGACCTAGTGGATACGGACCAGGAGCAGCTGCAGCAGCTGCGGCAGGCGGCGCTGGACCT
GGAAGACAACAAGCATATGGACCAGGTGGTTCTGGAGCAGCAGCGGCAGCAGCAGCTGGTGGACCAGGATATGG
AGGTCAACAAGGTTACGGACCAGGAGGAGCAGGTGCAGCAGCAGCAGCTGCCGCAGGAGGATCTGGACCTGGAG
GTTACGGACAAGGACCATCAGGTTACGGCCCATCAGGATCTGGTGGACAAGGTTACGGACAAGGAGGATCTGGA
GCAGCAGCCGCGGCAGCAGGTGGAGCAGGACCTGGTAGACAACAAGGATATGGACCAGGAAGTTCTGGAGCAGC
AGCGGCAGCAGCAGCTGGTGGACCAGGATTTGGAGGTCAACAAGGTTACGGACCAGGAGGATCAGGTGCAGCAG
CAGCAGCGGCAGCTGGTGGTGCAGGACCTGGTAGGCAACAAGCATATGGACCAGGAGGATCAGGAGCAGCAGCT
GCAGCAGCCGCTGCCGCAGGCTCAGGACCCAGTGGATACGGACCATCAGCAGCAGGACCAAGTGGACCAGGAGG
ATCAGGTGCCGCAGGTGGATCTGGCCCTGGAGGTTTTGGTCAAGGACCAGCAGGTTATGGTCCCTCAGGACCTG
GTGGACAACAAGGATACGGGCCAGGTGCATCAGGTGCTGCAGCGGCAGCAGCAGCTAGTGGATCAGGTGGATAT
GGTCCTTCACAATATGTTCCTAGCTCTGTTGCTTCTAGTGCTGCATCAGCAGCCTCAGCTTTATCTTCACCGAC
AACGCATGCTAGAATTTCTTCCCATGCATCAACTCTATTATCAAGTGGGCCAACTAATGCGGCAGCTCTTTCTA
ATGTCATTAGTAATGCCGTTTCCCAAGTCAGTGCAAGTAATCCAGGATCTTCCTCTTGTGATGTCCTTGTTCAA
GCACTTCTTGAAATAATTACTGCATTAATTAGTATACTAGATTCCTCTAGTGTTGGACAAGTTAATTACGGTTC
TTCAGGACAGTATGCACAAATTGTAGGGCAGTCTATGCAACAGGCTATGGGTGAAGCCTTATGTTTTGATTTC
TTATAATGAATCCGTGTAATTTGTAGTTTTAATTTCAGAATAAATTTTCAAAGCATTCTTTATTTGTTTGTCTT
CTCTATGGTTTCAGAAGTAAGGTCATTTCTGATGTATTATATGTATAATTTAAGCGTTTATTATTCTACATGAT
TTCTATAAAAAATTATTTTCTAAATATATTCTAAATCCTGGTACAGTCAAAAATGCGAAAATGTATTCATAATT
TAAATTGTAGATGAATTTTTTGTTGATAGTTGATATTTTTCATAAATTTTTAAATTATGTAGATATAAGACATG
TCAATCATGTTTCCTATCGTTTAAATTTGTAAAATGAAGTGGTCAATATCTAACTGTTAAATACTGAAATTTAT
CAGGAATTTTGTTTTACGTCCATCATATTTGGCATTAGTATTTAAACCAGTAAATTTTCAGTCATAGTATTTTC
AATAAAATTCTAAAAACAGATTTAGCTGTCATTTTAAGAAAAAGTTTCTGTAAAAAAATTGATTGATAGATTAT
TTTAATAAATTTTTAGGAAAAACCTAATCTTGAATTTTTCTCGATTTAAATTCATAAATAATTATTGGGAGTTT
ATTTATCTCCTTGGATTCTGTAAGCGATTCGTTTTTATCTATATTCAGAATACAATTTTATCAAAACTGTCTTT
CTTATCAATTCATGCGAACAACTGAGTGAGATCATTGATCCAGGCATTTTATTTAACCGTTAAGTGAAAAAGTA
AGTTTCAATGATTTCATTAGAACACTTTTCAACAGTTAAATAATTTTTCTCATGAGTCGTAAAGAAAGTTAAAA
AGGATATATCGTTTGCATTTGAATACGTTTTCCATAATTTGTCATAGTCATAAATTTACTTATTTTCAAAAGAA
TGATAGAATGCATAGTTTTCATGTTGTGATAAAATGATTGAGTATTATGTTTACAAAAATTGACAGATCAAGTA
AAATTGTTTATGGATTTAATGGTAATTTCATTCTTTGGTAATTCTACTCCACGGAATTAGTCATTAGAATTAAT

FIGURE 7 (cont'd)

AATAAAAAATACATTTGGGAGAGTTTCTGGAAATTCTTTAGGATGTTCAATGTTTAGCCAAAACGCTTCCTCTT
TAAAGATATTAATATGCATTAAATAATATTTTCAATTCCATTTTTTATAGAAAATATGTCCTGGTAATTTCTTT
AAAATAGTCCAAGTTAATTTTAGAGAAATAATTTTTCTAATATATACCTTTCACATGATAATAGTTAGGCATAA
TATCAATATTAATTTTTCGCATAGTGAAACCCAATGTTTGCCGAAAATCAGTGACCATTGCTTTTATGAACGTA
AACTTTTTCACGAACATTTAGATTTTATTGGTATTATTTTTTCCTGGGCAGAAAGGAAACAATGATGCAGTGGT
TTCCTTACTGAGAAAAACTTAATCGGACGACATACCTTGGGATTATAGACATAAATGCATTTTCAGATGTTCAT
GGTTCAGTTTGTCAAATGATATGTCGAATAGATACGAATAGATAAAAATAACAAATTAAATAGAGATTGTGATA
GAATAAAAAATTGTTCCAAAAAAAGAAACCACTTAGGGAGTTTGTTGTACTTATTGTAATCAAACGCCGATGTA
TATACATACACTACTGGCCATTAAAATTGCTACACCAAGAAGGAATGCAAATAACAAAAAGATATTTATTGGAC
ACTTACATTATAGTGGAAAGAACAAGTGATTAGATTTACAGGAAATTAGGATGTACAGATCTTCGACGCCGCAG
GCGGACAGCCTACTCGCGAAGCGAGTGTAAGGCTGTTAATGTCCGCTGCGTAGAGAAAAAAACCCATCACGGAG
AGGCAACAAGCCACCCCCGCCGGGCATGGAAATGAGAGCTGATCCAGTAGCCGGTTTGAACAGACGGGTTATTG
CTCTGACTGACCGATGATCTGGTCTGTCATCTAAAGTCTCTGGGCTCGATTCCGGAACAAACCAGAAAAGCCAC
TCCACCAACCCAACGTGTATGCATCATTCCCCGTTTATTGAAACTTTTTATCACATTACTAAGCCCGAACGCGA
GGTGAGGCCCACGCAGTGAGCGTCACCTTTACATGTGCAGGCTGGGGTTTGAATGCCTTCATGGGGGACTTTGT
GGGAAGGTGAGCCGTATTTACGCTAGTCTGGAGGGAAACCATGAAAACCTCTAGAACTCACCCCGAGCTGACTT
GCAACTCTACTGCGGTTACAGGAAGAGCTGCAGTACGCTCTATGACGCTAGTCTTGTTACATTGTAGATTTGGT
CTCCGGAATAAAAGTTCAAGTCGTCGACCTCTTCCTTTGTCTAAATTTGGGTTGGTGGACGCGGTTGAATTTAC
CTTGCTGTAGCAGTAAAGTTCACTTCAGTTTTGCAAGGCGTCATTCTCGCGTGTCCTGTGTGACTGCAGGTGAT
GCCGCTATCCTCTGGATCAAAGTTCATCACATTGAATGCGCACACACACTTGCTTGTAGTTTTCAGAACATGTT
GAACATTGATCGTCTGAGAAACCACAGCTGTGGCCGATCAATGTCAACTTTCACTAATGTATTGGATTGTCTCT
GAAAGCACACATTTGCATTGGTGGCACTACACAAAAGTTTGTAAGAAACTGCCGCTGTGAGAAATCAGTACCCA
GAGCAGCCAACTCTGGCTGCAATAACAGCATTTATCCGCCCAGGCATGGAGTCAAACAGAAATTGTATGGCATG
TACGGGGATCTCAGTCCATGCAGCTTCAACCCTATGCCACAGTTCATCGACAGTAGTAGATGGTGAGTGATGGC
GTGCCAATCGTTCGGCAACCATTGACCACACGTTCTCAATTGGTGACAGATCAGGAGAACGTGCTAGCCAGGTT
AACAATCGAATCTGTTCTGTATCAAAGAAGTTCAGAACAGTACGAACATATGGTCGTGCATTATCCTGTTGAAA
CAAAGCATTAGGGAGGCCTCGAAGATAGGGCAGAGCCACGGGCCTTAACACATCGGAAATGTAACGGTTGCTGT
TTAAAGTACAGGTAATGCGAACAAGAGGTTATCGAGACGTGTATCCAATGGCACCCCATACCATCACTCCAGCA
GATGGGCCAGTATGGCGATGTCTAATGCAAGCTGGCAATGCGCGTTCTCCACGATGCCTCCAAACACGGATGCG
GCCCTCATGGTCCTGTATACAGGACCATGAGGTATAAACCGAGATTCATCTGTAAAGATGACATGACGCCAATC
CCGCGTCCAGGTTCGTCGCGGATCACACCATTGAAGGCGCTCCTGTCTGTGACGCAGCGTCAATGGTAGCCGAA
GCCATGGTCGCCGTGCAGAAAATCCATGCTGCTGCAAACGTCTTCGAACTGTTCGAACAGAAACTTGTTGCCTT
GCAAATGACTCCATTTCTCAACTCAGGGTTCGTGACGTGGCTGTACGATCCCTTGTGACCATGCGAATAAGATG
TCTGTCTTCTCTGCTATTAGTGATGGGGGGTCACTGAGATCCTGCATGACGTTCCGTATGATTGTCCTGAACCC
ATCGATTCCATATTCTGCTAACAGTCATGGGGTCTCGACCGACGCGAGCAGCAATATTGCGGTACGATAAACCG
CAATCCCGGTAGGCTATAATCCTTCCTCGATCAAAGTCAGACACGTGCTGATAGGCATTTCTTTTTCTTACTCG
AAGCATTACAACAAATTTCTTTGCCGAAAACAACATTGAAACGGAAATTGAATATTAGAAAACTGCTGTCAAAT
CTCTGGTTTTATACACATTGTAGATGTCACTACTATCGCCTGCTTTGTATGAATGCCCTGAAAATCTAATCATT
TGCATACCACAGCAAGTTCTACCTATTATGCAAATTTCACGTGTGTGGTGTGCCGATTTCCTGGTGTAGCAATT
ATAATGGCCAGTAGTATATATTATTGCTATTATATTGCATTACTCTCCTAATTTCATACAAATTATTTTGCTGA
AATCTCTTTCTTTCGAATCTCATAAATAGTTGAAGAACGAACTTGCCCTCAAAAAACTTGTATATATTAACAAA
AATTTTCTATTACATAAATATTTTTACAATTCCTTTTTTATTTGATTATAAACAGTAAAAACACTGAATAGAAC
AATTATCCAAAATTTCTATTATTTAGTGACTAGACCAGTATTACAGTAAACTACTGCCAATTGAATTACAAAGA
AATTGGAATTTAATAATGAAAGTTGAACACAAAGTTTAAGGGCACTTTTTCATTTTTATCTTTCTAAGCCAAGA
AATAATGTCTGAAAGTGAAGCCGAAAAATCAATTTTTTTCATTAAAATGTAAAAAATTTCAAATACTAATGATA
AAGAATATTCGCGGCAACACTTGTCACACTTCTTCATCATTTTATCAATGTAACCATGAATGAATCTTCCACAT
GGTAGGAATAGAGGTTTTTGCACTTTAAAATGAAAAATATTTCAGAAAACTAGGTAAAAATAATGTACGATTGT
TCTGTAATAATATGATCGCTTATAATCTTTTTCCACAATCACTACTTATGCTTCCGATAAGGAGGACTGTGTAA
AATATTACGCTCCCCACTTTTAAAATATCCTTCCATTATTTGAATGTAGAGGGAAGTAAGCAATAAGTGCTAAA
TGTTTTTACCAGTGTTCATTAGATGGAATCATTTGAATTTCTGAATTTAGTTACAGGAAAGGTTTCTGAAGTAA
TATGTCAATAGTAGATTAGTATTAGTCTGGATTACCGCTTTTATTTGTTATTGCCTCTAGTTTAATTAGTTTCA
GCATTACCTTTTTACTTCATTCAATTTTATGGAAATATTGACGATACCAAGGTAATTAATGTAACTTGAAAGGT
CCAATTATACTGATTCTTTTGAGTAATAGTGTCAGAGGCGAGAGTAATTCATTAATTCCGTAATGTTTTTTTCA
TTGCAAAGGTTATGAGTGGTTTTTAGGCTTCAAACAACTGAGAAAATTATATCTTTTGAATATTCATCAGTTTT
GTTCCCTTAATTTCAATTTAACAGTTCTTTAACAGAGAAATATTTTGTGAAGTTTCCTTACATTAGCAGTATTT
ACATGATTTGACCATGAGAATTAAATAAAATATTCAGTACAAGTTTCTGAAAAGTGAAAGGGGTAATATTTTTC
TGCAAAAAATTACTTTTTGTGAAACGACGCCACTGTATTGTATGACAATATTGTAGTCAACAAACTTAGGTTCT

FIGURE 7 (cont'd)

ACTTGGAAGGGAATTCCTTCGATAAATTAAGACAATTGGACAGTATTGAAATTTAGGAGTATACAAAAATTTAA
TATAGAAAATCAAATAAAATATTTTTAAATCATCAAAGACCAACGTTGAATTATAACTTCCTGATAATCTCATA
TTTTTAAATATAAAAATTATCCCATAGCAATATAAAATATTAAATTTATATTCAAATATTTTAATTGGCTCAGA
AAAATTGATTTGGTATTTAGTTATATTATATAATTAATAATTATATATAGTTTGCCGCTATTTATTTGAAAATT
TTCAGTAAATTTAAATATGCTGCCACAATCCACTGGTAAACTTTAATAAATCAAAGAATTTAGAATATTATATT
TGGAACACGAAGTGCATAATTTCTGAGGACTTTATTATCTTTGGACTTTTGCTTTTAAAGACATCAATTTGATA
TGATTAGGAAAATTAATTTTATTTTTCCATGTGTTCTAGTTATTAAAATGAAAGAAAATATTCATAATTTTTAA
TTTATAATTAAAATATTAATTTAAATTTATTTATTTTCAACTATGATCTCTAATAATTTCTGAAAAATAATTAA
ACTAAAATTCTAACCAGTAAATAAGTTTAAAAAATTTAATAAATTCTTCAAAAAATCTCTACGTTGTTTAATCT
CCCAGAAAAAGTAATTTTAAGTGTCTGCATTTATTACTATACACTCAAATTGCATGCATTCTTATGAGTCTCCG
AATCATAAGAATCATAATTCGAATCATAAGAATCCGAATCACACGCTTACACAAATCACTTATATATAATGATA
AATTTCTCATGCAACTACAGCAACAAAATGAAGATTTTATTTATAGTTACCCATAATCTTCTCGCATTATGTGT
TTGATTAATAAATCTTTTTGAAACTGATTAAAAACTTCTGAATTAATTTAATATATAATTGTTTTATTTTTAAA
GGGTGTTTGTGGAAATTTTAAATTTAACTTCATATCATGCTTTTAACTTTTAAGTAAAATTTTAATGTCACGTT
TCCTTGGGAACCCTGATACCTTTTTATTAAAATATTCTTACACAAAGACTAAACATATATAAAGTAAATACTTC
ACGAAATGTTGATTAATGTATCGTTCTGAATATTGGAAGGTTGTGCTTTCGAGTCCCGACTTTACCGNAAATCC
GTGGTCATCACTAAAATCGACTATGGCACGTTTAATATATCGTAGTTGCAATGTCCTCCAAGTGAAATTATGTC
TTTAAATTGCAGGGCATGTATAGGGAGTCTTAATTGGTTCCTGCTTCCAAATTACGAAGACTCCCACACCTCTG
ATTCCAACTGACTGATAGGGTTAAACTCAGGGCAAGTATTGCAAAACATGCAACAAGGAACTAAAACCCTAAAG
AGTATATTTTGATTCATTTTGATAATACATTCCATTTAGTCAAACGCATAAGTTTACTGTTCATATTCAAAGAA
ATACTTCTTGAAAAAGCATAAGTTTACTCATTGCATATTTATCAGTATTAATTACTTAGTTAAGTCATCACGAG
CACGCGTCATATTTCATAATTTTTAAACTTACGAATATACCTTTAGCATATTTCATTTCTGTTTCTTAAATACT
GAAACATTTCCTTCTCTAATTTTACTTGAGAGCAAAGCTTAGCTTTATTTTATAAATCCTTATATTGAATGAAA
TTTACGAAAAGACACATTTCTTTTTTTTTATTAGAGAAATTAGTTATTATATGCTTATTTATTTCAACACCAAA
TTAGTTTTAAAAGCGCAATGAATTGATAAAAGCTACAAGCTGAGAATTGCGCTAAGAATTTTTGTGATTAATTC
ATTATTCATATATATATTCTAATTTTAGGAATTAGGTGCGTAAAAGTCATAATACGTAACTAGATAGATATGAA
ATGAGTTACATGTAACTGATATCTGATGCTATAGATTTCATGTCTAAGCAATATTATATAACCTATTTTCATCT
ATGTAAACTAGTAAACTAGGACTTTCTTTTGAAAAAAAATCAGCACTGATTTGAATTTTTGACTTCTACATATA
TATATATAATATATATATATATATATATATATATATATATATATATATATATATATATATATATATATATATAT
TAATAAATTCATATGAGAAATCTACTATTCGATAAAATATATTAAATTAAAATTTAAAATTTCATTGTGTTCTT
TTATTACCTAATTGTAAAATAATTCATAAATTTCCTCACTTTAATCTCACAGGGCAGTATAAAGTTTTCACTAA
GTATATATATAGTTTTAAATAAATTATTTGAAGACTATGCTAGGCTTGATTTATTTACACATTCTTAAGAATCT
TCTATTGTTGTTCGTATTTTTTACGTTATAAAATTCTTTTCAATACTGAAGTTCATTTTAAGCTTGTTATAGTA
AAATAGTCCATGCATATATACTGAAAAAAATTACATTTACTAGACTGATTCCTTAATTTATATAAACTGCTCAA
TAATATAACATTATTTGAAGCAACATTGCTTATACAGATTACTCTGCATAAATGATTAATTATTGGTTGATGTG
TGTGTTTACATTAAAAAAACAATCTAAGTTTATTTAATCTACTTAATATATAATGTACAGTAAGAAACTATATA
TACCTTAAAAAATTATACATCACTATATTGCATTTCTAATTGGTTCACGTTGATTTGCCCATTTCCAATTTACA
CGTTGACACAAGCTACTTAACTTTGGTTCATTGATTTCGGATATGTTATATTCAGTTTAGGTGATGAATCGGCA
GATTCAGCTCCTTCGATTTGAAATTGTTTGGGTCAGTGTTCCTGGAAAATATCGTATTCAAACCCGAATCCCAT
AATAATTTTTCCCAAGTGATTTGGAATGGATTTAAGCACGTTAAGCCCAGCCGATCACATCCATTCATCATCCA
AAATGAAGCATCACATCCATTTTGGATGCTGAATTCGTGTCATCGACAAGTTCGATTTAAAGTCCAAAAGTTGT
TGAGCAATATTTTGTTCTTAAAACATTGGTTTTTCCACGAACACCAAAACAATAGTTCCTCAAGACACTTAAAA
TTGATTTGAGCCCCGTGTATGTTGATATACGCGGTTTAATCACAGTCACATGACTTTGGATACATTACATTTAT
TTTAGGTGGTGAATCCGTGGTTCACATTCCTTCGATTTAAAGTACAAAAGTTATTGAAAAATAATTTGTTCTTA
ATACATTGATTGTTCTG

FIGURE 7 (cont'd)

>16D22 [organism=*Latrodectus hesperus*] [molecule=DNA] [moltype=Genomic DNA] [location=genomic] [clone=16D22] *Latrodectus hesperus* major ampullate spidroin 1 (MaSp1) gene, complete cds shown in bold-uderline TTCATTCATCTATTTATCTGAACAGAAAAATTACTATGAAACGAAAAATTTTACACCAAAGAAGGAGTTTTAAG
AAACCATCAAAATTAAGACGCACAATTTCACTAAAAATATAATCAATTGAGGAACGAATCTACTTCCCTGCTGT
GTATAAATTATAACAAGTAAAAATAATATTTCACAACTAAATTAACTTTTTAAAATGTTTCATTGGAAAGTTTA
TTTGGAAACGACAAATATACCTGCAATAAAAATAGCGCTTTCAATAGTTTAATATAAAGATAGTTAAAAAAAAA
CATTTGAAATTTTGGAATTTAATATGGAGTTATTTTTCAATATTAAAATAATTAAATAAGTAAAAATAAATGCA
TACTTTAATAACCTAACTATGAAAAAAATAACAATAAAATCATGTATCTTGAAAATCTATTGACACCATAATTT
TATTAACTTTTCTCAGAAACGTTAAATCACATTGCACTACAAAAAAGGTGAACGTCTATGCATCAGATAACTCT
TGTTTCAGAAAGCAATATATCACTTCCAGACTAATACTGGACTGAGGAATTGGCTTAGCATACATTTTACACAA
CATAGAAAGTGGTAATCACAGCCAAGGATCACATTCCGCCAACTAAACGTACTTTCTAAGGCCAAGCTCATTAC
CAATCCATTCTACGTGGCTAGGTTTATGATTTCATAAAAGAGAATAATTGTAGGTGTAAACTTGGAATAAACAA
TAAGTAATGCGCATGAAAATCTATCCTATTCAACAAATGACACCGGAAATACGATTGGGACAATGTTGATGTAC
ACATTACTTCAATCAGATAGTTCGATGTCCCTGAACATTTATGGCCACAAAAGATCAAAAATATTTTCAGGTGG
CTGATTGAATATCATTAGATTCTGCTCTGGTGAGATAGCGTAAATGCTATAATTTCTTCTTTAATTTGTGTTGC
TGAAACCTATTTTCAACCAACCGATTTCTCAGAGATTATGACATAACTGTTTGCAAAATTGTACAAAAGAGTGT
TTTGAAAATATTTAATAGATTTAATCACAATTAGATACATTTGATCCATGTTAGAAAAATGATAAACGACATTT
GAAATATGGTAAAATTTCGCTTGTTGTAAAGAACAGTGGAATCGAATGTGAAAGAAACTGAGAATTTCATAAAT
TTCAAACGTTGTAATGTATCTAAAGGAATATTTTTATTCGGAGGAAGGAATAATTAAGCTTATGAAAATTTGCT
TGCACTCTTAAAGAGAAAAAAGACTAAGAAATATATAATATAAAATTCCACACGCTTTAATCCATACGTTATGA
TGTAATATGTATATTACTTATAACATTCTTTTCACATGTAAATGCCAACGTTATAAAACTTCTCAAACAATCGT
AAATGTAGTAAAAATTATGTGCTATATTCAATGCCTAATTTTCTTGAGTTTAAAATTTGATATTCGTGGTAAAT
ACTTTTGATAAGCTATACCTTAAAATTAAACCTTTTATCATTTTAAAATAAAAATCATTAACAGACAAAATGTG
AAAATTCGATATTCTGTCTTCGATATTCAGAAACCATAAAATTGATAGTATACTTCTCTTAGATGTATCAAATT
CAGTAATTTTATACAAGAAAGATTTAAAACATTTTTGGGGTATTTTATAAAAAAAAGTATTTAAAATCGGCTAT
AAGACTAGAAAGTTGCATGCTAGGAAGTTTGTTATTCATGAGTATTAGGTAATATATGCTTTTGCTCTTCAAAA
TGATCTACTTTATTGGAATGTATACATGAATCAAAATCTCATACGATAATCCATTTAAGTAAAAATTAAATATG
AATTTTGATGAAGATTATGCACTATTTAATTTGTTTATGTTAACCTTTTTATGATAAAAGGAAAATAAATTTAA
AAAAACTAAAAGCTTGAAATTCACTGTATTAACAGATATAAATAATATAATCATGCGTCAGTAGATTTTATTAA
AATTAGTTTATCAACTCAAATCTCCATTAAATAAAACTTATTATTGTGCCATAGAAATTTTAAAAAGAAAATAG
TTGACTGATTTGAAAGAAATGCTTTAAATGTCTAATGTATGACGCGATGTCTCAAAAATTACTATTACATTATT
TCCTAAAATAGCACAACTTAAGCGCTGTGCCTTTCAGTTATAATTACTCTTAAGGAAATAAGTATAATAAAAGC
GAAATTTAATTGTAGCATTGAAGCGTAGTGTTTAAATGTAGTTTATTTGCGCATTCGGAAATTGATATTTTTTT
AGTTTCTAACACTTAAATTATACATAGCGAATATGCACACTTTCATACAGCTTGGGATCTATTTGAGTTGAAAA
CATAAATCAAGAAAAATGCAGAAATAAATGAGAGCATAAATTAATGCAGATAAGTAATGTAAGAACGAAAAGTA
GAAAATTTACTAGACCAAATAAAATGAAATTACCAATCATTTTGTAGTTTTGCTCTTGAAAATAGTGTTTCAAA
TTTATATAATTTCCTCATATTTTATCAAAAATAATTTGTATGGTAGTATGTGCAATTTGTTCTATAAACTCACT
GTGAATGTAAAAGGGGGAGCATATAATGTTTTGCTTTTGTTACTGTTTTACTTCTTTTCACAATTTTATACATA
CAGTTAATTTGAAAAAAAAGTATTATGAAAATAGAATATTAATTGCCTGCCCCAATTAAAATAATTTTCGATTA
TGGAACACATATATTGTACTGTCAATGGTAATAATGTCTCTTCGCTGCGAAGTATATTTCAAAGCATATAAATG
TAGATAAAAAAATTAGAAATTAGAAACTTTAAATTAAAGAATATTAATTCTTCACAAATTCTTATTTAAATTTG
TTAAATGAATAAGCATTAAGTATTTCTTAAGCATATTTTGTTTGCAGTATTATATTTTAAAATATACATACCTC
AGGTATTAAAAATATTGAAAAGTAATACTTATTTTCCACCTGTAAAAAGAACAAGCAAAATATCCTGCAAACTA
AATTTTAAATTAAATTAATTTAAGCAAAACCCGACAATTCTGCAGATTTTTTAAATATTATATTTTTATTTAACA
CTTTTAGCAAAATAAAGTGAAAAGAAAACTATTTTTCTTTTTAATTTTAAGAGGAAAAATAAATTGAAAAATAA
ACTTCCAGATCAGTTTTTATATTTTTGAAAAATATACATTAATTTTTTAAAATGTTTCTCCTAGGTAGTTTTTT
TTAAAGAAATTGTTTTCTTCATGGATCTCCAATGAGCTTTTTTTTAACAGACAACATAATTGCATATAAATCGC
CTAAATATCATTGCTTGGCTAAAACTTAACAAAAAATATTAGATAGAGCAATTCATTAGGTTACGAATAAATAA
TTTTTTAGACATTTTTGCCCTATTTCATAAATTAATTGACGAAAACTTGTATACGCTAGAAAGCAGATCTTAAT
ACTAATTCTATTTTATACCGTTGAGTATCCTTGATTTGTATGTACATAAAATATTTTTCCCTGTAAACTAAAAC
TTTTTTAAAGGTTGATAAAAATTCAAGATTTACGAAGATTTTTTTATATAAAGGAATTAAGATGACTTTTTTTT
AAATTAAAGATTTTATATTTTTTTAAAGATTTTTTCTCACGATACCCTTGTATACAAATTACAAGGAAATTTAA
AAATTTACGTAATATAATAATTTTATGAGAAATTATTGGGACATTTATGTGATTTAAACAAGTTTTAAACATTA
ATAAATGCTGTTTTTTCATCAAAAATCATTTATATATCGATTATTTACGTAAATTGTAAAAAATTTCATGGAAT
CTCATAAATAATCAAACTATTTTATTCCAAATATTTGCTAAAAGTGTTTGCTTCTAATATATTTTAAATATGTA
AATCTTTCAAGCGATAAACTTAAAAAAAACCTTTCTGTAATTAATAAAAAAATAATATTTCATGTAAATATATT FIGURE 7 (cont'd)

TGCGTAAAATTATTCTAAAGTAAGCCTTCTGAGTTTAAAGCAAGCTCATTCATCTGTTTCTTTTGACATTCATT
CAATTAAATATAAATTAATACTTAGCATGCAAACTTTTTTTTATTTATCAGAAATTAGATAAAAATTATGTTGG
AAATTTTAAATTAGAAAATCACAAAGAAAACAAAATAATCAAGAAAAATGATGCAGAATATTTGTGCATTTCTT
AAACATTTATAAAAAAAAAAGCTTTTAGGACAAACAAAACATTTTTCTATCATTTAAGTAAAGTAATTTCGAGA
TAATTAAGTACAAATAAGCACAACTTTGATATTTAAAAAAATTAATTTGTAGTTCCTTTTCAACATTATTTTAA
TTTCTTTTCATTCTACAGAATATTCTGCAGAATGTGTGGTGATGAAGTCAATGAATATTCTATTGGAATATATT
GTGATGAAAAAAATGGAAAGTTATAATTTATACTTTCCGCATTTTTCATCGCAATACATACCCTAAATTGTATT
CATATTTACTGGATAAGAGCAACTTAAACTCCTTTTTTTTAAATGAAATAAAATGGTTCAGAAAATAGTATTCA
AAATAATATTTCTTAATATATTCATTGGGAAATGAGAAATTTATATTTACTTGACAAATGTATAAAATATTGCA
CGAAAAATATCCAAAGTAATTTTATTGAATGAAAAATTAGCTTTTGATGTCTGAATAAGCTATATTATTTTTAT
TTTAATTAACTTCCTGCGATTTCATTAAAGTTTATTCTTGTAATTTAGTTTTCTCTTCCAGATTCAATACAAGA
CGTAAATACGCAAGTAACATATAAATTAAATTGTCAAATATTTTATAAAAATCTTCAATTGTCCTTTATTGATG
ATTAAATCTTGCTTTAGAAATCTTTCATCTATCGTAAAGATTATGGCATTAAAATTAATTCTCAATGCTATTAA
TTCATTTTAATTCATAAGGAACAATTTAATTAGTTACATCCATCAAGCATTTAAGATTAACAATTTCATTCTGC
CGTAATTAATTATTTGAAATAAATCGGAAAATGCATGCGAAATTTTGCTCGACTCCGATAAAAGGTATGATTGT
GACAAATAATCACATTTCCTTTTTTACATAAAACTGTTCCTTAATTGTTTAATTTATTCATGAAGAACTTTAAC
ATAATTTTCAGTAAAAGAAAATATTTATTCATGATCATAATAAGCAAGTGCTTAAAATTTCGTGTGAAAACATT
TAATACTTCCAAAACGTTGTATTGTACTCATTTTCTTTTACTTTCTATTACTATCTTCTGGAGAAGTCAACAAA
GTTTTAGTAAAATAATTAACCTTTTACAATTCCAGGATTTTTATATTAGTTTTTACTTTGGTTCCGAGAATTTG
ATTACTGATTATCATTTCACAAAAAACCAAACAGTTTTTAAATGCAGTTCACTATTCTTATTTAATGGTTAACA
TGTAACGCAAATTTTGCGTGCCAACAAATATCATTAGCAAAACATGTATTGATTAAAAAGGGTAAACGCAATAT
AGACAGACCTAGGTGAATTATTCCATTTTGGCAAAATTGTACAATTTATTTTTCCTTCATTACTTATGTTTTTA
CGTGATTATTAACAGCTTCTTAATTGATTCTTTCAGTCTTTCTAGGTGACATCTTTCAAATTTCAGAGGAATTC
GTCAAATGACAATAATGCAATAATAATTTGCATATAAATATCGAACATAATGAGGATTGTTAAATATATTTTTA
TAACTCGACTACAATACACTTCTAAAACTTTCCACCAAGAGTGCCTTTGAATTTCAGTTTAAAAGTATAAATAC
TTAATATATATGTACGATATCATCTCAATTAAATATAAATTTGCTGCAAAGAATTTATTTTTTCTAAGCTTTAT
TTAACTAACTAATTGCAATCTAAAATAGTTAAATTTTTATCTAATAAAGTACTTAAGATAGTTAAATTTTTCAC
AACACATATCCTAAAATATATTCATATTTATGAAAAAAAAACAACAACTTATATTCACTTTCAAAATGAATAAA
GTGTTTCAGCAAAGTATTCGGAATATATTCATAGGAAATGAAAAAGAAGAAAGCGAACACTTTTTAACCTTTAC
GATGGAATGTTTAATAAAAACATTGGCTACACACACTTACATTTTTATATTTTTCTTATTTTCTCATTCTTCAA
CATTATTTTTATCGAATTTTTTTCAATGTTTGTCCCAAAATTTTTTTTTCTAATTGTATCGTATAACATTTCTT
TAAGATACTAACCTGAAGTAGTTGCTATAACGGAGGAAAATAGCATGTCTCAAAAAGATTGGAGTAAAAAAGAA
TGCGCAAGATTTGGGATGAATAGAGTCAGATTCGATAAACAAAATGTTTGTAAAGCCCTGAAGTATTTTCATAT
TGAAATGCATTACAAACATTGGCATCACGAATCTAGAAATTCTAGAAAACACGTTATTGTCTCAGCTTTATTGC
TGACGCAGTTAACAAGCGTTGATGCAGATTCCATGGACAACATTTTTATGTATTTATGCGATTACTGGCCTAGA
TTTCCAATACAATTTTTGTGGGAAGAAGTGTTTATTCAGTTGAATTTAATTCGCAAAATCAAGATATATTTTAA
AAGCATGCCTCTTTAAAAATTTTAAAATTCAGAAATCATTTACAAAAATTTATTAACAACTTGTATCTTGATTA
CAAGAATTCAGTTTTTTGTAATGGAATTTAAAAACATTAAAAAAGAAAGAAATATCTAGCGAAATTAATTAATT
TTAAGGAAATAATAATCATTAAATATTAAATAGAATATTCATTAAATATAGAACTTAAGGAATGCTAGTAAACT
TTACATTTCAATACAGCACATTTAAGTATTTTTCTCTAAATTACACAAAAATATTTTGAATTACAAATACAAAA
TTATATGAACCAAAAAACGTGAAATATGTTTATGAATTGCAACATACTCATAAAACTCATATATGGTAATAAAA
TCAGTAACACATTTGAAATTATTTGTTTCAAAATAACGAATGTTTGCAAAGGTAAATTTCTAAAATTTCCTTTA
TACATATTAAATTATCTAGGTGTATAAATTTCCTTTTTTGTATTGCAACAAGTATTATGTTTATGTATTAAAAC
ACATATTTATGAAACTTATTTCAACTAATAAAATCAGTAACACATTTAATACTATTAGTTTCAAAATAACGAAT
GTTTGCAAACGCAAATTTCTGAAATTTCCTATATATAGATGGAAATATCTTGGTATATAAATTTATTATATAAA
CTTATTTCGTGTTTTTTGTTACTTGATATTAATTAGGTACATACTAATAATAGTTAGGTACATATAAGTATAGT
GGAAAATCAAAAGATCGATCTTTTTCATTGATTACACAAACAATAGATGTGTCCTGCACACACATCAATCGGAA
TCAATACAACAATGTTTCTGTTTTTTTTTTACGTCACGTTAATAAGACTGGTAAGAAATGATTAATTGAAATGC
AGTTTGCTGTATCTACCCAAATATTTTGCACAATTTAAAAAAAAACTGTTAAAGCAACTTAAAGGCTGACTATC
AAAAGTTAATTATTAATATTTTCAACAATTAGCCTTTAAGGAGTCTCTATTTCAAATGAATGTGTCATCAAAAA
TTTAAAAGTAAAAATATGATAGAAGATAAGCAGTCAGAAAATGTGATGTCTGAAGAAAGGAGAACTTTTTAATC
ATAATACTAGACTTTCTGTAAAAAGGAATAATTTTAGAAAAAATTTAATACATAACTTTAATATATATAACAATTT
TGAAAATTATCTTATTACGTATACCTATATATCACTTAATATTCAAAAATTATTAATCTTATAAGTAATGCTTT
GTGTGCGTTATCACAATTTAAGATTAATATATCGTTTAATTCAGTACAAGTAAAAGTATTTTAGTGATTACTTT
TGTGTACTGTGTAAATATATACATCATTAGTAATATTATGCATTAACTTTAAGAAGGGATGAACAATCGATACA
TTTGAATGTTTAAAATGTACTAAAACAGAAATTGCAAACTAATATACACGAGGATTTTTGTCTAAAATAAGAAA
TTTGAGCAATATGTTTTATCAGATAACAGGGTCACATTTTCTACTGACACATACATAACACGTAGATAGAGCAT

FIGURE 7 (cont'd)

TGTTAAAAAATCACGAAAATCGGAGGACAATTTATTGAATATTTAAAAATCCTAATTTGTGAAGTAATGTGATT
TCAATTCATAAATCAACATTTCAAAAACATTAATAACCTACACACTATACATGATAGAAAATCTTTTTTTACCA
GAAAAAGATCAATGATTGCAAAAAACACATTTTATAAGCACTGAAATAAATGAAAATTGATTGTATTAATCTTT
TGGAATACTAAAACAAAAGCACAATGTGATGAAATTCTCGCAATTACTGTATAAATAAACTGTTTACAACAAAA
CAAATGAAATTGAGTCTTGACTAACGAAGAATTATGGTGTTTGTAGTTCAGAACGATAAAGATTTATGTAAGAA
CAAGTAATAGTAGGAATGGTCTATAGGTTGATAATTGAATTTTGTAATTTAACAAAATGAAATTAAATGACACC
ATTAGAACAAAAATATCCATAGATAATATACCACCTTATCATTTTTAAAATATACTTGAATTGCAACTTGAATG
CTTAAGTTTATAAAAGAAGGATAAAACATTTTAAAACAAATGGCGAAGATATCATCGTAGTGGCTAACAGCTGC
GGACTTCCAGCATTTTATATGAAGTGATTAGAAATAAGCGATGTTCCAGAGAATAAAAATTTGTGTTGAGGTAG
TGACTAAGAAATATATACTCTCGACTTTTCTCATAATTTTTCATTTTATTATAAATATTTTTCTTATTTTTTAA
AAATTTGCATTTATTTATACTTATAATTTATTCTTCGTAAGCAGTGATTATGATAGTTTAAAACTTTCTAATGC
TTTTATTTCAAACCCTAAAGGTTAAATATTCAAATGTTAAATCTAAATTAGGGTATTCGCGAAAAGAAATAGTT
TAAATTCACTTCAATCAGAAAGTACCAGCCGAATTAACAAACGAATTACGGTATAATCTGGAAACACTTAAGTG
CGGAGTAATTGTAAATGTAGTTCTAGCAGATTGTAATTTTTTAATAATAAGCACTGAAAAGTGTTTTGTAATTT
CGGGTAATATCTTCTATAAAATGAATAGATAATAATTAGCTTAGAAAAAAAAACATTAACATTTCCAAAGACTT
CAAAAGTTCAACTGTAGAATTAAAATTATTGGAAGAATCCAATCAAAAATAATTTGCGTCAATGGATTAAATTG
TCAGATTTTCTAATGATAGTACACTTACAATTAAATGAGTGCTAATAAATAAATTAAAAAGAAAAATGGTGTGT
AATTATTATAGATGAAATAAGAATCAATTTGATATTTTTATCATGAATTTAAAATTTAGAACGACGATGTTATT
CGAATCAATCCAAATTTAATGAAAAATTATTCAATAAAATATCTCTAAATTTATCATAAAATTTATAAACTAAA
TAAAGCAATTATAGTTCCAATAAAAGGCAAAGTTATTAAGTAAAGTTTAATGCAAAATACCAAAAATGATATTA
AACACGTAAGTATTCGCATGTAAAAACATAAGAAAACTTGCATTTCACCTTGGAAAAAACAGGTGACTAAATTC
AAACAAGAAGTACACACGTCATCTTAGCACGCGGACATGACACAATTGTCTGCATATCTCCAGGTGTATTGAAA
AACCTGCTGCACAGCACGACCAATCATTGTATAAAAGAGGCAATCAATCAGCGTACAGTATTCAGTCGGGATTT
TCCAACTACTACAATGACTTGGTCAACTCGACTTGCCTTATCATTTCTTTTCGTGCTCTGCACTCAGAGCCTGT
ACGCTTTGGCGCAAGCCAACACGCCATGGTCAAGTAAAGCGAATGCTGATGCTTTTATCAATTCCTTTATTTCG
GCAGCTTCGAATACTGGATCCTTCTCCCAAGATCAGATGGAAGATATGTCATTGATTGGTAATACATTAATGGC
AGCAATGGATAATATGGGTGGAAGAATTACGCCATCCAAATTACAGGCTTTAGATATGGCTTTCGCATCATCTG
TAGCAGAAATTGCTGCTTCGGAAGGAGGAGACTTAGGAGTAACAACAAATGCAATTGCAGATGCTTTAACGTCA
GCTTTCTATCAAACAACCGGAGTAGTTAATAGCAGATTTATAAGCGAAATTAGAAGTTTGATTGGCATGTTTGC
ACAGGCATCTGCCAACGATGTATACGCCTCAGCAGGTTCCAGCGGTGGAGGAGGGTATGGAGCATCTTCTGCAA
GTGCAGCATCTGCAAGCGCAGCAGCACCATCAGGTGTCGCATATCAAGCTCCAGCACAAGCACAAATTTCCTTC
ACTTTGAGAGGACAACAGCCAGTTAGTTATGGTCAAGGAGGCGCTGGACCAGGAGGAGCTGGAGCAGCAGCGGC
AGCCGCAGCAGCAGCTGGAGGAGCGGGTCAAGGAGGACAAGGAGGGTATGGACAAGGAGGATACGGTCAAGGAG
GTGCCGGACAAGGTGGATCTGGAGCAGCAGCAGCGGCAGCAGCAGCAGCTGGAGGCACCGGTCAAGGAGGTGCT
GGACAAGGTGGAGCAGGAGCAGCAGCGGCAGCCGCAGCAGCAGCTGGAGGTGCAGGTCAAGGAGGACAAGGTGG
CTATGGACAAGGAGGATACGGTCAAGGAGGTACCGGACAAGGTGGAGCTGGAGCAGCAGCAGCGGCAGCAGCAG
CCGGAGGTGCAGGTCAAGGAGGACAAGGTGGATATGGACAAGGAGGATATGGACAAGGAGGATACGGACAAGGT
GGATCTGGAGCAGCAGCAGCGGCAGCAGCAGCAGCCGGAGGTGCAGGTCAAGGTGGACAAGGTGGCTATGGACA
AGGAGGTTACGGTCAAGGAGGTGCCGGACAAGGTGGAGCTGGAGCCGCAGCGGCAGCAGCAGCTGCAGCTGGTG
GAGCCGGACAAGGAGGATATGGCCGAGGTGGAGCAGGACAAGGGGGAGCAGCAGCAGCCGCTGCTGCAGCCGCA
GGAGCTGGTCAAGGTGGTTATGGAGGACAAGGTGCCGGACAAGGTGGATCTGGAGCTGCAGCCGCAGCAGCAGC
TGCTGGAGGGGCAGGTCAAGGAGGACAAGGTGGATATGGACAAGGAGGATACGGACAAGGTGGATCTGGAGCAG
CGGCAGCAGCAGCAGCAGCCGGAGGTGCAGGTCAAGGAGGACAAGGTGGCTATGGACAAGGAGGTTACGGTCAA
GGAGGTGCCGGACAAGGTGGAGCTGGAGCAGCAGCAGCGGCAGCTGCAGCCGGAGGTGCCGGTCAAGGAGGACA
AGGTGGCTATGGACAAGGAGGTTACGGTCAAGGAGGTGCCGGACAAGGTGGAGCTGGAGCAGCAGCAGCGGCAG
CTGCAGCCGGAGGTGCAGGTCAAGGAGGACAAGGTGGCTATGGACAAGGAGGTTACGGTCAAGGAGGTGCCGGA
CAAGGTGGAGCTGGAGCGGCAGCCGCAGCAGCAGCAGCCGGAGGTGCAGGTCAAGGAGGACAAGGTGGCTATGG
ACAAGGAGGTTACGGTCAAGGAGGTGCAGGACAAGGTGGAGCCGCAGCGGCAGCAGCAGCAGCAGCTGGTGGAG
CAGGACAAGGAGGATATGGCAGAGGTGGAGCAGGACAAGGTGGAGCAGCAGCCGCCGCTGGAGCTGGTCAAGGT
GGTTATGGAGGTCAAGGTGCCGGACAAGGTGGAGCTGGAGCTGCAGCCGCAGCAGCAGCAGCCGGAGGTGCAGG
TCAAGGAGGACAAGGTGGCTATGGACGAGGAGGTTACGGTCAAGGAGGTGCCGGACAAGGTGGAGCTGGAGCAG
CAGCAGCGGCAGCAGCAGCCGGAGGTGCAGGTCAAGGAGGACAAGGTGGCTATGGACAAGGAGGTTACGGTCAA
GGAGGCGCAGGACAAGGTGGAGCCGCAGCAGCAGCAGCAGCAGCTGGTGGAGCAGGACAAGGAGGATATGGCAG
AGGTGGAGCAGGACAAGGTGGAGCAGCAGCAGCCGCTGCTGCAGCCGCTGGAGCTGGTCAAGGTGGTTATGGAG
GTCAAGGTGCCGGACAAGGTGGAGCTGGAGCTGCAGCCGCAGCAGCAGCAGCCGGAGGTGCAGGTCAAGGAGGA
CAAGGTGACTATGGACGAGGAGGTTATGGTCAAGGAGGTGCCGGACAAGGCGGAGCTGGAGCAGCAGCAGCGGC

FIGURE 7 (cont'd)

AGCAGCAGCCGGAGGTGCAGGTCAAGGAGGACAAGGTGGCTATGGACAAGGAGGTTACGGTCAAGGAGGTGCAG
GACAAGGTGGAGCCGCAGCGGCAGCATCAGCAGCAGCAGCTGGTGGAGCAGGACAAGGAGGATATGGCAGAGGT
GGAGCAGGACAAGGTGGAGCAGCAGCAGCCGCTGGAGCTGGTCAAGGTGGTTATGGAGGTCAAGGTGCCGGACA
AGGTGGAGCTGGAGCTGCAGCCGCAGCAGCAGCAGCCGGAGGTGCAGGTCAAGGAGGACAAGGTGGCTATGGAC
GAGGAGGTTACGGTCAAGGAGGTGCCGGACAAGGCGGAGCTGGAGCAGCAGCAGCGGCAACAGCAGCCGGAGGT
GCAGGTCAAGGAGGACAAGGTGGCTATGGACAAGGAGGTTATGGTCAAGGAGGCGCAGGACAAGGTGGAGCCGC
AGCGGCAGCAGCAGCAGCAGCTGGTGGAGCAGGACAAGGAGGATATGGCAGAGGTGGAGCAGGACAAGGTGGAG
CAGCAGCAGCCGCTGCTGCAGCCGCTGGAGCTGGTCAAGGTGGTTATGGAGGTCAAGGTGCCGGACAAGGTGGA
GCTGGAGCTGCAGCAGCAGCAGCAGGAGGTGCAGGTCAAGGAGGACAAGGTGGCTATGGACGAGGAGGTTACGG
TCAAGGAGGTGCCGGACAAGGCGGAGCTGGAGCAGCAGCAGCGGCAGCAGCAGCCGGAGGTGCAGGTCAAGGAG
GACAAGGTGGCTATGGACAAGGAGGTTACGGTCAAGGAGGCGCAGGACAAGGTGGAGCCGCAGCGGCAGCAGCA
GCAGCAGCTGGTGGAGCAGGACAAGGAGGATATGGCAGAGGTGGAGCAGGACAAGGTGGAGCAGCAGCAGCCGC
TGGAGCTGGTCAAGGTGGTTATGGAGGTCAAGGTGCTGGACAAGGTGGAGCTGGAGCTGCAGCAGCAGCATCCA
GAGGTGCAGGTCAAGGAGGTCAGGGTGGCTATGGACGAGGAGGTTACGGTCAAGGAGGTGCCGGACAAGGCGGA
GCTGGAGCAGCAGCAGCGGCCGCAGCAGCCGGAGGTGCAGGTCAAGGAGGACAAGGTGGCTATGGACAAGGAGG
TTACGGTCAAGGAGGTGCAGGACAAGGTGGAGCGGCAGCAGCAGCAGCAGCCGCTGGTGGAGCAGGACAAGGAG
GATATGGCAGAGGTGGAGCAGGACAAGGTGGAGCAGCAGCAGCCGCTGGAGCTGGTCAAGGTGGTTATGGAGGT
CAAGGTGCCGGACAAGGTGGAGCTGGAGCTGCAGCCGCAGCAGCAGCAGCCGGAGGTGCAGGTCAAGGAGGACA
AGGTGGCTATGGACGAGGAGGTTACGGTCAAGGAGGTGCCGGACAAGGCGGAGCTGGAGCAGCAGCAGCGGCAG
CAGCAGCCGGAGGTGCAGGTCAAGGAGGACAAGGTGGCTATGGACAAGGAGGTTACGGTCAAGGAGGCGCAGGA
CAAGGTGGAGCCGCAGCGGCAGCAGCAGCAGCAGCTGGTGGAGCAGGACAAGGAGGATATGGCAGAGGTGGAGC
AGGACAAGGTGGAGCAGCAGCAGCCGCTGCTGCAGCCGCTGGATCTGGTCAAGGTGGTTATGGAGGTCAAGGTG
CCGGACAAGGTGGAGCTGGAGCTGCAGCCGCAGCAGCAGCAGCCGGAGGTGCAGGTCAAGGAGGACAAGGTGGC
TATGGACGAGGAGGTTACGGTCAAGGAGGTGCCGGACAAGGCGGAGCTGGAGCAGCAGCAGCGGCAGCAGCAGC
CGGAGGTGCAGGTCAAGGAGGACAAGGTGGCTATGGACAAGGAGGTTACGGTCAAGGAGGTGCAGGACAAGGTG
GAGCCGCAGCGGCAGCAGCAGCAGCAGCCGCTGGTGGAGCAGGACAAGGAGGATATGGCAGAGGTGGAGCAGGA
CAAGGTGGAGCAGCAGCAGCCGCTGGAGCTGGTCAAGGTGGTTATGGAGGTCAAGGTGCCGGACAAGGTGGAGC
TGGAGCTGCAGCCGCAGCAGCAGCAGCCGGAGGTGCAGGTCAAGGAGGACAAGGTGGCTATGGACGAGGAGGTT
ACGGTCAAGGAGGTGCCGGACAAGGCGGAGCAGGAACAGCAGCAGCGGCAGCAGCAGCCGGAGGTGCAGGTCAA
GGAGGACAAGGTGGCTATGGTCAAGGAGGTTATGGTCAAGGAGGCGCAGGACAAGGTGGAGCCGCAGCGGCAGC
AGCAGCAGCAGCTGGTGGAGCAGGACAAGGAGGATATGGCAGAGGTGGAGCAGGTCAAGGTGGAGCAGCAGCAG
CCGCTGCTGCAGCCGCTGGAGCTGGTCAAGGTGGTTATGGAGGTCAAGGTGCCGGACAAGGTGGAGCTGGAGCT
GCAGCTGCAGCAGCAGCAGCCGGAGGTGCAGGTCAAGGAGGACAAGGTGGCTATGGACGAGGGGGTTACGGTCA
AGGAGGTGCCGGACAAGGCGGAGCTGGAGCAGCAGCAGCGGCAGCAGCAGCCGGAGGTGCAAGTCAAGGAGGAC
AAGGTGGCTATGGACAAGGAGATTACGGTCAAGGAGGTGCAGGACAAGGTGGAGCCGCAGCGGCAGCAGCAGCA
GCTGGTGGAGCAGGACAAGGAGGATATGGCAGAGGTGGAGCAGGACAAGGTGGAGCAGCAGCAGCCGCTGGAGC
TGGTCAAGGTGGTTATGGAGGTCAAGGTGCCGGACAAGGTGGAGCTGGAGCTGCAGCCGCAGCAGCAGCAGCCG
GAGGTGCAGGTAGAGGAGGACAAGGTGGCTATGGACGAGGAGGTTACGGTCAAGGAGGTGCCGGACAAGGCGGA
GCTGGAGCAGCAGCAGCGGCAGCAGCAGCCGGAGGTGCAGGTCAAGGAGGACAAGGTGGCTATGGACAAGGAGG
TTACGGTCAAGGAGGCACAGGACAAGGTGGAGCCGCAGCGGCAGCAGCAGCAGCAGCTGGTGGAGCAGGACAAG
GAGGATATGGCAGAGGTGGAGCAGGACAAGGTGGAGCAGCAGCAGCCGCTGCTGCAGCCGCTGGAGCTGGTCAA
GGTGGTTATGGAGGTCAAGGTGCTGGACAAGGTGGAGCTGGAGCTGCAGCCGCAGCAGCAGCAGCCGGAGGTGC
AGGTCAAGGAGGTCAGGGTGGCTATGGACGAGGAGGTTACGGTCAAGGAGGTGCCGGACAAGGCGGAGCTGGAG
CAGCAGCAGCGGCCGCAGCAGCCGGAGGTGCAGGTCAAGGAGGACAAGGTGGCTATGGACAAGGAGGTTACGGT
CAAGGAGGTTACGGTCAAGGAGGTGCAGGACAAGGTGGAGCGGCAGCAGCAGCAGCAGCCGCTGGTGGAGCAGG
ACAAGGAGGATATGGCAGAGGTGGAGCAGGACAAGGTGGAGCAGCAGCAGCCGCTGGAGCTGGTCAAGGTGGTT
ATGGAGGTCAAGGTGCCGGACAAGGTGGAGCTGGAGCTGCAGCCGCAGCAGCAGCAGCCGGAGGTGCAGGTCAA
GGAGGACAAGGTGGCTATGGACGAGGAGGTTACGGTCAAGGAGGTGCCGGACAAGGCGGAGCTGGAGCAGCAGC
AGCGGCAGCAGCAGCCGGAGGTGCAGGTCAAGGAGGACAAGGTGGCTATGGACAAGGAGGTTACGGTCAAGGAG
GCGCAGGACAAGGTGGAGCCGCAGCGGCAGCAGCAGCAGCAGCTGGTGGAGCAGGACAAGGAGGATATGGCAGA
GGTGGAGCAGGACAAGGTGGAGCAGCTGCAGCCGCTGCTGCAGCCGCTGGATCTGGTCAAGGTGGTTATGGAGG
TCAAGGTGCCGGACAAGGTGGAGCTGGAGCTGCAGCCGCAGCAGCAGCAGCCGGAGGTGCAGGTCAAGGAGGAC
AAGGTGGCTATGGACGAGGAGGTTACGGTCAAGGAGGTGCCGGACAAGGCGGAGCTGGAGCAGCAGCAGCGGCA
GCAGCAGCCGGAGGTGCAGGTCAAGGAGGACAAGGTGGCTATGGACAAGGAGGTTACGGTCAAGGAGGTTACGG
TCAAGGAGGTGCAGGACAAGGTGGAGCCGCAGCGGCAGCAGCAGCAGCAGCCGCTGGTGGAGCAGGACAAGGAG
GATATGGCAGAGGTGGAGCAGGACAAGGTGGAGCAGCAGCAGCCGCTGGAGCTGGTCAAGGTGGTTATGGAGGT

FIGURE 7 (cont'd)

CAAGGTGCCGGACAAGGTGGAGCTGGAGCTGCAGCCGCAGCAGCAGCAGCCGGAGGTGCAGGTCAAGGAGGACA
AGGTGGCTATGGACGAGGAGGTTACGGTCAAGGAGGTGCCGGACAAGGCGGAGCTGGAGCAGCAGCAGCGGCAG
CAGCAGCCGGAGGTGCAGGTCAAGGAGGACAAGGTGGCTATGGACAAGGAGGTAATGGTCAAGGAGGCGCAGGA
CAAGGTGGAGCCGCAGCAGCAGCAGCAGCAGCTGGTGGAGCAGGACAAGGAGGATATGGCAGAGGTGGAGCAGG
ACAAGGTGGAGCAGCAGCAGCCGCTGCTGCAGCCGCTGGAGCTGGTCAAGGTGGTTATGGAGGTCAAGGTGCCG
GACAAGGTGGAGCTGGAGCTGCAGCCGCAGCAGCAGCAGCCGGAGGTGCAGGTCAAGGAGGACAAGGTGGCTAT
GGACGAGGAGGTTACGGTCAAGGAGGTGCCGGACAAGGCGGAGCTGGAGCAGCAGCAGCGGCAGCAGCAGCCGG
AGGTGCAAGTCAAGGAGGACAAGGTGGCTATGGACAAGGAGATTACGGTCAAGGAGGTGCAGGACAAGGTGGAG
CCGCAGCGGCAGCAGCAGCAGCTGGTGGAGCAGGACAAGGAGGATATGGCAGAGGTGGAGCAGGACAAGGTGGA
GCAGCAGCAGCCGCTGGAGCTGGTCAAGGTGGTTATGGAGGTCAAGGTGCCGGACAAGGTGGAGCTGGAGCTGC
AGCCGCAGCAGCAGCAGCCGGAGGTGCAGGTAGAGGAGGACAAGGTGGCTATGGACGAGGAGGTTACGGTCAAG
GAGGTGCCGGACAAGGTGGAGCTGGAGCAGCAGCAGCGGCAGCAGCAGCTGGAGGTGCAGGTCAAGGAGGACAA
GGTGGCTATGGACAAGGAGGTTATGGTCAAGGAGGCGCAGGACAAGGTGGAGCCGCAGCGGCAGCAGCAGCAGC
AGCTGGTGGAGCAGGACAAGGAGGATATGGCAGAGGTGGAGCAGGACAAGGTGGAGCAGCAGCAGCCGCTGGAG
CTGGTCAAGGTGGTTATGGAGGTCAAGGTGCCGGACAAGGTGGAGCTGGAGCTGCAGCCGCAGCAGCAGCAGCC
GGAGGTGCAGGTAGAGGAGGACAAGGTGGCTATGGACGAGGAGGTTACGGTCAAGGAGGTGCCGGACAAGGCGG
AGCTGGAGCAGCAGCAGCGGCAGCAGCAGCTGGAGGTGCAGGTCAAGGAGGACAAGGTGGCTATGGACAAGGAG
GTTATGGTCAAGGAGGCGCAGGACAAGGTGGAGCCGCAGCGGCAGCAGCAGCAGCAGTTGGTGGAGCAGGACAA
GGAGGATATGGCAGAGGTGGAGCAGGACAAGGTGGAGCAGCAGCAGCAGCCGCTGCTGCAGCCGCTGGATCTGG
TCAAGGTGGTTATGGAGGTCAAGGTGCCGGACAAGGTGGAGCTGGAGCTGCAGCCGCAGCAGCAGCAGCTGGAG
GTGCAGGTCAAGGAGGACAAGGTGGCTATGGAGGAGGAGGTTACGGTCAAGGAGGTGCCGGACAAGGCGGAGCT
GGAGCAGCAGCAGCGGCAGCAGCAGCCGGAGGTGCAGGTCAAGGAGGACAAGGTGGCTATGGACAAGGAGGTTA
CGGTCAAGGAGGTGCAGGACAAGGTGGAGCCGCAGCGGCAGCAGCAGCAGCAGCTGGTGGAGCAGGACAAGGAG
GATATGGCAGAGGTGGAGCAGGACAAGGGGGAGCAGCAGCAGCCACTGGAGCTGGTCAAGGTGGTTATGGAGGT
CAAGGTGCCGGACAAGGTGGAGCTGGAGCTGCAGCCGCAGCAGCAGCAGCCGGAGGTGCAGGTCAAGGAGGACA
AGGTGGCTATGGACGAGGAGGTTACGGTCAAGGAGGTGCCGGACAAGGTGGAGCTGGAGCAGCAGCAGCGGCAG
CAGCAGCCGGAGGTGCAGGTCAAGGAGGACAAGGTGGCTATGGACAAGGAGGTTACGGTCAAGGAGGTGCAGGA
CAAGGTGGAGCCGCAGCGGCAGCAGCAGCAGCTGGTGGAGCAGGACAAGGAGGATATGGCAGAGGTGGAGCAGG
ACAAGGTGGAGCAGCAGCAGCCGCTGCTGCAGCCGCTGGAGCTGGTCAAGGTGGTTATGGAGGTCAAGGTGCCG
GACAAGGTGGAGCTGGAGCTGCAGCCGCAGCAGCAGCAGCCGGAGGTGCAGGTCAAGGAGGACAAGGTGGCTAT
GGACGAGGAGGTTACGGTCAAGGAGGTGCCGGACAAGGCGGAGCTGGAGCAGCAGCAGCCGGAGGTGCAGGTCA
AGGAGGACAAGGTGGCTATGGACAAGGAGGTTACGGTCAAGGAGGTGCCGGACAAGGTGGAGCTGCAGCCGCAG
CGGCAGCAGCTGCAGCTGGAGGAGCAGGACAAGGAGGATATGGTGGATACGGTCAACAAGGTGGAGCAGGAGCC
GCAGCAGCAGCTGCTAGTGGACCTGGTCAAATTTATTATGGACCCCAATCTGTTGCTGCTCCAGCAGCAGCAGC
AGCTTCTGCTTTGGCAGCTCCAGCTACAAGCGCGAGAATTTCTTCACACGCCTCAGCTCTTCTTTCAAATGGAC
CTACTAACCCTGCTTCTATTTCAAACGTTATTAGTAATGCTGTATCCCAAATTAGTTCCAGCAATCCAGGAGCG
TCTGCGTGTGATGTTCTCGTTCAAGCTCTTCTTGAACTTGTTACTGCTTTGCTCACCATTATTGGATCATCAAA
TATTGGCAGTGTTAATTATGATTCTTCAGGCCAATATGCGCAAGTTGTTACTCAATCTGTTCAAAATGCATTCG
CTTGATTCTAAAACGTTGCTTAAGCATTCATTTTATAAAATGTACTAATATAATATGCATTGAGTAATTCTGAT
ATTGAATAAAGCATTTATCTTCTCTATAATCTCATTTGCCTAATTATATTTTTGTTTTTTTACTTCTGTCCTGA
GATCAGTTTCTTATATATGGTAATTCAGGCATTTTAACATTGTAATATATTATTGAATTGTAACATCTGCGGAA
AAAATATTTACAGAATACAAGTTGTAGAATTCAAATTAATTAACTTTTTTAAATGAAAATAAATTGAACTTAAT
TTTGAGGACTTTATGATATGGTTTCTAAATATTTTTATTTTCACGCTGGTTTTCCTGGAGAAATCAATAATTTC
CAACATAATATGTGTTTATTATAACTGCGTAGTCCCATTCCTTACTTTTCAGGTATACGCTTTAGTGTACTGTA
CTTCTGCAGTGTCTTAATATTGACCTGAAACGTATTAGATGATTTCGATCTTTGAATGAAAGAATAATACTAAA
AACTTTTTAAGTTCTTAAAATAATTTATTATATCACCAGATTTCTTTCAAAAGGACAGGTGTCATTTTGTAATT
GAAAGAAGAAATTTTGAAATTGAATAAAGAATTTTGAGTGGTTTGCTGCCTAATCAGCTTTGCACATAAGAATT
ATTTTTTGGCCTTTATTTGTTATATTTCTCAATGCACGGTGTGAAATTCCTTTGCATTTAAAATCAAAAATAGT
TGGTTTTCAAACATTTTAAATGCAAGTTTCAATAAAAGGAAAATAATTATAGTGTCTGTTGCTTATATTAATTT
TTATGTTTTTGAAATTATTATTTCTAATTAATTTCCAAAATATATCATGGTGATTGCAAGAGAAATAGCTAACT
TTTAAATAAAAATTTAGTAAAAAAATTTTTTTTGGTCGCTTTATAAATTAGAAGTAAATATAACTTCTAAACCA
AAATTTTCCTAATTTTGTCTTTCTAGACCAAATTGTCTCTGAAAGATGAGAGAAAGTGATAAGAAACTCTCGTA
GACTAAATCCATAACAGATTTCCAATACCAAACTAAAGAGGTTTATGTATTCGTATTAGCTAACAAAATAAGAA
AGAAATTAAAATTTTTCAGATTTTTTTTTTTACATATTCGTTAGTATACACTAGGATTTAAATAAAAAATGTAT
GAGATATATATTCTGCATTTACAATAGAAATTCACAAAAATTACAAAATCCGTTTAAATTGGCCCAAAACATTG
GTGATTTGAATATGATTATAAAAAATTCTTCTGTACATAAAATGTCAGGTGACAATATTTTATAAGTCTACAA

FIGURE 7 (cont'd)

TAAAATGTCCTTTAATCTGACACACTGGCGACAGCCTTTTAGTAAGGAAATGAACAAACTTATTAAAAAAATAT
AGTTATATTTTAGATAATAAGAATGAAATTATTAATCTATCTTTTTAAAATTGCACGCTTTCTGAGGGAAGACA
AAGCTCATCATATTAAAACCATTATTTACATTTTAATAATATGTTTGAGAATATTAAAATTAAGATTGACTCTG
TACCGACTCCGAAAAATTGTAACTGTTTTTCAGAAAAGAGTATCCCATTTTAAAGATTCAAGTAACCGTTGATT
TAATAAATGTGAAATAATGAATTGCAGTAGTAATATCTTTAATTTAATGTATAAAATCCAATAAAAATATGAAA
TGGAACCCTACACATTTCACAGAAAAAATTACTTTATTATCTCATATTTTATTTTGTAAAAACTTAAGAGAACA
GAAAAAACTATGAAATTGGCAACTTATTATAATAAATTAATGTATTCAAGTGATGTGCATAATATTTAAATGTA
AACTTTACAGAATTATTTCATTTATAAAATATTCATCAATTTTACAAATAATAAAACTTTTCAATTTATGAAAA
GTATAAATTGAAAATATTTAATATTTCTTCTTCATAAATCTTACTAACAATATAAATTTTACAATTCTATTTTA
TTTTTTATGACTGAATACAAGCATTATTTTGCATAAATAGTTTTCATTCATTATCACTGTTACGCAAATTAAAA
ACAAGGAATTCTATTTTAATCTTAGTGAATTCATTAAATGAAAGAAATAGTAAAATTCATTAATAAATATTAAA
ACACCAAAGTACAAGACATATATTTTTTTGTCGTGTCATGTCGTATCAAATATATATATAATGTCGAGAATACT
TATTATGGCTTCTGTAATTTCTTCAATGTTTTCGACATGTAAGTCAACCAAGGAAAATGGAAAATTCCGATTCT
CCTTATATCAGTTCTTATTGCTGGGCAGTCAAAAACGTAGTCTGGTGTCCTTTGCGAGTCTGGGCATGTATTAT
AGTTCCAAATAAGTTATTTTATTAATAATTAAAATGAAATGCAATGCAAGTGTAGTAATTTTAATCTGATATTA
TTTGGTTTTTATAAAATACTGTTGTTGTTATTACTTATGACACTTGCACAAGCCAATTACGCAATGCTGTTGGC
TATGCGAATTTAAGTCAGTAGGATGAATCTTTTTCGTTTAACTAGAGCACCACGTAGGTTGCAGTGATTTAGAT
GCCGTAAGTCAGATTTTTTTTATCACCGACGAAAATAGTGAATAGAATAATACTCCAAAAAAGTGAACAAACT
TTCATAAGCAGTAGGAGGTGAAGTGCATGCTACAAGAACAACGGTACACGTTACAAGATTATATAATCAGTTAG
TTACAATTTAGTTACAGTTTTAAGCAAGGTTGAGTACTTTACATAAGTGCATAAAGTTAGTTTTTCTGTGCCGC
TAGGTTGGCACGTCAGGTGGGGAGATGCGGTGGTGTATGGCATGGCCACCGCAGTACCTCCTTCCCAGCGTAAC
AGTTAGTTTAGTTGTGCTGCAAAGTGCACATGACGAGTCGAACGGGTACGTCGATTTCTGTTCGATGCTGTAGT
CTACGGAGGTAAGTCTTTTGTGGTGATCTCGTTGCTTGGTTGTAAAGGAGTCCGTTGGTTCCTGTTCGCATAAG
AGATAGGCTGGCTTCACTCTGTCCACTGAGATGAAAACCTCTTTGTTGTTCTTCAGTACCTTGAACACTTTGTC
CGTTTTGTCAAGGACCGGGAACGGCCCATCGTAAGGTGGATGTTGTACGGCGTCAAGCCGTATGAAGACGTGAG
TGCATTTTTTGAGAACCTGTGGAATGAATATTCTGTCCTTACCATGATTGGTGGTTTTTGGTGGTGAAAATGCG
CTCATTATGTCCCTCAGGTGGTTAATAAAATCTGCAGCGTTGAAACCTATTTTGCTAGGAACGAAAAACTCACC
TGGCAACCTCAAAGAGCTGCCATACACTAGCTCTGTGGTTGAGGCTTAGATTGTTTCACGAAATGCAGAATGTA
AACCCAGCTATGCCGTTGATAGGATTATTGTCCAACGATTGGTGAGTCGGGGGTCAGATAGCTGAGATTTAAGA
ACAGATTTCAAGGATCTATACCAATTTTCCACTAAGCCATTAGACTTGGGGTGGTATGCAGTGGTATGGATATG
CTTGATACCTAAAAGCTGTGTGAGAGCTCGAAACAAGTAAGATTCAAACTGTCTGCCCTGATCAGTAATCACTA
CACTGGGTACACCAAAACGAGTTACCCAACTGGCGTAGAAGTTTTTAGCAATTGTCTCAGCAGTTATATTAGAA
ATTGGTCTCGTTTCCACCCAACGGGCATATCTATCAATCATTATTCAATCACATTTAACAGACCGTATATCCGT
ACTAAATTGTCCGATTAAGTCCAGATACCTTAACTGACGAGGAGTGCACTTGTCTAGCTTTTCTTTGAACGCAA
ATATTAAGAGTCTGTGGTCTGTATAGATAAAAAAGTGTTGACCCTCTAACATATGTTTGAAATTCTTTATCGCT
GCGTATATTGCGTAAAGCTTCCTATCAAAAGTTGACCATTTCTGCTGAGCCGGAGTAAGCTTAGCCGAGAAGAA
TACGAGCGGTTCATACTTCGGTGAATCTACATTTTTGCTCTGGTTTAACGTTGCTCCTATCGCCATATCACTGG
CATAACAAGAAAGCATTAATTGCGCTTCAGAACAAGGAGGAGCTAGCATAGCGGCGTTCGCCAGTTGTTGCTGA
CACAATTCAAATGGAGCAATTTGTTCGGTACTCCATATTAATGCGCTGTTTTTTATTAACTTTAAGTGTATTTC
ATTTAATGATGCTTGCATATGCGCAGCATGTTTGATATTACCCCTACAGTAATTTAGTAAACCTAAAAATCGTT
GAAGTTGTTTTACTGTTTGAGGTAATGGGCAATCGAGTATAGGTTTCACTTTGTCAGAGGGAGGTTTAATACCA
TTTTTGCTGACAGAATATCCTACAAAACGATGCTTGGCAACTCCGAAAACACATTTACCTAAATTTATACGAAT
TCCGTACTCTGTCAGGCGCTTGAGTACCATTTCTAGATGTAGTTTGTGTTTCGATTTGGAATTGCTTGCGATTA
ATATATCATCCAGGTATGCGAATACAAAGTCAAATCCACGTAAGACTTCATTAATAAACCTTTGGAAAGTTTGA
GGTGCATTGGCCAAACCGAATGGAGTAAATAGAAATTCAAATAATCCAAAAGGTGTAGTGATTGCAGCTTTTTG
GACGTCGTCTGGGTGGACAGGAATTTGATGGTAAGCTTTTACCAAATCTATTTTTGAAAAGATTACTCTATTAT
GTAACTGATTCTAAAAGTCTTGAATGTGGGGGAGCGGATACCCATCAGGAATAGTAATTCTGTTAAGGGCTCTG
TAGTCACCAGTCGGACGAAAGTCGGTACCTGATGACTTGGGTACTAAATGCAAGGGGGATGACCAATTTGACAT
ACTAGGTCTACATATGCCTTGCTCTAACATATATTCAAACTCTTTCTTGGCAATTGCCAATTTTGTGGATGTA
ATCTTCGCGGCTTTAAAAATACAGACTGCCCGTTAGTTATAATACTATAGGTTAAAGTATGCTTTATTATTCGC
TTTGAAGGGTATGGGCGAATTACCTCATTGTATTTTTCCAAGATCTGCCTAAAAGGAAACGACAAAGATGGTGC
ACCGACCCACCCTAGGGTATGCGGTGAAAGAACGCGTGCAATAGTAGTCAGTACTTCAGAACTCGGTGGACACA
AGGTCAGGAAAAAGTCCAAACTGTGCAGAAGAGATGGCACCAAAGCCAAGATCTCCTGGAGTCCAAAAAGAGGG
AAAGTTAACGTCTCAAAAGAAGGCGTTCTATTCTATTACTCTGATCGGAAGATTGGGCATAACAGGCCTTTAT
TTTCTAGTTTACAATACAATATGATATAATAATATAAGATAATAATACAAAGTGGAAAAGTATATACATGTTTT
CAGTAGAGAGATTACAACAGTTATGATTTGTCAAAGTTAGGTACAGTTTGTTTGATTAATTGTTTGGCTGTCTG

FIGURE 7 (cont'd)

TGGAGGTGGTGTCCCTCATCTGATATTGTAGCTCTTGCTGTATGATTTCCCTGATGCCAATTTGCACCCTTGGG
ATTTGTAGAGCTGAAGATAACTTATGGTCGTATGTTGTTTCGGGAACCACTTATCTCTCATGTGTTGATACTTT
GTGCATCTCAAGATGAGGTGTTCGGAGTCGCAGGGTTCATCGTCATGTAGGCAAAGTTCCGATTTGCTATGGAA
TCTATTTCTGTAATATCCAAAAACTCCGTGTCCAGTGAAAGCTTGATTCAGAAAGAAATCCCCCTAAAGTCTGG
CTTTGGAAACTTTGGAGCAGAAACTATAGAGCCTTCTGGTCTTTTCGGAGTTATCCCAAATGTGTTGCCAGCGC
ATTAAAATGTGGTCCTGAATTAACTTTTTAGTTTGCTGTTTGCTTATCCTGACTTGTATTTCAATTGACTCTAA
GGTGGTTGCTTCCTTTGCCGCAGCGTCTGCTTCCTCATTTTGCTTTATGCCACAGTGGGCCTCGACCCAATGAA
ATGTGAAGCTGTGTTTGTGTTGTTCTAGTAGATTCTGGATGTCCCTAATTGTGTGGCTTAGGGTGTCGGGTGTG
GAAAGTGCCTGGATGACAGAGCAGGAATCTGTATGAATGTGGAATGTCTAATCTATTTCGATAATTTGATTTAT
GGTACCTAGGATGGCTTAGGCTTCCGCCTCGAAGACGTTGGCCTCATCATTGAGCCTCATTTGGTACTTTGAAC
TTGTTCTTGACCTCTAAAGATTAGTGCAGCACAGCCTGTTTGATTATTCATACGAGAACCATTTGTAAACGCAA
ATGTACCGTTGTGATTGGTGAGGAAGTCCCACTCAATGTGTTGGATCTGCCATGGGGGGTTTATCGTGCTGGAA
AAAGTCCACGCATTGTTTGGGTTGAATGCGATCGTGTTTAAGTTAATTTCCTTTCCTCTTCTCCAAAGTATGTA
CCTGAGTTGGAGTCCCTCAGCTTTGAGTTGGATGGGAGGGCAGCCTGATAGTACTTGGAGGGCGTGAGTTGATG
TGGTCTTATATGATTTAGCAATCTTTAATAAGGCAATTCTTTGGATTTGTTGAAGCTTAATACTTTGTTTTACA
GTGCTATTGTACCACGCAGGGGATCCATACAGTATGATGCTCTCGAAAGCAATGTTGTAGATCAATTTATTACT
GAGGGATTTAACCCCAAGTTCCTCTGGTGATTCTGGCTAGTTTGTTAGTTACATTATTGATCGAATCCTTAACC
TTGGTAAGATGACTATTCCAAGTTAGTTTTGGGTCACGCGTGATTCCTAGATACTTCATTTTTCTGGTGTAGGC
CAACTTCTTTCCTCCTATACTAATTCCCTGTCTTCTTGTGATATCCATTCCGAATTCAAATGTAGTATATTTGC
ATTTGTTAATGCTTAATTGGAGACCGTGTTTGAGGGTCCAACTTTCGACTATGTTGAGAGGTTTTCTAGATTGT
ATAGTGAACTTAAAGTAGGAGGAGTTGGAGAGAAGAAGTGCTATATCGTCTGCGAAAGCTTGGCAGGAGACTTG
AGGTTCAAAGTCCTGGATAAATAATTCATTTGCAATTAGTAACCAGAGAAAGGGTCCTAGGCTGGATCCTTGGG
GGACTCCGTTCATGTATTTTACAGGTTTGAATTGTGCGTTGAAATAGGTTCTATTATCCAAGAACGAGCAGATT
GTTTTGAAGATGTTGTTTGGAAATGGGAAATTCTATAATGGTCTCATGAGGTTCGTCCATCTCGCTGAATTAAA
GACATTTTTGATGTCTAAGGAAATCAGGCAATTGTATTGCTTGTTTTGCTGGTTAGTCTTGATGGTATTGGCAA
TTTGATAGATCGCATCTGAGGTACTCTTCCGTTTCCTGAACCCAAATTGGTTTTGTTGGAGGAGGGAGTTCGCC
TGGAAGAAGTAGCTAACTCTTTTATGTAGAATCTTATCGAGGATTTTTCCCCAGATGGGTAATAGGCAAATAGG
ACTATGTGAATCATATTTAGAAAGATCTTTGCCGTCTTTGAAAAATAGAATAACAGTTGCCTGTTTCCAGATTC
GGGGAAAGATGCCATTCCGTATGGATAAATTAAGTATTCCCGTGAACCATCCCTTGTCTTGTATTAATTCCTCA
TAAGTATCTAGACTTATGTCGTTGTATCCTGGTGCCTTTTTGCTGCCCATGGAACTTATGATTTCCCTAACTTT
ATCAATGGTGACCGGCGGGTCATCGGACATCGCCGTGGAGTTCAATTGACTTTGAATTGGGTTATTGGGAAAGT
GGAACTTGAGAATTTCGTTTGTTGCTTCTTCCGGGGAATTGGGGAAACTGCCGTCCATGAAAAGAATGCGATTT
ATGTGTTTCGGTCTTTTAATATTATCTCTGACAATTTTATAGGTGCCGCTGAAGGCATTGCGTTCAGTTATAGT
CCCTAAGTACTGCTCAAAGTGCCGGTAATGCGAACAAGAGGTGATCGAGATGTGTACCCAATGGCATCCCATAC
CATCACTCCAGCAGATGGGCTAGTATGGTGATGTCCAATGCAAGCTGGCAATGCGCGTTCTCCACGATGCTTCC
AAACACGGATGCGCTCCTGTCTGTGACGTAGCGTCAATGGTAGCCGAAGCCATAGTCGCCGTGCAGACAATCCA
TACTGCTGCAAACGTCGTCGAACTGCTCGAGCAGAAACTTGCTGCCTTGAAAATGACGCCATTTCTCGACTCAG
GGTTCGTGACGTGGCTGTACGATCCCTTGTGACCATGCGGATAAGATGTCTGTCTTCTCTGCTGTTAGTAATAG
GGCGGGGGGTCGCTGAGATCCTGCATGACTTTCCGTATGATTGTCGTGAAACCATCGATTCCATATTCTGCTAA
CATTCATGGGGTCTCGACCGACACGAGCAGCAATATTGCGGTACGATAAATCGGAATCCCGGTAGGCTATAATC
CTTCCTCGATCAAAGTCAGACATATGCTGATAGGCATTTCTTCTTCTTACAAGAGGCATTACAATTTCTTTATC
GAAAACAACGTTGAAACGGAAATTGAGTATGAGGAAACTGCTGTCAAATCTCGGGTTTTATACACATTGTAGAT
GTCGCTACTGTTGCCTGTTTTGTATGAATGCGCTGAAAATCTAATTATTTGCATATCACAGCAAGTTCTACCTG
TCATGCAAATTTCACGTATGTGGTGTGCCGCTTTCCTGGTGTAGCAATTTTCATGGCCAGTAGCGTGTAGGGCT
GCTGCCTTTTTAAATTACGCCTTTCGTAAATCGCGTTTAGGATTGTCCGTTTCTGCTTGAAATCTACCCCTAAG
TGCCCTGACTCAACTTCGTTCTTCAGTTAAAGCTGGGGTCCACCAATAGTTGGTGTTAGTCTTATGTATTTGCT
TCCTCTTGTGTTTTTTACAGAGTTCTTGTATGTTATGTTCGACTGTTTCTATGTGTCCTTTTCAATATTCTCTA
ATTTTTAGATTGGGAATTGTACTGGTATGCTCTTTAATTCATTCTTGAATTCTACCCAATTTAATGAGTTTGAA
TTGTATCTGAACTTAGTTTTAAAATAAGCTTTAACATTAGTGAGATTAAATGTCATGAGCTGAAGATCGCTGGC
TGAGAATTTGTCATTGATAGACCAGTTGGAGATATTGTTGCTATTTAAAATTTTTGTGATTAGTAAGTCTATCC
AGCTTTCTCCTAGTGTACTAAGGTACGTTGGTTTGCTGTTGGGATCATTTTCAAAGATCAGTTAGAGTTTAGAG
GCGAATTCGATTAGTGTGTGTCGTCTTTGATCTGTGTTCCTTGGACTCCAAATTGTGGAATTTGCGTTGAAATC
GCCTAAGATAATCCACTTTTGGTTATGATAAATCGCTAGAAGTTCACCTAACTCTTTAATGGATTCATTGATGT
TGCGAGACGGTGGACAGTAAATTGAGCATATATTGAAAGTGTCTTTATTATATTTAGTTTGAATTAAAACAAGG
TCTTCTGAGACATGAATCGGTGAGACGAGATATTGTTTGTTGCTGATCACAGCCGTTTTCCGGTAGTTACTAGC
AGTGATAGTGAGGCTCAGTGGGAAGCCGGAAATTTTTCCTTCAAAAGTGAACGGATCATTAATTGAAATAAAGT
CTAAGTTTAATTCCTTGATATCTTGGGAGAGAGTTAAGTTAGCTGCTCGGCGGTGATTAAGGTTGAAGTGGGCA

FIGURE 7 (cont'd)

AATTTTATTAGATTGTTAGAAGACATGTTAGTCATAGTTAGTTTGAATGATTAATTTGTTGATCTCTTTTTTAT
AAATCGGGCTTTTTTTATCGTTTGCTAGGTGATTAATTTTGTATTTAGTTTTATACTTATAATTGCTCTCCTCA
CAATTTTTGCATTTGATATCTTTATCGCAGTTTTAATCAACATGCGCTCCTGAGCATCTTCTACAAGAGTTCTC
TCCTTTGCAGTCTCTGGATATATGTCCATAACGGAGACATTTAAAGCACTGGCTTATTCTTATGTATTCTCTAA
ATTGGACCGTAGTCCATCCCACACAAAAATATCTTATTCCTTTTATTTAATTCATTTAGGGCTGCTCCATTGAG
TGTCATTATCCAGTTTATTCCATACCTGCCTTTAAAACTATGGACGGCTTCAACACTTAGGGAATTTTGGTTAA
TAATTCTTTCCACAATTTTTTCTTTTTTTAACTTCTTTATCTACATTGTAAAGAATTATTCTAGGCTCCTTTAG
TTCGGGCTTCTTAACTTCTACAATTTCTGTAAGTTTATCATTATTTTTAATCTCTGCGATTAATTTTTTTTATT
TTTTCCATGGAGCTAGTTTCAAGAACTATTCATCCTTTACGGACTGGGCGGATTTTCTTAACTTTTAATCCTAG
TTTAATTGGGTTTATAGCATTTTTTATTATTTTTGTAGTGTCTTCCGAGGAAGACTCTTTCTTAGGATACACCA
AAACAACGTTATCCTTTCTTTGACGACATTTATCTCGTCTAGACCTGCTTCTACTTCTCATTCTTAAAGTTTTG
TTGCCTTTCAGCATACCTTTCTTAACTGCCTCAGCAAAGGTTTTTGTCTGTTTTATCGGTAACTCATCTTTTGC
TTTTAATTGTCCTTCAAGAAAAGCATTTTTTTTTCTATCTGCTGCAAGGCAATGTGTAGAATGTCAGAAATGCC
TTGTCTAATTTTTTGTTGTATGGTACTGCTCGCCTTACTGGCTGAAAGAGCCTGTTGTATCTCTCTTTCTGTCT
CTAACAAATTTAGAATTTCTGATTTAATCCCATTGTTCGCTGTCTCACAATCATACACAGCGAACTCCCTTTCG
GGAGACTGTTTGTGTTGCCATGGGGGAAAGAGTTAAAGCCGTGTCCACTCGTTATAATTTGAGCTTAAAGCAGT
GTCAGCTCTTATAAGTCCCTCTGCTTTCGTTAGCCGCCAGTAAACTGACGTTTCCAGGAGCCACCACGAGGAAG
TGGAGGTCAGATGGTTTCGGAGAACAGAGAACTTGACAAGCAAAACCCGAAGGAATTGAAACGCCAAGACAGAG
TTAGCACTTTCCGGATAGACTCTAGGCCGTTGTCCGGAAACATATTAATCTCAAAATTACTTAAGTTCTCGCTG
CGGGGCTGGCTCCCTGCCTAAAAGGAAAAGTATCCGTAATTAAAGTTACATGGGATACATCGTGAACGGTTTTA
CCTGATGTAATTAAATTAGTTTTACTATCCCTAAGACACGCATGCTTCAAATCAATTAGTAAACCAAAATGCTT
GAGAAAATCTGCACCAATAATAGGTTTATTTACATCAGCAATTATAAAATACCAAGGAAACTTTCTGCGAAGAT
TCAAACTTACAGTAATAACTTAATTCCGTAAGTTTTGATTGTAGAGCAACTAGCTGAATATAACTTAAATTTGC
TATTACTCTGCTTTGAAAATTTGCATTTTGAGCGTGGTAAAACACAAGTCACTACCACTGTCGACTAGATAAGT
TAAATTTGTAATTGGGTCTGATACAAAAAGGCGGCTTGTATTGTCGAATTTGAAATTGTATTGTGCCAGGTCAT
ACAATTTTGCTATTAAATTTCCGATATTGTAAATGAACAAGGAAATTTGCAACGTTTAGCAGCCGAACCGAATT
TGAAATGATACCAGCACTGATAGTGAGTTTTTCTTTTGGGTGTTCGAGAGCGTTGGCGGGGAGGAGAAACTCGG
TTTTCCGGGTCCCGTGATTTGTGCCTGCGACCTTAAGATAAACTTTTAATTTATTTTCTAAGTTTCGCAATTTG
CATTTATAATTCGCTTAATTCACGAGATGAAATTTTGGGGACTTGAATTTCTTTAACAATCGCGTTTGAGGTAT
CATGGATTTTATCACCATTATAGCAAGCTTGTCGAACTTATCCTCGGAAACTGAAAGAATAGCTTGAGACTAAG
GAGTTAGACGCTGCAACCAAAGCATTTTAGGAAATCTTCACTTACAGTTTTACCCGCTAATTGCCTCATCTTGC
GTAGTAAGTGAGAAGGCTTGTCTCCTAGAATTAGTTCTGAAATTAGAGTTTTAATGCGTCGTCGCTCTGAATCT
GAGAATTCCTCAACGAGTCGAGATTTTAAAGTTTCATATTTATTTCCCTCAGGTGGCGTGAACACAATACCACT
AACGTAATTTAAAATACCCGACGTTAAAGCGGAAATAAACGAATAATATTTAGTCGAGTCCTGTGTAATACCAG
AAATTATAAACTGTGCCTCTATATTTGCAAACTATAGCACGGGATGTTTATCCAAGAAAAGTGGTAATTTTAGG
CTTACTCTAGCTATATTAGCCTCCACCCAGTCGTTTGGCATGATAACAGCGACATAAATAAAATGCCTGTTACA
AAATTTGAAATAGATAATATGTGTGAATGATACTGCCGTTTTTAGACTTTTCTTCTCCATAGATACTTGAAGTA
GGAAATTATCATTGATATTCTTCCAGCGAGAGACATTATTCCAACGTAGTAAAATCATCCGGTTCACCAGTGCA
GTGATTTAGAGGTCAAAAGTCAGATATTTTATATCACCGACGAAATTGGCGATTAGAATATTACTCCATAAAAG
TGAACAAATTTTTATTAGCAGTAGGAGGTGAAGTGCGTGCTACAAGAATAACAGTACACGTTAAAAGATTATAT
AATCAATTAGTTACAATACAATTACAGTTTCCAAGCAAGGTTGAGTAATTTACATAAGTGCATAAAGTTAGTTT
TTCCGTGCCGCCAGGTTGGCATGCCAGGTCGGGAATTGCGGTGGTGTATGGCATGGCCACCGCAAGGTGAAAGT
ACAACTGTGCTTTAAACTTCTTCGATAGATGGCACCACCAGCAAACCCACTTAAATCAATTATGACATTAATCT
GGAGGGGGAGGAAATTTTCTCCAGACAATTACACCCATGATAACTGCTCAACGAGCAACCACAGGACTTTCAAT
TCCACAGATTTAACGAGCACGTATATCGCATGTACTAGGTGGATCTTTGGTGGCATTCTGAGTAGAATTCTGCT
CTTCCGGACTGAAGGCTGATGCTCTAACCATTAGGCTACCACAGCTTATATGATCATTGCATTCAACAACACCA
TGAGTAGCTAAATTATAAGGTAAGTGCCCAGATGTTGTATTTTTTTCAATCTGCATGTTTGTCCTGTACATTTTG
ATATTTAATTTGTATTAATAGTACAATTGGGGCCAAAGTTGTTAAGCACTTAATAACTGTAAATTTTTCATGTT
TTTTGTCGTCTTCTCTAAAATTATTAATGTACTATTGTAATTACCATTTAATAACTTTGGAGCTGATTGTCCTA
TCTCATTGAAATTAATTTTAACGTGGAGTGGATAAGCTAAGCTTTTAAATTACATCTAATTTATGATTGTAGAT
TTAATAGTTTTCTCTCAATAATTTTTCAAAATTTAACATTGCTCAAAAATTTTTATGTATTTTTGCCTTATTTG
TATACAATTTTAATTTCAAAACTGCCTTAAAATTTTAAATATTAATCAATCCACTCCAATATTTCTAAATTAAT
TCAGAGCCGATTTCTGTGATTCAGAATATATTATTCTTTTTATTAATTTTTTAAATAATTAATAGTTAAAAAGT
TATCAATTTTATGTAGAATGTAATTGTATCTTTCACTGTTTTTTCCCCATTTCGACCAATGTAACTTCAGTGCT
CCCCTTTGTATATGTATTGCGGCTGTGATTTCATCTATGTCCGACCATTAGCAGGGTGATGGTCCCTCTCTTTC
ATCCTCCTCTTAATTCCGGCATTAATTAATTACTTTAATCAATTTTTAATTAGCGAATTTCTCACCTCCTAATT

FIGURE 7 (cont'd)

GTCCCAGAGACGCAGAACTAAATTCATTGGGTTCATTTGGCGTTTTCTCAACTCCCCATTAGTCTCAGAGACTC
GGGACTAATCTCTAATTTTGTTATTTAATAATGAGCTTCTAACGAGACCACTTAGTTGCCATTATTACAAAATT
ATCCCATTTTCCTTATATTGATGGATTGGATTTTTTTTAATTATTCATTTTTATTTTTACTTATTTATTTATTT
ATTTATTTATTTTTTGACGTTCGTCGCTAAGCCTATTTCCAAGACTTTAACTTGTCTCCATTAAATTGCCTTGA
TATTCAGTCAACTATCACACTACTATTATAACTATTTTAAGTTTATCATCCTGGCCAATTAATTAAATTAAGGG
CTAACTATATGCCCAATTAATCCTTAAATAGTTTAATTAACTTAAATATTCATCTTTGGAAAGGCCTATCATGG
GGGTCTGTGGCTCGATACAGTATGCAGGGGGAGTAGTGAACACAGATTGTATCCCACAACTTCTAAACTTTCAT
TAAAACCGTTTCTAAGACAATTAGCTTGTAAAGGAATAATTTTATTCAACTAGCATTTACTATTAACCAAATTA
CAAAAACACATTTTAAGTAAATTCGAGTTTTTTTAAATATTTTTTATTTTATTTATTTATTTTTTTTTATTTATT
TATTTTTTTATTTTATTTTTTATTTTTTTTATTTAATGGGACCAGATTTAACTTAGCTTAATTCACCCCTCTTT
AAATTTAACTACCAAGTATTTAACTGAACGAAACAAATTTTGCAATCGAATGGGTTGGTCACCTCCCCATAGTA
ATATTGTATCTCATGGCACAATTTTTTTAGAGAGATGGAACTAAGATCATTCTTCACCCTAACCTCCCACTAGCA
TATACAA

FIGURE 7 (cont'd)

SPIDER SILK DRAGLINE POLYNUCLEOTIDES, POLYPEPTIDES AND METHODS OF USE THEREOF

CROSS REFERENCE TO RELATED APPLICATIONS

This application is a U.S. National Stage Application filed under 35 U.S.C. 371 and claims priority to International Application No. PCT/US08/66448, filed Jun. 10, 2008, which application claims priority under 35 U.S.C. §119 from Provisional Application Ser. No. 60/943,107, filed Jun. 11, 2007, the disclosures of which is are incorporated herein by reference.

STATEMENT AS TO FEDERALLY SPONSORED RESEARCH

The U.S. Government has certain rights in this disclosure pursuant to Grant No DAAD19-02-1-0358 and W911NF-06-1-0455 awarded by the Army Research Office (DAAD19-02-1-0358 and W911NF-06-1-0455) Grant No. DEB-0236020 awarded by the National Science Foundation.

FIELD OF THE DISCLOSURE

The disclosure relates to spider silk dragline polypeptides, polynucleotides and uses thereof.

BACKGROUND

Ever increasing demands for materials and fabrics that are both light-weight and flexible without compromising strength and durability has created a need for new fibers possessing higher tolerances for such properties as elasticity, denier, tensile strength and modulus. The search for a better fiber has led to the investigation of fibers produced in nature, some of which possess remarkable qualities.

SUMMARY

The spider dragline compositions provided herein find uses in the textile industry (e.g., as filaments, yarns, ropes, and woven material). Such materials made using the methods and compositions described herein will take advantage of the extreme toughness, tensile strength, and extensibility of silk. In addition, the polypeptides of the disclosure can be used in pliant energy absorbing devices including armor and bumpers. Besides the mechanical properties of spider silk, silk is proteinaceous (thus not petroleum-based like nylon or para-aramid synthetic fibers, e.g., Kevlar®). Accordingly, the polypeptides of the disclosure provide biocompatible and biodegradable material useful in various industries including textiles and medicine. For example, the supercontraction ability of dragline silk can be beneficial for sutures that can tighten, compression bandages, or space minimizing packaging. Additionally the polypeptides can be used in the generation of scaffolds and material in tissue engineering, implants and other cell scaffold-based materials.

The disclosure provides a number of isolated full-length spider silk polynucleotides and their flanking regions. The polynucleotides encode the MaSp1 and MaSp2 proteins from the black widow's high-performance dragline silk. Each polynucleotide includes a single enormous exon (>9000 base pairs) that translates into a highly repetitive polypeptide. Patterns of variation among sequence repeats at the amino acid and nucleotide levels indicate that the interaction of selection, intergenic recombination, and intragenic recombination governs the evolution of these highly unusual, modular proteins. Phylogenetic footprinting revealed putative regulatory elements in non-coding flanking sequences. Conservation of both upstream and downstream flanking sequences was present between the two paralogous black widow major ampullate silk genes. Because these genes are co-expressed within the same silk gland, there may have been selection for similarity in regulatory regions.

The disclosure provides complete templates for synthesis of recombinant silk proteins that significantly improve the degree to which artificial silks mimic natural spider dragline fibers. The disclosure provides MaSp1 and MaSp2 polynucleotide sequences as well as adjacent non-coding regions. The polynucleotides of the disclosure have a higher-order repeat units that range from ~70 to over 2,000 bp, and show that the repetitive sequences of MaSp1 are more homogenized than those of MaSp2. The disclosure also demonstrate marked evolutionary conservation of N-terminal and upstream non-coding regions between paralogs within a species and across orthologs from divergent species. Based on these multi-gene comparisons, putative regulatory sequences that may be involved in co-expression of the two major ampullate silk genes. The data provide templates for complete recombinant major ampullate fibroins and illustrate the dramatic effects of intragenic and intergenic recombination in the evolution of these modular genes.

The details of one or more embodiments of the disclosure are set forth in the accompanying drawings and the description below. Other features, objects, and advantages of the disclosure will be apparent from the description and drawings, and from the claims.

BRIEF DESCRIPTION OF THE DRAWINGS

FIG. 1A(i)(ii)-B shows ensemble repeats encoded by *Latrodectus hesperus* (FIG. 1A(i)) and *Latrodectus geometricus* (FIG. 1A(ii)) MaSp1 loci. MaSp1 is characterized by GGX and poly-A aa motifs. For *L. hesperus*, exemplar ensemble types a-d are shown. The ordering of colored ovals depicts the arrangement of these ensemble types in each locus. For the *L. geometricus* loci, LgMaSp1_L1-2, the entirety of the sequenced repeats is shown. Fifty percent majority rule ensemble repeats are shown for the *L. geometricus* MaSp1 cDNA sequence (LgMaSp1_cDNA) and the third *Latrodectus geometricus* locus (LgMaSp1_L3). aa found in LgMaSp1_L3 but not in the other loci are highlighted with gray boxes.

FIG. 7 depicts the gene sequences of MaSp1 (SEQ ID NO:60) and MaSp2 (SEQ ID NO:59).

DETAILED DESCRIPTION

Figure 1B:
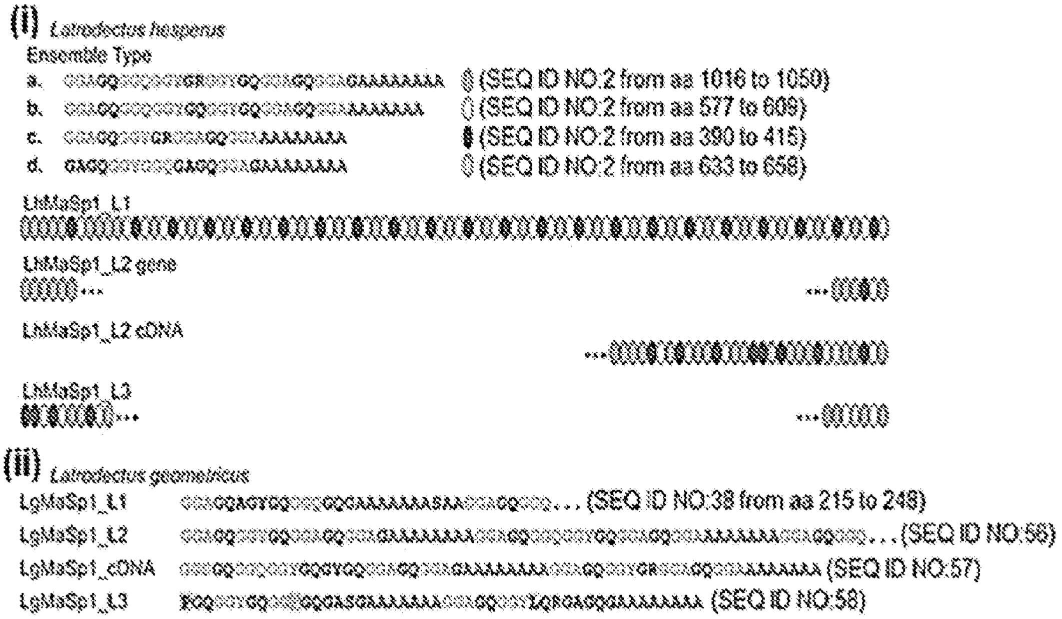
FIG. 1B shows a Comparison of the predicted aa composition of the repetitive regions encoded by MaSp1 loci in 2 *Latrodectus* species. The 10 most prevalent aa are shown. aa that differ most between LgMaSp1_L3 and the other loci are outlined in black (G, S, V, P, F, and L). The numbers of characterized aa are shown above the bars. Only LhMaSp1_L1 has been fully sequenced. *For LhMaSp1_L2, the predicted aa composition of the cDNA is shown because more of its repetitive region than that of the genomic clone has been sequenced.

As used herein and in the appended claims, the singular forms "a," "and," and "the" include plural referents unless the context clearly dictates otherwise. Thus, for example, reference to "MaSp" includes a plurality of such genes and variants and reference to "the peptide" includes reference to one or more peptides known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

Spider silks have been demonstrated to have several desirable characteristics. The orb-web-spinning spiders can produce silk from six different types of glands. Each of the six fibers has different mechanical properties. However, they all have several features in common. They are (i) composed predominantly or completely of protein; (ii) undergo a transition from a soluble to an insoluble form that is virtually irreversible; (iii) composed of amino acids dominated by alanine, serine, and glycine and have substantial quantities of other amino acids, such as glutamine, tyrosine, leucine, and valine. The spider dragline silk fiber has been proposed to consist of pseudocrystalline regions of antiparallel, β-sheet structure interspersed with elastic amorphous segments.

The spider silks range from those displaying a tensile strength greater than steel (7.8 vs 3.4 G/denier) and those with an elasticity greater than wool, to others characterized by energy-to-break limits that are greater than KEVLAR®. Given these characteristics spider silk could be used as a light-weight, high strength fiber for various textile applications.

Spider dragline silk has a number of unusual properties. These include a tensile strength greater than steel or carbon fibers (200 ksi), elasticity as great as some nylon (35%), a stiffness as low as silk (0.6 msi), and the ability to supercontract in water (up to 60% decrease in length). These properties are unmatched by any other material.

When spun into fibers, which can be done by dissolving spider silk in an appropriate solvent and forcing it through a small orifice, spider silk can have numerous uses. For example, one large volume use is for clothing. Silk with elasticity would have a unique place in the market even at high prices. It may also be applicable for certain kinds of high strength uses such as rope, surgical sutures, flexible tie downs for certain electrical components and even as a biomaterial for implantation (e.g., artificial ligaments or aortic banding). Thus, there are numerous applications including high-tech clothing, rope, sutures, medical coverings and others where various combinations of strength and elasticity are required. It is also possible to modify the properties of the silk fibers by altering the protein sequence.

Considerable difficulty has been encountered in attempting to solubilize and purify natural spider silk while retaining the molecular-weight integrity of the fiber. The silk fibers are insoluble except in very harsh agents such as LiSCN, $LiClO_4$, or 88% (vol/vol) formic acid. Once dissolved, the protein precipitates if dialyzed or if diluted with typical buffers. Another disadvantage of spider silk protein is that only small amounts are available from cultivated spiders, making commercially useful quantities of silk protein unattainable at a reasonable cost. Additionally, multiple forms of spider silks are produced simultaneously by any given spider. The resulting mixture has less application than a single isolated silk because the different spider-silk proteins have different properties and, due to solubilization problems, are not easily separated by methods based on their physical characteristics. Hence the prospect of producing commercial quantities of spider silk from natural sources has not previously been a practical one and there remains a need for an alternate mode of production. The technology of recombinant genetics provides one such mode.

By the use of recombinant molecular biology techniques it is now possible to transfer polynucleotides between different organisms for the purposes of expressing desired proteins in commercially useful quantities. Such transfer usually involves joining appropriate polynucleotides to a vector molecule, which is then introduced into a host cell or organism by transformation or transfection. Transformants are selected by a known marker on the vector, or by a genetic or biochemical screen to identify the cloned fragment. Vectors contain sequences that enable autonomous replication within the host cell, or allow integration into a chromosome in the host.

While many of the problems of efficient transcription and translation have been generally recognized and for the most part, overcome, the synthesis of fiber-forming foreign polypeptides containing high numbers of repeating units poses unique problems. Genes encoding proteins of this type are prone to genetic instability due to the repeating nucleic acid sequences. Ideally, they encode proteins of high molecular weight, consisting of at least 800 amino acid residues, and generally with restricted amino acid compositions. While *E. coli* produces endogenous proteins in excess of 1000 residues, production of long proteins of restricted amino acid composition appears to place an unbalanced strain on the biosynthetic system, resulting in the production of truncated products, probably due to abortive translation.

Progress has also been made in the cloning and expression of spider silk proteins. Xu et al., Proc. Natl, Acad. Sci. U.S.A., 87, 7120, (1990) report the determination of the sequence for a portion of the repetitive sequence of a dragline silk protein, Spidroin 1, from the spider *Nephila clavipes*, based on a partial cDNA clone. The repeating unit is a maximum of 34 amino acids long and is not rigidly conserved. The repeat unit is composed of two different segments: (i) a 10 amino acid segment dominated by a polyalanine sequence of 5-7 residues; (ii) a 24 amino acid segment that is conserved in sequence but has deletions of multiples of 3 amino acids in many of the repeats. The latter sequence consists predominantly of GlyXaaGly motifs, with Xaa being alanine, tyrosine, leucine, or glutamine. The codon usage for this DNA is highly selective, avoiding the use of cytosine or guanine in the third position.

Hinman and Lewis, J. Biol. Chem. 267, 19320 (1992) report the sequence of a partial cDNA clone encoding a portion of the repeating sequence of a second fibroin protein, Spidroin 2, from dragline silk of *Nephila clavipes*. The repeating unit of Spidroin 2 is a maximum of 51 amino acids long and is also not rigidly conserved. The frequency of codon usage of the Spidroin 2 cDNA is very similar to Spidroin 1.

Lewis et al. (EP 452925) disclose the expression of spider silk proteins including protein fragments and variants, of *Nephila clavipes* from transformed *E. coli*. Two distinct proteins were independently identified and cloned and were distinguished as silk protein 1 (Spidroin 1) and silk protein 2 (Spidroin 2).

Lombardi et al. (WO 9116351) teach the production of recombinant spider silk protein comprising an amorphous domain or subunit and a crystalline domain or subunit where the domain or subunit refers to a portion of the protein containing a repeating amino acid sequence that provides a particular mechanostructural property.

As used herein an "MaSp1 and MaSp2 polypeptide" means a polypeptide that contains or comprises an amino acid sequence as set forth in FIGS. 1A(i)-(ii) and 2; polypeptides having substantial homology or substantial identity to the sequences set forth in SEQ ID Nos: 2, 4, 6, 8, 10, 12, 14, 16, 18, 20, 22, 24, 26, 28, 30, 32, 34, 36, 38, 40, 42, 44, 46, and 48); polypeptides comprising up to 100 conservative amino acid substitutions or from 1-50 (e.g., from 1-40, 1-30, 1-20, 1-15 or 1-10) conservative amino acid substitutions to any of the foregoing sequences; fragments of the foregoing sequences; and conservative and naturally occurring variants (see, e.g., SEQ ID NOs: 6, 8, 10, 12, 14, 16, 18, 20, 22, 24, 26, 28, 30, 32, 34, 36, 38, 40, 42, 44, 46, and 48) of the foregoing, wherein the polypeptide comprises a spider silk structure motif. The disclosure provides polypeptides having a sequence as set forth in SEQ ID Nos: 2, 4 6, 8, 10, 12, 14, 16, 18, 20, 22, 24, 26, 28, 30, 32, 34, 36, 38, 40, 42, 44, 46, and 48 alone or fused to a second polypeptide.

As used herein an "MiSp polypeptide" means a polypeptide that contains or comprises an amino acid sequence as set forth in SEQ ID NO:50; polypeptides having substantial homology or substantial identity to the sequences set forth in SEQ ID NO:50; polypeptides comprising from 1-50 (e.g., from 1-40, 1-30, 1-20, 1-15 or 1-10 conservative amino acid substitutions to SEQ ID NO:50; fragments of the foregoing sequences; and conservative and naturally occurring variants of the foregoing, wherein the polypeptide comprises a spider silk structure motif. The disclosure provides polypeptides having a sequence as set forth in SEQ ID NO:50 alone or fused to a second polypeptide.

A polypeptide of the disclosure encompasses an amino acid sequence that has a sufficient or a substantial degree of identity or similarity to a sequence set forth in FIG. 1A(i)-(ii) or 2 or SEQ ID NOs: 2, 4, 6, 8, 10, 12, 14, 16, 18, 20, 22, 24, 26, 28, 30, 32, 34, 36, 38, 40, 42, 44, 46, 48 and 50. Substantially identical sequences can be identified by those of skill in the art as having structural domains and/or having biological activity in common with a MaSp1, MaSp2, or MiSp polypeptides. Methods of determining similarity or identity may employ computer algorithms such as, e.g., BLAST, FASTA, and the like.

Polypeptides derived from the MaSp1, MaSp2 and MiSp polypeptides of the disclosure by any type of alteration (e.g., insertions, deletions, or substitutions of amino acids; changes in the state of glycosylation of the polypeptide; refolding or isomerization to change its three-dimensional structure or self-association state; and changes to its association with other polypeptides or molecules) are also encompassed by the disclosure. Therefore, the polypeptides provided by the disclosure include polypeptides characterized by amino acid sequences similar to those as set forth in SEQ ID NOs:2, 4, 6, 8, 10, 12, 14, 16, 18, 20, 22, 14, 26, 28, 30, 32, 34, 36, 38, 40, 42, 44, 26, 48, or 50, but into which modifications are naturally provided or deliberately engineered. A polypeptide that shares biological activities in common with a polypeptide comprising a sequence as set forth in SEQ ID NOs:2, 4, 6, 8, 10, 12, 14, 16, 18, 20, 22, 14, 26, 28, 30, 32, 34, 36, 38, 40, 42, 44, 26, 48, or 50 having silk dragline characteristics or activity are encompassed by the disclosure.

Figure 2:
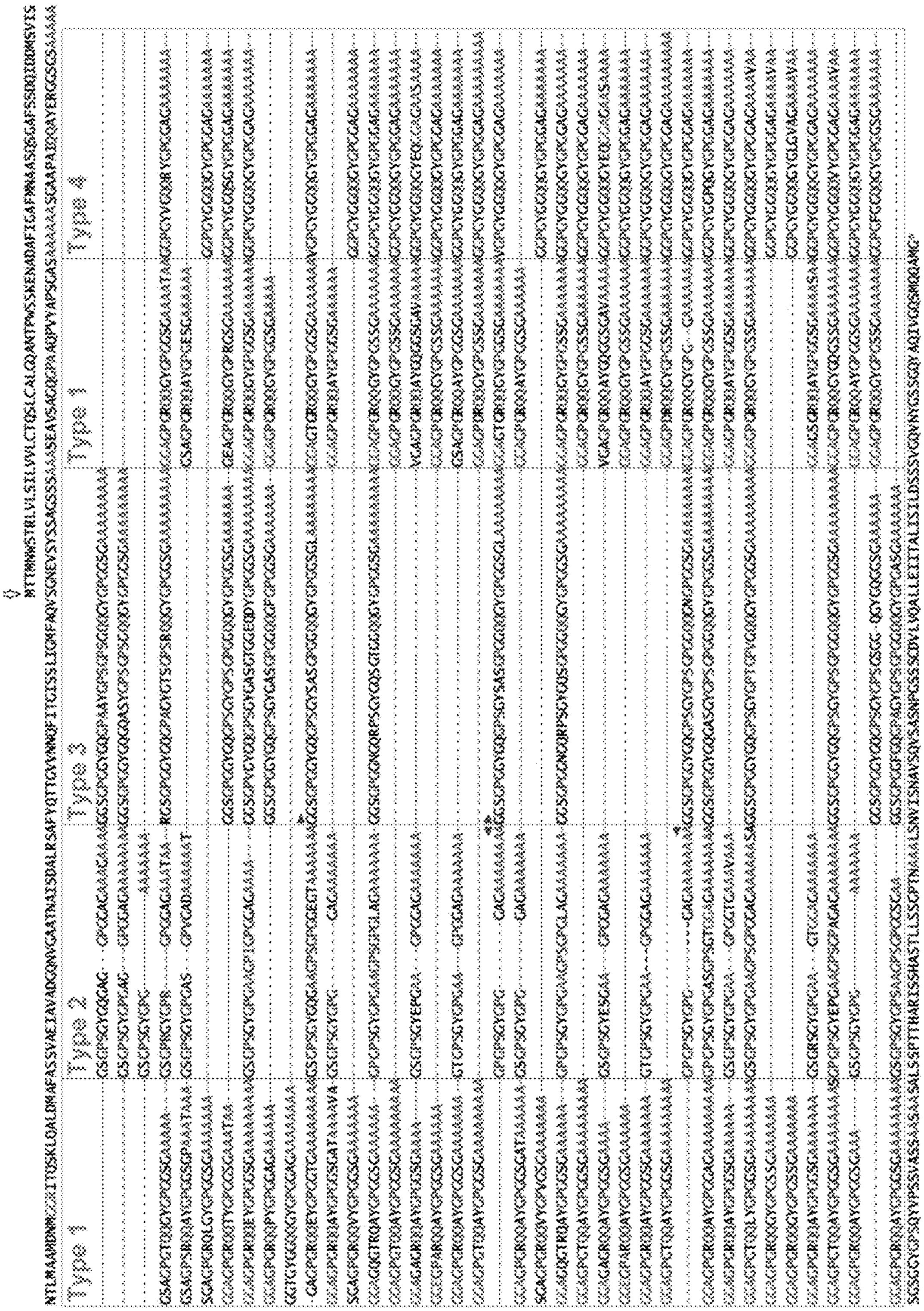
FIG. 2 shows a complete amino acid sequence for *L. hesperus* major ampullate spidroin 2 (MaSp2). The sequence is read from left to right and then top to bottom. Start position, stop position, and alignment gaps are indicated as for MaSp1 (FIG. 1C). MaSp2 is characterized by poly-A (red), GGX (green), GPX (blue), and QQ (purple) motifs. There are four types of ensemble repeats. Repeats of each type are aligned within a box, except for Type 1, which is separated into two boxes because it is approximately twice as prevalent as any other repeat type. Right and left pointing arrows mark beginnings and ends of two near-perfect repeats of 778 aa.

The disclosure encompasses various forms of MaSp1 and MaSp2 domains that retain at least one activity or characteristic ("silk dragline characteristics") selected from the group consisting (i) four distinct repeat units, termed ensemble repeats; and (ii) ensemble repeat units of about 30 amino acids, which are glycine-rich interspersed with alanine-rich regions. The polypeptides of the disclosure can be from 30 to at least about 3000 amino acids long. In another aspect, the four types of ensemble repeats are strung together to form an approximate 120 amino acid long, higher-level repeat unit. This large aggregate is tandemly arrayed about twenty times and the iterations share high identity at both the amino acid and nucleotide level (98.1% and 97.5% mean pairwise identity, respectively). MaSp2 has more sequence and length variation among its ensemble repeats than in MaSp1 (FIG. 2, Table 2). MaSp2, however, has a tandem repetition of 778 amino acids that is >99.7% identical over the 2,334 encoding nucleotides (FIG. 2). The modular architectures of MaSp1 and MaSp2 likely reflect concerted evolution within a single gene, as has been implicated in maintaining similarity among Flag (~440 aa) ensemble repeats and the long repeats of TuSp1 (~200 aa) and AcSp1 (aciniform silk; 200 aa). MiSp similarly has ensemble repeats as will be readily apparent by one of skill in the art upon review of SEQ ID N0:50.

A "unit repeat" constitutes a repetitive short sequence. Thus, the primary structure of the spider silk proteins is considered to consist mostly of a series of small variations of a unit repeat. The unit repeats in the naturally occurring proteins are often distinct from each other. That is, there is little or no exact duplication of the unit repeats along the length of the protein. Synthetic spider silks, however, can be made wherein the primary structure of the protein comprises a number of exact repetitions of a single unit repeat. Additional synthetic spider silks can be synthesized which comprise a number of repetitions of one unit repeat together with a number of repetitions of a second unit repeat. Such a structure would be similar to a typical block copolymer fiber. Unit repeats of several different sequences can also be combined to provide a synthetic spider silk protein having properties suited to a particular application. The term "direct repeat" as used herein is a repeat in tandem (head-to-tail arrangement) with a similar repeat.

The disclosure provides both full-length and mature forms of MaSp1, MaSp2 and MiSp polypeptides. The polypeptide and polynucleotides of the disclosure were identified from the widow spider family (e.g., *Latrodectus hesperus* or *Lactrodectus geometricus*). Full-length polypeptides are those having the complete primary amino acid sequence of the polypeptide as initially translated. The amino acid sequences of full-length polypeptides can be obtained, for example, by translation of the complete open reading frame ("ORF") of a cDNA molecule. Several full-length polypeptides may be encoded by a single genetic locus if multiple mRNA forms are produced from that locus by alternative splicing or by the use of multiple translation initiation sites. The "mature form" of a polypeptide refers to a polypeptide that has undergone post-translational processing steps, if any, such as, for example, cleavage of the signal sequence or proteolytic cleavage to remove a prodomain. Multiple mature forms of a particular full-length polypeptide may be produced, for example, by imprecise cleavage of the signal sequence, or by differential regulation of proteases that cleave the polypeptide. The mature form(s) of such polypeptide may be obtained by expression, in a suitable insect or mammalian cell or other host cell, of a polynucleotide that encodes the full-length polypeptide. The sequence of the mature form of the polypeptide may also be determinable from the amino acid sequence of the full-length form, through identification of signal sequences or protease cleavage sites. The MaSp1 and MaSp2 polypeptides of the disclosure also include polypeptides that result from posttranscriptional or post-translational processing events such as alternate mRNA processing which can yield a truncated but biologically active polypeptide. Also encompassed within the disclosure are variations attributable to proteolysis such as differences in the N- or C-termini upon expression in different types of host cells, due to proteolytic removal of one or more terminal amino acids from the polypeptide (generally from 1-5 terminal amino acids).

A polypeptide of the disclosure may be prepared by culturing transformed or recombinant host cells under culture conditions suitable to express a polypeptide of the disclosure. The resulting expressed polypeptide may then be purified from such culture using known purification processes. The purification of the polypeptide may also include an affinity column containing agents which will bind to the polypeptide; one or more column steps over such affinity resins as concanavalin A-agarose, Heparin-Toyopearl® or Cibacrom blue 3GA Sepharose®; one or more steps involving hydrophobic interaction chromatography using such resins as phenyl ether, butyl ether, or propyl ether; or immunoaffinity chromatography. Alternatively, the polypeptide of the disclosure may also be expressed in a form that will facilitate purification. For example, it may be expressed as a fusion polypeptide, such as those of maltose binding polypeptide (MBP), glutathione-5-transferase (GST) or thioredoxin (TRSX). Kits for expression and purification of such fusion polypeptides are commercially available from New England BioLab (Beverly, Mass.), Pharmacia (Piscataway, N.J.), and Invitrogen, respectively. The polypeptide can also be tagged with an epitope and subsequently purified by using a specific antibody directed to such epitope. Finally, one or more reverse-phase high performance liquid chromatography (RP-HPLC) steps employing hydrophobic RP-HPLC media, e.g., silica gel having pendant methyl or other aliphatic groups, can be employed to further purify the polypeptide. Some or all of the foregoing purification steps, in various combinations, can also be employed to provide a substantially homogeneous recombinant polypeptide. The polypeptide thus purified is substantially free of other insect, plant, bacterial or mammalian polypeptides and is defined in accordance with the disclosure as a "substantially purified polypeptide"; such purified polypeptides include MaSp1, MaSp2, or MiSp polypeptides, fragment, variant, and the like. A polypeptide of the disclosure may also be expressed as a product of transgenic animals or insects, which are characterized by somatic or germ cells containing a polynucleotide encoding a polypeptide of the disclosure.

It is also possible to utilize an affinity column such as a monoclonal antibody generated against polypeptides of the disclosure, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the disclosure. In this aspect of the disclosure, proteins that bind a polypeptide of the disclosure (e.g., an anti-MaSp1, MaSp2, MiSp antibody of the disclosure) can be bound to a solid phase support or a similar substrate suitable for identifying, separating, or purifying cells that express polypeptides of the disclosure on their surface. Adherence of, for example, an anti-MaSp1, anti-MaSp2 or anti-MiSp antibody of the disclosure to a solid phase surface can be accomplished by any means, for example, magnetic microspheres can be coated with these polypeptide-binding proteins and held in the incubation vessel through a magnetic field.

A polypeptide of the disclosure may also be produced by known conventional chemical synthesis. Methods for constructing the polypeptides of the disclosure by synthetic means are known to those skilled in the art. The synthetically-constructed polypeptide sequences, by virtue of sharing primary, secondary or tertiary structural and/or conformational characteristics with a native polypeptides may possess biological properties in common therewith, including biological activity.

The desired degree of purity depends on the intended use of the polypeptide. A relatively high degree of purity is desired when the polypeptide is to be administered in vivo, for example. In such a case, the polypeptides are purified such that no polypeptide bands corresponding to other polypeptides are detectable upon analysis by SDS-polyacrylamide gel electrophoresis (SDS-PAGE). It will be recognized by one skilled in the pertinent field that multiple bands corresponding to the polypeptide can be visualized by SDS-PAGE, due to differential glycosylation, differential post-translational processing, and the like. Typically, the polypeptide of the disclosure is purified to substantial homogeneity, as indicated by a single polypeptide band upon analysis by SDS-PAGE. The polypeptide band can be visualized by silver staining, Coomassie blue staining, or (if the polypeptide is radiolabeled) by autoradiography.

Species homologues of MaSp1, MaSp2 and MiSp polypeptides and polynucleotides encoding the polypeptides are also provided by the disclosure. As used herein, a “species homologue” is a polypeptide or polynucleotide with a different species of origin from that of a given polypeptide or polynucleotide, but with significant sequence similarity to the given polypeptide or polynucleotide. Species homologues may be isolated and identified by making suitable probes or primers from polynucleotides encoding the polypeptides provided herein and screening a suitable nucleic acid source from the desired species. Alternatively, homologues may be identified by screening a genome database containing sequences from one or more species utilizing a sequence (e.g., nucleic acid or amino acid sequence) of an MaSp1, MaSp2 or MiSp of the disclosure. Such genome databases are readily available for a number of species (e.g., on the world wide web (www) at tigr.org/tdb; genetics.wisc.edu; stanford.edu/.about.ball; hiv-web.lanl.gov; ncbi.nlm.nig.gov; ebi.ac.uk; and pasteur.fr/other/biology). For example, the disclosure provides homologues of *Latrodectus hesperus* and *Latrodectus geometricus*. The disclosure also encompasses multi-locus and allelic variants of MaSp1, MaSp2, and MiSp polypeptides and nucleic acids encoding them that are naturally-occurring alternative forms of such polypeptides and polynucleotides in which differences in amino acid or nucleotide sequence are attributable to genetic polymorphism.

Intermediate Sequence Search (ISS) can be used to identify closely related as well as distant homologs by connecting two proteins through one or more intermediate sequences. ISS repetitively uses the results of the previous query as new search seeds. Saturated BLAST is a package that performs ISS. Starting with a protein sequence, Saturated BLAST runs a BLAST search and identifies representative sequences for the next generation of searches. The procedure is run until convergence or until some predefined criteria are met. Saturated BLAST is available on the world wide web (www) at: bioinformatics.burnham-inst.org/xblast (see also, Li et al. Bioinformatics 16(12): 1105, 2000).

Fragments of the MaSp1, MaSp2 and MiSp polypeptides of the disclosure are encompassed by the disclosure and may be in linear form or cyclized using known methods (see, e.g., H. U. Saragovi, et al., Bio/Technology 10, 773 (1992); and R. S. McDowell, et al., J. Amer. Chem. Soc. 114:9245 (1992), both of which are incorporated by reference herein). Peptide fragments of MaSp1, MaSp2 and MiSp polypeptides of the disclosure, and polynucleotides encoding such fragments include amino acid or nucleotide sequence lengths that are at least 25% (typically at least 50%, 60%, or 70%, and commonly at least 80%) of the length of an MaSp1, MaSp2 or MiSp polypeptide or polynucleotide. Typically such sequences will have at least 60% sequence identity (more typically at least 70%-75%, 80%-85%, 90%-95%, at least 97.5%, or at least 99%, and most commonly at least 99.5%) with an MaSp1 and MaSp2 polypeptide or polynucleotide when aligned so as to maximize overlap and identity while minimizing sequence gaps. Also included in the disclosure are polypeptides, peptide fragments, and polynucleotides encoding them, that contain or encode a segment comprising at least 8 to 10, typically at least 20, at least 30, or most commonly at least 40 contiguous amino acids. Such polypeptides and fragments may also contain a segment that shares at least 70% (at least 75%, 80%-85%, 90%-95%, at least 97.5%, or at least 99%, and commonly at least 99.5%) with any such segment of any of the MaSp family polypeptides or MiSp family of polypeptides, when aligned so as to maximize overlap and identity while minimizing sequence gaps. Visual inspection, mathematical calculation, or computer algorithms can determine the percent identity.

The polypeptides of the disclosure comprise Black and Brown widow dragline silk, an exceptionally tough biomaterial, even compared to the high-performance draglines spun by other spiders. The disclosure provides isolated polynucleotides and the polynucleotide sequences for the MaSp1, MaSp2 and MiSp fibroins that form this silk. In one aspect, the polynucleotides of the disclosure lack introns and thus MaSp1, MaSp2 and MiSp each possess only one enormous exon containing 9,390 by (MaSp1), 11,340 by (MaSp2) or 6,564 by (MiSp) of coding sequence. Alternatively, the polynucleotide encoding the polypeptides of the disclosure may comprise gaps or non-coding sequences. For example, the following accession numbers (each of which is incorporated herein by reference) provide additional coding sequence information and gaps found in the polynucleotides of the disclosure:

>EU177648 [clone=113P20] [cds=952-2188,gap,2189-3210; note=coding region disrupted by sequencing gap of unknown length] *Latrodectus hesperus* major ampullate spidroin 1 locus 3 (LhMaSp1_L3) gene, partial cds (SEQ ID NO: 5);

>EU177649 [clone=110A1] [cds=637-1560,gap,1561-2529; note=coding region disrupted by sequencing gap of unknown length] *Latrodectus hesperus* major ampullate spidroin 1 locus 1 (LhMaSp1_L1) gene, partial cds (SEQ ID NO:7);

>EU177650 [clone=89K13] [cds=1379-2521,gap,2522-3472; note=coding region disrupted by sequencing gap of unknown length] *Latrodectus hesperus* major ampullate spidroin 1 locus 3 (LhMaSp1_L3) gene, partial cds (SEQ ID NO:9);

>EU177651 [clone=63L5] [cds=846-2036,gap,2037-2687; note=coding region disrupted by sequencing gap of unknown length] *Latrodectus hesperus* major ampullate spidroin 1 locus 2 (LhMaSp1_L2) gene, partial cds (SEQ ID NO:11);

>EU177653 [clone=1416] [cds=846-1949,gap,1950-2875; note=coding region disrupted by sequencing gap of unknown length] *Latrodectus hesperus* major ampullate spidroin 1 locus 2 (LhMaSp1_L2) gene, partial cds (SEQ ID NO:13);

>EU177654 [clone=14C24] [cds=231-1348,gap,1349-2046; note=coding region disrupted by sequencing gap of unknown length] *Latrodectus hesperus* major ampullate spidroin 1 locus 1 (LhMaSp1_L1) gene, partial cds (SEQ ID NO:15);

>EU177655 [clone=11E24] [cds=399-1655,gap,1656-2588; note=coding region disrupted by sequencing gap of unknown length] *Latrodectus hesperus* major ampullate spidroin 1 locus 1 (LhMaSp1_L1) gene, partial cds (SEQ ID NO:17);

>EU177652 [clone=38E21] [cds=509-1547,gap,1548-2249; note=coding region disrupted by sequencing gap of unknown length] *Latrodectus hesperus* major ampullate spidroin 2 (MaSp2) gene, partial cds (SEQ ID NO:19);

>EU177661, *Latrodectus hesperus* major ampullate spidroin 1 locus 1 (LhMaSp1_L1) gene, partial cds (SEQ ID NO:21);

>EU177662, *Latrodectus hesperus* major ampullate spidroin 1 locus 2 (LhMaSp1_L2) gene, partial cds (SEQ ID NO:23);

>EU177663, *Latrodectus hesperus* major ampullate spidroin 1 locus 1 (LhMaSp1_L1) gene, partial cds (SEQ ID NO:25);

>EU177664, *Latrodectus hesperus* major ampullate spidroin 1 locus 2 (LhMaSp1_L2) gene, partial cds (SEQ ID NO:27);

>EU177665, *Latrodectus hesperus* major ampullate spidroin 1 locus 2 (LhMaSp1_L2) gene, partial cds (SEQ ID NO:29);

>EU177658, *Latrodectus hesperus* major ampullate spidroin 1 locus 1 (LhMaSp1_L1) gene, partial cds (SEQ ID NO:31);

>EU177659, *Latrodectus hesperus* major ampullate spidroin 1 locus 3 (LhMaSp1_L3) gene, partial cds (SEQ ID NO:33);

>EU177656 *Latrodectus hesperus* major ampullate spidroin 2 (MaSp2) gene, partial cds (SEQ ID NO:35);

>EU177666, *Latrodectus geometricus* major ampullate spidroin 1 locus 1 (LgMaSp1_L1) variant 1 gene, partial cds (SEQ ID NO:37);

>EU177667, *Latrodectus geometricus* major ampullate spidroin 1 locus 1 (LgMaSp1_L1) variant 2 gene, partial cds (SEQ ID NO: 39);

>EU177668, *Latrodectus geometricus* major ampullate spidroin 1 locus 2 (LgMaSp1_L2) variant 1 gene, partial cds (SEQ ID NO:41);

>EU177669, *Latrodectus geometricus* major ampullate spidroin 1 locus 2 (LgMaSp1_L2) variant 2 gene, partial cds (SEQ ID NO:43);

>EU177657 *Latrodectus geometricus* major ampullate spidroin 2 (MaSp2) gene, partial cds (SEQ ID NO:45); and >EU177660, *Latrodectus geometricus* major ampullate spidroin 1 locus 3 (LgMaSp1_L3) gene, partial cds (SEQ ID NO:47).

In eukaryotes, proteins encoded by single exons are rare and strongly biased towards sizes much smaller (<1,000 aa) than the spider silk proteins (>3,000 aa). Intron-less genes may reflect one type of gene duplication process that led to the diversification of the spider silk gene family; retroposition of mRNA transcripts (inherently intron-less) into the genome can give rise to functional gene duplicates. Alternatively, intron-less genes may be selectively favored. Intron length is negatively correlated with expression level and major ampullate silk genes must be highly expressed throughout the lifetime of a spider. However, once an intron invades a silk gene, the intron can be rapidly propagated throughout the gene due to unequal crossing over, which appears to be common in silk genes (see FIG. 2).

Figure 1B:
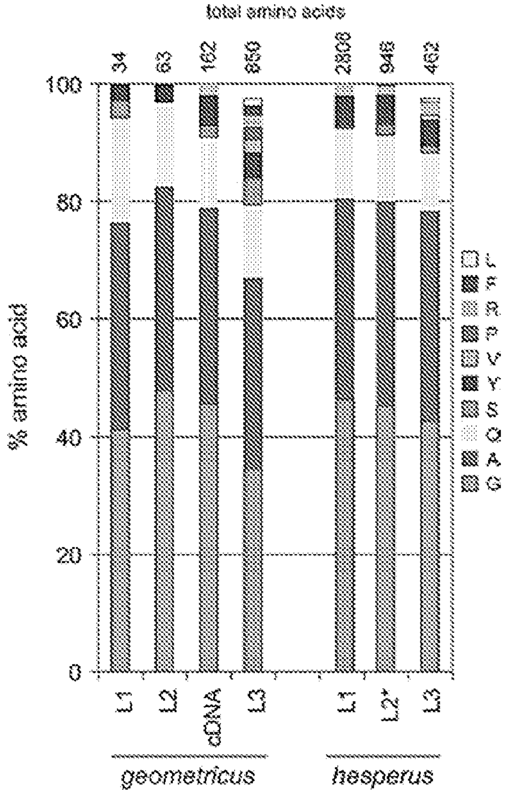
Figure 1C:
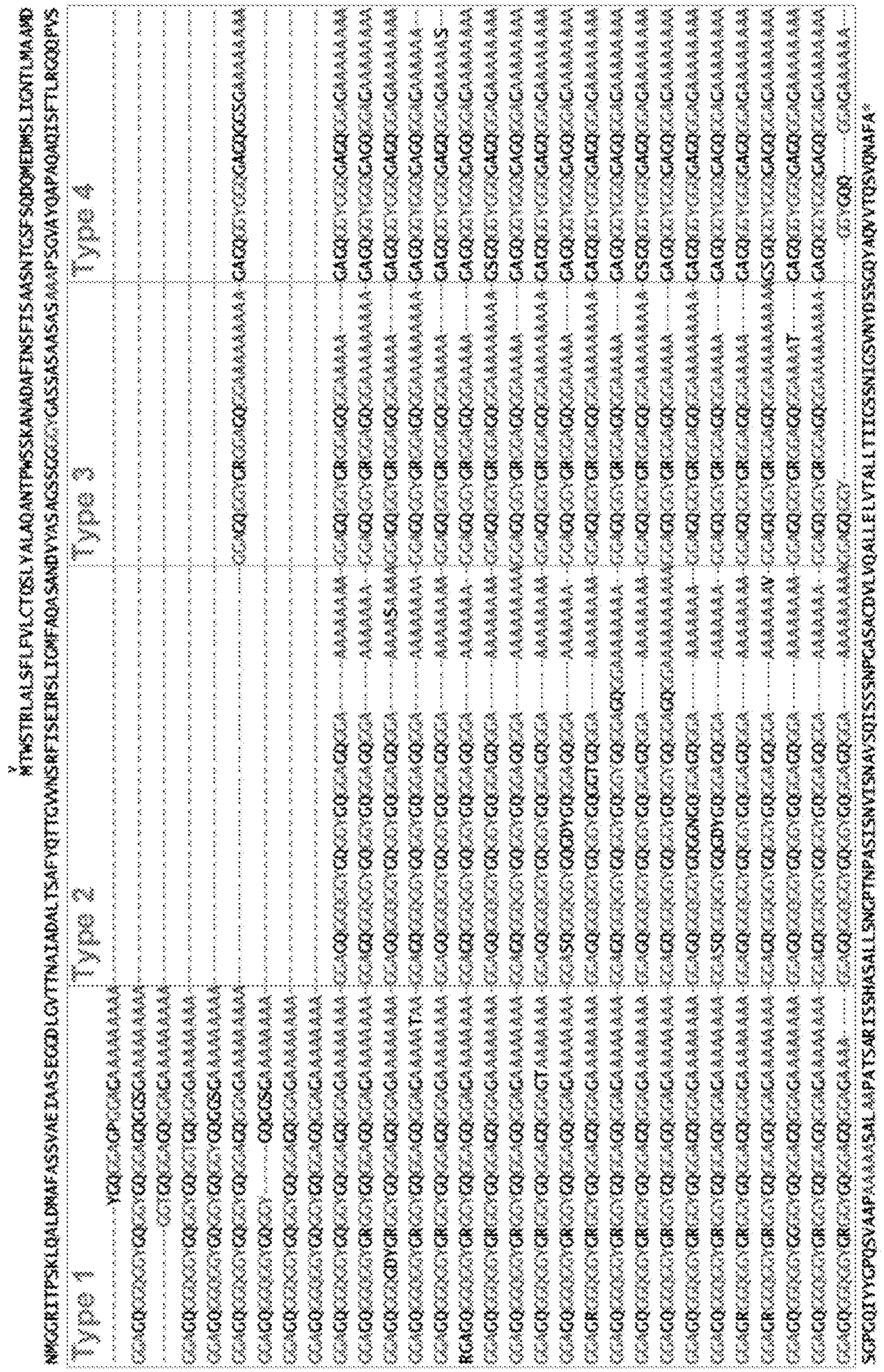
FIG. 1C shows the complete amino acid sequence for *L. hesperus* major ampullate spidroin 1 (MaSp1). The sequence is read from left to right and then top to bottom. The diamond marks the start position and the asterisk denotes the stop position. The protein is dominated by poly-A (red) and GGX (green) motifs. The majority of the sequence can be categorized into four types of ensemble repeat units. Repeats of each type are aligned within a box. Gaps (–) have been inserted in order to align repeat units within a type.

MaSp1 and MaSp2 are almost entirely composed of a small suite of amino acid sequence motifs, such as GGX and poly-A, which are repeated many times throughout both fibroins (FIGS. 1, 2). In each fibroin, the frequency and arrangement of these motifs occur in four distinct types of repeat units, termed ensemble repeats. Although the ensemble repeats of both MaSp1 and MaSp2 are similar in length (~30 aa) and composition (glycine-rich regions interspersed with alanine-rich regions), no repeat units from one protein are found in the other (FIGS. 1, 2). These results confirm that distinct genes encode each silk protein, rather than posttranscriptional processing of a single gene leading to silk protein diversity.

The amino acid sequence of a fragment of MaSp1 is repetitive and rich in glycine and alanine, but is otherwise unlike any previously known amino acid sequence. The repetitive nature of the protein and the pattern of variation among the individual repeats are emphasized by FIG. 1A(i)-(ii). The "consensus" sequence of a single repeat of Type 1 or Type 2, viewed in this way, is:

(SEQ ID NO: 51)

$Xaa_1GAGXaa_2GGQGXaa_3YGXaa_4GXaa_5Xaa_6GXaa_7GGXaa_8$ $GXaa_9GGXaa_{10}Xaa_{11}$ where $Xaa_1$ is R or G, $Xaa_2$ is Q or R, $Xaa_3$ is P or G, $Xaa_4$ is Q or R, $Xaa_5$ is D or G, $Xaa_6$ is Y or T, $Xaa_7$ is Q or P, $Xaa_8$ is A, T or Y, $Xaa_9$ is Q or P, $Xaa_{10}$ is A or S, and $Xaa_{11}$ is G or poly A of 4 to 10 residues. Other consensus repeats can be obtained from Type 3 and 4 repeats as shown in FIG. 1A(i)-ii) and for MaSp1. Consensus repeats for MaSp2 can be obtained by review of FIG. 2 as shown for Types 1, 2, 3, and 4.

*L. hesperus* and *L. geometricus* MaSp1 and MaSp2 have glycine and alanine-rich motifs that occur in ensemble repeats, but the fibroins differ in their higher-level repeat organization (repetitiveness) and similarity of repeat copies (homogenization). In MaSp1, the four types of ensemble repeats are strung together to form an approximate 120 amino acid long, higher-level repeat unit. This large aggregate is tandemly arrayed twenty times and the iterations share high identity at both the amino acid and nucleotide level (98.1% and 97.5% mean pairwise identity, respectively). In contrast, MaSp2 does not have clearly discernible higher-level repeats and has more sequence and length variation among its ensemble repeats than in MaSp1 (FIG. 2, Table 2). MaSp2, however, has a tandem repetition of about 778 aa that is >99.7% identical over the 2,334 encoding nucleotides (FIG. 2).

Modular architecture is also hypothesized to facilitate replication slippage in silk genes that have tandem arrays of codons for simple amino acid sequence motifs (e.g., poly-A, GGX, GA). Replication slippage would result in length variation among the ensemble repeats within a gene, as has been observed in MaSp1 and MaSp2.

Figure 4:
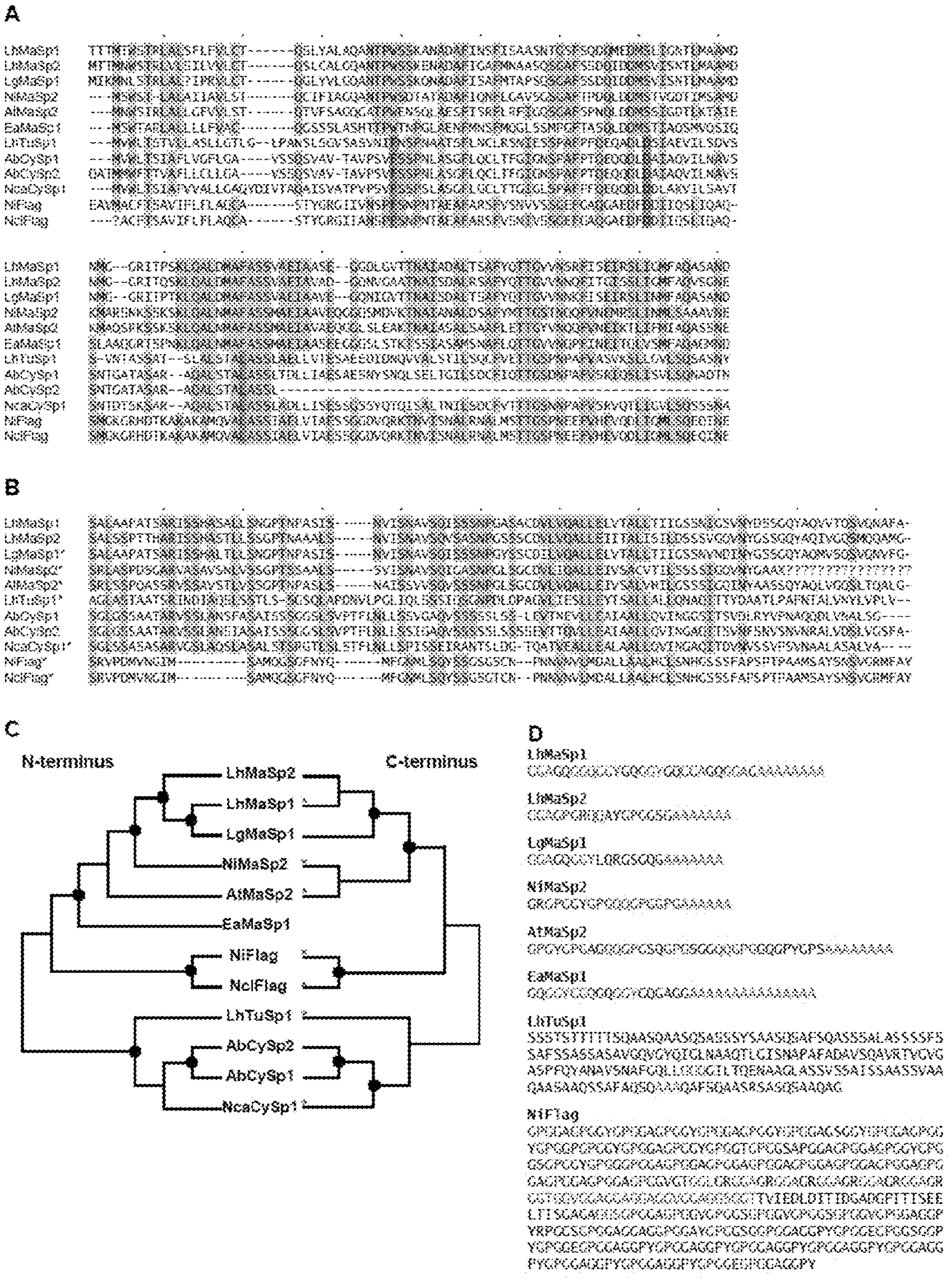
FIG. 4A-D shows a comparison of N-termini, C-termini and repeat units of spider silk proteins. (A) Alignment of published N-terminal amino acid sequences. Amino acids shared by >50% of proteins are highlighted in grey. Gaps are represented by dashes and missing characters by question marks. (B) Alignment of corresponding C-terminal amino acid sequences. Taxa with an asterisk result from partial sequencing and are presumed to belong to the same locus as the N-terminal sequences. (C) MP trees of N and C-terminal encoding sequences treating gaps as a fifth state and employing midpoint rooting. Left tree length=1449 (N-terminus); Right tree length=838 (C-terminus). Dots represent nodes with >75% bootstrap support in all MP and ML analyses and >95% Bayesian posterior probability. (D) Exemplar repeat units for each of the major ampullate fibroins and representative TuSp1 and Flag repeats. Amino acid motifs are colored as in FIG. 2. Abbreviations: LhMaSp2, *Latrodectus hesperus* MaSp2 (EF595245); LhMaSp1, *L. hesperus* MaSp1 (EF595246); LgMaSp1, *Latrodectus geometricus* MaSp1 (5' sequence: DQ059133S1, 3' sequence: DQ059133S2); NiMaSp2, *Nephila inaurata* madagascariensis MaSp2 (5' sequence: DQ059135, 3' sequence: AF350278); AtMaSp2, *Argiope trifasciata* MaSp2 (5' sequence: DQ059136, 3' sequence: AF350266); EaMaSp1; *Euprosthenops australis* MaSp1 (AM259067); LhTuSp1, *L. hesperus* TuSp1 (5' sequence: DQ379383, 3' sequence: AY953070); AbCySp1, *A. bruennichi* CySp1 AB242144; AbCySp2, *A. bruennichi* CySp2 (AB242145); NcaCySp1, *N. clavata* CySp1 (5' sequence: AB218974, 3' sequence: AB218973); NiFlag, N. i. madagascariensis Flag (5' sequence: AF218623S1, 3' sequence: AF218623S2); NclFlag, *N. clavipes* Flag (5' sequence: AF027972, 3' sequence: AF027973).
Figure 6:
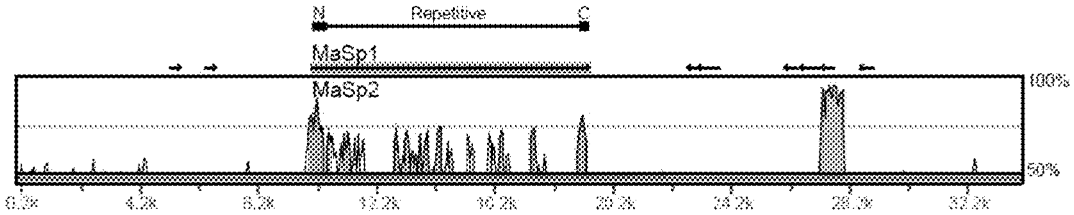
FIG. 6 shows a Global AVID alignment of *L. hesperus* genomic clones containing MaSp1 and MaSp2 visualized with VISTA. The MaSp1-containing clone was used as the reference sequence. Peak height corresponds to level of identity between the two clones. Regions exceeding 70% conservation over a window length of 100 by are colored (blue for exons, red for non-coding sequence). The red peak corresponds to a putative transposable element found in both clones. Arrows mark open reading frames (ORFs) on the clone containing MaSp1.

Attempts to reconstruct evolutionary relationships among members of the spider silk gene family have relied exclusively on the non-repetitive C-terminus, but the N-terminus has great promise for phylogenetic reconstruction. In the data demonstrated herein, there was extensive congruence between trees based on N- and C-termini of silk gene family members (FIG. 4C). A curious relationship found in both the N- and C-terminal phylogenetic trees is the grouping of *Latrodectus* major ampullate silk genes rather than a Glade of MaSp1 from all species separate from a MaSp2 Glade (FIG. 4C). A similar sister relationship between MaSp1 and MaSp2 C-termini has been found for other species. Given the striking conservation of repetitive amino acid motifs for each fibroin across divergent species, it seems unlikely that this pattern could result from independent duplication and convergence events. To explain the similarities in the repetitive regions by these means requires the convergence of thousands of nucleotides within a silk gene to encode either entirely MaSp1 or MaSp2 motifs, and for such convergences to have occurred multiple times in different spider lineages. Instead, recombination, selection, or the interaction of these two processes more likely explains the similarity of MaSp1 and MaSp2 N- and C-termini within species. Intergenic pairing during meiosis could be facilitated by the stretches of DNA coding for similar amino acid motifs, such as poly-A and GGX, in both MaSp1 and MaSp2. For example, pairwise comparisons of the *L. hesperus* MaSp1 and MaSp2 genes show that they contain multiple regions of significant similarity spanning at least 100 by (FIG. 6). If recombination occurs between these two genes, it is less frequent than speciation events; MaSp1 of *L. geometricus* and *L. hesperus* were clustered in the N-terminal trees and the C-terminal ML tree. Thus far, no single gene has been described that contains repeat units typical of both genes, which would provide the most convincing evidence for intergenic recombination. There could be strong selection against proteins with a mixture of repeat units, while terminal recombinants may be tolerated. Convergent evolution could alternatively explain the grouping of MaSp1 and MaSp2 paralogs by their N- and C-termini. Selection could drive convergence of terminal amino acid sequences within species if similarity in these regions is necessary for accurate assembly of the two fibroins into a single fiber. Both proteins are exposed to the same environments, such as salt and pH gradients in the silk gland and duct, which could also favor evolutionary convergence of terminal domains.

Non-coding sequences upstream of major ampullate silk genes from different genera were too divergent to reliably align or identify regulatory elements other than the conserved motif CACG and the TATA-box. Although phylogenetic footprinting is a powerful tool for identifying novel regulatory elements, the appropriate level of divergence among species is also important. The genera examined here, *Latrodectus, Nephila*, and *Argiope*, belong to three different families that shared a common ancestor ~135-160 million years ago (MYA).

Figure 5:
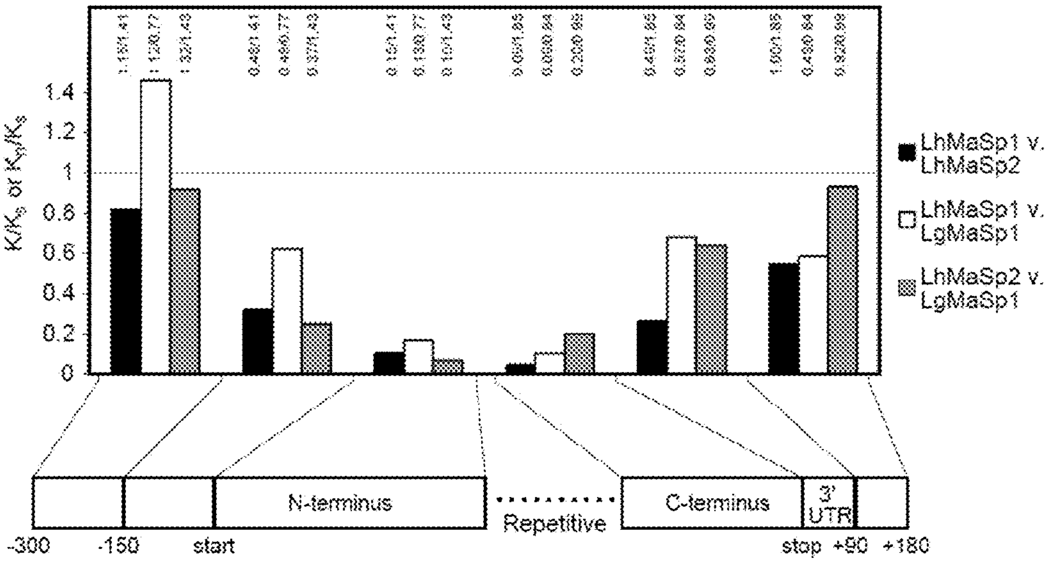
FIG. 5 shows K/Ks or Kn/Ks for flanking and terminal regions of *Latrodectus* major ampullate silk genes. Ks (N-terminus) is the denominator for upstream ratios; Ks (C-terminus) is the denominator for downstream ratios. Actual K values shown above bars. Gene abbreviations are the same as for FIG. 4.

In *Latrodectus,* ~300 by of upstream sequence could be reliably aligned. However, the ~150 by directly upstream of the start codon are more conserved than the adjacent, upstream non-coding sequence or synonymous sites in coding regions of the genes (FIG. 5). A conserved motif in this region that matches the binding site for the Achaete-Scute family of transcription factors, which regulate neurogenesis and sensory mother cell development in *Drosophila* was identified. A homolog of this transcription factor family, called SGSF, shows a silk gland-restricted pattern of expression in *L. hesperus*, specifically to the tubuliform and major ampullate silk glands. These are the only glands that appear to express MaSp1 and MaSp2 in appreciable quantities. Experimental manipulation is needed to elucidate if SGSF or a related protein is, in fact, involved with regulating major ampullate silk gene expression in black widows and other spider species.

The conserved, upstream non-coding regions and the 3' UTRs of *L. hesperus* MaSp1 and *L. hesperus* MaSp2 show evidence for stronger selective constraints than do *L. hesperus* MaSp1 and *Latrodectus geometricus* MaSp1 (lower K/Ks, FIG. 5). Although regulatory element evolution in the 3' UTR has received less attention than in promoter regions, many genes display significantly conserved sequence motifs in the 3' UTR. Additionally, experimental evidence has shown that elements in the 3' UTR bind factors involved in posttranscriptional regulation. A striking example of 3' regulation is in *Drosophila*'s Enhancer of split Complex, which belongs to the same class of genes (beta helix-loop-helix) as achaete and scute. Taken together, these data demonstrate selection on non-coding sequences for co-regulation of the paralogous dragline silk genes, MaSp1 and MaSp2.

The polypeptides of the disclosure can be made by direct synthesis or by expression from cloned polynucleotide of the disclosure. Means for expressing cloned polynucleotides are described herein and are generally known in the art. The following considerations are recommended for the design of expression vectors used to express polynucleotides encoding the spider silk polypeptides of the disclosure.

Because spider silk proteins are highly repetitive in their structure, cloned polynucleotides should be propagated and expressed in host cell strains that can maintain repetitive sequences in extrachromosomal elements. The prevalence of specific amino acids (e.g., alanine, glycine, proline, and glutamine) also suggests that it might be advantageous to use a host cell that overexpresses tRNA for these amino acids.

The proteins of the disclosure can otherwise be expressed using vectors (described more fully elsewhere herein) providing for high level transcription, fusion proteins allowing affinity purification through an epitope tag, and the like. The hosts can be either bacterial or eukaryotic or plant cells. Eukaryotic cells such as yeast, especially *Saccharomyces cerevisisae*, or insect cells might be particularly useful eukaryotic hosts. Expression of an engineered minor ampullate silk protein is described in U.S. Pat. No. 5,756,677, incorporated by reference herein. Such an approach can be used to express proteins of the disclosure.

In one aspect, a MaSp1, MaSp2, MiSp or any combination thereof may be expressed in a plant cell. For example, crop plants can be engineered to express spider silk genes. In one embodiment, standard molecular biology techniques are used to generated transgenes that are transformed into a suitable plant host cell. The transgene constructs can comprise (from 5' to 3') the cauliflower mosaic virus promoter, signal peptide, silk protein-coding region, together with a 6Xhis tag (for detection with His antibody and protein purification) and KDEL signal (to assure retention in the ER) at the carboxy-termini. The chimeric silk protein construct will be inserted into the vector pMDC32. This vector will be used in *Agrobacterium*-mediated transformation of crop plants such as tobacco and tomato.

Alternatively, plastid transformation is an effective mechanism to over-produce recombinant proteins in plants. One advantage of plastid transformation is the fact that plastids are not found in most pollen grains and therefore there is a limited capacity for transgene flow to related weeds or crops. More importantly, a wide array of proteins from animals, plants and microbes have been expressed to high levels in plant chloroplasts with protein levels ranging from 0.6% to 31%. This high level of protein accumulation is attributed to the approximate 10,000 plastid genomes present per plant mesophyll cell. In addition, there are examples where protein accumulation is toxic in the cytosol or vesicles, but was non-toxic when the protein accumulated in the chloroplast. To date, tobacco plastid transformation is almost routine and tomato plastid transformation is now feasible. In one embodiment polynucleotides of the disclosure are introduced into plastids using the pRB94 vector. The coding region will be expressed from the strong Prrn protomer. The chimeric silk transgenes will be introduced into plant leaf segments using particle bombardment. *Solanum lycopersicum* cvMoney maker and *Nicotiana tabacum* Xanthi can be used as parent plants. Spectinomycin-resistant tomato callus transformants can be selected for and serially propagated. For example, while one transgenic chloroplast tomato line is recovered after bombardment of 10 plates, 14 transgenic tobacco homoplasmic lines are recovered. With each transfer to new media, transgenic calli will be screened using genomic DNA digests and DNA blots to detect parental and transgenic genomes. Homoplasmic lines (lines containing only the transgenic genomes) will be further characterized. The accumulation of silk proteins in the homoplasmic lines will be determined by immunoblots blots using His-tag antiserum and/or antibodies specific to peptides or polypeptides in the recombinant protein.

The levels of silk protein achieved in tobacco or tomato chloroplasts may partially be based on the codon usage in plant chloroplasts vs. spiders. There is a good correlation of codon usage in the silk protein RNA and codons utilized in tobacco chloroplasts.

A useful spider silk protein or fragment thereof may be (1) insoluble inside a cell in which it is expressed or (2) capable of being formed into an insoluble fiber under normal conditions by which fibers are made. Typically, the protein is insoluble under conditions (1) and (2). Specifically, the protein or fragment may be insoluble in a solvent such as water, alcohol (methanol, ethanol, etc.), acetone and/or organic acids, etc. The MaSp1 and MaSp2 polypeptides or fragment thereof should be capable of being formed into a fiber having high tensile strength. A fragment or variant may have substantially the same characteristics as a natural spider silk. The natural protein may be particularly insoluble when in fiber form and resistant to degradation by most enzymes.

Recombinant spider silk proteins may be recovered from cultures by lysing cells to release spider silk proteins expressed therein. Initially, cell debris can be separated by centrifugation. Clarified cell lysate comprised of debris and supernatant can then be repeatedly extracted with solvents in which MaSp1, MaSp2 and MiSp polypeptides are insoluble, but cellular debris is soluble. These procedures can be repeated and combined with other procedures including filtration, dialysis and/or chromatography to obtain a pure product.

Fibrillar aggregates will form from solutions by spontaneous self-assembly of spider silk proteins when the protein concentration exceeds a critical value. The aggregates can be gathered and mechanically spun into macroscopic fibers. For example, the spider silk polypeptides can be viewed as derivatized polyamides. Accordingly, methods for producing fiber from soluble spider silk proteins are similar to those used to produce typical polyamide fibers, e.g. nylons, and the like. In one aspect, the MaSp1, MaSp2, MiSp or any combination thereof polypeptides can be solubilized in a strongly polar solvent. The protein concentration of such a protein solution should typically be greater than 5% and is typically between 8 and 20%.

Fibers are spun from solutions having properties characteristic of a liquid crystal phase. The fiber concentration at which phase transition can occur is dependent on the polypeptide composition of a protein or combination of proteins present in the solution. Phase transition, however, can be detected by monitoring the clarity and birefringence of the solution. Onset of a liquid crystal phase can be detected when the solution acquires a translucent appearance and registers birefringence when viewed through crossed polarizing filters.

The solvent used to dissolve an MaSp1, MaSp2, or MiSp polypeptide should be polar. Such solvents are exemplified by di- and tri-haloacetic acids, and haloalcohols (e.g. hexafluoroisopropanol). In some instances, co-solvents such as acetone are useful. Solutions of chaotropic agents, such as lithium thiocyanate, guanidine thiocyanate or urea can also be used.

In one fiber-forming technique, fibers can first be extruded from the protein solution through an orifice into methanol, until a length sufficient to be picked up by a mechanical means is produced. Then a fiber can be pulled by such mechanical means through a methanol solution, collected, and dried.

As mentioned above, the MaSp1, MaSp2 and MiSp polypeptides of the disclosure have primary structures dominated by repeating units. Synthetic spider silks can be generated wherein the primary structure of a synthetic spider silk protein can be described as a number of exact repetitions of a single unit repeat. Such a structure would be similar to a typical block copolymer. The disclosure also encompasses generation of synthetic spider silk proteins comprising unit repeats derived from several different spider silk sequences (naturally occurring variants or genetically engineered variants thereof) as copolymer fibers.

Figure 3:
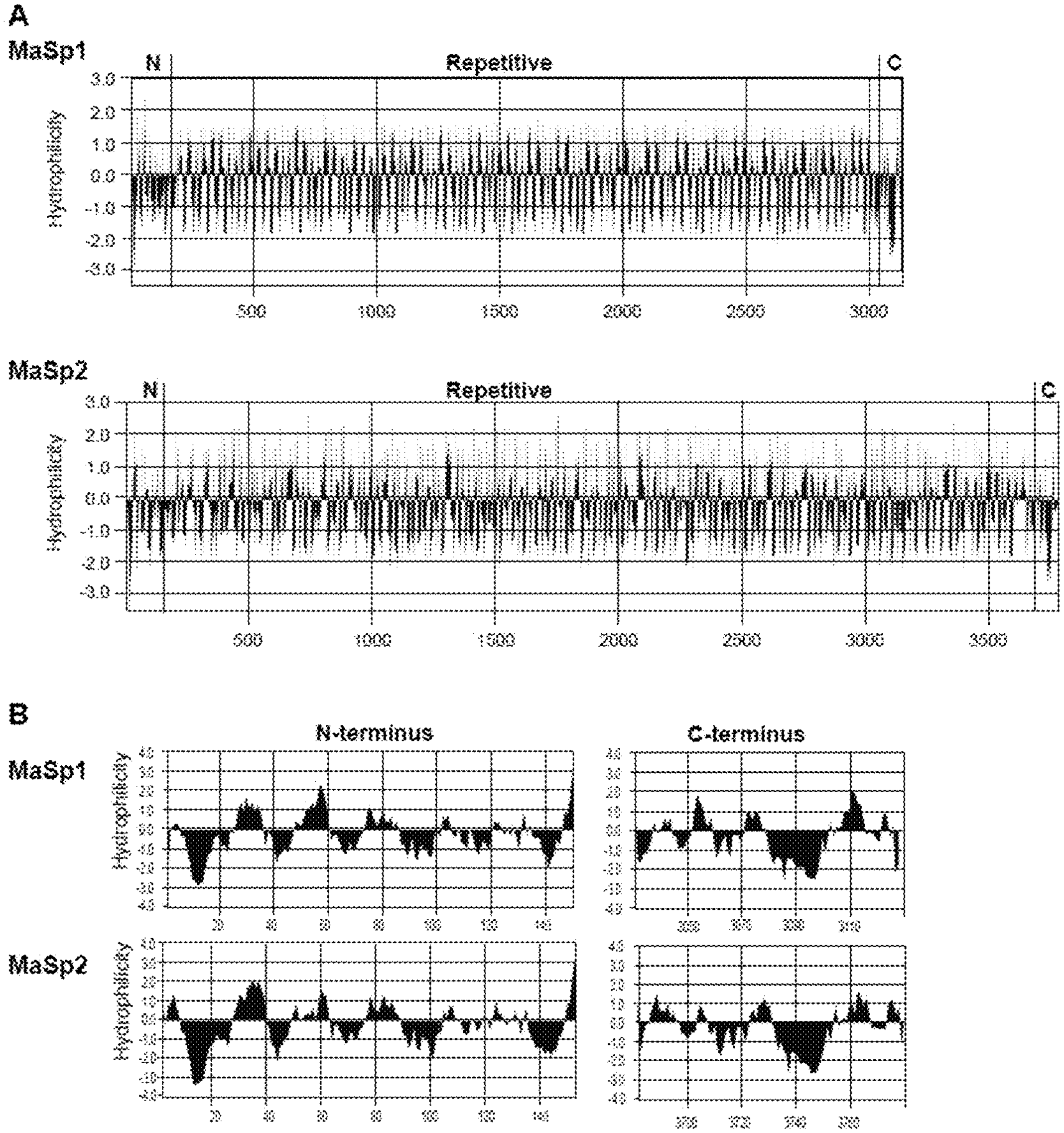
FIG. 3A-B shows a Kyte and Doolittle hydrophilicity plots for *L. hesperus* MaSp1 and MaSp2. Scan window size=7. Negative values indicate hydrophobicity. (A) Complete proteins. (B) Non-repetitive terminal regions.

Experiments on recombinant silks made with and without the C-terminal region showed that the C-terminus was required for fibroins to form aggregates. Protein aggregation is an essential step in the precipitation of liquid spinning dope into a solid silk fiber. The C-terminus is necessary for aggregation of recombinant fibroins, and for the formation of the characteristic crystalline structures that impart strength to dragline silk fibers. As has been proposed for the C-terminus, the evolutionary conservation of the N-terminus suggests that this region is also functionally significant. For example, N-termini may play a central role in the proper transport of fibroins from secretory cells to silk gland lumen, aid in fiber formation, and contribute to the structural properties of silk fibers. In both *L. hesperus* MaSp1 and MaSp2, the N-terminal domain contains the most hydrophobic region of the entire fibroin (FIG. 3). The next most hydrophobic region is the C-terminus. The hydrophobicity of the C-terminus was a key characteristic for its role in fibroin aggregation. The hydrophobic N-terminal region could thus similarly enhance silk fiber formation and mechanical properties. Another evolutionarily conserved aspect of spider fibroins is their extremely large size, which is also a feature of independently evolved insect fibroins. Thus, large size has been repeatedly selected for in the evolution of fibroin genes. Therefore, a complete silk gene, with full representation of the N- and C-terminal regions, the intervening repetitive sequence, and the transitions among these domains, should dramatically improve recombinant silk performance.

In another aspect of the disclosure, a polypeptide may comprise various combinations of fibroin polypeptide domains (e.g., repeat domains of MaSp1 and MaSp2). Accordingly, polypeptides of the disclosure and polynucleotides include those comprising or encoding two or more copies of a domain such Type 1 domain of MaSp1, two or more copies of a domain such as the Type 2 domain of MaSp2, or at least one copy of each domain, and these domains may be presented in any order within such polypeptides. Also included are recombinant polypeptides and the polynucleotides encoding the polypeptides wherein the recombinant polypeptides are "chimeric polypeptides" or "fusion polypeptides" and comprise an MaSp1 or MaSp2 sequence as set forth, for example, in SEQ ID Nos:2, 4, 6, 8, 10, 12, 14, 16, 18, 20, 22, 24, 26, 28, 30, 32, 34, 36, 38, 40, 42, 44, 26, or 48, operatively linked to a second polypeptide. The second polypeptide can be any polypeptide of interest having an activity or function independent of, or related to, the function of an MaSp1, MaSp2, or MiSp polypeptide. For example, the second polypeptide can be a domain of a related but distinct member of the fibroin family of polypeptides. The term "operatively linked" is intended to indicate that the MaSp1, MaSp2 or MiSp sequence and the second polypeptide sequence are fused in-frame to each other. The second polypeptide can be fused to the N-terminus or C-terminus of an MaSp1, MaSp2 or MiSp sequence as set forth in FIGS. 1C and 2. For example, in one embodiment, the fusion polypeptide is a GST-MaSp1 or MaSp2 fusion polypeptide in which the MaSp1 or MaSp2 sequences are fused to the C-terminus of the GST sequences. Such fusion polypeptides can facilitate the purification of recombinant MaSp1 or MaSp2 polypeptides. In another embodiment, the fusion polypeptide comprises an MaSp1 or MaSp2 sequence comprising a heterologous signal sequence at its N-terminus. In certain host cells (e.g., mammalian host cells), expression and/or secretion of an MaSp1 and MaSp2 polypeptide can be increased through use of a heterologous signal sequence. As another example, an MaSp1 and MaSp2 polypeptide or fragment thereof may be fused to a hexa-histidine tag to facilitate purification of bacterially expressed protein, or to a hemagglutinin tag to facilitate purification of protein expressed in eukaryotic cells. Further, fusion polypeptides can comprise, for example, poly-His or the antigenic identification peptides described in U.S. Pat. No. 5,011,912 and in Hopp et al., Bio/Technology 6:1204, 1988. One such peptide is the FLAG® peptide, which is highly antigenic and provides an epitope reversibly bound by a specific monoclonal antibody, enabling rapid assay and facile purification of expressed recombinant polypeptide. A murine hybridoma designated 4E11 produces a monoclonal antibody that binds the FLAG peptide in the presence of certain divalent metal cations, as described in U.S. Pat. No. 5,011,912, hereby incorporated by reference. The 4E11 hybridoma cell line has been deposited with the ATCC under accession no. HB9259. Monoclonal antibodies that bind the FLAG peptide are available from Eastman Kodak Co., Scientific Imaging Systems Division, New Haven, Conn.

Encompassed by the disclosure are oligomers or fusion polypeptides that contain an MaSp1, MaSp2 or MiSp polypeptide or repeat fragment thereof. Oligomers that can be used as fusion partners can be in the form of covalently linked or non-covalently-linked multimers, including dimers, trimers, or higher oligomers. In an alternative embodiment the disclosure is directed to oligomers comprising multiple polypeptides joined via covalent or non-covalent interactions between peptide moieties fused to the polypeptides. Such peptides can be peptide linkers (spacers), or peptides that have the property of promoting oligomerization. Leucine zippers and certain polypeptides derived from antibodies are among the peptides that can promote oligomerization of the polypeptides attached thereto, as described in more detail below.

Typically a linker will be a peptide linker moiety. The length of the linker moiety is chosen to optimize the biological activity of the polypeptide having an MaSp1 and MaSp2 sequence and can be determined empirically without undue experimentation. The linker moiety should be long enough and flexible enough to allow an MaSp1 and MaSp2 moiety to freely interact with a substrate or ligand. The linker moiety is typically a peptide between about one and 30 amino acid residues in length. Linking moieties are described, for example, in Huston, J. S., et al., PNAS 85:5879 (1988), Whitlow, M., et al., Protein Engineering 6:989 (1993), and Newton, D. L., et al., Biochemistry 35:545 (1996). Other suitable peptide linkers are those described in U.S. Pat. Nos. 4,751,180 and 4,935,233, which are hereby incorporated by reference. A DNA sequence encoding a desired peptide linker can be inserted between, and in the same reading frame as, DNA sequences of the disclosure, using any suitable conventional technique. For example, a chemically synthesized oligonucleotide encoding the linker can be ligated between the sequences. In particular embodiments, a fusion polypeptide comprises from two to four or more MaSp1, MaSp2, MiSp or chimeric polypeptides, separated by peptide linkers.

The MaSp1, MaSp2 or MiSp polypeptides of the disclosure can also include a localization sequence to direct the polypeptide to particular cellular sites by fusion to appropriate organellar targeting signals or localized host proteins. A polynucleotide encoding a localization sequence, or signal sequence, can be ligated or fused at the 5' terminus of a polynucleotide encoding an MaSp1, MaSp2 or MiSp polypeptide such that the signal peptide is located at the amino terminal end of the resulting fusion polynucleotide/polypeptide. In eukaryotes, the signal peptide functions to transport a polypeptide across the endoplasmic reticulum. The secretory protein is then transported through the Golgi apparatus, into secretory vesicles and into the extracellular space or the external environment. Signal peptides include pre-pro peptides that contain a proteolytic enzyme recognition site.

The localization sequence can be a nuclear-, an endoplasmic reticulum-, a peroxisome-, or a mitochondrial-localization sequence, or a localized protein. Localization sequences can be targeting sequences that are described, for example, in "Protein Targeting", chapter 35 of Stryer, L., Biochemistry (4th ed.). W.H. Freeman, 1995. Some important localization sequences include those targeting the nucleus, mitochondria, endoplasmic reticulum, peroxisome (SKF), plasma membrane, CC, CXC and the like, cytoplasmic side of plasma membrane (fusion to SNAP-25), or the Golgi apparatus (fusion to furin).

A chimeric or fusion polypeptide of the disclosure can be produced by standard recombinant molecular biology techniques. In one embodiment, polynucleotide fragments coding for the different polypeptide sequences are ligated together in-frame in accordance with conventional techniques, for example, by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. Examples of polynucleotides encoding all or portions of the MaSp1, MaSp2 and MiSp polypeptides are set for in SEQ ID NOs:1, 3, 5, 7, 9, 1, 13, 15, 17, 19, 21, 23, 25, 27, 29, 31, 33, 35, 37, 39, 41, 43, 45, 47 and 49. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g., a GST polypeptide).

The disclosure further includes polypeptides with or without associated native-pattern glycosylation. Polypeptides expressed in yeast or mammalian expression systems (e.g., COS-1 or CHO cells) can be similar to or significantly different from a native polypeptide in molecular weight and glycosylation pattern, depending upon the choice of expression system. Expression of polypeptides of the disclosure in bacterial expression systems, such as *E. coli*, provides non-glycosylated molecules. Further, a given preparation can include multiple differentially glycosylated species of the polypeptide. Glycosyl groups can be removed through conventional methods, in particular those utilizing glycopeptidase.

Additional variants within the scope of the disclosure include polypeptides that can be modified to create derivatives thereof by forming covalent or aggregative conjugates with other chemical moieties, such as glycosyl groups, lipids, phosphate, acetyl groups and the like. Covalent derivatives can be prepared by linking the chemical moieties to functional groups on amino acid side chains or at the N-terminus or C-terminus of a polypeptide. Conjugates comprising diagnostic (detectable) or therapeutic agents attached thereto are contemplated herein. Preferably, such alteration, substitution, replacement, insertion or deletion retains the desired activity of the polypeptide.

The disclosure also provides polynucleotides encoding MaSp1, MaSp2 and MiSp polypeptides. The term "polynucleotide" refers to a polymeric form of nucleotides of at least 10 bases in length. The nucleotides can be ribonucleotides, deoxyribonucleotides, or modified forms of either type of nucleotide. The term includes single and double stranded forms of DNA or RNA. DNA includes, for example, cDNA, genomic DNA, chemically synthesized DNA, DNA amplified by PCR, and combinations thereof. The polynucleotides of the disclosure include full-length genes and cDNA molecules as well as a combination of fragments thereof. The polynucleotides of the disclosure are preferentially derived from human sources, but the disclosure includes those derived from non-human species, as well.

A polynucleotide of the disclosure will generally contain phosphodiester bonds, although in some cases, nucleic acid analogs are included that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g. to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

A variety of references disclose such nucleic acid analogs, including, for example, phosphoramidate (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within one definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference.

Other analogs include peptide nucleic acids (PNA) which are peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature ($T_m$) for mismatched versus perfectly matched basepairs. DNA and RNA typically exhibit a 2-4° C. drop in $T_m$ for an internal mismatch. With the non-ionic PNA backbone, the drop is closer to 7-9° C. Similarly, due to their non-ionic nature, hybridization of the bases attached to these backbones is relatively insensitive to salt concentration. In addition, PNAs are not degraded by cellular enzymes, and thus can be more stable.

As described above, the nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc. "Transcript" typically refers to a naturally occurring RNA, e.g., a pre-mRNA, hnRNA, or mRNA. As used herein, the term "nucleoside" includes nucleotides and nucleoside and nucleotide analogs, and modified nucleosides such as amino modified nucleosides. In addition, "nucleoside" includes non-naturally occurring analog structures. Thus, e.g. the individual units of a peptide nucleic acid, each containing a base, are referred to herein as a nucleoside.

By “isolated polynucleotide” is meant a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant polynucleotide molecule, which is incorporated into a vector, e.g., an expression vector; into an autonomously replicating plasmid or virus; or into the genomic DNA of a prokaryote or eukaryote, or which exists as a separate molecule (e.g., a cDNA) independent of other sequences.

An MaSp1 and MaSp2 polynucleotide of the disclosure (1) encodes a polypeptide comprising a sequence as set forth in SEQ ID Nos:2, 4, 6, 8, 10, 12, 14, 16, 18, 20, 22, 24, 26, 28, 30, 32, 34, 36, 38, 40, 42, 44, 46, or 48; (2) has a sequence as set forth in SEQ ID Nos:1, 3, 5, 7, 9, 11, 13, 15, 17, 19, 21, 23, 25, 27, 29, 31, 33, 35, 37, 39, 41, 43, 45, or 47; (3) has sequences complementary to a sequence as set forth in SEQ ID Nos: 1, 3, 5, 7, 9, 11, 13, 15, 17, 19, 21, 23, 25, 27, 29, 31, 33, 35, 37, 39, 41, 43, 45, or 47; (4) fragments of SEQ ID Nos: 1, 3, 5, 7, 9, 11, 13, 15, 17, 19, 21, 23, 25, 27, 29, 31, 33, 35, 37, 39, 41, 43, 45, or 47 or their complements that specifically hybridize to the polynucleotide of (2) or (3) under moderate to highly stringent conditions; and (5) polynucleotides of (1), (2), (3), or (4) wherein T can also be U (e.g., RNA sequences). The polynucleotides of (1), (2), (3), (4) or (5) encode polypeptides that have fibrous strength characteristic similar to a widow spider’s silk or an ensemble repeat found in a widow spider’s silk. Also encompassed by the disclosure are homologs of an MaSp1 and MaSp2 polynucleotide of the disclosure. These polynucleotides can be identified in several ways, including isolation of genomic or cDNA molecules from a suitable source, or computer searches of available sequence databases. Oligonucleotides or polynucleotides corresponding to the amino acid sequences described herein can be used as probes or primers for the isolation of polynucleotide homologs or as query sequences for database searches. Degenerate oligonucleotide sequences can be obtained by “back-translation” from the amino acid sequences of the disclosure. The polymerase chain reaction (PCR) procedure can be employed to isolate and amplify a DNA sequence encoding an fibroin polypeptide or a desired combination of fibroin polypeptide fragments. Oligonucleotides that define the desired termini of a target DNA molecule are employed as 5' and 3' primers. Accordingly, fragments of the polynucleotides of the disclosure are useful as probes and primers to identify or amplify related sequence or obtain full-length sequences of an MaSp1 and MaSp2 of the disclosure. The oligonucleotides can additionally contain recognition sites for restriction endonucleases, to facilitate insertion of the amplified combination of DNA fragments into an expression vector. PCR techniques are known in the art (see, e.g., PCR Protocols: A Guide to Methods and Applications, Innis et. al., eds., Academic Press, Inc. (1990)).

An MiSp polynucleotide of the disclosure (1) encodes a polypeptide comprising a sequence as set forth in SEQ ID NO:50; (2) has a sequence as set forth in SEQ ID NO:49; (3) has sequences complementary to a sequence as set forth in SEQ ID NO:49; (4) fragments of SEQ ID NO:49 or their complements that specifically hybridize to the polynucleotide of (2) or (3) under moderate to highly stringent conditions; and (5) polynucleotides of (1), (2), (3), or (4) wherein T can also be U (e.g., RNA sequences). The polynucleotides of (1), (2), (3), (4) or (5) encode polypeptides that have fibrous strength characteristic similar to a widow spider’s silk or an ensemble repeat found in a widow spider’s silk. Also encompassed by the disclosure are homologs of an MaSp1 and MaSp2 polynucleotide of the disclosure. These polynucleotides can be identified in several ways, including isolation of genomic or cDNA molecules from a suitable source, or computer searches of available sequence databases. Oligonucleotides or polynucleotides corresponding to the amino acid sequences described herein can be used as probes or primers for the isolation of polynucleotide homologs or as query sequences for database searches. Degenerate oligonucleotide sequences can be obtained by “back-translation” from the amino acid sequences of the disclosure. The polymerase chain reaction (PCR) procedure can be employed to isolate and amplify a DNA sequence encoding an fibroin polypeptide or a desired combination of fibroin polypeptide fragments. Oligonucleotides that define the desired termini of a target DNA molecule are employed as 5' and 3' primers. Accordingly, fragments of the polynucleotides of the disclosure are useful as probes and primers to identify or amplify related sequence or obtain full-length sequences of an MaSp1 and MaSp2 of the disclosure. The oligonucleotides can additionally contain recognition sites for restriction endonucleases, to facilitate insertion of the amplified combination of DNA fragments into an expression vector. PCR techniques are known in the art (see, e.g., PCR Protocols: A Guide to Methods and Applications, Innis et. al., eds., Academic Press, Inc. (1990)).

Among the uses of the disclosed MaSp1, MaSp2 and MiSp polynucleotides, and combinations of fragments thereof, is the use of fragments as probes or primers. Such fragments generally comprise at least about 17 contiguous nucleotides of a DNA sequence. In other embodiments, a DNA fragment comprises at least 30, or at least 60 contiguous nucleotides of a DNA sequence. The basic parameters affecting the choice of hybridization conditions and guidance for devising suitable conditions are set forth by Sambrook et al., 1989 and are described in detail above. Using knowledge of the genetic code in combination with the amino acid sequences set forth above, sets of degenerate oligonucleotides can be prepared. Such oligonucleotides are useful as primers, e.g., in polymerase chain reactions (PCR), whereby DNA fragments are isolated and amplified. In certain embodiments, degenerate primers can be used as probes for non-human genetic libraries. Such libraries would include but are not limited to cDNA libraries, genomic libraries, and even electronic EST (express sequence tag) or DNA libraries. Homologous sequences identified by this method would then be used as probes to identify non-human homologues of the MaSp1, MaSp2 or MiSp sequence identified herein.

The disclosure also includes polynucleotides and oligonucleotides that hybridize under reduced stringency conditions, typically moderately stringent conditions, and commonly highly stringent conditions, to MaSp1, MaSp2, or MiSp polynucleotides described herein. The basic parameters affecting the choice of hybridization conditions and guidance for devising suitable conditions are set forth by Sambrook, J., E. F. Fritsch, and T. Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, F. M. Ausubel et al., eds., John Wiley & Sons, Inc., sections 2.10 and 6.3-6.4, incorporated herein by reference), and can be readily determined by those having ordinary skill in the art based on, for example, the length and/or base composition of the polynucleotide. One way of achieving moderately stringent conditions involves the use of a prewashing solution containing 5×SSC, 0.5% SDS, 1.0 mM EDTA (pH 8.0), hybridization buffer of about 50% formamide, 6×SSC, and a hybridization temperature of about 55° C. (or other similar hybridization solutions, such as one containing about 50% formamide, with a hybridization temperature of about 42° C.), and washing conditions of about 60° C., in 0.5×SSC, 0.1% SDS. Generally, highly stringent conditions are defined as hybridization conditions as above, but with washing at approximately 68° C., 0.2×SSC, 0.1% SDS, SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes after hybridization is complete. It should be understood that the wash temperature and wash salt concentration can be adjusted as necessary to achieve a desired degree of stringency by applying the basic principles that govern hybridization reactions and duplex stability, as known to those skilled in the art and described further below (see, e.g., Sambrook et al., 1989). When hybridizing a nucleic acid to a target polynucleotide of unknown sequence, the hybrid length is assumed to be that of the hybridizing nucleic acid. When nucleic acids of known sequence are hybridized, the hybrid length can be determined by aligning the sequences of the nucleic acids and identifying the region or regions of optimal sequence complementarity. The hybridization temperature for hybrids anticipated to be less than 50 base pairs in length should be 5 to 10° C. less than the melting temperature ($T_m$) of the hybrid, where $T_m$ is determined according to the following equations. For hybrids less than 18 base pairs in length, $T_m$ (° C.)=2(# of A+T bases)+4(# of G+C bases). For hybrids above 18 base pairs in length, $T_m$ (° C.)=81.5+16.6($\log_{10}$ [$Na^+$])+0.41(% G+C)−(600/N), where N is the number of bases in the hybrid, and [$Na^+$] is the concentration of sodium ions in the hybridization buffer ([$Na^{+]}$ for 1×SSC=0.165M). Preferably, each such hybridizing nucleic acid has a length that is at least 25% (more preferably at least 50%, 60%, or 70%, and most preferably at least 80%) of the length of a polynucleotide of the disclosure to which it hybridizes, and has at least 60% sequence identity (more preferably at least 70%, 75%, 80%, 85%, 90%, 95%, 97.5%, or at least 99%, and most preferably at least 99.5%) with a polynucleotide of the disclosure to which it hybridizes.

"Conservatively modified variants" applies to both polypeptide and polynucleotide. With respect to particular polynucleotide, conservatively modified variants refer to codons in the polynucleotide which encode identical or essentially identical amino acids. Because of the degeneracy of the genetic code, a large number of functionally identical polynucleotides encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such variations are "silent variations," which are one species of conservatively modified variations. Every polynucleotide sequence herein that encodes a polypeptide also describes every possible silent variation of the nucleic acid. One of skill will recognize that each codon in a polynucleotide (except AUG, which is ordinarily the only codon for methionine) can be modified to yield a functionally identical molecule. Accordingly, each silent variation of a nucleic acid that encodes a polypeptide is implicit in each described sequence.

The disclosure also provides methodology for analysis of polynucleotides of the disclosure on "DNA chips" as described in Hacia et al., Nature Genetics, 14:441-447 (1996). For example, high-density arrays of oligonucleotides consisting of a sequence as set forth in SEQ ID Nos:1, 3, 5, 7, 9, 11, 13, 15, 17, 19, 21, 23, 25, 27, 29, 31, 33, 35, 37, 39, 41, 43, 45, 47, 49, or a variant or mutant thereof are applied and immobilized to the chip and can be used to detect sequence variations in a population. Polynucleotides in a test sample are hybridized to the immobilized oligonucleotides. The hybridization profile of the target polynucleotide to the immobilized probe is quantitated and compared to a reference profile. The resulting genetic information can be used in molecular identification. The density of oligonucleotides on DNA chips can be modified as needed.

The disclosure also provides genes corresponding to the polynucleotides disclosed herein. "Corresponding genes" are the regions of the genome that are transcribed to produce the mRNAs from which cDNA molecules are derived and may include contiguous regions of the genome necessary for the regulated expression of such genes. Corresponding genes may therefore include but are not limited to coding sequences, 5' and 3' untranslated regions, alternatively spliced exons, introns, promoters, enhancers, and silencer or suppressor elements. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials.

The complete polynucleotides and polynucleotide sequences described here highlight the extraordinary molecular characteristics of spider silks. Black widow major ampullate silk genes are highly modular, exhibiting a hierarchical organization of iterated short motifs and ensemble repeats (groups of motifs). By characterizing full-length MaSp1, MaSp2 and MiSp genes, the disclosure identifies higher-level repeats (aggregates of ensemble repeats) and uncover a striking difference in the degree of repeat homogenization between MaSp1 and MaSp2. The extreme modularity of MaSp1 (FIG. 1) may reflect selection on the MaSp1 fibroin for perfect repeats, perhaps important for rapid and consistent spinning of high quality silk fibers. Sequence homogenization, however, is also due to molecular mechanisms, such as unequal crossing over (e.g., two large tandem repeats in FIG. 2). The disclosure also provides putative regulatory elements that may enhance expression of transgenic silks. Accordingly, the disclosure also provides non-coding regions of MaSp1, MaSp2 and MiSp that are useful in expression of transgenic silks. Thus, the clones sequenced here provide the complete genetic blueprints for the primary protein components of the major ampullate silk fiber. These designs hold critical information for the mass production of artificial fibers that accurately mimic the spectacular high-performance properties of native spider silk.

Expression, isolation, and purification of the polypeptides and fragments of the disclosure can be accomplished by any suitable technique, including but not limited to the following methods and those described elsewhere herein.

The isolated polynucleotides of the disclosure may be operably linked to an expression control sequence such as the pMT2 or pED expression vectors disclosed in Kaufman et al., Nucleic Acids Res. 19:4485 (1991); and Pouwels et al. Cloning Vectors: A Laboratory Manual, Elsevier, N.Y., (1985, and Supplements), in order to produce a polypeptide of the disclosure recombinantly. Many suitable expression control sequences are known in the art. General methods of expressing recombinant polypeptides are also known and are exemplified in R. Kaufman, Methods in Enzymology 185:537 (1990). As defined herein "operably linked" means that an isolated polynucleotide of the disclosure and an expression control sequence are situated within a vector or cell in such a way that the polypeptide encoded by the polynucleotide is expressed by a host cell which has been transformed (transfected) with the vector or polynucleotide operably linked to the control sequence.

For example, expression of the spider dragline protein can be performed in *E. coli* by inserting the polynucleotide encoding MaSp1 and/or MaSp2 into plasmid vectors pFP202 and pFP204, which can be derived from the well-known vector pET11a. In these vectors, the dragline protein-coding gene is inserted in such a manner as to be operably linked to a promoter derived from bacteriophage T7. This promoter is joined with sequences derived from the lac operator of *E. coli*, which confers regulation by lactose or analogs (IPTG). The *E. coli* host strain BL21(DE3) contains a lambda prophage which carries a gene encoding bacteriophage T7 RNA polymerase. This gene is controlled by a promoter which is also regulated by lactose or analogs. In addition to the phage T7 promoter, the vectors pFP202 and pFP204 provide sequences which encode a C-terminal tail containing six consecutive histidine residues appended to the dragline protein-coding sequences. This tail provides a means of affinity purification of the protein under denaturing conditions through its adsorption to resins bearing immobilized Ni ions.

In addition, a sequence encoding an appropriate signal peptide (native or heterologous) can be incorporated into expression vectors. The choice of signal peptide or leader can depend on factors such as the type of host cells in which the recombinant polypeptide is to be produced. Examples of heterologous signal peptides that are functional in mammalian host cells include the signal sequence for interleukin (IL)-7 (see, U.S. Pat. No. 4,965,195); the signal sequence for IL-2 receptor (see, Cosman et al., Nature 312:768, 1984); the IL4 receptor signal peptide (see, EP 367,566); the type I IL-1 receptor signal peptide (see, U.S. Pat. No. 4,968,607); and the type II IL-1 receptor signal peptide (see, EP 460,846). A signal peptide that is functional in the intended host cells promotes extracellular secretion of the polypeptide. The signal peptide is cleaved from the polypeptide upon secretion of a polypeptide from the cell. A polypeptide preparation can include a mixture of polypeptide molecules having different N-terminal amino acids, resulting from cleavage of the signal peptide at more than one site.

Established methods for introducing DNA into mammalian cells have been described (Kaufman, R. J., Large Scale Mammalian Cell Culture, 1990, pp. 15-69). Additional protocols using commercially available reagents, such as Lipofectamine or Lipofectamine-Plus lipid reagent (Gibco/BRL), can be used to transfect cells (Felgner et al., Proc. Natl. Acad. Sci. USA 84:7413, 1987). In addition, electroporation can be used to transfect mammalian cells using conventional procedures, such as those in Sambrook et al. (Molecular Cloning: A Laboratory Manual, 2 ed. Vol. 1-3, Cold Spring Harbor Laboratory Press, 1989). Selection of stable transformants can be performed using methods known in the art, such as, for example, resistance to cytotoxic drugs. Kaufman et al., Meth. in Enzymology 185:487, 1990, describes several selection schemes, such as dihydrofolate reductase (DHFR) resistance. A suitable strain for DHFR selection can be CHO strain DX-B11, which is deficient in DHFR (Urlaub et al., Proc. Natl. Acad. Sci. USA 77:4216, 1980). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector are selected on the basis of resistance to these compounds.

Alternatively, gene products can be obtained via homologous recombination, or "gene targeting" techniques. Such techniques employ the introduction of exogenous transcription control elements (such as the CMV promoter or the like) in a particular predetermined site on the genome, to induce expression of an endogenous MaSp1 and MaSp2 of the disclosure. The location of integration into a host chromosome or genome can be easily determined by one of skill in the art, given the known location and sequence of the gene. In a preferred embodiment, the disclosure also contemplates the introduction of exogenous transcriptional control elements in conjunction with an amplifiable gene, to produce increased amounts of the gene product. The practice of homologous recombination or gene targeting is explained by Chappel in U.S. Pat. No. 5,272,071 (see also Schimke, et al. "Amplification of Genes in Somatic Mammalian cells," Methods in Enzymology 151:85 (1987), and by Capecchi, et al., "The New Mouse Genetics: Altering the Genome by Gene Targeting," TIG 5:70 (1989)).

Suitable host cells for expression of the polypeptide include eukaryotic, insect, plant and prokaryotic cells. Mammalian host cells include, for example, the COS-7 line of monkey kidney cells (ATCC CRL 1651) (Gluzman et al., Cell 23:175, 1981), L cells, C127 cells, 3T3 cells (ATCC CCL 163), Chinese hamster ovary (CHO) cells, HeLa cells, BHK (ATCC CRL 10) cell lines, the CV1/EBNA cell line derived from the African green monkey kidney cell line CV1 (ATCC CCL 70) (see, McMahan et al. EMBO J. 10: 2821, 1991), human kidney 293 cells, human epidermal A431 cells, human Colo205 cells, other transformed primate cell lines, normal diploid cells, cell strains derived from in vitro culture of primary tissue, primary explants, HL-60, U937, HaK or Jurkat cells. Alternatively, it may be possible to produce the polypeptide in lower eukaryotes such as yeast or in prokaryotes such as bacteria. Potentially suitable yeast strains include *Saccharomyces cerevisiae, Schizosaccharomyces pombe, Kluyveromyces* strains, *Candida*, or any yeast strain capable of expressing heterologous polypeptides. Potentially suitable bacterial strains include, for example, *Escherichia coli, Bacillus subtilis, Salmonella typhimurium*, or any bacterial strain capable of expressing heterologous polypeptides. If the polypeptide is made in yeast or bacteria, it may be necessary to modify the polypeptide produced therein, for example by phosphorylation or glycosylation of the appropriate sites, in order to obtain the functional polypeptide. Such covalent attachments may be accomplished using known chemical or enzymatic methods. The polypeptide may also be produced by operably linking a polynucleotide of the disclosure to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), as well as methods described in Summers and Smith, Texas Agricultural Experiment Station Bulletin No. 1555 (1987), and Luckow and Summers, Bio/Technology 6:47 (1988), incorporated herein by reference. Cell-free translation systems could also be employed to produce polypeptides using RNAs derived from nucleic acid constructs disclosed herein. A host cell that comprises an isolated polynucleotide of the disclosure, preferably operably linked to at least one expression control sequence, is a "recombinant host cell".

In one embodiment, antagonists can be designed to reduce the level of endogenous MaSp1, MaSp2 and MiSp expression, e.g., using known antisense or ribozyme approaches to inhibit or prevent translation of MaSp1, MaSp2, or MiSp mRNA transcripts; triple helix approaches to inhibit transcription of MaSp1 and MaSp2 genes; or targeted homologous recombination to inactivate or "knock out" the MaSp1 and MaSp2 genes or their endogenous promoters or enhancer elements. Such antisense, ribozyme, and triple helix antagonists may be designed to reduce or inhibit either unimpaired or, if appropriate, mutant MaSp1 and MaSp2 activity. Such antagonists can be used as anti-insecticidals.

Antisense RNA and DNA molecules act to directly block the translation of mRNA by hybridizing to targeted mRNA and preventing polypeptide translation. Antisense approaches involve the design of oligonucleotides (either DNA or RNA) that are complementary to a mRNA having an MaSp1 and MaSp2 polynucleotide sequence. Absolute complementarity, although preferred, is not required. Oligonucleotides that are complementary to the 5' end of the message, e.g., the 5' untranslated sequence up to, and including, the AUG initiation codon, should work most efficiently at inhibiting translation. Antisense nucleic acids are preferably oligonucleotides ranging from 6 to about 50 nucleotides in length. The oligonucleotides can be DNA, RNA, chimeric mixtures, derivatives or modified versions thereof, single-stranded or double-stranded. The oligonucleotide can be modified at the base moiety, sugar moiety, or phosphate backbone, for example, to improve stability of the molecule, hybridization, and the like. The oligonucleotide may include other appended groups such as peptides (e.g., for targeting host cell receptors in vivo), or agents facilitating transport across the cell membrane (see, e.g., Letsinger et al., Proc. Natl. Acad. Sci. U.S.A. 86:6553, 1989; Lemaitre et al., Proc. Natl. Acad. Sci. 84:648, 1987; PCT Publication No. WO88/09810), or hybridization-triggered cleavage agents or intercalating agents (see, e.g., Zon, Pharm. Res. 5:539, 1988). The antisense molecules are delivered to cells, which express a transcript having an MaSp1 and MaSp2 polynucleotide sequence in vivo by, for example, direct injection into the tissue or cell derivation site, or modified antisense molecules, designed to target the desired cells (e.g., antisense linked to peptides or antibodies that specifically bind receptors or antigens expressed on the target cell surface) can be administered systemically. Preferred approach utilizes a recombinant DNA construct in which the antisense oligonucleotide is placed under the control of a strong pol III or pol II promoter.

Ribozyme molecules designed to catalytically cleave mRNA transcripts having an MaSp1, MaSp2 or MiSp polynucleotide sequence prevent translation of MaSp1, MaSp2, or MiSp mRNA (see, e.g., PCT International Publication WO90/11364; U.S. Pat. No. 5,824,519). Ribozymes are RNA molecules possessing the ability to specifically cleave other single-stranded RNA. Because ribozymes are sequence-specific, only mRNAs with particular sequences are inactivated. There are two basic types of ribozymes namely, tetrahymena-type (Hasselhoff, Nature, 334:585, 1988) and "hammerhead"-type. Tetrahymena-type ribozymes recognize sequences, which are four bases in length, while "hammerhead"-type ribozymes recognize base sequences 11-18 bases in length. The longer the recognition sequence, the greater the likelihood that the sequence will occur exclusively in the target mRNA species. Consequently, hammerhead-type ribozymes are preferable to tetrahymena-type ribozymes. As in the antisense approach, ribozymes can be composed of modified oligonucleotides and delivered using a DNA construct "encoding" the ribozyme under the control of a strong constitutive pol III or pol II promoter.

Alternatively, endogenous MaSp1, MaSp2 or MiSp expression can be reduced by targeting DNA sequences complementary to a regulatory region of the target gene (e.g., the target gene promoter and/or enhancers) to form triple helical structures that prevent transcription of the target gene (see generally, Helene, Anticancer Drug Des., 6(6), 569, 1991; Helene, et al., Ann. N.Y. Acad. Sci., 660:27, 1992; and Maher, Bioassays 14(12), 807, 1992).

Antisense, ribozyme, and triple helix molecules of the disclosure may be prepared by any method known in the art for the synthesis of DNA and RNA molecules and include techniques for chemically synthesizing oligodeoxyribonucleotides and oligoribonucleotides such as, for example, solid phase phosphoramidite chemical synthesis using an automated DNA synthesizer available from Biosearch, Applied Biosystems. Phosphorothioate oligonucleotides may be synthesized by the method of Stein et al., Nucl. Acids Res. 16:3209, 1988. Methylphosphonate oligonucleotides can be prepared by use of controlled pore glass polymer supports (Sarin et al., Proc. Natl. Acad. Sci. U.S.A. 85:7448, 1988). Alternatively, RNA molecules may be generated by in vitro and in vivo transcription of DNA sequences encoding the antisense RNA molecule.

As used herein, a "transgenic organism" is a non-human organism that includes a transgene that is inserted into an embryonal cell and becomes a part of the genome of the organism that develops from that cell, or an offspring of such an organisms. Any non-human organism that can be produced by transgenic technology is included in the disclosure. Typical organisms can include non-human animals, silk worms and other insects, and plant cells into which an MaSp1, MaSp2, and/or MiSp transgene has been inserted.

A "transgene" is a polynucleotide that comprises one or more selected sequences (e.g., encoding an MaSp1, MaSp2, and/or MiSp, encoding ribozymes that cleave MaSp1, MaSp2, or MiSp mRNA, encoding an antisense molecule to an MaSp1, MaSp2 or MiSp mRNA, encoding a mutant MaSp1, MaSp2 or MiSp sequence, and the like) to be expressed in a transgenic organism. The polynucleotide is partly or entirely heterologous, i.e., foreign, to the transgenic animal, plant or insect, or homologous to an endogenous gene of the transgenic animal, plant or insect, but which is designed to be inserted into the genome at a location which differs from that of the natural gene. A transgene may include one or more promoters and any other DNA sequences, such as introns, necessary for expression of the selected DNA, all operably linked to the selected DNA, and may include an enhancer sequence.

The transgenic organism can be used for the production of spider silk dragline comprising an MaSp1, MaSp2 and/or MiSp polypeptide or fragment thereof. For example, a transgenic organism can be used for large scale production of silk materials using the polynucleotides of the disclosure. Such silk materials can be harvested and used for the generation of textiles, biomaterials and the like. In another aspect, the transgenic organism can be used in order to identify the impact of increased or decreased MaSp1, MaSp2 or MiSp levels on a particular pathway or phenotype. Protocols useful in producing such transgenic animals are known in the art (see, e.g., Brinster, et al., Proc. Natl. Acad. Sci. USA 82:4438, 1985; Jaenisch, Proc. Natl. Acad. Sci. USA 73:1260, 1976; Hogan, et al., 1986, Manipulating the Mouse Embryo, Cold Spring Harbor Laboratory Press, Cold Spring Harbor, N.Y.; Jahner, et al., Proc. Natl. Acad. Sci. USA 82:6927, 1985; Van der Putten, et al., Proc Natl. Acad. Sci. USA 82:6148; Steward, et al., EMBO J., 6:383, 1987; Jahner, et al., Nature, 298:623, 1982).

In another embodiment, antibodies that are immunoreactive with the polypeptides of the disclosure are provided herein. The MaSp1, MaSp2, or MiSp polypeptides, fragments, variants, fusion polypeptides, and the like, as set forth above, can be employed as "immunogens" in producing antibodies immunoreactive therewith. Such antibodies specifically bind to the polypeptides via the antigen-binding sites of the antibody. Specifically binding antibodies are those that will specifically recognize and bind with MaSp1, MaSp2 or MiSp family polypeptides, homologues, and variants, but not with other molecules. In one embodiment, the antibodies are specific for polypeptides having an MaSp1, MaSp2, or MiSp amino acid sequence of the disclosure and do not cross-react with other polypeptides.

More specifically, the polypeptides, fragment, variants, fusion polypeptides, and the like contain antigenic determinants or epitopes that elicit the formation of antibodies. These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon polypeptide folding. Epitopes can be identified by any of the methods known in the art. Additionally, epitopes from the polypeptides of the disclosure can be used as research reagents, in assays, and to purify specific binding antibodies from substances such as polyclonal sera or supernatants from cultured hybridomas. Such epitopes or variants thereof can be produced using techniques known in the art such as solid-phase synthesis, chemical or enzymatic cleavage of a polypeptide, or using recombinant DNA technology.

Both polyclonal and monoclonal antibodies to the polypeptides of the disclosure can be prepared by conventional techniques. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988); Kohler and Milstein, (U.S. Pat. No. 4,376,110); the human B-cell hybridoma technique (Kosbor et al., Immunology Today 4:72, 1983; Cole et al., Proc. Natl. Acad. Sci. USA 80:2026, 1983); and the EBV-hybridoma technique (Cole et al., 1985, Monoclonal Antibodies And Cancer Therapy, Alan R. Liss, Inc., pp. 77-96). Hybridoma cell lines that produce monoclonal antibodies specific for the polypeptides of the disclosure are also contemplated herein. Such hybridomas can be produced and identified by conventional techniques. For the production of antibodies, various host animals may be immunized by injection with an MaSp1 and MaSp2 polypeptide, fragment, variant, or mutants thereof. Such host animals may include, but are not limited to, rabbits, mice, and rats, to name a few. Various adjutants may be used to increase the immunological response. Depending on the host species, such adjutants include, but are not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjutants such as BCG (bacille Calmette-Guerin) and *Corynebacterium parvum*. The monoclonal antibodies can be recovered by conventional techniques. Such monoclonal antibodies may be of any immunoglobulin class including IgG, IgM, IgE, IgA, IgD, and any subclass thereof.

Antibody fragments, which recognize specific epitopes, may be generated by known techniques. For example, such fragments include but are not limited to: the $F(ab')_2$ fragments which can be produced by pepsin digestion of the antibody molecule and the Fab fragments which can be generated by reducing the disulfide bridges of the $(ab')_2$ fragments. Alternatively, Fab expression libraries may be constructed (Huse et al., Science, 246:1275, 1989) to allow rapid and easy identification of monoclonal Fab fragments with the desired specificity. Techniques described for the production of single chain antibodies (U.S. Pat. No. 4,946,778; Bird, Science 242:423, 1988; Huston et al., Proc. Natl. Acad. Sci. USA 85:5879, 1988; and Ward et al., Nature 334:544, 1989) can also be adapted to produce single chain antibodies against polypeptides containing MaSp1 and MaSp2 amino acid sequences.

The antibodies of the disclosure can also be used in assays to detect the presence of the polypeptides or fragments of the disclosure, either in vitro or in vivo. The antibodies also can be employed in purifying polypeptides or fragments of the disclosure by immunoaffinity chromatography.

The disclosure provides methods for identifying agents that modulate MaSp1 and MaSp2 activity or expression. Such methods included contacting a sample containing an MaSp1, MaSp2 or MiSp polypeptide or polynucleotide with a test agent under conditions that allow for the test agent and the polypeptide or polynucleotide to interact and measuring the expression or activity of an MaSp1, MaSp2 or MiSp polypeptide in the presence or absence of the test agent.

In one embodiment, a cell containing an MaSp1 and/or MaSp2 polynucleotide is contacted with a test agent under conditions such that the cell and test agent are allowed to interact. Such conditions typically include normal cell culture conditions consistent with the particular cell type being utilized and which are known in the art. It may be desirable to allow the test agent and cell to interact under conditions associated with increased temperature or in the presence of regents that facilitate the uptake of the test agent by the cell. A control is treated similarly but in the absence of the test agent. Alternatively, the MaSp1 and/or MaSp2 activity or expression may be measured prior to contact with the test agent (e.g., the standard or control measurement) and then again following contact with the test agent. The treated cell is then compared to the control and a difference in the expression or activity of MaSp1 and MaSp2 compared to the control is indicative of an agent that modulates MaSp1, MaSp2 or MiSp activity or expression.

When MaSp1, MaSp2 or MiSp expression is being measured, detecting the amount of mRNA encoding an MaSp1, MaSp2, or MiSp polypeptide in the cell can be quantified by, for example, RT-PCR or Northern blot. Where a change in the amount of MaSp1, MaSp2 or MiSp polypeptide in the sample is being measured, detecting MaSp1, MaSp2 or MiSp by use of anti-MaSp1, MaSp2, MiSp antibodies can be used to quantify the amount of MaSp1, MaSp2 or MiSp polypeptide in the cell using known techniques.

A test agent can be any molecule typically used in the modulation of protein activity or expression and includes, for example, small molecules, chemicals, peptidomimetics, antibodies, peptides, polynucleotides (e.g., antisense or ribozyme molecules), and the like. Accordingly, agents developed by computer based design can be tested in the laboratory using the assay and methods described herein to determine the activity of the agent on the modulation of MaSp1, MaSp2 or MiSp activity or expression. Modulation of MaSp1, MaSp2 or MiSp includes an increase or decrease in activity or expression or strength of the resulting fibrous material.

Uses of MaSp1, MaSp2 and MiSp polypeptides and peptide fragments thereof include, but are not limited to, the following: delivery agents; textile materials; biomaterials for wound repair; biomaterials for tissue engineering; puncture resistant materials; molecular weight and isoelectric focusing markers; and preparation of antibodies.

The spider dragline compositions provided herein find uses in the textile industry (e.g., as filaments, yarns, ropes, and woven material). Such materials made using the methods and compositions described herein will take advantage of the extreme toughness, tensile strength, and extensibility of silk. In addition, the polypeptides of the disclosure can be used in pliant energy absorbing devices including armor and bumpers. Besides the mechanical properties of spider silk, silk is proteinaceous (thus not petroleum-based like nylon or Kevlar). Accordingly, the polypeptides of the disclosure provide biocompatible and biodegradable material useful in various industries including textiles and medicine. For example, the supercontraction ability of dragline silk can be beneficial for sutures that can tighten, compression bandages, or space minimizing packaging. Additionally the polypeptides can be used in the generation of scaffolds and material in tissue engineering, implants and other cell scaffold-based materials. The polypeptides of the disclosure can be used in the generation of biomaterials comprising other proteinacious substances (e.g., as a collagen and silk material combination).

For compositions of the disclosure which are useful for tissue repair or regeneration, the therapeutic method includes administering or contacting a site in need of wound repair with a biomaterial comprising a MaSp1, MaSp2 or MiSp polypeptide or fragment, physiologically acceptable form of the composition can be used topically, systematically, locally or in association with an implant or device.

Further encompassed by the disclosure are systems and methods for analyzing MaSp1 and/or MaSp2 polypeptides comprising identifying and/or characterizing one or more MaSp1 and/or MaSp2 polypeptides, encoding nucleic acids, and corresponding genes, these systems and methods comprise a data set representing a set of one or more MaSp1 and/or MaSp2 molecules, or the use thereof. Accordingly, the disclosure provides a computer readable medium having stored thereon a member selected from the group consisting of a polynucleotide comprising a sequence as set forth in SEQ ID Nos: 1, 3, 5, 7, 9, 11, 13, 15, 17, 19, 21, 23, 25, 27, 29, 31, 33, 35, 37, 39, 41, 43, 45, 47, or 49; a polypeptide comprising a sequence as set forth in SEQ ID Nos:2, 4, 6, 8, 10, 12, 14, 16, 18, 20, 22, 24, 26, 28, 30, 32, 34, 36, 28, 40, 42, 44, 46, 48 or 50; a set of polynucleotide sequences wherein at least one of said sequences comprises a sequence as set forth in SEQ ID Nos: 1, 3, 5, 7, 9, 11, 13, 15, 17, 19, 21, 23, 25, 27, 29, 31, 33, 35, 37, 39, 41, 43, 45, 47, or 49; and a set of polypeptide sequences wherein at least one of said sequences comprises a sequence as set forth in SEQ ID Nos: 2, 4, 6, 8, 10, 12, 14, 16, 18, 20, 22, 24, 26, 28, 30, 32, 34, 36, 28, 40, 42, 44, 46, 48 or 50.

One embodiment of the disclosure comprises a computing environment and a plurality of algorithms selectively executed to analyze a polypeptide or polynucleotide of the disclosure. Examples of analyses of an MaSp1, MaSp2 or MiSp polypeptide include, without limitation, displaying the amino acid sequence of a polypeptide in the set, comparing the amino acid sequence of one polypeptide in the set to the amino acid sequence of another polypeptide in the set, predicting the structure of a polypeptide in the set, determining the nucleotide sequences of nucleic acids encoding a polypeptide in the set, and identifying a gene corresponding to a polypeptide in the set.

The following examples are meant to illustrate the disclosure but should not be construed as limiting it in any way.

EXAMPLES

Genomic Library Construction and Screening

The disclosure targeted black widow silk genes because in addition to the exemplary properties of their silk, *Latrodectus hesperus* has one of the smallest known genome sizes for a spider (C-value of 1.29 picograms), meaning that fewer genomic clones must be screened to find a gene of interest. Individuals were collected from a single locality in Riverside, Calif. (USA), live frozen in liquid nitrogen, and stored at −80° C. High-molecular-weight DNA was isolated from the cephalothoraxes of eight individuals using a modified method of Sambrook and Russell. Following isolation, DNA was mechanically sheared through a pipette tip and subsequently treated with End-Repair Enzyme Mix (Epicentre) to produce blunt 5' phosphorylated ends. Fragments ranging from 38-50 kilobases were gel excised, purified, and ligated into pCC1FOS™ vector (Epicentre). Resulting fosmids were packaged using MaxPlax™ Lambda Packaging Extracts and transfected into Epi300-T1R *E. coli* cells following protocols for the CopyControl™ Fosmid Library Production kit (Epicentre). Approximately 100,000 recombinant *E. coli* colonies were picked and arrayed into 276 culture plates each containing 384 wells using a QPIX robotic picker (Genetix). Each culture plate was replicated and original stock plates containing 7.5% glycerol were stored at −80° C.

To efficiently screen the genomic library, fosmid DNA was extracted from cell cultures combined from a single 384-well plate, and such extractions were done for every plate in the library. Polymerase chain reaction (PCR) experiments targeting genes of interest were used to identify which plate contained one or more positive clones. Once the plate was identified, that plate was replicated twice, and cell cultures from the rows were combined to form 16 templates, while cell cultures from the columns were combined to form 24 templates. Templates were then PCR screened to identify individual clones containing the gene of interest. Primers targeting MaSp1 and MaSp2 were designed from *L. hesperus* cDNA clones (MaSp1—N-terminal clone, EF595247; MaSp2—C-terminal clone, AY953075). The primers, LhMaSp1NF254, 5'-TGGCTTTCGCATCATCTGTAGC-3' (SEQ ID NO:52) and LhMaSp1NR607, 5'-CTCCTTGACCATAACTAACTGGCTG-3' (SEQ ID NO:53) amplified a 350 by portion of the MaSp1 5' region. Primers LhMaSp2__1086F, 5'-CATCAGCAGCAGGACCAAGTG-3' (SEQ ID NO:54), and LhMaSp2__1337R, 5'-GCGTTGTCGGTGAAGATAAAGC-3' (SEQ ID NO:55), amplified a 250 by portion of the MaSp2 3' region.

Seven MaSp1-positive clones and three MaSp2-positive clones were found after screening half of the library. One positive clone for each gene was shotgun sequenced and assembled by Qiagen (Hilden, Germany) to 6× coverage for the MaSp2-positive clone and 8× coverage for the MaSp1-positive clone. This resulted in three contiguous sequences (contigs) for the MaSp2-positive clone with two gaps within the coding sequence and one directly after the stop codon. The 707 by gap between the stop codon and the downstream contig was closed by sequencing directly off the fosmid clone using primers designed from the C-terminal coding region of MaSp2 and for the beginning of the downstream contig (all primer sequences used in this study are available upon request). Primer walking to close the two gaps within the MaSp2 coding sequence was not possible due to its repetitive nature. Instead the clone was digested with NotI and BamHI (New England Biolabs) and a 9 kb restriction fragment containing almost the entire repetitive portion of MaSp2 was subcloned into pZErO™-2 plasmids (Invitrogen) and electroporated into Epi-400 *E. coli* (Epicentre). The subclone was partially digested with PstI (New England Biolabs) and 2000-3000 by fragments were gel excised and ligated into PstI digested and dephosphorylated pZErO™-2. Ligation products were electroporated into TOP10 *E. coli* (Invitrogen). A library of 96 PstI partial-digest clones were arrayed and sequenced in one direction. Sequences were assembled independently and using the fosmid contigs as a backbone in SEQUENCHER v4.5 (Gene Codes Corp.), requiring 100% identity for high-quality bases. Ten clones spanned the first gap (111 bp) and 18 clones spanned the second gap (632 bp) with no less than 5× sequence coverage of any base along the length of the NotI-BamHI subclone. No disagreement between the sequences of the subclone and the fosmid contigs was found.

Shotgun sequencing of a MaSp1-positive clone resulted in a single contig containing the entire coding sequence of MaSp1 and the vector. However, this contig was ~7000 by smaller than expected based on restriction digests. This missing sequence was determined by PCR amplifying with AccuPrime™ Taq DNA Polymerase High Fidelity (Invitrogen) and primers designed from both ends of the contig. The 7890 by PCR product was sequenced with at least 2× coverage by primer walking. Additionally, the fosmid was directly sequenced at intervals along the gap to ensure that no mutations had been introduced by the PCR amplification. Experimental restriction digests of the MaSp1-positive and MaSp2-positive clones matched predicted restriction sites in the final sequences, verifying that assembly had not erroneously excluded repetitive sequence.

*Latrodectus geometricus* was also examined for multiple MaSp1 loci. Two different PCR reactions were performed on DNA extracted from a single individual. The products were gel excised and cloned with the TOPO TA Cloning kit (Invitrogen, Carlsbad, Calif.). Forward primers for these reactions were designed from conserved regions of the N-termini of putative *Latrodectus hesperus* MaSp1 loci and the published *Latrodectus geometricus* MaSp1-like genomic clone (5' partial length, DQ059133S1; Motriuk-Smith et al. 2005). The reverse primer was designed from the repetitive region of the full-length *Latrodectus hesperus* MaSp1 sequence. Seventy clones were amplified using universal primers (M13 forward and M13 reverse), and inserts of the expected size (500-700 or 700-900 bp) were sequenced.

DNA sequences were aligned in SEQUENCHER v.4.5 (Gene Codes, Ann Arbor, Mich.), and a Neighbor-Joining tree (constructed in PAUP*v.4.0B10; Swofford 2002) revealed clusters of highly similar sequences. A consensus sequence for each cluster was calculated in SEQUENCHER.

The alignment of the TOPO TA clones with direct sequences of the original PCR products was inspected to verify that all base calls could be accounted for by the original PCR. Any polymorphic positions in the alignment of the clones that could not be accounted for by the original PCR were considered cloning error. Individual clones differed from the consensus sequence at 0-5 sites and typically, only 1 clone differed from the consensus sequence at any one position. However, at one position in the alignment of the third cluster, 16 clones displayed a T, 10 displayed a C, and the direct PCR sequences were polymorphic (i.e., multiple peaks at that position in the chromatographs). This polymorphism was thus considered a true allelic difference. A third PCR reaction was performed on the same individual as above with primers designed to specifically amplify the *Latrodectus geometricus* MaSp1-like sequence, and this PCR product was directly sequenced.

Nucleotide sequences were conceptually translated using the standard genetic code. Base composition, amino acid content, codon usage, and Kyte and Doolittle hydrophilicity predictions were calculated in MacVector™ (Oxford Molecular Group). Amino acid sequences were considered to start at the first methionine in frame. The first M on the MaSp1 sequence corresponded to the conserved start position (see FIG. 4A). The MaSp2 sequence also displayed an M at this position, but the first in frame M codon was 9 by upstream (FIG. 4A). Pairwise K, Ks, and Kn were calculated using DnaSp v4.0 [101] excluding gaps and missing data.

Predicted amino acid sequences of all currently published N-termini were aligned (FIG. 4A), making corrections to the nucleotide sequences of *Latrodectus geometricus* MaSp1, *A. bruennichi* CySp2, and *N. clavipes* Flag. Alignments of N- and C-terminal amino acid sequences were made separately using default parameters in ClustalW (MacVector™). The C-terminal alignment was modified slightly such that the first position of the C-terminal Flag sequences aligned with the first position of the other sequences (FIG. 4B). Amino acid alignments were used to guide nucleotide alignments, which formed the basis for phylogenetic analyses. Heuristic ML and MP searches were performed in PAUP* using TBR (tree bisection reconnection) branch swapping and 10,000 (MP) or 100 (ML) random stepwise addition replicates. Support for clades was evaluated with 1000 (MP) or 100 (ML) bootstrap pseudoreplicates (of all characters), and 100 (MP) or 1 (ML) random stepwise addition replicates per pseudoreplicate. ML analyses treated gaps as missing data. MP analyses were performed treating gaps as missing data and as a 5th state. Optimal model parameters for ML analyses were calculated with MODELTEST. The N-termini fit the HKY+G model of evolution (transitions/transversions=1.24; gamma=0.9058). The C-termini fit the TrN+G [105] model of evolution (A< >G=2.34; C< >T=1.27; transversions=1; gamma=1.34). To further evaluate tree structure and Glade support in a model-based framework, Bayesian analyses were carried out using MRBAYES v.3.1.2. The same model of evolution determined by MODELTEST was used but parameter values were evaluated during the Bayesian analysis. Default priors and Metropolis-coupled, Markov-chain, Monte Carlo (MCMC) sampling procedures were executed for two independent runs, sampled every 100th generation, carried out simultaneously. Convergence was assessed every 1000th generation and the posterior distribution was considered adequately sampled when the standard deviation of split frequencies of these two runs dropped below 0.01 (<1 million generations). A second analysis was run for 10 million generations (sampling every 500) to ensure that a longer sampling time did not change the results. For each run, the first 50% of sampled trees were discarded as burnin prior to calculating the majority rule consensus tree.

Comparisons of genes with MultiPipMaker were done using the "high sensitivity low time limit" option. Each major ampullate silk gene with upstream sequence was sequentially input as the reference to obtain maximal pairwise alignments. AVID alignments were made using default parameters and viewed on the VISTA browser <www-gsd.lbl.gov/vista/> [107-108]. Global alignments of conserved non-coding sequence identified by MultiPipMaker were made using default parameters in ClustalW and modified manually. Approximately 300 by of upstream sequence were scanned against insect transcription factor binding sites in the TRANSFAC 6.0 database using the program PATCH™ v1.0 with a minimum match of 6 and a maximum mismatch of 2.

Open reading frames on the black widow genomic clones were identified using the ORFFinder program on the NCBI website <[http://]www.ncbi.nlm.nih.gov/gorf/gorf.html>, with a minimum cutoff of 300 nucleotides.

Two fosmid clones were sequenced each containing ~37,000 by of the black widow genome. One clone (GenBank accession EF595246) encompassed the complete coding sequence for the dragline silk gene MaSp1 as well as 9,928 by upstream of its start codon and 14,728 by downstream of its stop codon. The MaSp1 gene is composed of a single exon with 9,390 by encoding 3,129 aa (FIG. 1). The second clone (EF595245) includes the entire coding sequence for MaSp2 plus 17,205 by of upstream and 8,546 by of downstream flanking sequence. Like MaSp1, the MaSp2 gene contains one enormous exon with 11,340 by encoding 3,779 aa (FIG. 2). Both MaSp1 and MaSp2 genes contain sequences that match partial-length cDNAs from *L. hesperus* silk gland expression libraries, indicating that these genes are transcribed. The C-terminal coding region (~300 bp) of the MaSp1 gene is 97% identical to the corresponding 3' partial MaSp1 cDNA clones (AY953074, DQ409057) and the N-terminal coding region (~450 bp) is 99.8% identical to our 5' partial cDNA clone (EF595247). Both the C-terminal coding region and the 3' untranslated region (UTR) of the MaSp2 gene share 99% sequence identity with 3' partial MaSp2 cDNA clones (AY953075, DQ409058). Similarly, the N-terminal coding regions of the MaSp2 gene and our 5' partial cDNA (EF595248) are 95.5% identical.

Glycine and alanine are by far the most abundant amino acids in our predicted *L. hesperus* MaSp1 and MaSp2 fibroins. These two amino acids constitute greater than 64% of both sequences, followed by glutamine in MaSp1 and proline in MaSp2 (Table 1). These values closely match published amino acid compositions of major ampullate silk from black widows and other araneoid spiders, further confirming that our genes encode the two dominant protein components of major ampullate silk. Because the first two codon positions for alanine, glycine, and proline are guanine or cytosine, the base compositions of these genes are guanine/cytosine-rich (MaSp1—61%; MaSp2—59%). However, overall base compositions are not highly skewed because the third positions for these codons in the *L. hesperus* MaSp1 and MaSp2 are extremely biased towards adenine and also strongly biased, but less dramatically, towards thymine (86% of MaSp1, 91% of MaSp2 glycine, alanine, and proline codons end with adenine or thymine; Table 1).

TABLE 1

Amino acid content and codon usage for the most common amino acids of black widow MaSp1 and MaSp2.

| | | MaSp1 | | MaSp2 | |
|---|---|---|---|---|---|
| Amino Acid | Codon | % aa | % codon | % aa | % codon |
| Glycine | GGA | 42.3 | 54 | 33.5 | 65 |
| | GGT | | 38 | | 30 |
| | GGC | | 7 | | 4 |
| | GGG | | 1 | | 1 |
| Alanine | GCA | 32.7 | 59 | 31.1 | 66 |
| | GCT | | 18 | | 18 |
| | GCC | | 17 | | 7 |
| | GCG | | 6 | | 9 |
| Glutamine | CAA | 11.3 | 98 | 6.9 | 97 |
| | CAG | | 2 | | 3 |
| Proline | CCA | 0.4 | 69 | 8.6 | 64 |
| | CCT | | 23 | | 33 |
| | CCC | | 8 | | 1 |
| | CCG | | 0 | | 2 |

The repetitive region of the *L. hesperus* MaSp1 translation is dominated by amino acid sequence motifs commonly found in MaSp1 of other spider species: GGX (X=A, Q, or Y), GX (X=Q, A, or R), and poly-A (4-10 consecutive alanines, mean number=7.7). These motifs are organized into four types of ensemble (higher order) repeat units, with each ensemble consisting of a glycine-rich region followed by a poly-A region (FIG. 1). Starting at residue 542, the different ensemble types are tandemly arrayed in a consistent pattern, and this aggregate of four ensembles is iterated 20 times with near perfect fidelity. Pairwise amino acid differences between aggregates are extremely low, ranging from 0.0 to 4.3% and averaging 1.9%. This remarkable sequence homogeneity is also maintained at the nucleotide level with average uncorrected pairwise differences of only 2.5% (range=0.3-6.3%).

The repetitive region of the *L. hesperus* MaSp2 amino acid sequence is characterized by a larger suite of motifs than MaSp1. The common MaSp2 motifs include GPX (X=G or S), QQ, GGX (X is usually A), GSG, and poly-A (3-9 consecutive alanines, mean number=6.7). Similar to MaSp1, these motifs are organized into four types of ensemble repeat units that each contain one poly-A motif (FIG. 2). However, the four types of MaSp2 ensembles are more variable than those of MaSp1, with pairwise amino acid differences between ensembles of the same type as high as 36% (Table 2). In addition, the MaSp2 ensemble types are not always strung together in the same order and do not form clearly discernible higher-level aggregates (FIG. 2). Nevertheless, there is a pair of 778 amino acid long tandem repeats that differ by a scant five aa (FIG. 2). The 2,334 nucleotides encoding each repeat vary at only six positions (>99.7% identity).

TABLE 2

Prevalence (#) and average pairwise amino acid differences between MaSp2 ensemble repeats of the same type.

| Ensemble Type* | # | Average % aa difference (min-max) |
|---|---|---|
| 1 | 62 | 11.8 (0.0-36.0) |
| 2 | 24 | 11.7 (0.0-28.0) |
| 3 | 16 | 11.4 (0.0-22.0) |
| 4 | 30 | 5.6 (0.0-20.8) |

*Ensemble repeat types shown in FIG. 2.

Using the method of Kyte and Doolittle, the hydrophilicity of *L. hesperus* MaSp1 and MaSp2 was predicted. Both fibroins show regions of hydrophobicity (corresponding to the poly-A motifs) and hydrophilicity (corresponding to the glycine-rich regions) that alternate throughout the entire repetitive portions of the two proteins (FIG. 3A). Both MaSp1 and MaSp2 repetitive regions are slightly hydrophilic when averaged across all residues (MaSp1 average=0.13 on the Kyte-Doolittle scale; MaSp2 average=0.14) but MaSp2 displays higher amplitude of hydrophilicity (MaSp1 max=2.0; MaSp2 max=2.6) (FIG. 3A). The N- and C-terminal domains show a similar pattern of alternating hydrophobicity and hydrophilicity but are generally more hydrophobic than the repetitive regions (average hydrophilicity across residues: MaSp1 N-terminus=−0.29, C-terminus=−0.44; MaSp2 N-terminus=−0.34; C-terminus=−0.31; negative values indicate degree of hydrophobicity). The most hydrophobic region of both fibroins is found at the beginning of the N-terminus (FIG. 3B).

Congruence between silk N- and C-termini evolutionary relationships. The N-terminal regions of *L. hesperus* MaSp1 and MaSp2 were aligned with N-termini from other spider fibroins (FIG. 4A). These proteins are constituents of three spider silk fiber types: the dragline silk composed of MaSp1 and MaSp2, the capture spiral filament of flagelliform silk protein (Flag), and the eggcase fibers produced from tubuliform (also called cylindrical) gland proteins (TuSp1, CySp1 and CySp2). For each of these N-termini, the corresponding C-termini was also aligned, if available (FIG. 4B). However, only in the case of the *L. hesperus* MaSp1 and MaSp2, and the full-length CySp1 and CySp2 cDNAs from *Argiope bruennichi*, is it certain that the N- and C-termini coding regions belong to the same gene. All others were partial 5' or 3' sequences that were assumed to represent the ends of the same gene.

The evolutionary relationships were assessed among the N-termini and C-termini encoding sequences using maximum likelihood (ML), maximum parsimony (MP), and Bayesian phylogenetic methods. All methods produced similar relationships among N-terminal sequences (FIG. 4C). A Glade of eggcase silks (TuSp1, CySp1 and CySp2) was always well-supported. A major ampullate silk Glade (MaSp1 and MaSp2) was consistently recovered with greater than 90% bootstrap support and 100% posterior probability. Despite the distinct differences between the repetitive portions of MaSp1 and MaSp2 (FIGS. 1, 2, 4D), all N-termini analyses strongly supported a grouping of *Latrodectus* MaSp1 and MaSp2, rather than a multi-species MaSp1 Glade that is distinct from a MaSp2 Glade. Within *Latrodectus*, however, *L. hesperus* MaSp1 grouped with *Latrodectus geometricus* MaSp1.

Relationships among the corresponding C-terminal encoding sequences typically mirrored those of the N-terminal encoding sequences (FIG. 4C). However, placement of the *L. hesperus* TuSp1 C-terminus was unstable. Depending on the type of analysis, it grouped with Flag, CySp1 and CySp2, or MaSp1 and MaSp2, but always with low support (less than 75% bootstrap support or 95% posterior probability). A MaSp1 and MaSp2 C-terminal Glade was consistently recovered with high support values, and nested within it, a *Latrodectus* MaSp1 and MaSp2 sub-Glade. The only difference among analyses was that *L. hesperus* MaSp1 grouped with either *Latrodectus geometricus* MaSp1 (ML and Bayesian trees) or *L. hesperus* MaSp2 (in the MP trees).

Multi-species comparisons identify conserved non-coding sequences. Phylogenetic footprinting is a powerful approach for discovering putative gene regulatory regions. This method generally relies on alignments of orthologous, non-coding sequences from multiple species [51]. The presence of conserved non-coding nucleotide stretches implies that a region is under selective constraint and therefore is likely to perform an important function. A similar approach can be applied to the non-coding sequences of co-regulated genes. The flanking sequences of *L. hesperus* MaSp1 and MaSp2 were compared, paralogous genes which are simultaneously expressed. These sequences were also analyzed with available flanking sequences of MaSp1 and MaSp2 from other spider species. Because the *L. hesperus* MaSp2 clone contained another open reading frame (ORF) 2,611 by upstream of the MaSp2 start codon, the comparisons used ~2,500 by of upstream sequence. Using MultiPipMaker, the regions that could be reliably aligned among *L. hesperus* MaSp1 and MaSp2, *Latrodectus geometricus* MaSp1 (5': DQ059133S1, 3': DQ059133S2), Argiope trifasciata MaSp2 (DQ059136), and Nephila inaurata madagascariensis MaSp2 (DQ059135 were analyzed; only 700 by upstream sequence available). Downstream genomic sequences were not available for Argiope and Nephila MaSp2. MultiPipMaker generates local alignments using the BLASTZ algorithm and only produces an alignment if identity among sequences exceeds a threshold, below which alignments are considered random. Margulies et al. argued that pairwise alignments are unreliable for detecting regulatory elements. Conserved regions found in at least three sequences were analyzed. When attempting to align only upstream non-coding sequence, MultiPipMaker produced alignments among *Latrodectus* sequences but not between *Latrodectus* and *Argiope* or *Nephila*. When the coding sequences were included as an anchor, a span of ~90 by directly upstream of the start codon could be aligned among all 5 genes. This region included the conserved motif CACG and the TATA box, which were also identified by Motriuk-Smith et al. While the TATA box is thought to guide RNA polymerase II to the transcription initiation site in many eukaryotic genes, the motif CACG represents a potentially novel regulatory element for spider silk genes. Approximately 150 by of sequence upstream from the start codon could be aligned among the three *Latrodectus* genes and ~300 by upstream sequence between *L. hesperus* MaSp1 and MaSp2. Additionally, ~180 by of sequence downstream of the stop codon could be aligned among all three *Latrodectus* genes.

The regions of similarity identified among the *Latrodectus* non-coding sequences were analyzed by creating global alignments of the ~300 by region upstream of the start codon and of the ~180 by segment downstream of the stop codon. In addition to the CACG motif and TATA box found among all sequences examined, the three *Latrodectus* upstream sequences share a 15 by motif found ~110 by upstream of the start codon that has only 2 variable positions. When scanned against the TRANSFAC database, this conserved region perfectly matches a 6 by binding site for the Achaete-Scute family of transcription factors.

The nucleotide substitution rates for various regions of the *Latrodectus* sequences were compared (FIG. 5). To detect selection on protein coding sequences, the ratio of the number of nonsynonymous substitutions per nonsynonymous site (Kn) were compared to the number of synonymous substitutions per synonymous site (Ks). As expected for evolutionarily conserved proteins, the data show Kn/Ks was very low, ranging from 0.05 to 0.20 for *Latrodectus* MaSp1 and MaSp2 terminal coding regions, suggesting strong purifying selection (FIG. 5). A similar approach was applied to estimate selective pressures in non-coding sequences by calculating the ratio of the number of substitutions per site (K) to Ks for the adjacent coding sequence. The data demonstrate K (150 by upstream)/Ks (N-terminus) ranged from 0.26 to 0.63, which is higher than for coding sequence but still considerably less than 1. In contrast, K (300-150 by upstream)/Ks (N-terminus) ranged from 0.82 to 1.45 (FIG. 5), suggesting that the 150 by directly upstream of coding sequence are under selective constraints while regions farther upstream are not. The data also demonstrate K (3' UTR)/Ks (C-terminus) =0.27 for *L. hesperus* MaSp1 and MaSp2, consistent with strong purifying selection on the 3' UTR.

Global comparisons of genomic clones. The entire clones containing MaSp1 (34,046 bp) and MaSp2 (37,092 bp) were compared using MultiPipMaker and the global alignment program AVID. The flanking sequences of the genes were also compared using BLASTN to search for repetitive elements in the *L. hesperus* genome. As expected, the N- and C-terminal coding regions are significantly conserved between the two genes (FIG. 6). Within the genes themselves, there are also multiple regions of significant similarity at the DNA level. These regions correspond to the poly-A, GG, GGXG and GQ motifs found in both proteins. Additionally, there were numerous significant matches between regions of non-silk-protein-coding sequence. Each of these regions, when translated, was similar to transposable elements in the NCBI nr protein database (based on BLASTX scores: E<e-10). Most notably, there is a significantly conserved region spanning ~700 by that is found ~10,000 by downstream of the MaSp1 and MaSp2 ORFs (FIG. 6). The translated sequence of this region from the MaSp2 clone significantly matched TCb1-transposase. The translated sequence from the MaSp1 clone significantly matched gag-pol polyprotein, which contains a retrotransposon. Although both clones contain ORFs in this region, they do not encode full-length proteins. Thus, these genomic regions appear to be inactive transposable elements.

Naturally occurring variants were identified using the techniques described herein as well as homologues form *Latrodectus geometricus*. Partial sequencing of *Latrodectus hesperus* MaSp1-positive genomic clones revealed that they fit into 4 categories, each presumed to represent a different locus. Three of these loci appear functional (no premature stop codons were detected) and will be referred to as LhMaSp1_L1-3 for the remainder of the paper. The fourth locus, LhMaSp1 pseudo, is a pseudogene represented by a single fosmid clone (EU177647).

Conceptual translation of this sequence reveals a stop codon after 153 aa that correspond to the N-terminus and 11 aa of repetitive spidroin sequence. After the stop codon, there are 18 consecutive codons for repetitive sequence before the conceptual translation fails to recover recognizable spidroin sequence in any frame. Sequencing reactions targeting the C-terminus failed. Additionally, the pairwise Ka/Ks value between the N-terminus of LhMaSp1_pseudo and the locus most similar to it, LhMaSp1_L3, is 0.96, suggesting a loss of functional constraints on this locus. In contrast, pairwise Ka/Ks values for all *Latrodectus* MaSp1 loci and MaSp2 comparisons, excluding LhMaSp1 pseudo, are typically below 0.2, indicating strong functional constraints on the remaining loci. Four fosmid clones (EU177649, EU177654, EU177655, and EF595246), including the fully sequenced clone, belong to LhMaSp1_L1. Two clones (EU177651 and EU177653) belong to LhMaSp1_L2 and 2 (EU177648 and EU177650) to LhMaSp1_L3. Pairwise differences between clones belonging to a single locus range from 0% to 1.2% (including all available sequence: noncoding, N- and C-termini, and repetitive sequence). In contrast, pairwise differences between loci range from 10.8% to 36.3% (excluding repetitive sequence). The N- and C-terminal coding sequences of clones within a locus were either identical or only differed at one position. The only difference between the genomic clone and these cDNA sequences is the presence of a gap in the repetitive region, and thus, these cDNA sequences are assumed to represent allelic variants of LhMaSp1_L2.

The amplification of MaSp1 from an individual spider's genomic DNA with locus-specific PCR primers shows that differences among the loci cannot be explained by allelic variation. Direct sequencing of the locus-specific PCR products results in a few (~1.0%) polymorphic base calls, which are visualized as positions with multiple peaks on chromatographs (EU177658, EU177659, EU177661, EU177662, EU177663, EU177664, and EU177665). These polymorphic positions are interpreted as allelic variation, and their low frequency and specific locations cannot account for the variation seen among MaSp1 loci.

At least 3 loci are also present in *L. geometricus*. The cloned PCR products can be assigned to 4 categories of MaSp1 sequences. Because PCR reactions were carried out on genomic DNA from a single individual and spiders are diploid, at least 2 loci must exist to account for these 4 alleles. Two alleles are identical in the N-terminal coding region and differ at only a few nucleotide positions in the repetitive region (1.8% of 284 nt). These alleles are considered to belong to a single locus, LgMaSp1_L1 (EU177666 and EU177667). The other 2 alleles differ at only one position (876 nt) and are referred to as LgMaSp1_L2 (EU177668 and EU177669).

The existence of all 3 loci in the genome of a single individual is confirmed by sequencing PCR products generated with LgMaSp1__3 locus-specific primers (EU177660).

The presence of at least 3 copies of MaSp1 in both *Latrodectus geometricus* and *Latrodectus hesperus* suggests that multiple loci encode MaSp1 in all widow spiders. These 2 species represent the extent of divergence in *Latrodectus*, which is split into 2 primary clades with *Latrodectus hesperus* belonging to one and *Latrodectus geometricus* belonging to the other.

In contrast to MaSp1, the *Latrodectus hesperus* MaSp2 clones (EF595245 and EU177652) are very similar (99% identity over 3030 bp). In addition, sequences of *Latrodectus hesperus* and *Latrodectus geometricus* MaSp2 PCR products (EU177656 and EU177657, respectively) reveal 3 and 0 polymorphic base calls, respectively, indicating low allelic diversity.

The conceptual translations of the repetitive portions of each *Latrodectus hesperus* and *Latrodectus geometricus* locus contain aa motifs typical of MaSp1, such as GGX (X 5 A, Q, Y, S, L, I, or F), GX (X 5 Q, A, R, E, or L), and poly-A (FIG. 1A(i)-(ii)). In *Latrodectus hesperus*, these aa motifs are combined to form 4 different ensemble repeat types possessed by each putatively functional locus. However, the 3 loci (LhMaSp1_L1-3) differ in the arrangement of the ensemble types. LhMaSp1_L1 displays a consistent aggregate repetition of ensemble types "a," "b," "c," and "d" in that order (FIG. 1A(i)). In contrast, LhMaSp1_L2 and L3 do not display a consistent aggregate repeat of ensemble types, at least over the sequenced portions (FIG. 1A(i)).

*Latrodectus geometricus* LgMaSp1_L1, L2, and the cDNA sequence have very similar ensemble repeats (FIG. 1A(ii)). However, these sequences are directly adjacent to the N-termini (L1 and L2) or C-terminus (cDNA) and more regular ensemble types may be found in the central portions of the genes. LgMaSp1_L3 shares aa motifs with the other loci, but the ensemble repeats are distinct (FIG. 1A(ii)). A striking difference between LgMaSp1_L3 and the other loci is that its repetitive sequence has a more diverse aa composition (FIG. 1A(ii)). Especially notable is the lower proportion of G and the higher proportions of S, P, L, V, and F in the ensemble repeats of LgMaSp1_L3 compared with the other *Latrodectus geometricus* and *Latrodectus hesperus* loci.

A number of non-limiting examples and embodiment have been described. The foregoing description is not intended to limit the invention and one of skill in the art will readily ascertain additional embodiments encompassed by the following claims in view of the foregoing description.

What is claimed is:

1. An engineered and purified silk polypeptide comprising at least four distinct units, each unit termed an ensemble repeat comprising the amino acid sequence of SEQ ID NO:51, said ensemble repeat comprising about 30 amino acids, having a glycine-rich region followed by an alanine-rich region and wherein the purified silk polypeptide has at least 97.5% sequence identity to the sequence of SEQ ID NO:2 and has a tensile strength of greater than 3.4 G/denier, an elasticity as great as 35% and a stiffness as low as 0.6 msi.

2. A copolymer fiber comprising the silk polypeptide of claim 1.

* * * * *

SEQUENCE LISTING

```
<160> NUMBER OF SEQ ID NOS: 60

<210> SEQ ID NO 1
<211> LENGTH: 9390
```

```
<212> TYPE: DNA
<213> ORGANISM: Latrodectus hesperus
<220> FEATURE:
<221> NAME/KEY: CDS
<222> LOCATION: (1)..(9390)

<400> SEQUENCE: 1

atg act tgg tca act cga ctt gcc tta tca ttt ctt ttc gtg ctc tgc       48
Met Thr Trp Ser Thr Arg Leu Ala Leu Ser Phe Leu Phe Val Leu Cys
1               5                   10                  15

act cag agc ctg tac gct ttg gcg caa gcc aac acg cca tgg tca agt       96
Thr Gln Ser Leu Tyr Ala Leu Ala Gln Ala Asn Thr Pro Trp Ser Ser
            20                  25                  30

aaa gcg aat gct gat gct ttt atc aat tcc ttt att tcg gca gct tcg      144
Lys Ala Asn Ala Asp Ala Phe Ile Asn Ser Phe Ile Ser Ala Ala Ser
        35                  40                  45

aat act gga tcc ttc tcc caa gat cag atg gaa gat atg tca ttg att      192
Asn Thr Gly Ser Phe Ser Gln Asp Gln Met Glu Asp Met Ser Leu Ile
    50                  55                  60

ggt aat aca tta atg gca gca atg gat aat atg ggt gga aga att acg      240
Gly Asn Thr Leu Met Ala Ala Met Asp Asn Met Gly Gly Arg Ile Thr
65                  70                  75                  80

cca tcc aaa tta cag gct tta gat atg gct ttc gca tca tct gta gca      288
Pro Ser Lys Leu Gln Ala Leu Asp Met Ala Phe Ala Ser Ser Val Ala
                85                  90                  95

gaa att gct gct tcg gaa gga gga gac tta gga gta aca aca aat gca      336
Glu Ile Ala Ala Ser Glu Gly Gly Asp Leu Gly Val Thr Thr Asn Ala
            100                 105                 110

att gca gat gct tta acg tca gct ttc tat caa aca acc gga gta gtt      384
Ile Ala Asp Ala Leu Thr Ser Ala Phe Tyr Gln Thr Thr Gly Val Val
        115                 120                 125

aat agc aga ttt ata agc gaa att aga agt ttg att ggc atg ttt gca      432
Asn Ser Arg Phe Ile Ser Glu Ile Arg Ser Leu Ile Gly Met Phe Ala
    130                 135                 140

cag gca tct gcc aac gat gta tac gcc tca gca ggt tcc agc ggt gga      480
Gln Ala Ser Ala Asn Asp Val Tyr Ala Ser Ala Gly Ser Ser Gly Gly
145                 150                 155                 160

gga ggg tat gga gca tct tct gca agt gca gca tct gca agc gca gca      528
Gly Gly Tyr Gly Ala Ser Ser Ala Ser Ala Ala Ser Ala Ser Ala Ala
                165                 170                 175

gca cca tca ggt gtc gca tat caa gct cca gca caa gca caa att tcc      576
Ala Pro Ser Gly Val Ala Tyr Gln Ala Pro Ala Gln Ala Gln Ile Ser
            180                 185                 190

ttc act ttg aga gga caa cag cca gtt agt tat ggt caa gga ggc gct      624
Phe Thr Leu Arg Gly Gln Gln Pro Val Ser Tyr Gly Gln Gly Gly Ala
        195                 200                 205

gga cca gga gga gct gga gca gca gcg gca gcc gca gca gca gct gga      672
Gly Pro Gly Gly Ala Gly Ala Ala Ala Ala Ala Ala Ala Ala Ala Gly
    210                 215                 220

gga gcg ggt caa gga gga caa gga ggg tat gga caa gga gga tac ggt      720
Gly Ala Gly Gln Gly Gly Gln Gly Gly Tyr Gly Gln Gly Gly Tyr Gly
225                 230                 235                 240

caa gga ggt gcc gga caa ggt gga tct gga gca gca gca gcg gca gca      768
Gln Gly Gly Ala Gly Gln Gly Gly Ser Gly Ala Ala Ala Ala Ala Ala
                245                 250                 255

gca gca gct gga ggc acc ggt caa gga ggt gct gga caa ggt gga gca      816
Ala Ala Ala Gly Gly Thr Gly Gln Gly Gly Ala Gly Gln Gly Gly Ala
            260                 265                 270

gga gca gca gcg gca gcc gca gca gca gct gga ggt gca ggt caa gga      864
Gly Ala Ala Ala Ala Ala Ala Ala Ala Ala Gly Gly Ala Gly Gln Gly
        275                 280                 285
```

-continued

```
gga caa ggt ggc tat gga caa gga gga tac ggt caa gga ggt acc gga      912
Gly Gln Gly Gly Tyr Gly Gln Gly Gly Tyr Gly Gln Gly Gly Thr Gly
    290                 295                 300

caa ggt gga gct gga gca gca gca gcg gca gca gca gcc gga ggt gca      960
Gln Gly Gly Ala Gly Ala Ala Ala Ala Ala Ala Ala Ala Gly Gly Ala
305                 310                 315                 320

ggt caa gga gga caa ggt gga tat gga caa gga gga tat gga caa gga     1008
Gly Gln Gly Gly Gln Gly Gly Tyr Gly Gln Gly Gly Tyr Gly Gln Gly
                325                 330                 335

gga tac gga caa ggt gga tct gga gca gca gca gcg gca gca gca gca     1056
Gly Tyr Gly Gln Gly Gly Ser Gly Ala Ala Ala Ala Ala Ala Ala Ala
            340                 345                 350

gcc gga ggt gca ggt caa ggt gga caa ggt ggc tat gga caa gga ggt     1104
Ala Gly Gly Ala Gly Gln Gly Gly Gln Gly Gly Tyr Gly Gln Gly Gly
        355                 360                 365

tac ggt caa gga ggt gcc gga caa ggt gga gct gga gcc gca gcg gca     1152
Tyr Gly Gln Gly Gly Ala Gly Gln Gly Gly Ala Gly Ala Ala Ala Ala
    370                 375                 380

gca gca gct gca gct ggt gga gcc gga caa gga gga tat ggc cga ggt     1200
Ala Ala Ala Ala Ala Gly Gly Ala Gly Gln Gly Gly Tyr Gly Arg Gly
385                 390                 395                 400

gga gca gga caa ggg gga gca gca gca gcc gct gct gca gcc gca gga     1248
Gly Ala Gly Gln Gly Gly Ala Ala Ala Ala Ala Ala Ala Ala Ala Gly
                405                 410                 415

gct ggt caa ggt ggt tat gga gga caa ggt gcc gga caa ggt gga tct     1296
Ala Gly Gln Gly Gly Tyr Gly Gly Gln Gly Ala Gly Gln Gly Gly Ser
            420                 425                 430

gga gct gca gcc gca gca gca gct gct gga ggg gca ggt caa gga gga     1344
Gly Ala Ala Ala Ala Ala Ala Ala Ala Gly Gly Ala Gly Gln Gly Gly
        435                 440                 445

caa ggt gga tat gga caa gga gga tac gga caa ggt gga tct gga gca     1392
Gln Gly Gly Tyr Gly Gln Gly Gly Tyr Gly Gln Gly Gly Ser Gly Ala
    450                 455                 460

gcg gca gca gca gca gca gcc gga ggt gca ggt caa gga gga caa ggt     1440
Ala Ala Ala Ala Ala Ala Ala Gly Gly Ala Gly Gln Gly Gly Gln Gly
465                 470                 475                 480

ggc tat gga caa gga ggt tac ggt caa gga ggt gcc gga caa ggt gga     1488
Gly Tyr Gly Gln Gly Gly Tyr Gly Gln Gly Gly Ala Gly Gln Gly Gly
                485                 490                 495

gct gga gca gca gca gcg gca gct gca gcc gga ggt gcc ggt caa gga     1536
Ala Gly Ala Ala Ala Ala Ala Ala Ala Ala Gly Gly Ala Gly Gln Gly
            500                 505                 510

gga caa ggt ggc tat gga caa gga ggt tac ggt caa gga ggt gcc gga     1584
Gly Gln Gly Gly Tyr Gly Gln Gly Gly Tyr Gly Gln Gly Gly Ala Gly
        515                 520                 525

caa ggt gga gct gga gca gca gca gcg gca gct gca gcc gga ggt gca     1632
Gln Gly Gly Ala Gly Ala Ala Ala Ala Ala Ala Ala Ala Gly Gly Ala
    530                 535                 540

ggt caa gga gga caa ggt ggc tat gga caa gga ggt tac ggt caa gga     1680
Gly Gln Gly Gly Gln Gly Gly Tyr Gly Gln Gly Gly Tyr Gly Gln Gly
545                 550                 555                 560

ggt gcc gga caa ggt gga gct gga gcg gca gcc gca gca gca gca gcc     1728
Gly Ala Gly Gln Gly Gly Ala Gly Ala Ala Ala Ala Ala Ala Ala Ala
                565                 570                 575

gga ggt gca ggt caa gga gga caa ggt ggc tat gga caa gga ggt tac     1776
Gly Gly Ala Gly Gln Gly Gly Gln Gly Gly Tyr Gly Gln Gly Gly Tyr
            580                 585                 590

ggt caa gga ggt gca gga caa ggt gga gcc gca gcg gca gca gca gca     1824
Gly Gln Gly Gly Ala Gly Gln Gly Gly Ala Ala Ala Ala Ala Ala Ala
```

-continued

```
        595                 600                 605

gca gct ggt gga gca gga caa gga gga tat ggc aga ggt gga gca gga      1872
Ala Ala Gly Gly Ala Gly Gln Gly Gly Tyr Gly Arg Gly Gly Ala Gly
    610                 615                 620

caa ggt gga gca gca gcc gcc gct gga gct ggt caa ggt ggt tat gga      1920
Gln Gly Gly Ala Ala Ala Ala Ala Gly Ala Gly Gln Gly Gly Tyr Gly
625                 630                 635                 640

ggt caa ggt gcc gga caa ggt gga gct gga gct gca gcc gca gca gca      1968
Gly Gln Gly Ala Gly Gln Gly Gly Ala Gly Ala Ala Ala Ala Ala Ala
                645                 650                 655

gca gcc gga ggt gca ggt caa gga gga caa ggt ggc tat gga cga gga      2016
Ala Ala Gly Gly Ala Gly Gln Gly Gly Gln Gly Gly Tyr Gly Arg Gly
            660                 665                 670

ggt tac ggt caa gga ggt gcc gga caa ggt gga gct gga gca gca gca      2064
Gly Tyr Gly Gln Gly Gly Ala Gly Gln Gly Gly Ala Gly Ala Ala Ala
        675                 680                 685

gcg gca gca gca gcc gga ggt gca ggt caa gga gga caa ggt ggc tat      2112
Ala Ala Ala Ala Ala Gly Gly Ala Gly Gln Gly Gly Gln Gly Gly Tyr
    690                 695                 700

gga caa gga ggt tac ggt caa gga ggc gca gga caa ggt gga gcc gca      2160
Gly Gln Gly Gly Tyr Gly Gln Gly Gly Ala Gly Gln Gly Gly Ala Ala
705                 710                 715                 720

gca gca gca gca gca gct ggt gga gca gga caa gga gga tat ggc aga      2208
Ala Ala Ala Ala Ala Ala Gly Gly Ala Gly Gln Gly Gly Tyr Gly Arg
                725                 730                 735

ggt gga gca gga caa ggt gga gca gca gca gcc gct gct gca gcc gct      2256
Gly Gly Ala Gly Gln Gly Gly Ala Ala Ala Ala Ala Ala Ala Ala Ala
            740                 745                 750

gga gct ggt caa ggt ggt tat gga ggt caa ggt gcc gga caa ggt gga      2304
Gly Ala Gly Gln Gly Gly Tyr Gly Gly Gln Gly Ala Gly Gln Gly Gly
        755                 760                 765

gct gga gct gca gcc gca gca gca gca gcc gga ggt gca ggt caa gga      2352
Ala Gly Ala Ala Ala Ala Ala Ala Ala Ala Gly Gly Ala Gly Gln Gly
    770                 775                 780

gga caa ggt gac tat gga cga gga ggt tat ggt caa gga ggt gcc gga      2400
Gly Gln Gly Asp Tyr Gly Arg Gly Gly Tyr Gly Gln Gly Gly Ala Gly
785                 790                 795                 800

caa ggc gga gct gga gca gca gca gcg gca gca gca gcc gga ggt gca      2448
Gln Gly Gly Ala Gly Ala Ala Ala Ala Ala Ala Ala Ala Gly Gly Ala
                805                 810                 815

ggt caa gga gga caa ggt ggc tat gga caa gga ggt tac ggt caa gga      2496
Gly Gln Gly Gly Gln Gly Gly Tyr Gly Gln Gly Gly Tyr Gly Gln Gly
            820                 825                 830

ggt gca gga caa ggt gga gcc gca gcg gca gca tca gca gca gca gct      2544
Gly Ala Gly Gln Gly Gly Ala Ala Ala Ala Ala Ser Ala Ala Ala Ala
        835                 840                 845

ggt gga gca gga caa gga gga tat ggc aga ggt gga gca gga caa ggt      2592
Gly Gly Ala Gly Gln Gly Gly Tyr Gly Arg Gly Gly Ala Gly Gln Gly
    850                 855                 860

gga gca gca gca gcc gct gga gct ggt caa ggt ggt tat gga ggt caa      2640
Gly Ala Ala Ala Ala Ala Gly Ala Gly Gln Gly Gly Tyr Gly Gly Gln
865                 870                 875                 880

ggt gcc gga caa ggt gga gct gga gct gca gcc gca gca gca gca gcc      2688
Gly Ala Gly Gln Gly Gly Ala Gly Ala Ala Ala Ala Ala Ala Ala Ala
                885                 890                 895

gga ggt gca ggt caa gga gga caa ggt ggc tat gga cga gga ggt tac      2736
Gly Gly Ala Gly Gln Gly Gly Gln Gly Gly Tyr Gly Arg Gly Gly Tyr
            900                 905                 910

ggt caa gga ggt gcc gga caa ggc gga gct gga gca gca gca gcg gca      2784
```

-continued

```
Gly Gln Gly Gly Ala Gly Gln Gly Gly Ala Gly Ala Ala Ala Ala Ala
        915                 920                 925

aca gca gcc gga ggt gca ggt caa gga gga caa ggt ggc tat gga caa     2832
Thr Ala Ala Gly Gly Ala Gly Gln Gly Gly Gln Gly Gly Tyr Gly Gln
    930                 935                 940

gga ggt tat ggt caa gga ggc gca gga caa ggt gga gcc gca gcg gca     2880
Gly Gly Tyr Gly Gln Gly Gly Ala Gly Gln Gly Gly Ala Ala Ala Ala
945                 950                 955                 960

gca gca gca gca gct ggt gga gca gga caa gga gga tat ggc aga ggt     2928
Ala Ala Ala Ala Ala Gly Gly Ala Gly Gln Gly Gly Tyr Gly Arg Gly
                965                 970                 975

gga gca gga caa ggt gga gca gca gca gcc gct gct gca gcc gct gga     2976
Gly Ala Gly Gln Gly Gly Ala Ala Ala Ala Ala Ala Ala Ala Ala Gly
            980                 985                 990

gct ggt caa ggt ggt tat gga ggt  caa ggt gcc gga caa  ggt gga gct   3024
Ala Gly Gln Gly Gly Tyr Gly Gly  Gln Gly Ala Gly Gln  Gly Gly Ala
        995                 1000                 1005

gga gct  gca gca gca gca gca  gga ggt gca ggt caa  gga gga caa      3069
Gly Ala  Ala Ala Ala Ala Ala  Gly Gly Ala Gly Gln  Gly Gly Gln
    1010                 1015                 1020

ggt ggc  tat gga cga gga ggt  tac ggt caa gga ggt  gcc gga caa      3114
Gly Gly  Tyr Gly Arg Gly Gly  Tyr Gly Gln Gly Gly  Ala Gly Gln
    1025                 1030                 1035

ggc gga  gct gga gca gca gca  gcg gca gca gca gcc  gga ggt gca      3159
Gly Gly  Ala Gly Ala Ala Ala  Ala Ala Ala Ala Ala  Gly Gly Ala
    1040                 1045                 1050

ggt caa  gga gga caa ggt ggc  tat gga caa gga ggt  tac ggt caa      3204
Gly Gln  Gly Gly Gln Gly Gly  Tyr Gly Gln Gly Gly  Tyr Gly Gln
    1055                 1060                 1065

gga ggc  gca gga caa ggt gga  gcc gca gcg gca gca  gca gca gca      3249
Gly Gly  Ala Gly Gln Gly Gly  Ala Ala Ala Ala Ala  Ala Ala Ala
    1070                 1075                 1080

gct ggt  gga gca gga caa gga  gga tat ggc aga ggt  gga gca gga      3294
Ala Gly  Gly Ala Gly Gln Gly  Gly Tyr Gly Arg Gly  Gly Ala Gly
    1085                 1090                 1095

caa ggt  gga gca gca gca gcc  gct gga gct ggt caa  ggt ggt tat      3339
Gln Gly  Gly Ala Ala Ala Ala  Ala Gly Ala Gly Gln  Gly Gly Tyr
    1100                 1105                 1110

gga ggt  caa ggt gct gga caa  ggt gga gct gga gct  gca gca gca      3384
Gly Gly  Gln Gly Ala Gly Gln  Gly Gly Ala Gly Ala  Ala Ala Ala
    1115                 1120                 1125

gca tcc  aga ggt gca ggt caa  gga ggt cag ggt ggc  tat gga cga      3429
Ala Ser  Arg Gly Ala Gly Gln  Gly Gly Gln Gly Gly  Tyr Gly Arg
    1130                 1135                 1140

gga ggt  tac ggt caa gga ggt  gcc gga caa ggc gga  gct gga gca      3474
Gly Gly  Tyr Gly Gln Gly Gly  Ala Gly Gln Gly Gly  Ala Gly Ala
    1145                 1150                 1155

gca gca  gcg gcc gca gca gcc  gga ggt gca ggt caa  gga gga caa      3519
Ala Ala  Ala Ala Ala Ala Ala  Gly Gly Ala Gly Gln  Gly Gly Gln
    1160                 1165                 1170

ggt ggc  tat gga caa gga ggt  tac ggt caa gga ggt  gca gga caa      3564
Gly Gly  Tyr Gly Gln Gly Gly  Tyr Gly Gln Gly Gly  Ala Gly Gln
    1175                 1180                 1185

ggt gga  gcg gca gca gca gca  gca gcc gct ggt gga  gca gga caa      3609
Gly Gly  Ala Ala Ala Ala Ala  Ala Ala Ala Gly Gly  Ala Gly Gln
    1190                 1195                 1200

gga gga  tat ggc aga ggt gga  gca gga caa ggt gga  gca gca gca      3654
Gly Gly  Tyr Gly Arg Gly Gly  Ala Gly Gln Gly Gly  Ala Ala Ala
    1205                 1210                 1215
```

-continued gcc gct gga gct ggt caa ggt ggt tat gga ggt caa ggt gcc gga 3699
Ala Ala Gly Ala Gly Gln Gly Gly Tyr Gly Gly Gln Gly Ala Gly
1220 1225 1230 caa ggt gga gct gga gct gca gcc gca gca gca gca gcc gga ggt 3744
Gln Gly Gly Ala Gly Ala Ala Ala Ala Ala Ala Ala Ala Gly Gly
1235 1240 1245 gca ggt caa gga gga caa ggt ggc tat gga cga gga ggt tac ggt 3789
Ala Gly Gln Gly Gly Gln Gly Gly Tyr Gly Arg Gly Gly Tyr Gly
1250 1255 1260 caa gga ggt gcc gga caa ggc gga gct gga gca gca gca gcg gca 3834
Gln Gly Gly Ala Gly Gln Gly Gly Ala Gly Ala Ala Ala Ala Ala
1265 1270 1275 gca gca gcc gga ggt gca ggt caa gga gga caa ggt ggc tat gga 3879
Ala Ala Ala Gly Gly Ala Gly Gln Gly Gly Gln Gly Gly Tyr Gly
1280 1285 1290 caa gga ggt tac ggt caa gga ggc gca gga caa ggt gga gcc gca 3924
Gln Gly Gly Tyr Gly Gln Gly Gly Ala Gly Gln Gly Gly Ala Ala
1295 1300 1305 gcg gca gca gca gca gca gct ggt gga gca gga caa gga gga tat 3969
Ala Ala Ala Ala Ala Ala Ala Gly Gly Ala Gly Gln Gly Gly Tyr
1310 1315 1320 ggc aga ggt gga gca gga caa ggt gga gca gca gca gcc gct gct 4014
Gly Arg Gly Gly Ala Gly Gln Gly Gly Ala Ala Ala Ala Ala Ala
1325 1330 1335 gca gcc gct gga tct ggt caa ggt ggt tat gga ggt caa ggt gcc 4059
Ala Ala Ala Gly Ser Gly Gln Gly Gly Tyr Gly Gly Gln Gly Ala
1340 1345 1350 gga caa ggt gga gct gga gct gca gcc gca gca gca gca gcc gga 4104
Gly Gln Gly Gly Ala Gly Ala Ala Ala Ala Ala Ala Ala Ala Gly
1355 1360 1365 ggt gca ggt caa gga gga caa ggt ggc tat gga cga gga ggt tac 4149
Gly Ala Gly Gln Gly Gly Gln Gly Gly Tyr Gly Arg Gly Gly Tyr
1370 1375 1380 ggt caa gga ggt gcc gga caa ggc gga gct gga gca gca gca gcg 4194
Gly Gln Gly Gly Ala Gly Gln Gly Gly Ala Gly Ala Ala Ala Ala
1385 1390 1395 gca gca gca gcc gga ggt gca ggt caa gga gga caa ggt ggc tat 4239
Ala Ala Ala Ala Gly Gly Ala Gly Gln Gly Gly Gln Gly Gly Tyr
1400 1405 1410 gga caa gga ggt tac ggt caa gga ggt gca gga caa ggt gga gcc 4284
Gly Gln Gly Gly Tyr Gly Gln Gly Gly Ala Gly Gln Gly Gly Ala
1415 1420 1425 gca gcg gca gca gca gca gca gcc gct ggt gga gca gga caa gga 4329
Ala Ala Ala Ala Ala Ala Ala Ala Ala Gly Gly Ala Gly Gln Gly
1430 1435 1440 gga tat ggc aga ggt gga gca gga caa ggt gga gca gca gca gcc 4374
Gly Tyr Gly Arg Gly Gly Ala Gly Gln Gly Gly Ala Ala Ala Ala
1445 1450 1455 gct gga gct ggt caa ggt ggt tat gga ggt caa ggt gcc gga caa 4419
Ala Gly Ala Gly Gln Gly Gly Tyr Gly Gly Gln Gly Ala Gly Gln
1460 1465 1470 ggt gga gct gga gct gca gcc gca gca gca gca gcc gga ggt gca 4464
Gly Gly Ala Gly Ala Ala Ala Ala Ala Ala Ala Ala Gly Gly Ala
1475 1480 1485 ggt caa gga gga caa ggt ggc tat gga cga gga ggt tac ggt caa 4509
Gly Gln Gly Gly Gln Gly Gly Tyr Gly Arg Gly Gly Tyr Gly Gln
1490 1495 1500 gga ggt gcc gga caa ggc gga gca gga aca gca gca gcg gca gca 4554
Gly Gly Ala Gly Gln Gly Gly Ala Gly Thr Ala Ala Ala Ala Ala
1505 1510 1515

-continued

```
gca gcc  gga ggt gca ggt caa  gga gga caa ggt ggc  tat ggt caa      4599
Ala Ala  Gly Gly Ala Gly Gln  Gly Gly Gln Gly Gly  Tyr Gly Gln
    1520                 1525                 1530

gga ggt  tat ggt caa gga ggc  gca gga caa ggt gga  gcc gca gcg      4644
Gly Gly  Tyr Gly Gln Gly Gly  Ala Gly Gln Gly Gly  Ala Ala Ala
    1535                 1540                 1545

gca gca  gca gca gca gct ggt  gga gca gga caa gga  gga tat ggc      4689
Ala Ala  Ala Ala Ala Ala Gly  Gly Ala Gly Gln Gly  Gly Tyr Gly
    1550                 1555                 1560

aga ggt  gga gca ggt caa ggt  gga gca gca gca gcc  gct gct gca      4734
Arg Gly  Gly Ala Gly Gln Gly  Gly Ala Ala Ala Ala  Ala Ala Ala
    1565                 1570                 1575

gcc gct  gga gct ggt caa ggt  ggt tat gga ggt caa  ggt gcc gga      4779
Ala Ala  Gly Ala Gly Gln Gly  Gly Tyr Gly Gly Gln  Gly Ala Gly
    1580                 1585                 1590

caa ggt  gga gct gga gct gca  gct gca gca gca gca  gcc gga ggt      4824
Gln Gly  Gly Ala Gly Ala Ala  Ala Ala Ala Ala Ala  Ala Gly Gly
    1595                 1600                 1605

gca ggt  caa gga gga caa ggt  ggc tat gga cga ggg  ggt tac ggt      4869
Ala Gly  Gln Gly Gly Gln Gly  Gly Tyr Gly Arg Gly  Gly Tyr Gly
    1610                 1615                 1620

caa gga  ggt gcc gga caa ggc  gga gct gga gca gca  gca gcg gca      4914
Gln Gly  Gly Ala Gly Gln Gly  Gly Ala Gly Ala Ala  Ala Ala Ala
    1625                 1630                 1635

gca gca  gcc gga ggt gca agt  caa gga gga caa ggt  ggc tat gga      4959
Ala Ala  Ala Gly Gly Ala Ser  Gln Gly Gly Gln Gly  Gly Tyr Gly
    1640                 1645                 1650

caa gga  gat tac ggt caa gga  ggt gca gga caa ggt  gga gcc gca      5004
Gln Gly  Asp Tyr Gly Gln Gly  Gly Ala Gly Gln Gly  Gly Ala Ala
    1655                 1660                 1665

gcg gca  gca gca gca gct ggt  gga gca gga caa gga  gga tat ggc      5049
Ala Ala  Ala Ala Ala Ala Gly  Gly Ala Gly Gln Gly  Gly Tyr Gly
    1670                 1675                 1680

aga ggt  gga gca gga caa ggt  gga gca gca gca gcc  gct gga gct      5094
Arg Gly  Gly Ala Gly Gln Gly  Gly Ala Ala Ala Ala  Ala Gly Ala
    1685                 1690                 1695

ggt caa  ggt ggt tat gga ggt  caa ggt gcc gga caa  ggt gga gct      5139
Gly Gln  Gly Gly Tyr Gly Gly  Gln Gly Ala Gly Gln  Gly Gly Ala
    1700                 1705                 1710

gga gct  gca gcc gca gca gca  gca gcc gga ggt gca  ggt aga gga      5184
Gly Ala  Ala Ala Ala Ala Ala  Ala Ala Gly Gly Ala  Gly Arg Gly
    1715                 1720                 1725

gga caa  ggt ggc tat gga cga  gga ggt tac ggt caa  gga ggt gcc      5229
Gly Gln  Gly Gly Tyr Gly Arg  Gly Gly Tyr Gly Gln  Gly Gly Ala
    1730                 1735                 1740

gga caa  ggc gga gct gga gca  gca gca gcg gca gca  gca gcc gga      5274
Gly Gln  Gly Gly Ala Gly Ala  Ala Ala Ala Ala Ala  Ala Ala Gly
    1745                 1750                 1755

ggt gca  ggt caa gga gga caa  ggt ggc tat gga caa  gga ggt tac      5319
Gly Ala  Gly Gln Gly Gly Gln  Gly Gly Tyr Gly Gln  Gly Gly Tyr
    1760                 1765                 1770

ggt caa  gga ggc aca gga caa  ggt gga gcc gca gcg  gca gca gca      5364
Gly Gln  Gly Gly Thr Gly Gln  Gly Gly Ala Ala Ala  Ala Ala Ala
    1775                 1780                 1785

gca gca  gct ggt gga gca gga  caa gga gga tat ggc  aga ggt gga      5409
Ala Ala  Ala Gly Gly Ala Gly  Gln Gly Gly Tyr Gly  Arg Gly Gly
    1790                 1795                 1800

gca gga  caa ggt gga gca gca  gca gcc gct gct gca  gcc gct gga      5454
Ala Gly  Gln Gly Gly Ala Ala  Ala Ala Ala Ala Ala  Ala Ala Gly
```

```
    1805                1810                1815

gct ggt  caa ggt ggt tat gga  ggt caa ggt gct gga  caa ggt gga      5499
Ala Gly  Gln Gly Gly Tyr Gly  Gly Gln Gly Ala Gly  Gln Gly Gly
    1820                1825                1830

gct gga  gct gca gcc gca gca  gca gca gcc gga ggt  gca ggt caa      5544
Ala Gly  Ala Ala Ala Ala Ala  Ala Ala Ala Gly Gly  Ala Gly Gln
    1835                1840                1845

gga ggt  cag ggt ggc tat gga  cga gga ggt tac ggt  caa gga ggt      5589
Gly Gly  Gln Gly Gly Tyr Gly  Arg Gly Gly Tyr Gly  Gln Gly Gly
    1850                1855                1860

gcc gga  caa ggc gga gct gga  gca gca gca gcg gcc  gca gca gcc      5634
Ala Gly  Gln Gly Gly Ala Gly  Ala Ala Ala Ala Ala  Ala Ala Ala
    1865                1870                1875

gga ggt  gca ggt caa gga gga  caa ggt ggc tat gga  caa gga ggt      5679
Gly Gly  Ala Gly Gln Gly Gly  Gln Gly Gly Tyr Gly  Gln Gly Gly
    1880                1885                1890

tac ggt  caa gga ggt tac ggt  caa gga ggt gca gga  caa ggt gga      5724
Tyr Gly  Gln Gly Gly Tyr Gly  Gln Gly Gly Ala Gly  Gln Gly Gly
    1895                1900                1905

gcg gca  gca gca gca gca gcc  gct ggt gga gca gga  caa gga gga      5769
Ala Ala  Ala Ala Ala Ala Ala  Ala Gly Gly Ala Gly  Gln Gly Gly
    1910                1915                1920

tat ggc  aga ggt gga gca gga  caa ggt gga gca gca  gca gcc gct      5814
Tyr Gly  Arg Gly Gly Ala Gly  Gln Gly Gly Ala Ala  Ala Ala Ala
    1925                1930                1935

gga gct  ggt caa ggt ggt tat  gga ggt caa ggt gcc  gga caa ggt      5859
Gly Ala  Gly Gln Gly Gly Tyr  Gly Gly Gln Gly Ala  Gly Gln Gly
    1940                1945                1950

gga gct  gga gct gca gcc gca  gca gca gca gcc gga  ggt gca ggt      5904
Gly Ala  Gly Ala Ala Ala Ala  Ala Ala Ala Ala Gly  Gly Ala Gly
    1955                1960                1965

caa gga  gga caa ggt ggc tat  gga cga gga ggt tac  ggt caa gga      5949
Gln Gly  Gly Gln Gly Gly Tyr  Gly Arg Gly Gly Tyr  Gly Gln Gly
    1970                1975                1980

ggt gcc  gga caa ggc gga gct  gga gca gca gca gcg  gca gca gca      5994
Gly Ala  Gly Gln Gly Gly Ala  Gly Ala Ala Ala Ala  Ala Ala Ala
    1985                1990                1995

gcc gga  ggt gca ggt caa gga  gga caa ggt ggc tat  gga caa gga      6039
Ala Gly  Gly Ala Gly Gln Gly  Gly Gln Gly Gly Tyr  Gly Gln Gly
    2000                2005                2010

ggt tac  ggt caa gga ggc gca  gga caa ggt gga gcc  gca gcg gca      6084
Gly Tyr  Gly Gln Gly Gly Ala  Gly Gln Gly Gly Ala  Ala Ala Ala
    2015                2020                2025

gca gca  gca gca gct ggt gga  gca gga caa gga gga  tat ggc aga      6129
Ala Ala  Ala Ala Ala Gly Gly  Ala Gly Gln Gly Gly  Tyr Gly Arg
    2030                2035                2040

ggt gga  gca gga caa ggt gga  gca gct gca gcc gct  gct gca gcc      6174
Gly Gly  Ala Gly Gln Gly Gly  Ala Ala Ala Ala Ala  Ala Ala Ala
    2045                2050                2055

gct gga  tct ggt caa ggt ggt  tat gga ggt caa ggt  gcc gga caa      6219
Ala Gly  Ser Gly Gln Gly Gly  Tyr Gly Gly Gln Gly  Ala Gly Gln
    2060                2065                2070

ggt gga  gct gga gct gca gcc  gca gca gca gca gcc  gga ggt gca      6264
Gly Gly  Ala Gly Ala Ala Ala  Ala Ala Ala Ala Ala  Gly Gly Ala
    2075                2080                2085

ggt caa  gga gga caa ggt ggc  tat gga cga gga ggt  tac ggt caa      6309
Gly Gln  Gly Gly Gln Gly Gly  Tyr Gly Arg Gly Gly  Tyr Gly Gln
    2090                2095                2100

gga ggt  gcc gga caa ggc gga  gct gga gca gca gca  gcg gca gca      6354
```

-continued

```
Gly Gly  Ala Gly Gln Gly Gly  Ala Gly Ala Ala Ala  Ala Ala Ala
    2105                 2110                 2115

gca gcc  gga ggt gca ggt caa  gga gga caa ggt ggc  tat gga caa      6399
Ala Ala  Gly Gly Ala Gly Gln  Gly Gly Gln Gly Gly  Tyr Gly Gln
    2120                 2125                 2130

gga ggt  tac ggt caa gga ggt  tac ggt caa gga ggt  gca gga caa      6444
Gly Gly  Tyr Gly Gln Gly Gly  Tyr Gly Gln Gly Gly  Ala Gly Gln
    2135                 2140                 2145

ggt gga  gcc gca gcg gca gca  gca gca gca gcc gct  ggt gga gca      6489
Gly Gly  Ala Ala Ala Ala Ala  Ala Ala Ala Ala Ala  Gly Gly Ala
    2150                 2155                 2160

gga caa  gga gga tat ggc aga  ggt gga gca gga caa  ggt gga gca      6534
Gly Gln  Gly Gly Tyr Gly Arg  Gly Gly Ala Gly Gln  Gly Gly Ala
    2165                 2170                 2175

gca gca  gcc gct gga gct ggt  caa ggt ggt tat gga  ggt caa ggt      6579
Ala Ala  Ala Ala Gly Ala Gly  Gln Gly Gly Tyr Gly  Gly Gln Gly
    2180                 2185                 2190

gcc gga  caa ggt gga gct gga  gct gca gcc gca gca  gca gca gcc      6624
Ala Gly  Gln Gly Gly Ala Gly  Ala Ala Ala Ala Ala  Ala Ala Ala
    2195                 2200                 2205

gga ggt  gca ggt caa gga gga  caa ggt ggc tat gga  cga gga ggt      6669
Gly Gly  Ala Gly Gln Gly Gly  Gln Gly Gly Tyr Gly  Arg Gly Gly
    2210                 2215                 2220

tac ggt  caa gga ggt gcc gga  caa ggc gga gct gga  gca gca gca      6714
Tyr Gly  Gln Gly Gly Ala Gly  Gln Gly Gly Ala Gly  Ala Ala Ala
    2225                 2230                 2235

gcg gca  gca gca gcc gga ggt  gca ggt caa gga gga  caa ggt ggc      6759
Ala Ala  Ala Ala Ala Gly Gly  Ala Gly Gln Gly Gly  Gln Gly Gly
    2240                 2245                 2250

tat gga  caa gga ggt aat ggt  caa gga ggc gca gga  caa ggt gga      6804
Tyr Gly  Gln Gly Gly Asn Gly  Gln Gly Gly Ala Gly  Gln Gly Gly
    2255                 2260                 2265

gcc gca  gca gca gca gca gca  gct ggt gga gca gga  caa gga gga      6849
Ala Ala  Ala Ala Ala Ala Ala  Ala Gly Gly Ala Gly  Gln Gly Gly
    2270                 2275                 2280

tat ggc  aga ggt gga gca gga  caa ggt gga gca gca  gca gcc gct      6894
Tyr Gly  Arg Gly Gly Ala Gly  Gln Gly Gly Ala Ala  Ala Ala Ala
    2285                 2290                 2295

gct gca  gcc gct gga gct ggt  caa ggt ggt tat gga  ggt caa ggt      6939
Ala Ala  Ala Ala Gly Ala Gly  Gln Gly Gly Tyr Gly  Gly Gln Gly
    2300                 2305                 2310

gcc gga  caa ggt gga gct gga  gct gca gcc gca gca  gca gca gcc      6984
Ala Gly  Gln Gly Gly Ala Gly  Ala Ala Ala Ala Ala  Ala Ala Ala
    2315                 2320                 2325

gga ggt  gca ggt caa gga gga  caa ggt ggc tat gga  cga gga ggt      7029
Gly Gly  Ala Gly Gln Gly Gly  Gln Gly Gly Tyr Gly  Arg Gly Gly
    2330                 2335                 2340

tac ggt  caa gga ggt gcc gga  caa ggc gga gct gga  gca gca gca      7074
Tyr Gly  Gln Gly Gly Ala Gly  Gln Gly Gly Ala Gly  Ala Ala Ala
    2345                 2350                 2355

gcg gca  gca gca gcc gga ggt  gca agt caa gga gga  caa ggt ggc      7119
Ala Ala  Ala Ala Ala Gly Gly  Ala Ser Gln Gly Gly  Gln Gly Gly
    2360                 2365                 2370

tat gga  caa gga gat tac ggt  caa gga ggt gca gga  caa ggt gga      7164
Tyr Gly  Gln Gly Asp Tyr Gly  Gln Gly Gly Ala Gly  Gln Gly Gly
    2375                 2380                 2385

gcc gca  gcg gca gca gca gca  gct ggt gga gca gga  caa gga gga      7209
Ala Ala  Ala Ala Ala Ala Ala  Ala Gly Gly Ala Gly  Gln Gly Gly
    2390                 2395                 2400
```

```
tat ggc  aga ggt gga gca gga  caa ggt gga gca gca  gca gcc gct      7254
Tyr Gly  Arg Gly Gly Ala Gly  Gln Gly Gly Ala Ala  Ala Ala Ala
    2405                 2410                 2415

gga gct  ggt caa ggt ggt tat  gga ggt caa ggt gcc  gga caa ggt      7299
Gly Ala  Gly Gln Gly Gly Tyr  Gly Gly Gln Gly Ala  Gly Gln Gly
    2420                 2425                 2430

gga gct  gga gct gca gcc gca  gca gca gca gcc gga  ggt gca ggt      7344
Gly Ala  Gly Ala Ala Ala Ala  Ala Ala Ala Ala Gly  Gly Ala Gly
    2435                 2440                 2445

aga gga  gga caa ggt ggc tat  gga cga gga ggt tac  ggt caa gga      7389
Arg Gly  Gly Gln Gly Gly Tyr  Gly Arg Gly Gly Tyr  Gly Gln Gly
    2450                 2455                 2460

ggt gcc  gga caa ggt gga gct  gga gca gca gca gcg  gca gca gca      7434
Gly Ala  Gly Gln Gly Gly Ala  Gly Ala Ala Ala Ala  Ala Ala Ala
    2465                 2470                 2475

gct gga  ggt gca ggt caa gga  gga caa ggt ggc tat  gga caa gga      7479
Ala Gly  Gly Ala Gly Gln Gly  Gly Gln Gly Gly Tyr  Gly Gln Gly
    2480                 2485                 2490

ggt tat  ggt caa gga ggc gca  gga caa ggt gga gcc  gca gcg gca      7524
Gly Tyr  Gly Gln Gly Gly Ala  Gly Gln Gly Gly Ala  Ala Ala Ala
    2495                 2500                 2505

gca gca  gca gca gct ggt gga  gca gga caa gga gga  tat ggc aga      7569
Ala Ala  Ala Ala Ala Gly Gly  Ala Gly Gln Gly Gly  Tyr Gly Arg
    2510                 2515                 2520

ggt gga  gca gga caa ggt gga  gca gca gca gcc gct  gga gct ggt      7614
Gly Gly  Ala Gly Gln Gly Gly  Ala Ala Ala Ala Ala  Gly Ala Gly
    2525                 2530                 2535

caa ggt  ggt tat gga ggt caa  ggt gcc gga caa ggt  gga gct gga      7659
Gln Gly  Gly Tyr Gly Gly Gln  Gly Ala Gly Gln Gly  Gly Ala Gly
    2540                 2545                 2550

gct gca  gcc gca gca gca gca  gcc gga ggt gca ggt  aga gga gga      7704
Ala Ala  Ala Ala Ala Ala Ala  Ala Gly Gly Ala Gly  Arg Gly Gly
    2555                 2560                 2565

caa ggt  ggc tat gga cga gga  ggt tac ggt caa gga  ggt gcc gga      7749
Gln Gly  Gly Tyr Gly Arg Gly  Gly Tyr Gly Gln Gly  Gly Ala Gly
    2570                 2575                 2580

caa ggc  gga gct gga gca gca  gca gcg gca gca gca  gct gga ggt      7794
Gln Gly  Gly Ala Gly Ala Ala  Ala Ala Ala Ala Ala  Ala Gly Gly
    2585                 2590                 2595

gca ggt  caa gga gga caa ggt  ggc tat gga caa gga  ggt tat ggt      7839
Ala Gly  Gln Gly Gly Gln Gly  Gly Tyr Gly Gln Gly  Gly Tyr Gly
    2600                 2605                 2610

caa gga  ggc gca gga caa ggt  gga gcc gca gcg gca  gca gca gca      7884
Gln Gly  Gly Ala Gly Gln Gly  Gly Ala Ala Ala Ala  Ala Ala Ala
    2615                 2620                 2625

gca gtt  ggt gga gca gga caa  gga gga tat ggc aga  ggt gga gca      7929
Ala Val  Gly Gly Ala Gly Gln  Gly Gly Tyr Gly Arg  Gly Gly Ala
    2630                 2635                 2640

gga caa  ggt gga gca gca gca  gca gcc gct gct gca  gcc gct gga      7974
Gly Gln  Gly Gly Ala Ala Ala  Ala Ala Ala Ala Ala  Ala Ala Gly
    2645                 2650                 2655

tct ggt  caa ggt ggt tat gga  ggt caa ggt gcc gga  caa ggt gga      8019
Ser Gly  Gln Gly Gly Tyr Gly  Gly Gln Gly Ala Gly  Gln Gly Gly
    2660                 2665                 2670

gct gga  gct gca gcc gca gca  gca gca gct gga ggt  gca ggt caa      8064
Ala Gly  Ala Ala Ala Ala Ala  Ala Ala Ala Gly Gly  Ala Gly Gln
    2675                 2680                 2685

gga gga  caa ggt ggc tat gga  gga gga ggt tac ggt  caa gga ggt      8109
Gly Gly  Gln Gly Gly Tyr Gly  Gly Gly Gly Tyr Gly  Gln Gly Gly
    2690                 2695                 2700
```

```
gcc gga  caa ggc gga gct gga  gca gca gca gcg gca  gca gca gcc      8154
Ala Gly  Gln Gly Gly Ala Gly  Ala Ala Ala Ala Ala  Ala Ala Ala
    2705                2710                2715

gga ggt  gca ggt caa gga gga  caa ggt ggc tat gga  caa gga ggt      8199
Gly Gly  Ala Gly Gln Gly Gly  Gln Gly Gly Tyr Gly  Gln Gly Gly
    2720                2725                2730

tac ggt  caa gga ggt gca gga  caa ggt gga gcc gca  gcg gca gca      8244
Tyr Gly  Gln Gly Gly Ala Gly  Gln Gly Gly Ala Ala  Ala Ala Ala
    2735                2740                2745

gca gca  gca gct ggt gga gca  gga caa gga gga tat  ggc aga ggt      8289
Ala Ala  Ala Ala Gly Gly Ala  Gly Gln Gly Gly Tyr  Gly Arg Gly
    2750                2755                2760

gga gca  gga caa ggg gga gca  gca gca gcc act gga  gct ggt caa      8334
Gly Ala  Gly Gln Gly Gly Ala  Ala Ala Ala Thr Gly  Ala Gly Gln
    2765                2770                2775

ggt ggt  tat gga ggt caa ggt  gcc gga caa ggt gga  gct gga gct      8379
Gly Gly  Tyr Gly Gly Gln Gly  Ala Gly Gln Gly Gly  Ala Gly Ala
    2780                2785                2790

gca gcc  gca gca gca gca gcc  gga ggt gca ggt caa  gga gga caa      8424
Ala Ala  Ala Ala Ala Ala Ala  Gly Gly Ala Gly Gln  Gly Gly Gln
    2795                2800                2805

ggt ggc  tat gga cga gga ggt  tac ggt caa gga ggt  gcc gga caa      8469
Gly Gly  Tyr Gly Arg Gly Gly  Tyr Gly Gln Gly Gly  Ala Gly Gln
    2810                2815                2820

ggt gga  gct gga gca gca gca  gcg gca gca gca gcc  gga ggt gca      8514
Gly Gly  Ala Gly Ala Ala Ala  Ala Ala Ala Ala Ala  Gly Gly Ala
    2825                2830                2835

ggt caa  gga gga caa ggt ggc  tat gga caa gga ggt  tac ggt caa      8559
Gly Gln  Gly Gly Gln Gly Gly  Tyr Gly Gln Gly Gly  Tyr Gly Gln
    2840                2845                2850

gga ggt  gca gga caa ggt gga  gcc gca gcg gca gca  gca gca gct      8604
Gly Gly  Ala Gly Gln Gly Gly  Ala Ala Ala Ala Ala  Ala Ala Ala
    2855                2860                2865

ggt gga  gca gga caa gga gga  tat ggc aga ggt gga  gca gga caa      8649
Gly Gly  Ala Gly Gln Gly Gly  Tyr Gly Arg Gly Gly  Ala Gly Gln
    2870                2875                2880

ggt gga  gca gca gca gcc gct  gct gca gcc gct gga  gct ggt caa      8694
Gly Gly  Ala Ala Ala Ala Ala  Ala Ala Ala Ala Gly  Ala Gly Gln
    2885                2890                2895

ggt ggt  tat gga ggt caa ggt  gcc gga caa ggt gga  gct gga gct      8739
Gly Gly  Tyr Gly Gly Gln Gly  Ala Gly Gln Gly Gly  Ala Gly Ala
    2900                2905                2910

gca gcc  gca gca gca gca gcc  gga ggt gca ggt caa  gga gga caa      8784
Ala Ala  Ala Ala Ala Ala Ala  Gly Gly Ala Gly Gln  Gly Gly Gln
    2915                2920                2925

ggt ggc  tat gga cga gga ggt  tac ggt caa gga ggt  gcc gga caa      8829
Gly Gly  Tyr Gly Arg Gly Gly  Tyr Gly Gln Gly Gly  Ala Gly Gln
    2930                2935                2940

ggc gga  gct gga gca gca gca  gcc gga ggt gca ggt  caa gga gga      8874
Gly Gly  Ala Gly Ala Ala Ala  Ala Gly Gly Ala Gly  Gln Gly Gly
    2945                2950                2955

caa ggt  ggc tat gga caa gga  ggt tac ggt caa gga  ggt gcc gga      8919
Gln Gly  Gly Tyr Gly Gln Gly  Gly Tyr Gly Gln Gly  Gly Ala Gly
    2960                2965                2970

caa ggt  gga gct gca gcc gca  gcg gca gca gct gca  gct gga gga      8964
Gln Gly  Gly Ala Ala Ala Ala  Ala Ala Ala Ala Ala  Ala Gly Gly
    2975                2980                2985

gca gga  caa gga gga tat ggt  gga tac ggt caa caa  ggt gga gca      9009
Ala Gly  Gln Gly Gly Tyr Gly  Gly Tyr Gly Gln Gln  Gly Gly Ala
```

```
    2990                2995                3000

gga gcc  gca gca gca gct gct  agt gga cct ggt caa  att tat tat      9054
Gly Ala  Ala Ala Ala Ala Ala  Ser Gly Pro Gly Gln  Ile Tyr Tyr
    3005                3010                3015

gga ccc  caa tct gtt gct gct  cca gca gca gca gca  gct tct gct      9099
Gly Pro  Gln Ser Val Ala Ala  Pro Ala Ala Ala Ala  Ala Ser Ala
    3020                3025                3030

ttg gca  gct cca gct aca agc  gcg aga att tct tca  cac gcc tca      9144
Leu Ala  Ala Pro Ala Thr Ser  Ala Arg Ile Ser Ser  His Ala Ser
    3035                3040                3045

gct ctt  ctt tca aat gga cct  act aac cct gct tct  att tca aac      9189
Ala Leu  Leu Ser Asn Gly Pro  Thr Asn Pro Ala Ser  Ile Ser Asn
    3050                3055                3060

gtt att  agt aat gct gta tcc  caa att agt tcc agc  aat cca gga      9234
Val Ile  Ser Asn Ala Val Ser  Gln Ile Ser Ser Ser  Asn Pro Gly
    3065                3070                3075

gcg tct  gcg tgt gat gtt ctc  gtt caa gct ctt ctt  gaa ctt gtt      9279
Ala Ser  Ala Cys Asp Val Leu  Val Gln Ala Leu Leu  Glu Leu Val
    3080                3085                3090

act gct  ttg ctc acc att att  gga tca tca aat att  ggc agt gtt      9324
Thr Ala  Leu Leu Thr Ile Ile  Gly Ser Ser Asn Ile  Gly Ser Val
    3095                3100                3105

aat tat  gat tct tca ggc caa  tat gcg caa gtt gtt  act caa tct      9369
Asn Tyr  Asp Ser Ser Gly Gln  Tyr Ala Gln Val Val  Thr Gln Ser
    3110                3115                3120

gtt caa  aat gca ttc gct tga                                        9390
Val Gln  Asn Ala Phe Ala
    3125


<210> SEQ ID NO 2
<211> LENGTH: 3129
<212> TYPE: PRT
<213> ORGANISM: Latrodectus hesperus

<400> SEQUENCE: 2

Met Thr Trp Ser Thr Arg Leu Ala Leu Ser Phe Leu Phe Val Leu Cys
1               5                   10                  15

Thr Gln Ser Leu Tyr Ala Leu Ala Gln Ala Asn Thr Pro Trp Ser Ser
            20                  25                  30

Lys Ala Asn Ala Asp Ala Phe Ile Asn Ser Phe Ile Ser Ala Ala Ser
        35                  40                  45

Asn Thr Gly Ser Phe Ser Gln Asp Gln Met Glu Asp Met Ser Leu Ile
    50                  55                  60

Gly Asn Thr Leu Met Ala Ala Met Asp Asn Met Gly Gly Arg Ile Thr
65                  70                  75                  80

Pro Ser Lys Leu Gln Ala Leu Asp Met Ala Phe Ala Ser Ser Val Ala
                85                  90                  95

Glu Ile Ala Ala Ser Glu Gly Gly Asp Leu Gly Val Thr Thr Asn Ala
            100                 105                 110

Ile Ala Asp Ala Leu Thr Ser Ala Phe Tyr Gln Thr Thr Gly Val Val
        115                 120                 125

Asn Ser Arg Phe Ile Ser Glu Ile Arg Ser Leu Ile Gly Met Phe Ala
    130                 135                 140

Gln Ala Ser Ala Asn Asp Val Tyr Ala Ser Ala Gly Ser Ser Gly Gly
145                 150                 155                 160

Gly Gly Tyr Gly Ala Ser Ser Ala Ser Ala Ala Ser Ala Ser Ala Ala
                165                 170                 175
```

-continued

```
Ala Pro Ser Gly Val Ala Tyr Gln Ala Pro Ala Gln Ala Gln Ile Ser
            180                 185                 190

Phe Thr Leu Arg Gly Gln Gln Pro Val Ser Tyr Gly Gln Gly Gly Ala
        195                 200                 205

Gly Pro Gly Gly Ala Gly Ala Ala Ala Ala Ala Ala Ala Ala Ala Gly
    210                 215                 220

Gly Ala Gly Gln Gly Gly Gln Gly Gly Tyr Gly Gln Gly Gly Tyr Gly
225                 230                 235                 240

Gln Gly Gly Ala Gly Gln Gly Gly Ser Gly Ala Ala Ala Ala Ala Ala
                245                 250                 255

Ala Ala Ala Gly Gly Thr Gly Gln Gly Gly Ala Gly Gln Gly Gly Ala
            260                 265                 270

Gly Ala Ala Ala Ala Ala Ala Ala Ala Ala Gly Gly Ala Gly Gln Gly
        275                 280                 285

Gly Gln Gly Gly Tyr Gly Gln Gly Gly Tyr Gly Gln Gly Gly Thr Gly
    290                 295                 300

Gln Gly Gly Ala Gly Ala Ala Ala Ala Ala Ala Ala Ala Gly Gly Ala
305                 310                 315                 320

Gly Gln Gly Gly Gln Gly Gly Tyr Gly Gln Gly Gly Tyr Gly Gln Gly
                325                 330                 335

Gly Tyr Gly Gln Gly Gly Ser Gly Ala Ala Ala Ala Ala Ala Ala Ala
            340                 345                 350

Ala Gly Gly Ala Gly Gln Gly Gly Gln Gly Gly Tyr Gly Gln Gly Gly
        355                 360                 365

Tyr Gly Gln Gly Gly Ala Gly Gln Gly Gly Ala Gly Ala Ala Ala Ala
    370                 375                 380

Ala Ala Ala Ala Ala Gly Gly Ala Gly Gln Gly Gly Tyr Gly Arg Gly
385                 390                 395                 400

Gly Ala Gly Gln Gly Gly Ala Ala Ala Ala Ala Ala Ala Ala Ala Gly
                405                 410                 415

Ala Gly Gln Gly Gly Tyr Gly Gly Gln Gly Ala Gly Gln Gly Gly Ser
            420                 425                 430

Gly Ala Ala Ala Ala Ala Ala Ala Ala Gly Gly Ala Gly Gln Gly Gly
        435                 440                 445

Gln Gly Gly Tyr Gly Gln Gly Gly Tyr Gly Gln Gly Gly Ser Gly Ala
    450                 455                 460

Ala Ala Ala Ala Ala Ala Ala Gly Gly Ala Gly Gln Gly Gly Gln Gly
465                 470                 475                 480

Gly Tyr Gly Gln Gly Gly Tyr Gly Gln Gly Gly Ala Gly Gln Gly Gly
                485                 490                 495

Ala Gly Ala Ala Ala Ala Ala Ala Ala Ala Gly Gly Ala Gly Gln Gly
            500                 505                 510

Gly Gln Gly Gly Tyr Gly Gln Gly Gly Tyr Gly Gln Gly Gly Ala Gly
        515                 520                 525

Gln Gly Gly Ala Gly Ala Ala Ala Ala Ala Ala Ala Ala Gly Gly Ala
    530                 535                 540

Gly Gln Gly Gly Gln Gly Gly Tyr Gly Gln Gly Gly Tyr Gly Gln Gly
545                 550                 555                 560

Gly Ala Gly Gln Gly Gly Ala Gly Ala Ala Ala Ala Ala Ala Ala Ala
                565                 570                 575

Gly Gly Ala Gly Gln Gly Gly Gln Gly Gly Tyr Gly Gln Gly Gly Tyr
            580                 585                 590

Gly Gln Gly Gly Ala Gly Gln Gly Gly Ala Ala Ala Ala Ala Ala Ala
```

-continued

```
        595                 600                 605

Ala Ala Gly Gly Ala Gly Gln Gly Gly Tyr Gly Arg Gly Gly Ala Gly
    610                 615                 620

Gln Gly Gly Ala Ala Ala Ala Ala Gly Ala Gly Gln Gly Gly Tyr Gly
625                 630                 635                 640

Gly Gln Gly Ala Gly Gln Gly Gly Ala Gly Ala Ala Ala Ala Ala Ala
                645                 650                 655

Ala Ala Gly Gly Ala Gly Gln Gly Gly Gln Gly Gly Tyr Gly Arg Gly
            660                 665                 670

Gly Tyr Gly Gln Gly Gly Ala Gly Gln Gly Gly Ala Gly Ala Ala Ala
        675                 680                 685

Ala Ala Ala Ala Ala Gly Gly Ala Gly Gln Gly Gly Gln Gly Gly Tyr
    690                 695                 700

Gly Gln Gly Gly Tyr Gly Gln Gly Gly Ala Gly Gln Gly Gly Ala Ala
705                 710                 715                 720

Ala Ala Ala Ala Ala Ala Gly Gly Ala Gly Gln Gly Gly Tyr Gly Arg
                725                 730                 735

Gly Gly Ala Gly Gln Gly Gly Ala Ala Ala Ala Ala Ala Ala Ala Ala
            740                 745                 750

Gly Ala Gly Gln Gly Gly Tyr Gly Gly Gln Gly Ala Gly Gln Gly Gly
        755                 760                 765

Ala Gly Ala Ala Ala Ala Ala Ala Ala Ala Gly Gly Ala Gly Gln Gly
    770                 775                 780

Gly Gln Gly Asp Tyr Gly Arg Gly Gly Tyr Gly Gln Gly Gly Ala Gly
785                 790                 795                 800

Gln Gly Gly Ala Gly Ala Ala Ala Ala Ala Ala Ala Ala Gly Gly Ala
                805                 810                 815

Gly Gln Gly Gly Gln Gly Gly Tyr Gly Gln Gly Gly Tyr Gly Gln Gly
            820                 825                 830

Gly Ala Gly Gln Gly Gly Ala Ala Ala Ala Ala Ser Ala Ala Ala Ala
        835                 840                 845

Gly Gly Ala Gly Gln Gly Gly Tyr Gly Arg Gly Gly Ala Gly Gln Gly
    850                 855                 860

Gly Ala Ala Ala Ala Ala Gly Ala Gly Gln Gly Gly Tyr Gly Gly Gln
865                 870                 875                 880

Gly Ala Gly Gln Gly Gly Ala Gly Ala Ala Ala Ala Ala Ala Ala Ala
                885                 890                 895

Gly Gly Ala Gly Gln Gly Gly Gln Gly Gly Tyr Gly Arg Gly Gly Tyr
            900                 905                 910

Gly Gln Gly Gly Ala Gly Gln Gly Gly Ala Gly Ala Ala Ala Ala Ala
        915                 920                 925

Thr Ala Ala Gly Gly Ala Gly Gln Gly Gly Gln Gly Gly Tyr Gly Gln
    930                 935                 940

Gly Gly Tyr Gly Gln Gly Gly Ala Gly Gln Gly Gly Ala Ala Ala Ala
945                 950                 955                 960

Ala Ala Ala Ala Ala Gly Gly Ala Gly Gln Gly Gly Tyr Gly Arg Gly
                965                 970                 975

Gly Ala Gly Gln Gly Gly Ala Ala Ala Ala Ala Ala Ala Ala Ala Gly
            980                 985                 990

Ala Gly Gln Gly Gly Tyr Gly Gly  Gln Gly Ala Gly Gln  Gly Gly Ala
        995                 1000                1005

Gly Ala  Ala Ala Ala Ala Ala  Gly Gly Ala Gly Gln  Gly Gly Gln
    1010                1015                1020
```

-continued

```
Gly Gly  Tyr Gly Arg Gly Gly  Tyr Gly Gln Gly Gly  Ala Gly Gln
    1025                 1030                 1035

Gly Gly  Ala Gly Ala Ala Ala  Ala Ala Ala Ala Ala  Gly Gly Ala
    1040                 1045                 1050

Gly Gln  Gly Gly Gln Gly Gly  Tyr Gly Gln Gly Gly  Tyr Gly Gln
    1055                 1060                 1065

Gly Gly  Ala Gly Gln Gly Gly  Ala Ala Ala Ala Ala  Ala Ala Ala
    1070                 1075                 1080

Ala Gly  Gly Ala Gly Gln Gly  Gly Tyr Gly Arg Gly  Gly Ala Gly
    1085                 1090                 1095

Gln Gly  Gly Ala Ala Ala Ala  Ala Gly Ala Gly Gln  Gly Gly Tyr
    1100                 1105                 1110

Gly Gly  Gln Gly Ala Gly Gln  Gly Gly Ala Gly Ala  Ala Ala Ala
    1115                 1120                 1125

Ala Ser  Arg Gly Ala Gly Gln  Gly Gly Gln Gly Gly  Tyr Gly Arg
    1130                 1135                 1140

Gly Gly  Tyr Gly Gln Gly Gly  Ala Gly Gln Gly Gly  Ala Gly Ala
    1145                 1150                 1155

Ala Ala  Ala Ala Ala Ala Ala  Gly Gly Ala Gly Gln  Gly Gly Gln
    1160                 1165                 1170

Gly Gly  Tyr Gly Gln Gly Gly  Tyr Gly Gln Gly Gly  Ala Gly Gln
    1175                 1180                 1185

Gly Gly  Ala Ala Ala Ala Ala  Ala Ala Ala Gly Gly  Ala Gly Gln
    1190                 1195                 1200

Gly Gly  Tyr Gly Arg Gly Gly  Ala Gly Gln Gly Gly  Ala Ala Ala
    1205                 1210                 1215

Ala Ala  Gly Ala Gly Gln Gly  Gly Tyr Gly Gly Gln  Gly Ala Gly
    1220                 1225                 1230

Gln Gly  Gly Ala Gly Ala Ala  Ala Ala Ala Ala Ala  Ala Gly Gly
    1235                 1240                 1245

Ala Gly  Gln Gly Gly Gln Gly  Gly Tyr Gly Arg Gly  Gly Tyr Gly
    1250                 1255                 1260

Gln Gly  Gly Ala Gly Gln Gly  Gly Ala Gly Ala Ala  Ala Ala Ala
    1265                 1270                 1275

Ala Ala  Ala Gly Gly Ala Gly  Gln Gly Gly Gln Gly  Gly Tyr Gly
    1280                 1285                 1290

Gln Gly  Gly Tyr Gly Gln Gly  Gly Ala Gly Gln Gly  Gly Ala Ala
    1295                 1300                 1305

Ala Ala  Ala Ala Ala Ala Ala  Gly Gly Ala Gly Gln  Gly Gly Tyr
    1310                 1315                 1320

Gly Arg  Gly Gly Ala Gly Gln  Gly Gly Ala Ala Ala  Ala Ala Ala
    1325                 1330                 1335

Ala Ala  Ala Gly Ser Gly Gln  Gly Gly Tyr Gly Gly  Gln Gly Ala
    1340                 1345                 1350

Gly Gln  Gly Gly Ala Gly Ala  Ala Ala Ala Ala Ala  Ala Ala Gly
    1355                 1360                 1365

Gly Ala  Gly Gln Gly Gly Gln  Gly Gly Tyr Gly Arg  Gly Gly Tyr
    1370                 1375                 1380

Gly Gln  Gly Gly Ala Gly Gln  Gly Gly Ala Gly Ala  Ala Ala Ala
    1385                 1390                 1395

Ala Ala  Ala Ala Gly Gly Ala  Gly Gln Gly Gly Gln  Gly Gly Tyr
    1400                 1405                 1410
```

-continued

```
Gly Gln  Gly Gly Tyr Gly Gln  Gly Gly Ala Gly Gln  Gly Gly Ala
    1415                 1420                 1425

Ala Ala  Ala Ala Ala Ala Ala  Ala Ala Gly Gly Ala  Gly Gln Gly
    1430                 1435                 1440

Gly Tyr  Gly Arg Gly Gly Ala  Gly Gln Gly Gly Ala  Ala Ala Ala
    1445                 1450                 1455

Ala Gly  Ala Gly Gln Gly Gly  Tyr Gly Gly Gln Gly  Ala Gly Gln
    1460                 1465                 1470

Gly Gly  Ala Gly Ala Ala Ala  Ala Ala Ala Ala Ala  Gly Gly Ala
    1475                 1480                 1485

Gly Gln  Gly Gly Gln Gly Gly  Tyr Gly Arg Gly Gly  Tyr Gly Gln
    1490                 1495                 1500

Gly Gly  Ala Gly Gln Gly Gly  Ala Gly Thr Ala Ala  Ala Ala Ala
    1505                 1510                 1515

Ala Ala  Gly Gly Ala Gly Gln  Gly Gly Gln Gly Gly  Tyr Gly Gln
    1520                 1525                 1530

Gly Gly  Tyr Gly Gln Gly Gly  Ala Gly Gln Gly Gly  Ala Ala Ala
    1535                 1540                 1545

Ala Ala  Ala Ala Ala Ala Gly  Gly Ala Gly Gln Gly  Gly Tyr Gly
    1550                 1555                 1560

Arg Gly  Gly Ala Gly Gln Gly  Gly Ala Ala Ala Ala  Ala Ala Ala
    1565                 1570                 1575

Ala Ala  Gly Ala Gly Gln Gly  Gly Tyr Gly Gly Gln  Gly Ala Gly
    1580                 1585                 1590

Gln Gly  Gly Ala Gly Ala Ala  Ala Ala Ala Ala Ala  Ala Gly Gly
    1595                 1600                 1605

Ala Gly  Gln Gly Gly Gln Gly  Gly Tyr Gly Arg Gly  Gly Tyr Gly
    1610                 1615                 1620

Gln Gly  Gly Ala Gly Gln Gly  Gly Ala Gly Ala Ala  Ala Ala Ala
    1625                 1630                 1635

Ala Ala  Ala Gly Gly Ala Ser  Gln Gly Gly Gln Gly  Gly Tyr Gly
    1640                 1645                 1650

Gln Gly  Asp Tyr Gly Gln Gly  Gly Ala Gly Gln Gly  Gly Ala Ala
    1655                 1660                 1665

Ala Ala  Ala Ala Ala Ala Gly  Gly Ala Gly Gln Gly  Gly Tyr Gly
    1670                 1675                 1680

Arg Gly  Gly Ala Gly Gln Gly  Gly Ala Ala Ala Ala  Ala Gly Ala
    1685                 1690                 1695

Gly Gln  Gly Gly Tyr Gly Gly  Gln Gly Ala Gly Gln  Gly Gly Ala
    1700                 1705                 1710

Gly Ala  Ala Ala Ala Ala Ala  Ala Ala Gly Gly Ala  Gly Arg Gly
    1715                 1720                 1725

Gly Gln  Gly Gly Tyr Gly Arg  Gly Gly Tyr Gly Gln  Gly Gly Ala
    1730                 1735                 1740

Gly Gln  Gly Gly Ala Gly Ala  Ala Ala Ala Ala Ala  Ala Ala Gly
    1745                 1750                 1755

Gly Ala  Gly Gln Gly Gly Gln  Gly Gly Tyr Gly Gln  Gly Gly Tyr
    1760                 1765                 1770

Gly Gln  Gly Gly Thr Gly Gln  Gly Gly Ala Ala Ala  Ala Ala Ala
    1775                 1780                 1785

Ala Ala  Ala Gly Gly Ala Gly  Gln Gly Gly Tyr Gly  Arg Gly Gly
    1790                 1795                 1800

Ala Gly  Gln Gly Gly Ala Ala  Ala Ala Ala Ala Ala  Ala Ala Gly
```

-continued

```
    1805                1810                1815

Ala Gly  Gln Gly Gly Tyr Gly  Gly Gln Gly Ala Gly  Gln Gly Gly
    1820                1825                1830

Ala Gly  Ala Ala Ala Ala Ala  Ala Ala Ala Gly Gly  Ala Gly Gln
    1835                1840                1845

Gly Gly  Gln Gly Gly Tyr Gly  Arg Gly Gly Tyr Gly  Gln Gly Gly
    1850                1855                1860

Ala Gly  Gln Gly Gly Ala Gly  Ala Ala Ala Ala Ala  Ala Ala Ala
    1865                1870                1875

Gly Gly  Ala Gly Gln Gly Gly  Gln Gly Gly Tyr Gly  Gln Gly Gly
    1880                1885                1890

Tyr Gly  Gln Gly Gly Tyr Gly  Gln Gly Gly Ala Gly  Gln Gly Gly
    1895                1900                1905

Ala Ala  Ala Ala Ala Ala Ala  Ala Gly Gly Ala Gly  Gln Gly Gly
    1910                1915                1920

Tyr Gly  Arg Gly Gly Ala Gly  Gln Gly Gly Ala Ala  Ala Ala Ala
    1925                1930                1935

Gly Ala  Gly Gln Gly Gly Tyr  Gly Gly Gln Gly Ala  Gly Gln Gly
    1940                1945                1950

Gly Ala  Gly Ala Ala Ala Ala  Ala Ala Ala Ala Gly  Gly Ala Gly
    1955                1960                1965

Gln Gly  Gly Gln Gly Gly Tyr  Gly Arg Gly Gly Tyr  Gly Gln Gly
    1970                1975                1980

Gly Ala  Gly Gln Gly Gly Ala  Gly Ala Ala Ala Ala  Ala Ala Ala
    1985                1990                1995

Ala Gly  Gly Ala Gly Gln Gly  Gly Gln Gly Gly Tyr  Gly Gln Gly
    2000                2005                2010

Gly Tyr  Gly Gln Gly Gly Ala  Gly Gln Gly Gly Ala  Ala Ala Ala
    2015                2020                2025

Ala Ala  Ala Ala Ala Gly Gly  Ala Gly Gln Gly Gly  Tyr Gly Arg
    2030                2035                2040

Gly Gly  Ala Gly Gln Gly Gly  Ala Ala Ala Ala Ala  Ala Ala Ala
    2045                2050                2055

Ala Gly  Ser Gly Gln Gly Gly  Tyr Gly Gly Gln Gly  Ala Gly Gln
    2060                2065                2070

Gly Gly  Ala Gly Ala Ala Ala  Ala Ala Ala Ala Ala  Gly Gly Ala
    2075                2080                2085

Gly Gln  Gly Gly Gln Gly Gly  Tyr Gly Arg Gly Gly  Tyr Gly Gln
    2090                2095                2100

Gly Gly  Ala Gly Gln Gly Gly  Ala Gly Ala Ala Ala  Ala Ala Ala
    2105                2110                2115

Ala Ala  Gly Gly Ala Gly Gln  Gly Gly Gln Gly Gly  Tyr Gly Gln
    2120                2125                2130

Gly Gly  Tyr Gly Gln Gly Gly  Tyr Gly Gln Gly Gly  Ala Gly Gln
    2135                2140                2145

Gly Gly  Ala Ala Ala Ala Ala  Ala Ala Ala Ala Ala  Gly Gly Ala
    2150                2155                2160

Gly Gln  Gly Gly Tyr Gly Arg  Gly Gly Ala Gly Gln  Gly Gly Ala
    2165                2170                2175

Ala Ala  Ala Ala Gly Ala Gly  Gln Gly Gly Tyr Gly  Gly Gln Gly
    2180                2185                2190

Ala Gly  Gln Gly Gly Ala Gly  Ala Ala Ala Ala Ala  Ala Ala Ala
    2195                2200                2205
```

```
Gly Gly  Ala Gly Gln Gly Gly  Gln Gly Gly Tyr Gly  Arg Gly Gly
    2210                 2215                 2220

Tyr Gly  Gln Gly Gly Ala Gly  Gln Gly Gly Ala Gly  Ala Ala Ala
    2225                 2230                 2235

Ala Ala  Ala Ala Ala Gly Gly  Ala Gly Gln Gly Gly  Gln Gly Gly
    2240                 2245                 2250

Tyr Gly  Gln Gly Gly Asn Gly  Gln Gly Gly Ala Gly  Gln Gly Gly
    2255                 2260                 2265

Ala Ala  Ala Ala Ala Ala Ala  Ala Gly Gly Ala Gly  Gln Gly Gly
    2270                 2275                 2280

Tyr Gly  Arg Gly Gly Ala Gly  Gln Gly Gly Ala Ala  Ala Ala Ala
    2285                 2290                 2295

Ala Ala  Ala Ala Gly Ala Gly  Gln Gly Gly Tyr Gly  Gly Gln Gly
    2300                 2305                 2310

Ala Gly  Gln Gly Gly Ala Gly  Ala Ala Ala Ala Ala  Ala Ala Ala
    2315                 2320                 2325

Gly Gly  Ala Gly Gln Gly Gly  Gln Gly Gly Tyr Gly  Arg Gly Gly
    2330                 2335                 2340

Tyr Gly  Gln Gly Gly Ala Gly  Gln Gly Gly Ala Gly  Ala Ala Ala
    2345                 2350                 2355

Ala Ala  Ala Ala Ala Gly Gly  Ala Ser Gln Gly Gly  Gln Gly Gly
    2360                 2365                 2370

Tyr Gly  Gln Gly Asp Tyr Gly  Gln Gly Gly Ala Gly  Gln Gly Gly
    2375                 2380                 2385

Ala Ala  Ala Ala Ala Ala Ala  Ala Gly Gly Ala Gly  Gln Gly Gly
    2390                 2395                 2400

Tyr Gly  Arg Gly Gly Ala Gly  Gln Gly Gly Ala Ala  Ala Ala Ala
    2405                 2410                 2415

Gly Ala  Gly Gln Gly Gly Tyr  Gly Gly Gln Gly Ala  Gly Gln Gly
    2420                 2425                 2430

Gly Ala  Gly Ala Ala Ala Ala  Ala Ala Ala Ala Gly  Gly Ala Gly
    2435                 2440                 2445

Arg Gly  Gly Gln Gly Gly Tyr  Gly Arg Gly Gly Tyr  Gly Gln Gly
    2450                 2455                 2460

Gly Ala  Gly Gln Gly Gly Ala  Gly Ala Ala Ala Ala  Ala Ala Ala
    2465                 2470                 2475

Ala Gly  Gly Ala Gly Gln Gly  Gly Gln Gly Gly Tyr  Gly Gln Gly
    2480                 2485                 2490

Gly Tyr  Gly Gln Gly Gly Ala  Gly Gln Gly Gly Ala  Ala Ala Ala
    2495                 2500                 2505

Ala Ala  Ala Ala Ala Gly Gly  Ala Gly Gln Gly Gly  Tyr Gly Arg
    2510                 2515                 2520

Gly Gly  Ala Gly Gln Gly Gly  Ala Ala Ala Ala Ala  Gly Ala Gly
    2525                 2530                 2535

Gln Gly  Gly Tyr Gly Gly Gln  Gly Ala Gly Gln Gly  Gly Ala Gly
    2540                 2545                 2550

Ala Ala  Ala Ala Ala Ala Ala  Ala Gly Gly Ala Gly  Arg Gly Gly
    2555                 2560                 2565

Gln Gly  Gly Tyr Gly Arg Gly  Gly Tyr Gly Gln Gly  Gly Ala Gly
    2570                 2575                 2580

Gln Gly  Gly Ala Gly Ala Ala  Ala Ala Ala Ala Ala  Ala Gly Gly
    2585                 2590                 2595
```

```
Ala Gly  Gln Gly Gly Gln Gly  Gly Tyr Gly Gln Gly  Gly Tyr Gly
    2600                 2605                 2610

Gln Gly  Gly Ala Gly Gln Gly  Gly Ala Ala Ala Ala  Ala Ala Ala
    2615                 2620                 2625

Ala Val  Gly Gly Ala Gly Gln  Gly Gly Tyr Gly Arg  Gly Gly Ala
    2630                 2635                 2640

Gly Gln  Gly Gly Ala Ala Ala  Ala Ala Ala Ala Ala  Ala Ala Gly
    2645                 2650                 2655

Ser Gly  Gln Gly Gly Tyr Gly  Gly Gln Gly Ala Gly  Gln Gly Gly
    2660                 2665                 2670

Ala Gly  Ala Ala Ala Ala Ala  Ala Ala Ala Gly Gly  Ala Gly Gln
    2675                 2680                 2685

Gly Gly  Gln Gly Gly Tyr Gly  Gly Gly Gly Tyr Gly  Gln Gly Gly
    2690                 2695                 2700

Ala Gly  Gln Gly Gly Ala Gly  Ala Ala Ala Ala Ala  Ala Ala Ala
    2705                 2710                 2715

Gly Gly  Ala Gly Gln Gly Gly  Gln Gly Gly Tyr Gly  Gln Gly Gly
    2720                 2725                 2730

Tyr Gly  Gln Gly Gly Ala Gly  Gln Gly Gly Ala Ala  Ala Ala Ala
    2735                 2740                 2745

Ala Ala  Ala Ala Gly Gly Ala  Gly Gln Gly Gly Tyr  Gly Arg Gly
    2750                 2755                 2760

Gly Ala  Gly Gln Gly Gly Ala  Ala Ala Ala Thr Gly  Ala Gly Gln
    2765                 2770                 2775

Gly Gly  Tyr Gly Gly Gln Gly  Ala Gly Gln Gly Gly  Ala Gly Ala
    2780                 2785                 2790

Ala Ala  Ala Ala Ala Ala Ala  Gly Gly Ala Gly Gln  Gly Gly Gln
    2795                 2800                 2805

Gly Gly  Tyr Gly Arg Gly Gly  Tyr Gly Gln Gly Gly  Ala Gly Gln
    2810                 2815                 2820

Gly Gly  Ala Gly Ala Ala Ala  Ala Ala Ala Ala Ala  Gly Gly Ala
    2825                 2830                 2835

Gly Gln  Gly Gly Gln Gly Gly  Tyr Gly Gln Gly Gly  Tyr Gly Gln
    2840                 2845                 2850

Gly Gly  Ala Gly Gln Gly Gly  Ala Ala Ala Ala Ala  Ala Ala Ala
    2855                 2860                 2865

Gly Gly  Ala Gly Gln Gly Gly  Tyr Gly Arg Gly Gly  Ala Gly Gln
    2870                 2875                 2880

Gly Gly  Ala Ala Ala Ala Ala  Ala Ala Ala Ala Gly  Ala Gly Gln
    2885                 2890                 2895

Gly Gly  Tyr Gly Gly Gln Gly  Ala Gly Gln Gly Gly  Ala Gly Ala
    2900                 2905                 2910

Ala Ala  Ala Ala Ala Ala Ala  Gly Gly Ala Gly Gln  Gly Gly Gln
    2915                 2920                 2925

Gly Gly  Tyr Gly Arg Gly Gly  Tyr Gly Gln Gly Gly  Ala Gly Gln
    2930                 2935                 2940

Gly Gly  Ala Gly Ala Ala Ala  Ala Gly Gly Ala Gly  Gln Gly Gly
    2945                 2950                 2955

Gln Gly  Gly Tyr Gly Gln Gly  Gly Tyr Gly Gln Gly  Gly Ala Gly
    2960                 2965                 2970

Gln Gly  Gly Ala Ala Ala Ala  Ala Ala Ala Ala Ala  Ala Gly Gly
    2975                 2980                 2985

Ala Gly  Gln Gly Gly Tyr Gly  Gly Tyr Gly Gln Gln  Gly Gly Ala
```

-continued

```
    2990                2995                3000

Gly Ala  Ala Ala Ala Ala Ala  Ser Gly Pro Gly Gln  Ile Tyr Tyr
    3005                3010                3015

Gly Pro  Gln Ser Val Ala Ala  Pro Ala Ala Ala Ala  Ala Ser Ala
    3020                3025                3030

Leu Ala  Ala Pro Ala Thr Ser  Ala Arg Ile Ser Ser  His Ala Ser
    3035                3040                3045

Ala Leu  Leu Ser Asn Gly Pro  Thr Asn Pro Ala Ser  Ile Ser Asn
    3050                3055                3060

Val Ile  Ser Asn Ala Val Ser  Gln Ile Ser Ser Ser  Asn Pro Gly
    3065                3070                3075

Ala Ser  Ala Cys Asp Val Leu  Val Gln Ala Leu Leu  Glu Leu Val
    3080                3085                3090

Thr Ala  Leu Leu Thr Ile Ile  Gly Ser Ser Asn Ile  Gly Ser Val
    3095                3100                3105

Asn Tyr  Asp Ser Ser Gly Gln  Tyr Ala Gln Val Val  Thr Gln Ser
    3110                3115                3120

Val Gln  Asn Ala Phe Ala
    3125


<210> SEQ ID NO 3
<211> LENGTH: 11340
<212> TYPE: DNA
<213> ORGANISM: Latrodectus hesperus
<220> FEATURE:
<221> NAME/KEY: CDS
<222> LOCATION: (1)..(11340)

<400> SEQUENCE: 3

atg act aca atg aat tgg tct act cga ctt gtg ttg tca ata ctc gta       48
Met Thr Thr Met Asn Trp Ser Thr Arg Leu Val Leu Ser Ile Leu Val
1               5                   10                  15

gtg ctt tgc act cag agc ctc tgt gct ctg gga caa gca aac act ccg       96
Val Leu Cys Thr Gln Ser Leu Cys Ala Leu Gly Gln Ala Asn Thr Pro
            20                  25                  30

tgg tcc agt aaa gaa aac gct gac gct ttt ata ggc gca ttt atg aat      144
Trp Ser Ser Lys Glu Asn Ala Asp Ala Phe Ile Gly Ala Phe Met Asn
        35                  40                  45

gct gct tca caa agt gga gca ttt tca tcg gat cag ata gat gat atg      192
Ala Ala Ser Gln Ser Gly Ala Phe Ser Ser Asp Gln Ile Asp Asp Met
    50                  55                  60

tca gtt att agt aat aca ttg atg gct gca atg gac aac atg ggt gga      240
Ser Val Ile Ser Asn Thr Leu Met Ala Ala Met Asp Asn Met Gly Gly
65                  70                  75                  80

aga atc aca caa tca aaa tta cag gct tta gat atg gct ttt gca tca      288
Arg Ile Thr Gln Ser Lys Leu Gln Ala Leu Asp Met Ala Phe Ala Ser
                85                  90                  95

tcc gtg gca gaa ata gct gta gct gat ggc caa aac gtt gga gcc gct      336
Ser Val Ala Glu Ile Ala Val Ala Asp Gly Gln Asn Val Gly Ala Ala
            100                 105                 110

acg aat gcc ata tca gac gca tta cgg tca gcc ttc tat caa act acc      384
Thr Asn Ala Ile Ser Asp Ala Leu Arg Ser Ala Phe Tyr Gln Thr Thr
        115                 120                 125

gga gtg gta aac aat caa ttt att act ggg ata agt agc cta att ggc      432
Gly Val Val Asn Asn Gln Phe Ile Thr Gly Ile Ser Ser Leu Ile Gly
    130                 135                 140

atg ttt gcc caa gta tca ggc aat gaa gtt tct tat tca tca gct ggg      480
Met Phe Ala Gln Val Ser Gly Asn Glu Val Ser Tyr Ser Ser Ala Gly
145                 150                 155                 160
```

-continued

```
tca tcc agc gcc gca gct tca gaa gca gtc tca gca gga caa gga cca      528
Ser Ser Ser Ala Ala Ala Ser Glu Ala Val Ser Ala Gly Gln Gly Pro
                165                 170                 175

gca gca caa cca gtt tac gca cca agc gga gca agt gca gct gca gca      576
Ala Ala Gln Pro Val Tyr Ala Pro Ser Gly Ala Ser Ala Ala Ala Ala
            180                 185                 190

gcg gct agt gga gca gca cct gca ata caa caa gca tat gaa cga gga      624
Ala Ala Ser Gly Ala Ala Pro Ala Ile Gln Gln Ala Tyr Glu Arg Gly
        195                 200                 205

ggt tca gga tca gca gct gca gca gca ggc tca gga cca agt gga tac      672
Gly Ser Gly Ser Ala Ala Ala Ala Ala Gly Ser Gly Pro Ser Gly Tyr
    210                 215                 220

gga caa gga gca gga gga cca gga gga gca ggt gct gca gca gga gcg      720
Gly Gln Gly Ala Gly Gly Pro Gly Gly Ala Gly Ala Ala Ala Gly Ala
225                 230                 235                 240

gct gcc gca gga gga tct ggc cct gga gga tac gga caa gga cca gct      768
Ala Ala Ala Gly Gly Ser Gly Pro Gly Gly Tyr Gly Gln Gly Pro Ala
                245                 250                 255

gct tat ggc cca tca gga cct agt gga caa caa ggt tac gga cca ggt      816
Ala Tyr Gly Pro Ser Gly Pro Ser Gly Gln Gln Gly Tyr Gly Pro Gly
            260                 265                 270

gga tca gga gca gca gct gcc gca gcc gca gca gca ggc tca gga cct      864
Gly Ser Gly Ala Ala Ala Ala Ala Ala Ala Ala Ala Gly Ser Gly Pro
        275                 280                 285

agt gga tac gga cca gga gca ggt gga cca gga gga gca ggt gct gca      912
Ser Gly Tyr Gly Pro Gly Ala Gly Gly Pro Gly Gly Ala Gly Ala Ala
    290                 295                 300

gca gca gcg gct gcc gca gga gga tct ggc cct gga gga tac gga caa      960
Ala Ala Ala Ala Ala Ala Gly Gly Ser Gly Pro Gly Gly Tyr Gly Gln
305                 310                 315                 320

gga caa gct agt tat ggc ccg tca gga cct agt gga caa caa ggt tac     1008
Gly Gln Ala Ser Tyr Gly Pro Ser Gly Pro Ser Gly Gln Gln Gly Tyr
                325                 330                 335

gga cca ggt gga tca gga gca gca gct gcc gca gcc gca gca gca gga     1056
Gly Pro Gly Gly Ser Gly Ala Ala Ala Ala Ala Ala Ala Ala Ala Gly
            340                 345                 350

tca gga cct agt gga tac gga cca gga gca gct gca gca gct gcg gca     1104
Ser Gly Pro Ser Gly Tyr Gly Pro Gly Ala Ala Ala Ala Ala Ala Ala
        355                 360                 365

ggc agc gct gga cct gga aca caa caa gga tat gga cca gga gga tca     1152
Gly Ser Ala Gly Pro Gly Thr Gln Gln Gly Tyr Gly Pro Gly Gly Ser
    370                 375                 380

ggt gca gcc gct gcc gca ggt tca gga cct aga gga tac gga cca aga     1200
Gly Ala Ala Ala Ala Ala Gly Ser Gly Pro Arg Gly Tyr Gly Pro Arg
385                 390                 395                 400

gga cca gga gga gca ggt gca gca gca act gcc gca aga gga tct ggc     1248
Gly Pro Gly Gly Ala Gly Ala Ala Ala Thr Ala Ala Arg Gly Ser Gly
                405                 410                 415

cct gga gga tac gga caa gga cca gct ggt tat ggt aca tca gga cct     1296
Pro Gly Gly Tyr Gly Gln Gly Pro Ala Gly Tyr Gly Thr Ser Gly Pro
            420                 425                 430

agt aga caa caa ggt tac gga cca gga gga tct gga gca gca gcc gca     1344
Ser Arg Gln Gln Gly Tyr Gly Pro Gly Gly Ser Gly Ala Ala Ala Ala
        435                 440                 445

gca gct gcg gca gca ggt gga gca gga cct ggt aga caa caa gga tat     1392
Ala Ala Ala Ala Ala Gly Gly Ala Gly Pro Gly Arg Gln Gln Gly Tyr
    450                 455                 460

gga cca gga ggt tct gga gca gca gct gca aca gca gct ggt gga cca     1440
Gly Pro Gly Gly Ser Gly Ala Ala Ala Ala Thr Ala Ala Gly Gly Pro
```

-continued

```
465                 470                 475                 480

gga tat gta ggt caa caa agg tac gga cca gga gga gca ggt gca gca     1488
Gly Tyr Val Gly Gln Gln Arg Tyr Gly Pro Gly Gly Ala Gly Ala Ala
                485                 490                 495

gca gcg gca gca gct ggt agt gca gga cct agt aga caa caa gca tat     1536
Ala Ala Ala Ala Ala Gly Ser Ala Gly Pro Ser Arg Gln Gln Ala Tyr
            500                 505                 510

gga cca gga gga tca ggt cca gca gct gca aca gca gca gca ggc tca     1584
Gly Pro Gly Gly Ser Gly Pro Ala Ala Ala Thr Ala Ala Ala Gly Ser
        515                 520                 525

gga cct agt gga tac ggt cca gga gca agt gga cca gta gga gca gat     1632
Gly Pro Ser Gly Tyr Gly Pro Gly Ala Ser Gly Pro Val Gly Ala Asp
    530                 535                 540

gca gct gca gca gct gcg aca ggc agc gct gga cct gga aga caa caa     1680
Ala Ala Ala Ala Ala Ala Thr Gly Ser Ala Gly Pro Gly Arg Gln Gln
545                 550                 555                 560

gca tat gga cca gga gaa tct gga gca gca gcc gcg gca gca agt gga     1728
Ala Tyr Gly Pro Gly Glu Ser Gly Ala Ala Ala Ala Ala Ala Ser Gly
                565                 570                 575

gca gga cct ggt aga caa cta gga tat gga cca gga ggt tct gga gca     1776
Ala Gly Pro Gly Arg Gln Leu Gly Tyr Gly Pro Gly Gly Ser Gly Ala
            580                 585                 590

gca gcg gca gca gca gct ggt gga cca gga tat gga ggt caa caa ggt     1824
Ala Ala Ala Ala Ala Ala Gly Gly Pro Gly Tyr Gly Gly Gln Gln Gly
        595                 600                 605

tac ggt cca gga gga gca ggt gca gca gca gcg gcg gca gct ggt ggt     1872
Tyr Gly Pro Gly Gly Ala Gly Ala Ala Ala Ala Ala Ala Ala Gly Gly
    610                 615                 620

gca gga cct ggt aga caa caa aca tat gga cca gga gga tcc ggt gca     1920
Ala Gly Pro Gly Arg Gln Gln Thr Tyr Gly Pro Gly Gly Ser Gly Ala
625                 630                 635                 640

gca gca act gcc gca gga gga tct gga cct gga ggt tac gga caa gga     1968
Ala Ala Thr Ala Ala Gly Gly Ser Gly Pro Gly Gly Tyr Gly Gln Gly
                645                 650                 655

cca tca ggt tac ggc cca tca gga cct ggt gga caa caa ggt tac gga     2016
Pro Ser Gly Tyr Gly Pro Ser Gly Pro Gly Gly Gln Gln Gly Tyr Gly
            660                 665                 670

cca gga gga tct gga gca gca gca gcc gcg gca gca ggt gaa gca gga     2064
Pro Gly Gly Ser Gly Ala Ala Ala Ala Ala Ala Ala Gly Glu Ala Gly
        675                 680                 685

cct ggt aga caa caa gga tat gga cca aga ggt tct gga gca gca gcg     2112
Pro Gly Arg Gln Gln Gly Tyr Gly Pro Arg Gly Ser Gly Ala Ala Ala
    690                 695                 700

gca gca gca gct ggt gga cca gga tat gga ggt caa tca ggt tac gga     2160
Ala Ala Ala Ala Gly Gly Pro Gly Tyr Gly Gly Gln Ser Gly Tyr Gly
705                 710                 715                 720

cct gga gga gca ggt gca gca gca gcg gcg gca gct ggt ggt gca gga     2208
Pro Gly Gly Ala Gly Ala Ala Ala Ala Ala Ala Ala Gly Gly Ala Gly
                725                 730                 735

cct ggt aga caa caa gaa tat gga cca gga gga tca ggt gca gca gct     2256
Pro Gly Arg Gln Gln Glu Tyr Gly Pro Gly Gly Ser Gly Ala Ala Ala
            740                 745                 750

gca gca gcc gct gcc gca ggg tca gga cct agt gga tac gga cca gga     2304
Ala Ala Ala Ala Ala Ala Gly Ser Gly Pro Ser Gly Tyr Gly Pro Gly
        755                 760                 765

gca gca gga cca att gga cca gga gga gca ggt gca gct gcc gca gga     2352
Ala Ala Gly Pro Ile Gly Pro Gly Gly Ala Gly Ala Ala Ala Ala Gly
    770                 775                 780

gga tct gga cct gta ggt tac gga caa gga cca tca ggt tac ggc gca     2400
```

```
Gly Ser Gly Pro Val Gly Tyr Gly Gln Gly Pro Ser Gly Tyr Gly Ala
785                 790                 795                 800

tca gga act ggt gga gaa caa gat tat gga cca gga gga tct gga gca      2448
Ser Gly Thr Gly Gly Glu Gln Asp Tyr Gly Pro Gly Gly Ser Gly Ala
                805                 810                 815

gca gcc gca gca gct gcg gca gca ggt gga gca gga cct ggt aga caa      2496
Ala Ala Ala Ala Ala Ala Ala Ala Gly Gly Ala Gly Pro Gly Arg Gln
            820                 825                 830

caa gga tat gga cca gga ggt tct gga gca gca gcg gca gca gca gct      2544
Gln Gly Tyr Gly Pro Gly Gly Ser Gly Ala Ala Ala Ala Ala Ala Ala
        835                 840                 845

ggt gga cca gga tat gga ggt caa caa ggt tac gga cca gga gga gca      2592
Gly Gly Pro Gly Tyr Gly Gly Gln Gln Gly Tyr Gly Pro Gly Gly Ala
    850                 855                 860

ggt gca gca gca gcg gcg gca gct ggt ggt gca gga cct ggt aga caa      2640
Gly Ala Ala Ala Ala Ala Ala Ala Gly Gly Ala Gly Pro Gly Arg Gln
865                 870                 875                 880

caa cca tat gga cca gga gga gca ggt gca gca gca gct gcc gca gga      2688
Gln Pro Tyr Gly Pro Gly Gly Ala Gly Ala Ala Ala Ala Ala Ala Gly
                885                 890                 895

gga tct gga cct gga ggt tac gga caa gga cca tca ggt tac ggc gca      2736
Gly Ser Gly Pro Gly Gly Tyr Gly Gln Gly Pro Ser Gly Tyr Gly Ala
            900                 905                 910

tca gga cct ggt gga caa caa ggt ttc gga cca gga gga tct gga gca      2784
Ser Gly Pro Gly Gly Gln Gln Gly Phe Gly Pro Gly Gly Ser Gly Ala
        915                 920                 925

gca gca gcc gcg gca gca ggt gga gca gga cct ggt aga caa caa gga      2832
Ala Ala Ala Ala Ala Ala Gly Gly Ala Gly Pro Gly Arg Gln Gln Gly
    930                 935                 940

tat gga cca gga ggt tct gga gca gca gca gca gct ggt gga aca gga      2880
Tyr Gly Pro Gly Gly Ser Gly Ala Ala Ala Ala Ala Gly Gly Thr Gly
945                 950                 955                 960

tat gga ggt caa caa ggt tac gga cca gga gga gca ggt gca gca gca      2928
Tyr Gly Gly Gln Gln Gly Tyr Gly Pro Gly Gly Ala Gly Ala Ala Ala
                965                 970                 975

gcg gcg gca gct gct ggt gca gga cct ggt aga caa caa gaa tat gga      2976
Ala Ala Ala Ala Ala Gly Ala Gly Pro Gly Arg Gln Gln Glu Tyr Gly
            980                 985                 990

cca gga gga aca ggt gca gca gct  gca gca gcc gct gcc  gca ggg tca    3024
Pro Gly Gly Thr Gly Ala Ala Ala  Ala Ala Ala Ala Ala  Ala Gly Ser
        995                1000                 1005

gga cct  agt gga tac gga caa  gga gca gcc gga cca  agt gga cca      3069
Gly Pro  Ser Gly Tyr Gly Gln  Gly Ala Ala Gly Pro  Ser Gly Pro
    1010                 1015                 1020

gga gga  gaa ggt aca gca gca  gca gca gct gct gca  gga gga tct      3114
Gly Gly  Glu Gly Thr Ala Ala  Ala Ala Ala Ala Ala  Gly Gly Ser
    1025                 1030                 1035

gga cct  gga ggt tac gga caa  gga cca tca ggt tac  agc gca tca      3159
Gly Pro  Gly Gly Tyr Gly Gln  Gly Pro Ser Gly Tyr  Ser Ala Ser
    1040                 1045                 1050

gga cct  ggt gga caa caa gga  tac gga cca ggg gga  tct gga cta      3204
Gly Pro  Gly Gly Gln Gln Gly  Tyr Gly Pro Gly Gly  Ser Gly Leu
    1055                 1060                 1065

gca gcc  gca gca gct gcg gca  gca ggt gga gca gga  act ggt aga      3249
Ala Ala  Ala Ala Ala Ala Ala  Ala Gly Gly Ala Gly  Thr Gly Arg
    1070                 1075                 1080

caa caa  gga tat gga cct ggt  ggt tct gga gca gca  gcg gca gca      3294
Gln Gln  Gly Tyr Gly Pro Gly  Gly Ser Gly Ala Ala  Ala Ala Ala
    1085                 1090                 1095
```

-continued

```
gca gct  gtt gga cca gga tat  gga ggt caa caa ggt  tac gga cca      3339
Ala Ala  Val Gly Pro Gly Tyr  Gly Gly Gln Gln Gly  Tyr Gly Pro
    1100                 1105                 1110

gga gga  gca ggt gca gca gca  gct gcg gca gct ggt  ggt gca ggt      3384
Gly Gly  Ala Gly Ala Ala Ala  Ala Ala Ala Ala Gly  Gly Ala Gly
    1115                 1120                 1125

cct ggt  aga caa cag gca tat  gga cca gga gga tca  ggt gca aca      3429
Pro Gly  Arg Gln Gln Ala Tyr  Gly Pro Gly Gly Ser  Gly Ala Thr
    1130                 1135                 1140

gcc gct  gca gca gta gca ggg  tca gga cct agt gga  tac gga cca      3474
Ala Ala  Ala Ala Val Ala Gly  Ser Gly Pro Ser Gly  Tyr Gly Pro
    1145                 1150                 1155

gga gga  gca ggt gca gca gca  gca gct gcg gca ggc  ggc gct ggt      3519
Gly Gly  Ala Gly Ala Ala Ala  Ala Ala Ala Ala Gly  Gly Ala Gly
    1160                 1165                 1170

cct gga  aga caa caa gca tat  gga cca gga gga tct  gga gca gca      3564
Pro Gly  Arg Gln Gln Ala Tyr  Gly Pro Gly Gly Ser  Gly Ala Ala
    1175                 1180                 1185

gcc gcg  gca gca agt gga gca  gga cct ggt aga caa  caa gta tat      3609
Ala Ala  Ala Ala Ser Gly Ala  Gly Pro Gly Arg Gln  Gln Val Tyr
    1190                 1195                 1200

gga cca  ggt ggt tct gga gca  gca gcg gca gca gca  gct ggt gga      3654
Gly Pro  Gly Gly Ser Gly Ala  Ala Ala Ala Ala Ala  Ala Gly Gly
    1205                 1210                 1215

cca gga  tat gga ggt caa caa  ggt tac gga cca gga  gga gca ggt      3699
Pro Gly  Tyr Gly Gly Gln Gln  Gly Tyr Gly Pro Gly  Gly Ala Gly
    1220                 1225                 1230

gca gca  gct gcg gcg gca gct  ggt ggt gca gga caa  ggt aca aga      3744
Ala Ala  Ala Ala Ala Ala Ala  Gly Gly Ala Gly Gln  Gly Thr Arg
    1235                 1240                 1245

caa gca  tat gga cca gga gga  tca ggt gca gca gcc  gct gcc gca      3789
Gln Ala  Tyr Gly Pro Gly Gly  Ser Gly Ala Ala Ala  Ala Ala Ala
    1250                 1255                 1260

ggg cca  gga cct agt gga tac  gga cca gga gca gca  gga cca agt      3834
Gly Pro  Gly Pro Ser Gly Tyr  Gly Pro Gly Ala Ala  Gly Pro Ser
    1265                 1270                 1275

gga cca  gga tta gca ggt gca  gca gca gca gct gcc  gca gga gga      3879
Gly Pro  Gly Leu Ala Gly Ala  Ala Ala Ala Ala Ala  Ala Gly Gly
    1280                 1285                 1290

tct gga  cct gga ggt aat gga  caa aga cca tca ggt  tac ggc caa      3924
Ser Gly  Pro Gly Gly Asn Gly  Gln Arg Pro Ser Gly  Tyr Gly Gln
    1295                 1300                 1305

tca gga  act ggt gga caa caa  ggt tat gga cca gga  gga tct gga      3969
Ser Gly  Thr Gly Gly Gln Gln  Gly Tyr Gly Pro Gly  Gly Ser Gly
    1310                 1315                 1320

gca gcc  gct gca gca gcc gcg  gca gca ggt gga gcc  gga cct ggt      4014
Ala Ala  Ala Ala Ala Ala Ala  Ala Ala Gly Gly Ala  Gly Pro Gly
    1325                 1330                 1335

aga caa  caa gga tat gga cca  gga agt tct gga gca  gca gcg gca      4059
Arg Gln  Gln Gly Tyr Gly Pro  Gly Ser Ser Gly Ala  Ala Ala Ala
    1340                 1345                 1350

gca gca  gct ggt gga cca gga  tat gga ggt caa caa  ggt tac gga      4104
Ala Ala  Ala Gly Gly Pro Gly  Tyr Gly Gly Gln Gln  Gly Tyr Gly
    1355                 1360                 1365

cca gga  gga gca ggt gca gca  gct gcg gcg gca gct  ggt ggt gca      4149
Pro Gly  Gly Ala Gly Ala Ala  Ala Ala Ala Ala Ala  Gly Gly Ala
    1370                 1375                 1380

gga cct  ggt aca caa caa gca  tat gga cca gga gga  tct gga gca      4194
Gly Pro  Gly Thr Gln Gln Ala  Tyr Gly Pro Gly Gly  Ser Gly Ala
    1385                 1390                 1395
```

-continued

```
gca gct  gca gca gcc gcg gca  gca ggt gga gcc gga  cct ggt aga      4239
Ala Ala  Ala Ala Ala Ala Ala  Ala Gly Gly Ala Gly  Pro Gly Arg
    1400                 1405                 1410

caa caa  gga tat gga cca gga  agt tct gga gca gca  gcg gca gca      4284
Gln Gln  Gly Tyr Gly Pro Gly  Ser Ser Gly Ala Ala  Ala Ala Ala
    1415                 1420                 1425

gca gct  ggt gga cca gga tat  gga ggt caa caa ggt  tac gga cca      4329
Ala Ala  Gly Gly Pro Gly Tyr  Gly Gly Gln Gln Gly  Tyr Gly Pro
    1430                 1435                 1440

gga gga  gca ggt gca gca gca  gcg gcg gca gct gga  ggt gca gga      4374
Gly Gly  Ala Gly Ala Ala Ala  Ala Ala Ala Ala Gly  Gly Ala Gly
    1445                 1450                 1455

gct ggt  aga caa caa gca tat  gga cca gga gga tca  ggt gca gca      4419
Ala Gly  Arg Gln Gln Ala Tyr  Gly Pro Gly Gly Ser  Gly Ala Ala
    1460                 1465                 1470

gca gca  ggc tca gga cct agt  gga tac gaa cca gga  gca gct gga      4464
Ala Ala  Gly Ser Gly Pro Ser  Gly Tyr Glu Pro Gly  Ala Ala Gly
    1475                 1480                 1485

cca gga  gga gca ggt gca gct  gca gca gct gcg gct  gtc ggc gct      4509
Pro Gly  Gly Ala Gly Ala Ala  Ala Ala Ala Ala Ala  Val Gly Ala
    1490                 1495                 1500

gga cct  gga aga caa caa gca  tat gga caa ggt ggt  tct gga gca      4554
Gly Pro  Gly Arg Gln Gln Ala  Tyr Gly Gln Gly Gly  Ser Gly Ala
    1505                 1510                 1515

gta gcg  gca gca gca gct ggt  gga cca gga tat gga  ggt caa caa      4599
Val Ala  Ala Ala Ala Ala Gly  Gly Pro Gly Tyr Gly  Gly Gln Gln
    1520                 1525                 1530

ggt tac  gaa caa gga gga gca  ggt gca gca tca gcg  gcg gca gct      4644
Gly Tyr  Glu Gln Gly Gly Ala  Gly Ala Ala Ser Ala  Ala Ala Ala
    1535                 1540                 1545

gga ggt  gaa gga cct gct aga  caa caa gca tat gga  cca gga gga      4689
Gly Gly  Glu Gly Pro Ala Arg  Gln Gln Ala Tyr Gly  Pro Gly Gly
    1550                 1555                 1560

tca ggt  gca gca gct gca gca  gca ggt gga gca gga  cct ggt aga      4734
Ser Gly  Ala Ala Ala Ala Ala  Ala Gly Gly Ala Gly  Pro Gly Arg
    1565                 1570                 1575

caa caa  gga tat gga cca gga  agt tct gga gca gca  gcg gca gca      4779
Gln Gln  Gly Tyr Gly Pro Gly  Ser Ser Gly Ala Ala  Ala Ala Ala
    1580                 1585                 1590

gca gct  ggt gga cca gga tat  gga ggt caa caa ggt  tac gga cca      4824
Ala Ala  Gly Gly Pro Gly Tyr  Gly Gly Gln Gln Gly  Tyr Gly Pro
    1595                 1600                 1605

gga gga  gca ggt gca gca gca  gcg gcg gca gct ggt  ggt gca gga      4869
Gly Gly  Ala Gly Ala Ala Ala  Ala Ala Ala Ala Gly  Gly Ala Gly
    1610                 1615                 1620

cca ggt  aga caa caa gca tat  gga cca gga gga tca  ggt gca gca      4914
Pro Gly  Arg Gln Gln Ala Tyr  Gly Pro Gly Gly Ser  Gly Ala Ala
    1625                 1630                 1635

gct gca  gca gca gca ggc aca  gga cct agt gga tac  gga cca gga      4959
Ala Ala  Ala Ala Ala Gly Thr  Gly Pro Ser Gly Tyr  Gly Pro Gly
    1640                 1645                 1650

gca gct  gga ccg gga gga gca  ggt gca gct gca gca  gct gcg gca      5004
Ala Ala  Gly Pro Gly Gly Ala  Gly Ala Ala Ala Ala  Ala Ala Ala
    1655                 1660                 1665

ggc agc  gct gga cct gga aga  caa caa gca tat gga  cca ggt ggt      5049
Gly Ser  Ala Gly Pro Gly Arg  Gln Gln Ala Tyr Gly  Pro Gly Gly
    1670                 1675                 1680

tct gga  gca gca gcg gca gca  gct gct ggt gga cca  ggt tat gga      5094
Ser Gly  Ala Ala Ala Ala Ala  Ala Ala Gly Gly Pro  Gly Tyr Gly
```

```
    1685                1690                1695

ggt caa  caa ggt tac gga cca  gga gga gca ggt gca  gca gct gcg      5139
Gly Gln  Gln Gly Tyr Gly Pro  Gly Gly Ala Gly Ala  Ala Ala Ala
    1700                1705                1710

gcg gca  gct ggt ggt gca gga  cct ggt aca caa caa  gca tat gga      5184
Ala Ala  Ala Gly Gly Ala Gly  Pro Gly Thr Gln Gln  Ala Tyr Gly
    1715                1720                1725

cca gga  gga tct gga gca gca  gct gca gca gcc gcg  gca gca ggt      5229
Pro Gly  Gly Ser Gly Ala Ala  Ala Ala Ala Ala Ala  Ala Ala Gly
    1730                1735                1740

gga gca  gga cct gat aga caa  caa gga tat gga cca  gga agt tct      5274
Gly Ala  Gly Pro Asp Arg Gln  Gln Gly Tyr Gly Pro  Gly Ser Ser
    1745                1750                1755

gga gca  gca gcg gca gca gca  gct ggt gga cca gga  tat gga ggt      5319
Gly Ala  Ala Ala Ala Ala Ala  Ala Gly Gly Pro Gly  Tyr Gly Gly
    1760                1765                1770

caa caa  ggt tat gga cca gga  gga gca ggt gca gca  gct gct gca      5364
Gln Gln  Gly Tyr Gly Pro Gly  Gly Ala Gly Ala Ala  Ala Ala Ala
    1775                1780                1785

gcc gct  gcc gca ggg cca gga  cct agt gga tac gga  cca gga gga      5409
Ala Ala  Ala Ala Gly Pro Gly  Pro Ser Gly Tyr Gly  Pro Gly Gly
    1790                1795                1800

gca ggt  gca gca gca gca gca  gct gct gca gga gga  tct gga cct      5454
Ala Gly  Ala Ala Ala Ala Ala  Ala Ala Ala Gly Gly  Ser Gly Pro
    1805                1810                1815

gga ggt  tac gga caa gga cca  tca ggt tac agc gca  tca gga cct      5499
Gly Gly  Tyr Gly Gln Gly Pro  Ser Gly Tyr Ser Ala  Ser Gly Pro
    1820                1825                1830

ggt gga  caa caa gga tac gga  cca ggg gga tct gga  cta gca gcc      5544
Gly Gly  Gln Gln Gly Tyr Gly  Pro Gly Gly Ser Gly  Leu Ala Ala
    1835                1840                1845

gca gca  gct gcg gca gca ggt  gga gca gga act ggt  aga caa caa      5589
Ala Ala  Ala Ala Ala Ala Gly  Gly Ala Gly Thr Gly  Arg Gln Gln
    1850                1855                1860

gga tat  gga cct ggt ggt tct  gga gca gca gcg gca  gca gca gct      5634
Gly Tyr  Gly Pro Gly Gly Ser  Gly Ala Ala Ala Ala  Ala Ala Ala
    1865                1870                1875

gtt gga  cca gga tat gga ggt  caa caa ggt tac gga  cca gga gga      5679
Val Gly  Pro Gly Tyr Gly Gly  Gln Gln Gly Tyr Gly  Pro Gly Gly
    1880                1885                1890

gca ggt  gca gca gca gct gcg  gca gct ggt ggt gca  ggt cct ggt      5724
Ala Gly  Ala Ala Ala Ala Ala  Ala Ala Gly Gly Ala  Gly Pro Gly
    1895                1900                1905

aga caa  cag gca tat gga cca  gga gga tca ggt gca  aca gcc gct      5769
Arg Gln  Gln Ala Tyr Gly Pro  Gly Gly Ser Gly Ala  Thr Ala Ala
    1910                1915                1920

gca gca  gca gca ggg tca gga  cct agt gga tac gga  cca gga gga      5814
Ala Ala  Ala Ala Gly Ser Gly  Pro Ser Gly Tyr Gly  Pro Gly Gly
    1925                1930                1935

gca ggt  gca gca gca gca gct  gcg gca ggc ggc gct  ggt cct gga      5859
Ala Gly  Ala Ala Ala Ala Ala  Ala Ala Gly Gly Ala  Gly Pro Gly
    1940                1945                1950

aga caa  caa gca tat gga cca  gga gga tct gga gca  gca gcc gcg      5904
Arg Gln  Gln Ala Tyr Gly Pro  Gly Gly Ser Gly Ala  Ala Ala Ala
    1955                1960                1965

gca gca  agt gga gca gga cct  ggt aga caa caa gta  tat gga cca      5949
Ala Ala  Ser Gly Ala Gly Pro  Gly Arg Gln Gln Val  Tyr Gly Pro
    1970                1975                1980

gtt ggt  tct gga gca gca gcg  gca gca gca gct ggt  gga cca gga      5994
```

```
Val Gly  Ser Gly Ala Ala Ala  Ala Ala Ala Ala Gly  Gly Pro Gly
    1985                 1990                 1995

tat gga  ggt caa caa ggt tac  gga cca gga gga gca  ggt gca gca      6039
Tyr Gly  Gly Gln Gln Gly Tyr  Gly Pro Gly Gly Ala  Gly Ala Ala
    2000                 2005                 2010

gct gcg  gcg gca gct ggt ggt  gca gga caa ggt aca  aga caa gca      6084
Ala Ala  Ala Ala Ala Gly Gly  Ala Gly Gln Gly Thr  Arg Gln Ala
    2015                 2020                 2025

tat gga  cca gga gga tca ggt  gca gca gcc gct gcc  gca ggg cca      6129
Tyr Gly  Pro Gly Gly Ser Gly  Ala Ala Ala Ala Ala  Ala Gly Pro
    2030                 2035                 2040

gga cct  agt gga tac gga cca  gga gca gca gga cca  agt gga cca      6174
Gly Pro  Ser Gly Tyr Gly Pro  Gly Ala Ala Gly Pro  Ser Gly Pro
    2045                 2050                 2055

gga tta  gca ggt gca gca gca  gca gct gcc gca gga  gga tct gga      6219
Gly Leu  Ala Gly Ala Ala Ala  Ala Ala Ala Ala Gly  Gly Ser Gly
    2060                 2065                 2070

cct gga  ggt aat gga caa aga  cca tca ggt tac ggc  caa tca gga      6264
Pro Gly  Gly Asn Gly Gln Arg  Pro Ser Gly Tyr Gly  Gln Ser Gly
    2075                 2080                 2085

cct ggt  gga caa caa ggt tat  gga cca gga gga tct  gga gca gcc      6309
Pro Gly  Gly Gln Gln Gly Tyr  Gly Pro Gly Gly Ser  Gly Ala Ala
    2090                 2095                 2100

gct gca  gca gcc gcg gca gca  ggt gga gcc gga cct  ggt aga caa      6354
Ala Ala  Ala Ala Ala Ala Ala  Gly Gly Ala Gly Pro  Gly Arg Gln
    2105                 2110                 2115

caa gga  tat gga cca gga agt  tct gga gca gca gcg  gca gca gca      6399
Gln Gly  Tyr Gly Pro Gly Ser  Ser Gly Ala Ala Ala  Ala Ala Ala
    2120                 2125                 2130

gct ggt  gga cca gga tat gga  ggt caa caa ggt tac  gga cca gga      6444
Ala Gly  Gly Pro Gly Tyr Gly  Gly Gln Gln Gly Tyr  Gly Pro Gly
    2135                 2140                 2145

gga gca  ggt gca gca gct gcg  gcg gca gct ggt ggt  gca gga cct      6489
Gly Ala  Gly Ala Ala Ala Ala  Ala Ala Ala Gly Gly  Ala Gly Pro
    2150                 2155                 2160

ggt aca  caa caa gca tat gga  cca gga gga tct gga  gca gca gct      6534
Gly Thr  Gln Gln Ala Tyr Gly  Pro Gly Gly Ser Gly  Ala Ala Ala
    2165                 2170                 2175

gca gca  gcc gcg gca gca ggt  gga gcc gga cct ggt  aga caa caa      6579
Ala Ala  Ala Ala Ala Ala Gly  Gly Ala Gly Pro Gly  Arg Gln Gln
    2180                 2185                 2190

gga tat  gga cca gga agt tct  gga gca gca gcg gca  gca gca gct      6624
Gly Tyr  Gly Pro Gly Ser Ser  Gly Ala Ala Ala Ala  Ala Ala Ala
    2195                 2200                 2205

ggt gga  cca gga tat gga ggt  caa caa ggt tac gga  cca gga gga      6669
Gly Gly  Pro Gly Tyr Gly Gly  Gln Gln Gly Tyr Gly  Pro Gly Gly
    2210                 2215                 2220

gca ggt  gca gca gca gcg gcg  gca gct gga ggt gca  gga gct ggt      6714
Ala Gly  Ala Ala Ala Ala Ala  Ala Ala Gly Gly Ala  Gly Ala Gly
    2225                 2230                 2235

aga caa  caa gca tat gga cca  gga gga tca ggt gca  gca gca gca      6759
Arg Gln  Gln Ala Tyr Gly Pro  Gly Gly Ser Gly Ala  Ala Ala Ala
    2240                 2245                 2250

ggc tca  gga cct agt gga tac  gaa tca gga gca gct  gga cca gga      6804
Gly Ser  Gly Pro Ser Gly Tyr  Glu Ser Gly Ala Ala  Gly Pro Gly
    2255                 2260                 2265

gga gca  ggt gca gct gca gca  gct gcg gct gtc ggc  gct gga cct      6849
Gly Ala  Gly Ala Ala Ala Ala  Ala Ala Ala Val Gly  Ala Gly Pro
    2270                 2275                 2280
```

```
gga aga  caa caa gca tat gga  caa ggt ggt tct gga  gca gta gcg      6894
Gly Arg  Gln Gln Ala Tyr Gly  Gln Gly Gly Ser Gly  Ala Val Ala
    2285                 2290                 2295

gca gca  gca gct ggt gga cca  gga tat gga ggt caa  caa ggt tac      6939
Ala Ala  Ala Ala Gly Gly Pro  Gly Tyr Gly Gly Gln  Gln Gly Tyr
    2300                 2305                 2310

gaa caa  gga gga gca ggt gca  gca tca gcg gcg gca  gct gga ggt      6984
Glu Gln  Gly Gly Ala Gly Ala  Ala Ser Ala Ala Ala  Ala Gly Gly
    2315                 2320                 2325

gaa gga  cct gct aga caa caa  gca tat gga cca gga  gga tca ggt      7029
Glu Gly  Pro Ala Arg Gln Gln  Ala Tyr Gly Pro Gly  Gly Ser Gly
    2330                 2335                 2340

gca gca  gct gca gca gca ggt  gga gca gga cct ggt  aga caa caa      7074
Ala Ala  Ala Ala Ala Ala Gly  Gly Ala Gly Pro Gly  Arg Gln Gln
    2345                 2350                 2355

gga tat  gga cca gga agt tct  gga gca gca gcg gca  gca gca gct      7119
Gly Tyr  Gly Pro Gly Ser Ser  Gly Ala Ala Ala Ala  Ala Ala Ala
    2360                 2365                 2370

ggt gga  cca gga tat gga ggt  caa caa ggt tac gga  cca gga gga      7164
Gly Gly  Pro Gly Tyr Gly Gly  Gln Gln Gly Tyr Gly  Pro Gly Gly
    2375                 2380                 2385

gca ggt  gca gca gca gcg gcg  gca gct ggt ggt gca  gga cca ggt      7209
Ala Gly  Ala Ala Ala Ala Ala  Ala Ala Gly Gly Ala  Gly Pro Gly
    2390                 2395                 2400

aga caa  caa gca tat gga cca  gga gga tca ggt gca  gca gct gca      7254
Arg Gln  Gln Ala Tyr Gly Pro  Gly Gly Ser Gly Ala  Ala Ala Ala
    2405                 2410                 2415

gca gca  gca ggc aca gga cct  agt gga tac gga cca  gga gca gct      7299
Ala Ala  Ala Gly Thr Gly Pro  Ser Gly Tyr Gly Pro  Gly Ala Ala
    2420                 2425                 2430

gga ccg  gga gga gca ggt gca  gct gca gca gct gcg  gca ggc ggc      7344
Gly Pro  Gly Gly Ala Gly Ala  Ala Ala Ala Ala Ala  Ala Gly Gly
    2435                 2440                 2445

gct gga  cct gga aga caa caa  gca tat gga cca ggt  ggt tct gga      7389
Ala Gly  Pro Gly Arg Gln Gln  Ala Tyr Gly Pro Gly  Gly Ser Gly
    2450                 2455                 2460

gca gca  gcg gca gca gct gct  ggt gga cca ggt tat  gga ggt caa      7434
Ala Ala  Ala Ala Ala Ala Ala  Gly Gly Pro Gly Tyr  Gly Gly Gln
    2465                 2470                 2475

caa ggt  tac gga cca gga gga  gca ggt gca gca gct  gcg gcg gca      7479
Gln Gly  Tyr Gly Pro Gly Gly  Ala Gly Ala Ala Ala  Ala Ala Ala
    2480                 2485                 2490

gct ggt  ggt gca gga cct ggt  aca caa caa gca tat  gga cca gga      7524
Ala Gly  Gly Ala Gly Pro Gly  Thr Gln Gln Ala Tyr  Gly Pro Gly
    2495                 2500                 2505

gga tct  gga gca gca gct gca  gca gcc gcg gca gca  ggt gga gca      7569
Gly Ser  Gly Ala Ala Ala Ala  Ala Ala Ala Ala Ala  Gly Gly Ala
    2510                 2515                 2520

gga cct  gat aga caa caa gga  tat gga cca gga agt  tct gga gca      7614
Gly Pro  Asp Arg Gln Gln Gly  Tyr Gly Pro Gly Ser  Ser Gly Ala
    2525                 2530                 2535

gca gcg  gca gca gca gct ggt  gga cca gga tat gga  ggt caa caa      7659
Ala Ala  Ala Ala Ala Ala Gly  Gly Pro Gly Tyr Gly  Gly Gln Gln
    2540                 2545                 2550

ggt tat  gga cca gga gga gca  ggt gca gca gct gct  gca gcc gct      7704
Gly Tyr  Gly Pro Gly Gly Ala  Gly Ala Ala Ala Ala  Ala Ala Ala
    2555                 2560                 2565

gcc gca  ggg cca gga cct agt  gga tac gga cca gga  gga gca ggt      7749
Ala Ala  Gly Pro Gly Pro Ser  Gly Tyr Gly Pro Gly  Gly Ala Gly
    2570                 2575                 2580
```

```
gca gca  gca gca gca gct gcc  gca gga gga tct gga  cct gga ggt      7794
Ala Ala  Ala Ala Ala Ala Ala  Ala Gly Gly Ser Gly  Pro Gly Gly
    2585                 2590                 2595

tac gga  caa gga cca tca ggt  tac ggc cca tca gga  cct ggt gga      7839
Tyr Gly  Gln Gly Pro Ser Gly  Tyr Gly Pro Ser Gly  Pro Gly Gly
    2600                 2605                 2610

caa caa  ggt aac gga cca gga  gga tct gga gca gca  gct gca gca      7884
Gln Gln  Gly Asn Gly Pro Gly  Gly Ser Gly Ala Ala  Ala Ala Ala
    2615                 2620                 2625

gcc gcg  gca gca ggt gga gca  gga cct ggt aga caa  caa gga tat      7929
Ala Ala  Ala Ala Gly Gly Ala  Gly Pro Gly Arg Gln  Gln Gly Tyr
    2630                 2635                 2640

gga cca  gga gga gca gca gcg  gca gcc gca gct ggt  gga cca gga      7974
Gly Pro  Gly Gly Ala Ala Ala  Ala Ala Ala Ala Gly  Gly Pro Gly
    2645                 2650                 2655

tat gga  ggt caa caa ggt tac  gga cca gga gga gca  ggt gca gca      8019
Tyr Gly  Gly Gln Gln Gly Tyr  Gly Pro Gly Gly Ala  Gly Ala Ala
    2660                 2665                 2670

gca gcg  gcg gca gct ggt ggt  gca gga cca ggt aga  caa caa gca      8064
Ala Ala  Ala Ala Ala Gly Gly  Ala Gly Pro Gly Arg  Gln Gln Ala
    2675                 2680                 2685

tat gga  cca gga gga gca ggt  gca gca gct gct gca  gcc gct gcc      8109
Tyr Gly  Pro Gly Gly Ala Gly  Ala Ala Ala Ala Ala  Ala Ala Ala
    2690                 2695                 2700

gca ggt  cca gga cct agt gga  tac gga cca gga gca  tca gga cca      8154
Ala Gly  Pro Gly Pro Ser Gly  Tyr Gly Pro Gly Ala  Ser Gly Pro
    2705                 2710                 2715

agt gga  aca gga gga gca ggt  gca gca gca gca gca  gct gcc gca      8199
Ser Gly  Thr Gly Gly Ala Gly  Ala Ala Ala Ala Ala  Ala Ala Ala
    2720                 2725                 2730

gga gga  tct gga cct gga ggt  tac gga caa gga gca  tca ggt tac      8244
Gly Gly  Ser Gly Pro Gly Gly  Tyr Gly Gln Gly Ala  Ser Gly Tyr
    2735                 2740                 2745

ggc cca  tct gga cct ggt gga  caa caa ggt tat gga  cca gga gga      8289
Gly Pro  Ser Gly Pro Gly Gly  Gln Gln Gly Tyr Gly  Pro Gly Gly
    2750                 2755                 2760

tct gga  gca gca gct gca gca  gcc gcg gca gca ggt  gga gca gga      8334
Ser Gly  Ala Ala Ala Ala Ala  Ala Ala Ala Ala Gly  Gly Ala Gly
    2765                 2770                 2775

cct ggt  aga caa caa gga tat  gga cca gga agt tct  gga gcc gca      8379
Pro Gly  Arg Gln Gln Gly Tyr  Gly Pro Gly Ser Ser  Gly Ala Ala
    2780                 2785                 2790

gcg gca  gca gca gct ggt gga  cca gga tat gga ggt  cca caa gga      8424
Ala Ala  Ala Ala Ala Gly Gly  Pro Gly Tyr Gly Gly  Pro Gln Gly
    2795                 2800                 2805

tac gga  cca gga gga gca ggt  gca gca gca gcg gcg  gca gct ggt      8469
Tyr Gly  Pro Gly Gly Ala Gly  Ala Ala Ala Ala Ala  Ala Ala Gly
    2810                 2815                 2820

ggt gca  gga cct ggt aga caa  caa gca tat gga cca  gga gga tca      8514
Gly Ala  Gly Pro Gly Arg Gln  Gln Ala Tyr Gly Pro  Gly Gly Ser
    2825                 2830                 2835

ggt gca  gca gct gca gca gca  ggc tca gga cct agt  gga tac gga      8559
Gly Ala  Ala Ala Ala Ala Ala  Gly Ser Gly Pro Ser  Gly Tyr Gly
    2840                 2845                 2850

cca gga  gca gct gga cca gga  gga aca ggt gca gca  gca gta gct      8604
Pro Gly  Ala Ala Gly Pro Gly  Gly Thr Gly Ala Ala  Ala Val Ala
    2855                 2860                 2865

gcg gca  ggt ggt gct ggt cct  gga aga caa caa gca  tat gga cca      8649
Ala Ala  Gly Gly Ala Gly Pro  Gly Arg Gln Gln Ala  Tyr Gly Pro
```

```
    2870                2875                2880

ggt ggt  tct gga gca gca gcg  gca gca gca gct ggt  gga cca gga      8694
Gly Gly  Ser Gly Ala Ala Ala  Ala Ala Ala Ala Gly  Gly Pro Gly
    2885                2890                2895

tat gga  ggt caa caa ggt tac  gga cca gga gga gca  ggt gca gca      8739
Tyr Gly  Gly Gln Gln Gly Tyr  Gly Pro Gly Gly Ala  Gly Ala Ala
    2900                2905                2910

gct gcg  gcg gca gct ggt ggt  gca gga cct ggt aca  caa caa tta      8784
Ala Ala  Ala Ala Ala Gly Gly  Ala Gly Pro Gly Thr  Gln Gln Leu
    2915                2920                2925

tat gga  cca gga gga tct ggt  gca gca gct gca gca  gcc gct gcc      8829
Tyr Gly  Pro Gly Gly Ser Gly  Ala Ala Ala Ala Ala  Ala Ala Ala
    2930                2935                2940

gca ggg  tca gga cct agt gga  tac gga cca gga gca  gca gga cca      8874
Ala Gly  Ser Gly Pro Ser Gly  Tyr Gly Pro Gly Ala  Ala Gly Pro
    2945                2950                2955

agt gga  cca gga gga gca ggt  gca gca gca gca gca  gct tcc gca      8919
Ser Gly  Pro Gly Gly Ala Gly  Ala Ala Ala Ala Ala  Ala Ser Ala
    2960                2965                2970

gga gga  tct gga cct gga ggt  tac gga caa gga cca  tca ggt tac      8964
Gly Gly  Ser Gly Pro Gly Gly  Tyr Gly Gln Gly Pro  Ser Gly Tyr
    2975                2980                2985

ggc cca  aca gga cct gtt gga  caa caa ggt tat gga  cca gga gga      9009
Gly Pro  Thr Gly Pro Val Gly  Gln Gln Gly Tyr Gly  Pro Gly Gly
    2990                2995                3000

tct gga  gca gca gct gca gca  gcc gcg gca gca ggt  gga gca gga      9054
Ser Gly  Ala Ala Ala Ala Ala  Ala Ala Ala Ala Gly  Gly Ala Gly
    3005                3010                3015

cct ggt  aga caa caa gga tat  gga cca gga agt tct  gga gca gca      9099
Pro Gly  Arg Gln Gln Gly Tyr  Gly Pro Gly Ser Ser  Gly Ala Ala
    3020                3025                3030

gcg gca  gca gca gct ggt gga  cca gga tat gga ggt  caa caa ggt      9144
Ala Ala  Ala Ala Ala Gly Gly  Pro Gly Tyr Gly Gly  Gln Gln Gly
    3035                3040                3045

tac gga  cca gga gga gca ggt  gca gca gca gcg gtg  gca gct ggt      9189
Tyr Gly  Pro Gly Gly Ala Gly  Ala Ala Ala Ala Val  Ala Ala Gly
    3050                3055                3060

ggt gca  gga cct ggt aga caa  caa gga tat gga cca  gga agt tct      9234
Gly Ala  Gly Pro Gly Arg Gln  Gln Gly Tyr Gly Pro  Gly Ser Ser
    3065                3070                3075

gga gca  gca gcg gca gca gca  gct ggt gga cca gga  tat gga ggt      9279
Gly Ala  Ala Ala Ala Ala Ala  Ala Gly Gly Pro Gly  Tyr Gly Gly
    3080                3085                3090

caa caa  ggt tac gga cca gga  gga gca ggt gca gca  gca gcg gtg      9324
Gln Gln  Gly Tyr Gly Pro Gly  Gly Ala Gly Ala Ala  Ala Ala Val
    3095                3100                3105

gca gct  ggt ggt gca gga cct  ggt aga caa caa gga  tat gga cca      9369
Ala Ala  Gly Gly Ala Gly Pro  Gly Arg Gln Gln Gly  Tyr Gly Pro
    3110                3115                3120

gga agt  tct gga gca gca gcg  gca gca gca gct ggt  gga cca gga      9414
Gly Ser  Ser Gly Ala Ala Ala  Ala Ala Ala Ala Gly  Gly Pro Gly
    3125                3130                3135

tat gga  ggt caa caa ggt tac  gga tta gga gta gca  ggt gca gca      9459
Tyr Gly  Gly Gln Gln Gly Tyr  Gly Leu Gly Val Ala  Gly Ala Ala
    3140                3145                3150

gca gcg  gtg gca gct ggt ggt  gca gga cct ggt aga  caa caa gca      9504
Ala Ala  Val Ala Ala Gly Gly  Ala Gly Pro Gly Arg  Gln Gln Ala
    3155                3160                3165

tat gga  cca gga gga tca ggt  gca gca gct gcc gca  gca gca ggc      9549
```

```
Tyr Gly  Pro Gly Gly Ser Gly  Ala Ala Ala Ala Ala  Ala Ala Gly
    3170                 3175                 3180

tca gga  cgt agt gga tac gga  cca gga gca gct gga  aca gga gga      9594
Ser Gly  Arg Ser Gly Tyr Gly  Pro Gly Ala Ala Gly  Thr Gly Gly
    3185                 3190                 3195

gca ggt  gca gca gca gca gct  gcg gca ggt ggc gct  ggt tct gga      9639
Ala Gly  Ala Ala Ala Ala Ala  Ala Ala Gly Gly Ala  Gly Ser Gly
    3200                 3205                 3210

aga caa  caa gca tat gga cca  ggt ggt tct gga gca  gca gcg gca      9684
Arg Gln  Gln Ala Tyr Gly Pro  Gly Gly Ser Gly Ala  Ala Ala Ala
    3215                 3220                 3225

tca gca  gct ggt gga cca gga  tat gga ggt caa caa  ggt tac gga      9729
Ser Ala  Ala Gly Gly Pro Gly  Tyr Gly Gly Gln Gln  Gly Tyr Gly
    3230                 3235                 3240

cca gga  gga gca ggt gca gca  gct gcg gcg gca gct  ggt ggt gca      9774
Pro Gly  Gly Ala Gly Ala Ala  Ala Ala Ala Ala Ala  Gly Gly Ala
    3245                 3250                 3255

gga cct  ggt aca caa caa gca  tat gga cca gga gga  tca ggt gca      9819
Gly Pro  Gly Thr Gln Gln Ala  Tyr Gly Pro Gly Gly  Ser Gly Ala
    3260                 3265                 3270

gca gct  gca gca gcc gct gcc  tca ggg cca gga cct  agt gga tac      9864
Ala Ala  Ala Ala Ala Ala Ala  Ser Gly Pro Gly Pro  Ser Gly Tyr
    3275                 3280                 3285

gaa cca  gga gca gca gga cca  agt gga cca gca gga  gca ggt gca      9909
Glu Pro  Gly Ala Ala Gly Pro  Ser Gly Pro Ala Gly  Ala Gly Ala
    3290                 3295                 3300

gca gca  gca gca gct gcc gca  gga gga tct gga cct  gga ggt tac      9954
Ala Ala  Ala Ala Ala Ala Ala  Gly Gly Ser Gly Pro  Gly Gly Tyr
    3305                 3310                 3315

gga caa  gga cca tca ggt tac  ggc cca tca gga cct  ggt gga caa      9999
Gly Gln  Gly Pro Ser Gly Tyr  Gly Pro Ser Gly Pro  Gly Gly Gln
    3320                 3325                 3330

caa ggt  tac gga cca gga gga  tct gga gca gca gct  gca gca gcc     10044
Gln Gly  Tyr Gly Pro Gly Gly  Ser Gly Ala Ala Ala  Ala Ala Ala
    3335                 3340                 3345

gcg gca  gca ggt gga gca gga  cct ggt aga caa caa  gga tat gga     10089
Ala Ala  Ala Gly Gly Ala Gly  Pro Gly Arg Gln Gln  Gly Tyr Gly
    3350                 3355                 3360

caa gga  agt tct gga gca gca  gcg gcc gca gca gct  ggt gga cca     10134
Gln Gly  Ser Ser Gly Ala Ala  Ala Ala Ala Ala Ala  Gly Gly Pro
    3365                 3370                 3375

gga tat  gga ggt caa caa gtt  tac gga cca gga gga  gca ggt gca     10179
Gly Tyr  Gly Gly Gln Gln Val  Tyr Gly Pro Gly Gly  Ala Gly Ala
    3380                 3385                 3390

gca gca  gcg gtg gca gct ggt  ggt gca gga cct ggt  aga caa caa     10224
Ala Ala  Ala Val Ala Ala Gly  Gly Ala Gly Pro Gly  Arg Gln Gln
    3395                 3400                 3405

gca tat  gga cca gga gga tca  ggt gca gca gca ggc  tca gga cct     10269
Ala Tyr  Gly Pro Gly Gly Ser  Gly Ala Ala Ala Gly  Ser Gly Pro
    3410                 3415                 3420

agt gga  tac gga cca gga gca  gct gca gca gct gcg  gca ggc ggc     10314
Ser Gly  Tyr Gly Pro Gly Ala  Ala Ala Ala Ala Ala  Ala Gly Gly
    3425                 3430                 3435

gct gga  cct gga aga caa caa  gca tat gga cca ggt  ggt tct gga     10359
Ala Gly  Pro Gly Arg Gln Gln  Ala Tyr Gly Pro Gly  Gly Ser Gly
    3440                 3445                 3450

gca gca  gcg gca gca gca gct  ggt gga cca gga tat  gga ggt caa     10404
Ala Ala  Ala Ala Ala Ala Ala  Gly Gly Pro Gly Tyr  Gly Gly Gln
    3455                 3460                 3465
```

-continued

```
caa ggt  tac gga cca gga gga  gca ggt gca gca gca  gca gct gcc      10449
Gln Gly  Tyr Gly Pro Gly Gly  Ala Gly Ala Ala Ala  Ala Ala Ala
    3470                 3475                 3480

gca gga  gga tct gga cct gga  ggt tac gga caa gga  cca tca ggt      10494
Ala Gly  Gly Ser Gly Pro Gly  Gly Tyr Gly Gln Gly  Pro Ser Gly
    3485                 3490                 3495

tac ggc  cca tca gga tct ggt  gga caa ggt tac gga  caa gga gga      10539
Tyr Gly  Pro Ser Gly Ser Gly  Gly Gln Gly Tyr Gly  Gln Gly Gly
    3500                 3505                 3510

tct gga  gca gca gcc gcg gca  gca ggt gga gca gga  cct ggt aga      10584
Ser Gly  Ala Ala Ala Ala Ala  Ala Gly Gly Ala Gly  Pro Gly Arg
    3515                 3520                 3525

caa caa  gga tat gga cca gga  agt tct gga gca gca  gcg gca gca      10629
Gln Gln  Gly Tyr Gly Pro Gly  Ser Ser Gly Ala Ala  Ala Ala Ala
    3530                 3535                 3540

gca gct  ggt gga cca gga ttt  gga ggt caa caa ggt  tac gga cca      10674
Ala Ala  Gly Gly Pro Gly Phe  Gly Gly Gln Gln Gly  Tyr Gly Pro
    3545                 3550                 3555

gga gga  tca ggt gca gca gca  gca gcg gca gct ggt  ggt gca gga      10719
Gly Gly  Ser Gly Ala Ala Ala  Ala Ala Ala Ala Gly  Gly Ala Gly
    3560                 3565                 3570

cct ggt  agg caa caa gca tat  gga cca gga gga tca  gga gca gca      10764
Pro Gly  Arg Gln Gln Ala Tyr  Gly Pro Gly Gly Ser  Gly Ala Ala
    3575                 3580                 3585

gct gca  gca gcc gct gcc gca  ggc tca gga ccc agt  gga tac gga      10809
Ala Ala  Ala Ala Ala Ala Ala  Gly Ser Gly Pro Ser  Gly Tyr Gly
    3590                 3595                 3600

cca tca  gca gca gga cca agt  gga cca gga gga tca  ggt gcc gca      10854
Pro Ser  Ala Ala Gly Pro Ser  Gly Pro Gly Gly Ser  Gly Ala Ala
    3605                 3610                 3615

ggt gga  tct ggc cct gga ggt  ttt ggt caa gga cca  gca ggt tat      10899
Gly Gly  Ser Gly Pro Gly Gly  Phe Gly Gln Gly Pro  Ala Gly Tyr
    3620                 3625                 3630

ggt ccc  tca gga cct ggt gga  caa caa gga tac ggg  cca ggt gca      10944
Gly Pro  Ser Gly Pro Gly Gly  Gln Gln Gly Tyr Gly  Pro Gly Ala
    3635                 3640                 3645

tca ggt  gct gca gcg gca gca  gca gct agt gga tca  ggt gga tat      10989
Ser Gly  Ala Ala Ala Ala Ala  Ala Ala Ser Gly Ser  Gly Gly Tyr
    3650                 3655                 3660

ggt cct  tca caa tat gtt cct  agc tct gtt gct tct  agt gct gca      11034
Gly Pro  Ser Gln Tyr Val Pro  Ser Ser Val Ala Ser  Ser Ala Ala
    3665                 3670                 3675

tca gca  gcc tca gct tta tct  tca ccg aca acg cat  gct aga att      11079
Ser Ala  Ala Ser Ala Leu Ser  Ser Pro Thr Thr His  Ala Arg Ile
    3680                 3685                 3690

tct tcc  cat gca tca act cta  tta tca agt ggg cca  act aat gcg      11124
Ser Ser  His Ala Ser Thr Leu  Leu Ser Ser Gly Pro  Thr Asn Ala
    3695                 3700                 3705

gca gct  ctt tct aat gtc att  agt aat gcc gtt tcc  caa gtc agt      11169
Ala Ala  Leu Ser Asn Val Ile  Ser Asn Ala Val Ser  Gln Val Ser
    3710                 3715                 3720

gca agt  aat cca gga tct tcc  tct tgt gat gtc ctt  gtt caa gca      11214
Ala Ser  Asn Pro Gly Ser Ser  Ser Cys Asp Val Leu  Val Gln Ala
    3725                 3730                 3735

ctt ctt  gaa ata att act gca  tta att agt ata cta  gat tcc tct      11259
Leu Leu  Glu Ile Ile Thr Ala  Leu Ile Ser Ile Leu  Asp Ser Ser
    3740                 3745                 3750

agt gtt  gga caa gtt aat tac  ggt tct tca gga cag  tat gca caa      11304
Ser Val  Gly Gln Val Asn Tyr  Gly Ser Ser Gly Gln  Tyr Ala Gln
    3755                 3760                 3765
```

```
att gta  ggg cag tct atg caa  cag gct atg ggg tga                 11340
Ile Val  Gly Gln Ser Met Gln  Gln Ala Met Gly
    3770                 3775


<210> SEQ ID NO 4
<211> LENGTH: 3779
<212> TYPE: PRT
<213> ORGANISM: Latrodectus hesperus

<400> SEQUENCE: 4

Met Thr Thr Met Asn Trp Ser Thr Arg Leu Val Leu Ser Ile Leu Val
1               5                   10                  15

Val Leu Cys Thr Gln Ser Leu Cys Ala Leu Gly Gln Ala Asn Thr Pro
            20                  25                  30

Trp Ser Ser Lys Glu Asn Ala Asp Ala Phe Ile Gly Ala Phe Met Asn
        35                  40                  45

Ala Ala Ser Gln Ser Gly Ala Phe Ser Ser Asp Gln Ile Asp Asp Met
    50                  55                  60

Ser Val Ile Ser Asn Thr Leu Met Ala Ala Met Asp Asn Met Gly Gly
65                  70                  75                  80

Arg Ile Thr Gln Ser Lys Leu Gln Ala Leu Asp Met Ala Phe Ala Ser
                85                  90                  95

Ser Val Ala Glu Ile Ala Val Ala Asp Gly Gln Asn Val Gly Ala Ala
            100                 105                 110

Thr Asn Ala Ile Ser Asp Ala Leu Arg Ser Ala Phe Tyr Gln Thr Thr
        115                 120                 125

Gly Val Val Asn Asn Gln Phe Ile Thr Gly Ile Ser Ser Leu Ile Gly
    130                 135                 140

Met Phe Ala Gln Val Ser Gly Asn Glu Val Ser Tyr Ser Ser Ala Gly
145                 150                 155                 160

Ser Ser Ser Ala Ala Ala Ser Glu Ala Val Ser Ala Gly Gln Gly Pro
                165                 170                 175

Ala Ala Gln Pro Val Tyr Ala Pro Ser Gly Ala Ser Ala Ala Ala Ala
            180                 185                 190

Ala Ala Ser Gly Ala Ala Pro Ala Ile Gln Gln Ala Tyr Glu Arg Gly
        195                 200                 205

Gly Ser Gly Ser Ala Ala Ala Ala Ala Gly Ser Gly Pro Ser Gly Tyr
    210                 215                 220

Gly Gln Gly Ala Gly Gly Pro Gly Gly Ala Gly Ala Ala Ala Gly Ala
225                 230                 235                 240

Ala Ala Ala Gly Gly Ser Gly Pro Gly Gly Tyr Gly Gln Gly Pro Ala
                245                 250                 255

Ala Tyr Gly Pro Ser Gly Pro Ser Gly Gln Gln Gly Tyr Gly Pro Gly
            260                 265                 270

Gly Ser Gly Ala Ala Ala Ala Ala Ala Ala Ala Ala Gly Ser Gly Pro
        275                 280                 285

Ser Gly Tyr Gly Pro Gly Ala Gly Gly Pro Gly Gly Ala Gly Ala Ala
    290                 295                 300

Ala Ala Ala Ala Ala Ala Gly Gly Ser Gly Pro Gly Gly Tyr Gly Gln
305                 310                 315                 320

Gly Gln Ala Ser Tyr Gly Pro Ser Gly Pro Ser Gly Gln Gln Gly Tyr
                325                 330                 335

Gly Pro Gly Gly Ser Gly Ala Ala Ala Ala Ala Ala Ala Ala Ala Gly
            340                 345                 350
```

-continued

```
Ser Gly Pro Ser Gly Tyr Gly Pro Gly Ala Ala Ala Ala Ala Ala Ala
        355                 360                 365

Gly Ser Ala Gly Pro Gly Thr Gln Gln Gly Tyr Gly Pro Gly Gly Ser
    370                 375                 380

Gly Ala Ala Ala Ala Ala Gly Ser Gly Pro Arg Gly Tyr Gly Pro Arg
385                 390                 395                 400

Gly Pro Gly Gly Ala Gly Ala Ala Ala Thr Ala Ala Arg Gly Ser Gly
                405                 410                 415

Pro Gly Gly Tyr Gly Gln Gly Pro Ala Gly Tyr Gly Thr Ser Gly Pro
            420                 425                 430

Ser Arg Gln Gln Gly Tyr Gly Pro Gly Gly Ser Gly Ala Ala Ala Ala
        435                 440                 445

Ala Ala Ala Ala Ala Gly Gly Ala Gly Pro Gly Arg Gln Gln Gly Tyr
    450                 455                 460

Gly Pro Gly Gly Ser Gly Ala Ala Ala Ala Thr Ala Ala Gly Gly Pro
465                 470                 475                 480

Gly Tyr Val Gly Gln Gln Arg Tyr Gly Pro Gly Gly Ala Gly Ala Ala
                485                 490                 495

Ala Ala Ala Ala Ala Gly Ser Ala Gly Pro Ser Arg Gln Gln Ala Tyr
            500                 505                 510

Gly Pro Gly Gly Ser Gly Pro Ala Ala Ala Thr Ala Ala Ala Gly Ser
        515                 520                 525

Gly Pro Ser Gly Tyr Gly Pro Gly Ala Ser Gly Pro Val Gly Ala Asp
    530                 535                 540

Ala Ala Ala Ala Ala Ala Thr Gly Ser Ala Gly Pro Gly Arg Gln Gln
545                 550                 555                 560

Ala Tyr Gly Pro Gly Glu Ser Gly Ala Ala Ala Ala Ala Ala Ser Gly
                565                 570                 575

Ala Gly Pro Gly Arg Gln Leu Gly Tyr Gly Pro Gly Gly Ser Gly Ala
            580                 585                 590

Ala Ala Ala Ala Ala Ala Gly Gly Pro Gly Tyr Gly Gly Gln Gln Gly
        595                 600                 605

Tyr Gly Pro Gly Gly Ala Gly Ala Ala Ala Ala Ala Ala Ala Gly Gly
    610                 615                 620

Ala Gly Pro Gly Arg Gln Gln Thr Tyr Gly Pro Gly Gly Ser Gly Ala
625                 630                 635                 640

Ala Ala Thr Ala Ala Gly Gly Ser Gly Pro Gly Gly Tyr Gly Gln Gly
                645                 650                 655

Pro Ser Gly Tyr Gly Pro Ser Gly Pro Gly Gly Gln Gln Gly Tyr Gly
            660                 665                 670

Pro Gly Gly Ser Gly Ala Ala Ala Ala Ala Ala Ala Gly Glu Ala Gly
        675                 680                 685

Pro Gly Arg Gln Gln Gly Tyr Gly Pro Arg Gly Ser Gly Ala Ala Ala
    690                 695                 700

Ala Ala Ala Ala Gly Gly Pro Gly Tyr Gly Gly Gln Ser Gly Tyr Gly
705                 710                 715                 720

Pro Gly Gly Ala Gly Ala Ala Ala Ala Ala Ala Ala Gly Gly Ala Gly
                725                 730                 735

Pro Gly Arg Gln Gln Glu Tyr Gly Pro Gly Gly Ser Gly Ala Ala Ala
            740                 745                 750

Ala Ala Ala Ala Ala Ala Gly Ser Gly Pro Ser Gly Tyr Gly Pro Gly
        755                 760                 765

Ala Ala Gly Pro Ile Gly Pro Gly Gly Ala Gly Ala Ala Ala Ala Gly
```

-continued

```
    770                 775                 780

Gly Ser Gly Pro Val Gly Tyr Gly Gln Gly Pro Ser Gly Tyr Gly Ala
785                 790                 795                 800

Ser Gly Thr Gly Gly Glu Gln Asp Tyr Gly Pro Gly Gly Ser Gly Ala
                805                 810                 815

Ala Ala Ala Ala Ala Ala Ala Ala Gly Gly Ala Gly Pro Gly Arg Gln
            820                 825                 830

Gln Gly Tyr Gly Pro Gly Gly Ser Gly Ala Ala Ala Ala Ala Ala Ala
        835                 840                 845

Gly Gly Pro Gly Tyr Gly Gly Gln Gln Gly Tyr Gly Pro Gly Gly Ala
    850                 855                 860

Gly Ala Ala Ala Ala Ala Ala Ala Gly Gly Ala Gly Pro Gly Arg Gln
865                 870                 875                 880

Gln Pro Tyr Gly Pro Gly Gly Ala Gly Ala Ala Ala Ala Ala Ala Gly
                885                 890                 895

Gly Ser Gly Pro Gly Gly Tyr Gly Gln Gly Pro Ser Gly Tyr Gly Ala
            900                 905                 910

Ser Gly Pro Gly Gly Gln Gln Gly Phe Gly Pro Gly Gly Ser Gly Ala
        915                 920                 925

Ala Ala Ala Ala Ala Ala Gly Gly Ala Gly Pro Gly Arg Gln Gln Gly
    930                 935                 940

Tyr Gly Pro Gly Gly Ser Gly Ala Ala Ala Ala Ala Gly Gly Thr Gly
945                 950                 955                 960

Tyr Gly Gly Gln Gln Gly Tyr Gly Pro Gly Gly Ala Gly Ala Ala Ala
                965                 970                 975

Ala Ala Ala Ala Ala Gly Ala Gly Pro Gly Arg Gln Gln Glu Tyr Gly
            980                 985                 990

Pro Gly Gly Thr Gly Ala Ala Ala  Ala Ala Ala Ala Ala  Ala Gly Ser
        995                 1000                1005

Gly Pro  Ser Gly Tyr Gly Gln  Gly Ala Ala Gly Pro  Ser Gly Pro
    1010                1015                1020

Gly Gly  Glu Gly Thr Ala Ala  Ala Ala Ala Ala Ala  Gly Gly Ser
    1025                1030                1035

Gly Pro  Gly Gly Tyr Gly Gln  Gly Pro Ser Gly Tyr  Ser Ala Ser
    1040                1045                1050

Gly Pro  Gly Gly Gln Gln Gly  Tyr Gly Pro Gly Gly  Ser Gly Leu
    1055                1060                1065

Ala Ala  Ala Ala Ala Ala Ala  Ala Gly Gly Ala Gly  Thr Gly Arg
    1070                1075                1080

Gln Gln  Gly Tyr Gly Pro Gly  Gly Ser Gly Ala Ala  Ala Ala Ala
    1085                1090                1095

Ala Ala  Val Gly Pro Gly Tyr  Gly Gly Gln Gln Gly  Tyr Gly Pro
    1100                1105                1110

Gly Gly  Ala Gly Ala Ala Ala  Ala Ala Ala Ala Gly  Gly Ala Gly
    1115                1120                1125

Pro Gly  Arg Gln Gln Ala Tyr  Gly Pro Gly Gly Ser  Gly Ala Thr
    1130                1135                1140

Ala Ala  Ala Ala Val Ala Gly  Ser Gly Pro Ser Gly  Tyr Gly Pro
    1145                1150                1155

Gly Gly  Ala Gly Ala Ala Ala  Ala Ala Ala Ala Gly  Gly Ala Gly
    1160                1165                1170

Pro Gly  Arg Gln Gln Ala Tyr  Gly Pro Gly Gly Ser  Gly Ala Ala
    1175                1180                1185
```

```
Ala Ala Ala Ala Ser Gly Ala Gly Pro Gly Arg Gln Gln Val Tyr
    1190                1195                1200

Gly Pro Gly Gly Ser Gly Ala Ala Ala Ala Ala Ala Ala Gly Gly
    1205                1210                1215

Pro Gly Tyr Gly Gly Gln Gln Gly Tyr Gly Pro Gly Gly Ala Gly
    1220                1225                1230

Ala Ala Ala Ala Ala Ala Ala Gly Gly Ala Gly Gln Gly Thr Arg
    1235                1240                1245

Gln Ala Tyr Gly Pro Gly Gly Ser Gly Ala Ala Ala Ala Ala Ala
    1250                1255                1260

Gly Pro Gly Pro Ser Gly Tyr Gly Pro Gly Ala Ala Gly Pro Ser
    1265                1270                1275

Gly Pro Gly Leu Ala Gly Ala Ala Ala Ala Ala Ala Ala Gly Gly
    1280                1285                1290

Ser Gly Pro Gly Gly Asn Gly Gln Arg Pro Ser Gly Tyr Gly Gln
    1295                1300                1305

Ser Gly Thr Gly Gly Gln Gln Gly Tyr Gly Pro Gly Gly Ser Gly
    1310                1315                1320

Ala Ala Ala Ala Ala Ala Ala Ala Ala Gly Gly Ala Gly Pro Gly
    1325                1330                1335

Arg Gln Gln Gly Tyr Gly Pro Gly Ser Ser Gly Ala Ala Ala Ala
    1340                1345                1350

Ala Ala Ala Gly Gly Pro Gly Tyr Gly Gly Gln Gln Gly Tyr Gly
    1355                1360                1365

Pro Gly Gly Ala Gly Ala Ala Ala Ala Ala Ala Ala Gly Gly Ala
    1370                1375                1380

Gly Pro Gly Thr Gln Gln Ala Tyr Gly Pro Gly Gly Ser Gly Ala
    1385                1390                1395

Ala Ala Ala Ala Ala Ala Ala Ala Gly Gly Ala Gly Pro Gly Arg
    1400                1405                1410

Gln Gln Gly Tyr Gly Pro Gly Ser Ser Gly Ala Ala Ala Ala Ala
    1415                1420                1425

Ala Ala Gly Gly Pro Gly Tyr Gly Gly Gln Gln Gly Tyr Gly Pro
    1430                1435                1440

Gly Gly Ala Gly Ala Ala Ala Ala Ala Ala Ala Gly Gly Ala Gly
    1445                1450                1455

Ala Gly Arg Gln Gln Ala Tyr Gly Pro Gly Gly Ser Gly Ala Ala
    1460                1465                1470

Ala Ala Gly Ser Gly Pro Ser Gly Tyr Glu Pro Gly Ala Ala Gly
    1475                1480                1485

Pro Gly Gly Ala Gly Ala Ala Ala Ala Ala Ala Ala Val Gly Ala
    1490                1495                1500

Gly Pro Gly Arg Gln Gln Ala Tyr Gly Gln Gly Gly Ser Gly Ala
    1505                1510                1515

Val Ala Ala Ala Ala Ala Gly Gly Pro Gly Tyr Gly Gly Gln Gln
    1520                1525                1530

Gly Tyr Glu Gln Gly Gly Ala Gly Ala Ala Ser Ala Ala Ala Ala
    1535                1540                1545

Gly Gly Glu Gly Pro Ala Arg Gln Gln Ala Tyr Gly Pro Gly Gly
    1550                1555                1560

Ser Gly Ala Ala Ala Ala Ala Ala Gly Gly Ala Gly Pro Gly Arg
    1565                1570                1575
```

-continued

```
Gln Gln Gly Tyr Gly Pro Gly Ser Ser Gly Ala Ala Ala Ala Ala
    1580                1585                1590

Ala Ala Gly Gly Pro Gly Tyr Gly Gly Gln Gln Gly Tyr Gly Pro
    1595                1600                1605

Gly Gly Ala Gly Ala Ala Ala Ala Ala Ala Ala Gly Gly Ala Gly
    1610                1615                1620

Pro Gly Arg Gln Gln Ala Tyr Gly Pro Gly Gly Ser Gly Ala Ala
    1625                1630                1635

Ala Ala Ala Ala Ala Gly Thr Gly Pro Ser Gly Tyr Gly Pro Gly
    1640                1645                1650

Ala Ala Gly Pro Gly Gly Ala Gly Ala Ala Ala Ala Ala Ala Ala
    1655                1660                1665

Gly Ser Ala Gly Pro Gly Arg Gln Gln Ala Tyr Gly Pro Gly Gly
    1670                1675                1680

Ser Gly Ala Ala Ala Ala Ala Ala Ala Gly Gly Pro Gly Tyr Gly
    1685                1690                1695

Gly Gln Gln Gly Tyr Gly Pro Gly Gly Ala Gly Ala Ala Ala Ala
    1700                1705                1710

Ala Ala Ala Gly Gly Ala Gly Pro Gly Thr Gln Gln Ala Tyr Gly
    1715                1720                1725

Pro Gly Gly Ser Gly Ala Ala Ala Ala Ala Ala Ala Ala Ala Gly
    1730                1735                1740

Gly Ala Gly Pro Asp Arg Gln Gln Gly Tyr Gly Pro Gly Ser Ser
    1745                1750                1755

Gly Ala Ala Ala Ala Ala Ala Ala Gly Gly Pro Gly Tyr Gly Gly
    1760                1765                1770

Gln Gln Gly Tyr Gly Pro Gly Gly Ala Gly Ala Ala Ala Ala Ala
    1775                1780                1785

Ala Ala Ala Ala Gly Pro Gly Pro Ser Gly Tyr Gly Pro Gly Gly
    1790                1795                1800

Ala Gly Ala Ala Ala Ala Ala Ala Ala Ala Gly Gly Ser Gly Pro
    1805                1810                1815

Gly Gly Tyr Gly Gln Gly Pro Ser Gly Tyr Ser Ala Ser Gly Pro
    1820                1825                1830

Gly Gly Gln Gln Gly Tyr Gly Pro Gly Gly Ser Gly Leu Ala Ala
    1835                1840                1845

Ala Ala Ala Ala Ala Ala Gly Gly Ala Gly Thr Gly Arg Gln Gln
    1850                1855                1860

Gly Tyr Gly Pro Gly Gly Ser Gly Ala Ala Ala Ala Ala Ala Ala
    1865                1870                1875

Val Gly Pro Gly Tyr Gly Gly Gln Gln Gly Tyr Gly Pro Gly Gly
    1880                1885                1890

Ala Gly Ala Ala Ala Ala Ala Ala Ala Gly Gly Ala Gly Pro Gly
    1895                1900                1905

Arg Gln Gln Ala Tyr Gly Pro Gly Gly Ser Gly Ala Thr Ala Ala
    1910                1915                1920

Ala Ala Ala Ala Gly Ser Gly Pro Ser Gly Tyr Gly Pro Gly Gly
    1925                1930                1935

Ala Gly Ala Ala Ala Ala Ala Ala Ala Gly Gly Ala Gly Pro Gly
    1940                1945                1950

Arg Gln Gln Ala Tyr Gly Pro Gly Gly Ser Gly Ala Ala Ala Ala
    1955                1960                1965

Ala Ala Ser Gly Ala Gly Pro Gly Arg Gln Gln Val Tyr Gly Pro
```

```
    1970                1975                1980

Val Gly  Ser Gly Ala Ala Ala  Ala Ala Ala Ala Gly  Gly Pro Gly
    1985                1990                1995

Tyr Gly  Gly Gln Gln Gly Tyr  Gly Pro Gly Gly Ala  Gly Ala Ala
    2000                2005                2010

Ala Ala  Ala Ala Ala Gly Gly  Ala Gly Gln Gly Thr  Arg Gln Ala
    2015                2020                2025

Tyr Gly  Pro Gly Gly Ser Gly  Ala Ala Ala Ala Ala  Ala Gly Pro
    2030                2035                2040

Gly Pro  Ser Gly Tyr Gly Pro  Gly Ala Ala Gly Pro  Ser Gly Pro
    2045                2050                2055

Gly Leu  Ala Gly Ala Ala Ala  Ala Ala Ala Ala Gly  Gly Ser Gly
    2060                2065                2070

Pro Gly  Gly Asn Gly Gln Arg  Pro Ser Gly Tyr Gly  Gln Ser Gly
    2075                2080                2085

Pro Gly  Gly Gln Gln Gly Tyr  Gly Pro Gly Gly Ser  Gly Ala Ala
    2090                2095                2100

Ala Ala  Ala Ala Ala Ala Ala  Gly Gly Ala Gly Pro  Gly Arg Gln
    2105                2110                2115

Gln Gly  Tyr Gly Pro Gly Ser  Ser Gly Ala Ala Ala  Ala Ala Ala
    2120                2125                2130

Ala Gly  Gly Pro Gly Tyr Gly  Gly Gln Gln Gly Tyr  Gly Pro Gly
    2135                2140                2145

Gly Ala  Gly Ala Ala Ala Ala  Ala Ala Ala Gly Gly  Ala Gly Pro
    2150                2155                2160

Gly Thr  Gln Gln Ala Tyr Gly  Pro Gly Gly Ser Gly  Ala Ala Ala
    2165                2170                2175

Ala Ala  Ala Ala Ala Ala Gly  Gly Ala Gly Pro Gly  Arg Gln Gln
    2180                2185                2190

Gly Tyr  Gly Pro Gly Ser Ser  Gly Ala Ala Ala Ala  Ala Ala Ala
    2195                2200                2205

Gly Gly  Pro Gly Tyr Gly Gly  Gln Gln Gly Tyr Gly  Pro Gly Gly
    2210                2215                2220

Ala Gly  Ala Ala Ala Ala Ala  Ala Ala Gly Gly Ala  Gly Ala Gly
    2225                2230                2235

Arg Gln  Gln Ala Tyr Gly Pro  Gly Gly Ser Gly Ala  Ala Ala Ala
    2240                2245                2250

Gly Ser  Gly Pro Ser Gly Tyr  Glu Ser Gly Ala Ala  Gly Pro Gly
    2255                2260                2265

Gly Ala  Gly Ala Ala Ala Ala  Ala Ala Ala Val Gly  Ala Gly Pro
    2270                2275                2280

Gly Arg  Gln Gln Ala Tyr Gly  Gln Gly Gly Ser Gly  Ala Val Ala
    2285                2290                2295

Ala Ala  Ala Ala Gly Gly Pro  Gly Tyr Gly Gly Gln  Gln Gly Tyr
    2300                2305                2310

Glu Gln  Gly Gly Ala Gly Ala  Ala Ser Ala Ala Ala  Ala Gly Gly
    2315                2320                2325

Glu Gly  Pro Ala Arg Gln Gln  Ala Tyr Gly Pro Gly  Gly Ser Gly
    2330                2335                2340

Ala Ala  Ala Ala Ala Ala Gly  Gly Ala Gly Pro Gly  Arg Gln Gln
    2345                2350                2355

Gly Tyr  Gly Pro Gly Ser Ser  Gly Ala Ala Ala Ala  Ala Ala Ala
    2360                2365                2370
```

```
Gly Gly Pro Gly Tyr Gly Gly Gln Gln Gly Tyr Gly Pro Gly Gly
    2375                2380                2385

Ala Gly Ala Ala Ala Ala Ala Ala Ala Gly Gly Ala Gly Pro Gly
    2390                2395                2400

Arg Gln Gln Ala Tyr Gly Pro Gly Gly Ser Gly Ala Ala Ala Ala
    2405                2410                2415

Ala Ala Ala Gly Thr Gly Pro Ser Gly Tyr Gly Pro Gly Ala Ala
    2420                2425                2430

Gly Pro Gly Gly Ala Gly Ala Ala Ala Ala Ala Ala Ala Gly Gly
    2435                2440                2445

Ala Gly Pro Gly Arg Gln Gln Ala Tyr Gly Pro Gly Gly Ser Gly
    2450                2455                2460

Ala Ala Ala Ala Ala Ala Ala Gly Gly Pro Gly Tyr Gly Gly Gln
    2465                2470                2475

Gln Gly Tyr Gly Pro Gly Gly Ala Gly Ala Ala Ala Ala Ala Ala
    2480                2485                2490

Ala Gly Gly Ala Gly Pro Gly Thr Gln Gln Ala Tyr Gly Pro Gly
    2495                2500                2505

Gly Ser Gly Ala Ala Ala Ala Ala Ala Ala Ala Ala Gly Gly Ala
    2510                2515                2520

Gly Pro Asp Arg Gln Gln Gly Tyr Gly Pro Gly Ser Ser Gly Ala
    2525                2530                2535

Ala Ala Ala Ala Ala Ala Gly Gly Pro Gly Tyr Gly Gly Gln Gln
    2540                2545                2550

Gly Tyr Gly Pro Gly Gly Ala Gly Ala Ala Ala Ala Ala Ala Ala
    2555                2560                2565

Ala Ala Gly Pro Gly Pro Ser Gly Tyr Gly Pro Gly Gly Ala Gly
    2570                2575                2580

Ala Ala Ala Ala Ala Ala Ala Ala Gly Gly Ser Gly Pro Gly Gly
    2585                2590                2595

Tyr Gly Gln Gly Pro Ser Gly Tyr Gly Pro Ser Gly Pro Gly Gly
    2600                2605                2610

Gln Gln Gly Asn Gly Pro Gly Gly Ser Gly Ala Ala Ala Ala Ala
    2615                2620                2625

Ala Ala Ala Ala Gly Gly Ala Gly Pro Gly Arg Gln Gln Gly Tyr
    2630                2635                2640

Gly Pro Gly Gly Ala Ala Ala Ala Ala Ala Ala Gly Gly Pro Gly
    2645                2650                2655

Tyr Gly Gly Gln Gln Gly Tyr Gly Pro Gly Gly Ala Gly Ala Ala
    2660                2665                2670

Ala Ala Ala Ala Ala Gly Gly Ala Gly Pro Gly Arg Gln Gln Ala
    2675                2680                2685

Tyr Gly Pro Gly Gly Ala Gly Ala Ala Ala Ala Ala Ala Ala Ala
    2690                2695                2700

Ala Gly Pro Gly Pro Ser Gly Tyr Gly Pro Gly Ala Ser Gly Pro
    2705                2710                2715

Ser Gly Thr Gly Gly Ala Gly Ala Ala Ala Ala Ala Ala Ala Ala
    2720                2725                2730

Gly Gly Ser Gly Pro Gly Gly Tyr Gly Gln Gly Ala Ser Gly Tyr
    2735                2740                2745

Gly Pro Ser Gly Pro Gly Gly Gln Gln Gly Tyr Gly Pro Gly Gly
    2750                2755                2760
```

```
Ser Gly  Ala Ala Ala Ala Ala  Ala Ala Ala Ala Gly  Gly Ala Gly
    2765                 2770                 2775

Pro Gly  Arg Gln Gln Gly Tyr  Gly Pro Gly Ser Ser  Gly Ala Ala
    2780                 2785                 2790

Ala Ala  Ala Ala Ala Gly Gly  Pro Gly Tyr Gly Gly  Pro Gln Gly
    2795                 2800                 2805

Tyr Gly  Pro Gly Gly Ala Gly  Ala Ala Ala Ala Ala  Ala Ala Gly
    2810                 2815                 2820

Gly Ala  Gly Pro Gly Arg Gln  Gln Ala Tyr Gly Pro  Gly Gly Ser
    2825                 2830                 2835

Gly Ala  Ala Ala Ala Ala Ala  Gly Ser Gly Pro Ser  Gly Tyr Gly
    2840                 2845                 2850

Pro Gly  Ala Ala Gly Pro Gly  Gly Thr Gly Ala Ala  Ala Val Ala
    2855                 2860                 2865

Ala Ala  Gly Gly Ala Gly Pro  Gly Arg Gln Gln Ala  Tyr Gly Pro
    2870                 2875                 2880

Gly Gly  Ser Gly Ala Ala Ala  Ala Ala Ala Ala Gly  Gly Pro Gly
    2885                 2890                 2895

Tyr Gly  Gly Gln Gln Gly Tyr  Gly Pro Gly Gly Ala  Gly Ala Ala
    2900                 2905                 2910

Ala Ala  Ala Ala Ala Gly Gly  Ala Gly Pro Gly Thr  Gln Gln Leu
    2915                 2920                 2925

Tyr Gly  Pro Gly Gly Ser Gly  Ala Ala Ala Ala Ala  Ala Ala Ala
    2930                 2935                 2940

Ala Gly  Ser Gly Pro Ser Gly  Tyr Gly Pro Gly Ala  Ala Gly Pro
    2945                 2950                 2955

Ser Gly  Pro Gly Gly Ala Gly  Ala Ala Ala Ala Ala  Ala Ser Ala
    2960                 2965                 2970

Gly Gly  Ser Gly Pro Gly Gly  Tyr Gly Gln Gly Pro  Ser Gly Tyr
    2975                 2980                 2985

Gly Pro  Thr Gly Pro Val Gly  Gln Gln Gly Tyr Gly  Pro Gly Gly
    2990                 2995                 3000

Ser Gly  Ala Ala Ala Ala Ala  Ala Ala Ala Ala Gly  Gly Ala Gly
    3005                 3010                 3015

Pro Gly  Arg Gln Gln Gly Tyr  Gly Pro Gly Ser Ser  Gly Ala Ala
    3020                 3025                 3030

Ala Ala  Ala Ala Ala Gly Gly  Pro Gly Tyr Gly Gly  Gln Gln Gly
    3035                 3040                 3045

Tyr Gly  Pro Gly Gly Ala Gly  Ala Ala Ala Ala Val  Ala Ala Gly
    3050                 3055                 3060

Gly Ala  Gly Pro Gly Arg Gln  Gln Gly Tyr Gly Pro  Gly Ser Ser
    3065                 3070                 3075

Gly Ala  Ala Ala Ala Ala Ala  Ala Gly Gly Pro Gly  Tyr Gly Gly
    3080                 3085                 3090

Gln Gln  Gly Tyr Gly Pro Gly  Gly Ala Gly Ala Ala  Ala Ala Val
    3095                 3100                 3105

Ala Ala  Gly Gly Ala Gly Pro  Gly Arg Gln Gln Gly  Tyr Gly Pro
    3110                 3115                 3120

Gly Ser  Ser Gly Ala Ala Ala  Ala Ala Ala Ala Gly  Gly Pro Gly
    3125                 3130                 3135

Tyr Gly  Gly Gln Gln Gly Tyr  Gly Leu Gly Val Ala  Gly Ala Ala
    3140                 3145                 3150

Ala Ala  Val Ala Ala Gly Gly  Ala Gly Pro Gly Arg  Gln Gln Ala
```

```
    3155                3160                3165

Tyr Gly Pro Gly Gly Ser Gly Ala Ala Ala Ala Ala Ala Ala Gly
    3170                3175                3180

Ser Gly Arg Ser Gly Tyr Gly Pro Gly Ala Ala Gly Thr Gly Gly
    3185                3190                3195

Ala Gly Ala Ala Ala Ala Ala Ala Ala Gly Gly Ala Gly Ser Gly
    3200                3205                3210

Arg Gln Gln Ala Tyr Gly Pro Gly Gly Ser Gly Ala Ala Ala Ala
    3215                3220                3225

Ser Ala Ala Gly Gly Pro Gly Tyr Gly Gly Gln Gln Gly Tyr Gly
    3230                3235                3240

Pro Gly Gly Ala Gly Ala Ala Ala Ala Ala Ala Ala Gly Gly Ala
    3245                3250                3255

Gly Pro Gly Thr Gln Gln Ala Tyr Gly Pro Gly Gly Ser Gly Ala
    3260                3265                3270

Ala Ala Ala Ala Ala Ala Ala Ser Gly Pro Gly Pro Ser Gly Tyr
    3275                3280                3285

Glu Pro Gly Ala Ala Gly Pro Ser Gly Pro Ala Gly Ala Gly Ala
    3290                3295                3300

Ala Ala Ala Ala Ala Ala Ala Gly Gly Ser Gly Pro Gly Gly Tyr
    3305                3310                3315

Gly Gln Gly Pro Ser Gly Tyr Gly Pro Ser Gly Pro Gly Gly Gln
    3320                3325                3330

Gln Gly Tyr Gly Pro Gly Gly Ser Gly Ala Ala Ala Ala Ala Ala
    3335                3340                3345

Ala Ala Ala Gly Gly Ala Gly Pro Gly Arg Gln Gln Gly Tyr Gly
    3350                3355                3360

Gln Gly Ser Ser Gly Ala Ala Ala Ala Ala Ala Ala Gly Gly Pro
    3365                3370                3375

Gly Tyr Gly Gly Gln Gln Val Tyr Gly Pro Gly Gly Ala Gly Ala
    3380                3385                3390

Ala Ala Ala Val Ala Ala Gly Gly Ala Gly Pro Gly Arg Gln Gln
    3395                3400                3405

Ala Tyr Gly Pro Gly Gly Ser Gly Ala Ala Ala Gly Ser Gly Pro
    3410                3415                3420

Ser Gly Tyr Gly Pro Gly Ala Ala Ala Ala Ala Ala Ala Gly Gly
    3425                3430                3435

Ala Gly Pro Gly Arg Gln Gln Ala Tyr Gly Pro Gly Gly Ser Gly
    3440                3445                3450

Ala Ala Ala Ala Ala Ala Ala Gly Gly Pro Gly Tyr Gly Gly Gln
    3455                3460                3465

Gln Gly Tyr Gly Pro Gly Gly Ala Gly Ala Ala Ala Ala Ala Ala
    3470                3475                3480

Ala Gly Gly Ser Gly Pro Gly Gly Tyr Gly Gln Gly Pro Ser Gly
    3485                3490                3495

Tyr Gly Pro Ser Gly Ser Gly Gly Gln Gly Tyr Gly Gln Gly Gly
    3500                3505                3510

Ser Gly Ala Ala Ala Ala Ala Ala Gly Gly Ala Gly Pro Gly Arg
    3515                3520                3525

Gln Gln Gly Tyr Gly Pro Gly Ser Ser Gly Ala Ala Ala Ala Ala
    3530                3535                3540

Ala Ala Gly Gly Pro Gly Phe Gly Gly Gln Gln Gly Tyr Gly Pro
    3545                3550                3555
```

```
Gly Gly  Ser Gly Ala Ala Ala  Ala Ala Ala Ala Gly  Gly Ala Gly
    3560                 3565                 3570

Pro Gly  Arg Gln Gln Ala Tyr  Gly Pro Gly Gly Ser  Gly Ala Ala
    3575                 3580                 3585

Ala Ala  Ala Ala Ala Ala Ala  Gly Ser Gly Pro Ser  Gly Tyr Gly
    3590                 3595                 3600

Pro Ser  Ala Ala Gly Pro Ser  Gly Pro Gly Gly Ser  Gly Ala Ala
    3605                 3610                 3615

Gly Gly  Ser Gly Pro Gly Gly  Phe Gly Gln Gly Pro  Ala Gly Tyr
    3620                 3625                 3630

Gly Pro  Ser Gly Pro Gly Gly  Gln Gln Gly Tyr Gly  Pro Gly Ala
    3635                 3640                 3645

Ser Gly  Ala Ala Ala Ala Ala  Ala Ala Ser Gly Ser  Gly Gly Tyr
    3650                 3655                 3660

Gly Pro  Ser Gln Tyr Val Pro  Ser Ser Val Ala Ser  Ser Ala Ala
    3665                 3670                 3675

Ser Ala  Ala Ser Ala Leu Ser  Ser Pro Thr Thr His  Ala Arg Ile
    3680                 3685                 3690

Ser Ser  His Ala Ser Thr Leu  Leu Ser Ser Gly Pro  Thr Asn Ala
    3695                 3700                 3705

Ala Ala  Leu Ser Asn Val Ile  Ser Asn Ala Val Ser  Gln Val Ser
    3710                 3715                 3720

Ala Ser  Asn Pro Gly Ser Ser  Ser Cys Asp Val Leu  Val Gln Ala
    3725                 3730                 3735

Leu Leu  Glu Ile Ile Thr Ala  Leu Ile Ser Ile Leu  Asp Ser Ser
    3740                 3745                 3750

Ser Val  Gly Gln Val Asn Tyr  Gly Ser Ser Gly Gln  Tyr Ala Gln
    3755                 3760                 3765

Ile Val  Gly Gln Ser Met Gln  Gln Ala Met Gly
    3770                 3775


<210> SEQ ID NO 5
<211> LENGTH: 2256
<212> TYPE: DNA
<213> ORGANISM: Latrodectus hesperus
<220> FEATURE:
<221> NAME/KEY: CDS
<222> LOCATION: (1)..(2256)

<400> SEQUENCE: 5

atg agg aga atg tac agc cta agt att cag tcg gat ttt cca act act       48
Met Arg Arg Met Tyr Ser Leu Ser Ile Gln Ser Asp Phe Pro Thr Thr
1               5                   10                  15

aca atg acc tgg tct act cga ctt gct tta tca ttc ttc gca gtg atc       96
Thr Met Thr Trp Ser Thr Arg Leu Ala Leu Ser Phe Phe Ala Val Ile
            20                  25                  30

tgc aca caa agc att tat gct cta ggg cag gga aac act cca tgg tct      144
Cys Thr Gln Ser Ile Tyr Ala Leu Gly Gln Gly Asn Thr Pro Trp Ser
        35                  40                  45

act aaa gca aat gct gat aat ttt atg aac gga ttt ttg agt gct tgt      192
Thr Lys Ala Asn Ala Asp Asn Phe Met Asn Gly Phe Leu Ser Ala Cys
    50                  55                  60

gca caa agt gga gta ttt tca gca gat cag gta gac gat atg acc acg      240
Ala Gln Ser Gly Val Phe Ser Ala Asp Gln Val Asp Asp Met Thr Thr
65                  70                  75                  80

att ggt aaa aca tta atg ata gct atg gat aaa atg ggt gga aaa att      288
Ile Gly Lys Thr Leu Met Ile Ala Met Asp Lys Met Gly Gly Lys Ile
```

-continued

```
                85                  90                  95

tcc tcc tca aag cta caa gcc ttg gat atg gcc ttt gca tca tct gta      336
Ser Ser Ser Lys Leu Gln Ala Leu Asp Met Ala Phe Ala Ser Ser Val
            100                 105                 110

gca gaa atc gct act gca gaa gga ggt gcc aac ata aat gac att aca      384
Ala Glu Ile Ala Thr Ala Glu Gly Gly Ala Asn Ile Asn Asp Ile Thr
        115                 120                 125

gat gca att cga tat gct ttg caa aac gca ttt tat caa aca aca gga      432
Asp Ala Ile Arg Tyr Ala Leu Gln Asn Ala Phe Tyr Gln Thr Thr Gly
    130                 135                 140

gcg gtt aat tcc aaa ttt att aat gaa att tca aat tta ata tat atg      480
Ala Val Asn Ser Lys Phe Ile Asn Glu Ile Ser Asn Leu Ile Tyr Met
145                 150                 155                 160

ttc gct caa aca aac ata aat gat gtc aat ggg gga gga gga tac ggt      528
Phe Ala Gln Thr Asn Ile Asn Asp Val Asn Gly Gly Gly Gly Tyr Gly
                165                 170                 175

caa gga ggt gca gga caa ggt gga gcc gca gca gca gca gct ggt gga      576
Gln Gly Gly Ala Gly Gln Gly Gly Ala Ala Ala Ala Ala Ala Gly Gly
            180                 185                 190

gca gga caa gga gga tat ggc aga ggt gga gcc aga caa ggt gga gca      624
Ala Gly Gln Gly Gly Tyr Gly Arg Gly Gly Ala Arg Gln Gly Gly Ala
        195                 200                 205

gca gca gcc gct gga gct ggt caa ggt ggt tat gga gat caa ggt gcc      672
Ala Ala Ala Ala Gly Ala Gly Gln Gly Gly Tyr Gly Asp Gln Gly Ala
    210                 215                 220

gga caa ggg gga gct gga gcc gca gcg gca gca gca act gca tct ggt      720
Gly Gln Gly Gly Ala Gly Ala Ala Ala Ala Ala Ala Thr Ala Ser Gly
225                 230                 235                 240

gga gcc gga caa gga gga tat ggc cga ggt gga gca gga caa ggt gga      768
Gly Ala Gly Gln Gly Gly Tyr Gly Arg Gly Gly Ala Gly Gln Gly Gly
                245                 250                 255

gca gca gca gcc gct gct gca gcc gca gga gct ggt caa ggt ggt tat      816
Ala Ala Ala Ala Ala Ala Ala Ala Ala Gly Ala Gly Gln Gly Gly Tyr
            260                 265                 270

gga gga caa ggg gcc gca caa ggt gga gct gga gct gca gcc gca gca      864
Gly Gly Gln Gly Ala Ala Gln Gly Gly Ala Gly Ala Ala Ala Ala Ala
        275                 280                 285

gca gca gcc gga ggt gca ggt cta gga gga cta ggt gga tac gga caa      912
Ala Ala Ala Gly Gly Ala Gly Leu Gly Gly Leu Gly Gly Tyr Gly Gln
    290                 295                 300

ggt gga tct gga gca gca gca gca gcc gga gga gca ggt caa gga gga      960
Gly Gly Ser Gly Ala Ala Ala Ala Ala Gly Gly Ala Gly Gln Gly Gly
305                 310                 315                 320

gaa ggt ggc gtt gga caa gga ggt tac ggt caa aga ggt gcc gga caa     1008
Glu Gly Gly Val Gly Gln Gly Gly Tyr Gly Gln Arg Gly Ala Gly Gln
                325                 330                 335

ggt gga gta gga gcc gca gcg gct gca gca gct gca gct ggt gga gcc     1056
Gly Gly Val Gly Ala Ala Ala Ala Ala Ala Ala Ala Ala Gly Gly Ala
            340                 345                 350

gga caa gga gaa tat ggc cga ggt gga gca gga aaa ggt gga gca gca     1104
Gly Gln Gly Glu Tyr Gly Arg Gly Gly Ala Gly Lys Gly Gly Ala Ala
        355                 360                 365

gca gcc gct gct gca gcc gca gga gct ggt caa ggt gga tat gga gga     1152
Ala Ala Ala Ala Ala Ala Ala Gly Ala Gly Gln Gly Gly Tyr Gly Gly
    370                 375                 380

caa ggt gga gct gga gct gca gcc gca gca gca gct gct gga gga gca     1200
Gln Gly Gly Ala Gly Ala Ala Ala Ala Ala Ala Ala Ala Gly Gly Ala
385                 390                 395                 400

ggt cta gga gga aaa gga gga tat gga caa gga gga gct gga gct gca     1248
```

-continued

```
Gly Leu Gly Gly Lys Gly Gly Tyr Gly Gln Gly Gly Ala Gly Ala Ala
                405                 410                 415

gcc gca gca gca gca gcc gga ggt gca ggt caa gga gga caa ggt ggc      1296
Ala Ala Ala Ala Ala Ala Gly Gly Ala Gly Gln Gly Gly Gln Gly Gly
            420                 425                 430

tat gga cga gga ggt tac ggt cga gga ggt gcc gga caa ggc gga gct      1344
Tyr Gly Arg Gly Gly Tyr Gly Arg Gly Gly Ala Gly Gln Gly Gly Ala
        435                 440                 445

gga gca gca gca gcg gca gca gca gcc gga ggt gca ggt caa gta gga      1392
Gly Ala Ala Ala Ala Ala Ala Ala Ala Gly Gly Ala Gly Gln Val Gly
    450                 455                 460

caa agt ggc tat gga caa gaa ggt tac ggt caa gga ggt gcc gga caa      1440
Gln Ser Gly Tyr Gly Gln Glu Gly Tyr Gly Gln Gly Gly Ala Gly Gln
465                 470                 475                 480

ggt gga gct gga gcc gca gcg gcg gca gct gct gca gct ggt gga gcc      1488
Gly Gly Ala Gly Ala Ala Ala Ala Ala Ala Ala Ala Ala Gly Gly Ala
                485                 490                 495

gga caa ggt gga tat ggc cga ggt gga gca gga caa ggt gaa gca gca      1536
Gly Gln Gly Gly Tyr Gly Arg Gly Gly Ala Gly Gln Gly Glu Ala Ala
            500                 505                 510

gca gcc gct gct gca gcc gca gga gct ggt caa ggt ggt tat gga gga      1584
Ala Ala Ala Ala Ala Ala Ala Gly Ala Gly Gln Gly Gly Tyr Gly Gly
        515                 520                 525

caa ggt gcc gga caa ggt aga gct gga gct gca gcc gca gca gca gct      1632
Gln Gly Ala Gly Gln Gly Arg Ala Gly Ala Ala Ala Ala Ala Ala Ala
    530                 535                 540

gct gga ggg gca ggt caa gga gga caa ggt gga tat gga caa gga gga      1680
Ala Gly Gly Ala Gly Gln Gly Gly Gln Gly Gly Tyr Gly Gln Gly Gly
545                 550                 555                 560

tac gga caa ggt gga tct gga gca gct gca gcg gca gca gca gca gcc      1728
Tyr Gly Gln Gly Gly Ser Gly Ala Ala Ala Ala Ala Ala Ala Ala Ala
                565                 570                 575

gga ggt gca ggt caa gga gga caa ggt ggc tat gga caa gga ggt tac      1776
Gly Gly Ala Gly Gln Gly Gly Gln Gly Gly Tyr Gly Gln Gly Gly Tyr
            580                 585                 590

ggt caa gga ggt gcc gga caa ggt gga gct gca gcc gta gca gca gca      1824
Gly Gln Gly Gly Ala Gly Gln Gly Gly Ala Ala Ala Val Ala Ala Ala
        595                 600                 605

gct gca gct gga gga gca gga caa gga gga tac ggt cca caa ggt gga      1872
Ala Ala Ala Gly Gly Ala Gly Gln Gly Gly Tyr Gly Pro Gln Gly Gly
    610                 615                 620

gca gga gcc aca gca gca tca gct agt gga cct gtt caa att tat tat      1920
Ala Gly Ala Thr Ala Ala Ser Ala Ser Gly Pro Val Gln Ile Tyr Tyr
625                 630                 635                 640

gga ccc caa tct gtt gtt gct cca gca gct gca gca gct tct gcc ttg      1968
Gly Pro Gln Ser Val Val Ala Pro Ala Ala Ala Ala Ala Ser Ala Leu
                645                 650                 655

gca gct cca gct aca agt gcg aga att tct tca cac gcc tca gct ctt      2016
Ala Ala Pro Ala Thr Ser Ala Arg Ile Ser Ser His Ala Ser Ala Leu
            660                 665                 670

ctt tca aat gga cct act aac cct gct tct att tca aac gtt att agt      2064
Leu Ser Asn Gly Pro Thr Asn Pro Ala Ser Ile Ser Asn Val Ile Ser
        675                 680                 685

aat gct gta tcc caa att agt tcc agc aat cca gga gcg tct gcg tgt      2112
Asn Ala Val Ser Gln Ile Ser Ser Ser Asn Pro Gly Ala Ser Ala Cys
    690                 695                 700

gat gtt ctc gtt caa gct ctt ctt gaa ctt gtt act gct ttg ctc acc      2160
Asp Val Leu Val Gln Ala Leu Leu Glu Leu Val Thr Ala Leu Leu Thr
705                 710                 715                 720
```

-continued

```
att att gga tca tca aat att ggc agt gtt aat tat gat tct tca ggc      2208
Ile Ile Gly Ser Ser Asn Ile Gly Ser Val Asn Tyr Asp Ser Ser Gly
                725                 730                 735

caa tat gcg caa gtt gtt act caa tct gta caa aat gca ttc gct tga      2256
Gln Tyr Ala Gln Val Val Thr Gln Ser Val Gln Asn Ala Phe Ala
            740                 745                 750


<210> SEQ ID NO 6
<211> LENGTH: 751
<212> TYPE: PRT
<213> ORGANISM: Latrodectus hesperus

<400> SEQUENCE: 6

Met Arg Arg Met Tyr Ser Leu Ser Ile Gln Ser Asp Phe Pro Thr Thr
1               5                   10                  15

Thr Met Thr Trp Ser Thr Arg Leu Ala Leu Ser Phe Phe Ala Val Ile
            20                  25                  30

Cys Thr Gln Ser Ile Tyr Ala Leu Gly Gln Gly Asn Thr Pro Trp Ser
        35                  40                  45

Thr Lys Ala Asn Ala Asp Asn Phe Met Asn Gly Phe Leu Ser Ala Cys
    50                  55                  60

Ala Gln Ser Gly Val Phe Ser Ala Asp Gln Val Asp Asp Met Thr Thr
65                  70                  75                  80

Ile Gly Lys Thr Leu Met Ile Ala Met Asp Lys Met Gly Gly Lys Ile
                85                  90                  95

Ser Ser Ser Lys Leu Gln Ala Leu Asp Met Ala Phe Ala Ser Ser Val
            100                 105                 110

Ala Glu Ile Ala Thr Ala Glu Gly Gly Ala Asn Ile Asn Asp Ile Thr
        115                 120                 125

Asp Ala Ile Arg Tyr Ala Leu Gln Asn Ala Phe Tyr Gln Thr Thr Gly
    130                 135                 140

Ala Val Asn Ser Lys Phe Ile Asn Glu Ile Ser Asn Leu Ile Tyr Met
145                 150                 155                 160

Phe Ala Gln Thr Asn Ile Asn Asp Val Asn Gly Gly Gly Gly Tyr Gly
                165                 170                 175

Gln Gly Gly Ala Gly Gln Gly Gly Ala Ala Ala Ala Ala Ala Gly Gly
            180                 185                 190

Ala Gly Gln Gly Gly Tyr Gly Arg Gly Gly Ala Arg Gln Gly Gly Ala
        195                 200                 205

Ala Ala Ala Ala Gly Ala Gly Gln Gly Gly Tyr Gly Asp Gln Gly Ala
    210                 215                 220

Gly Gln Gly Gly Ala Gly Ala Ala Ala Ala Ala Ala Thr Ala Ser Gly
225                 230                 235                 240

Gly Ala Gly Gln Gly Gly Tyr Gly Arg Gly Gly Ala Gly Gln Gly Gly
                245                 250                 255

Ala Ala Ala Ala Ala Ala Ala Ala Ala Gly Ala Gly Gln Gly Gly Tyr
            260                 265                 270

Gly Gly Gln Gly Ala Ala Gln Gly Gly Ala Gly Ala Ala Ala Ala Ala
        275                 280                 285

Ala Ala Ala Gly Gly Ala Gly Leu Gly Gly Leu Gly Gly Tyr Gly Gln
    290                 295                 300

Gly Gly Ser Gly Ala Ala Ala Ala Ala Gly Gly Ala Gly Gln Gly Gly
305                 310                 315                 320

Glu Gly Gly Val Gly Gln Gly Gly Tyr Gly Gln Arg Gly Ala Gly Gln
                325                 330                 335
```

-continued

```
Gly Gly Val Gly Ala Ala Ala Ala Ala Ala Ala Ala Ala Gly Gly Ala
            340                 345                 350

Gly Gln Gly Glu Tyr Gly Arg Gly Gly Ala Gly Lys Gly Gly Ala Ala
        355                 360                 365

Ala Ala Ala Ala Ala Ala Ala Gly Ala Gly Gln Gly Gly Tyr Gly Gly
    370                 375                 380

Gln Gly Gly Ala Gly Ala Ala Ala Ala Ala Ala Ala Ala Gly Gly Ala
385                 390                 395                 400

Gly Leu Gly Gly Lys Gly Gly Tyr Gly Gln Gly Gly Ala Gly Ala Ala
                405                 410                 415

Ala Ala Ala Ala Ala Ala Gly Gly Ala Gly Gln Gly Gly Gln Gly Gly
            420                 425                 430

Tyr Gly Arg Gly Gly Tyr Gly Arg Gly Gly Ala Gly Gln Gly Gly Ala
        435                 440                 445

Gly Ala Ala Ala Ala Ala Ala Ala Ala Gly Gly Ala Gly Gln Val Gly
    450                 455                 460

Gln Ser Gly Tyr Gly Gln Glu Gly Tyr Gly Gln Gly Gly Ala Gly Gln
465                 470                 475                 480

Gly Gly Ala Gly Ala Ala Ala Ala Ala Ala Ala Ala Ala Gly Gly Ala
                485                 490                 495

Gly Gln Gly Gly Tyr Gly Arg Gly Gly Ala Gly Gln Gly Glu Ala Ala
            500                 505                 510

Ala Ala Ala Ala Ala Ala Ala Gly Ala Gly Gln Gly Gly Tyr Gly Gly
        515                 520                 525

Gln Gly Ala Gly Gln Gly Arg Ala Gly Ala Ala Ala Ala Ala Ala Ala
    530                 535                 540

Ala Gly Gly Ala Gly Gln Gly Gly Gln Gly Gly Tyr Gly Gln Gly Gly
545                 550                 555                 560

Tyr Gly Gln Gly Gly Ser Gly Ala Ala Ala Ala Ala Ala Ala Ala Ala
                565                 570                 575

Gly Gly Ala Gly Gln Gly Gly Gln Gly Gly Tyr Gly Gln Gly Gly Tyr
            580                 585                 590

Gly Gln Gly Gly Ala Gly Gln Gly Gly Ala Ala Ala Val Ala Ala Ala
        595                 600                 605

Ala Ala Ala Gly Gly Ala Gly Gln Gly Gly Tyr Gly Pro Gln Gly Gly
    610                 615                 620

Ala Gly Ala Thr Ala Ala Ser Ala Ser Gly Pro Val Gln Ile Tyr Tyr
625                 630                 635                 640

Gly Pro Gln Ser Val Val Ala Pro Ala Ala Ala Ala Ala Ser Ala Leu
                645                 650                 655

Ala Ala Pro Ala Thr Ser Ala Arg Ile Ser Ser His Ala Ser Ala Leu
            660                 665                 670

Leu Ser Asn Gly Pro Thr Asn Pro Ala Ser Ile Ser Asn Val Ile Ser
        675                 680                 685

Asn Ala Val Ser Gln Ile Ser Ser Ser Asn Pro Gly Ala Ser Ala Cys
    690                 695                 700

Asp Val Leu Val Gln Ala Leu Leu Glu Leu Val Thr Ala Leu Leu Thr
705                 710                 715                 720

Ile Ile Gly Ser Ser Asn Ile Gly Ser Val Asn Tyr Asp Ser Ser Gly
                725                 730                 735

Gln Tyr Ala Gln Val Val Thr Gln Ser Val Gln Asn Ala Phe Ala
            740                 745                 750
```

```
<210> SEQ ID NO 7
<211> LENGTH: 3200
<212> TYPE: DNA
<213> ORGANISM: Latrodectus hesperus
<220> FEATURE:
<221> NAME/KEY: CDS
<222> LOCATION: (637)..(2529)
<220> FEATURE:
<221> NAME/KEY: misc_feature
<222> LOCATION: (1620)..(1620)
<223> OTHER INFORMATION: n is a, c, g, or t

<400> SEQUENCE: 7

gctcggtacc cggggatccc acgaaaaaaa aacattaaca tttccaaaga cttcaaaagt      60

tcaactgtag aattaaaatt attggaagaa tccaatcaaa aataatttgc gtcaatggat     120

taaattgtca gattttctaa tgatagtaca cttacaatta aatgagtgca aataaataaa     180

ttaaaaagaa aaatggtgtg taattattat agatgaaata agaatcaatt tgatattttt     240

atcatgaatt taaaatttag aacgacgatg ttattcgaat caatccaaat ttaatgaaaa     300

attattcaat aaaatatctt tctaaattta tcataaaatt tataaactaa ataaagcaat     360

tatagttcca ataaaaggca aagttattaa gtaaagttta atgcaaaata ccaaaaatga     420

tattaaacac gtaagtattc gcatgtaaaa acataagaaa acttgcattt caccttggaa     480

aaaacaggtg actaaattca aacaagaagt acacacgtca tcttagcacg cggacatgac     540

acaattgtct gcatatctcc aggtgtattg aaaaacctgc tgcacagcac gaccaatcat     600

tgtataaaag aggcaatcaa tcagcgtaca gtattc agt cgg gat ttt cca act      654
                                        Ser Arg Asp Phe Pro Thr
                                        1               5

act aca atg act tgg tca act cga ctt gcc tta tca ttt ctt ttc gtg      702
Thr Thr Met Thr Trp Ser Thr Arg Leu Ala Leu Ser Phe Leu Phe Val
            10                  15                  20

ctc tgc act cag agc ctg tac gct ttg gcg caa gcc aac acg cca tgg      750
Leu Cys Thr Gln Ser Leu Tyr Ala Leu Ala Gln Ala Asn Thr Pro Trp
        25                  30                  35

tca agt aaa gcg aat gct gat gct ttt atc aat tcc ttt att tcg gca      798
Ser Ser Lys Ala Asn Ala Asp Ala Phe Ile Asn Ser Phe Ile Ser Ala
    40                  45                  50

gct tcg aat act gga tcc ttc tcc caa gat cag atg gaa gat atg tca      846
Ala Ser Asn Thr Gly Ser Phe Ser Gln Asp Gln Met Glu Asp Met Ser
55                  60                  65                  70

ttg att ggt aat aca tta atg gca gca atg gat aat atg ggt gga aga      894
Leu Ile Gly Asn Thr Leu Met Ala Ala Met Asp Asn Met Gly Gly Arg
                75                  80                  85

att acg cca tcc aaa tta cag gct tta gat atg gct ttc gca tca tct      942
Ile Thr Pro Ser Lys Leu Gln Ala Leu Asp Met Ala Phe Ala Ser Ser
            90                  95                  100

gta gca gaa att gct gct tcg gaa gga gga gac tta gga gta aca aca      990
Val Ala Glu Ile Ala Ala Ser Glu Gly Gly Asp Leu Gly Val Thr Thr
        105                 110                 115

aat gca att gca gat gct tta acg tca gct ttc tat caa aca acc gga     1038
Asn Ala Ile Ala Asp Ala Leu Thr Ser Ala Phe Tyr Gln Thr Thr Gly
    120                 125                 130

gta gtt aat agc aga ttt att agc gaa att aga agt ttg att ggc atg     1086
Val Val Asn Ser Arg Phe Ile Ser Glu Ile Arg Ser Leu Ile Gly Met
135                 140                 145                 150

ttt gca cag gca tct gcc aac gat gta tac gcc tca gca ggt tcc agc     1134
Phe Ala Gln Ala Ser Ala Asn Asp Val Tyr Ala Ser Ala Gly Ser Ser
                155                 160                 165

ggt gga gga ggg tat gga gca tct tct gca agt gca gca tct gca agc     1182
```

-continued

```
Gly Gly Gly Gly Tyr Gly Ala Ser Ser Ala Ser Ala Ala Ser Ala Ser
            170                 175                 180

gca gca gca cca tca ggt gtc gca tat caa gct cca gca caa gca caa      1230
Ala Ala Ala Pro Ser Gly Val Ala Tyr Gln Ala Pro Ala Gln Ala Gln
        185                 190                 195

att tcc ttc act ttg aga gga caa cag cca gtt agt tat ggt caa gga      1278
Ile Ser Phe Thr Leu Arg Gly Gln Gln Pro Val Ser Tyr Gly Gln Gly
    200                 205                 210

ggc gct gga cca gga gga gct gga gca gca gcg gca gcc gca gca gca      1326
Gly Ala Gly Pro Gly Gly Ala Gly Ala Ala Ala Ala Ala Ala Ala Ala
215                 220                 225                 230

gct gga gga gcg ggt caa gga gga caa gga ggg tat gga caa gga gga      1374
Ala Gly Gly Ala Gly Gln Gly Gly Gln Gly Gly Tyr Gly Gln Gly Gly
                235                 240                 245

tat ggt caa gga ggt gcc gga caa ggt gga tct gga gca gca gca gca      1422
Tyr Gly Gln Gly Gly Ala Gly Gln Gly Gly Ser Gly Ala Ala Ala Ala
            250                 255                 260

gct gga ggc acc ggt caa gga ggt gct gga caa ggt gga gca gga gca      1470
Ala Gly Gly Thr Gly Gln Gly Gly Ala Gly Gln Gly Gly Ala Gly Ala
        265                 270                 275

gca gcg gca gcc gca gca gca gct gga ggt gca ggt caa gga gga caa      1518
Ala Ala Ala Ala Ala Ala Ala Ala Gly Gly Ala Gly Gln Gly Gly Gln
    280                 285                 290

ggt ggc tat gga caa gga gga tac ggt caa gga ggt acc gga caa ggt      1566
Gly Gly Tyr Gly Gln Gly Gly Tyr Gly Gln Gly Gly Thr Gly Gln Gly
295                 300                 305                 310

gga gct gga gca gca gca cga gga ggt tac ggt caa gga ggt gcc gga      1614
Gly Ala Gly Ala Ala Ala Arg Gly Gly Tyr Gly Gln Gly Gly Ala Gly
                315                 320                 325

caa ggn gga gct gga gca gca gca gcg gca gca gca gcc gga ggt gca      1662
Gln Gly Gly Ala Gly Ala Ala Ala Ala Ala Ala Ala Ala Gly Gly Ala
            330                 335                 340

ggt caa gga gga caa ggt ggc tat gga caa gga ggt tac ggt caa gga      1710
Gly Gln Gly Gly Gln Gly Gly Tyr Gly Gln Gly Gly Tyr Gly Gln Gly
        345                 350                 355

ggt gca gga caa ggt gga gcc gca gcg gca gca gca gca gct ggt gga      1758
Gly Ala Gly Gln Gly Gly Ala Ala Ala Ala Ala Ala Ala Ala Gly Gly
    360                 365                 370

gca gga caa gga gga tat ggc aga ggt gga gca gga caa ggt gga gca      1806
Ala Gly Gln Gly Gly Tyr Gly Arg Gly Gly Ala Gly Gln Gly Gly Ala
375                 380                 385                 390

gca gca gcc gct gct gca gcc gct gga gct ggt caa ggt ggt tat gga      1854
Ala Ala Ala Ala Ala Ala Ala Ala Gly Ala Gly Gln Gly Gly Tyr Gly
                395                 400                 405

ggt caa ggt gcc gga caa ggt gga gct gga gct gca gcc gca gca gca      1902
Gly Gln Gly Ala Gly Gln Gly Gly Ala Gly Ala Ala Ala Ala Ala Ala
            410                 415                 420

gca gcc gga ggt gca ggt caa gga gga caa ggt ggc tat gga cga gga      1950
Ala Ala Gly Gly Ala Gly Gln Gly Gly Gln Gly Gly Tyr Gly Arg Gly
        425                 430                 435

ggt tac ggt caa gga ggt gct gga caa ggc gga gct gga gca gca gca      1998
Gly Tyr Gly Gln Gly Gly Ala Gly Gln Gly Gly Ala Gly Ala Ala Ala
    440                 445                 450

gcg gca gca gca gca gcc gga ggt gca ggt caa gga gga caa ggt ggc      2046
Ala Ala Ala Ala Ala Ala Gly Gly Ala Gly Gln Gly Gly Gln Gly Gly
455                 460                 465                 470

tat gga caa gga ggt tac ggt caa gga ggt gcc gga caa ggt gga gct      2094
Tyr Gly Gln Gly Gly Tyr Gly Gln Gly Gly Ala Gly Gln Gly Gly Ala
                475                 480                 485
```

```
gca gcc gca gcg gca gca gct gca gct gga gga gca gga caa gga gga     2142
Ala Ala Ala Ala Ala Ala Ala Ala Ala Gly Gly Ala Gly Gln Gly Gly
            490                 495                 500

tat ggt gga tac ggt caa caa ggt gga gca gga gcc gca gca gca gct     2190
Tyr Gly Gly Tyr Gly Gln Gln Gly Gly Ala Gly Ala Ala Ala Ala Ala
        505                 510                 515

gct agt gga cct ggt caa att tat tat gga ccc caa tct gtt gct gct     2238
Ala Ser Gly Pro Gly Gln Ile Tyr Tyr Gly Pro Gln Ser Val Ala Ala
    520                 525                 530

cca gca gca gca gca gct tct gct ttg gca gct cca gct aca agc gcg     2286
Pro Ala Ala Ala Ala Ala Ser Ala Leu Ala Ala Pro Ala Thr Ser Ala
535                 540                 545                 550

aga att tct tca cac gcc tca gct ctt ctt tca aat gga cct act aac     2334
Arg Ile Ser Ser His Ala Ser Ala Leu Leu Ser Asn Gly Pro Thr Asn
                555                 560                 565

cct gct tct att tca aac gtt att agt aat gct gta tcc caa att agt     2382
Pro Ala Ser Ile Ser Asn Val Ile Ser Asn Ala Val Ser Gln Ile Ser
            570                 575                 580

tcc agc aat cca gga gcg tct gcg tgt gat gtt ctc gtt caa gct ctt     2430
Ser Ser Asn Pro Gly Ala Ser Ala Cys Asp Val Leu Val Gln Ala Leu
        585                 590                 595

ctt gaa ctt gtt act gct ttg ctc acc att att gga tca tca aat att     2478
Leu Glu Leu Val Thr Ala Leu Leu Thr Ile Ile Gly Ser Ser Asn Ile
    600                 605                 610

ggc agt gtt aat tat gat tct tca ggc caa tat gcg caa gtt gtt act     2526
Gly Ser Val Asn Tyr Asp Ser Ser Gly Gln Tyr Ala Gln Val Val Thr
615                 620                 625                 630

caa tctgttcaaa atgcattcgc ttgattctaa aacgttgctt aagcattcat          2579
Gln

tttataaaat gtactaatat aatatgtatt gagtaattct gatattgaat aaagcattta   2639

tcttctctat aatctcattt gcctaattat atttttgttt ttttacttct gtcctgagat   2699

cagtttctta tatatggtaa ttcaggcatt ttaacattgt aatatattat tgaattgtaa   2759

catctgcgga aaaaatattt acagaataca agttgtagaa ttcaaattaa ttaacttttt   2819

taaatgaaaa taaattgaac ttaattttga ggactttatg atatggtttc taaatatttt   2879

tattttcacg ctggttttcc tggagaaatc aataatttcc aacataatat gtgtttatta   2939

taactgcgta gtcccattcc ttacttttca ggtatacgct ttagtgtact gtacttctgc   2999

agtgtcttaa tattgacctg aaacgtatta gatgatttcg atctttgaat gaaagaataa   3059

tactaaaaac tttttaagtt cttaaaataa tttattatat caccagattt ctttccaaaa   3119

ggacaggtgt cattttgtaa ttgaaaagaa gaaattttga aattgaataa agaattttga   3179

gtggtttgct gcctaatcag c                                              3200


<210> SEQ ID NO 8
<211> LENGTH: 631
<212> TYPE: PRT
<213> ORGANISM: Latrodectus hesperus

<400> SEQUENCE: 8

Ser Arg Asp Phe Pro Thr Thr Thr Met Thr Trp Ser Thr Arg Leu Ala
1               5                   10                  15

Leu Ser Phe Leu Phe Val Leu Cys Thr Gln Ser Leu Tyr Ala Leu Ala
            20                  25                  30

Gln Ala Asn Thr Pro Trp Ser Ser Lys Ala Asn Ala Asp Ala Phe Ile
        35                  40                  45

Asn Ser Phe Ile Ser Ala Ala Ser Asn Thr Gly Ser Phe Ser Gln Asp
```

-continued

```
    50                  55                  60

Gln Met Glu Asp Met Ser Leu Ile Gly Asn Thr Leu Met Ala Ala Met
65                  70                  75                  80

Asp Asn Met Gly Gly Arg Ile Thr Pro Ser Lys Leu Gln Ala Leu Asp
                85                  90                  95

Met Ala Phe Ala Ser Ser Val Ala Glu Ile Ala Ala Ser Glu Gly Gly
            100                 105                 110

Asp Leu Gly Val Thr Thr Asn Ala Ile Ala Asp Ala Leu Thr Ser Ala
        115                 120                 125

Phe Tyr Gln Thr Thr Gly Val Val Asn Ser Arg Phe Ile Ser Glu Ile
    130                 135                 140

Arg Ser Leu Ile Gly Met Phe Ala Gln Ala Ser Ala Asn Asp Val Tyr
145                 150                 155                 160

Ala Ser Ala Gly Ser Ser Gly Gly Gly Gly Tyr Gly Ala Ser Ser Ala
                165                 170                 175

Ser Ala Ala Ser Ala Ser Ala Ala Ala Pro Ser Gly Val Ala Tyr Gln
            180                 185                 190

Ala Pro Ala Gln Ala Gln Ile Ser Phe Thr Leu Arg Gly Gln Gln Pro
        195                 200                 205

Val Ser Tyr Gly Gln Gly Gly Ala Gly Pro Gly Gly Ala Gly Ala Ala
    210                 215                 220

Ala Ala Ala Ala Ala Ala Ala Gly Gly Ala Gly Gln Gly Gly Gln Gly
225                 230                 235                 240

Gly Tyr Gly Gln Gly Gly Tyr Gly Gln Gly Gly Ala Gly Gln Gly Gly
                245                 250                 255

Ser Gly Ala Ala Ala Ala Ala Gly Gly Thr Gly Gln Gly Gly Ala Gly
            260                 265                 270

Gln Gly Gly Ala Gly Ala Ala Ala Ala Ala Ala Ala Ala Ala Gly Gly
        275                 280                 285

Ala Gly Gln Gly Gly Gln Gly Gly Tyr Gly Gln Gly Gly Tyr Gly Gln
    290                 295                 300

Gly Gly Thr Gly Gln Gly Gly Ala Gly Ala Ala Ala Arg Gly Gly Tyr
305                 310                 315                 320

Gly Gln Gly Gly Ala Gly Gln Gly Gly Ala Gly Ala Ala Ala Ala Ala
                325                 330                 335

Ala Ala Ala Gly Gly Ala Gly Gln Gly Gly Gln Gly Gly Tyr Gly Gln
            340                 345                 350

Gly Gly Tyr Gly Gln Gly Gly Ala Gly Gln Gly Gly Ala Ala Ala Ala
        355                 360                 365

Ala Ala Ala Ala Gly Gly Ala Gly Gln Gly Gly Tyr Gly Arg Gly Gly
    370                 375                 380

Ala Gly Gln Gly Gly Ala Ala Ala Ala Ala Ala Ala Ala Ala Gly Ala
385                 390                 395                 400

Gly Gln Gly Gly Tyr Gly Gly Gln Gly Ala Gly Gln Gly Gly Ala Gly
                405                 410                 415

Ala Ala Ala Ala Ala Ala Ala Ala Gly Gly Ala Gly Gln Gly Gly Gln
            420                 425                 430

Gly Gly Tyr Gly Arg Gly Gly Tyr Gly Gln Gly Gly Ala Gly Gln Gly
        435                 440                 445

Gly Ala Gly Ala Ala Ala Ala Ala Ala Ala Ala Ala Gly Gly Ala Gly
    450                 455                 460

Gln Gly Gly Gln Gly Gly Tyr Gly Gln Gly Gly Tyr Gly Gln Gly Gly
465                 470                 475                 480
```

```
Ala Gly Gln Gly Gly Ala Ala Ala Ala Ala Ala Ala Ala Ala Ala Gly
                485                 490                 495

Gly Ala Gly Gln Gly Gly Tyr Gly Gly Tyr Gly Gln Gln Gly Gly Ala
            500                 505                 510

Gly Ala Ala Ala Ala Ala Ala Ser Gly Pro Gly Gln Ile Tyr Tyr Gly
        515                 520                 525

Pro Gln Ser Val Ala Ala Pro Ala Ala Ala Ala Ala Ser Ala Leu Ala
    530                 535                 540

Ala Pro Ala Thr Ser Ala Arg Ile Ser Ser His Ala Ser Ala Leu Leu
545                 550                 555                 560

Ser Asn Gly Pro Thr Asn Pro Ala Ser Ile Ser Asn Val Ile Ser Asn
                565                 570                 575

Ala Val Ser Gln Ile Ser Ser Ser Asn Pro Gly Ala Ser Ala Cys Asp
            580                 585                 590

Val Leu Val Gln Ala Leu Leu Glu Leu Val Thr Ala Leu Leu Thr Ile
        595                 600                 605

Ile Gly Ser Ser Asn Ile Gly Ser Val Asn Tyr Asp Ser Ser Gly Gln
    610                 615                 620

Tyr Ala Gln Val Val Thr Gln
625                 630


<210> SEQ ID NO 9
<211> LENGTH: 4183
<212> TYPE: DNA
<213> ORGANISM: Latrodectus hesperus
<220> FEATURE:
<221> NAME/KEY: CDS
<222> LOCATION: (1379)..(3472)

<400> SEQUENCE: 9

tgaatgatct aataatcaga aaagaatatt aagcgctgtt tgaagctgat aactcaattc     60

atgttaccac gaggattgct ttgatttgtt tgcctgtctg gggtaacttt tacaagatta    120

atcagacagg gaactaaaat taaaagtaaa ttcctgacaa atacaaaaca ttcattccta    180

aagagaatgc tgaactcaaa acgagttgat tcgtattcca actgaattta aaagagatga    240

taaataggaa ccagaaagag aatgaaagag atgatatatc agtcactatg aaaaaatact    300

ctctattttt cacagcaggt ttcaataaat gcttatagca cattctacat tttttatagt    360

tactgaaacc gcgaatttaa attactgaat attttcaaat attcagtaat tcaaattcca    420

ctttggaaag gaattatggt tgtaagaaat actgtttgat atacggagag agagtgtgag    480

agtgaaagag agagagagga gtagttgaag aagcattcat ataaacaaat acaaactata    540

gttagcattt gtttcagata aacaaaacat tcaataataa caattcatat aaacaaatgc    600

taactatata gtatagttag cattcaacaa aaaatatttc atttttatcg ctatgtgatt    660

agatttattt cacaattgaa ttttttggga aatcagaaac caaattgcca aatgtttctt    720

tcaatatatc ctaggaataa gaattgacag taatattgta aagtatttac tttagttaaa    780

agttataaat catgacacac attctttcta cactttaaat gccactctcg atagaaatgc    840

ttaaaaatat acgagaaaaa tatgaataaa taaagtagga atattctgat tctaaagatt    900

gctgtacttc aaatctagaa taaaaattat gtaattaagc tcgatagaat agttttgaat    960

aatagctgta acaataagat tataaaaaat tgtaacataa tttcgcatca attaaatgca   1020

actatatgtt atacgaatat taaatttaca aaagctaatg atataatttt attaggcgta   1080

acacaaatta attaatcatt aaaactaatt atagttactt tgaaagcaca tttaaactga   1140
```

```
agcctaaata tcaatatctg aaaagattaa ctaaaaatat aaaggaaatc tcaaacataa   1200

aataatatta aggtattcaa cttcctaact gcgaaataca ggtgtacaaa ttataatgtc   1260

aatcataaga tacatacgtc atttaaaaac gtggggataa catcattcct taaatatttc   1320

caggtgtatt gataaaacct gctgcaaatc acgaccaatc gttgtataaa taaggaga     1378

atg tac agc cta agt att cag tcg gat ttt cca act act aca atg acc     1426
Met Tyr Ser Leu Ser Ile Gln Ser Asp Phe Pro Thr Thr Thr Met Thr
1               5                   10                  15

tgg tct act cga ctt gct tta tca ttc ttc gca gtg atc tgc aca caa     1474
Trp Ser Thr Arg Leu Ala Leu Ser Phe Phe Ala Val Ile Cys Thr Gln
            20                  25                  30

agc att tat gct cta ggg cag gga aac act cca tgg tct act aaa gca     1522
Ser Ile Tyr Ala Leu Gly Gln Gly Asn Thr Pro Trp Ser Thr Lys Ala
        35                  40                  45

aat gct gat aat ttt atg aac gga ttt ttg agt gct tgt gca caa agt     1570
Asn Ala Asp Asn Phe Met Asn Gly Phe Leu Ser Ala Cys Ala Gln Ser
    50                  55                  60

gga gta ttt tca gca gat cag gta gac gat atg acc acg att ggt aaa     1618
Gly Val Phe Ser Ala Asp Gln Val Asp Asp Met Thr Thr Ile Gly Lys
65                  70                  75                  80

aca tta atg ata gct atg gat aaa atg ggt gga aaa att tcc tcc tca     1666
Thr Leu Met Ile Ala Met Asp Lys Met Gly Gly Lys Ile Ser Ser Ser
                85                  90                  95

aag cta caa gcc ttg gat atg gcc ttt gca tca tct gta gca gaa atc     1714
Lys Leu Gln Ala Leu Asp Met Ala Phe Ala Ser Ser Val Ala Glu Ile
            100                 105                 110

gct act gca gaa gga ggt gcc aac ata aat gac att aca gat gca att     1762
Ala Thr Ala Glu Gly Gly Ala Asn Ile Asn Asp Ile Thr Asp Ala Ile
        115                 120                 125

cga tat gct ttg caa aac gca ttt tat caa aca aca gga gcg gtt aat     1810
Arg Tyr Ala Leu Gln Asn Ala Phe Tyr Gln Thr Thr Gly Ala Val Asn
    130                 135                 140

tcc aaa ttt att aat gaa att tca aat tta ata tat atg ttc gct caa     1858
Ser Lys Phe Ile Asn Glu Ile Ser Asn Leu Ile Tyr Met Phe Ala Gln
145                 150                 155                 160

aca aac ata aat gat gtc aat ggg gga gga gga tac ggt caa gga ggt     1906
Thr Asn Ile Asn Asp Val Asn Gly Gly Gly Gly Tyr Gly Gln Gly Gly
                165                 170                 175

gca gga caa ggt gga gcc gca gca gca gca gct ggt gga gca gga caa     1954
Ala Gly Gln Gly Gly Ala Ala Ala Ala Ala Ala Gly Gly Ala Gly Gln
            180                 185                 190

gga gga tat ggc aga ggt gga gcc gga caa ggt gga gca gca gca gcc     2002
Gly Gly Tyr Gly Arg Gly Gly Ala Gly Gln Gly Gly Ala Ala Ala Ala
        195                 200                 205

gct gga gct ggt caa ggt ggt tat gga gat caa ggt gcc gga caa ggt     2050
Ala Gly Ala Gly Gln Gly Gly Tyr Gly Asp Gln Gly Ala Gly Gln Gly
    210                 215                 220

gga gct gga gcc gca gcg gca gca gca act gca tct ggt gga gcc gga     2098
Gly Ala Gly Ala Ala Ala Ala Ala Ala Thr Ala Ser Gly Gly Ala Gly
225                 230                 235                 240

caa gga gga tat ggc cga ggt gga gca gga caa ggt gga gaa gca gca     2146
Gln Gly Gly Tyr Gly Arg Gly Gly Ala Gly Gln Gly Gly Glu Ala Ala
                245                 250                 255

gcc gct gct gca gcc gcc gga gct ggt caa ggt ggt tat gga gga caa     2194
Ala Ala Ala Ala Ala Ala Gly Ala Gly Gln Gly Gly Tyr Gly Gly Gln
            260                 265                 270

gag gcc gca caa ggt gga gct gga gct gca gcc gca gca gca gca gcc     2242
Glu Ala Ala Gln Gly Gly Ala Gly Ala Ala Ala Ala Ala Ala Ala Ala
```

-continued

```
        275                 280                 285

gga ggt gca ggt cta gga gga cta ggt gga tac gga caa ggt gga tct      2290
Gly Gly Ala Gly Leu Gly Gly Leu Gly Gly Tyr Gly Gln Gly Gly Ser
    290                 295                 300

gga gca gca gca gca gcc gga gga gca ggt caa gga gga gaa ggt ggc      2338
Gly Ala Ala Ala Ala Ala Gly Gly Ala Gly Gln Gly Gly Glu Gly Gly
305                 310                 315                 320

gtt gga caa gga ggt tac ggt caa aga ggt gcc gga caa ggt gga gca      2386
Val Gly Gln Gly Gly Tyr Gly Gln Arg Gly Ala Gly Gln Gly Gly Ala
                325                 330                 335

gga gcc gca gca gct gca gct ggt gga gcc gga caa gga gaa tat ggc      2434
Gly Ala Ala Ala Ala Ala Ala Gly Gly Ala Gly Gln Gly Glu Tyr Gly
            340                 345                 350

cga ggt gga gca gga caa ggt aga gca gca gca gcc gct gct gca gcc      2482
Arg Gly Gly Ala Gly Gln Gly Arg Ala Ala Ala Ala Ala Ala Ala Ala
        355                 360                 365

gcc gga gct ggt caa ggt agt tat gga gga caa ggt gcc gga ggt tac      2530
Ala Gly Ala Gly Gln Gly Ser Tyr Gly Gly Gln Gly Ala Gly Gly Tyr
    370                 375                 380

ggt cga gga ggt gcc gga caa ggc gga gct gga gca gca gca gcg gca      2578
Gly Arg Gly Gly Ala Gly Gln Gly Gly Ala Gly Ala Ala Ala Ala Ala
385                 390                 395                 400

gca gca gcc gga ggt gca ggt caa gta gga caa agt ggc tat gga caa      2626
Ala Ala Ala Gly Gly Ala Gly Gln Val Gly Gln Ser Gly Tyr Gly Gln
                405                 410                 415

gaa ggt tac ggt caa gga ggt gcc gga caa ggt gga gct gga gct gca      2674
Glu Gly Tyr Gly Gln Gly Gly Ala Gly Gln Gly Gly Ala Gly Ala Ala
            420                 425                 430

gcg gcg gca gca gct gca gct ggt gga gcc gga caa ggt gga tat ggc      2722
Ala Ala Ala Ala Ala Ala Ala Gly Gly Ala Gly Gln Gly Gly Tyr Gly
        435                 440                 445

cga ggt gga gca gga caa ggt gga gca gca gca gcc gct gct gca gcc      2770
Arg Gly Gly Ala Gly Gln Gly Gly Ala Ala Ala Ala Ala Ala Ala Ala
    450                 455                 460

gca gga gct ggt caa ggt ggt tat gga gga caa ggt gcc gga caa ggt      2818
Ala Gly Ala Gly Gln Gly Gly Tyr Gly Gly Gln Gly Ala Gly Gln Gly
465                 470                 475                 480

gga gct gga gct gca gcc gca gca gca gct gct gga tgg gca ggt caa      2866
Gly Ala Gly Ala Ala Ala Ala Ala Ala Ala Ala Gly Trp Ala Gly Gln
                485                 490                 495

gga gga caa ggt gga tat gga caa gga gga tac gga caa ggt gga tct      2914
Gly Gly Gln Gly Gly Tyr Gly Gln Gly Gly Tyr Gly Gln Gly Gly Ser
            500                 505                 510

gga gca gct gca gcg gca gca gca gca gcc gga ggt gca ggt caa gga      2962
Gly Ala Ala Ala Ala Ala Ala Ala Ala Ala Gly Gly Ala Gly Gln Gly
        515                 520                 525

gga caa ggt ggc tat gga caa gga ggt tac gat caa gga ggt gcc gga      3010
Gly Gln Gly Gly Tyr Gly Gln Gly Gly Tyr Asp Gln Gly Gly Ala Gly
    530                 535                 540

caa ggt gga gct gca gcc gta gca gca gca gct gca gct gga gga gca      3058
Gln Gly Gly Ala Ala Ala Val Ala Ala Ala Ala Ala Ala Gly Gly Ala
545                 550                 555                 560

gga caa gga gga tac ggt cca caa ggt gga gca gga gcc gca gca gca      3106
Gly Gln Gly Gly Tyr Gly Pro Gln Gly Gly Ala Gly Ala Ala Ala Ala
                565                 570                 575

tca gct agt gga cct gtt caa att tat tat gga ccc caa tct gtt gct      3154
Ser Ala Ser Gly Pro Val Gln Ile Tyr Tyr Gly Pro Gln Ser Val Ala
            580                 585                 590

gct cca gca gct gca gca gct tct gcc ttg gca gct cca gct aca agt      3202
```

```
Ala Pro Ala Ala Ala Ala Ala Ser Ala Leu Ala Ala Pro Ala Thr Ser
        595                 600                 605

gcg aga att tct tca cac gcc tca gct ctt ctt tca aat gga cct act     3250
Ala Arg Ile Ser Ser His Ala Ser Ala Leu Leu Ser Asn Gly Pro Thr
    610                 615                 620

aac cct gct tct att tca aac gtt att agt aat gct gta tcc caa att     3298
Asn Pro Ala Ser Ile Ser Asn Val Ile Ser Asn Ala Val Ser Gln Ile
625                 630                 635                 640

agt tcc agc aat cca gga gcg tct gcg tgt gat gtt ctc gtt caa gct     3346
Ser Ser Ser Asn Pro Gly Ala Ser Ala Cys Asp Val Leu Val Gln Ala
                645                 650                 655

ctt ctt gaa ctt gtt act gct ttg ctc acc att att gga tca tca aat     3394
Leu Leu Glu Leu Val Thr Ala Leu Leu Thr Ile Ile Gly Ser Ser Asn
            660                 665                 670

att ggc agt gtt aat tat gat tct tca ggc caa tat gcg caa gtt gtt     3442
Ile Gly Ser Val Asn Tyr Asp Ser Ser Gly Gln Tyr Ala Gln Val Val
        675                 680                 685

act caa tct gta caa aat gca ttc gct tga ttctaaaaag ttgcttaagc       3492
Thr Gln Ser Val Gln Asn Ala Phe Ala
    690                 695

attcatttta taaaatatac taatgtaaca tgcattgagt aattctgata ttgaataaag   3552

catttatctt ctctataatc tcatttgcct aattattttt ttgttttttt acttctgtcc   3612

tgagatcagt ttcttatata tggtaattca ggcattttaa catattaata tattattcaa   3672

ttgtaatatc tgcggaaaaa tatgtacaga atacaagttg tagaattcaa attaattaac   3732

tttttaaat gaaaataaat tgaacttaat tttgaggact ttatgatatg gtttctaaat    3792

atttttattt tcacgctggt tttcctggag aaatcattaa tttccaatat aatatatgtt   3852

tattataact gcgtagtccc attccttact tttcaggtaa acgctttagt ttactatact   3912

tctgcagttt tttaatattg aactgaaacg tattagatga tttcgatctt tgaatgaaag   3972

tataatacta aaaacatttt aaatacttaa taatatttat tatgtcacca gatatctctc   4032

aaaatgacag ggtcatttt gtaattgaaa gaagaaattt tgaaattgaa taatgaattt    4092

tgagtggttt actgccaaat cagctttgca cataagaatg atattttggt gcgagatgag   4152

aatagcgttt ctggaaatgc ttttcctttg c                                  4183


<210> SEQ ID NO 10
<211> LENGTH: 697
<212> TYPE: PRT
<213> ORGANISM: Latrodectus hesperus

<400> SEQUENCE: 10

Met Tyr Ser Leu Ser Ile Gln Ser Asp Phe Pro Thr Thr Thr Met Thr
1               5                   10                  15

Trp Ser Thr Arg Leu Ala Leu Ser Phe Phe Ala Val Ile Cys Thr Gln
            20                  25                  30

Ser Ile Tyr Ala Leu Gly Gln Gly Asn Thr Pro Trp Ser Thr Lys Ala
        35                  40                  45

Asn Ala Asp Asn Phe Met Asn Gly Phe Leu Ser Ala Cys Ala Gln Ser
    50                  55                  60

Gly Val Phe Ser Ala Asp Gln Val Asp Asp Met Thr Thr Ile Gly Lys
65                  70                  75                  80

Thr Leu Met Ile Ala Met Asp Lys Met Gly Gly Lys Ile Ser Ser Ser
                85                  90                  95

Lys Leu Gln Ala Leu Asp Met Ala Phe Ala Ser Ser Val Ala Glu Ile
            100                 105                 110
```

-continued

```
Ala Thr Ala Glu Gly Gly Ala Asn Ile Asn Asp Ile Thr Asp Ala Ile
        115                 120                 125

Arg Tyr Ala Leu Gln Asn Ala Phe Tyr Gln Thr Thr Gly Ala Val Asn
    130                 135                 140

Ser Lys Phe Ile Asn Glu Ile Ser Asn Leu Ile Tyr Met Phe Ala Gln
145                 150                 155                 160

Thr Asn Ile Asn Asp Val Asn Gly Gly Gly Gly Tyr Gly Gln Gly Gly
                165                 170                 175

Ala Gly Gln Gly Gly Ala Ala Ala Ala Ala Ala Gly Gly Ala Gly Gln
            180                 185                 190

Gly Gly Tyr Gly Arg Gly Gly Ala Gly Gln Gly Gly Ala Ala Ala Ala
        195                 200                 205

Ala Gly Ala Gly Gln Gly Gly Tyr Gly Asp Gln Gly Ala Gly Gln Gly
    210                 215                 220

Gly Ala Gly Ala Ala Ala Ala Ala Ala Thr Ala Ser Gly Gly Ala Gly
225                 230                 235                 240

Gln Gly Gly Tyr Gly Arg Gly Gly Ala Gly Gln Gly Gly Glu Ala Ala
                245                 250                 255

Ala Ala Ala Ala Ala Ala Gly Ala Gly Gln Gly Gly Tyr Gly Gly Gln
            260                 265                 270

Glu Ala Ala Gln Gly Gly Ala Gly Ala Ala Ala Ala Ala Ala Ala Ala
        275                 280                 285

Gly Gly Ala Gly Leu Gly Gly Leu Gly Gly Tyr Gly Gln Gly Gly Ser
    290                 295                 300

Gly Ala Ala Ala Ala Ala Gly Gly Ala Gly Gln Gly Gly Glu Gly Gly
305                 310                 315                 320

Val Gly Gln Gly Gly Tyr Gly Gln Arg Gly Ala Gly Gln Gly Gly Ala
                325                 330                 335

Gly Ala Ala Ala Ala Ala Ala Gly Gly Ala Gly Gln Gly Glu Tyr Gly
            340                 345                 350

Arg Gly Gly Ala Gly Gln Gly Arg Ala Ala Ala Ala Ala Ala Ala Ala
        355                 360                 365

Ala Gly Ala Gly Gln Gly Ser Tyr Gly Gly Gln Gly Ala Gly Gly Tyr
    370                 375                 380

Gly Arg Gly Gly Ala Gly Gln Gly Gly Ala Gly Ala Ala Ala Ala Ala
385                 390                 395                 400

Ala Ala Ala Gly Gly Ala Gly Gln Val Gly Gln Ser Gly Tyr Gly Gln
                405                 410                 415

Glu Gly Tyr Gly Gln Gly Gly Ala Gly Gln Gly Gly Ala Gly Ala Ala
            420                 425                 430

Ala Ala Ala Ala Ala Ala Ala Gly Gly Ala Gly Gln Gly Gly Tyr Gly
        435                 440                 445

Arg Gly Gly Ala Gly Gln Gly Gly Ala Ala Ala Ala Ala Ala Ala Ala
    450                 455                 460

Ala Gly Ala Gly Gln Gly Gly Tyr Gly Gly Gln Gly Ala Gly Gln Gly
465                 470                 475                 480

Gly Ala Gly Ala Ala Ala Ala Ala Ala Ala Ala Gly Trp Ala Gly Gln
                485                 490                 495

Gly Gly Gln Gly Gly Tyr Gly Gln Gly Gly Tyr Gly Gln Gly Gly Ser
            500                 505                 510

Gly Ala Ala Ala Ala Ala Ala Ala Ala Ala Gly Gly Ala Gly Gln Gly
        515                 520                 525
```

```
Gly Gln Gly Gly Tyr Gly Gln Gly Gly Tyr Asp Gln Gly Gly Ala Gly
    530                 535                 540

Gln Gly Gly Ala Ala Ala Val Ala Ala Ala Ala Ala Ala Gly Gly Ala
545                 550                 555                 560

Gly Gln Gly Gly Tyr Gly Pro Gln Gly Gly Ala Gly Ala Ala Ala Ala
                565                 570                 575

Ser Ala Ser Gly Pro Val Gln Ile Tyr Tyr Gly Pro Gln Ser Val Ala
            580                 585                 590

Ala Pro Ala Ala Ala Ala Ala Ser Ala Leu Ala Ala Pro Ala Thr Ser
        595                 600                 605

Ala Arg Ile Ser Ser His Ala Ser Ala Leu Leu Ser Asn Gly Pro Thr
    610                 615                 620

Asn Pro Ala Ser Ile Ser Asn Val Ile Ser Asn Ala Val Ser Gln Ile
625                 630                 635                 640

Ser Ser Ser Asn Pro Gly Ala Ser Ala Cys Asp Val Leu Val Gln Ala
                645                 650                 655

Leu Leu Glu Leu Val Thr Ala Leu Leu Thr Ile Ile Gly Ser Ser Asn
            660                 665                 670

Ile Gly Ser Val Asn Tyr Asp Ser Ser Gly Gln Tyr Ala Gln Val Val
        675                 680                 685

Thr Gln Ser Val Gln Asn Ala Phe Ala
    690                 695
```

<210> SEQ ID NO 11
<211> LENGTH: 2687
<212> TYPE: DNA
<213> ORGANISM: Latrodectus hesperus
<220> FEATURE:
<221> NAME/KEY: CDS
<222> LOCATION: (846)..(2687)
<220> FEATURE:
<221> NAME/KEY: misc_feature
<222> LOCATION: (2095)..(2095)
<223> OTHER INFORMATION: n is a, c, g, or t
<220> FEATURE:
<221> NAME/KEY: misc_feature
<222> LOCATION: (2600)..(2602)
<223> OTHER INFORMATION: n is a, c, g, or t
<220> FEATURE:
<221> NAME/KEY: misc_feature
<222> LOCATION: (2639)..(2644)
<223> OTHER INFORMATION: n is a, c, g, or t

<400> SEQUENCE: 11

```
gaggattttt tttcattata ttttttctca ctggtatcga aaatgttttc aataaagagc     60

aatttttcta tcaacctctt ttacacaata agtattagaa cattttatgc ttagaattaa    120

ccctttaaaa acattcagca gcacaataag ctgcttacac attttacact taaatagaca    180

ggattactta gctttcttca aaattaaaaa cttatttcat taaagaattg tatgaatcgg    240

aaatttaaga catcgaatta ttcaatagaa agaaaatctc tgtattttta agatccttat    300

attttttaaa cttggaataa aaatgacgtt aaattataaa aagtttttgt ctatctgctc    360

taacttacaa attatcaaac atgcgtcatt aattattaca aattcggaac agagaagtat    420

gttgtattaa aacgaggaaa tgatactcat aatattacat taaaaaagta attaatcaat    480

aaaacagttc gacaaaatat aattaaattt ttaaagaata atattgattg cctattatgg    540

ctacacagaa actaaagatt ttaaaatttg taaaaattaa tatacaaaaa taattactaa    600

atctaaaaca ggaaatacgt caaagcataa aaaacatcca cgacgtttgc attcgacctt    660

agaaaaacag atgagtaaat gaaagtgaaa cgtacatacg tcaattcaac tgggcgagat    720
```

-continued

```
gaaatcgtag actgcatatt tccaggtata ttgatacacc tgctgcacat cacgaacaat    780

cagtgtataa aagaggagaa cgatcagcgt aaagtattct cagtcgggat tttccaacta    840

ctaca atg act tgg tct act cga ctt gcc tta tca ttt ctt tta gtg ctc    890
      Met Thr Trp Ser Thr Arg Leu Ala Leu Ser Phe Leu Leu Val Leu
      1               5                   10                  15

tgc act cag agc att tat gct ctg gcg caa gcc aac acg cca tgg tca      938
Cys Thr Gln Ser Ile Tyr Ala Leu Ala Gln Ala Asn Thr Pro Trp Ser
                20                  25                  30

agt aaa gcg aat gct gat gct ttt atc aat tcc ttt att tcg gca gct      986
Ser Lys Ala Asn Ala Asp Ala Phe Ile Asn Ser Phe Ile Ser Ala Ala
            35                  40                  45

tcg aat act gga tcc ttc tcc caa gat cag atg gaa gat atg tca ttg     1034
Ser Asn Thr Gly Ser Phe Ser Gln Asp Gln Met Glu Asp Met Ser Leu
        50                  55                  60

att ggt aat aca tta atg gca gca atg gat aat atg ggt gga aga att     1082
Ile Gly Asn Thr Leu Met Ala Ala Met Asp Asn Met Gly Gly Arg Ile
    65                  70                  75

acg cca tcc aaa tta cag gct tta gat atg gct ttc gca tca tct gta     1130
Thr Pro Ser Lys Leu Gln Ala Leu Asp Met Ala Phe Ala Ser Ser Val
80                  85                  90                  95

gca gaa att gct gct tcg gaa gga gga gac tta gga gta aca aca aat     1178
Ala Glu Ile Ala Ala Ser Glu Gly Gly Asp Leu Gly Val Thr Thr Asn
                100                 105                 110

gca att gca gat gct tta aca tca gct ttc tat caa aca acc gga gta     1226
Ala Ile Ala Asp Ala Leu Thr Ser Ala Phe Tyr Gln Thr Thr Gly Val
            115                 120                 125

gtt aat agc aga ttt att agc gaa att aga agt ttg att ggc atg ttt     1274
Val Asn Ser Arg Phe Ile Ser Glu Ile Arg Ser Leu Ile Gly Met Phe
        130                 135                 140

gca cag gca tct gcc aac gat gta tac gcc tca gca ggt tcc agc ggt     1322
Ala Gln Ala Ser Ala Asn Asp Val Tyr Ala Ser Ala Gly Ser Ser Gly
    145                 150                 155

gga gga ggg tat gga gca tct tct gca agt gca gca tct gca agc gca     1370
Gly Gly Gly Tyr Gly Ala Ser Ser Ala Ser Ala Ala Ser Ala Ser Ala
160                 165                 170                 175

gca gca cca tca ggt gtc gca tac caa gct cca gca caa gca caa att     1418
Ala Ala Pro Ser Gly Val Ala Tyr Gln Ala Pro Ala Gln Ala Gln Ile
                180                 185                 190

tcc ttc tct ttg aga gga caa cag cca gtt agt tat ggt caa gga gga     1466
Ser Phe Ser Leu Arg Gly Gln Gln Pro Val Ser Tyr Gly Gln Gly Gly
            195                 200                 205

gct agc gca gct tca gga gca gcg gct ggt caa gga ggc gca gga cca     1514
Ala Ser Ala Ala Ser Gly Ala Ala Ala Gly Gln Gly Gly Ala Gly Pro
        210                 215                 220

gga gga gct gga gca gca gcg gca gcg gca gca gca gct gga gga gcg     1562
Gly Gly Ala Gly Ala Ala Ala Ala Ala Ala Ala Ala Ala Gly Gly Ala
    225                 230                 235

ggt caa gga gga caa gga gga tat gga caa gga gga tac ggt caa gga     1610
Gly Gln Gly Gly Gln Gly Gly Tyr Gly Gln Gly Gly Tyr Gly Gln Gly
240                 245                 250                 255

ggt gcc gga caa ggt gga tct gga gca gca gca gcg gca gca gca gca     1658
Gly Ala Gly Gln Gly Gly Ser Gly Ala Ala Ala Ala Ala Ala Ala Ala
                260                 265                 270

gct gga ggc acc ggt caa gga ggt gct gga caa ggt gga gca gga gca     1706
Ala Gly Gly Thr Gly Gln Gly Gly Ala Gly Gln Gly Gly Ala Gly Ala
            275                 280                 285

gca gcg gca gcc gca gca gca gct gga gat gca ggt caa gga gga caa     1754
Ala Ala Ala Ala Ala Ala Ala Ala Gly Asp Ala Gly Gln Gly Gly Gln
```

-continued

```
        290                 295                 300

ggt gga tat gga caa gga gga tac gga caa ggt gga tct gga gca gca      1802
Gly Gly Tyr Gly Gln Gly Gly Tyr Gly Gln Gly Gly Ser Gly Ala Ala
    305                 310                 315

gca gcg gca gca gca gca gcc gga ggt gca ggt caa ggt gga caa ggt      1850
Ala Ala Ala Ala Ala Ala Ala Gly Gly Ala Gly Gln Gly Gly Gln Gly
320                 325                 330                 335

ggc tat gga caa gga ggt tac ggt caa gga ggt gcc gga caa ggt gga      1898
Gly Tyr Gly Gln Gly Gly Tyr Gly Gln Gly Gly Ala Gly Gln Gly Gly
                340                 345                 350

gat gga gcc gca gcg gca gca gca gct gca gct ggt gga gcc gga caa      1946
Asp Gly Ala Ala Ala Ala Ala Ala Ala Ala Ala Gly Gly Ala Gly Gln
            355                 360                 365

gga gga tat ggc cga ggt gga gca gga caa ggt gga gca gcc gca gcc      1994
Gly Gly Tyr Gly Arg Gly Gly Ala Gly Gln Gly Gly Ala Ala Ala Ala
        370                 375                 380

gct gct gca gcc gca gga gct ggt caa ggt ggc tat gga gga gga gca      2042
Ala Ala Ala Ala Ala Gly Ala Gly Gln Gly Gly Tyr Gly Gly Gly Ala
    385                 390                 395

gca gca gcg gca gca gca gca gcc gga ggt gca ggt caa gga gga caa      2090
Ala Ala Ala Ala Ala Ala Ala Ala Gly Gly Ala Gly Gln Gly Gly Gln
400                 405                 410                 415

ggt gnc tat gga caa gga ggt tac gga caa ggt gga tct gga gca gca      2138
Gly Xaa Tyr Gly Gln Gly Gly Tyr Gly Gln Gly Gly Ser Gly Ala Ala
                420                 425                 430

gca gcg gca gca gca gca gcc gga ggt gca ggt caa ggt gga caa ggt      2186
Ala Ala Ala Ala Ala Ala Ala Gly Gly Ala Gly Gln Gly Gly Gln Gly
            435                 440                 445

ggc tat gga caa gga ggt tac ggt caa gga ggt gcc gga caa ggt gga      2234
Gly Tyr Gly Gln Gly Gly Tyr Gly Gln Gly Gly Ala Gly Gln Gly Gly
        450                 455                 460

gct ggg gcc gca gcg gca gca gca gct gca gct ggt gga gcc gga caa      2282
Ala Gly Ala Ala Ala Ala Ala Ala Ala Ala Ala Gly Gly Ala Gly Gln
    465                 470                 475

gga gga tat ggc cga ggt gga gca gga caa ggt gga gca gca gca gcc      2330
Gly Gly Tyr Gly Arg Gly Gly Ala Gly Gln Gly Gly Ala Ala Ala Ala
480                 485                 490                 495

gct gct gca gcc gca gga gca ggt caa cgt ggt tat gga gga caa ggt      2378
Ala Ala Ala Ala Ala Gly Ala Gly Gln Arg Gly Tyr Gly Gly Gln Gly
                500                 505                 510

gcc gga caa ggt gga gct gga gct gca gcc gca gca gca gct gct gga      2426
Ala Gly Gln Gly Gly Ala Gly Ala Ala Ala Ala Ala Ala Ala Ala Gly
            515                 520                 525

ggt gca ggt caa gga gga caa cgt gga tat gga caa gga gga tac gga      2474
Gly Ala Gly Gln Gly Gly Gln Arg Gly Tyr Gly Gln Gly Gly Tyr Gly
        530                 535                 540

caa ggt gga tct gga gca gca gca gcg gca gca gca gct agt gga cct      2522
Gln Gly Gly Ser Gly Ala Ala Ala Ala Ala Ala Ala Ala Ser Gly Pro
    545                 550                 555

ggt caa gtt tat tat gga ccc caa tct ttt gca gct cca gca gct gca      2570
Gly Gln Val Tyr Tyr Gly Pro Gln Ser Phe Ala Ala Pro Ala Ala Ala
560                 565                 570                 575

gca gct tct gct ttg tca gct cca gct acn nnc gcg aga att tct tca      2618
Ala Ala Ser Ala Leu Ser Ala Pro Ala Thr Xaa Ala Arg Ile Ser Ser
                580                 585                 590

cac gcc tca gct ctt ctt tcn nnn nna cca act aac cct gct tct att      2666
His Ala Ser Ala Leu Leu Xaa Xaa Xaa Pro Thr Asn Pro Ala Ser Ile
            595                 600                 605

tca aac gtt att agt aat gct                                          2687
```

```
Ser Asn Val Ile Ser Asn Ala
        610


<210> SEQ ID NO 12
<211> LENGTH: 614
<212> TYPE: PRT
<213> ORGANISM: Latrodectus hesperus
<220> FEATURE:
<221> NAME/KEY: misc_feature
<222> LOCATION: (417)..(417)
<223> OTHER INFORMATION: The 'Xaa' at location 417 stands for Asp, Gly,
      Ala, or Val.
<220> FEATURE:
<221> NAME/KEY: misc_feature
<222> LOCATION: (586)..(586)
<223> OTHER INFORMATION: The 'Xaa' at location 586 stands for Asn, Ser,
      Thr, Ile, Asp, Gly, Ala, Val, His, Arg, Pro, Leu, Tyr, Cys, or
      Phe.
<220> FEATURE:
<221> NAME/KEY: misc_feature
<222> LOCATION: (598)..(598)
<223> OTHER INFORMATION: The 'Xaa' at location 598 stands for Ser.
<220> FEATURE:
<221> NAME/KEY: misc_feature
<222> LOCATION: (599)..(599)
<223> OTHER INFORMATION: The 'Xaa' at location 599 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (600)..(600)
<223> OTHER INFORMATION: The 'Xaa' at location 600 stands for Lys, Arg,
      Thr, Ile, Glu, Gly, Ala, Val, Gln, Pro, Leu, or Ser.

<400> SEQUENCE: 12

Met Thr Trp Ser Thr Arg Leu Ala Leu Ser Phe Leu Leu Val Leu Cys
1               5                   10                  15

Thr Gln Ser Ile Tyr Ala Leu Ala Gln Ala Asn Thr Pro Trp Ser Ser
            20                  25                  30

Lys Ala Asn Ala Asp Ala Phe Ile Asn Ser Phe Ile Ser Ala Ala Ser
        35                  40                  45

Asn Thr Gly Ser Phe Ser Gln Asp Gln Met Glu Asp Met Ser Leu Ile
    50                  55                  60

Gly Asn Thr Leu Met Ala Ala Met Asp Asn Met Gly Gly Arg Ile Thr
65                  70                  75                  80

Pro Ser Lys Leu Gln Ala Leu Asp Met Ala Phe Ala Ser Ser Val Ala
                85                  90                  95

Glu Ile Ala Ala Ser Glu Gly Gly Asp Leu Gly Val Thr Thr Asn Ala
            100                 105                 110

Ile Ala Asp Ala Leu Thr Ser Ala Phe Tyr Gln Thr Thr Gly Val Val
        115                 120                 125

Asn Ser Arg Phe Ile Ser Glu Ile Arg Ser Leu Ile Gly Met Phe Ala
    130                 135                 140

Gln Ala Ser Ala Asn Asp Val Tyr Ala Ser Ala Gly Ser Ser Gly Gly
145                 150                 155                 160

Gly Gly Tyr Gly Ala Ser Ser Ala Ser Ala Ala Ser Ala Ser Ala Ala
                165                 170                 175

Ala Pro Ser Gly Val Ala Tyr Gln Ala Pro Ala Gln Ala Gln Ile Ser
            180                 185                 190

Phe Ser Leu Arg Gly Gln Gln Pro Val Ser Tyr Gly Gln Gly Gly Ala
        195                 200                 205

Ser Ala Ala Ser Gly Ala Ala Ala Gly Gln Gly Gly Ala Gly Pro Gly
    210                 215                 220
```

-continued

```
Gly Ala Gly Ala Ala Ala Ala Ala Ala Ala Ala Ala Gly Gly Ala Gly
225                 230                 235                 240

Gln Gly Gly Gln Gly Gly Tyr Gly Gln Gly Gly Tyr Gly Gln Gly Gly
                245                 250                 255

Ala Gly Gln Gly Gly Ser Gly Ala Ala Ala Ala Ala Ala Ala Ala Ala
            260                 265                 270

Gly Gly Thr Gly Gln Gly Gly Ala Gly Gln Gly Gly Ala Gly Ala Ala
        275                 280                 285

Ala Ala Ala Ala Ala Ala Ala Gly Asp Ala Gly Gln Gly Gly Gln Gly
    290                 295                 300

Gly Tyr Gly Gln Gly Gly Tyr Gly Gln Gly Gly Ser Gly Ala Ala Ala
305                 310                 315                 320

Ala Ala Ala Ala Ala Ala Gly Gly Ala Gly Gln Gly Gly Gln Gly Gly
                325                 330                 335

Tyr Gly Gln Gly Gly Tyr Gly Gln Gly Gly Ala Gly Gln Gly Gly Asp
            340                 345                 350

Gly Ala Ala Ala Ala Ala Ala Ala Ala Ala Gly Gly Ala Gly Gln Gly
        355                 360                 365

Gly Tyr Gly Arg Gly Gly Ala Gly Gln Gly Gly Ala Ala Ala Ala Ala
    370                 375                 380

Ala Ala Ala Ala Gly Ala Gly Gln Gly Gly Tyr Gly Gly Gly Ala Ala
385                 390                 395                 400

Ala Ala Ala Ala Ala Ala Ala Gly Gly Ala Gly Gln Gly Gly Gln Gly
                405                 410                 415

Xaa Tyr Gly Gln Gly Gly Tyr Gly Gln Gly Gly Ser Gly Ala Ala Ala
            420                 425                 430

Ala Ala Ala Ala Ala Ala Gly Gly Ala Gly Gln Gly Gly Gln Gly Gly
        435                 440                 445

Tyr Gly Gln Gly Gly Tyr Gly Gln Gly Gly Ala Gly Gln Gly Gly Ala
    450                 455                 460

Gly Ala Ala Ala Ala Ala Ala Ala Ala Ala Gly Gly Ala Gly Gln Gly
465                 470                 475                 480

Gly Tyr Gly Arg Gly Gly Ala Gly Gln Gly Gly Ala Ala Ala Ala Ala
                485                 490                 495

Ala Ala Ala Ala Gly Ala Gly Gln Arg Gly Tyr Gly Gly Gln Gly Ala
            500                 505                 510

Gly Gln Gly Gly Ala Gly Ala Ala Ala Ala Ala Ala Ala Ala Gly Gly
        515                 520                 525

Ala Gly Gln Gly Gly Gln Arg Gly Tyr Gly Gln Gly Gly Tyr Gly Gln
    530                 535                 540

Gly Gly Ser Gly Ala Ala Ala Ala Ala Ala Ala Ala Ser Gly Pro Gly
545                 550                 555                 560

Gln Val Tyr Tyr Gly Pro Gln Ser Phe Ala Ala Pro Ala Ala Ala Ala
                565                 570                 575

Ala Ser Ala Leu Ser Ala Pro Ala Thr Xaa Ala Arg Ile Ser Ser His
            580                 585                 590

Ala Ser Ala Leu Leu Xaa Xaa Xaa Pro Thr Asn Pro Ala Ser Ile Ser
        595                 600                 605

Asn Val Ile Ser Asn Ala
    610
```

<210> SEQ ID NO 13
<211> LENGTH: 3611
<212> TYPE: DNA

```
<213> ORGANISM: Latrodectus hesperus
<220> FEATURE:
<221> NAME/KEY: CDS
<222> LOCATION: (846)..(2873)

<400> SEQUENCE: 13

gaggattttt tttcattata ttttttctca ctggtatcga aaatgttttc aataaagagc      60

aatttttcta tcaacctctt ttacacaata agtattagaa cattttatgc ttagaattaa     120

ccctttaaaa acattcagca gcacaataag ctgcttacac attttacact taaatagaca     180

ggattactta gctttcttca aaattaaaaa cttatttgat taaagaattg tatggatcgg     240

aaattttaga catcaaatta ttcaatagaa agaaaatctc tgtattttta agatccttat     300

atttttaaa cttgaaataa aaatgacgtt aaattataaa aagtttttgt ctatctgctc      360

taacttacaa attatcaaac atgcgtcatt aattattaca aattcagaac agagatgtat     420

gttgtattaa aacgagaaaa tgatactcat aatattacat taaaaaagca attaatcaat     480

aaaacagttc gacaaaatat aattaaactt ttaaagaata atattgattg cctattatgg     540

ctacatagaa actaatgatt ttaaaatttg taaaaattaa tatacaaaaa taattactat     600

atctaaaaca ggaaatacgt aaaagcataa aaatcatcca cgacgtttgc attcgacctt     660

agaaaagcag atgagtaaat gaaagtgaaa cgtacatacg tcaattcaac tgggcgagat     720

gaaatcgtag actgcatatt tccaggtata ttgatacacc tgctgcacat cacgaacaat     780

cagtgtataa aagaggagaa cgatcagcgt aaagtattct cagtcgggat tttccaacta     840

ctaca atg act tgg tct act cga ctt gcc tta tca ttt ctt tta gtg ctc      890
      Met Thr Trp Ser Thr Arg Leu Ala Leu Ser Phe Leu Leu Val Leu
      1               5                   10                  15

tgc act cag agc att tat gct ctg gcg caa gcc aac acg cca tgg tca       938
Cys Thr Gln Ser Ile Tyr Ala Leu Ala Gln Ala Asn Thr Pro Trp Ser
                20                  25                  30

agt aaa gcg aat gct gat gct ttt atc aat tcc ttt att tcg gca gct       986
Ser Lys Ala Asn Ala Asp Ala Phe Ile Asn Ser Phe Ile Ser Ala Ala
            35                  40                  45

tcg aat act gga tcc ttc tcc caa gat cag atg gaa gat atg tca ttg      1034
Ser Asn Thr Gly Ser Phe Ser Gln Asp Gln Met Glu Asp Met Ser Leu
        50                  55                  60

att ggt aat aca tta atg gca gca atg gat aat atg ggt gga aga att      1082
Ile Gly Asn Thr Leu Met Ala Ala Met Asp Asn Met Gly Gly Arg Ile
    65                  70                  75

acg cca tcc aaa tta cag gct tta gac atg gct ttc gca tca tct gta      1130
Thr Pro Ser Lys Leu Gln Ala Leu Asp Met Ala Phe Ala Ser Ser Val
80                  85                  90                  95

gca gaa att gct gct tcg gaa gga gga gac tta gga gta aca aca aat      1178
Ala Glu Ile Ala Ala Ser Glu Gly Gly Asp Leu Gly Val Thr Thr Asn
                100                 105                 110

gca att gca gat gct tta aca tca gct ttc tat caa aca acc gga gta      1226
Ala Ile Ala Asp Ala Leu Thr Ser Ala Phe Tyr Gln Thr Thr Gly Val
            115                 120                 125

gtt aat agc aga ttt att agc gaa att aga agt ttg att ggc atg ttt      1274
Val Asn Ser Arg Phe Ile Ser Glu Ile Arg Ser Leu Ile Gly Met Phe
        130                 135                 140

gca cag gca tct gcc aac gat gta tac gcc tca gca ggt tcc agc ggt      1322
Ala Gln Ala Ser Ala Asn Asp Val Tyr Ala Ser Ala Gly Ser Ser Gly
    145                 150                 155

gga gga ggg tat gga gca tct tct gca agt gca gca tct gca agc gca      1370
Gly Gly Gly Tyr Gly Ala Ser Ser Ala Ser Ala Ala Ser Ala Ser Ala
160                 165                 170                 175
```

-continued

```
gca gca cca tca ggt gtc gca tac caa gct cca gca caa gca caa att     1418
Ala Ala Pro Ser Gly Val Ala Tyr Gln Ala Pro Ala Gln Ala Gln Ile
                180                 185                 190

tcc ttc tct ttg aga gga caa cag cca gtt ggt tat ggt caa gga gga     1466
Ser Phe Ser Leu Arg Gly Gln Gln Pro Val Gly Tyr Gly Gln Gly Gly
            195                 200                 205

gct agc gca gcc tca gga gca gcg gct ggt caa gga ggc gca gga cca     1514
Ala Ser Ala Ala Ser Gly Ala Ala Ala Gly Gln Gly Gly Ala Gly Pro
        210                 215                 220

gga gga gct ggg gca gca gca gct gga gga gcg ggt caa gga gga caa     1562
Gly Gly Ala Gly Ala Ala Ala Ala Gly Gly Ala Gly Gln Gly Gly Gln
    225                 230                 235

gga gga tat gga caa gga gga tac ggt caa gga ggt gcc gga caa ggt     1610
Gly Gly Tyr Gly Gln Gly Gly Tyr Gly Gln Gly Gly Ala Gly Gln Gly
240                 245                 250                 255

gga tct gga gca gca gca gcg gca gca gca gca gct gga ggc acc ggt     1658
Gly Ser Gly Ala Ala Ala Ala Ala Ala Ala Ala Ala Gly Gly Thr Gly
                260                 265                 270

caa gga ggt gct gga caa ggt gga gca gga gca gca gcg gca gcc gca     1706
Gln Gly Gly Ala Gly Gln Gly Gly Ala Gly Ala Ala Ala Ala Ala Ala
            275                 280                 285

gca gca gct gga ggt gca ggt caa gga gga caa ggt gga tat gga caa     1754
Ala Ala Ala Gly Gly Ala Gly Gln Gly Gly Gln Gly Gly Tyr Gly Gln
        290                 295                 300

gga gga tac gga caa ggt gga tca gga gca gca gca gcg gca gca gca     1802
Gly Gly Tyr Gly Gln Gly Gly Ser Gly Ala Ala Ala Ala Ala Ala Ala
    305                 310                 315

gca gcc gga ggt gca ggt caa ggt gga caa ggt gac tat gga caa gga     1850
Ala Ala Gly Gly Ala Gly Gln Gly Gly Gln Gly Asp Tyr Gly Gln Gly
320                 325                 330                 335

ggt tac ggt caa gga ggt gcc gga caa ggt gga gct gga gcc gca gcg     1898
Gly Tyr Gly Gln Gly Gly Ala Gly Gln Gly Gly Ala Gly Ala Ala Ala
                340                 345                 350

gca gca gca gct gca gct ggt gga gcc gga caa gga gga tat ggc cga     1946
Ala Ala Ala Ala Ala Ala Gly Gly Ala Gly Gln Gly Gly Tyr Gly Arg
            355                 360                 365

ggt gca gca gcg gca gca gca gca gcc gga ggt gca ggt caa gga gga     1994
Gly Ala Ala Ala Ala Ala Ala Ala Ala Gly Gly Ala Gly Gln Gly Gly
        370                 375                 380

caa ggt ggc tat gga caa gga ggt tac gga caa ggt gga tct gga gca     2042
Gln Gly Gly Tyr Gly Gln Gly Gly Tyr Gly Gln Gly Gly Ser Gly Ala
    385                 390                 395

gca gca gcg gca gca gca gca gcc gga ggt gca ggt caa gga gga caa     2090
Ala Ala Ala Ala Ala Ala Ala Ala Gly Gly Ala Gly Gln Gly Gly Gln
400                 405                 410                 415

ggt ggc tat gga caa gga ggt tac gga caa ggt gga tct gga gca gca     2138
Gly Gly Tyr Gly Gln Gly Gly Tyr Gly Gln Gly Gly Ser Gly Ala Ala
                420                 425                 430

gca gcg gca gca gca gca gcc gga ggt gca ggt caa ggt gga caa ggt     2186
Ala Ala Ala Ala Ala Ala Ala Gly Gly Ala Gly Gln Gly Gly Gln Gly
            435                 440                 445

ggc tat gga caa gga ggt tac ggt caa gga ggt gcc gga caa ggt gga     2234
Gly Tyr Gly Gln Gly Gly Tyr Gly Gln Gly Gly Ala Gly Gln Gly Gly
        450                 455                 460

gct ggg gcc gca gcg gca gca gca gct gca gct ggt gga gcc gga caa     2282
Ala Gly Ala Ala Ala Ala Ala Ala Ala Ala Ala Gly Gly Ala Gly Gln
    465                 470                 475

gga gga tat ggc cga ggt gga gca gga caa ggt gga gca gca gca gcc     2330
Gly Gly Tyr Gly Arg Gly Gly Ala Gly Gln Gly Gly Ala Ala Ala Ala
480                 485                 490                 495
```

```
gct gct gca gcc gca gga gca ggt caa cgt ggt tat gga gga caa ggt      2378
Ala Ala Ala Ala Ala Gly Ala Gly Gln Arg Gly Tyr Gly Gly Gln Gly
                500                 505                 510

gcc gga caa ggt gga gct gga gct gca gcc gca gca gca gct gct gga      2426
Ala Gly Gln Gly Gly Ala Gly Ala Ala Ala Ala Ala Ala Ala Ala Gly
            515                 520                 525

ggt gca ggt caa gga gga caa cgt gga tat gga caa gga gga tac gga      2474
Gly Ala Gly Gln Gly Gly Gln Arg Gly Tyr Gly Gln Gly Gly Tyr Gly
        530                 535                 540

caa ggt gga tct gga gca gca gca gcg gca gca gca gct agt gga cct      2522
Gln Gly Gly Ser Gly Ala Ala Ala Ala Ala Ala Ala Ala Ser Gly Pro
    545                 550                 555

ggt caa gtt tat tat gga ccc caa tct ttt gca gct cca gca gct gca      2570
Gly Gln Val Tyr Tyr Gly Pro Gln Ser Phe Ala Ala Pro Ala Ala Ala
560                 565                 570                 575

gca gct tct gct ttg tca gct cca gct aca agc gcg aga att tct tca      2618
Ala Ala Ser Ala Leu Ser Ala Pro Ala Thr Ser Ala Arg Ile Ser Ser
                580                 585                 590

cac gcc tca gct ctt ctt tca agt gga cca act aac cct gct tct att      2666
His Ala Ser Ala Leu Leu Ser Ser Gly Pro Thr Asn Pro Ala Ser Ile
            595                 600                 605

tca aac gtt att agt aat gct gta tcc caa att agt tcc agc aat cca      2714
Ser Asn Val Ile Ser Asn Ala Val Ser Gln Ile Ser Ser Ser Asn Pro
        610                 615                 620

gga gcg tct gcg tgt gat gtt ctc gtt caa gct ctt ctt gaa ctt gtt      2762
Gly Ala Ser Ala Cys Asp Val Leu Val Gln Ala Leu Leu Glu Leu Val
    625                 630                 635

aca gct ttg ctc acc att att gga tca tca aat att ggc agt gtt aat      2810
Thr Ala Leu Leu Thr Ile Ile Gly Ser Ser Asn Ile Gly Ser Val Asn
640                 645                 650                 655

tat gat tct tca ggc caa tat gcg caa gtt gtt act cag tct gta caa      2858
Tyr Asp Ser Ser Gly Gln Tyr Ala Gln Val Val Thr Gln Ser Val Gln
                660                 665                 670

aat gta ttc ggt tga ttctaaggag atttttatgc attaattttt cctaaatata      2913
Asn Val Phe Gly
            675

gtgatatgta ctgagtaatt ctaatagcga ataaagtaat tatcttctct ttaatagtct   2973

cctcaattat atattagttt ttttccttct atcctgaaat cagtgtcata catatggttg   3033

tccttgcatt ttaagtatgt aatattttgt ccaactgtaa gttttacaca agaaaatgtt   3093

tacaaactac aagtttcttc gatgaaatta attatcgatt ataaataaaa attaatgaaa   3153

cctaattttt aggactttat tgtcgtattt ttaaaattta atgattatta gctaatttaa   3213

ttatggattt cattaatttc ctatttatat gtttgtttgt gtttcaaatt gcaaaactcc   3273

acttgttcct ttttggattt tatgttattc tgtttttata atggcttaat atttaaaatg   3333

tattagctta tttcgatcgt cgaatataaa tataaaattt aaaacaatat taagtaaata   3393

atattatttg ttacgttatc ggatttttca aaaatatggc agatttcatg aaattttaaa   3453

ttttactaaa gttttttttt actttcagtc caatgagatg tgtttattga tgtctaccta   3513

taagaaaact taataaaatt tattaactct tcacagaatg ctacttccct tattttgaaa   3573

ccacgtgact acagaaacct tcagatgtta ctttcaaa                           3611
```

```
<210> SEQ ID NO 14
<211> LENGTH: 675
<212> TYPE: PRT
<213> ORGANISM: Latrodectus hesperus
```

-continued

<400> SEQUENCE: 14

```
Met Thr Trp Ser Thr Arg Leu Ala Leu Ser Phe Leu Leu Val Leu Cys
1               5                   10                  15

Thr Gln Ser Ile Tyr Ala Leu Ala Gln Ala Asn Thr Pro Trp Ser Ser
            20                  25                  30

Lys Ala Asn Ala Asp Ala Phe Ile Asn Ser Phe Ile Ser Ala Ala Ser
        35                  40                  45

Asn Thr Gly Ser Phe Ser Gln Asp Gln Met Glu Asp Met Ser Leu Ile
    50                  55                  60

Gly Asn Thr Leu Met Ala Ala Met Asp Asn Met Gly Gly Arg Ile Thr
65                  70                  75                  80

Pro Ser Lys Leu Gln Ala Leu Asp Met Ala Phe Ala Ser Ser Val Ala
                85                  90                  95

Glu Ile Ala Ala Ser Glu Gly Gly Asp Leu Gly Val Thr Thr Asn Ala
            100                 105                 110

Ile Ala Asp Ala Leu Thr Ser Ala Phe Tyr Gln Thr Thr Gly Val Val
        115                 120                 125

Asn Ser Arg Phe Ile Ser Glu Ile Arg Ser Leu Ile Gly Met Phe Ala
    130                 135                 140

Gln Ala Ser Ala Asn Asp Val Tyr Ala Ser Ala Gly Ser Ser Gly Gly
145                 150                 155                 160

Gly Gly Tyr Gly Ala Ser Ser Ala Ser Ala Ala Ser Ala Ser Ala Ala
                165                 170                 175

Ala Pro Ser Gly Val Ala Tyr Gln Ala Pro Ala Gln Ala Gln Ile Ser
            180                 185                 190

Phe Ser Leu Arg Gly Gln Gln Pro Val Gly Tyr Gly Gln Gly Gly Ala
        195                 200                 205

Ser Ala Ala Ser Gly Ala Ala Ala Gly Gln Gly Gly Ala Gly Pro Gly
    210                 215                 220

Gly Ala Gly Ala Ala Ala Ala Gly Gly Ala Gly Gln Gly Gly Gln Gly
225                 230                 235                 240

Gly Tyr Gly Gln Gly Gly Tyr Gly Gln Gly Gly Ala Gly Gln Gly Gly
                245                 250                 255

Ser Gly Ala Ala Ala Ala Ala Ala Ala Ala Ala Gly Gly Thr Gly Gln
            260                 265                 270

Gly Gly Ala Gly Gln Gly Gly Ala Gly Ala Ala Ala Ala Ala Ala Ala
        275                 280                 285

Ala Ala Gly Gly Ala Gly Gln Gly Gly Gln Gly Gly Tyr Gly Gln Gly
    290                 295                 300

Gly Tyr Gly Gln Gly Gly Ser Gly Ala Ala Ala Ala Ala Ala Ala Ala
305                 310                 315                 320

Ala Gly Gly Ala Gly Gln Gly Gly Gln Gly Asp Tyr Gly Gln Gly Gly
                325                 330                 335

Tyr Gly Gln Gly Gly Ala Gly Gln Gly Gly Ala Gly Ala Ala Ala Ala
            340                 345                 350

Ala Ala Ala Ala Ala Gly Gly Ala Gly Gln Gly Gly Tyr Gly Arg Gly
        355                 360                 365

Ala Ala Ala Ala Ala Ala Ala Ala Gly Gly Ala Gly Gln Gly Gly Gln
    370                 375                 380

Gly Gly Tyr Gly Gln Gly Gly Tyr Gly Gln Gly Gly Ser Gly Ala Ala
385                 390                 395                 400

Ala Ala Ala Ala Ala Ala Ala Gly Gly Ala Gly Gln Gly Gly Gln Gly
                405                 410                 415
```

```
Gly Tyr Gly Gln Gly Gly Tyr Gly Gln Gly Gly Ser Gly Ala Ala Ala
            420                 425                 430

Ala Ala Ala Ala Ala Ala Gly Gly Ala Gly Gln Gly Gly Gln Gly Gly
        435                 440                 445

Tyr Gly Gln Gly Gly Tyr Gly Gln Gly Gly Ala Gly Gln Gly Gly Ala
    450                 455                 460

Gly Ala Ala Ala Ala Ala Ala Ala Ala Ala Gly Gly Ala Gly Gln Gly
465                 470                 475                 480

Gly Tyr Gly Arg Gly Gly Ala Gly Gln Gly Gly Ala Ala Ala Ala Ala
                485                 490                 495

Ala Ala Ala Ala Gly Ala Gly Gln Arg Gly Tyr Gly Gly Gln Gly Ala
            500                 505                 510

Gly Gln Gly Gly Ala Gly Ala Ala Ala Ala Ala Ala Ala Ala Gly Gly
        515                 520                 525

Ala Gly Gln Gly Gly Gln Arg Gly Tyr Gly Gln Gly Gly Tyr Gly Gln
    530                 535                 540

Gly Gly Ser Gly Ala Ala Ala Ala Ala Ala Ala Ala Ser Gly Pro Gly
545                 550                 555                 560

Gln Val Tyr Tyr Gly Pro Gln Ser Phe Ala Ala Pro Ala Ala Ala Ala
                565                 570                 575

Ala Ser Ala Leu Ser Ala Pro Ala Thr Ser Ala Arg Ile Ser Ser His
            580                 585                 590

Ala Ser Ala Leu Leu Ser Ser Gly Pro Thr Asn Pro Ala Ser Ile Ser
        595                 600                 605

Asn Val Ile Ser Asn Ala Val Ser Gln Ile Ser Ser Ser Asn Pro Gly
    610                 615                 620

Ala Ser Ala Cys Asp Val Leu Val Gln Ala Leu Leu Glu Leu Val Thr
625                 630                 635                 640

Ala Leu Leu Thr Ile Ile Gly Ser Ser Asn Ile Gly Ser Val Asn Tyr
                645                 650                 655

Asp Ser Ser Gly Gln Tyr Ala Gln Val Val Thr Gln Ser Val Gln Asn
            660                 665                 670

Val Phe Gly
        675


<210> SEQ ID NO 15
<211> LENGTH: 1815
<212> TYPE: DNA
<213> ORGANISM: Latrodectus hesperus
<220> FEATURE:
<221> NAME/KEY: CDS
<222> LOCATION: (1)..(1815)

<400> SEQUENCE: 15

atg act tgg tca act cga ctt gcc tta tca ttt ctt ttc gtg ctc tgc       48
Met Thr Trp Ser Thr Arg Leu Ala Leu Ser Phe Leu Phe Val Leu Cys
1               5                   10                  15

act cag agc ctg tac gct ttg gcg caa gcc aac acg cca tgg tca agt       96
Thr Gln Ser Leu Tyr Ala Leu Ala Gln Ala Asn Thr Pro Trp Ser Ser
            20                  25                  30

aaa gcg aat gct gat gct ttt atc aat tcc ttt att tcg gca gct tcg      144
Lys Ala Asn Ala Asp Ala Phe Ile Asn Ser Phe Ile Ser Ala Ala Ser
        35                  40                  45

aat act gga tcc ttc tcc caa gat cag atg gaa gat atg tca ttg att      192
Asn Thr Gly Ser Phe Ser Gln Asp Gln Met Glu Asp Met Ser Leu Ile
    50                  55                  60
```

-continued

```
ggt aat aca tta atg gca gca atg gat aat atg ggt gga aga att acg      240
Gly Asn Thr Leu Met Ala Ala Met Asp Asn Met Gly Gly Arg Ile Thr
65                  70                  75                  80

cca tcc aaa tta cag gct tta gat atg gct ttc gca tca tct gta gca      288
Pro Ser Lys Leu Gln Ala Leu Asp Met Ala Phe Ala Ser Ser Val Ala
                85                  90                  95

gaa att gct gct tcg gaa gga gga gac tta gga gta aca aca aat gca      336
Glu Ile Ala Ala Ser Glu Gly Gly Asp Leu Gly Val Thr Thr Asn Ala
            100                 105                 110

att gca gat gct tta acg tca gct ttc tat caa aca acc gga gta gtt      384
Ile Ala Asp Ala Leu Thr Ser Ala Phe Tyr Gln Thr Thr Gly Val Val
        115                 120                 125

aat agc aga ttt att agc gaa att aga agt ttg att ggc atg ttt gca      432
Asn Ser Arg Phe Ile Ser Glu Ile Arg Ser Leu Ile Gly Met Phe Ala
    130                 135                 140

cag gca tct gcc aac gat gta tac gcc tca gca ggt tcc agc ggt gga      480
Gln Ala Ser Ala Asn Asp Val Tyr Ala Ser Ala Gly Ser Ser Gly Gly
145                 150                 155                 160

gga ggg tat gga gca tct tct gca agt gca gca tct gca agc gca gca      528
Gly Gly Tyr Gly Ala Ser Ser Ala Ser Ala Ala Ser Ala Ser Ala Ala
                165                 170                 175

gca cca tca ggt gtc gca tat caa gct cca gca caa gca caa att tcc      576
Ala Pro Ser Gly Val Ala Tyr Gln Ala Pro Ala Gln Ala Gln Ile Ser
            180                 185                 190

ttc act ttg aga gga caa cag cca gtt agt tat ggt caa gga ggc gct      624
Phe Thr Leu Arg Gly Gln Gln Pro Val Ser Tyr Gly Gln Gly Gly Ala
        195                 200                 205

gga cca gga gga gct gga gca gca gcg gca gcc gca gca gca gct gga      672
Gly Pro Gly Gly Ala Gly Ala Ala Ala Ala Ala Ala Ala Ala Ala Gly
    210                 215                 220

gga gcg ggt caa gga gga caa gga ggg tat gga caa gga gga tac ggt      720
Gly Ala Gly Gln Gly Gly Gln Gly Gly Tyr Gly Gln Gly Gly Tyr Gly
225                 230                 235                 240

caa gga ggt gcc gga caa ggt gga tct gga gca gca gca gca gct gga      768
Gln Gly Gly Ala Gly Gln Gly Gly Ser Gly Ala Ala Ala Ala Ala Gly
                245                 250                 255

ggc acc ggt caa gga ggt gct gga caa ggt gga gca gga gca gca gcg      816
Gly Thr Gly Gln Gly Gly Ala Gly Gln Gly Gly Ala Gly Ala Ala Ala
            260                 265                 270

gca gcc gca gca gca gct gga ggt gca ggt caa gga gga caa ggt ggc      864
Ala Ala Ala Ala Ala Ala Gly Gly Ala Gly Gln Gly Gly Gln Gly Gly
        275                 280                 285

tat gga caa gga gga tac ggt caa gga ggt acc gga caa ggt gga gct      912
Tyr Gly Gln Gly Gly Tyr Gly Gln Gly Gly Thr Gly Gln Gly Gly Ala
    290                 295                 300

gga gca gca gca gcg gca gca gca gcc gga ggt gca ggt caa gga gga      960
Gly Ala Ala Ala Ala Ala Ala Ala Ala Gly Gly Ala Gly Gln Gly Gly
305                 310                 315                 320

caa ggt gga tat gga caa gga gga tac gga caa ggt gga tct gga gca     1008
Gln Gly Gly Tyr Gly Gln Gly Gly Tyr Gly Gln Gly Gly Ser Gly Ala
                325                 330                 335

gca gca gcg gca gca gca gca gcc gga ggt gca ggt caa ggt gga caa     1056
Ala Ala Ala Ala Ala Ala Ala Ala Gly Gly Ala Gly Gln Gly Gly Gln
            340                 345                 350

ggt ggc tat gga caa gga ggt tac ggt caa gga ggt gcc gga caa ggt     1104
Gly Gly Tyr Gly Gln Gly Gly Tyr Gly Gln Gly Gly Ala Gly Gln Gly
        355                 360                 365

gga gct gga gcc gca gga caa ggt ggc tat gga caa gga ggt tac ggt     1152
Gly Ala Gly Ala Ala Gly Gln Gly Gly Tyr Gly Gln Gly Gly Tyr Gly
    370                 375                 380
```

```
caa gga ggt gca gga caa ggt gga gcc gca gcg gca gca gca gca gct      1200
Gln Gly Gly Ala Gly Gln Gly Gly Ala Ala Ala Ala Ala Ala Ala Ala
385                 390                 395                 400

ggt gga gca gga caa gga gga tat ggc aga ggt gga gca gga caa ggt      1248
Gly Gly Ala Gly Gln Gly Gly Tyr Gly Arg Gly Gly Ala Gly Gln Gly
                405                 410                 415

gga gca gca gca gcc gct gct gca gcc gct gga gct ggt caa ggt ggt      1296
Gly Ala Ala Ala Ala Ala Ala Ala Ala Ala Gly Ala Gly Gln Gly Gly
            420                 425                 430

tat gga ggt caa ggt gcc gga caa ggt gga gct gga gct gca gcc gca      1344
Tyr Gly Gly Gln Gly Ala Gly Gln Gly Gly Ala Gly Ala Ala Ala Ala
        435                 440                 445

gca gca gca gcc gga ggt gca ggt caa gga gga caa ggt ggc tat gga      1392
Ala Ala Ala Ala Gly Gly Ala Gly Gln Gly Gly Gln Gly Gly Tyr Gly
    450                 455                 460

cga gga ggt tac gat caa gga ggt gct gga caa ggc gga gct gga gca      1440
Arg Gly Gly Tyr Asp Gln Gly Gly Ala Gly Gln Gly Gly Ala Gly Ala
465                 470                 475                 480

gca gca gcg gca gca gca gca gcc gga ggt gca ggt caa gga gga caa      1488
Ala Ala Ala Ala Ala Ala Ala Ala Gly Gly Ala Gly Gln Gly Gly Gln
                485                 490                 495

ggt ggc tat gga caa gga ggt tac ggt caa gga ggt gcc gga caa ggt      1536
Gly Gly Tyr Gly Gln Gly Gly Tyr Gly Gln Gly Gly Ala Gly Gln Gly
            500                 505                 510

gga gct gca gcc gca gcg gca gca gct gca gct gga gga gca gga caa      1584
Gly Ala Ala Ala Ala Ala Ala Ala Ala Ala Ala Gly Gly Ala Gly Gln
        515                 520                 525

gga gga tat ggt gga tac ggt caa caa ggt gga gca gga gcc gca gca      1632
Gly Gly Tyr Gly Gly Tyr Gly Gln Gln Gly Gly Ala Gly Ala Ala Ala
    530                 535                 540

gca gct gct agt gga cct ggt caa att tat tat gga ccc caa tct gtt      1680
Ala Ala Ala Ser Gly Pro Gly Gln Ile Tyr Tyr Gly Pro Gln Ser Val
545                 550                 555                 560

gct gct cca gca gca gca gca gct tct gct ttg gca gct cca gct aca      1728
Ala Ala Pro Ala Ala Ala Ala Ala Ser Ala Leu Ala Ala Pro Ala Thr
                565                 570                 575

agc gcg aga att tct tca cac gcc tca gct ctt ctt tca aat gga cct      1776
Ser Ala Arg Ile Ser Ser His Ala Ser Ala Leu Leu Ser Asn Gly Pro
            580                 585                 590

act aac cct gct tct att tca aac gtt att agt aat gct                  1815
Thr Asn Pro Ala Ser Ile Ser Asn Val Ile Ser Asn Ala
        595                 600                 605


<210> SEQ ID NO 16
<211> LENGTH: 605
<212> TYPE: PRT
<213> ORGANISM: Latrodectus hesperus

<400> SEQUENCE: 16

Met Thr Trp Ser Thr Arg Leu Ala Leu Ser Phe Leu Phe Val Leu Cys
1               5                   10                  15

Thr Gln Ser Leu Tyr Ala Leu Ala Gln Ala Asn Thr Pro Trp Ser Ser
            20                  25                  30

Lys Ala Asn Ala Asp Ala Phe Ile Asn Ser Phe Ile Ser Ala Ala Ser
        35                  40                  45

Asn Thr Gly Ser Phe Ser Gln Asp Gln Met Glu Asp Met Ser Leu Ile
    50                  55                  60

Gly Asn Thr Leu Met Ala Ala Met Asp Asn Met Gly Gly Arg Ile Thr
65                  70                  75                  80
```

-continued

```
Pro Ser Lys Leu Gln Ala Leu Asp Met Ala Phe Ala Ser Ser Val Ala
                85                  90                  95

Glu Ile Ala Ala Ser Glu Gly Gly Asp Leu Gly Val Thr Thr Asn Ala
            100                 105                 110

Ile Ala Asp Ala Leu Thr Ser Ala Phe Tyr Gln Thr Thr Gly Val Val
        115                 120                 125

Asn Ser Arg Phe Ile Ser Glu Ile Arg Ser Leu Ile Gly Met Phe Ala
    130                 135                 140

Gln Ala Ser Ala Asn Asp Val Tyr Ala Ser Ala Gly Ser Ser Gly Gly
145                 150                 155                 160

Gly Gly Tyr Gly Ala Ser Ser Ala Ser Ala Ala Ser Ala Ser Ala Ala
                165                 170                 175

Ala Pro Ser Gly Val Ala Tyr Gln Ala Pro Ala Gln Ala Gln Ile Ser
            180                 185                 190

Phe Thr Leu Arg Gly Gln Gln Pro Val Ser Tyr Gly Gln Gly Gly Ala
        195                 200                 205

Gly Pro Gly Gly Ala Gly Ala Ala Ala Ala Ala Ala Ala Ala Ala Gly
    210                 215                 220

Gly Ala Gly Gln Gly Gly Gln Gly Gly Tyr Gly Gln Gly Gly Tyr Gly
225                 230                 235                 240

Gln Gly Gly Ala Gly Gln Gly Gly Ser Gly Ala Ala Ala Ala Ala Gly
                245                 250                 255

Gly Thr Gly Gln Gly Gly Ala Gly Gln Gly Gly Ala Gly Ala Ala Ala
            260                 265                 270

Ala Ala Ala Ala Ala Ala Gly Gly Ala Gly Gln Gly Gly Gln Gly Gly
        275                 280                 285

Tyr Gly Gln Gly Gly Tyr Gly Gln Gly Gly Thr Gly Gln Gly Gly Ala
    290                 295                 300

Gly Ala Ala Ala Ala Ala Ala Ala Ala Gly Gly Ala Gly Gln Gly Gly
305                 310                 315                 320

Gln Gly Gly Tyr Gly Gln Gly Gly Tyr Gly Gln Gly Gly Ser Gly Ala
                325                 330                 335

Ala Ala Ala Ala Ala Ala Ala Ala Gly Gly Ala Gly Gln Gly Gly Gln
            340                 345                 350

Gly Gly Tyr Gly Gln Gly Gly Tyr Gly Gln Gly Gly Ala Gly Gln Gly
        355                 360                 365

Gly Ala Gly Ala Ala Gly Gln Gly Gly Tyr Gly Gln Gly Gly Tyr Gly
    370                 375                 380

Gln Gly Gly Ala Gly Gln Gly Gly Ala Ala Ala Ala Ala Ala Ala Ala
385                 390                 395                 400

Gly Gly Ala Gly Gln Gly Gly Tyr Gly Arg Gly Gly Ala Gly Gln Gly
                405                 410                 415

Gly Ala Ala Ala Ala Ala Ala Ala Ala Ala Gly Ala Gly Gln Gly Gly
            420                 425                 430

Tyr Gly Gly Gln Gly Ala Gly Gln Gly Gly Ala Gly Ala Ala Ala Ala
        435                 440                 445

Ala Ala Ala Ala Gly Gly Ala Gly Gln Gly Gly Gln Gly Gly Tyr Gly
    450                 455                 460

Arg Gly Gly Tyr Asp Gln Gly Gly Ala Gly Gln Gly Gly Ala Gly Ala
465                 470                 475                 480

Ala Ala Ala Ala Ala Ala Ala Ala Gly Gly Ala Gly Gln Gly Gly Gln
                485                 490                 495
```

```
Gly Gly Tyr Gly Gln Gly Gly Tyr Gly Gln Gly Gly Ala Gly Gln Gly
            500                 505                 510

Gly Ala Ala Ala Ala Ala Ala Ala Ala Ala Ala Gly Gly Ala Gly Gln
        515                 520                 525

Gly Gly Tyr Gly Gly Tyr Gly Gln Gln Gly Gly Ala Gly Ala Ala Ala
    530                 535                 540

Ala Ala Ala Ser Gly Pro Gly Gln Ile Tyr Tyr Gly Pro Gln Ser Val
545                 550                 555                 560

Ala Ala Pro Ala Ala Ala Ala Ala Ser Ala Leu Ala Ala Pro Ala Thr
                565                 570                 575

Ser Ala Arg Ile Ser Ser His Ala Ser Ala Leu Leu Ser Asn Gly Pro
            580                 585                 590

Thr Asn Pro Ala Ser Ile Ser Asn Val Ile Ser Asn Ala
        595                 600                 605


<210> SEQ ID NO 17
<211> LENGTH: 3148
<212> TYPE: DNA
<213> ORGANISM: Latrodectus hesperus
<220> FEATURE:
<221> NAME/KEY: CDS
<222> LOCATION: (399)..(2588)

<400> SEQUENCE: 17

cgacgatgtt attcgaatca atccaaattt aatgaaaaat tattcaataa aatatctttc      60

taaatttatc ataaaattta taaactaaat aaagcaatta tagttccaat aaaaggcaaa     120

gttattaagt aaagtttaat gcaaaatacc aaaaatgata ttaaacacgt aagtattcgc     180

atgtaaaaac ataagaaaac ttgcatttca ccttggaaaa aacaggtgac taaattcaaa     240

caagaagtac acacgtcatc ttagcacgcg gacatgacac aattgtctgc atatctccag     300

gtgtattgaa aaacctgctg cacagcacga ccaatcattg tataaaagag gcaatcaatc     360

agcgtacagt attcagtcgg gattttccaa ctactaca atg act tgg tca act cga     416
                                          Met Thr Trp Ser Thr Arg
                                          1               5

ctt gcc tta tca ttt ctt ttc gtg ctc tgc act cag agc ctg tac gct      464
Leu Ala Leu Ser Phe Leu Phe Val Leu Cys Thr Gln Ser Leu Tyr Ala
            10                  15                  20

ttg gcg caa gcc aac acg cca tgg tca agt aaa gcg aat gct gat gct      512
Leu Ala Gln Ala Asn Thr Pro Trp Ser Ser Lys Ala Asn Ala Asp Ala
        25                  30                  35

ttt atc aat tcc ttt att tcg gca gct tcg aat act gga tcc ttc tcc      560
Phe Ile Asn Ser Phe Ile Ser Ala Ala Ser Asn Thr Gly Ser Phe Ser
    40                  45                  50

caa gat cag atg gaa gat atg tca ttg att ggt aat aca tta atg gca      608
Gln Asp Gln Met Glu Asp Met Ser Leu Ile Gly Asn Thr Leu Met Ala
55                  60                  65                  70

gca atg gat aat atg ggt gga aga att acg cca tcc aaa tta cag gct      656
Ala Met Asp Asn Met Gly Gly Arg Ile Thr Pro Ser Lys Leu Gln Ala
                75                  80                  85

tta gat atg gct ttc gca tca tct gta gca gaa att gct gct tcg gaa      704
Leu Asp Met Ala Phe Ala Ser Ser Val Ala Glu Ile Ala Ala Ser Glu
            90                  95                  100

gga gga gac tta gga gta aca aca aat gca att gca gat gct tta acg      752
Gly Gly Asp Leu Gly Val Thr Thr Asn Ala Ile Ala Asp Ala Leu Thr
        105                 110                 115

tca gct ttc tat caa aca acc gga gta gtt aat agc aga ttt att agc      800
Ser Ala Phe Tyr Gln Thr Thr Gly Val Val Asn Ser Arg Phe Ile Ser
    120                 125                 130
```

-continued

```
gaa att aga agt ttg att ggc atg ttt gca cag gca tct gcc aac gat      848
Glu Ile Arg Ser Leu Ile Gly Met Phe Ala Gln Ala Ser Ala Asn Asp
135                 140                 145                 150

gta tac gcc tca gca ggt tcc agc ggt gga gga ggg tat gga gca tct      896
Val Tyr Ala Ser Ala Gly Ser Ser Gly Gly Gly Gly Tyr Gly Ala Ser
                155                 160                 165

tct gca agt gca gca tct gca agc gca gca gca cca tca ggt gtc gca      944
Ser Ala Ser Ala Ala Ser Ala Ser Ala Ala Ala Pro Ser Gly Val Ala
            170                 175                 180

tat caa gct cca gca caa gca caa att tcc ttc act ttg aga gga caa      992
Tyr Gln Ala Pro Ala Gln Ala Gln Ile Ser Phe Thr Leu Arg Gly Gln
        185                 190                 195

cag cca gtt agt tat ggt caa gga ggc gct gga cca gga gga gct gga     1040
Gln Pro Val Ser Tyr Gly Gln Gly Gly Ala Gly Pro Gly Gly Ala Gly
    200                 205                 210

gca gca gcg gca gcc gca gca gca gct gga gga gcg ggt caa gga gga     1088
Ala Ala Ala Ala Ala Ala Ala Ala Ala Gly Gly Ala Gly Gln Gly Gly
215                 220                 225                 230

caa gga ggg tat gga caa gga gga tac ggt caa gga ggt gcc gga caa     1136
Gln Gly Gly Tyr Gly Gln Gly Gly Tyr Gly Gln Gly Gly Ala Gly Gln
                235                 240                 245

ggt gga tct gga gca gca gca gca gct gga ggc acc ggt caa gga ggt     1184
Gly Gly Ser Gly Ala Ala Ala Ala Ala Gly Gly Thr Gly Gln Gly Gly
            250                 255                 260

gct gga caa ggt gga gca gga gca gca gcg gca gcc gca gca gca gct     1232
Ala Gly Gln Gly Gly Ala Gly Ala Ala Ala Ala Ala Ala Ala Ala Ala
        265                 270                 275

gga ggt gca ggt caa gga gga caa ggt ggc tat gga caa gga gga tac     1280
Gly Gly Ala Gly Gln Gly Gly Gln Gly Gly Tyr Gly Gln Gly Gly Tyr
    280                 285                 290

ggt caa gga ggt acc gga caa ggt gga gct gga gca gca gca gcg gca     1328
Gly Gln Gly Gly Thr Gly Gln Gly Gly Ala Gly Ala Ala Ala Ala Ala
295                 300                 305                 310

gca gca gcc gga ggt gca ggt caa gga gga caa ggt gga tat gga caa     1376
Ala Ala Ala Gly Gly Ala Gly Gln Gly Gly Gln Gly Gly Tyr Gly Gln
                315                 320                 325

gga gga tac gga caa ggt gga tct gga gca gca gca gcg gca gca gca     1424
Gly Gly Tyr Gly Gln Gly Gly Ser Gly Ala Ala Ala Ala Ala Ala Ala
            330                 335                 340

gca gcc gga ggt gca ggt caa ggt gga caa ggt ggc tat gga caa gga     1472
Ala Ala Gly Gly Ala Gly Gln Gly Gly Gln Gly Gly Tyr Gly Gln Gly
        345                 350                 355

ggt tac ggt caa gga ggt gcc gga caa ggt gga gct gga gcc gca gcg     1520
Gly Tyr Gly Gln Gly Gly Ala Gly Gln Gly Gly Ala Gly Ala Ala Ala
    360                 365                 370

gca gca gca gct gca gct ggt gga gcc gga caa gga gga tat ggc cga     1568
Ala Ala Ala Ala Ala Ala Gly Gly Ala Gly Gln Gly Gly Tyr Gly Arg
375                 380                 385                 390

ggt gga gca gga caa ggg gga gca gca gca gcc gct gct gca gcc gca     1616
Gly Gly Ala Gly Gln Gly Gly Ala Ala Ala Ala Ala Ala Ala Ala Ala
                395                 400                 405

gga gct ggt caa ggt ggt tat gga gga caa ggt gcc gga gga gct gga     1664
Gly Ala Gly Gln Gly Gly Tyr Gly Gly Gln Gly Ala Gly Gly Ala Gly
            410                 415                 420

gca gca gca gcg gca gca gca gcc gga ggt gca ggt caa gga gga caa     1712
Ala Ala Ala Ala Ala Ala Ala Ala Gly Gly Ala Gly Gln Gly Gly Gln
        425                 430                 435

ggt ggc tat gga caa gga ggt tac ggt caa gga ggt gca gga caa ggt     1760
Gly Gly Tyr Gly Gln Gly Gly Tyr Gly Gln Gly Gly Ala Gly Gln Gly
```

-continued

```
    440                 445                 450

gga gcc gca gcg gca gca gca gca gct ggt gga gca gga caa gga gga      1808
Gly Ala Ala Ala Ala Ala Ala Ala Ala Gly Gly Ala Gly Gln Gly Gly
455                 460                 465                 470

tat ggc aga ggt gga gca gga caa ggt gga gca gca gca gcc gct gct      1856
Tyr Gly Arg Gly Gly Ala Gly Gln Gly Gly Ala Ala Ala Ala Ala Ala
                475                 480                 485

gca gcc gct gga gct ggt caa ggt ggt tat gga ggt caa ggt gcc gga      1904
Ala Ala Ala Gly Ala Gly Gln Gly Gly Tyr Gly Gly Gln Gly Ala Gly
            490                 495                 500

caa ggt gga gct gga gct gca gcc gca gca gca gca gcc gga ggt gca      1952
Gln Gly Gly Ala Gly Ala Ala Ala Ala Ala Ala Ala Ala Gly Gly Ala
        505                 510                 515

ggt caa gga gga caa ggt ggc tat gga cga gga ggt tac gat caa gga      2000
Gly Gln Gly Gly Gln Gly Gly Tyr Gly Arg Gly Gly Tyr Asp Gln Gly
    520                 525                 530

ggt gct gga caa ggc gga gct gga gca gca gca gcg gca gca gca gca      2048
Gly Ala Gly Gln Gly Gly Ala Gly Ala Ala Ala Ala Ala Ala Ala Ala
535                 540                 545                 550

gcc gga ggt gca ggt caa gga gga caa ggt ggc tat gga caa gga ggt      2096
Ala Gly Gly Ala Gly Gln Gly Gly Gln Gly Gly Tyr Gly Gln Gly Gly
                555                 560                 565

tac ggt caa gga ggt gcc gga caa ggt gga gct gca gcc gca gcg gca      2144
Tyr Gly Gln Gly Gly Ala Gly Gln Gly Gly Ala Ala Ala Ala Ala Ala
            570                 575                 580

gca gct gca gct gga gga gca gga caa gga gga tat ggt gga tac ggt      2192
Ala Ala Ala Ala Gly Gly Ala Gly Gln Gly Gly Tyr Gly Gly Tyr Gly
        585                 590                 595

caa caa ggt gga gca gga gcc gca gca gca gct gct agt gga cct ggt      2240
Gln Gln Gly Gly Ala Gly Ala Ala Ala Ala Ala Ala Ser Gly Pro Gly
    600                 605                 610

caa att tat tat gga ccc caa tct gtt gct gct cca gca gca gca gca      2288
Gln Ile Tyr Tyr Gly Pro Gln Ser Val Ala Ala Pro Ala Ala Ala Ala
615                 620                 625                 630

gct tct gct ttg gca gct cca gct aca agc gcg aga att tct tca cac      2336
Ala Ser Ala Leu Ala Ala Pro Ala Thr Ser Ala Arg Ile Ser Ser His
                635                 640                 645

gcc tca gct ctt ctt tca aat gga cct act aac cct gct tct att tca      2384
Ala Ser Ala Leu Leu Ser Asn Gly Pro Thr Asn Pro Ala Ser Ile Ser
            650                 655                 660

aac gtt att agt aat gct gta tcc caa att agt tcc agc aat cca gga      2432
Asn Val Ile Ser Asn Ala Val Ser Gln Ile Ser Ser Ser Asn Pro Gly
        665                 670                 675

gcg tct gcg tgt gat gtt ctc gtt caa gct ctt ctt gaa ctt gtt act      2480
Ala Ser Ala Cys Asp Val Leu Val Gln Ala Leu Leu Glu Leu Val Thr
    680                 685                 690

gct ttg ctc acc att att gga tca tca aat att ggc agt gtt aat tat      2528
Ala Leu Leu Thr Ile Ile Gly Ser Ser Asn Ile Gly Ser Val Asn Tyr
695                 700                 705                 710

gat tct tca ggc caa tat gcg caa gtt gtt act caa tct gtt caa aat      2576
Asp Ser Ser Gly Gln Tyr Ala Gln Val Val Thr Gln Ser Val Gln Asn
                715                 720                 725

gca ttc gct tga ttctaaaacg ttgcttaagc attcatttta taaaatgtac          2628
Ala Phe Ala

taatataata tgtattgagt aattctgata ttgaataaag catttatctt ctctataatc   2688

tcatttgcct aattatattt ttgttttttt acttctgtcc tgagatcagt ttcttatata   2748

tggtaattca ggcattttaa cattgtaata tattattgaa ttgtaacatc tgcggaaaaa   2808
```

-continued

```
atatttacag aatacaagtt gtagaattca aattaattaa ctttttttaaa tgaaaataaa   2868

ttgaacttaa ttttgaggac tttatgatat ggtttctaaa tatttttatt ttcacgctgg   2928

ttttcctgga gaaatcaata atttccaaca taatatgtgt ttattataac tgcgtagtcc   2988

cattccttac ttttcaggta tacgctttag tgtactgtac ttctgcagtg tcttaatatt   3048

gacctgaaac gtattagatg atttcgatct ttgaatgaaa gaataatact aaaaactttt   3108

taagttctta aaataattta ttatatcacc agatttcttt                         3148


<210> SEQ ID NO 18
<211> LENGTH: 729
<212> TYPE: PRT
<213> ORGANISM: Latrodectus hesperus

<400> SEQUENCE: 18

Met Thr Trp Ser Thr Arg Leu Ala Leu Ser Phe Leu Phe Val Leu Cys
1               5                   10                  15

Thr Gln Ser Leu Tyr Ala Leu Ala Gln Ala Asn Thr Pro Trp Ser Ser
            20                  25                  30

Lys Ala Asn Ala Asp Ala Phe Ile Asn Ser Phe Ile Ser Ala Ala Ser
        35                  40                  45

Asn Thr Gly Ser Phe Ser Gln Asp Gln Met Glu Asp Met Ser Leu Ile
    50                  55                  60

Gly Asn Thr Leu Met Ala Ala Met Asp Asn Met Gly Gly Arg Ile Thr
65                  70                  75                  80

Pro Ser Lys Leu Gln Ala Leu Asp Met Ala Phe Ala Ser Ser Val Ala
                85                  90                  95

Glu Ile Ala Ala Ser Glu Gly Gly Asp Leu Gly Val Thr Thr Asn Ala
            100                 105                 110

Ile Ala Asp Ala Leu Thr Ser Ala Phe Tyr Gln Thr Thr Gly Val Val
        115                 120                 125

Asn Ser Arg Phe Ile Ser Glu Ile Arg Ser Leu Ile Gly Met Phe Ala
    130                 135                 140

Gln Ala Ser Ala Asn Asp Val Tyr Ala Ser Ala Gly Ser Ser Gly Gly
145                 150                 155                 160

Gly Gly Tyr Gly Ala Ser Ser Ala Ser Ala Ala Ser Ala Ser Ala Ala
                165                 170                 175

Ala Pro Ser Gly Val Ala Tyr Gln Ala Pro Ala Gln Ala Gln Ile Ser
            180                 185                 190

Phe Thr Leu Arg Gly Gln Gln Pro Val Ser Tyr Gly Gln Gly Gly Ala
        195                 200                 205

Gly Pro Gly Gly Ala Gly Ala Ala Ala Ala Ala Ala Ala Ala Ala Gly
    210                 215                 220

Gly Ala Gly Gln Gly Gly Gln Gly Gly Tyr Gly Gln Gly Gly Tyr Gly
225                 230                 235                 240

Gln Gly Gly Ala Gly Gln Gly Gly Ser Gly Ala Ala Ala Ala Ala Gly
                245                 250                 255

Gly Thr Gly Gln Gly Gly Ala Gly Gln Gly Gly Ala Gly Ala Ala Ala
            260                 265                 270

Ala Ala Ala Ala Ala Ala Gly Gly Ala Gly Gln Gly Gly Gln Gly Gly
        275                 280                 285

Tyr Gly Gln Gly Gly Tyr Gly Gln Gly Gly Thr Gly Gln Gly Gly Ala
    290                 295                 300

Gly Ala Ala Ala Ala Ala Ala Ala Ala Gly Gly Ala Gly Gln Gly Gly
305                 310                 315                 320
```

-continued

```
Gln Gly Gly Tyr Gly Gln Gly Gly Tyr Gly Gln Gly Gly Ser Gly Ala
                325                 330                 335

Ala Ala Ala Ala Ala Ala Ala Ala Gly Gly Ala Gly Gln Gly Gly Gln
            340                 345                 350

Gly Gly Tyr Gly Gln Gly Gly Tyr Gly Gln Gly Gly Ala Gly Gln Gly
        355                 360                 365

Gly Ala Gly Ala Ala Ala Ala Ala Ala Ala Ala Ala Gly Gly Ala Gly
    370                 375                 380

Gln Gly Gly Tyr Gly Arg Gly Gly Ala Gly Gln Gly Gly Ala Ala Ala
385                 390                 395                 400

Ala Ala Ala Ala Ala Ala Gly Ala Gly Gln Gly Gly Tyr Gly Gly Gln
                405                 410                 415

Gly Ala Gly Gly Ala Gly Ala Ala Ala Ala Ala Ala Ala Ala Gly Gly
            420                 425                 430

Ala Gly Gln Gly Gly Gln Gly Gly Tyr Gly Gln Gly Gly Tyr Gly Gln
        435                 440                 445

Gly Gly Ala Gly Gln Gly Gly Ala Ala Ala Ala Ala Ala Ala Ala Gly
    450                 455                 460

Gly Ala Gly Gln Gly Gly Tyr Gly Arg Gly Gly Ala Gly Gln Gly Gly
465                 470                 475                 480

Ala Ala Ala Ala Ala Ala Ala Ala Ala Gly Ala Gly Gln Gly Gly Tyr
                485                 490                 495

Gly Gly Gln Gly Ala Gly Gln Gly Gly Ala Gly Ala Ala Ala Ala Ala
            500                 505                 510

Ala Ala Ala Gly Gly Ala Gly Gln Gly Gly Gln Gly Gly Tyr Gly Arg
        515                 520                 525

Gly Gly Tyr Asp Gln Gly Gly Ala Gly Gln Gly Gly Ala Gly Ala Ala
    530                 535                 540

Ala Ala Ala Ala Ala Ala Ala Gly Gly Ala Gly Gln Gly Gly Gln Gly
545                 550                 555                 560

Gly Tyr Gly Gln Gly Gly Tyr Gly Gln Gly Gly Ala Gly Gln Gly Gly
                565                 570                 575

Ala Ala Ala Ala Ala Ala Ala Ala Ala Ala Gly Gly Ala Gly Gln Gly
            580                 585                 590

Gly Tyr Gly Gly Tyr Gly Gln Gln Gly Gly Ala Gly Ala Ala Ala Ala
        595                 600                 605

Ala Ala Ser Gly Pro Gly Gln Ile Tyr Tyr Gly Pro Gln Ser Val Ala
    610                 615                 620

Ala Pro Ala Ala Ala Ala Ala Ser Ala Leu Ala Ala Pro Ala Thr Ser
625                 630                 635                 640

Ala Arg Ile Ser Ser His Ala Ser Ala Leu Leu Ser Asn Gly Pro Thr
                645                 650                 655

Asn Pro Ala Ser Ile Ser Asn Val Ile Ser Asn Ala Val Ser Gln Ile
            660                 665                 670

Ser Ser Ser Asn Pro Gly Ala Ser Ala Cys Asp Val Leu Val Gln Ala
        675                 680                 685

Leu Leu Glu Leu Val Thr Ala Leu Leu Thr Ile Ile Gly Ser Ser Asn
    690                 695                 700

Ile Gly Ser Val Asn Tyr Asp Ser Ser Gly Gln Tyr Ala Gln Val Val
705                 710                 715                 720

Thr Gln Ser Val Gln Asn Ala Phe Ala
                725
```

<210> SEQ ID NO 19
<211> LENGTH: 1739
<212> TYPE: DNA
<213> ORGANISM: Latrodectus hesperus
<220> FEATURE:
<221> NAME/KEY: CDS
<222> LOCATION: (1)..(1737)
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (130)..(130)
<223> OTHER INFORMATION: n is a, c, g, or t
<220> FEATURE:
<221> NAME/KEY: misc_feature
<222> LOCATION: (133)..(133)
<223> OTHER INFORMATION: n is a, c, g, or t
<220> FEATURE:
<221> NAME/KEY: misc_feature
<222> LOCATION: (914)..(914)
<223> OTHER INFORMATION: n is a, c, g, or t
<220> FEATURE:
<221> NAME/KEY: misc_feature
<222> LOCATION: (931)..(931)
<223> OTHER INFORMATION: n is a, c, g, or t
<220> FEATURE:
<221> NAME/KEY: misc_feature
<222> LOCATION: (978)..(978)
<223> OTHER INFORMATION: n is a, c, g, or t
<220> FEATURE:
<221> NAME/KEY: misc_feature
<222> LOCATION: (992)..(992)

```
<223> OTHER INFORMATION: n is a, c, g, or t

<400> SEQUENCE: 19

atg nct aca atg aat tgg tct act cga ctt gtg tng tca nta ctn gtn       48
Met Xaa Thr Met Asn Trp Ser Thr Arg Leu Val Xaa Ser Xaa Xaa Val
1               5                   10                  15

gtn ctt tgc act cag ngc ctn tgt gct ntg gga caa gca anc act ccg       96
Val Leu Cys Thr Gln Xaa Xaa Cys Ala Xaa Gly Gln Ala Xaa Thr Pro
            20                  25                  30

tng tcc ant aaa gaa aac gct gac gct ttt ata ngc nca ttt atg aat      144
Xaa Ser Xaa Lys Glu Asn Ala Asp Ala Phe Ile Xaa Xaa Phe Met Asn
        35                  40                  45

gct gct tca caa agt gga gca ttt tca tcg gat cag ata gat gat atg      192
Ala Ala Ser Gln Ser Gly Ala Phe Ser Ser Asp Gln Ile Asp Asp Met
    50                  55                  60

tca gtt att agt aat aca ttg atg gct gca atg aac aac atg ggt gga      240
Ser Val Ile Ser Asn Thr Leu Met Ala Ala Met Asn Asn Met Gly Gly
65                  70                  75                  80

aga atc aca caa tca aaa tta cag gct tta gat atg gcc ttt gca tca      288
Arg Ile Thr Gln Ser Lys Leu Gln Ala Leu Asp Met Ala Phe Ala Ser
                85                  90                  95

tcc gtg gca gaa ata gct gta gct gat ggc caa aac gtt gga gcc gct      336
Ser Val Ala Glu Ile Ala Val Ala Asp Gly Gln Asn Val Gly Ala Ala
            100                 105                 110

acg aat gcc ata tca gac gca tta cgg tca gcc ttc tat caa act acc      384
Thr Asn Ala Ile Ser Asp Ala Leu Arg Ser Ala Phe Tyr Gln Thr Thr
        115                 120                 125

gga gtg gta aac aat caa ttt att act ggg ata agt agc cta att ggc      432
Gly Val Val Asn Asn Gln Phe Ile Thr Gly Ile Ser Ser Leu Ile Gly
    130                 135                 140

atg ttt gcc caa gta tca ggc aat gaa gtt tct tat tca tca gct ggg      480
Met Phe Ala Gln Val Ser Gly Asn Glu Val Ser Tyr Ser Ser Ala Gly
145                 150                 155                 160

tca tcc agc gcc gca gct tca gaa gca gtc tca gca gga caa gga cca      528
Ser Ser Ser Ala Ala Ala Ser Glu Ala Val Ser Ala Gly Gln Gly Pro
                165                 170                 175

gca gca caa cca gtt tac gca cca agc gga gca agt gca gct gca gca      576
Ala Ala Gln Pro Val Tyr Ala Pro Ser Gly Ala Ser Ala Ala Ala Ala
            180                 185                 190

gcg gct agt gga gca gca cct gca ata cta caa gca tat gaa cga gga      624
Ala Ala Ser Gly Ala Ala Pro Ala Ile Leu Gln Ala Tyr Glu Arg Gly
        195                 200                 205

ggt tca gga tca gca gct gca gca gca ggc tca gga cca agt gga tac      672
Gly Ser Gly Ser Ala Ala Ala Ala Ala Gly Ser Gly Pro Ser Gly Tyr
    210                 215                 220

gga caa gga gca gga gga cca gga gga gca ggt gct gca gca gga gcg      720
Gly Gln Gly Ala Gly Gly Pro Gly Gly Ala Gly Ala Ala Ala Gly Ala
225                 230                 235                 240

gct gcc gca gga gga tct ggc cct gga gga tac gga caa gga cca gct      768
Ala Ala Ala Gly Gly Ser Gly Pro Gly Gly Tyr Gly Gln Gly Pro Ala
                245                 250                 255

gct tat ggc cca tca gga cct agt gga caa caa ggt tac gga cca ggt      816
Ala Tyr Gly Pro Ser Gly Pro Ser Gly Gln Gln Gly Tyr Gly Pro Gly
            260                 265                 270

gga tca gga gca gca gct gcc gca gcc gca gca gca ggc tca gga cct      864
Gly Ser Gly Ala Ala Ala Ala Ala Ala Ala Ala Ala Gly Ser Gly Pro
        275                 280                 285

agt gga tac gga cca gga gca ggt gga cca gga gga gca ggt gct gca      912
Ser Gly Tyr Gly Pro Gly Ala Gly Gly Pro Gly Gly Ala Gly Ala Ala
    290                 295                 300
```

```
gna gca gcg gct gcc gca nga gga tct ggc cct gga gga tac gga caa      960
Xaa Ala Ala Ala Ala Ala Xaa Gly Ser Gly Pro Gly Gly Tyr Gly Gln
305                 310                 315                 320

gga caa gct agt tat ggn ccg tca gga cct ant gga caa caa ggt tac     1008
Gly Gln Ala Ser Tyr Gly Pro Ser Gly Pro Xaa Gly Gln Gln Gly Tyr
                325                 330                 335

gga cca ggt gaa tca gga gca gca gct gcc tct gga gca gca gcc gcg     1056
Gly Pro Gly Glu Ser Gly Ala Ala Ala Ala Ser Gly Ala Ala Ala Ala
            340                 345                 350

gca gca ggt gga gca gga cct ggt aga caa caa gga tat gga cca gga     1104
Ala Ala Gly Gly Ala Gly Pro Gly Arg Gln Gln Gly Tyr Gly Pro Gly
        355                 360                 365

agt tct gga gca gca gcg gca gca gca gct ggt gga cca gga tat gga     1152
Ser Ser Gly Ala Ala Ala Ala Ala Ala Ala Gly Gly Pro Gly Tyr Gly
    370                 375                 380

ggt caa caa ggt tac cga cca gga gga gca ggt gca gca gca gca gcg     1200
Gly Gln Gln Gly Tyr Arg Pro Gly Gly Ala Gly Ala Ala Ala Ala Ala
385                 390                 395                 400

gca gct ggt ggt gca gga cca ggt aga caa caa gca tat gga cca gga     1248
Ala Ala Gly Gly Ala Gly Pro Gly Arg Gln Gln Ala Tyr Gly Pro Gly
                405                 410                 415

gga tca ggt gca gca gct gca gca gca ggt gga gca gga cct ggt aga     1296
Gly Ser Gly Ala Ala Ala Ala Ala Ala Gly Gly Ala Gly Pro Gly Arg
            420                 425                 430

caa caa gga tat gga cca gga ggt tct gga gca gca gcg gta gca gca     1344
Gln Gln Gly Tyr Gly Pro Gly Gly Ser Gly Ala Ala Ala Val Ala Ala
        435                 440                 445

gca gct ggt gga cca gga tat gga ggt caa caa ggt tac gga cca gga     1392
Ala Ala Gly Gly Pro Gly Tyr Gly Gly Gln Gln Gly Tyr Gly Pro Gly
    450                 455                 460

gga tca ggt gca gca gca gca gcg gca gct ggt ggt gca gga cct ggt     1440
Gly Ser Gly Ala Ala Ala Ala Ala Ala Ala Gly Gly Ala Gly Pro Gly
465                 470                 475                 480

agg caa caa gca tat gga cca gga gga tca gga gca gca gct gca gca     1488
Arg Gln Gln Ala Tyr Gly Pro Gly Gly Ser Gly Ala Ala Ala Ala Ala
                485                 490                 495

gcc gct gcc gca ggc tca gga ccc agt gga tac gga cca tca gca gca     1536
Ala Ala Ala Ala Gly Ser Gly Pro Ser Gly Tyr Gly Pro Ser Ala Ala
            500                 505                 510

gga cca agt gga cca gga gga tca ggt gcc gca gca gcg gct gcc gca     1584
Gly Pro Ser Gly Pro Gly Gly Ser Gly Ala Ala Ala Ala Ala Ala Ala
        515                 520                 525

ggt gga tct ggc cct gga ggt ttt ggt caa gga cca gca ggt tat ggt     1632
Gly Gly Ser Gly Pro Gly Gly Phe Gly Gln Gly Pro Ala Gly Tyr Gly
    530                 535                 540

ccc tca gga cct ggt gga caa caa gga tac ggg cca ggt gca tca ggt     1680
Pro Ser Gly Pro Gly Gly Gln Gln Gly Tyr Gly Pro Gly Ala Ser Gly
545                 550                 555                 560

gct gca gcg gca gca gca gct agt gga tca ggt gga tat ggt cct tca     1728
Ala Ala Ala Ala Ala Ala Ala Ser Gly Ser Gly Gly Tyr Gly Pro Ser
                565                 570                 575

caa tat gtt cc                                                      1739
Gln Tyr Val
```

<210> SEQ ID NO 20
<211> LENGTH: 579
<212> TYPE: PRT
<213> ORGANISM: Latrodectus hesperus
<220> FEATURE:
<221> NAME/KEY: misc_feature
<222> LOCATION: (2)..(2)
<223> OTHER INFORMATION: The 'Xaa' at location 2 stands for Thr, Ala, Pro, or Ser.
<220> FEATURE:
<221> NAME/KEY: misc_feature
<222> LOCATION: (12)..(12)
<223> OTHER INFORMATION: The 'Xaa' at location 12 stands for Trp, Ser, or Leu.
<220> FEATURE:
<221> NAME/KEY: misc_feature
<222> LOCATION: (14)..(14)
<223> OTHER INFORMATION: The 'Xaa' at location 14 stands for Ile, Val, or Leu.
<220> FEATURE:
<221> NAME/KEY: misc_feature
<222> LOCATION: (15)..(15)
<223> OTHER INFORMATION: The 'Xaa' at location 15 stands for Leu.
<220> FEATURE:
<221> NAME/KEY: misc_feature
<222> LOCATION: (22)..(22)
<223> OTHER INFORMATION: The 'Xaa' at location 22 stands for Ser, Gly, Arg, or Cys.
<220> FEATURE:
<221> NAME/KEY: misc_feature
<222> LOCATION: (23)..(23)
<223> OTHER INFORMATION: The 'Xaa' at location 23 stands for Leu.
<220> FEATURE:
<221> NAME/KEY: misc_feature
<222> LOCATION: (26)..(26)
<223> OTHER INFORMATION: The 'Xaa' at location 26 stands for Met, Val, or Leu.
<220> FEATURE:
<221> NAME/KEY: misc_feature
<222> LOCATION: (30)..(30)
<223> OTHER INFORMATION: The 'Xaa' at location 30 stands for Asn, Ser, Thr, or Ile.
<220> FEATURE:
<221> NAME/KEY: misc_feature
<222> LOCATION: (33)..(33)
<223> OTHER INFORMATION: The 'Xaa' at location 33 stands for Trp, Ser, or Leu.
<220> FEATURE:
<221> NAME/KEY: misc_feature
<222> LOCATION: (35)..(35)
<223> OTHER INFORMATION: The 'Xaa' at location 35 stands for Asn, Ser, Thr, or Ile.
<220> FEATURE:
<221> NAME/KEY: misc_feature
<222> LOCATION: (44)..(44)
<223> OTHER INFORMATION: The 'Xaa' at location 44 stands for Ser, Gly, Arg, or Cys.
<220> FEATURE:
<221> NAME/KEY: misc_feature
<222> LOCATION: (45)..(45)
<223> OTHER INFORMATION: The 'Xaa' at location 45 stands for Thr, Ala, Pro, or Ser.
<220> FEATURE:
<221> NAME/KEY: misc_feature
<222> LOCATION: (305)..(305)
<223> OTHER INFORMATION: The 'Xaa' at location 305 stands for Glu, Gly, Ala, or Val.
<220> FEATURE:
<221> NAME/KEY: misc_feature
<222> LOCATION: (311)..(311)
<223> OTHER INFORMATION: The 'Xaa' at location 311 stands for Arg, or Gly.
<220> FEATURE:
<221> NAME/KEY: misc_feature
<222> LOCATION: (331)..(331)
<223> OTHER INFORMATION: The 'Xaa' at location 331 stands for Asn, Ser, Thr, or Ile.

<400> SEQUENCE: 20

```
Met Xaa Thr Met Asn Trp Ser Thr Arg Leu Val Xaa Ser Xaa Xaa Val
1               5                   10                  15

Val Leu Cys Thr Gln Xaa Xaa Cys Ala Xaa Gly Gln Ala Xaa Thr Pro
            20                  25                  30
```

-continued

```
Xaa Ser Xaa Lys Glu Asn Ala Asp Ala Phe Ile Xaa Xaa Phe Met Asn
        35                  40                  45

Ala Ala Ser Gln Ser Gly Ala Phe Ser Ser Asp Gln Ile Asp Asp Met
    50                  55                  60

Ser Val Ile Ser Asn Thr Leu Met Ala Ala Met Asn Asn Met Gly Gly
65                  70                  75                  80

Arg Ile Thr Gln Ser Lys Leu Gln Ala Leu Asp Met Ala Phe Ala Ser
                85                  90                  95

Ser Val Ala Glu Ile Ala Val Ala Asp Gly Gln Asn Val Gly Ala Ala
            100                 105                 110

Thr Asn Ala Ile Ser Asp Ala Leu Arg Ser Ala Phe Tyr Gln Thr Thr
        115                 120                 125

Gly Val Val Asn Asn Gln Phe Ile Thr Gly Ile Ser Ser Leu Ile Gly
    130                 135                 140

Met Phe Ala Gln Val Ser Gly Asn Glu Val Ser Tyr Ser Ser Ala Gly
145                 150                 155                 160

Ser Ser Ser Ala Ala Ala Ser Glu Ala Val Ser Ala Gly Gln Gly Pro
                165                 170                 175

Ala Ala Gln Pro Val Tyr Ala Pro Ser Gly Ala Ser Ala Ala Ala Ala
            180                 185                 190

Ala Ala Ser Gly Ala Ala Pro Ala Ile Leu Gln Ala Tyr Glu Arg Gly
        195                 200                 205

Gly Ser Gly Ser Ala Ala Ala Ala Ala Gly Ser Gly Pro Ser Gly Tyr
    210                 215                 220

Gly Gln Gly Ala Gly Gly Pro Gly Gly Ala Gly Ala Ala Ala Gly Ala
225                 230                 235                 240

Ala Ala Ala Gly Gly Ser Gly Pro Gly Gly Tyr Gly Gln Gly Pro Ala
                245                 250                 255

Ala Tyr Gly Pro Ser Gly Pro Ser Gly Gln Gln Gly Tyr Gly Pro Gly
            260                 265                 270

Gly Ser Gly Ala Ala Ala Ala Ala Ala Ala Ala Ala Gly Ser Gly Pro
        275                 280                 285

Ser Gly Tyr Gly Pro Gly Ala Gly Gly Pro Gly Gly Ala Gly Ala Ala
    290                 295                 300

Xaa Ala Ala Ala Ala Ala Xaa Gly Ser Gly Pro Gly Gly Tyr Gly Gln
305                 310                 315                 320

Gly Gln Ala Ser Tyr Gly Pro Ser Gly Pro Xaa Gly Gln Gln Gly Tyr
                325                 330                 335

Gly Pro Gly Glu Ser Gly Ala Ala Ala Ala Ser Gly Ala Ala Ala Ala
            340                 345                 350

Ala Ala Gly Gly Ala Gly Pro Gly Arg Gln Gln Gly Tyr Gly Pro Gly
        355                 360                 365

Ser Ser Gly Ala Ala Ala Ala Ala Ala Ala Gly Gly Pro Gly Tyr Gly
    370                 375                 380

Gly Gln Gln Gly Tyr Arg Pro Gly Gly Ala Gly Ala Ala Ala Ala Ala
385                 390                 395                 400

Ala Ala Gly Gly Ala Gly Pro Gly Arg Gln Gln Ala Tyr Gly Pro Gly
                405                 410                 415

Gly Ser Gly Ala Ala Ala Ala Ala Ala Gly Gly Ala Gly Pro Gly Arg
            420                 425                 430

Gln Gln Gly Tyr Gly Pro Gly Gly Ser Gly Ala Ala Ala Val Ala Ala
        435                 440                 445
```

```
Ala Ala Gly Gly Pro Gly Tyr Gly Gly Gln Gln Gly Tyr Gly Pro Gly
    450                 455                 460

Gly Ser Gly Ala Ala Ala Ala Ala Ala Ala Gly Gly Ala Gly Pro Gly
465                 470                 475                 480

Arg Gln Gln Ala Tyr Gly Pro Gly Gly Ser Gly Ala Ala Ala Ala Ala
                485                 490                 495

Ala Ala Ala Ala Gly Ser Gly Pro Ser Gly Tyr Gly Pro Ser Ala Ala
            500                 505                 510

Gly Pro Ser Gly Pro Gly Gly Ser Gly Ala Ala Ala Ala Ala Ala Ala
        515                 520                 525

Gly Gly Ser Gly Pro Gly Gly Phe Gly Gln Gly Pro Ala Gly Tyr Gly
    530                 535                 540

Pro Ser Gly Pro Gly Gly Gln Gln Gly Tyr Gly Pro Gly Ala Ser Gly
545                 550                 555                 560

Ala Ala Ala Ala Ala Ala Ala Ser Gly Ser Gly Gly Tyr Gly Pro Ser
                565                 570                 575

Gln Tyr Val


<210> SEQ ID NO 21
<211> LENGTH: 830
<212> TYPE: DNA
<213> ORGANISM: Latrodectus hesperus
<220> FEATURE:
<221> NAME/KEY: CDS
<222> LOCATION: (135)..(830)

<400> SEQUENCE: 21

cacgcggaca tgacacaatt gtctgcatat ctccaggtgt attgaaaaac ctgctgcaca      60

gcacgaccaa tcattgtata aaagaggcaa tcaatcagcg tacagtattc agtcgggatt     120

ttccaactac taca atg act tgg tca act cga ctt gcc tta tca ttt ctt       170
                Met Thr Trp Ser Thr Arg Leu Ala Leu Ser Phe Leu
                1               5                   10

ttc gtg ctc tgc act cag agc ctg tac gct ttg gcg caa gcc aac acg       218
Phe Val Leu Cys Thr Gln Ser Leu Tyr Ala Leu Ala Gln Ala Asn Thr
        15                  20                  25

cca tgg tca agt aaa gcg aat gct gat gct ttt atc aat tcc ttt att       266
Pro Trp Ser Ser Lys Ala Asn Ala Asp Ala Phe Ile Asn Ser Phe Ile
    30                  35                  40

tcg gca gct tcg aat act gga tcc ttc tcc caa gat cag atg gaa gat       314
Ser Ala Ala Ser Asn Thr Gly Ser Phe Ser Gln Asp Gln Met Glu Asp
45                  50                  55                  60

atg tca ttg att ggt aat aca tta atg gca gca atg gat aat atg ggt       362
Met Ser Leu Ile Gly Asn Thr Leu Met Ala Ala Met Asp Asn Met Gly
                65                  70                  75

gga aga att acg cca tcc aaa tta cag gct tta gat atg gct ttc gca       410
Gly Arg Ile Thr Pro Ser Lys Leu Gln Ala Leu Asp Met Ala Phe Ala
            80                  85                  90

tca tct gta gca gaa att gct gct tcg gaa gga gga gac tta gga gta       458
Ser Ser Val Ala Glu Ile Ala Ala Ser Glu Gly Gly Asp Leu Gly Val
        95                  100                 105

aca aca aat gca att gca gat gct tta acg tca gct ttc tat caa aca       506
Thr Thr Asn Ala Ile Ala Asp Ala Leu Thr Ser Ala Phe Tyr Gln Thr
    110                 115                 120

acc gga gta gtt aat agc aga ttt att agc gaa att aga agt ttg att       554
Thr Gly Val Val Asn Ser Arg Phe Ile Ser Glu Ile Arg Ser Leu Ile
125                 130                 135                 140

ggc atg ttt gca cag gca tct gcc aac gat gta tac gcc tca gca ggt       602
Gly Met Phe Ala Gln Ala Ser Ala Asn Asp Val Tyr Ala Ser Ala Gly
```

```
                145                 150                 155

tcc agc ggt gga gga ggg tat gga gca tct tct gca agt gca gca tct      650
Ser Ser Gly Gly Gly Gly Tyr Gly Ala Ser Ser Ala Ser Ala Ala Ser
            160                 165                 170

gca agc gca gca gca cca tca ggt gtc gca tat caa gct cca gca caa      698
Ala Ser Ala Ala Ala Pro Ser Gly Val Ala Tyr Gln Ala Pro Ala Gln
        175                 180                 185

gca caa att tcc ttc act ttg aga gga caa cag cca gtt agt tat ggt      746
Ala Gln Ile Ser Phe Thr Leu Arg Gly Gln Gln Pro Val Ser Tyr Gly
    190                 195                 200

caa gga ggm gct rgm sca gsy ksa gsw gsa gmr gcw gwk wma gwm gwc      794
Gln Gly Xaa Ala Xaa Xaa Xaa Xaa Xaa Xaa Xaa Ala Xaa Xaa Xaa Xaa
205                 210                 215                 220

gcw gsa scw gga gga gcw ggw sma gsa gsa sya gsy                      830
Ala Xaa Xaa Gly Gly Ala Xaa Xaa Xaa Xaa Xaa Xaa
                225                 230


<210> SEQ ID NO 22
<211> LENGTH: 232
<212> TYPE: PRT
<213> ORGANISM: Latrodectus hesperus
<220> FEATURE:
<221> NAME/KEY: misc_feature
<222> LOCATION: (207)..(207)
<223> OTHER INFORMATION: The 'Xaa' at location 207 stands for Gly.
<220> FEATURE:
<221> NAME/KEY: misc_feature
<222> LOCATION: (209)..(209)
<223> OTHER INFORMATION: The 'Xaa' at location 209 stands for Gly, Arg,
      or Ser.
<220> FEATURE:
<221> NAME/KEY: misc_feature
<222> LOCATION: (210)..(210)
<223> OTHER INFORMATION: The 'Xaa' at location 210 stands for Ala, or
      Pro.
<220> FEATURE:
<221> NAME/KEY: misc_feature
<222> LOCATION: (211)..(211)
<223> OTHER INFORMATION: The 'Xaa' at location 211 stands for Gly, or
      Ala.
<220> FEATURE:
<221> NAME/KEY: misc_feature
<222> LOCATION: (212)..(212)
<223> OTHER INFORMATION: The 'Xaa' at location 212 stands for Gly, Ala,
      or Ser.
<220> FEATURE:
<221> NAME/KEY: misc_feature
<222> LOCATION: (213)..(213)
<223> OTHER INFORMATION: The 'Xaa' at location 213 stands for Gly, or
      Ala.
<220> FEATURE:
<221> NAME/KEY: misc_feature
<222> LOCATION: (214)..(214)
<223> OTHER INFORMATION: The 'Xaa' at location 214 stands for Gly, or
      Ala.
<220> FEATURE:
<221> NAME/KEY: misc_feature
<222> LOCATION: (215)..(215)
<223> OTHER INFORMATION: The 'Xaa' at location 215 stands for Glu, or
      Ala.
<220> FEATURE:
<221> NAME/KEY: misc_feature
<222> LOCATION: (217)..(217)
<223> OTHER INFORMATION: The 'Xaa' at location 217 stands for Glu, Asp,
      or Val.
<220> FEATURE:
<221> NAME/KEY: misc_feature
<222> LOCATION: (218)..(218)
<223> OTHER INFORMATION: The 'Xaa' at location 218 stands for Lys, Thr,
      or Ser.
<220> FEATURE:
<221> NAME/KEY: misc_feature
<222> LOCATION: (219)..(219)
```

```
<223> OTHER INFORMATION: The 'Xaa' at location 219 stands for Glu, Asp,
      or Val.
<220> FEATURE:
<221> NAME/KEY: misc_feature
<222> LOCATION: (220)..(220)
<223> OTHER INFORMATION: The 'Xaa' at location 220 stands for Asp, or
      Val.
<220> FEATURE:
<221> NAME/KEY: misc_feature
<222> LOCATION: (222)..(222)
<223> OTHER INFORMATION: The 'Xaa' at location 222 stands for Gly, or
      Ala.
<220> FEATURE:
<221> NAME/KEY: misc_feature
<222> LOCATION: (223)..(223)
<223> OTHER INFORMATION: The 'Xaa' at location 223 stands for Ala, or
      Pro.
<220> FEATURE:
<221> NAME/KEY: misc_feature
<222> LOCATION: (227)..(227)
<223> OTHER INFORMATION: The 'Xaa' at location 227 stands for Gly.
<220> FEATURE:
<221> NAME/KEY: misc_feature
<222> LOCATION: (228)..(228)
<223> OTHER INFORMATION: The 'Xaa' at location 228 stands for Glu, Ala,
      Gln, or Pro.
<220> FEATURE:
<221> NAME/KEY: misc_feature
<222> LOCATION: (229)..(229)
<223> OTHER INFORMATION: The 'Xaa' at location 229 stands for Gly, or
      Ala.
<220> FEATURE:
<221> NAME/KEY: misc_feature
<222> LOCATION: (230)..(230)
<223> OTHER INFORMATION: The 'Xaa' at location 230 stands for Gly, or
      Ala.
<220> FEATURE:
<221> NAME/KEY: misc_feature
<222> LOCATION: (231)..(231)
<223> OTHER INFORMATION: The 'Xaa' at location 231 stands for Ala, Val,
      Pro, or Leu.
<220> FEATURE:
<221> NAME/KEY: misc_feature
<222> LOCATION: (232)..(232)
<223> OTHER INFORMATION: The 'Xaa' at location 232 stands for Gly, or
      Ala.

<400> SEQUENCE: 22

Met Thr Trp Ser Thr Arg Leu Ala Leu Ser Phe Leu Phe Val Leu Cys
1               5                   10                  15

Thr Gln Ser Leu Tyr Ala Leu Ala Gln Ala Asn Thr Pro Trp Ser Ser
            20                  25                  30

Lys Ala Asn Ala Asp Ala Phe Ile Asn Ser Phe Ile Ser Ala Ala Ser
        35                  40                  45

Asn Thr Gly Ser Phe Ser Gln Asp Gln Met Glu Asp Met Ser Leu Ile
    50                  55                  60

Gly Asn Thr Leu Met Ala Ala Met Asp Asn Met Gly Gly Arg Ile Thr
65                  70                  75                  80

Pro Ser Lys Leu Gln Ala Leu Asp Met Ala Phe Ala Ser Ser Val Ala
                85                  90                  95

Glu Ile Ala Ala Ser Glu Gly Gly Asp Leu Gly Val Thr Thr Asn Ala
            100                 105                 110

Ile Ala Asp Ala Leu Thr Ser Ala Phe Tyr Gln Thr Thr Gly Val Val
        115                 120                 125

Asn Ser Arg Phe Ile Ser Glu Ile Arg Ser Leu Ile Gly Met Phe Ala
    130                 135                 140

Gln Ala Ser Ala Asn Asp Val Tyr Ala Ser Ala Gly Ser Ser Gly Gly
145                 150                 155                 160
```

-continued

```
Gly Gly Tyr Gly Ala Ser Ser Ala Ser Ala Ala Ser Ala Ser Ala Ala
                165                 170                 175

Ala Pro Ser Gly Val Ala Tyr Gln Ala Pro Ala Gln Ala Gln Ile Ser
            180                 185                 190

Phe Thr Leu Arg Gly Gln Gln Pro Val Ser Tyr Gly Gln Gly Xaa Ala
        195                 200                 205

Xaa Xaa Xaa Xaa Xaa Xaa Xaa Ala Xaa Xaa Xaa Xaa Ala Xaa Xaa Gly
    210                 215                 220

Gly Ala Xaa Xaa Xaa Xaa Xaa Xaa
225                 230


<210> SEQ ID NO 23
<211> LENGTH: 1124
<212> TYPE: DNA
<213> ORGANISM: Latrodectus hesperus
<220> FEATURE:
<221> NAME/KEY: CDS
<222> LOCATION: (213)..(1124)
<220> FEATURE:
<221> NAME/KEY: misc_feature
<222> LOCATION: (959)..(959)
<223> OTHER INFORMATION: n is a, c, g, or t

<400> SEQUENCE: 23

catccacgaa cgtttgcatt cgaccttaga aaaacagatg agtaaatgaa agtgaaacgt      60

acatacgtca attcaactgg gcgagatgaa atcgtagact gcatatttcc aggtatattg     120

atacacctgc tgcacatcac gaacaatcag tgtataaaag aggagaacga tcagcgtaaa     180

gtattctcag tcgrgatttt ccaactacta ca atg act tgg tct act cga ctt       233
                                    Met Thr Trp Ser Thr Arg Leu
                                    1               5

gcc tta tca ttt ctt tta gtg ctc tgc act cag agc att tat gct ctg       281
Ala Leu Ser Phe Leu Leu Val Leu Cys Thr Gln Ser Ile Tyr Ala Leu
        10                  15                  20

gcg caa gcc aac acg cca tgg tca agt aaa gcg aat gct gat gct ttt       329
Ala Gln Ala Asn Thr Pro Trp Ser Ser Lys Ala Asn Ala Asp Ala Phe
    25                  30                  35

atc aat tcc ttt att tcg gca gct tcg aat act gga tcc ttc tcc caa       377
Ile Asn Ser Phe Ile Ser Ala Ala Ser Asn Thr Gly Ser Phe Ser Gln
40                  45                  50                  55

gat cag atg gaa gat atg tca ttg att ggt aat aca tta atg gca gca       425
Asp Gln Met Glu Asp Met Ser Leu Ile Gly Asn Thr Leu Met Ala Ala
                60                  65                  70

atg gat aat atg ggt gga aga att acg cca tcc aaa tta cag gct tta       473
Met Asp Asn Met Gly Gly Arg Ile Thr Pro Ser Lys Leu Gln Ala Leu
            75                  80                  85

gat atg gct ttc gca tca tct gta gca gaa att gct gct tcg gaa gga       521
Asp Met Ala Phe Ala Ser Ser Val Ala Glu Ile Ala Ala Ser Glu Gly
        90                  95                  100

gga gac tta gga gta aca aca aat gca att gca gat gct tta aca tca       569
Gly Asp Leu Gly Val Thr Thr Asn Ala Ile Ala Asp Ala Leu Thr Ser
    105                 110                 115

gct ttc tat caa aca acc gga gta gtt aat agc aga ttt att agc gaa       617
Ala Phe Tyr Gln Thr Thr Gly Val Val Asn Ser Arg Phe Ile Ser Glu
120                 125                 130                 135

att aga agt ttg att ggc atg ttt gca cag gca tct gcc aac gat gta       665
Ile Arg Ser Leu Ile Gly Met Phe Ala Gln Ala Ser Ala Asn Asp Val
                140                 145                 150

tac gcc tca gca ggt tcc agc ggt gga gga ggg tat gga gca tct tct       713
Tyr Ala Ser Ala Gly Ser Ser Gly Gly Gly Gly Tyr Gly Ala Ser Ser
            155                 160                 165
```

```
gca agt gca gca tct gca agc gca gca gca cca tca ggt gtc gca tac      761
Ala Ser Ala Ala Ser Ala Ser Ala Ala Ala Pro Ser Gly Val Ala Tyr
        170                 175                 180

caa gct cca gca caa gca caa att tcc ttc tct ttg aga gga caa cag      809
Gln Ala Pro Ala Gln Ala Gln Ile Ser Phe Ser Leu Arg Gly Gln Gln
    185                 190                 195

cca gtt agt tat ggt caa gga gga gct agc gca gct tca gga gca gcg      857
Pro Val Ser Tyr Gly Gln Gly Gly Ala Ser Ala Ala Ser Gly Ala Ala
200                 205                 210                 215

gct ggt caa gga ggc gca gga cca gga gga gct gga gca gca gcg gca      905
Ala Gly Gln Gly Gly Ala Gly Pro Gly Gly Ala Gly Ala Ala Ala Ala
                220                 225                 230

gcg gca gca gca gct gsa gga gcr ggt caa gga gga caa ggt gga tat      953
Ala Ala Ala Ala Ala Xaa Gly Ala Gly Gln Gly Gly Gln Gly Gly Tyr
            235                 240                 245

gga can gga gga tac ggt caa gga ggt gcc gga caa ggt gga tct gga     1001
Gly Xaa Gly Gly Tyr Gly Gln Gly Gly Ala Gly Gln Gly Gly Ser Gly
        250                 255                 260

gca gca gca gcg gca gca gca gca gct gga ggc acc ggt caa gga ggt     1049
Ala Ala Ala Ala Ala Ala Ala Ala Ala Gly Gly Thr Gly Gln Gly Gly
    265                 270                 275

gct gga caa ggt gga gca gga gca gca gcg gca gcc gca gca gca gct     1097
Ala Gly Gln Gly Gly Ala Gly Ala Ala Ala Ala Ala Ala Ala Ala Ala
280                 285                 290                 295

gga gat gca ggt caa gga gga caa ggt                                 1124
Gly Asp Ala Gly Gln Gly Gly Gln Gly
                300
```

<210> SEQ ID NO 24
<211> LENGTH: 304
<212> TYPE: PRT
<213> ORGANISM: Latrodectus hesperus
<220> FEATURE:
<221> NAME/KEY: misc_feature
<222> LOCATION: (237)..(237)
<223> OTHER INFORMATION: The 'Xaa' at location 237 stands for Gly, or Ala.
<220> FEATURE:
<221> NAME/KEY: misc_feature
<222> LOCATION: (249)..(249)
<223> OTHER INFORMATION: The 'Xaa' at location 249 stands for Gln, or His.

<400> SEQUENCE: 24

```
Met Thr Trp Ser Thr Arg Leu Ala Leu Ser Phe Leu Leu Val Leu Cys
1               5                   10                  15

Thr Gln Ser Ile Tyr Ala Leu Ala Gln Ala Asn Thr Pro Trp Ser Ser
            20                  25                  30

Lys Ala Asn Ala Asp Ala Phe Ile Asn Ser Phe Ile Ser Ala Ala Ser
        35                  40                  45

Asn Thr Gly Ser Phe Ser Gln Asp Gln Met Glu Asp Met Ser Leu Ile
    50                  55                  60

Gly Asn Thr Leu Met Ala Ala Met Asp Asn Met Gly Gly Arg Ile Thr
65                  70                  75                  80

Pro Ser Lys Leu Gln Ala Leu Asp Met Ala Phe Ala Ser Ser Val Ala
                85                  90                  95

Glu Ile Ala Ala Ser Glu Gly Gly Asp Leu Gly Val Thr Thr Asn Ala
            100                 105                 110

Ile Ala Asp Ala Leu Thr Ser Ala Phe Tyr Gln Thr Thr Gly Val Val
        115                 120                 125
```

```
Asn Ser Arg Phe Ile Ser Glu Ile Arg Ser Leu Ile Gly Met Phe Ala
    130                 135                 140

Gln Ala Ser Ala Asn Asp Val Tyr Ala Ser Ala Gly Ser Ser Gly Gly
145                 150                 155                 160

Gly Gly Tyr Gly Ala Ser Ser Ala Ser Ala Ala Ser Ala Ser Ala Ala
                165                 170                 175

Ala Pro Ser Gly Val Ala Tyr Gln Ala Pro Ala Gln Ala Gln Ile Ser
            180                 185                 190

Phe Ser Leu Arg Gly Gln Gln Pro Val Ser Tyr Gly Gln Gly Gly Ala
        195                 200                 205

Ser Ala Ala Ser Gly Ala Ala Ala Gly Gln Gly Gly Ala Gly Pro Gly
    210                 215                 220

Gly Ala Gly Ala Ala Ala Ala Ala Ala Ala Ala Ala Xaa Gly Ala Gly
225                 230                 235                 240

Gln Gly Gly Gln Gly Gly Tyr Gly Xaa Gly Gly Tyr Gly Gln Gly Gly
                245                 250                 255

Ala Gly Gln Gly Gly Ser Gly Ala Ala Ala Ala Ala Ala Ala Ala Ala
            260                 265                 270

Gly Gly Thr Gly Gln Gly Gly Ala Gly Gln Gly Gly Ala Gly Ala Ala
        275                 280                 285

Ala Ala Ala Ala Ala Ala Ala Gly Asp Ala Gly Gln Gly Gly Gln Gly
    290                 295                 300


<210> SEQ ID NO 25
<211> LENGTH: 832
<212> TYPE: DNA
<213> ORGANISM: Latrodectus hesperus
<220> FEATURE:
<221> NAME/KEY: CDS
<222> LOCATION: (98)..(832)

<400> SEQUENCE: 25

tgtattgaaa aacctgctgc acagcacgac caatcattgt ataaaagagg caatcaatca      60

gcgtacagta ttcagtcggg attttccaac tactaca atg act tgg tca act cga      115
                                         Met Thr Trp Ser Thr Arg
                                         1               5

ctt gcc tta tca ttt ctt ttc gtg ctc tgc act cag agc ctg tac gct      163
Leu Ala Leu Ser Phe Leu Phe Val Leu Cys Thr Gln Ser Leu Tyr Ala
            10                  15                  20

ttg gcg caa gcc aac acg cca tgg tca agt aaa gcg aat gct gat gct      211
Leu Ala Gln Ala Asn Thr Pro Trp Ser Ser Lys Ala Asn Ala Asp Ala
        25                  30                  35

ttt atc aat tcc ttt att tcg gca gct tcg aat act gga tcc ttc tcc      259
Phe Ile Asn Ser Phe Ile Ser Ala Ala Ser Asn Thr Gly Ser Phe Ser
    40                  45                  50

caa gat cag atg gaa gat atg tca ttg att ggt aat aca tta atg gca      307
Gln Asp Gln Met Glu Asp Met Ser Leu Ile Gly Asn Thr Leu Met Ala
55                  60                  65                  70

gca atg gat aat atg ggt gga aga att acg cca tcc aaa tta cag gct      355
Ala Met Asp Asn Met Gly Gly Arg Ile Thr Pro Ser Lys Leu Gln Ala
                75                  80                  85

tta gat atg gct ttc gca tca tct gta gca gaa att gct gct tcg gaa      403
Leu Asp Met Ala Phe Ala Ser Ser Val Ala Glu Ile Ala Ala Ser Glu
            90                  95                  100

gga gga gac tta gga gta aca aca aat gca att gca gat gct tta acg      451
Gly Gly Asp Leu Gly Val Thr Thr Asn Ala Ile Ala Asp Ala Leu Thr
        105                 110                 115

tca gct ttc tat caa aca acc gga gta gtt aat agc aga ttt att agc      499
```

-continued

```
Ser Ala Phe Tyr Gln Thr Thr Gly Val Val Asn Ser Arg Phe Ile Ser
    120                 125                 130

gaa att aga agt ttg att ggc atg ttt gca cag gca tct gcc aac gat      547
Glu Ile Arg Ser Leu Ile Gly Met Phe Ala Gln Ala Ser Ala Asn Asp
135                 140                 145                 150

gta tac gcc tca gca ggt tcc agc ggt gga gga ggg tat gga gca tct      595
Val Tyr Ala Ser Ala Gly Ser Ser Gly Gly Gly Gly Tyr Gly Ala Ser
                155                 160                 165

tct gca agt gca gca tct gca agc gca gca gca cca tca ggt gtc gca      643
Ser Ala Ser Ala Ala Ser Ala Ser Ala Ala Ala Pro Ser Gly Val Ala
            170                 175                 180

tat caa gct cca gca caa gca caa att tcc ttc act ttg aga gga caa      691
Tyr Gln Ala Pro Ala Gln Ala Gln Ile Ser Phe Thr Leu Arg Gly Gln
        185                 190                 195

cag cca gtt agt tat ggt caa gga gga gct agc gca gcc tca gga gca      739
Gln Pro Val Ser Tyr Gly Gln Gly Gly Ala Ser Ala Ala Ser Gly Ala
    200                 205                 210

gag gct ggt caa gga ggc gct gga cca gga gga gct gga gca gca gcg      787
Glu Ala Gly Gln Gly Gly Ala Gly Pro Gly Gly Ala Gly Ala Ala Ala
215                 220                 225                 230

gca gcc gca gca gca gct gga gga gca ggt caa gga gga caa ggt          832
Ala Ala Ala Ala Ala Ala Gly Gly Ala Gly Gln Gly Gly Gln Gly
                235                 240                 245


<210> SEQ ID NO 26
<211> LENGTH: 245
<212> TYPE: PRT
<213> ORGANISM: Latrodectus hesperus

<400> SEQUENCE: 26

Met Thr Trp Ser Thr Arg Leu Ala Leu Ser Phe Leu Phe Val Leu Cys
1               5                   10                  15

Thr Gln Ser Leu Tyr Ala Leu Ala Gln Ala Asn Thr Pro Trp Ser Ser
            20                  25                  30

Lys Ala Asn Ala Asp Ala Phe Ile Asn Ser Phe Ile Ser Ala Ala Ser
        35                  40                  45

Asn Thr Gly Ser Phe Ser Gln Asp Gln Met Glu Asp Met Ser Leu Ile
    50                  55                  60

Gly Asn Thr Leu Met Ala Ala Met Asp Asn Met Gly Gly Arg Ile Thr
65                  70                  75                  80

Pro Ser Lys Leu Gln Ala Leu Asp Met Ala Phe Ala Ser Ser Val Ala
                85                  90                  95

Glu Ile Ala Ala Ser Glu Gly Gly Asp Leu Gly Val Thr Thr Asn Ala
            100                 105                 110

Ile Ala Asp Ala Leu Thr Ser Ala Phe Tyr Gln Thr Thr Gly Val Val
        115                 120                 125

Asn Ser Arg Phe Ile Ser Glu Ile Arg Ser Leu Ile Gly Met Phe Ala
    130                 135                 140

Gln Ala Ser Ala Asn Asp Val Tyr Ala Ser Ala Gly Ser Ser Gly Gly
145                 150                 155                 160

Gly Gly Tyr Gly Ala Ser Ser Ala Ser Ala Ala Ser Ala Ser Ala Ala
                165                 170                 175

Ala Pro Ser Gly Val Ala Tyr Gln Ala Pro Ala Gln Ala Gln Ile Ser
            180                 185                 190

Phe Thr Leu Arg Gly Gln Gln Pro Val Ser Tyr Gly Gln Gly Gly Ala
        195                 200                 205

Ser Ala Ala Ser Gly Ala Glu Ala Gly Gln Gly Gly Ala Gly Pro Gly
```

-continued

```
    210                 215                 220

Gly Ala Gly Ala Ala Ala Ala Ala Ala Ala Ala Ala Gly Gly Ala Gly
225                 230                 235                 240

Gln Gly Gly Gln Gly
                245


<210> SEQ ID NO 27
<211> LENGTH: 955
<212> TYPE: DNA
<213> ORGANISM: Latrodectus hesperus
<220> FEATURE:
<221> NAME/KEY: CDS
<222> LOCATION: (220)..(954)

<400> SEQUENCE: 27

aaaaaaacat ccacgaacgt ttgcattcga ccttagaaaa acagatgagt aaatgaaagt      60

gaaacgtaca tacgtcaatt caactgggcg agatgaaatc gtagactgca tatttccagg     120

tatattgata cacctgctgc acatcacgaa caatcagtgt ataaaagagg agaacgatca     180

gcgtaaagta ttctcagtcg ggattttcca actactaca atg act tgg tct act       234
                                           Met Thr Trp Ser Thr
                                           1               5

cga ctt gcc tta tca ttt ctt tta gtg ctc tgc act cag agc att tat      282
Arg Leu Ala Leu Ser Phe Leu Leu Val Leu Cys Thr Gln Ser Ile Tyr
                10                  15                  20

gct ctg gcg caa gcc aac acg cca tgg tca agt aaa gcg aat gct gat      330
Ala Leu Ala Gln Ala Asn Thr Pro Trp Ser Ser Lys Ala Asn Ala Asp
            25                  30                  35

gct ttt atc aat tcc ttt att tcg gca gct tcg aat act gga tcc ttc      378
Ala Phe Ile Asn Ser Phe Ile Ser Ala Ala Ser Asn Thr Gly Ser Phe
        40                  45                  50

tcc caa gat cag atg gaa gat atg tca ttg att ggt aat aca tta atg      426
Ser Gln Asp Gln Met Glu Asp Met Ser Leu Ile Gly Asn Thr Leu Met
    55                  60                  65

gca gca atg gat aat atg ggt gga aga att acg cca tcc aaa tta cag      474
Ala Ala Met Asp Asn Met Gly Gly Arg Ile Thr Pro Ser Lys Leu Gln
70                  75                  80                  85

gct tta gat atg gct ttc gca tca tct gta gca gaa att gct gct tcg      522
Ala Leu Asp Met Ala Phe Ala Ser Ser Val Ala Glu Ile Ala Ala Ser
                90                  95                  100

gaa gga gga gac tta gga gta aca aca aat gca att gca gat gct tta      570
Glu Gly Gly Asp Leu Gly Val Thr Thr Asn Ala Ile Ala Asp Ala Leu
            105                 110                 115

aca tca gct ttc tat caa aca acc gga gta gtt aat agc aga ttt att      618
Thr Ser Ala Phe Tyr Gln Thr Thr Gly Val Val Asn Ser Arg Phe Ile
        120                 125                 130

agc gaa att aga agt ttg att ggc atg ttt gca cag gca tct gcc aac      666
Ser Glu Ile Arg Ser Leu Ile Gly Met Phe Ala Gln Ala Ser Ala Asn
    135                 140                 145

gat gta tac gcc tca gca ggt tcc agc ggt gga gga ggg tat gga gca      714
Asp Val Tyr Ala Ser Ala Gly Ser Ser Gly Gly Gly Gly Tyr Gly Ala
150                 155                 160                 165

tct tct gca agt gca gca tct gca agc gca gca gca cca tca ggt gtc      762
Ser Ser Ala Ser Ala Ala Ser Ala Ser Ala Ala Ala Pro Ser Gly Val
                170                 175                 180

gca tac caa gct cca gca caa gca caa att tcc ttc tct ttg aga gga      810
Ala Tyr Gln Ala Pro Ala Gln Ala Gln Ile Ser Phe Ser Leu Arg Gly
            185                 190                 195

caa cag cca gtt rgt tat ggt caa gga gga gct agc gca gcy tca gga      858
Gln Gln Pro Val Xaa Tyr Gly Gln Gly Gly Ala Ser Ala Ala Ser Gly
```

```
        200                 205                 210

gca gcg gct ggt caa gga ggc gca gga cca gga gga gct gga gca gca      906
Ala Ala Ala Gly Gln Gly Gly Ala Gly Pro Gly Gly Ala Gly Ala Ala
    215                 220                 225

gcg gca gcg gca gca gca gct gga gga gcr ggt caa gga gga caa ggt g    955
Ala Ala Ala Ala Ala Ala Ala Gly Gly Ala Gly Gln Gly Gly Gln Gly
230                 235                 240                 245


<210> SEQ ID NO 28
<211> LENGTH: 245
<212> TYPE: PRT
<213> ORGANISM: Latrodectus hesperus
<220> FEATURE:
<221> NAME/KEY: misc_feature
<222> LOCATION: (202)..(202)
<223> OTHER INFORMATION: The 'Xaa' at location 202 stands for Gly, or
      Ser.

<400> SEQUENCE: 28

Met Thr Trp Ser Thr Arg Leu Ala Leu Ser Phe Leu Leu Val Leu Cys
1               5                   10                  15

Thr Gln Ser Ile Tyr Ala Leu Ala Gln Ala Asn Thr Pro Trp Ser Ser
            20                  25                  30

Lys Ala Asn Ala Asp Ala Phe Ile Asn Ser Phe Ile Ser Ala Ala Ser
        35                  40                  45

Asn Thr Gly Ser Phe Ser Gln Asp Gln Met Glu Asp Met Ser Leu Ile
    50                  55                  60

Gly Asn Thr Leu Met Ala Ala Met Asp Asn Met Gly Gly Arg Ile Thr
65                  70                  75                  80

Pro Ser Lys Leu Gln Ala Leu Asp Met Ala Phe Ala Ser Ser Val Ala
                85                  90                  95

Glu Ile Ala Ala Ser Glu Gly Gly Asp Leu Gly Val Thr Thr Asn Ala
            100                 105                 110

Ile Ala Asp Ala Leu Thr Ser Ala Phe Tyr Gln Thr Thr Gly Val Val
        115                 120                 125

Asn Ser Arg Phe Ile Ser Glu Ile Arg Ser Leu Ile Gly Met Phe Ala
    130                 135                 140

Gln Ala Ser Ala Asn Asp Val Tyr Ala Ser Ala Gly Ser Ser Gly Gly
145                 150                 155                 160

Gly Gly Tyr Gly Ala Ser Ser Ala Ser Ala Ala Ser Ala Ser Ala Ala
                165                 170                 175

Ala Pro Ser Gly Val Ala Tyr Gln Ala Pro Ala Gln Ala Gln Ile Ser
            180                 185                 190

Phe Ser Leu Arg Gly Gln Gln Pro Val Xaa Tyr Gly Gln Gly Gly Ala
        195                 200                 205

Ser Ala Ala Ser Gly Ala Ala Ala Gly Gln Gly Gly Ala Gly Pro Gly
    210                 215                 220

Gly Ala Gly Ala Ala Ala Ala Ala Ala Ala Ala Ala Gly Gly Ala Gly
225                 230                 235                 240

Gln Gly Gly Gln Gly
                245


<210> SEQ ID NO 29
<211> LENGTH: 1028
<212> TYPE: DNA
<213> ORGANISM: Latrodectus hesperus
<220> FEATURE:
<221> NAME/KEY: CDS
<222> LOCATION: (220)..(1026)
```

<400> SEQUENCE: 29

```
aaaaaaacat ccacgaacgt ttgcattcga ccttagaaaa acagatgagt aaatgaaagt      60

gaaacgtaca tacgtcaatt caactgggcg agatgaaatc gtagactgca tatttccagg     120

tatattgata cacctgctgc acatcacgaa caatcagtgt ataaaagagg agaacgatca     180

gcgtaaagta ttctcagtcg ggattttcca actactaca atg act tgg tct act        234
                                          Met Thr Trp Ser Thr
                                          1               5

cga ctt gcc tta tca ttt ctt tta gtg ctc tgc act cag agc att tat       282
Arg Leu Ala Leu Ser Phe Leu Leu Val Leu Cys Thr Gln Ser Ile Tyr
                10                  15                  20

gct ctg gcg caa gcc aac acg cca tgg tca agt aaa gcg aat gct gat       330
Ala Leu Ala Gln Ala Asn Thr Pro Trp Ser Ser Lys Ala Asn Ala Asp
            25                  30                  35

gct ttt atc aat tcc ttt att tcg gca gct tcg aat act gga tcc ttc       378
Ala Phe Ile Asn Ser Phe Ile Ser Ala Ala Ser Asn Thr Gly Ser Phe
        40                  45                  50

tcc caa gat cag atg gaa gat atg tca ttg att ggt aat aca tta atg       426
Ser Gln Asp Gln Met Glu Asp Met Ser Leu Ile Gly Asn Thr Leu Met
    55                  60                  65

gca gca atg gat aat atg ggt gga aga att acg cca tcc aaa tta cag       474
Ala Ala Met Asp Asn Met Gly Gly Arg Ile Thr Pro Ser Lys Leu Gln
70                  75                  80                  85

gct tta gat atg gct ttc gca tca tct gta gca gaa att gct gct tcg       522
Ala Leu Asp Met Ala Phe Ala Ser Ser Val Ala Glu Ile Ala Ala Ser
                90                  95                  100

gaa gga gga gac tta gga gta aca aca aat gca att gca gat gct tta       570
Glu Gly Gly Asp Leu Gly Val Thr Thr Asn Ala Ile Ala Asp Ala Leu
            105                 110                 115

aca tca gct ttc tat caa aca acc gga gta gtt aat agc aga ttt att       618
Thr Ser Ala Phe Tyr Gln Thr Thr Gly Val Val Asn Ser Arg Phe Ile
        120                 125                 130

agc gaa att aga agt ttg att ggc atg ttt gca cag gca tct gcc aac       666
Ser Glu Ile Arg Ser Leu Ile Gly Met Phe Ala Gln Ala Ser Ala Asn
    135                 140                 145

gat gta tac gcc tca gca ggt tcc agc ggt gga gga ggg tat gga gca       714
Asp Val Tyr Ala Ser Ala Gly Ser Ser Gly Gly Gly Gly Tyr Gly Ala
150                 155                 160                 165

tct tct gca agy gca gca tct gca agc gca gca gca cca tca ggt gtc       762
Ser Ser Ala Xaa Ala Ala Ser Ala Ser Ala Ala Ala Pro Ser Gly Val
                170                 175                 180

gca tac caa gct cca gca caa gca caa att tcc ttc tct ttg aga gga       810
Ala Tyr Gln Ala Pro Ala Gln Ala Gln Ile Ser Phe Ser Leu Arg Gly
            185                 190                 195

caa cag cca gtt agt tat ggt caa gga gga gct agc gca gct tca gga       858
Gln Gln Pro Val Ser Tyr Gly Gln Gly Gly Ala Ser Ala Ala Ser Gly
        200                 205                 210

gca gcg gct ggt caa gga ggc gcw gga cca gga gga gct gga gca gca       906
Ala Ala Ala Gly Gln Gly Gly Ala Gly Pro Gly Gly Ala Gly Ala Ala
    215                 220                 225

gcg gca gcg gca gca gca gct gga gga gcr ggt caa gga gga caa ggt       954
Ala Ala Ala Ala Ala Ala Ala Gly Gly Ala Gly Gln Gly Gly Gln Gly
230                 235                 240                 245

gga tat gga caa gga gga tac ggt caa gga ggt gcc gga caa ggt gga      1002
Gly Tyr Gly Gln Gly Gly Tyr Gly Gln Gly Gly Ala Gly Gln Gly Gly
                250                 255                 260

tct gga gca gca gca gcg gca gca gc                                    1028
Ser Gly Ala Ala Ala Ala Ala Ala
```

265

<210> SEQ ID NO 30
<211> LENGTH: 269
<212> TYPE: PRT
<213> ORGANISM: Latrodectus hesperus
<220> FEATURE:
<221> NAME/KEY: misc_feature
<222> LOCATION: (169)..(169)
<223> OTHER INFORMATION: The 'Xaa' at location 169 stands for Ser.

<400> SEQUENCE: 30

```
Met Thr Trp Ser Thr Arg Leu Ala Leu Ser Phe Leu Leu Val Leu Cys
1               5                   10                  15

Thr Gln Ser Ile Tyr Ala Leu Ala Gln Ala Asn Thr Pro Trp Ser Ser
            20                  25                  30

Lys Ala Asn Ala Asp Ala Phe Ile Asn Ser Phe Ile Ser Ala Ala Ser
        35                  40                  45

Asn Thr Gly Ser Phe Ser Gln Asp Gln Met Glu Asp Met Ser Leu Ile
    50                  55                  60

Gly Asn Thr Leu Met Ala Ala Met Asp Asn Met Gly Gly Arg Ile Thr
65                  70                  75                  80

Pro Ser Lys Leu Gln Ala Leu Asp Met Ala Phe Ala Ser Ser Val Ala
                85                  90                  95

Glu Ile Ala Ala Ser Glu Gly Gly Asp Leu Gly Val Thr Thr Asn Ala
            100                 105                 110

Ile Ala Asp Ala Leu Thr Ser Ala Phe Tyr Gln Thr Thr Gly Val Val
        115                 120                 125

Asn Ser Arg Phe Ile Ser Glu Ile Arg Ser Leu Ile Gly Met Phe Ala
    130                 135                 140

Gln Ala Ser Ala Asn Asp Val Tyr Ala Ser Ala Gly Ser Ser Gly Gly
145                 150                 155                 160

Gly Gly Tyr Gly Ala Ser Ser Ala Xaa Ala Ala Ser Ala Ser Ala Ala
                165                 170                 175

Ala Pro Ser Gly Val Ala Tyr Gln Ala Pro Ala Gln Ala Gln Ile Ser
            180                 185                 190

Phe Ser Leu Arg Gly Gln Gln Pro Val Ser Tyr Gly Gln Gly Gly Ala
        195                 200                 205

Ser Ala Ala Ser Gly Ala Ala Ala Gly Gln Gly Gly Ala Gly Pro Gly
    210                 215                 220

Gly Ala Gly Ala Ala Ala Ala Ala Ala Ala Ala Ala Gly Gly Ala Gly
225                 230                 235                 240

Gln Gly Gly Gln Gly Gly Tyr Gly Gln Gly Gly Tyr Gly Gln Gly Gly
                245                 250                 255

Ala Gly Gln Gly Gly Ser Gly Ala Ala Ala Ala Ala Ala
            260                 265
```

<210> SEQ ID NO 31
<211> LENGTH: 403
<212> TYPE: DNA
<213> ORGANISM: Latrodectus hesperus
<220> FEATURE:
<221> NAME/KEY: CDS
<222> LOCATION: (2)..(403)
<220> FEATURE:
<221> NAME/KEY: misc_feature
<222> LOCATION: (401)..(401)
<223> OTHER INFORMATION: n is a, c, g, or t

<400> SEQUENCE: 31

```
t gca att gca gat gct tta acg tca gct ttc tat caa aca acc gga gta      49
  Ala Ile Ala Asp Ala Leu Thr Ser Ala Phe Tyr Gln Thr Thr Gly Val
  1               5                   10                  15

gtt aat agc aga ttt att agc gaa att aga agt ttg att ggc atg ttt       97
Val Asn Ser Arg Phe Ile Ser Glu Ile Arg Ser Leu Ile Gly Met Phe
            20                  25                  30

gca cag gca tct gcc aac gat gta tac gcc tca gca ggt tcc agc ggt      145
Ala Gln Ala Ser Ala Asn Asp Val Tyr Ala Ser Ala Gly Ser Ser Gly
        35                  40                  45

gga gga ggg tat gga gca tct tct gca agt gca gca tct gca agc gca      193
Gly Gly Gly Tyr Gly Ala Ser Ser Ala Ser Ala Ala Ser Ala Ser Ala
    50                  55                  60

gca gca cca tca ggt gtc gca tat caa gct cca gca caa gca caa att      241
Ala Ala Pro Ser Gly Val Ala Tyr Gln Ala Pro Ala Gln Ala Gln Ile
65                  70                  75                  80

tcc ttc act ttg aga gga caa cag cca gtt agt tat ggt caa gga ggc      289
Ser Phe Thr Leu Arg Gly Gln Gln Pro Val Ser Tyr Gly Gln Gly Gly
                85                  90                  95

gct gga cca gga gga gct gga gca gca gcg gca gcc gca gca gca gct      337
Ala Gly Pro Gly Gly Ala Gly Ala Ala Ala Ala Ala Ala Ala Ala Ala
            100                 105                 110

gga gga gca ggt caa gga gga caa ggt agg tat gga caa gga gga tac      385
Gly Gly Ala Gly Gln Gly Gly Gln Gly Arg Tyr Gly Gln Gly Gly Tyr
        115                 120                 125

ggt caa gga ggt gcc nga                                               403
Gly Gln Gly Gly Ala Xaa
    130


<210> SEQ ID NO 32
<211> LENGTH: 134
<212> TYPE: PRT
<213> ORGANISM: Latrodectus hesperus
<220> FEATURE:
<221> NAME/KEY: misc_feature
<222> LOCATION: (134)..(134)
<223> OTHER INFORMATION: The 'Xaa' at location 134 stands for Arg, or
      Gly.

<400> SEQUENCE: 32

Ala Ile Ala Asp Ala Leu Thr Ser Ala Phe Tyr Gln Thr Thr Gly Val
1               5                   10                  15

Val Asn Ser Arg Phe Ile Ser Glu Ile Arg Ser Leu Ile Gly Met Phe
            20                  25                  30

Ala Gln Ala Ser Ala Asn Asp Val Tyr Ala Ser Ala Gly Ser Ser Gly
        35                  40                  45

Gly Gly Gly Tyr Gly Ala Ser Ser Ala Ser Ala Ala Ser Ala Ser Ala
    50                  55                  60

Ala Ala Pro Ser Gly Val Ala Tyr Gln Ala Pro Ala Gln Ala Gln Ile
65                  70                  75                  80

Ser Phe Thr Leu Arg Gly Gln Gln Pro Val Ser Tyr Gly Gln Gly Gly
                85                  90                  95

Ala Gly Pro Gly Gly Ala Gly Ala Ala Ala Ala Ala Ala Ala Ala Ala
            100                 105                 110

Gly Gly Ala Gly Gln Gly Gly Gln Gly Arg Tyr Gly Gln Gly Gly Tyr
        115                 120                 125

Gly Gln Gly Gly Ala Xaa
    130


<210> SEQ ID NO 33
```

```
<211> LENGTH: 680
<212> TYPE: DNA
<213> ORGANISM: Latrodectus hesperus
<220> FEATURE:
<221> NAME/KEY: CDS
<222> LOCATION: (3)..(680)

<400> SEQUENCE: 33

tt tcc tcc tca aag cta cra gcc ttg gat atg gcc ttt gca tca tct        47
   Ser Ser Ser Lys Leu Xaa Ala Leu Asp Met Ala Phe Ala Ser Ser
   1               5                   10                  15

gta gca gaa atc gct act gca gaa gga ggw gcc aac ata aat gmc att       95
Val Ala Glu Ile Ala Thr Ala Glu Gly Xaa Ala Asn Ile Asn Xaa Ile
                20                  25                  30

aca gat gca att cga tat gct ttg caa aac gca ttt tat caa aca aca      143
Thr Asp Ala Ile Arg Tyr Ala Leu Gln Asn Ala Phe Tyr Gln Thr Thr
            35                  40                  45

gga gcg gtt aat tcc aaa ttt att aat gaa att tca aat tta ata tat      191
Gly Ala Val Asn Ser Lys Phe Ile Asn Glu Ile Ser Asn Leu Ile Tyr
        50                  55                  60

atg ttc gct caa aca aac ata aat gat gtc aat ggg gga gga gga tac      239
Met Phe Ala Gln Thr Asn Ile Asn Asp Val Asn Gly Gly Gly Gly Tyr
    65                  70                  75

ggt caa gga ggt gca gga caa ggt gga gcc gca gca gca gca gct ggt      287
Gly Gln Gly Gly Ala Gly Gln Gly Gly Ala Ala Ala Ala Ala Ala Gly
80                  85                  90                  95

gga gca gga caa gga gga tat ggc aga ggt gga gcc gga caa ggt gga      335
Gly Ala Gly Gln Gly Gly Tyr Gly Arg Gly Gly Ala Gly Gln Gly Gly
                100                 105                 110

gca gca gca gcc gct gga gct ggt caa ggt ggt tat gga gat caa ggt      383
Ala Ala Ala Ala Ala Gly Ala Gly Gln Gly Gly Tyr Gly Asp Gln Gly
            115                 120                 125

gcc gga caa ggk gga gct gga gcc gca gcg gca gca gma act gca tct      431
Ala Gly Gln Xaa Gly Ala Gly Ala Ala Ala Ala Ala Xaa Thr Ala Ser
        130                 135                 140

ggt gga gcc gga caa gga gga tat ggc cga ggt gga gca gga caa ggt      479
Gly Gly Ala Gly Gln Gly Gly Tyr Gly Arg Gly Gly Ala Gly Gln Gly
    145                 150                 155

gga gca gca gca gcc gct gct rca gcc gca gga gct ggt caa ggt ggt      527
Gly Ala Ala Ala Ala Ala Ala Xaa Ala Ala Gly Ala Gly Gln Gly Gly
160                 165                 170                 175

tat gga gga caa ggg gcc gca caa ggt gga gct gga gct gca gcc gca      575
Tyr Gly Gly Gln Gly Ala Ala Gln Gly Gly Ala Gly Ala Ala Ala Ala
                180                 185                 190

gca gca gca gcc gga ggt gca ggt cta gga gga cta ggt gga tac gga      623
Ala Ala Ala Ala Gly Gly Ala Gly Leu Gly Gly Leu Gly Gly Tyr Gly
            195                 200                 205

caa ggt gga tct gga gca gca gca gca gcy gga gga gca ggt caa gga      671
Gln Gly Gly Ser Gly Ala Ala Ala Ala Ala Gly Gly Ala Gly Gln Gly
        210                 215                 220

gga caa ggt                                                          680
Gly Gln Gly
    225


<210> SEQ ID NO 34
<211> LENGTH: 226
<212> TYPE: PRT
<213> ORGANISM: Latrodectus hesperus
<220> FEATURE:
<221> NAME/KEY: misc_feature
<222> LOCATION: (6)..(6)
<223> OTHER INFORMATION: The 'Xaa' at location 6 stands for Arg, or Gln.
<220> FEATURE:
```

<221> NAME/KEY: misc_feature
<222> LOCATION: (25)..(25)
<223> OTHER INFORMATION: The 'Xaa' at location 25 stands for Gly.
<220> FEATURE:
<221> NAME/KEY: misc_feature
<222> LOCATION: (30)..(30)
<223> OTHER INFORMATION: The 'Xaa' at location 30 stands for Asp, or Ala.
<220> FEATURE:
<221> NAME/KEY: misc_feature
<222> LOCATION: (131)..(131)
<223> OTHER INFORMATION: The 'Xaa' at location 131 stands for Gly.
<220> FEATURE:
<221> NAME/KEY: misc_feature
<222> LOCATION: (140)..(140)
<223> OTHER INFORMATION: The 'Xaa' at location 140 stands for Glu, or Ala.
<220> FEATURE:
<221> NAME/KEY: misc_feature
<222> LOCATION: (167)..(167)
<223> OTHER INFORMATION: The 'Xaa' at location 167 stands for Ala, or Thr.

<400> SEQUENCE: 34

```
Ser Ser Ser Lys Leu Xaa Ala Leu Asp Met Ala Phe Ala Ser Ser Val
1               5                   10                  15

Ala Glu Ile Ala Thr Ala Glu Gly Xaa Ala Asn Ile Asn Xaa Ile Thr
            20                  25                  30

Asp Ala Ile Arg Tyr Ala Leu Gln Asn Ala Phe Tyr Gln Thr Thr Gly
        35                  40                  45

Ala Val Asn Ser Lys Phe Ile Asn Glu Ile Ser Asn Leu Ile Tyr Met
    50                  55                  60

Phe Ala Gln Thr Asn Ile Asn Asp Val Asn Gly Gly Gly Gly Tyr Gly
65                  70                  75                  80

Gln Gly Gly Ala Gly Gln Gly Gly Ala Ala Ala Ala Ala Ala Gly Gly
                85                  90                  95

Ala Gly Gln Gly Gly Tyr Gly Arg Gly Gly Ala Gly Gln Gly Gly Ala
            100                 105                 110

Ala Ala Ala Ala Gly Ala Gly Gln Gly Gly Tyr Gly Asp Gln Gly Ala
        115                 120                 125

Gly Gln Xaa Gly Ala Gly Ala Ala Ala Ala Ala Xaa Thr Ala Ser Gly
    130                 135                 140

Gly Ala Gly Gln Gly Gly Tyr Gly Arg Gly Gly Ala Gly Gln Gly Gly
145                 150                 155                 160

Ala Ala Ala Ala Ala Ala Xaa Ala Ala Gly Ala Gly Gln Gly Gly Tyr
                165                 170                 175

Gly Gly Gln Gly Ala Ala Gln Gly Gly Ala Gly Ala Ala Ala Ala Ala
            180                 185                 190

Ala Ala Ala Gly Gly Ala Gly Leu Gly Gly Leu Gly Gly Tyr Gly Gln
        195                 200                 205

Gly Gly Ser Gly Ala Ala Ala Ala Ala Gly Gly Ala Gly Gln Gly Gly
    210                 215                 220

Gln Gly
225
```

<210> SEQ ID NO 35
<211> LENGTH: 273
<212> TYPE: DNA
<213> ORGANISM: Latrodectus hesperus
<220> FEATURE:
<221> NAME/KEY: CDS
<222> LOCATION: (3)..(272)

```
<400> SEQUENCE: 35

ca tca gca gca gga cca agt gga cca gga gga tca ggt gcc gca gca        47
   Ser Ala Ala Gly Pro Ser Gly Pro Gly Gly Ser Gly Ala Ala Ala
   1               5                   10                  15

gcg gct gcc gca ggt gga tct ggc cct gga ggt ttt ggt caa gga cca       95
Ala Ala Ala Ala Gly Gly Ser Gly Pro Gly Gly Phe Gly Gln Gly Pro
                20                  25                  30

rca ggt tat ggt ccc tca gga cct ggt gga caa caa gra tac ggg cca      143
Xaa Gly Tyr Gly Pro Ser Gly Pro Gly Gly Gln Gln Xaa Tyr Gly Pro
            35                  40                  45

ggt gca tca ggt gct gca gcg gca gca gca gct agt gga tca ggt gga      191
Gly Ala Ser Gly Ala Ala Ala Ala Ala Ala Ala Ser Gly Ser Gly Gly
        50                  55                  60

tat ggt cct tca caa tat gtt cct agc tct gtt gct tct agt rct gca      239
Tyr Gly Pro Ser Gln Tyr Val Pro Ser Ser Val Ala Ser Ser Xaa Ala
    65                  70                  75

tca gca gcc tca gct tta tct tcc ccg aca acg c                        273
Ser Ala Ala Ser Ala Leu Ser Ser Pro Thr Thr
80                  85                  90


<210> SEQ ID NO 36
<211> LENGTH: 90
<212> TYPE: PRT
<213> ORGANISM: Latrodectus hesperus
<220> FEATURE:
<221> NAME/KEY: misc_feature
<222> LOCATION: (32)..(32)
<223> OTHER INFORMATION: The 'Xaa' at location 32 stands for Ala, or
      Thr.
<220> FEATURE:
<221> NAME/KEY: misc_feature
<222> LOCATION: (44)..(44)
<223> OTHER INFORMATION: The 'Xaa' at location 44 stands for Gly, or
      Glu.
<220> FEATURE:
<221> NAME/KEY: misc_feature
<222> LOCATION: (78)..(78)
<223> OTHER INFORMATION: The 'Xaa' at location 78 stands for Ala, or
      Thr.

<400> SEQUENCE: 36

Ser Ala Ala Gly Pro Ser Gly Pro Gly Gly Ser Gly Ala Ala Ala Ala
1               5                   10                  15

Ala Ala Ala Gly Gly Ser Gly Pro Gly Gly Phe Gly Gln Gly Pro Xaa
            20                  25                  30

Gly Tyr Gly Pro Ser Gly Pro Gly Gly Gln Gln Xaa Tyr Gly Pro Gly
        35                  40                  45

Ala Ser Gly Ala Ala Ala Ala Ala Ala Ala Ser Gly Ser Gly Gly Tyr
    50                  55                  60

Gly Pro Ser Gln Tyr Val Pro Ser Ser Val Ala Ser Ser Xaa Ala Ser
65                  70                  75                  80

Ala Ala Ser Ala Leu Ser Ser Pro Thr Thr
                85                  90


<210> SEQ ID NO 37
<211> LENGTH: 765
<212> TYPE: DNA
<213> ORGANISM: Latrodectus geometricus
<220> FEATURE:
<221> NAME/KEY: CDS
<222> LOCATION: (20)..(763)

<400> SEQUENCE: 37

ggattttcca actactaca atg act tgg tct act cga ctt gcc tta tca gta      52
```

```
                    Met Thr Trp Ser Thr Arg Leu Ala Leu Ser Val
                    1               5                   10

ctt tta gtg ctc tgc act cag agc att tat gct ctg gcg caa gcc aac      100
Leu Leu Val Leu Cys Thr Gln Ser Ile Tyr Ala Leu Ala Gln Ala Asn
            15                  20                  25

acg cca tgg tca agt aaa gca aat gca gat gct ttt atc aat tcc ttt      148
Thr Pro Trp Ser Ser Lys Ala Asn Ala Asp Ala Phe Ile Asn Ser Phe
        30                  35                  40

att tca tct gct caa aat act gga tca ttt tca caa gat cag atg gac      196
Ile Ser Ser Ala Gln Asn Thr Gly Ser Phe Ser Gln Asp Gln Met Asp
    45                  50                  55

gat atg tca ttg att ggt aac aca tta atg aca gca atg gat aat atg      244
Asp Met Ser Leu Ile Gly Asn Thr Leu Met Thr Ala Met Asp Asn Met
60                  65                  70                  75

ggt gga aga att acg cct tcc aaa ttg caa gct tta gat atg gct ttc      292
Gly Gly Arg Ile Thr Pro Ser Lys Leu Gln Ala Leu Asp Met Ala Phe
                80                  85                  90

gca tca tct gta gca gaa atc gct gct tcg gaa gga gga gat tta gga      340
Ala Ser Ser Val Ala Glu Ile Ala Ala Ser Glu Gly Gly Asp Leu Gly
            95                  100                 105

gta aca aca aat gcc att gca gat gct ttg aca tca gct ttc tat caa      388
Val Thr Thr Asn Ala Ile Ala Asp Ala Leu Thr Ser Ala Phe Tyr Gln
        110                 115                 120

aca acc ggg gtt gtt aat aac aga ttt atc agc gaa att cga agt ttg      436
Thr Thr Gly Val Val Asn Asn Arg Phe Ile Ser Glu Ile Arg Ser Leu
    125                 130                 135

att agt atg ttt gcc cag gca tcc gca aat gat gta tac gcc tct gct      484
Ile Ser Met Phe Ala Gln Ala Ser Ala Asn Asp Val Tyr Ala Ser Ala
140                 145                 150                 155

gga tca agt ggt gga gga gga tac ggc gca gct tca tca tct gca agt      532
Gly Ser Ser Gly Gly Gly Gly Tyr Gly Ala Ala Ser Ser Ser Ala Ser
                160                 165                 170

gca gca gcg cca tca ggt gtc aca tat caa gct cca tca caa gcc caa      580
Ala Ala Ala Pro Ser Gly Val Thr Tyr Gln Ala Pro Ser Gln Ala Gln
            175                 180                 185

ata agc ttc tct atg aga gga caa caa cca gtt aat tat ggt caa tca      628
Ile Ser Phe Ser Met Arg Gly Gln Gln Pro Val Asn Tyr Gly Gln Ser
        190                 195                 200

gga act agt gct gca tca gca gca gca gca gct gga gga gct ggt caa      676
Gly Thr Ser Ala Ala Ser Ala Ala Ala Ala Ala Gly Gly Ala Gly Gln
    205                 210                 215

gca gga tat ggc caa gga gga caa gga caa ggt gca gca gca gca gcc      724
Ala Gly Tyr Gly Gln Gly Gly Gln Gly Gln Gly Ala Ala Ala Ala Ala
220                 225                 230                 235

gct gcc tca gca gct gga ggt gca ggt caa gga gga caa gg               765
Ala Ala Ser Ala Ala Gly Gly Ala Gly Gln Gly Gly Gln
                240                 245
```

<210> SEQ ID NO 38
<211> LENGTH: 248
<212> TYPE: PRT
<213> ORGANISM: Latrodectus geometricus

<400> SEQUENCE: 38

```
Met Thr Trp Ser Thr Arg Leu Ala Leu Ser Val Leu Leu Val Leu Cys
1               5                   10                  15

Thr Gln Ser Ile Tyr Ala Leu Ala Gln Ala Asn Thr Pro Trp Ser Ser
            20                  25                  30

Lys Ala Asn Ala Asp Ala Phe Ile Asn Ser Phe Ile Ser Ser Ala Gln
        35                  40                  45
```

```
Asn Thr Gly Ser Phe Ser Gln Asp Gln Met Asp Asp Met Ser Leu Ile
    50                  55                  60

Gly Asn Thr Leu Met Thr Ala Met Asp Asn Met Gly Gly Arg Ile Thr
65                  70                  75                  80

Pro Ser Lys Leu Gln Ala Leu Asp Met Ala Phe Ala Ser Ser Val Ala
                85                  90                  95

Glu Ile Ala Ala Ser Glu Gly Gly Asp Leu Gly Val Thr Thr Asn Ala
            100                 105                 110

Ile Ala Asp Ala Leu Thr Ser Ala Phe Tyr Gln Thr Thr Gly Val Val
        115                 120                 125

Asn Asn Arg Phe Ile Ser Glu Ile Arg Ser Leu Ile Ser Met Phe Ala
    130                 135                 140

Gln Ala Ser Ala Asn Asp Val Tyr Ala Ser Ala Gly Ser Ser Gly Gly
145                 150                 155                 160

Gly Gly Tyr Gly Ala Ala Ser Ser Ser Ala Ser Ala Ala Ala Pro Ser
                165                 170                 175

Gly Val Thr Tyr Gln Ala Pro Ser Gln Ala Gln Ile Ser Phe Ser Met
            180                 185                 190

Arg Gly Gln Gln Pro Val Asn Tyr Gly Gln Ser Gly Thr Ser Ala Ala
        195                 200                 205

Ser Ala Ala Ala Ala Ala Gly Gly Ala Gly Gln Ala Gly Tyr Gly Gln
    210                 215                 220

Gly Gly Gln Gly Gln Gly Ala Ala Ala Ala Ala Ala Ala Ser Ala Ala
225                 230                 235                 240

Gly Gly Ala Gly Gln Gly Gly Gln
                245


<210> SEQ ID NO 39
<211> LENGTH: 759
<212> TYPE: DNA
<213> ORGANISM: Latrodectus geometricus
<220> FEATURE:
<221> NAME/KEY: CDS
<222> LOCATION: (20)..(757)

<400> SEQUENCE: 39

ggattttcca actactaca atg act tgg tct act cga ctt gcc tta tca gta      52
                     Met Thr Trp Ser Thr Arg Leu Ala Leu Ser Val
                     1               5                   10

ctt tta gtg ctc tgc act cag agc att tat gct ctg gcg caa gcc aac      100
Leu Leu Val Leu Cys Thr Gln Ser Ile Tyr Ala Leu Ala Gln Ala Asn
            15                  20                  25

acg cca tgg tca agt aaa gca aat gca gat gct ttt atc aat tcc ttt      148
Thr Pro Trp Ser Ser Lys Ala Asn Ala Asp Ala Phe Ile Asn Ser Phe
        30                  35                  40

att tca tct gct caa aat act gga tca ttt tca caa gat cag atg gac      196
Ile Ser Ser Ala Gln Asn Thr Gly Ser Phe Ser Gln Asp Gln Met Asp
    45                  50                  55

gat atg tca ttg att ggt aac aca tta atg aca gca atg gat aat atg      244
Asp Met Ser Leu Ile Gly Asn Thr Leu Met Thr Ala Met Asp Asn Met
60                  65                  70                  75

ggt gga aga att acg cct tcc aaa ttg caa gct tta gat atg gct ttc      292
Gly Gly Arg Ile Thr Pro Ser Lys Leu Gln Ala Leu Asp Met Ala Phe
                80                  85                  90

gca tca tct gta gca gaa atc gct gct tcg gaa gga gga gat tta gga      340
Ala Ser Ser Val Ala Glu Ile Ala Ala Ser Glu Gly Gly Asp Leu Gly
            95                  100                 105
```

```
gta aca aca aat gcc att gca gat gct ttg aca tca gct ttc tat caa      388
Val Thr Thr Asn Ala Ile Ala Asp Ala Leu Thr Ser Ala Phe Tyr Gln
        110                 115                 120

aca acc ggg gtt gtt aat aac aga ttt atc agc gaa att cga agt ttg      436
Thr Thr Gly Val Val Asn Asn Arg Phe Ile Ser Glu Ile Arg Ser Leu
    125                 130                 135

att agt atg ttt gcc cag gca tcc gca aat gat gta tac gcc tct gct      484
Ile Ser Met Phe Ala Gln Ala Ser Ala Asn Asp Val Tyr Ala Ser Ala
140                 145                 150                 155

gga tca agt ggt gga gga gga tac ggc gca gct tca tca tct gca agt      532
Gly Ser Ser Gly Gly Gly Gly Tyr Gly Ala Ala Ser Ser Ser Ala Ser
                160                 165                 170

gca gca gcg cca tca ggt gtc aca tat caa gct cca tca caa gcc caa      580
Ala Ala Ala Pro Ser Gly Val Thr Tyr Gln Ala Pro Ser Gln Ala Gln
            175                 180                 185

ata agc ttc tct atg aga gga caa caa cca aat aat tat ggt caa tca      628
Ile Ser Phe Ser Met Arg Gly Gln Gln Pro Asn Asn Tyr Gly Gln Ser
        190                 195                 200

gga gct agt gct gga tca gca gca gct gga gga gct ggt caa gca gga      676
Gly Ala Ser Ala Gly Ser Ala Ala Ala Gly Gly Ala Gly Gln Ala Gly
    205                 210                 215

tat ggc caa aga gga caa gga caa ggt gca gca gca gca gcc gct gcc      724
Tyr Gly Gln Arg Gly Gln Gly Gln Gly Ala Ala Ala Ala Ala Ala Ala
220                 225                 230                 235

tca gca gct gga ggt gca ggt caa gga gga caa gg                       759
Ser Ala Ala Gly Gly Ala Gly Gln Gly Gly Gln
                240                 245


<210> SEQ ID NO 40
<211> LENGTH: 246
<212> TYPE: PRT
<213> ORGANISM: Latrodectus geometricus

<400> SEQUENCE: 40

Met Thr Trp Ser Thr Arg Leu Ala Leu Ser Val Leu Leu Val Leu Cys
1               5                   10                  15

Thr Gln Ser Ile Tyr Ala Leu Ala Gln Ala Asn Thr Pro Trp Ser Ser
            20                  25                  30

Lys Ala Asn Ala Asp Ala Phe Ile Asn Ser Phe Ile Ser Ser Ala Gln
        35                  40                  45

Asn Thr Gly Ser Phe Ser Gln Asp Gln Met Asp Asp Met Ser Leu Ile
    50                  55                  60

Gly Asn Thr Leu Met Thr Ala Met Asp Asn Met Gly Gly Arg Ile Thr
65                  70                  75                  80

Pro Ser Lys Leu Gln Ala Leu Asp Met Ala Phe Ala Ser Ser Val Ala
                85                  90                  95

Glu Ile Ala Ala Ser Glu Gly Gly Asp Leu Gly Val Thr Thr Asn Ala
            100                 105                 110

Ile Ala Asp Ala Leu Thr Ser Ala Phe Tyr Gln Thr Thr Gly Val Val
        115                 120                 125

Asn Asn Arg Phe Ile Ser Glu Ile Arg Ser Leu Ile Ser Met Phe Ala
    130                 135                 140

Gln Ala Ser Ala Asn Asp Val Tyr Ala Ser Ala Gly Ser Ser Gly Gly
145                 150                 155                 160

Gly Gly Tyr Gly Ala Ala Ser Ser Ser Ala Ser Ala Ala Ala Pro Ser
                165                 170                 175

Gly Val Thr Tyr Gln Ala Pro Ser Gln Ala Gln Ile Ser Phe Ser Met
            180                 185                 190
```

```
Arg Gly Gln Gln Pro Asn Asn Tyr Gly Gln Ser Gly Ala Ser Ala Gly
        195                 200                 205

Ser Ala Ala Ala Gly Gly Ala Gly Gln Ala Gly Tyr Gly Gln Arg Gly
    210                 215                 220

Gln Gly Gln Gly Ala Ala Ala Ala Ala Ala Ala Ser Ala Ala Gly Gly
225                 230                 235                 240

Ala Gly Gln Gly Gly Gln
                245


<210> SEQ ID NO 41
<211> LENGTH: 876
<212> TYPE: DNA
<213> ORGANISM: Latrodectus geometricus
<220> FEATURE:
<221> NAME/KEY: CDS
<222> LOCATION: (20)..(874)

<400> SEQUENCE: 41

ggattttcca actactaca atg act tgg tct act cga ctt gcc tta tca ttt      52
                     Met Thr Trp Ser Thr Arg Leu Ala Leu Ser Phe
                     1               5                   10

ctt tta gtg ctc tgc act cag agc att tat gct ctg gcg caa gcc aac      100
Leu Leu Val Leu Cys Thr Gln Ser Ile Tyr Ala Leu Ala Gln Ala Asn
            15                  20                  25

acg cca tgg tca agt aaa gcg aat gct gat gct ttt atc ggt tct ttt      148
Thr Pro Trp Ser Ser Lys Ala Asn Ala Asp Ala Phe Ile Gly Ser Phe
        30                  35                  40

att tcg tct gct caa aat aca gga gca ttt tca aca gat cag atg gac      196
Ile Ser Ser Ala Gln Asn Thr Gly Ala Phe Ser Thr Asp Gln Met Asp
    45                  50                  55

gat atg tct ttg att ggc aac aca tta atg gca gca atg gat aat atg      244
Asp Met Ser Leu Ile Gly Asn Thr Leu Met Ala Ala Met Asp Asn Met
60                  65                  70                  75

ggt gga aga att acg cct tcc aaa ttg caa gct tta gat atg gct ttc      292
Gly Gly Arg Ile Thr Pro Ser Lys Leu Gln Ala Leu Asp Met Ala Phe
                80                  85                  90

gca tca tct gta gca gaa atc gct gct gca gaa gga gga gat tta gga      340
Ala Ser Ser Val Ala Glu Ile Ala Ala Ala Glu Gly Gly Asp Leu Gly
            95                  100                 105

gta aca aca aat gcc ata gca gat gct tta aca tca gct ttc tat caa      388
Val Thr Thr Asn Ala Ile Ala Asp Ala Leu Thr Ser Ala Phe Tyr Gln
        110                 115                 120

aca acc gga gtt gtt aat agc aga ttt att agc gaa att cga agt ttg      436
Thr Thr Gly Val Val Asn Ser Arg Phe Ile Ser Glu Ile Arg Ser Leu
    125                 130                 135

att aat atg ttt gca cag gca tct gca aat gat gta tac gcc tca gct      484
Ile Asn Met Phe Ala Gln Ala Ser Ala Asn Asp Val Tyr Ala Ser Ala
140                 145                 150                 155

gga tca agt ggt gga gga gga tac gga gca gct tca tcg tct gca agt      532
Gly Ser Ser Gly Gly Gly Gly Tyr Gly Ala Ala Ser Ser Ser Ala Ser
                160                 165                 170

gca gca gct tca tca tct gca agt gca gca gca cca tca ggt gtc tca      580
Ala Ala Ala Ser Ser Ser Ala Ser Ala Ala Ala Pro Ser Gly Val Ser
            175                 180                 185

tat caa gct cca gca caa gca caa ata agc ttc tca ttg aca cga caa      628
Tyr Gln Ala Pro Ala Gln Ala Gln Ile Ser Phe Ser Leu Thr Arg Gln
        190                 195                 200

caa caa cca gtt aat tat ggt caa tca gga gct agc gct gca tca gca      676
Gln Gln Pro Val Asn Tyr Gly Gln Ser Gly Ala Ser Ala Ala Ser Ala
    205                 210                 215
```

```
gcg gca gct gga gga gca ggt caa gga ggc tat gga caa gga gga gct      724
Ala Ala Ala Gly Gly Ala Gly Gln Gly Gly Tyr Gly Gln Gly Gly Ala
220                 225                 230                 235

gga caa ggt gga gca gga gca gca gcc gcc gca gca gca gct gga gga      772
Gly Gln Gly Gly Ala Gly Ala Ala Ala Ala Ala Ala Ala Ala Gly Gly
            240                 245                 250

gca ggt caa gga gga caa ggt ggt tac gga caa gga ggt gcc gga caa      820
Ala Gly Gln Gly Gly Gln Gly Gly Tyr Gly Gln Gly Gly Ala Gly Gln
            255                 260                 265

ggt gga gca gca gca gct gca gca gca gct ggt gga gca ggt caa gga      868
Gly Gly Ala Ala Ala Ala Ala Ala Ala Ala Gly Gly Ala Gly Gln Gly
        270                 275                 280

gga caa gg                                                            876
Gly Gln
    285


<210> SEQ ID NO 42
<211> LENGTH: 285
<212> TYPE: PRT
<213> ORGANISM: Latrodectus geometricus

<400> SEQUENCE: 42

Met Thr Trp Ser Thr Arg Leu Ala Leu Ser Phe Leu Leu Val Leu Cys
1               5                   10                  15

Thr Gln Ser Ile Tyr Ala Leu Ala Gln Ala Asn Thr Pro Trp Ser Ser
            20                  25                  30

Lys Ala Asn Ala Asp Ala Phe Ile Gly Ser Phe Ile Ser Ser Ala Gln
        35                  40                  45

Asn Thr Gly Ala Phe Ser Thr Asp Gln Met Asp Asp Met Ser Leu Ile
    50                  55                  60

Gly Asn Thr Leu Met Ala Ala Met Asp Asn Met Gly Gly Arg Ile Thr
65                  70                  75                  80

Pro Ser Lys Leu Gln Ala Leu Asp Met Ala Phe Ala Ser Ser Val Ala
                85                  90                  95

Glu Ile Ala Ala Ala Glu Gly Gly Asp Leu Gly Val Thr Thr Asn Ala
            100                 105                 110

Ile Ala Asp Ala Leu Thr Ser Ala Phe Tyr Gln Thr Thr Gly Val Val
        115                 120                 125

Asn Ser Arg Phe Ile Ser Glu Ile Arg Ser Leu Ile Asn Met Phe Ala
    130                 135                 140

Gln Ala Ser Ala Asn Asp Val Tyr Ala Ser Ala Gly Ser Ser Gly Gly
145                 150                 155                 160

Gly Gly Tyr Gly Ala Ala Ser Ser Ser Ala Ser Ala Ala Ala Ser Ser
                165                 170                 175

Ser Ala Ser Ala Ala Ala Pro Ser Gly Val Ser Tyr Gln Ala Pro Ala
            180                 185                 190

Gln Ala Gln Ile Ser Phe Ser Leu Thr Arg Gln Gln Gln Pro Val Asn
        195                 200                 205

Tyr Gly Gln Ser Gly Ala Ser Ala Ala Ser Ala Ala Ala Gly Gly
    210                 215                 220

Ala Gly Gln Gly Gly Tyr Gly Gln Gly Gly Ala Gly Gln Gly Gly Ala
225                 230                 235                 240

Gly Ala Ala Ala Ala Ala Ala Ala Ala Gly Gly Ala Gly Gln Gly Gly
                245                 250                 255

Gln Gly Gly Tyr Gly Gln Gly Gly Ala Gly Gln Gly Gly Ala Ala Ala
            260                 265                 270
```

```
Ala Ala Ala Ala Ala Gly Gly Ala Gly Gln Gly Gly Gln
        275                 280                 285


<210> SEQ ID NO 43
<211> LENGTH: 876
<212> TYPE: DNA
<213> ORGANISM: Latrodectus geometricus
<220> FEATURE:
<221> NAME/KEY: CDS
<222> LOCATION: (20)..(874)

<400> SEQUENCE: 43

ggattttcca actactaca atg act tgg tct act cga ctt gcc tta tca ttt      52
                     Met Thr Trp Ser Thr Arg Leu Ala Leu Ser Phe
                     1               5                   10

ctt tta gtg ctc tgc act cag agc att tat gct ctg gcg caa gcc aac      100
Leu Leu Val Leu Cys Thr Gln Ser Ile Tyr Ala Leu Ala Gln Ala Asn
            15                  20                  25

acg cca tgg tca agt aaa gcg aat gct gat gct ttt atc ggt tcc ttt      148
Thr Pro Trp Ser Ser Lys Ala Asn Ala Asp Ala Phe Ile Gly Ser Phe
        30                  35                  40

att tcg tct gct caa aat aca gga gca ttt tca aca gat cag atg gac      196
Ile Ser Ser Ala Gln Asn Thr Gly Ala Phe Ser Thr Asp Gln Met Asp
    45                  50                  55

gat atg tct ttg att ggc aac aca tta atg gca gca atg gat aat atg      244
Asp Met Ser Leu Ile Gly Asn Thr Leu Met Ala Ala Met Asp Asn Met
60                  65                  70                  75

ggt gga aga att acg cct tcc aaa ttg caa gct tta gat atg gct ttc      292
Gly Gly Arg Ile Thr Pro Ser Lys Leu Gln Ala Leu Asp Met Ala Phe
                80                  85                  90

gca tca tct gta gca gaa atc gct gct gca gaa gga gga gat tta gga      340
Ala Ser Ser Val Ala Glu Ile Ala Ala Ala Glu Gly Gly Asp Leu Gly
            95                  100                 105

gta aca aca aat gcc ata gca gat gct tta aca tca gct ttc tat caa      388
Val Thr Thr Asn Ala Ile Ala Asp Ala Leu Thr Ser Ala Phe Tyr Gln
        110                 115                 120

aca acc gga gtt gtt aat agc aga ttt att agc gaa att cga agt ttg      436
Thr Thr Gly Val Val Asn Ser Arg Phe Ile Ser Glu Ile Arg Ser Leu
    125                 130                 135

att aat atg ttt gca cag gca tct gca aat gat gta tac gcc tca gct      484
Ile Asn Met Phe Ala Gln Ala Ser Ala Asn Asp Val Tyr Ala Ser Ala
140                 145                 150                 155

gga tca agt ggt gga gga gga tac gga gca gct tca tcg tct gca agt      532
Gly Ser Ser Gly Gly Gly Gly Tyr Gly Ala Ala Ser Ser Ser Ala Ser
                160                 165                 170

gca gca gct tca tca tct gca agt gca gca gca cca tca ggt gtc tca      580
Ala Ala Ala Ser Ser Ser Ala Ser Ala Ala Ala Pro Ser Gly Val Ser
            175                 180                 185

tat caa gct cca gca caa gca caa ata agc ttc tca ttg aca cga caa      628
Tyr Gln Ala Pro Ala Gln Ala Gln Ile Ser Phe Ser Leu Thr Arg Gln
        190                 195                 200

caa caa cca gtt aat tat ggt caa tca gga gct agc gct gca tca gca      676
Gln Gln Pro Val Asn Tyr Gly Gln Ser Gly Ala Ser Ala Ala Ser Ala
    205                 210                 215

gcg gca gct gga gga gca ggt caa gga ggc tat gga caa gga gga gct      724
Ala Ala Ala Gly Gly Ala Gly Gln Gly Gly Tyr Gly Gln Gly Gly Ala
220                 225                 230                 235

gga caa ggt gga gca gga gca gca gcc gcc gca gca gca gct gga gga      772
Gly Gln Gly Gly Ala Gly Ala Ala Ala Ala Ala Ala Ala Ala Gly Gly
                240                 245                 250
```

-continued

```
gca ggt caa gga gga caa ggt ggt tac gga caa gga ggt gcc gga caa      820
Ala Gly Gln Gly Gly Gln Gly Gly Tyr Gly Gln Gly Gly Ala Gly Gln
            255                 260                 265

ggt gga gca gca gca gct gca gca gca gct ggt gga gca ggt caa gga      868
Gly Gly Ala Ala Ala Ala Ala Ala Ala Ala Gly Gly Ala Gly Gln Gly
        270                 275                 280

gga caa gg                                                           876
Gly Gln
    285


<210> SEQ ID NO 44
<211> LENGTH: 285
<212> TYPE: PRT
<213> ORGANISM: Latrodectus geometricus

<400> SEQUENCE: 44

Met Thr Trp Ser Thr Arg Leu Ala Leu Ser Phe Leu Leu Val Leu Cys
1               5                   10                  15

Thr Gln Ser Ile Tyr Ala Leu Ala Gln Ala Asn Thr Pro Trp Ser Ser
            20                  25                  30

Lys Ala Asn Ala Asp Ala Phe Ile Gly Ser Phe Ile Ser Ser Ala Gln
        35                  40                  45

Asn Thr Gly Ala Phe Ser Thr Asp Gln Met Asp Asp Met Ser Leu Ile
    50                  55                  60

Gly Asn Thr Leu Met Ala Ala Met Asp Asn Met Gly Gly Arg Ile Thr
65                  70                  75                  80

Pro Ser Lys Leu Gln Ala Leu Asp Met Ala Phe Ala Ser Ser Val Ala
                85                  90                  95

Glu Ile Ala Ala Ala Glu Gly Gly Asp Leu Gly Val Thr Thr Asn Ala
            100                 105                 110

Ile Ala Asp Ala Leu Thr Ser Ala Phe Tyr Gln Thr Thr Gly Val Val
        115                 120                 125

Asn Ser Arg Phe Ile Ser Glu Ile Arg Ser Leu Ile Asn Met Phe Ala
    130                 135                 140

Gln Ala Ser Ala Asn Asp Val Tyr Ala Ser Ala Gly Ser Ser Gly Gly
145                 150                 155                 160

Gly Gly Tyr Gly Ala Ala Ser Ser Ser Ala Ser Ala Ala Ala Ser Ser
                165                 170                 175

Ser Ala Ser Ala Ala Ala Pro Ser Gly Val Ser Tyr Gln Ala Pro Ala
            180                 185                 190

Gln Ala Gln Ile Ser Phe Ser Leu Thr Arg Gln Gln Gln Pro Val Asn
        195                 200                 205

Tyr Gly Gln Ser Gly Ala Ser Ala Ala Ser Ala Ala Ala Ala Gly Gly
    210                 215                 220

Ala Gly Gln Gly Gly Tyr Gly Gln Gly Gly Ala Gly Gln Gly Gly Ala
225                 230                 235                 240

Gly Ala Ala Ala Ala Ala Ala Ala Ala Gly Gly Ala Gly Gln Gly Gly
                245                 250                 255

Gln Gly Gly Tyr Gly Gln Gly Gly Ala Gly Gln Gly Gly Ala Ala Ala
            260                 265                 270

Ala Ala Ala Ala Ala Gly Gly Ala Gly Gln Gly Gly Gln
        275                 280                 285


<210> SEQ ID NO 45
<211> LENGTH: 1164
<212> TYPE: DNA
<213> ORGANISM: Latrodectus geometricus
```

```
<220> FEATURE:
<221> NAME/KEY: CDS
<222> LOCATION: (1)..(1164)

<400> SEQUENCE: 45

ctc cgg tgg tct agt aaa gat aat gct gat aga ttt ata aac gca ttt      48
Leu Arg Trp Ser Ser Lys Asp Asn Ala Asp Arg Phe Ile Asn Ala Phe
1               5                   10                  15

ttg caa gct gct tca aac agt ggc gcc ttc tcc tca gat cag gtt gac      96
Leu Gln Ala Ala Ser Asn Ser Gly Ala Phe Ser Ser Asp Gln Val Asp
            20                  25                  30

gac atg tcg gtt att ggt aat aca tta atg act gca atg gac aac atg     144
Asp Met Ser Val Ile Gly Asn Thr Leu Met Thr Ala Met Asp Asn Met
        35                  40                  45

ggt gga aga att aca ccg tcc aaa ttg cag gct tta gat atg gct ttc     192
Gly Gly Arg Ile Thr Pro Ser Lys Leu Gln Ala Leu Asp Met Ala Phe
    50                  55                  60

gca tca tct gtt gca gaa ata gct gta gct gat ggc caa aat gtt gga     240
Ala Ser Ser Val Ala Glu Ile Ala Val Ala Asp Gly Gln Asn Val Gly
65                  70                  75                  80

ggg gcg aca aat gca att tca aat gca tta cgg tca gcc ttc tat caa     288
Gly Ala Thr Asn Ala Ile Ser Asn Ala Leu Arg Ser Ala Phe Tyr Gln
                85                  90                  95

aca aca gga gtg gtt aac aat caa ttt att tca gaa atc agt aat cta     336
Thr Thr Gly Val Val Asn Asn Gln Phe Ile Ser Glu Ile Ser Asn Leu
            100                 105                 110

att aat atg ttt gca caa gta tca gcc aat gaa gtt tct tat gca tca     384
Ile Asn Met Phe Ala Gln Val Ser Ala Asn Glu Val Ser Tyr Ala Ser
        115                 120                 125

ggt gga tca tct agc gcc gca gct tca gca gct gcc tca gca gga cca     432
Gly Gly Ser Ser Ser Ala Ala Ala Ser Ala Ala Ala Ser Ala Gly Pro
    130                 135                 140

gcg gca caa caa gtg tat gca cca agc gca gga gct cca gca gcc gca     480
Ala Ala Gln Gln Val Tyr Ala Pro Ser Ala Gly Ala Pro Ala Ala Ala
145                 150                 155                 160

aca gca agc tct gga cca ggc gca tat ggc cca agt gca cct gga gga     528
Thr Ala Ser Ser Gly Pro Gly Ala Tyr Gly Pro Ser Ala Pro Gly Gly
                165                 170                 175

cct agt gca gct gct gct gca gct gcg tct ggt gga gcc gga cca gga     576
Pro Ser Ala Ala Ala Ala Ala Ala Ala Ser Gly Gly Ala Gly Pro Gly
            180                 185                 190

aga caa cag tca tat gga cca gga gga tca gga gcc gcg gca gca gca     624
Arg Gln Gln Ser Tyr Gly Pro Gly Gly Ser Gly Ala Ala Ala Ala Ala
        195                 200                 205

gcc gcc act gga gga tct ggt cca gga gga tac gga caa gga cca gcc     672
Ala Ala Thr Gly Gly Ser Gly Pro Gly Gly Tyr Gly Gln Gly Pro Ala
    210                 215                 220

agt tac gcc cca tca gga cct ggt gga caa caa ggc tat gga cca gga     720
Ser Tyr Ala Pro Ser Gly Pro Gly Gly Gln Gln Gly Tyr Gly Pro Gly
225                 230                 235                 240

gga tca gga gca gca tct gca gca gcc gca gca gca agt tct gga cct     768
Gly Ser Gly Ala Ala Ser Ala Ala Ala Ala Ala Ala Ser Ser Gly Pro
                245                 250                 255

gga gga tat gga cca gga gca tca ggc cca gga agt tat ggt cca agt     816
Gly Gly Tyr Gly Pro Gly Ala Ser Gly Pro Gly Ser Tyr Gly Pro Ser
            260                 265                 270

gga cct gga gga tct ggt gca gct gcc gca gcc gct gct gct agt gca     864
Gly Pro Gly Gly Ser Gly Ala Ala Ala Ala Ala Ala Ala Ala Ser Ala
        275                 280                 285

cca gga gga caa caa gga tac gga cca ggt gga tct ggt gca gct gca     912
```

-continued

```
Pro Gly Gly Gln Gln Gly Tyr Gly Pro Gly Gly Ser Gly Ala Ala Ala
    290                 295                 300

gca gct gcg gct ggc gga gca ggt cct gga agc caa caa gca tat gga      960
Ala Ala Ala Ala Gly Gly Ala Gly Pro Gly Ser Gln Gln Ala Tyr Gly
305                 310                 315                 320

cca gga gga tca gga gcc gca gca gca gct gca gcc gga cca gga tct     1008
Pro Gly Gly Ser Gly Ala Ala Ala Ala Ala Ala Ala Gly Pro Gly Ser
                325                 330                 335

gga ggc caa caa gga tac gga cca gga gga tct gct gca gcc gca gca     1056
Gly Gly Gln Gln Gly Tyr Gly Pro Gly Gly Ser Ala Ala Ala Ala Ala
            340                 345                 350

gcc gcc gcc gct gga gga tct ggc cca gga gga tac gga caa gga cca     1104
Ala Ala Ala Ala Gly Gly Ser Gly Pro Gly Gly Tyr Gly Gln Gly Pro
        355                 360                 365

gcc ggt tac ggc cca tct gga cct ggt gca caa caa ggt tac gga cca     1152
Ala Gly Tyr Gly Pro Ser Gly Pro Gly Ala Gln Gln Gly Tyr Gly Pro
    370                 375                 380

gga ggc cca gga                                                     1164
Gly Gly Pro Gly
385


<210> SEQ ID NO 46
<211> LENGTH: 388
<212> TYPE: PRT
<213> ORGANISM: Latrodectus geometricus

<400> SEQUENCE: 46

Leu Arg Trp Ser Ser Lys Asp Asn Ala Asp Arg Phe Ile Asn Ala Phe
1               5                   10                  15

Leu Gln Ala Ala Ser Asn Ser Gly Ala Phe Ser Ser Asp Gln Val Asp
            20                  25                  30

Asp Met Ser Val Ile Gly Asn Thr Leu Met Thr Ala Met Asp Asn Met
        35                  40                  45

Gly Gly Arg Ile Thr Pro Ser Lys Leu Gln Ala Leu Asp Met Ala Phe
    50                  55                  60

Ala Ser Ser Val Ala Glu Ile Ala Val Ala Asp Gly Gln Asn Val Gly
65                  70                  75                  80

Gly Ala Thr Asn Ala Ile Ser Asn Ala Leu Arg Ser Ala Phe Tyr Gln
                85                  90                  95

Thr Thr Gly Val Val Asn Asn Gln Phe Ile Ser Glu Ile Ser Asn Leu
            100                 105                 110

Ile Asn Met Phe Ala Gln Val Ser Ala Asn Glu Val Ser Tyr Ala Ser
        115                 120                 125

Gly Gly Ser Ser Ser Ala Ala Ala Ser Ala Ala Ala Ser Ala Gly Pro
    130                 135                 140

Ala Ala Gln Gln Val Tyr Ala Pro Ser Ala Gly Ala Pro Ala Ala Ala
145                 150                 155                 160

Thr Ala Ser Ser Gly Pro Gly Ala Tyr Gly Pro Ser Ala Pro Gly Gly
                165                 170                 175

Pro Ser Ala Ala Ala Ala Ala Ala Ala Ser Gly Gly Ala Gly Pro Gly
            180                 185                 190

Arg Gln Gln Ser Tyr Gly Pro Gly Gly Ser Gly Ala Ala Ala Ala Ala
        195                 200                 205

Ala Ala Thr Gly Gly Ser Gly Pro Gly Gly Tyr Gly Gln Gly Pro Ala
    210                 215                 220

Ser Tyr Ala Pro Ser Gly Pro Gly Gly Gln Gln Gly Tyr Gly Pro Gly
225                 230                 235                 240
```

```
Gly Ser Gly Ala Ala Ser Ala Ala Ala Ala Ala Ala Ser Ser Gly Pro
                245                 250                 255

Gly Gly Tyr Gly Pro Gly Ala Ser Gly Pro Gly Ser Tyr Gly Pro Ser
            260                 265                 270

Gly Pro Gly Gly Ser Gly Ala Ala Ala Ala Ala Ala Ala Ala Ser Ala
        275                 280                 285

Pro Gly Gly Gln Gln Gly Tyr Gly Pro Gly Gly Ser Gly Ala Ala Ala
    290                 295                 300

Ala Ala Ala Ala Gly Gly Ala Gly Pro Gly Ser Gln Gln Ala Tyr Gly
305                 310                 315                 320

Pro Gly Gly Ser Gly Ala Ala Ala Ala Ala Ala Ala Gly Pro Gly Ser
                325                 330                 335

Gly Gly Gln Gln Gly Tyr Gly Pro Gly Gly Ser Ala Ala Ala Ala Ala
            340                 345                 350

Ala Ala Ala Ala Gly Gly Ser Gly Pro Gly Gly Tyr Gly Gln Gly Pro
        355                 360                 365

Ala Gly Tyr Gly Pro Ser Gly Pro Gly Ala Gln Gln Gly Tyr Gly Pro
    370                 375                 380

Gly Gly Pro Gly
385


<210> SEQ ID NO 47
<211> LENGTH: 569
<212> TYPE: DNA
<213> ORGANISM: Latrodectus geometricus
<220> FEATURE:
<221> NAME/KEY: CDS
<222> LOCATION: (2)..(568)

<400> SEQUENCE: 47

t atc att cct cgt gtg ctt tgc act caa ggt ctg tat gtt ctg gga caa      49
  Ile Ile Pro Arg Val Leu Cys Thr Gln Gly Leu Tyr Val Leu Gly Gln
  1               5                   10                  15

gca aac act cca tgg tct agt aag caa aat gct gac gct ttt ata agt       97
Ala Asn Thr Pro Trp Ser Ser Lys Gln Asn Ala Asp Ala Phe Ile Ser
            20                  25                  30

gca ttc atg act gct gct tca caa agt gga gca ttt tca tcg gat cag      145
Ala Phe Met Thr Ala Ala Ser Gln Ser Gly Ala Phe Ser Ser Asp Gln
        35                  40                  45

atc gat gac atg tct gtc atc agc aat aca tta atg gca gca atg gat      193
Ile Asp Asp Met Ser Val Ile Ser Asn Thr Leu Met Ala Ala Met Asp
    50                  55                  60

aat atg gga gga aga att aca ccc tcc aaa tta caa gcc tta gat atg      241
Asn Met Gly Gly Arg Ile Thr Pro Ser Lys Leu Gln Ala Leu Asp Met
65                  70                  75                  80

gct ttc gca tca tct gtg gca gaa att gct gct gtg gaa ggt caa aat      289
Ala Phe Ala Ser Ser Val Ala Glu Ile Ala Ala Val Glu Gly Gln Asn
                85                  90                  95

ata ggg gta act aca aat gca att tca gac gcc ttg aca tca gct ttc      337
Ile Gly Val Thr Thr Asn Ala Ile Ser Asp Ala Leu Thr Ser Ala Phe
            100                 105                 110

tat caa aca aca ggg gta gtt aat aac aaa ttt atc agc gaa att aga      385
Tyr Gln Thr Thr Gly Val Val Asn Asn Lys Phe Ile Ser Glu Ile Arg
        115                 120                 125

agt ttg att aat atg ttt gca caa gcg tct gca aat gat gtt tat tcc      433
Ser Leu Ile Asn Met Phe Ala Gln Ala Ser Ala Asn Asp Val Tyr Ser
    130                 135                 140

tca gct ggt gca agt agt gga tcg aaa ggt tat gga tca gtt tca tca      481
```

Ser Ala Gly Ala Ser Ser Gly Ser Lys Gly Tyr Gly Ser Val Ser Ser
145 150 155 160 tcc gta agt gct gca caa caa tca ggt atg ata tat caa gct cca gca 529
Ser Val Ser Ala Ala Gln Gln Ser Gly Met Ile Tyr Gln Ala Pro Ala
165 170 175 aaa gca caa gta acc ttc tct atg aca cga caa cag caa c 569
Lys Ala Gln Val Thr Phe Ser Met Thr Arg Gln Gln Gln
180 185

<210> SEQ ID NO 48
<211> LENGTH: 189
<212> TYPE: PRT
<213> ORGANISM: Latrodectus geometricus

<400> SEQUENCE: 48

Ile Ile Pro Arg Val Leu Cys Thr Gln Gly Leu Tyr Val Leu Gly Gln
1 5 10 15

Ala Asn Thr Pro Trp Ser Ser Lys Gln Asn Ala Asp Ala Phe Ile Ser
20 25 30

Ala Phe Met Thr Ala Ala Ser Gln Ser Gly Ala Phe Ser Ser Asp Gln
35 40 45

Ile Asp Asp Met Ser Val Ile Ser Asn Thr Leu Met Ala Ala Met Asp
50 55 60

Asn Met Gly Gly Arg Ile Thr Pro Ser Lys Leu Gln Ala Leu Asp Met
65 70 75 80

Ala Phe Ala Ser Ser Val Ala Glu Ile Ala Ala Val Glu Gly Gln Asn
85 90 95

Ile Gly Val Thr Thr Asn Ala Ile Ser Asp Ala Leu Thr Ser Ala Phe
100 105 110

Tyr Gln Thr Thr Gly Val Val Asn Asn Lys Phe Ile Ser Glu Ile Arg
115 120 125

Ser Leu Ile Asn Met Phe Ala Gln Ala Ser Ala Asn Asp Val Tyr Ser
130 135 140

Ser Ala Gly Ala Ser Ser Gly Ser Lys Gly Tyr Gly Ser Val Ser Ser
145 150 155 160

Ser Val Ser Ala Ala Gln Gln Ser Gly Met Ile Tyr Gln Ala Pro Ala
165 170 175

Lys Ala Gln Val Thr Phe Ser Met Thr Arg Gln Gln Gln
180 185

<210> SEQ ID NO 49
<211> LENGTH: 13421
<212> TYPE: DNA
<213> ORGANISM: Latrodectus hesperus
<220> FEATURE:
<221> NAME/KEY: CDS
<222> LOCATION: (4675)..(11238)

<400> SEQUENCE: 49
ataaaatatc aataactggt tgggaaataa aattaacacc tgcctttgct ataaaatgtt 60
caatatttga tgacgtcgca ataaaattaa gtgtgtctga ttacaatatt tcattttaaa 120
ttaaaatttg aacacataaa ttattcttta aaacaatata ttataatgaa atatctaatc 180
taaaaaataa agcatatgaa aacatttgtc atttattatc cttaatacca ggattaaatg 240
aaaaaattaa tacatacatt tcagcttaaa taataaatga ttaatatgtt agagtagttg 300
aaataagaaa ttaataaaca ttttaaaatt taagtatata caaatgaagt aagcacagat 360
aagcgcctat gtttaagatt cacatataaa attcctatgt aagttaaatt aaataacatt 420

```
acttaatatg tgtaccacac tcaaactttt gtttgaatta aaataacaaa tatagtgttt    480
agaagaaaaa gaaaatcaaa ttcacaatag aaacatcaaa gtaaaataac ttaaacagaa    540
ttaatatatc acaatatttt gtattccttt taatatcgac gttttgaatt caaagtaaat    600
tgattgtttt ttgttattta ttaagcactg tgatgcataa aacacatcat gtatgaatat    660
aatactataa atttaatggc tgtaatgtat tttgaaaaaa gtatttaatt aataaaataa    720
gacacttgaa aaaagtaggt ataaattcat taatgcattc aatttctata attatcaaat    780
gcaaaaaaaa aaaaacatta cattatacgt ttagttttta gcaaaaaaaa aacatgttta    840
aaaactaaga aaagtataaa ttaaattcat tgaaaaatat gttttttagt tctatactaa    900
ttttaacgca atatttggat atttctgtta catagcaatt ttgacgtaat ataaggatgc    960
acaaatttgc attctaactg aaattatatt agattataat agtttaaaac tgaatattat   1020
acaaagtgtt cataaaaacg cgatagaaat tatttaaagt ttttgatttg aaatgtatcg   1080
ataaatataa ttttttcata ttgtaatagc tgatatactg atagttgaag tggatgtttg   1140
actagtaact ataaacaata aaaagaaaca acaagctata tggattcatt gatcttggag   1200
aaagaattat ttatcgctag aggaaatttt gtgaaaaaac caaaaaatgt cacagtttga   1260
caagcaggtt gttcgaaaaa aaaggacacc tagtgaagtg gaaatcggcc aatatttgat   1320
catatattct ttaatggtat ggtgacagaa gtgaaacatt gagaacccta gaatgacttt   1380
agtcctaaag ttcagaatga aatgctggta ttgattcctg ctgaatgatt ttcgttatca   1440
ttgacatcgt gacattgttt ccccaattca atggaaaact tgaaatcggt catcagaagt   1500
tagaattatg tatttgattc caattcactc caggacatcg taactgaatt ttgctgacca   1560
ttgctgaccc aaattcgttg aaaaacttga aataggtcat cagaagaggg cattatgtac   1620
tccatgacat cacaattgaa ttccaaaaca ggatttatag cataatcgtc ggcagcgtct   1680
gacatttcga gcctgttata tattaaatgc cgtttgtatc tttattcaaa taaaaataat   1740
taaaaaataa aaataatgaa ttttttatga aagcaagaca ttaattttaa gatttaaaag   1800
ggataattta caaatattgc aattattaat ttaaaattct attaattaat gaaattttta   1860
aaaaatttaa ttagtccttg acgatttaaa ctaacccata aagtggatgt tttgtcttgt   1920
cttttccatt ttgctttttc ttctgttcta ttgtcaacga gtaaaattat tgaatcaatg   1980
gaaaacggct actcaaaccg atgctttggt ctttatataa gaaatcgttt tataagcaaa   2040
atgaacttcg acactattct cagacattcg atggtgaact tcgccttgtt tgctgccgtt   2100
cgaagaatgc aattagaaga cagacagcaa attcgtcgac acgtcggatt tacgacgcca   2160
tctcaatacg atgtcgtact taattatata tgtgggacat agatgaaatg ttatctgacg   2220
tcatggatat tttaaaccaa tgagaattgt gataaaggga tataaacata tgttctcaat   2280
tggaacgaaa ggaactacta cgttatggtt aaaaaatgtt ctcgcatgtt ttcttttttt   2340
tttaccgcaa tgatcgttta cgttctgcca tgcttttgga tcactcagta atatcactct   2400
ataataggag gttgtgaagt tattaataaa tgtgaagagt gtcatcaatt tattctaatc   2460
caaattatac aatactacat ccaaattatg tgcgcgtaaa taaaatcctt taaaaagata   2520
tcaattaaat aatctttaaa aaaggaaaaa agtatgaaat ttcaatttta aatcgattaa   2580
aatttagttc cactattctc tctctctctc tcacacacac acaggagtgt aaaactaatt   2640
acttgataat taactctttg aatgtaatgt tagaaatcaa tgcgaacatt gcataaaatg   2700
taaaattgat cttcacccaa tatgagcata cccatttgta taaaattcga aatataatta   2760
```

-continued

```
tgccacacca gtttaaataa aataagttaa ctaaaattag ttattaaata taattaataa   2820

ataaaattta atatataaat aaagacgaaa aatttttaat ttgtaactat gaaataaatg   2880

acttatgtgg gcccatagat tattaaaata taaaaaatat ttgtgcgcaa aaaatcgagt   2940

taaatataga gaagaacagt atttaatgca ttttaacccc aatcagccat tacttaaaag   3000

agatttcaaa attttgattg cttaagaggt atattatgaa aacttctaca tagttaaatt   3060

aattatataa attttaaatt tatgcgactg catattttct aaattaaaat taatttaact   3120

gtattcaata actgaaagca atttaaaaat tctttttaat atttttgatg atatttcata   3180

gttttaaatt atagatataa tttaacaaat agggtgtaga aatttgatgg tcaaagtttt   3240

ggaattgaac aggaatttgg acgatttcca aactatagca cagaataata ttgtattgtt   3300

tatcgaaatg ctaaataatg atttatctta acaaaagagg ttattaaaaa tatttatagc   3360

caaaaattta atcttgcagt gttgccataa aatataatat tcctcttttt gaagactgta   3420

attgagaaaa tataaactca ttccaattaa ttcagcaata aaggtgctat tcagagtgga   3480

atgtgccagg ttcgtacctt acagctattg aacaatggga gacagaaatt aagttttcca   3540

tttctgtttg gaactgctgc ttaagtaaga aacttttact gcagctctaa ctttttatac   3600

gacccactag gaatagttga tatctcttta ttattttttg cataactact tagaaataag   3660

agattattct tttaatactt cttttattaa tagaaatata aaattatata aaaaaaactt   3720

tactcttatc aaaaatttcg gttccgcttg gaaacttcat gcatacattt taagaaaaat   3780

aataaaattt cttgattttt tgcgcgaaat aataattgaa atatgtctgt tttgctcaag   3840

ccataaatga atgaaattgt agagtgtaaa ttgggaaaat aagaaaaatc cgctttttca   3900

attcgaaata catatatgct tatgcatttc gcgaataaga gaatatatat agaaaacttc   3960

aatttggtaa tagacaagta atttattttt ttagaaaatg gataaaaatt aaaaatgcaa   4020

gatactttgg gaatacgtgg catttttaag agttattata tatattcctc attttctaat   4080

gagtgaaaat tgttaattat aaaccaaata gaaaaaatgc ttaaaaattc taatttatta   4140

ttgttttatt acataaatat ggtaattctt ttacacaaaa cttgattttt gaatatttaa   4200

aaaaatttta ttattaactg aaagaagaaa tttcaattgt aacattataa ttattcctta   4260

gtatagactg ctattgtata aggacaaaaa aagaaaaaaa ataattccac ataatctaaa   4320

agaatataac aaaatacgtc aaaaataatt aaaggaataa ttaaataata attatgtatg   4380

ataacaaaaa attaatatta tcttagaata attaaaaaaa ttaaaaatct gaattctaaa   4440

tttgacggaa tacttggtga tgtgacgtat atcaatttaa tacccagcag actaaaatga   4500

taagatgaga atataaaatt ccaccaataa aaaagaagct tatgaatatg aaacagcagg   4560

tgatatttac tcataaaatc acttcttgtc acgtttctaa gagagcagtc acgaaaaaag   4620

gagtataaaa gatggtcgta ttcctccaac aaatcactcg attgagttga agta atg     4677
                                                            Met
                                                            1

att aca gca atc atg cat att cca gct cag tta tct tta ctc ttc ctt     4725
Ile Thr Ala Ile Met His Ile Pro Ala Gln Leu Ser Leu Leu Phe Leu
            5                   10                  15

ctt ctg tgc gcc cag agc ttc gtc tct tta gat gcc gcc agt gtc tgg     4773
Leu Leu Cys Ala Gln Ser Phe Val Ser Leu Asp Ala Ala Ser Val Trp
        20                  25                  30

gac agc aca gca aca gct gaa gct ttt att gga agc ttc aat tct ggc     4821
Asp Ser Thr Ala Thr Ala Glu Ala Phe Ile Gly Ser Phe Asn Ser Gly
    35                  40                  45

atg gaa aga tgt gga gtg ttg tca cgg tct cag atg gat gat atc tca     4869
```

-continued

```
Met Glu Arg Cys Gly Val Leu Ser Arg Ser Gln Met Asp Asp Ile Ser
50                  55                  60                  65

tcc att agc gac acc ata ata tct gcc att gaa aga aac cca aac aac      4917
Ser Ile Ser Asp Thr Ile Ile Ser Ala Ile Glu Arg Asn Pro Asn Asn
                70                  75                  80

tcc aaa tcg aaa ttg caa gct tta aac atg gct ttt gca tca tca gtt      4965
Ser Lys Ser Lys Leu Gln Ala Leu Asn Met Ala Phe Ala Ser Ser Val
            85                  90                  95

tcg gaa att gcg ttc tct gag aac aat gga att tca aac agt gct aaa      5013
Ser Glu Ile Ala Phe Ser Glu Asn Asn Gly Ile Ser Asn Ser Ala Lys
        100                 105                 110

ata caa gcc att att gat gca ctc aga gga gca ttt ctt caa act att      5061
Ile Gln Ala Ile Ile Asp Ala Leu Arg Gly Ala Phe Leu Gln Thr Ile
    115                 120                 125

gga acg gta gat caa acc ttt ttg aat gaa att tct agt ctc gtt aaa      5109
Gly Thr Val Asp Gln Thr Phe Leu Asn Glu Ile Ser Ser Leu Val Lys
130                 135                 140                 145

atg ttt tca cag gtt tca gca gaa aat gca gtt tca aca agt gct gga      5157
Met Phe Ser Gln Val Ser Ala Glu Asn Ala Val Ser Thr Ser Ala Gly
                150                 155                 160

gca gca gct act tcc att gga agc agt ggt ggt ggt tac gga cag caa      5205
Ala Ala Ala Thr Ser Ile Gly Ser Ser Gly Gly Gly Tyr Gly Gln Gln
            165                 170                 175

agt ggt ggg tac agt caa ggt tca gct gcg tca gcc tca tct tca gca      5253
Ser Gly Gly Tyr Ser Gln Gly Ser Ala Ala Ser Ala Ser Ser Ser Ala
        180                 185                 190

gga gaa aga acc tct gca ggc act act gga tat tct gct ggt tca aca      5301
Gly Glu Arg Thr Ser Ala Gly Thr Thr Gly Tyr Ser Ala Gly Ser Thr
    195                 200                 205

caa gtc tct tcc act gta tct tct aca agc caa gca gcg caa tca gca      5349
Gln Val Ser Ser Thr Val Ser Ser Thr Ser Gln Ala Ala Gln Ser Ala
210                 215                 220                 225

acc gca acc agt caa tat ggc caa gca caa agt gcc gga tca tat agt      5397
Thr Ala Thr Ser Gln Tyr Gly Gln Ala Gln Ser Ala Gly Ser Tyr Ser
                230                 235                 240

aac gcg gct gca gga gct aca ggt gct tat gca gga gga tac ggt cag      5445
Asn Ala Ala Ala Gly Ala Thr Gly Ala Tyr Ala Gly Gly Tyr Gly Gln
            245                 250                 255

ggt agt agt gct gca gca ggt gct gga gca gga gga tat aac cag ggc      5493
Gly Ser Ser Ala Ala Ala Gly Ala Gly Ala Gly Gly Tyr Asn Gln Gly
        260                 265                 270

gca gga agc tat gga caa ggt gct ggt gct gca gca aga acg gct gct      5541
Ala Gly Ser Tyr Gly Gln Gly Ala Gly Ala Ala Ala Arg Thr Ala Ala
    275                 280                 285

ggt gca gga gca gga gga tat ggt caa ggt gct gga ggc tac gga caa      5589
Gly Ala Gly Ala Gly Gly Tyr Gly Gln Gly Ala Gly Gly Tyr Gly Gln
290                 295                 300                 305

ggt gct ggt gct gca gct ggt gcg gct gct gga gca gga gca gga gga      5637
Gly Ala Gly Ala Ala Ala Gly Ala Ala Ala Gly Ala Gly Ala Gly Gly
                310                 315                 320

tat gga cga ggt gct ggt tct gca gca ggt gcg gct gct ggt gca gga      5685
Tyr Gly Arg Gly Ala Gly Ser Ala Ala Gly Ala Ala Ala Gly Ala Gly
            325                 330                 335

gta gga gaa tat ggc caa ggt gct gga ggc tac gga caa ggt gct ggt      5733
Val Gly Glu Tyr Gly Gln Gly Ala Gly Gly Tyr Gly Gln Gly Ala Gly
        340                 345                 350

gct gca gca ggt gca gct gct ggt gca gga gct gga gga tat ggt caa      5781
Ala Ala Ala Gly Ala Ala Ala Gly Ala Gly Ala Gly Gly Tyr Gly Gln
    355                 360                 365
```

-continued

```
ggt gct gga gga tac gga caa ggt gct gga gga tac gga caa ggt gct      5829
Gly Ala Gly Gly Tyr Gly Gln Gly Ala Gly Gly Tyr Gly Gln Gly Ala
370                 375                 380                 385

ggt gct gca gca ggt gca gga gcc gga agt tat ggt caa ggt gct gga      5877
Gly Ala Ala Ala Gly Ala Gly Ala Gly Ser Tyr Gly Gln Gly Ala Gly
                390                 395                 400

ggc tac gga caa ggt gct ggc gct gca gca gga gca gca gct ggt gca      5925
Gly Tyr Gly Gln Gly Ala Gly Ala Ala Ala Gly Ala Ala Ala Gly Ala
            405                 410                 415

gga gca gga gga tat ggt caa ggt gct gga ggc tac gga caa ggt gct      5973
Gly Ala Gly Gly Tyr Gly Gln Gly Ala Gly Gly Tyr Gly Gln Gly Ala
        420                 425                 430

ggt gct gca gca ggt gca gct gct ggt gca gga gcc gga gga tat ggt      6021
Gly Ala Ala Ala Gly Ala Ala Ala Gly Ala Gly Ala Gly Gly Tyr Gly
    435                 440                 445

caa ggt gct gga gga tac gga caa ggt gct ggt gct gca gct ggt gca      6069
Gln Gly Ala Gly Gly Tyr Gly Gln Gly Ala Gly Ala Ala Ala Gly Ala
450                 455                 460                 465

gga gca gga gga tat gga cga ggt gct ggt tct gca gca ggt gcg gct      6117
Gly Ala Gly Gly Tyr Gly Arg Gly Ala Gly Ser Ala Ala Gly Ala Ala
                470                 475                 480

gct ggt tca gga gca gga gga tat gga caa gga gct gga ggc tat gga      6165
Ala Gly Ser Gly Ala Gly Gly Tyr Gly Gln Gly Ala Gly Gly Tyr Gly
            485                 490                 495

caa gga gct ggt gct ggt gca gga gga tat ggt caa ggt gct ggt gct      6213
Gln Gly Ala Gly Ala Gly Ala Gly Gly Tyr Gly Gln Gly Ala Gly Ala
        500                 505                 510

tca aca ggt gca gca gct gga gca ggg gca ggt gga tat ggc caa ggt      6261
Ser Thr Gly Ala Ala Ala Gly Ala Gly Ala Gly Gly Tyr Gly Gln Gly
    515                 520                 525

gct ggg ggc tac gga caa ggt tct ggt gct gca gct gga gca gga gga      6309
Ala Gly Gly Tyr Gly Gln Gly Ser Gly Ala Ala Ala Gly Ala Gly Gly
530                 535                 540                 545

tat ggt caa gga tct caa ggc tac gaa caa ggt gct gct gca acc tca      6357
Tyr Gly Gln Gly Ser Gln Gly Tyr Glu Gln Gly Ala Ala Ala Thr Ser
                550                 555                 560

tcg gct gca gca ggg gca tct tca act ggt tat aca gaa aga caa aat      6405
Ser Ala Ala Ala Gly Ala Ser Ser Thr Gly Tyr Thr Glu Arg Gln Asn
            565                 570                 575

gaa gtt gtc act aca gtt act act aca cgt caa gaa ata gca gat cga      6453
Glu Val Val Thr Thr Val Thr Thr Thr Arg Gln Glu Ile Ala Asp Arg
        580                 585                 590

aga cag gca gca agc gcc tca ggt gca gta tca act tca gct gca gct      6501
Arg Gln Ala Ala Ser Ala Ser Gly Ala Val Ser Thr Ser Ala Ala Ala
    595                 600                 605

ggc tac ggc caa ggt gct gga aca gga gct gga gga tac ggt caa ggc      6549
Gly Tyr Gly Gln Gly Ala Gly Thr Gly Ala Gly Gly Tyr Gly Gln Gly
610                 615                 620                 625

gct ggt ggc tat gga caa aga gct ggt gct gca gca gga gga tac ggt      6597
Ala Gly Gly Tyr Gly Gln Arg Ala Gly Ala Ala Ala Gly Gly Tyr Gly
                630                 635                 640

caa ggg tct ggt ggc tat gga caa ggg gtt ggt gct gca gct agt gta      6645
Gln Gly Ser Gly Gly Tyr Gly Gln Gly Val Gly Ala Ala Ala Ser Val
            645                 650                 655

gct gct gga gga gct gga gca gga gga tac ggt tta ggt gct ggt ggc      6693
Ala Ala Gly Gly Ala Gly Ala Gly Gly Tyr Gly Leu Gly Ala Gly Gly
        660                 665                 670

tat gga aga ggt gct ggt gct gca gca gga gga tac ggt caa ggc gct      6741
Tyr Gly Arg Gly Ala Gly Ala Ala Ala Gly Gly Tyr Gly Gln Gly Ala
    675                 680                 685
```

```
ggt ggc tat gga caa ggt gct ggt gct gca gcg gga gca gga gca gga     6789
Gly Gly Tyr Gly Gln Gly Ala Gly Ala Ala Ala Gly Ala Gly Ala Gly
690                 695                 700                 705

gga tac gat caa ggc gct ggt ggc tat gga caa ggt gct ggt gct gca     6837
Gly Tyr Asp Gln Gly Ala Gly Gly Tyr Gly Gln Gly Ala Gly Ala Ala
                710                 715                 720

gct agt gta gct gct gga gga gct gga tca gga gga tac ggt cta ggt     6885
Ala Ser Val Ala Ala Gly Gly Ala Gly Ser Gly Gly Tyr Gly Leu Gly
            725                 730                 735

gct ggc att gga gca ggt gca gct gca ata gct gga gga tac gga caa     6933
Ala Gly Ile Gly Ala Gly Ala Ala Ala Ile Ala Gly Gly Tyr Gly Gln
        740                 745                 750

ggt gct ggt gct gca gca ggt gca gct gct ggt gca gga gcc gga agt     6981
Gly Ala Gly Ala Ala Ala Gly Ala Ala Ala Gly Ala Gly Ala Gly Ser
    755                 760                 765

tat ggt caa ggt gct gga ggc tac gga caa ggt gct ggc gct gca gca     7029
Tyr Gly Gln Gly Ala Gly Gly Tyr Gly Gln Gly Ala Gly Ala Ala Ala
770                 775                 780                 785

gga gca gca gct ggt gca gga gca gga gga tat ggt caa ggt gct gga     7077
Gly Ala Ala Ala Gly Ala Gly Ala Gly Gly Tyr Gly Gln Gly Ala Gly
                790                 795                 800

ggc tac gga caa ggt gct ggt gct gca gca ggt gca gct gct ggt gca     7125
Gly Tyr Gly Gln Gly Ala Gly Ala Ala Ala Gly Ala Ala Ala Gly Ala
            805                 810                 815

gga gcc gga gga tat ggt caa ggt gct gga ggc tac gga caa ggt gct     7173
Gly Ala Gly Gly Tyr Gly Gln Gly Ala Gly Gly Tyr Gly Gln Gly Ala
        820                 825                 830

ggt gca gga gca gga gga tat ggt caa ggt gct gga ggc tac gga caa     7221
Gly Ala Gly Ala Gly Gly Tyr Gly Gln Gly Ala Gly Gly Tyr Gly Gln
    835                 840                 845

ggt gct ggt gct gca gca ggt gca gct gct ggt gca gga gcc gga gga     7269
Gly Ala Gly Ala Ala Ala Gly Ala Ala Ala Gly Ala Gly Ala Gly Gly
850                 855                 860                 865

tat ggt caa ggt gct gga gga tac gga caa ggt gct ggt gca gga gca     7317
Tyr Gly Gln Gly Ala Gly Gly Tyr Gly Gln Gly Ala Gly Ala Gly Ala
                870                 875                 880

gga gga tat gga cga ggt gct ggt tct gca gca ggt gcg gct gct ggt     7365
Gly Gly Tyr Gly Arg Gly Ala Gly Ser Ala Ala Gly Ala Ala Ala Gly
            885                 890                 895

tca gga gca gga gga tat gga caa gga gct gga ggc tat gga caa gga     7413
Ser Gly Ala Gly Gly Tyr Gly Gln Gly Ala Gly Gly Tyr Gly Gln Gly
        900                 905                 910

gct ggt gct ggt gca gga gga tat ggt caa ggt gct ggt gct tca aca     7461
Ala Gly Ala Gly Ala Gly Gly Tyr Gly Gln Gly Ala Gly Ala Ser Thr
    915                 920                 925

ggt gca gca gct gga gca ggg gca ggt gga tat ggc caa ggt gct ggg     7509
Gly Ala Ala Ala Gly Ala Gly Ala Gly Gly Tyr Gly Gln Gly Ala Gly
930                 935                 940                 945

ggc tac gga caa ggt tct ggt gct gca gct gga gca gga gga tat ggt     7557
Gly Tyr Gly Gln Gly Ser Gly Ala Ala Ala Gly Ala Gly Gly Tyr Gly
                950                 955                 960

caa gga tct caa ggc tac gga caa ggt gct gct gca acc tca tcg gct     7605
Gln Gly Ser Gln Gly Tyr Gly Gln Gly Ala Ala Ala Thr Ser Ser Ala
            965                 970                 975

gca gca ggg gca tct tca act ggt tat aca gaa aga caa aat gaa gtt     7653
Ala Ala Gly Ala Ser Ser Thr Gly Tyr Thr Glu Arg Gln Asn Glu Val
        980                 985                 990

gtc act aca gtt act act aca  cgt caa gaa ata gca  gat cga aga cag   7701
Val Thr Thr Val Thr Thr Thr  Arg Gln Glu Ile Ala  Asp Arg Arg Gln
```

```
    995                 1000                1005

gca  gca agc gcc tca ggt  gca gta tca act tca  gct gca gct ggc      7746
Ala  Ala Ser Ala Ser Gly  Ala Val Ser Thr Ser  Ala Ala Ala Gly
1010                1015                1020

tac  ggc caa ggt gct gga  aca gga gct gga gga  tac ggt caa ggc      7791
Tyr  Gly Gln Gly Ala Gly  Thr Gly Ala Gly Gly  Tyr Gly Gln Gly
1025                1030                1035

gct  ggt ggc tat gga caa  aga gct ggt gct gca  gca gga gga tac      7836
Ala  Gly Gly Tyr Gly Gln  Arg Ala Gly Ala Ala  Ala Gly Gly Tyr
1040                1045                1050

ggt  caa ggg tct ggt ggc  tat gga caa ggg gtt  ggt act gca gct      7881
Gly  Gln Gly Ser Gly Gly  Tyr Gly Gln Gly Val  Gly Thr Ala Ala
1055                1060                1065

agt  gta gct gct gga gga  gct gga gca gga gga  tac ggt tta ggt      7926
Ser  Val Ala Ala Gly Gly  Ala Gly Ala Gly Gly  Tyr Gly Leu Gly
1070                1075                1080

gct  ggt ggc tat gga aga  ggt gct ggt gct gca  gca gga tct gga      7971
Ala  Gly Gly Tyr Gly Arg  Gly Ala Gly Ala Ala  Ala Gly Ser Gly
1085                1090                1095

gca  gga gga tac ggt caa  ggc gct ggt ggc tat  gga caa ggt gct      8016
Ala  Gly Gly Tyr Gly Gln  Gly Ala Gly Gly Tyr  Gly Gln Gly Ala
1100                1105                1110

ggt  gct gca gcg gga gct  gga gca gga gga tac  ggt caa ggc gct      8061
Gly  Ala Ala Ala Gly Ala  Gly Ala Gly Gly Tyr  Gly Gln Gly Ala
1115                1120                1125

ggt  ggc tat gga caa ggt  gct ggt gct gca gct  agt gta gct gct      8106
Gly  Gly Tyr Gly Gln Gly  Ala Gly Ala Ala Ala  Ser Val Ala Ala
1130                1135                1140

gga  gga gct gga gca gga  gga tac ggt tta ggt  gct ggt ggc tat      8151
Gly  Gly Ala Gly Ala Gly  Gly Tyr Gly Leu Gly  Ala Gly Gly Tyr
1145                1150                1155

gga  aga ggt gct ggt gct  gga gca ggt gca gct  gcc ggg tct gga      8196
Gly  Arg Gly Ala Gly Ala  Gly Ala Gly Ala Ala  Ala Gly Ser Gly
1160                1165                1170

gca  gga gga tac agt caa  ggc gct ggt ggc tat  gga caa cgt ggt      8241
Ala  Gly Gly Tyr Ser Gln  Gly Ala Gly Gly Tyr  Gly Gln Arg Gly
1175                1180                1185

ggt  gct gca gcc ggt gca  gct gct gga gga gct  gga tca gga gga      8286
Gly  Ala Ala Ala Gly Ala  Ala Ala Gly Gly Ala  Gly Ser Gly Gly
1190                1195                1200

tac  ggt cta ggt gct ggc  att gga gca ggt gca  gct gca ata gct      8331
Tyr  Gly Leu Gly Ala Gly  Ile Gly Ala Gly Ala  Ala Ala Ile Ala
1205                1210                1215

gga  gga tac ggt caa gga  gct gga ggc tac aaa  caa ggt gct ggt      8376
Gly  Gly Tyr Gly Gln Gly  Ala Gly Gly Tyr Lys  Gln Gly Ala Gly
1220                1225                1230

gct  gca gct ggt gca ggt  act gga gca gga ggt  tat ggt caa gga      8421
Ala  Ala Ala Gly Ala Gly  Thr Gly Ala Gly Gly  Tyr Gly Gln Gly
1235                1240                1245

gca  gga ggc tat gga caa  ggg gct gga gct gca  gca ggt gct agt      8466
Ala  Gly Gly Tyr Gly Gln  Gly Ala Gly Ala Ala  Ala Gly Ala Ser
1250                1255                1260

gct  ggt gca ata gct gga  gga tac ggt caa gga  gct gta ggc tac      8511
Ala  Gly Ala Ile Ala Gly  Gly Tyr Gly Gln Gly  Ala Val Gly Tyr
1265                1270                1275

ggt  caa gga act gga ggc  tac gga caa ggt gct  gca gct ggt gca      8556
Gly  Gln Gly Thr Gly Gly  Tyr Gly Gln Gly Ala  Ala Ala Gly Ala
1280                1285                1290

ggt  act gga gca gga ggt  tat ggt cag gga gct  ggt ggc tat gga      8601
```

```
Gly  Thr Gly Ala Gly Gly  Tyr Gly Gln Gly Ala  Gly Gly Tyr Gly
1295                1300                1305

caa  gct act gga gta gga  agc tac gga caa ggt  act ggt gac ggt      8646
Gln  Ala Thr Gly Val Gly  Ser Tyr Gly Gln Gly  Thr Gly Asp Gly
1310                1315                1320

gct  cga gga cct gca ggc  tat gga caa ggt gcg  ggt gtc ggt act      8691
Ala  Arg Gly Pro Ala Gly  Tyr Gly Gln Gly Ala  Gly Val Gly Thr
1325                1330                1335

ata  gga gca gta ggt tac  gga caa gga caa aca  gct gga gca tcc      8736
Ile  Gly Ala Val Gly Tyr  Gly Gln Gly Gln Thr  Ala Gly Ala Ser
1340                1345                1350

tct  tca aca gca gcc gga  gca gct tct act ggt  tat aca gaa aga      8781
Ser  Ser Thr Ala Ala Gly  Ala Ala Ser Thr Gly  Tyr Thr Glu Arg
1355                1360                1365

caa  aat gag gtt aca act  act gtt tct act aca  cgc aaa gaa aca      8826
Gln  Asn Glu Val Thr Thr  Thr Val Ser Thr Thr  Arg Lys Glu Thr
1370                1375                1380

gca  gat cga aga caa gca  gca agt gcc tca gct  gca gtt tcc act      8871
Ala  Asp Arg Arg Gln Ala  Ala Ser Ala Ser Ala  Ala Val Ser Thr
1385                1390                1395

tca  gct gca gct ggc tat  ggc aaa ggt act gga  ggc tat ggg caa      8916
Ser  Ala Ala Ala Gly Tyr  Gly Lys Gly Thr Gly  Gly Tyr Gly Gln
1400                1405                1410

ggt  gct ggc gca gca gca  gga gct gga gcg gga  gga tat gtt caa      8961
Gly  Ala Gly Ala Ala Ala  Gly Ala Gly Ala Gly  Gly Tyr Val Gln
1415                1420                1425

agt  tat ggt gct gca gca  ggt gca tcg gct att  gct gga gca ggt      9006
Ser  Tyr Gly Ala Ala Ala  Gly Ala Ser Ala Ile  Ala Gly Ala Gly
1430                1435                1440

aga  tat gga caa ggt gca  gga gca aca gga tac  ggt caa ggc gct      9051
Arg  Tyr Gly Gln Gly Ala  Gly Ala Thr Gly Tyr  Gly Gln Gly Ala
1445                1450                1455

ggt  ggc tat gga gga agt  gct ggt gct gga gca  ggg gca ggt gca      9096
Gly  Gly Tyr Gly Gly Ser  Ala Gly Ala Gly Ala  Gly Ala Gly Ala
1460                1465                1470

gct  tca gga gct gga gca  ggt gga tat ggt cga  ggc gct ggt ggc      9141
Ala  Ser Gly Ala Gly Ala  Gly Gly Tyr Gly Arg  Gly Ala Gly Gly
1475                1480                1485

tat  gga caa ggt gct ggt  gct gca ggt gca gct  gca gga gct gga      9186
Tyr  Gly Gln Gly Ala Gly  Ala Ala Gly Ala Ala  Ala Gly Ala Gly
1490                1495                1500

gga  tac gct caa gcc gct  ggt ggc tat gga caa  ggt tct gtt gct      9231
Gly  Tyr Ala Gln Ala Ala  Gly Gly Tyr Gly Gln  Gly Ser Val Ala
1505                1510                1515

gta  gca ggt gca gct gca  ggt gct ggt ggc tat  gga caa ggt gct      9276
Val  Ala Gly Ala Ala Ala  Gly Ala Gly Gly Tyr  Gly Gln Gly Ala
1520                1525                1530

agt  gct gca gca gga gct  gga gga tac ggt caa  gcc gct ggt gtc      9321
Ser  Ala Ala Ala Gly Ala  Gly Gly Tyr Gly Gln  Ala Ala Gly Val
1535                1540                1545

tat  gga caa ggt gct ggt  gct gca ggt gca gct  gca gga gct ggt      9366
Tyr  Gly Gln Gly Ala Gly  Ala Ala Gly Ala Ala  Ala Gly Ala Gly
1550                1555                1560

ggc  tat gga caa ggt gct  ggt gct gca gca ggt  gcc gct gca ggt      9411
Gly  Tyr Gly Gln Gly Ala  Gly Ala Ala Ala Gly  Ala Ala Ala Gly
1565                1570                1575

tct  ggt ggc tat gga caa  ggt gct ggt gct gta  gca ggt gca gct      9456
Ser  Gly Gly Tyr Gly Gln  Gly Ala Gly Ala Val  Ala Gly Ala Ala
1580                1585                1590
```

-continued

```
gca  ggt gct ggt ggc tat  gga caa ggt cct ggc  gct gca gca gat      9501
Ala  Gly Ala Gly Gly Tyr  Gly Gln Gly Pro Gly  Ala Ala Ala Asp
1595                1600                1605

gca  gca gca gga gct ggt  ggc tat gga caa ggt  acc gga ggg tat      9546
Ala  Ala Ala Gly Ala Gly  Gly Tyr Gly Gln Gly  Thr Gly Gly Tyr
1610                1615                1620

gga  caa ggt gct ggt gct  gca gga gct gga gca  ggt gga tat ggt      9591
Gly  Gln Gly Ala Gly Ala  Ala Gly Ala Gly Ala  Gly Gly Tyr Gly
1625                1630                1635

cga  ggc gct ggt ggc tat  gga caa gga gct gat  gct gca gga gct      9636
Arg  Gly Ala Gly Gly Tyr  Gly Gln Gly Ala Asp  Ala Ala Gly Ala
1640                1645                1650

gga  ggg tac ggt gga ggc  gct ggt ggc tat gga  caa ggt gcc aga      9681
Gly  Gly Tyr Gly Gly Gly  Ala Gly Gly Tyr Gly  Gln Gly Ala Arg
1655                1660                1665

ggc  tat gga caa ggc gct  ggt gct gct gca ggt  tcg ggt tca gga      9726
Gly  Tyr Gly Gln Gly Ala  Gly Ala Ala Ala Gly  Ser Gly Ser Gly
1670                1675                1680

gca  gga gga tac ggt caa  ggt ggt gtt gga gga  tat gga caa cgt      9771
Ala  Gly Gly Tyr Gly Gln  Gly Gly Val Gly Gly  Tyr Gly Gln Arg
1685                1690                1695

gct  ggt tca gga gca aca  ggt tat ggc caa ggt  act ggt gga tac      9816
Ala  Gly Ser Gly Ala Thr  Gly Tyr Gly Gln Gly  Thr Gly Gly Tyr
1700                1705                1710

ggt  caa ggt gct ggt gta  tca tcg gca gca gca  gga gca tcc tct      9861
Gly  Gln Gly Ala Gly Val  Ser Ser Ala Ala Ala  Gly Ala Ser Ser
1715                1720                1725

act  ggc tat gca gga aga  caa aat gaa gtt atc  act acg gtt act      9906
Thr  Gly Tyr Ala Gly Arg  Gln Asn Glu Val Ile  Thr Thr Val Thr
1730                1735                1740

act  aca cgc caa gaa act  gca gat tat gct aat  aaa caa gca gca      9951
Thr  Thr Arg Gln Glu Thr  Ala Asp Tyr Ala Asn  Lys Gln Ala Ala
1745                1750                1755

agt  tcc tca tca gca gca  gct tca gcg gct agt  ggt tat gct caa      9996
Ser  Ser Ser Ser Ala Ala  Ala Ser Ala Ala Ser  Gly Tyr Ala Gln
1760                1765                1770

ggt  gct ttt gca gga ggc  tac gga cga ggt ctc  ggc gct ggc gtc     10041
Gly  Ala Phe Ala Gly Gly  Tyr Gly Arg Gly Leu  Gly Ala Gly Val
1775                1780                1785

gaa  gga gat tct gca act  gga act tat ggt caa  ggt ggt ggt tct     10086
Glu  Gly Asp Ser Ala Thr  Gly Thr Tyr Gly Gln  Gly Gly Gly Ser
1790                1795                1800

gcc  gca ggt gca tca gct  aga gct gga gca gga  gct tat ggc caa     10131
Ala  Ala Gly Ala Ser Ala  Arg Ala Gly Ala Gly  Ala Tyr Gly Gln
1805                1810                1815

ggt  acc gga ggt tat gca  caa aga gct ggt gga  gca gca ggt gct     10176
Gly  Thr Gly Gly Tyr Ala  Gln Arg Ala Gly Gly  Ala Ala Gly Ala
1820                1825                1830

gct  gct ggc gct gga gtt  gga ggc tat gga gaa  gga gct ggt gca     10221
Ala  Ala Gly Ala Gly Val  Gly Gly Tyr Gly Glu  Gly Ala Gly Ala
1835                1840                1845

gca  gca ggt gcg gct gct  ggt act tgg gca gga  ggg tat gga caa     10266
Ala  Ala Gly Ala Ala Ala  Gly Thr Trp Ala Gly  Gly Tyr Gly Gln
1850                1855                1860

ggt  gct gga gtt ggt gct  gcc gca ggt gct gga  gct gga ggt tat     10311
Gly  Ala Gly Val Gly Ala  Ala Ala Gly Ala Gly  Ala Gly Gly Tyr
1865                1870                1875

gga  caa gga gct tta ttt  ggc caa gga gct gga  ggc tat gga caa     10356
Gly  Gln Gly Ala Leu Phe  Gly Gln Gly Ala Gly  Gly Tyr Gly Gln
1880                1885                1890
```

```
gca  gca ggt gtg gct gtt  ggt ggt gga gca gga  ggg tat gga caa     10401
Ala  Ala Gly Val Ala Val  Gly Gly Gly Ala Gly  Gly Tyr Gly Gln
1895                1900                 1905

ggc  gct gga gct ggt gct  gcc gca ggt gcg gct  gca agt act gga     10446
Gly  Ala Gly Ala Gly Ala  Ala Ala Gly Ala Ala  Ala Ser Thr Gly
1910                1915                 1920

gct  gga ggt tat gga caa  gga gct gca ggg tat  ggc caa gga gct     10491
Ala  Gly Gly Tyr Gly Gln  Gly Ala Ala Gly Tyr  Gly Gln Gly Ala
1925                1930                 1935

gga  gac tac gga cga gga  gct ggt gca gca gca  ggt gtg gct gct     10536
Gly  Asp Tyr Gly Arg Gly  Ala Gly Ala Ala Ala  Gly Val Ala Ala
1940                1945                 1950

aga  gct gga gca gga act  tat gtc caa ggt tca  gga ggc tat ggt     10581
Arg  Ala Gly Ala Gly Thr  Tyr Val Gln Gly Ser  Gly Gly Tyr Gly
1955                1960                 1965

caa  ggc caa gca gct ggt  gct gca gcc gct gca  gca gca gga ggt     10626
Gln  Gly Gln Ala Ala Gly  Ala Ala Ala Ala Ala  Ala Ala Gly Gly
1970                1975                 1980

ggt  gga gca gga aga tat  gga caa ggg gtt gga  gtg gca tcc gta     10671
Gly  Gly Ala Gly Arg Tyr  Gly Gln Gly Val Gly  Val Ala Ser Val
1985                1990                 1995

tca  gct ggt gga tat gga  caa gca caa gtt tca  cga gct tca agt     10716
Ser  Ala Gly Gly Tyr Gly  Gln Ala Gln Val Ser  Arg Ala Ser Ser
2000                2005                 2010

act  tcg gct gct gga act  tca acc tcg ggt tat  aca tct cag caa     10761
Thr  Ser Ala Ala Gly Thr  Ser Thr Ser Gly Tyr  Thr Ser Gln Gln
2015                2020                 2025

aca  caa act gca gga aca  tct tca gca gtt tca  aca tca ggc aca     10806
Thr  Gln Thr Ala Gly Thr  Ser Ser Ala Val Ser  Thr Ser Gly Thr
2030                2035                 2040

agt  ggt tat tct caa gta  agt gga ggc tac ggg  caa agt gca gca     10851
Ser  Gly Tyr Ser Gln Val  Ser Gly Gly Tyr Gly  Gln Ser Ala Ala
2045                2050                 2055

ggt  ggt caa gct ttt gca  ggt tat gga caa atg  caa ggt ggc gga     10896
Gly  Gly Gln Ala Phe Ala  Gly Tyr Gly Gln Met  Gln Gly Gly Gly
2060                2065                 2070

gct  gtt agt ggt aca agc  gca tca gcg act gtt  tca tct gca gca     10941
Ala  Val Ser Gly Thr Ser  Ala Ser Ala Thr Val  Ser Ser Ala Ala
2075                2080                 2085

tca  cga tta agt tct gct  tct tcc tct tcc aga  ata agc tct gca     10986
Ser  Arg Leu Ser Ser Ala  Ser Ser Ser Ser Arg  Ile Ser Ser Ala
2090                2095                 2100

gcg  tct agc ctt gca act  ggt gga gtg ttg aat  act gct gca ttg     11031
Ala  Ser Ser Leu Ala Thr  Gly Gly Val Leu Asn  Thr Ala Ala Leu
2105                2110                 2115

cct  tcg gta gtt tct aat  atg atg tcc caa gtt  tca gct agc agt     11076
Pro  Ser Val Val Ser Asn  Met Met Ser Gln Val  Ser Ala Ser Ser
2120                2125                 2130

cct  gga atg tca tca agt  gaa gtt gtt atc caa  gcc cta ctt gaa     11121
Pro  Gly Met Ser Ser Ser  Glu Val Val Ile Gln  Ala Leu Leu Glu
2135                2140                 2145

ttg  gtg tct tct ctt ata  cat att ctc agc tcc  gct aac atc ggt     11166
Leu  Val Ser Ser Leu Ile  His Ile Leu Ser Ser  Ala Asn Ile Gly
2150                2155                 2160

caa  gtt gac ttc aat tct  gtt gga aat aca gct  gct gtt gtt ggt     11211
Gln  Val Asp Phe Asn Ser  Val Gly Asn Thr Ala  Ala Val Val Gly
2165                2170                 2175

caa  tca ctt ggg gca gct  tta gga tga atatttttaa atcttgaaag        11258
Gln  Ser Leu Gly Ala Ala  Leu Gly
```

-continued 2180 2185 ttgtattttc acttaatctt attaacttga ttaactttag caaaattgaa tgaatatctt 11318 cagctaaata catactttgt tattatgact aataaaatat aaaatttaat gaaataattc 11378 gtctttttgt gtgtgttttc cccttttttt gtatgcactt aaaactatta acttgcttac 11438 actgatatgc gatatctata tgtcagtaga attgataaaa ttgtatgaac agtttttctg 11498 ttgttagagt aggatttgaa gaatctactt gcttcttagt atggattaaa ttttccagcg 11558 gtttgtcagg tattatattt taaaatatat aaacaacgct gttaatatga aaaataatta 11618 agtatgttaa atatttatac catactatta atgtataacc gttccgaaat gagaaaaaac 11678 ataaaaattc atattataca taaaataatg ctcagttctc atggaaattt ttaagtctga 11738 aaacttcatg aaaatatttt gtaaaaattt cagttatttt tgactgaaat atgagggaat 11798 tcttattcgt cagaattgaa attattatta ttaaattagt atagtagatg tgaattatgc 11858 acattgtcat ttcttaatta aaatgatttt atgaatatgt caattatatt ttgtttaagg 11918 agtaacaagt acctatagca tttgcacttt attacacagt tctataaatt gaaataattt 11978 ttagtttact tcaaatattt tttgagaatg cgcatgctaa atgtttttat ttgaaccttt 12038 tttcaattaa aacatttagc ttatccattc tctctaaaaa aaaaaaaaga aaaaaaaaga 12098 ttactttcat caaaatttta atctaatatt catctgtttc gttataattt aaaagaaata 12158 ttatttttgg aataaaggtt tgaataattg ttttttcaac caaggagtgt aatttataat 12218 tatatgaaat tatgtatata aatatacatg tagctcagtt aaaaataaga ttaattttgt 12278 tgaagtgtgt gtttaaatat aaaatttcat aaattagaat cattatgagc atctaaattt 12338 cccctaaaaa aaatttgtaa caaatttgca taaatgataa ataaaatata ttattaagta 12398 catggtttta gacacattgc atgcaacctt aattgactaa gtcaacaaaa taataagctt 12458 tacataatta atttaccgtg taacactaaa agcttatcat ttgctttaat ttatttcttg 12518 ggaaatgaag gagaatttgt tacatttgtg tagtcttttg ggagaagtgt atgtggtaga 12578 gtcaaagtca acggtataaa tctttttcac ggctaacgat tataagttat tgtaatctta 12638 ctcgtctcaa atattttttta tatttaacac ttgttgaaat tagtaaagga gaatcgttac 12698 ttctcatcac gactttttta attaaaattt ctcggaggtt gagtaggaaa ttaagaatga 12758 ttgcattgtt ttaatttact taactaagtt taatttaaga aaaaattctt atattgagat 12818 attaaaactt ttaaagtgta tacaatgctt gacgattgta acaagcattg catatacctc 12878 ataatttatt ttatagtctt cagtgctgtg tcatgtttga tttgcttaaa aaatccagta 12938 tcataaaaat attaaaactt attttattag ccgatcttaa aaattattta taaattaaac 12998 attggtatat gaaatactta tttgtaaata aaaaattaaa ttttaaaaac aatttaatta 13058 taaatttaag actttaatta agaaaataaa tatttatata agtattgtat ttatttcaaa 13118 attctgtgac acattcctat tattacaaat tattgaaata aatattattt ataaatagaa 13178 tattcaattg tgatcattta attatatgat ctgttcattt aattaattta tttttatcaa 13238 tatgttgtac acattctgtg cttctataat taaaaataaa aatattaaaa agtacaaact 13298 taaaattttt atatgcttat aaatttataa atttttcgct taatagtgct aatatatata 13358 taaatatata tatatatata tatatatata tatatatata tatatatata taagtgcaac 13418 att 13421

<210> SEQ ID NO 50
<211> LENGTH: 2187

```
<212> TYPE: PRT
<213> ORGANISM: Latrodectus hesperus

<400> SEQUENCE: 50

Met Ile Thr Ala Ile Met His Ile Pro Ala Gln Leu Ser Leu Leu Phe
1               5                   10                  15

Leu Leu Leu Cys Ala Gln Ser Phe Val Ser Leu Asp Ala Ala Ser Val
            20                  25                  30

Trp Asp Ser Thr Ala Thr Ala Glu Ala Phe Ile Gly Ser Phe Asn Ser
        35                  40                  45

Gly Met Glu Arg Cys Gly Val Leu Ser Arg Ser Gln Met Asp Asp Ile
    50                  55                  60

Ser Ser Ile Ser Asp Thr Ile Ile Ser Ala Ile Glu Arg Asn Pro Asn
65                  70                  75                  80

Asn Ser Lys Ser Lys Leu Gln Ala Leu Asn Met Ala Phe Ala Ser Ser
                85                  90                  95

Val Ser Glu Ile Ala Phe Ser Glu Asn Asn Gly Ile Ser Asn Ser Ala
            100                 105                 110

Lys Ile Gln Ala Ile Ile Asp Ala Leu Arg Gly Ala Phe Leu Gln Thr
        115                 120                 125

Ile Gly Thr Val Asp Gln Thr Phe Leu Asn Glu Ile Ser Ser Leu Val
    130                 135                 140

Lys Met Phe Ser Gln Val Ser Ala Glu Asn Ala Val Ser Thr Ser Ala
145                 150                 155                 160

Gly Ala Ala Ala Thr Ser Ile Gly Ser Ser Gly Gly Gly Tyr Gly Gln
                165                 170                 175

Gln Ser Gly Gly Tyr Ser Gln Gly Ser Ala Ala Ser Ala Ser Ser Ser
            180                 185                 190

Ala Gly Glu Arg Thr Ser Ala Gly Thr Thr Gly Tyr Ser Ala Gly Ser
        195                 200                 205

Thr Gln Val Ser Ser Thr Val Ser Ser Thr Ser Gln Ala Ala Gln Ser
    210                 215                 220

Ala Thr Ala Thr Ser Gln Tyr Gly Gln Ala Gln Ser Ala Gly Ser Tyr
225                 230                 235                 240

Ser Asn Ala Ala Ala Gly Ala Thr Gly Ala Tyr Ala Gly Gly Tyr Gly
                245                 250                 255

Gln Gly Ser Ser Ala Ala Ala Gly Ala Gly Ala Gly Gly Tyr Asn Gln
            260                 265                 270

Gly Ala Gly Ser Tyr Gly Gln Gly Ala Gly Ala Ala Ala Arg Thr Ala
        275                 280                 285

Ala Gly Ala Gly Ala Gly Gly Tyr Gly Gln Gly Ala Gly Gly Tyr Gly
    290                 295                 300

Gln Gly Ala Gly Ala Ala Ala Gly Ala Ala Ala Gly Ala Gly Ala Gly
305                 310                 315                 320

Gly Tyr Gly Arg Gly Ala Gly Ser Ala Ala Gly Ala Ala Ala Gly Ala
                325                 330                 335

Gly Val Gly Glu Tyr Gly Gln Gly Ala Gly Gly Tyr Gly Gln Gly Ala
            340                 345                 350

Gly Ala Ala Ala Gly Ala Ala Ala Gly Ala Gly Ala Gly Gly Tyr Gly
        355                 360                 365

Gln Gly Ala Gly Gly Tyr Gly Gln Gly Ala Gly Gly Tyr Gly Gln Gly
    370                 375                 380

Ala Gly Ala Ala Ala Gly Ala Gly Ala Gly Ser Tyr Gly Gln Gly Ala
385                 390                 395                 400
```

```
Gly Gly Tyr Gly Gln Gly Ala Gly Ala Ala Ala Gly Ala Ala Ala Gly
                405                 410                 415

Ala Gly Ala Gly Gly Tyr Gly Gln Gly Ala Gly Gly Tyr Gly Gln Gly
            420                 425                 430

Ala Gly Ala Ala Ala Gly Ala Ala Ala Gly Ala Gly Ala Gly Gly Tyr
        435                 440                 445

Gly Gln Gly Ala Gly Gly Tyr Gly Gln Gly Ala Gly Ala Ala Ala Gly
    450                 455                 460

Ala Gly Ala Gly Gly Tyr Gly Arg Gly Ala Gly Ser Ala Ala Gly Ala
465                 470                 475                 480

Ala Ala Gly Ser Gly Ala Gly Gly Tyr Gly Gln Gly Ala Gly Gly Tyr
                485                 490                 495

Gly Gln Gly Ala Gly Ala Gly Ala Gly Gly Tyr Gly Gln Gly Ala Gly
            500                 505                 510

Ala Ser Thr Gly Ala Ala Ala Gly Ala Gly Ala Gly Gly Tyr Gly Gln
        515                 520                 525

Gly Ala Gly Gly Tyr Gly Gln Gly Ser Gly Ala Ala Ala Gly Ala Gly
    530                 535                 540

Gly Tyr Gly Gln Gly Ser Gln Gly Tyr Glu Gln Gly Ala Ala Ala Thr
545                 550                 555                 560

Ser Ser Ala Ala Ala Gly Ala Ser Ser Thr Gly Tyr Thr Glu Arg Gln
                565                 570                 575

Asn Glu Val Val Thr Thr Val Thr Thr Thr Arg Gln Glu Ile Ala Asp
            580                 585                 590

Arg Arg Gln Ala Ala Ser Ala Ser Gly Ala Val Ser Thr Ser Ala Ala
        595                 600                 605

Ala Gly Tyr Gly Gln Gly Ala Gly Thr Gly Ala Gly Gly Tyr Gly Gln
    610                 615                 620

Gly Ala Gly Gly Tyr Gly Gln Arg Ala Gly Ala Ala Ala Gly Gly Tyr
625                 630                 635                 640

Gly Gln Gly Ser Gly Gly Tyr Gly Gln Gly Val Gly Ala Ala Ala Ser
                645                 650                 655

Val Ala Ala Gly Gly Ala Gly Ala Gly Gly Tyr Gly Leu Gly Ala Gly
            660                 665                 670

Gly Tyr Gly Arg Gly Ala Gly Ala Ala Ala Gly Gly Tyr Gly Gln Gly
        675                 680                 685

Ala Gly Gly Tyr Gly Gln Gly Ala Gly Ala Ala Ala Gly Ala Gly Ala
    690                 695                 700

Gly Gly Tyr Asp Gln Gly Ala Gly Gly Tyr Gly Gln Gly Ala Gly Ala
705                 710                 715                 720

Ala Ala Ser Val Ala Ala Gly Gly Ala Gly Ser Gly Gly Tyr Gly Leu
                725                 730                 735

Gly Ala Gly Ile Gly Ala Gly Ala Ala Ala Ile Ala Gly Gly Tyr Gly
            740                 745                 750

Gln Gly Ala Gly Ala Ala Ala Gly Ala Ala Ala Gly Ala Gly Ala Gly
        755                 760                 765

Ser Tyr Gly Gln Gly Ala Gly Gly Tyr Gly Gln Gly Ala Gly Ala Ala
    770                 775                 780

Ala Gly Ala Ala Ala Gly Ala Gly Ala Gly Gly Tyr Gly Gln Gly Ala
785                 790                 795                 800

Gly Gly Tyr Gly Gln Gly Ala Gly Ala Ala Ala Gly Ala Ala Ala Gly
                805                 810                 815
```

```
Ala Gly Ala Gly Gly Tyr Gly Gln Gly Ala Gly Gly Tyr Gly Gln Gly
            820                 825                 830

Ala Gly Ala Gly Ala Gly Gly Tyr Gly Gln Gly Ala Gly Gly Tyr Gly
        835                 840                 845

Gln Gly Ala Gly Ala Ala Ala Gly Ala Ala Ala Gly Ala Gly Ala Gly
    850                 855                 860

Gly Tyr Gly Gln Gly Ala Gly Gly Tyr Gly Gln Gly Ala Gly Ala Gly
865                 870                 875                 880

Ala Gly Gly Tyr Gly Arg Gly Ala Gly Ser Ala Ala Gly Ala Ala Ala
                885                 890                 895

Gly Ser Gly Ala Gly Gly Tyr Gly Gln Gly Ala Gly Gly Tyr Gly Gln
            900                 905                 910

Gly Ala Gly Ala Gly Ala Gly Gly Tyr Gly Gln Gly Ala Gly Ala Ser
        915                 920                 925

Thr Gly Ala Ala Ala Gly Ala Gly Ala Gly Gly Tyr Gly Gln Gly Ala
    930                 935                 940

Gly Gly Tyr Gly Gln Gly Ser Gly Ala Ala Ala Gly Ala Gly Gly Tyr
945                 950                 955                 960

Gly Gln Gly Ser Gln Gly Tyr Gly Gln Gly Ala Ala Ala Thr Ser Ser
                965                 970                 975

Ala Ala Ala Gly Ala Ser Ser Thr Gly Tyr Thr Glu Arg Gln Asn Glu
            980                 985                 990

Val Val Thr Thr Val Thr Thr Thr  Arg Gln Glu Ile Ala  Asp Arg Arg
        995                 1000                1005

Gln Ala  Ala Ser Ala Ser Gly  Ala Val Ser Thr Ser  Ala Ala Ala
    1010                1015                1020

Gly Tyr  Gly Gln Gly Ala Gly  Thr Gly Ala Gly Gly  Tyr Gly Gln
    1025                1030                1035

Gly Ala  Gly Gly Tyr Gly Gln  Arg Ala Gly Ala Ala  Ala Gly Gly
    1040                1045                1050

Tyr Gly  Gln Gly Ser Gly Gly  Tyr Gly Gln Gly Val  Gly Thr Ala
    1055                1060                1065

Ala Ser  Val Ala Ala Gly Gly  Ala Gly Ala Gly Gly  Tyr Gly Leu
    1070                1075                1080

Gly Ala  Gly Gly Tyr Gly Arg  Gly Ala Gly Ala Ala  Ala Gly Ser
    1085                1090                1095

Gly Ala  Gly Gly Tyr Gly Gln  Gly Ala Gly Gly Tyr  Gly Gln Gly
    1100                1105                1110

Ala Gly  Ala Ala Ala Gly Ala  Gly Ala Gly Gly Tyr  Gly Gln Gly
    1115                1120                1125

Ala Gly  Gly Tyr Gly Gln Gly  Ala Gly Ala Ala Ala  Ser Val Ala
    1130                1135                1140

Ala Gly  Gly Ala Gly Ala Gly  Gly Tyr Gly Leu Gly  Ala Gly Gly
    1145                1150                1155

Tyr Gly  Arg Gly Ala Gly Ala  Gly Ala Gly Ala Ala  Ala Gly Ser
    1160                1165                1170

Gly Ala  Gly Gly Tyr Ser Gln  Gly Ala Gly Gly Tyr  Gly Gln Arg
    1175                1180                1185

Gly Gly  Ala Ala Ala Gly Ala  Ala Ala Gly Gly Ala  Gly Ser Gly
    1190                1195                1200

Gly Tyr  Gly Leu Gly Ala Gly  Ile Gly Ala Gly Ala  Ala Ala Ile
    1205                1210                1215

Ala Gly  Gly Tyr Gly Gln Gly  Ala Gly Gly Tyr Lys  Gln Gly Ala
```

```
    1220                1225                1230

Gly Ala  Ala Ala Gly Ala Gly  Thr Gly Ala Gly Gly  Tyr Gly Gln
    1235                1240                1245

Gly Ala  Gly Gly Tyr Gly Gln  Gly Ala Gly Ala Ala  Ala Gly Ala
    1250                1255                1260

Ser Ala  Gly Ala Ile Ala Gly  Gly Tyr Gly Gln Gly  Ala Val Gly
    1265                1270                1275

Tyr Gly  Gln Gly Thr Gly Gly  Tyr Gly Gln Gly Ala  Ala Ala Gly
    1280                1285                1290

Ala Gly  Thr Gly Ala Gly Gly  Tyr Gly Gln Gly Ala  Gly Gly Tyr
    1295                1300                1305

Gly Gln  Ala Thr Gly Val Gly  Ser Tyr Gly Gln Gly  Thr Gly Asp
    1310                1315                1320

Gly Ala  Arg Gly Pro Ala Gly  Tyr Gly Gln Gly Ala  Gly Val Gly
    1325                1330                1335

Thr Ile  Gly Ala Val Gly Tyr  Gly Gln Gly Gln Thr  Ala Gly Ala
    1340                1345                1350

Ser Ser  Ser Thr Ala Ala Gly  Ala Ala Ser Thr Gly  Tyr Thr Glu
    1355                1360                1365

Arg Gln  Asn Glu Val Thr Thr  Thr Val Ser Thr Thr  Arg Lys Glu
    1370                1375                1380

Thr Ala  Asp Arg Arg Gln Ala  Ala Ser Ala Ser Ala  Ala Val Ser
    1385                1390                1395

Thr Ser  Ala Ala Ala Gly Tyr  Gly Lys Gly Thr Gly  Gly Tyr Gly
    1400                1405                1410

Gln Gly  Ala Gly Ala Ala Ala  Gly Ala Gly Ala Gly  Gly Tyr Val
    1415                1420                1425

Gln Ser  Tyr Gly Ala Ala Ala  Gly Ala Ser Ala Ile  Ala Gly Ala
    1430                1435                1440

Gly Arg  Tyr Gly Gln Gly Ala  Gly Ala Thr Gly Tyr  Gly Gln Gly
    1445                1450                1455

Ala Gly  Gly Tyr Gly Gly Ser  Ala Gly Ala Gly Ala  Gly Ala Gly
    1460                1465                1470

Ala Ala  Ser Gly Ala Gly Ala  Gly Gly Tyr Gly Arg  Gly Ala Gly
    1475                1480                1485

Gly Tyr  Gly Gln Gly Ala Gly  Ala Ala Gly Ala Ala  Ala Gly Ala
    1490                1495                1500

Gly Gly  Tyr Ala Gln Ala Ala  Gly Gly Tyr Gly Gln  Gly Ser Val
    1505                1510                1515

Ala Val  Ala Gly Ala Ala Ala  Gly Ala Gly Gly Tyr  Gly Gln Gly
    1520                1525                1530

Ala Ser  Ala Ala Ala Gly Ala  Gly Gly Tyr Gly Gln  Ala Ala Gly
    1535                1540                1545

Val Tyr  Gly Gln Gly Ala Gly  Ala Ala Gly Ala Ala  Ala Gly Ala
    1550                1555                1560

Gly Gly  Tyr Gly Gln Gly Ala  Gly Ala Ala Ala Gly  Ala Ala Ala
    1565                1570                1575

Gly Ser  Gly Gly Tyr Gly Gln  Gly Ala Gly Ala Val  Ala Gly Ala
    1580                1585                1590

Ala Ala  Gly Ala Gly Gly Tyr  Gly Gln Gly Pro Gly  Ala Ala Ala
    1595                1600                1605

Asp Ala  Ala Ala Gly Ala Gly  Gly Tyr Gly Gln Gly  Thr Gly Gly
    1610                1615                1620
```

```
Tyr Gly  Gln Gly Ala Gly Ala  Ala Gly Ala Gly Ala  Gly Gly Tyr
    1625                 1630                 1635

Gly Arg  Gly Ala Gly Gly Tyr  Gly Gln Gly Ala Asp  Ala Ala Gly
    1640                 1645                 1650

Ala Gly  Gly Tyr Gly Gly Gly  Ala Gly Gly Tyr Gly  Gln Gly Ala
    1655                 1660                 1665

Arg Gly  Tyr Gly Gln Gly Ala  Gly Ala Ala Ala Gly  Ser Gly Ser
    1670                 1675                 1680

Gly Ala  Gly Gly Tyr Gly Gln  Gly Gly Val Gly Gly  Tyr Gly Gln
    1685                 1690                 1695

Arg Ala  Gly Ser Gly Ala Thr  Gly Tyr Gly Gln Gly  Thr Gly Gly
    1700                 1705                 1710

Tyr Gly  Gln Gly Ala Gly Val  Ser Ser Ala Ala Ala  Gly Ala Ser
    1715                 1720                 1725

Ser Thr  Gly Tyr Ala Gly Arg  Gln Asn Glu Val Ile  Thr Thr Val
    1730                 1735                 1740

Thr Thr  Thr Arg Gln Glu Thr  Ala Asp Tyr Ala Asn  Lys Gln Ala
    1745                 1750                 1755

Ala Ser  Ser Ser Ser Ala Ala  Ala Ser Ala Ala Ser  Gly Tyr Ala
    1760                 1765                 1770

Gln Gly  Ala Phe Ala Gly Gly  Tyr Gly Arg Gly Leu  Gly Ala Gly
    1775                 1780                 1785

Val Glu  Gly Asp Ser Ala Thr  Gly Thr Tyr Gly Gln  Gly Gly Gly
    1790                 1795                 1800

Ser Ala  Ala Gly Ala Ser Ala  Arg Ala Gly Ala Gly  Ala Tyr Gly
    1805                 1810                 1815

Gln Gly  Thr Gly Gly Tyr Ala  Gln Arg Ala Gly Gly  Ala Ala Gly
    1820                 1825                 1830

Ala Ala  Ala Gly Ala Gly Val  Gly Gly Tyr Gly Glu  Gly Ala Gly
    1835                 1840                 1845

Ala Ala  Ala Gly Ala Ala Ala  Gly Thr Trp Ala Gly  Gly Tyr Gly
    1850                 1855                 1860

Gln Gly  Ala Gly Val Gly Ala  Ala Ala Gly Ala Gly  Ala Gly Gly
    1865                 1870                 1875

Tyr Gly  Gln Gly Ala Leu Phe  Gly Gln Gly Ala Gly  Gly Tyr Gly
    1880                 1885                 1890

Gln Ala  Ala Gly Val Ala Val  Gly Gly Gly Ala Gly  Gly Tyr Gly
    1895                 1900                 1905

Gln Gly  Ala Gly Ala Gly Ala  Ala Ala Gly Ala Ala  Ala Ser Thr
    1910                 1915                 1920

Gly Ala  Gly Gly Tyr Gly Gln  Gly Ala Ala Gly Tyr  Gly Gln Gly
    1925                 1930                 1935

Ala Gly  Asp Tyr Gly Arg Gly  Ala Gly Ala Ala Ala  Gly Val Ala
    1940                 1945                 1950

Ala Arg  Ala Gly Ala Gly Thr  Tyr Val Gln Gly Ser  Gly Gly Tyr
    1955                 1960                 1965

Gly Gln  Gly Gln Ala Ala Gly  Ala Ala Ala Ala Ala  Ala Ala Gly
    1970                 1975                 1980

Gly Gly  Gly Ala Gly Arg Tyr  Gly Gln Gly Val Gly  Val Ala Ser
    1985                 1990                 1995

Val Ser  Ala Gly Gly Tyr Gly  Gln Ala Gln Val Ser  Arg Ala Ser
    2000                 2005                 2010
```

```
Ser Thr  Ser Ala Ala Gly Thr  Ser Thr Ser Gly Tyr  Thr Ser Gln
    2015                 2020                 2025

Gln Thr  Gln Thr Ala Gly Thr  Ser Ser Ala Val Ser  Thr Ser Gly
    2030                 2035                 2040

Thr Ser  Gly Tyr Ser Gln Val  Ser Gly Gly Tyr Gly  Gln Ser Ala
    2045                 2050                 2055

Ala Gly  Gly Gln Ala Phe Ala  Gly Tyr Gly Gln Met  Gln Gly Gly
    2060                 2065                 2070

Gly Ala  Val Ser Gly Thr Ser  Ala Ser Ala Thr Val  Ser Ser Ala
    2075                 2080                 2085

Ala Ser  Arg Leu Ser Ser Ala  Ser Ser Ser Ser Arg  Ile Ser Ser
    2090                 2095                 2100

Ala Ala  Ser Ser Leu Ala Thr  Gly Gly Val Leu Asn  Thr Ala Ala
    2105                 2110                 2115

Leu Pro  Ser Val Val Ser Asn  Met Met Ser Gln Val  Ser Ala Ser
    2120                 2125                 2130

Ser Pro  Gly Met Ser Ser Ser  Glu Val Val Ile Gln  Ala Leu Leu
    2135                 2140                 2145

Glu Leu  Val Ser Ser Leu Ile  His Ile Leu Ser Ser  Ala Asn Ile
    2150                 2155                 2160

Gly Gln  Val Asp Phe Asn Ser  Val Gly Asn Thr Ala  Ala Val Val
    2165                 2170                 2175

Gly Gln  Ser Leu Gly Ala Ala  Leu Gly
    2180                 2185
```

<210> SEQ ID NO 51
<211> LENGTH: 27
<212> TYPE: PRT
<213> ORGANISM: Artificial Sequence
<220> FEATURE:
<223> OTHER INFORMATION: Consensus sequence
<220> FEATURE:
<221> NAME/KEY: misc
<222> LOCATION: (1)..(1)
<223> OTHER INFORMATION: X is R or G
<220> FEATURE:
<221> NAME/KEY: misc
<222> LOCATION: (5)..(5)
<223> OTHER INFORMATION: X is Q or R
<220> FEATURE:
<221> NAME/KEY: misc_feature
<222> LOCATION: (10)..(10)
<223> OTHER INFORMATION: X is P or G
<220> FEATURE:
<221> NAME/KEY: misc
<222> LOCATION: (13)..(13)
<223> OTHER INFORMATION: X is Q or R
<220> FEATURE:
<221> NAME/KEY: misc
<222> LOCATION: (15)..(15)
<223> OTHER INFORMATION: X is D or G
<220> FEATURE:
<221> NAME/KEY: misc
<222> LOCATION: (16)..(16)
<223> OTHER INFORMATION: X is Y or T
<220> FEATURE:
<221> NAME/KEY: misc
<222> LOCATION: (18)..(18)
<223> OTHER INFORMATION: X is Q or P
<220> FEATURE:
<221> NAME/KEY: misc
<222> LOCATION: (21)..(21)
<223> OTHER INFORMATION: X is A, T or Y
<220> FEATURE:
<221> NAME/KEY: misc
<222> LOCATION: (23)..(23)
<223> OTHER INFORMATION: X is Q or P
<220> FEATURE:
<221> NAME/KEY: misc
<222> LOCATION: (26)..(26)
<223> OTHER INFORMATION: X is A or S
<220> FEATURE:
<221> NAME/KEY: misc_feature
<222> LOCATION: (27)..(27)
<223> OTHER INFORMATION: Xaa is G or poly A of 4 to 10 residues

<400> SEQUENCE: 51

Xaa Gly Ala Gly Xaa Gly Gly Gln Gly Xaa Tyr Gly Xaa Gly Xaa Xaa
1 5 10 15

Gly Xaa Gly Gly Xaa Gly Xaa Gly Gly Xaa Xaa
20 25

<210> SEQ ID NO 52
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 52
tggctttcgc atcatctgta gc 22

<210> SEQ ID NO 53
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 53
ctccttgacc ataactaact ggctg 25

<210> SEQ ID NO 54
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 54
catcagcagc aggaccaagt g 21

<210> SEQ ID NO 55
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 55
gcgttgtcgg tgaagataaa gc 22

<210> SEQ ID NO 56
<211> LENGTH: 63
<212> TYPE: PRT
<213> ORGANISM: Latrodectus geometricus

<400> SEQUENCE: 56

Gly Gly Ala Gly Gln Gly Gly Tyr Gly Gln Gly Gly Ala Gly Gln Gly
1 5 10 15

Gly Ala Gly Ala Ala Ala Ala Ala Ala Ala Ala Gly Gly Ala Gly Gln
20 25 30

Gly Gly Gln Gly Gly Tyr Gly Gln Gly Gly Ala Gly Gln Gly Gly Ala
35 40 45

Ala Ala Ala Ala Ala Ala Ala Gly Gly Ala Gly Gln Gly Gly Gln
50 55 60

<210> SEQ ID NO 57
<211> LENGTH: 59
<212> TYPE: PRT
<213> ORGANISM: Latrodectus geometricus

<400> SEQUENCE: 57

Gly Gly Ser Gly Gln Gly Gly Gln Gly Gly Tyr Gly Gln Gly Tyr Gly
1 5 10 15

Gln Gly Gly Ala Gly Gln Gly Gly Ala Gly Ala Ala Ala Ala Ala Ala
20 25 30

Ala Ala Gly Gly Ala Gly Gln Gly Gly Tyr Gly Arg Gly Gly Ala Gly
35 40 45

Gln Gly Gly Ala Ala Ala Ala Ala Ala Ala Ala
50 55

<210> SEQ ID NO 58
<211> LENGTH: 48
<212> TYPE: PRT
<213> ORGANISM: Latrodectus geometricus

<400> SEQUENCE: 58

Pro Gly Gln Gly Gly Tyr Gly Gln Gly Gly Phe Gly Gln Gly Ala Ser
1 5 10 15

Gly Ala Ala Ala Ala Ala Ala Ala Gly Gly Ala Gly Gln Gly Gly Tyr
20 25 30

Leu Gln Arg Gly Ala Gly Gln Gly Ala Ala Ala Ala Ala Ala Ala Ala
35 40 45

<210> SEQ ID NO 59
<211> LENGTH: 37091
<212> TYPE: DNA
<213> ORGANISM: Latrodectus hesperus
<220> FEATURE:
<221> NAME/KEY: misc_feature
<222> LOCATION: (34996)..(34996)
<223> OTHER INFORMATION: n is a, c, g, or t

<400> SEQUENCE: 59
acttcgaaac attcacgcat ttcggtacca ttcagtacca ctacaaagag ccaactcgaa 60
gcaaaaataa gaaattcata attattcata ctattttcaa ttccatttgt atcacttatc 120
tttacaggtg ttacatcgta cacgtgattt tactgctgtt accttagtat ttgtgaaaag 180
caacagctat tcaaatacac agtatgtaaa aacgtctctt tgaataattt ctctgcacga 240
aatcatataa tatttcagaa aaagaagtat ttttagaaaa tataatcata tagagcaaac 300
ttgaaaggta tatggtgttt gagaaacctc gtggcagatt ccccacaaat gataaagcaa 360
acagtgtctg catgaactaa aatttttaga aaacaaaatt attgtttcag ccaatatcac 420
acggaattaa gattttaaga cgtagatacc aacagcatca tttctaactt taacgtaaat 480
tgtgacctaa attcaaataa tccattttac ttgaaatatc ttgcacgcga tagataattt 540
ctgaattaac acttgttgtc ttaatgaatg tcatttgata ataattatta attccgaaat 600
tcgcgaattt aaacaaacat taattcaggc atgcatacac aaatcaaatg ccacgaaatt 660
aattgacata aactttaaag cttaatctta ttttgcaaat ctttaaaaaa agtatttgga 720

-continued

```
cttaattata tataagcgaa tccatgattt gacagtactt tacatattta aaggagaata    780

atccgtccaa cgtgtctagt ggtcagtgtg tctgactgcg gatagtgagg tcctgggttc    840

gaatcccggt tcgggcatgg atgatctttc tctatctatc atgtttttgt tcttttttg    900

tatgaatgtg gaatgaatgc ttgcctaccc tgtaagcggg tacctatggc atttgtgtac    960

tgaggaagtc ggactccaca ccaaaatatg tttcagttgg aaaagtggag cagagcaccc   1020

catattgtgc cagcctggct ggcatacgac aacaacaaca acaaaggaga ataaaattgt   1080

ggaaattttt aacaccaatg aagtgggaca aaaatgtatc gtgtttaaga cgttgctcct   1140

tttaattata aacttcgcaa ttattggtta aatattaatt tgccattgaa ttgaacagtt   1200

taaattcttt aatgtattat ctagcttgta aatgtcagta actcattcaa ataacttata   1260

aaaatgtttt gaaactgcat attatctata gtttattata tccaattaaa agtatctcaa   1320

agttttatac ttagtgtatt tcactattga gatttagtaa tttggagagt aaagtgttgc   1380

taagatacag tgagcgcgat atcttaataa tcaaatggca tcgagggctt ttccccacaa   1440

aaagattcca tagggtcctg tgtccctcac atgatgggat gtgatgttga gaaaaatata   1500

caatattaga tgtcgaattg aggttcaaaa tttagtgaca gggctgtttc atcgatttgt   1560

ctcggcagaa ataagcagtt tgaattgtat cttaaatacc taaccttaac ttcgtttgtt   1620

tcaaatttca ctttaataaa ggtaagcttt taaaattaag aatagttatt tttatagtaa   1680

atttaaaccc attgaagatg aaaatctatg acaaatgcat cgtgatttta cgccgtttat   1740

tatccggtca ttttagaatc ttaaaattaa tttcaaatca gtcaaacaat tgactctaga   1800

tcttgtttgg tcatccaatg attacaatct aagtccatgc tagatcgata gtgttttcaa   1860

gcagaatcga agagtaattt cggtagtatt atcatccacg cgcgttttac aagcaatggc   1920

aaaaatataa ctgcaacaac tataccaagg ttcagacact ttaataaact atatacatga   1980

gtatcacacg cttcaattct acaccactga ccattaaaat tgcaagaagg aatgcaaata   2040

acagaacgat atttattgga cacatacgtt atagtggaaa gagcaagtga ttagatttac   2100

aggaaattag gatgtataga tcttgagaaa tcagtaccca gagcagcccc ctctggctgc   2160

aataacagca tttatccgcc taggcatgga gtcaaacaga gattgtatgg catgtacggg   2220

gatctcagtc catgcagctt caatactatg ccacagttca tcgacagtag tggatggtga   2280

gtgatggcgt gccaatcgtt cggcaaccat tgaccaaacg ttctcaattg gtgacagatc   2340

aggagaacgt gctagccagg gtaacagtgg aacctgttct gtatcaaggg agttaagaac   2400

agtacgggca acatgcggag gtgcattatc ctgttgaaac aaagcattag ggtggcctcg   2460

aagatagggc agagccatgg gccttaatac atcggaaatg taacggttgc tgttcaaagt   2520

gccggtaatg cgaacaagag gtgatcgaga cgtgtatcca atggcacccc ataccatcac   2580

tccagccgat gggccagtat ggcgatgtcc aatgcaagct ggcaatgcgc gttctccacg   2640

atgcctccaa acacggatgc ggccctcatg gtcctgtata caggaccatg aggtataaac   2700

cgagattcat ctgtaaagat gacatgacgc caatcccgcg tccaggttcg tcgcggatca   2760

caccattgaa ggcgctcctg tctgtgacgc agcgtcaatg gtagccgaag ccatggtcgc   2820

cgtgcagaca atccatgctg ctggaaacgt cgtcgaacgg agcagaaact tgttgccttg   2880

caaatgactc catttatcga ctcagggttc gtgacgtggc tgtacgatcc cttgtgacca   2940

tgcgataaga cgtctgtctt ctctgctgtt agtgatgggg ggtcgctgag atcctgcatg   3000

acgttccgta tgattgtcct gaacccatcg attccatatt ctgctaacag tcatggagtc   3060

tcgaccaacg cgagcagcaa tattgcggta cgataaaccg caatcccggt aggctataat   3120
```

-continued

```
ccttcttcga tcaaagtcag actcgtgctg ataggcattt cttcttctta catgaggcat   3180
tacaacaact ttctttgccg aaaacaacgc tgaaaacgga aattgagtat gagaaaactg   3240
ctgtcaaatc tctggtggtt ttatacacat tgtagatgtc gctactgtcg cctgctttgt   3300
atgaatgcgc tgaaaatcta atcatttgca tatcacagca agttctactt gtcatgcaat   3360
tttcacgtgt gtggtgtgac gctttccttt agtagcgttt ttaatggcca gtagtggata   3420
ttgtaattat tttttaagga acacgattgt agcagttcag cagatattta aattgtacga   3480
tctccgatag agtgacaaag tttaaataat gaatgagttg atatttactc aacaatatta   3540
tgacatgcgt tgcatttaat atgtgctgga gaattgaaga tatactacgt gacattaaaa   3600
atgcaacacc aagaatcagt gaccagaaaa ttatacaaat ttaaggttag acgtaccata   3660
catagttatg aaaatgatct gaaatatgga aactcttctg catacgtagg ataagataaa   3720
aggtgaggaa ctggcagaat gggaaatatt caccccgtta ttgctgcttc aaaaataatc   3780
cttgaaaatt tgttcctgtc ttaaagtacg cctgcaattc ccgagaataa taggccatcc   3840
tcgtcggagt caggtgcagc agactgacgt gtttacaagg gacatggtga tcgaactgag   3900
aaaagcaagt tggtccttac tacaaaccac agctaacaga cacctgtgcg cttccagtgc   3960
atcggctgtg cagaagatgt ttacaacaag gaactgtgga acgttggcgg ggtaccggta   4020
cagacagagt gacgtcagta cgcttggatc cacgtatcca atgggaagtg gtagcaattc   4080
cgtaaagcaa gtctaccaaa attctgcagc atgtgtaaga cacctaggat gataccgtat   4140
cgagcagaac actttgccaa cgattggttg ctagtgtcct gtggtcatag agtctgttaa   4200
gaagattggc attgacttaa catcttagac accaacgtcg gaaatggtgc cgaattagat   4260
agacatgtgg acgacggagc ggcaaaggat cgtcttctca gatgagtcac gcttctgttt   4320
tttcagtgat agtcgccgcg tacaagtgtg gcgtcgacat agagacaggt ccaatcttga   4380
agcaattaca gaactcccca cagcgtgaca acgtggcatc atggatagga gcaccattgc   4440
gtttgattac aggtaacctc taattcgtat ttacggccat gtgaaagcac aacattatgt   4500
ggataatatg gtgcggccag tggcacttcc caatcttcaa ggggtgtcca atgtatttta   4560
tcagcaggat gatgcccgac cgcacatttc tcggatcacc caacatgctt ttaaaggtgt   4620
aaagctgttt ccctgaccac cgtgctcgcc agatctctca ccaatcaagc acgtttggga   4680
tgttattgga tgctattaac agaccctgcc actgcctcct ttagaagaag cactttagca   4740
aatggttgac attcctcagg acggcatccg tattttcatt gattctgtgc ctagacgtgt   4800
tgcttcatgt atcgccgtcc acggtggtcc tactacctac tgatccgacc ctgctttcga   4860
tatgtagtat gcttatcatt tcgaaataca gatcactaat tttccgttgc tgtctctctg   4920
tggtcgcgga gtttcgtcac tttctggcaa ctccttcttg gtgttgcatt ttcaatatcg   4980
agcagtgtat atacaactta gagaacatca tacaatcaga agtgagttta aaacacatcg   5040
ggacaacatc taagcaagat atggattgcg tgtttcttat aacatttcct tatttaaatt   5100
ctggagccat acacaatagg tggagaattg attgtatttt cggtaaaaaa aaatttctta   5160
accaattgtg aacggttgat aattcattaa ttatataata tcggtgatat gcttcacctg   5220
ataccgcatc ctatttactc cactaatagt aaggtatcga ttaaagtttt tagatctaac   5280
tgacatgaaa tgcaccgtgt aggcacaaac aagcttttca cattataaaa aggattttac   5340
tgaataataa tgcagcacaa ataattgacg aaatggctca atccgtagca atttctttat   5400
atgaatactt aaaaagtctg aattttctat aaataatctt tgatataaaa gtccacttta   5460
```

-continued

```
caaaaaaaaa acaagtttta tttttaactt gtacaagagg gaaaattttc caaatattgt   5520
tagttactaa aagttttgaa atcattaatt aaagtgaaat gttattaacg aattaaaata   5580
tttttctata tacaatatat acctattccc agtaacattt cttttgatac tgtccgcctc   5640
aagggattaa cctttttttag gtaaacacgg gtgtcacaat cccgaggtac caagtgatct   5700
gtcctcttct ttaatttctt ctcatctcta ctcttctgct ttttcttcct tttcctcctc   5760
gttgtggttg cctcataaga agttgggagc taccccttgag tagagatttc gccgctatgt   5820
tgcaattagc tcctcatggg gactaaatca cacgcgtgtt tgcagtgcgt ggatacccgt   5880
gtccctggaa aggagggtcc tggtaattga ggacaccaga gaccaacaca ttactttgac   5940
ttctgcttca ggtaaacggg aaatgtattg tggtcagcag cacatcaatc ggctttatgg   6000
atcaagcaat cggtacatct ataggatgac tcgttaaggg tggagaccat ctcagggatg   6060
tactgtgagc gtataggacc tagcaagtac tggtgcagct ggtctgcatc cccttgttgg   6120
attcagtagt gggtggtgcg gtcaggtccc aaaatttaaa aaatattata atggcgaata   6180
aacattttaa atttctccca cgagagcaac agtttgaaaa cttaaatcct aaatttttca   6240
taatcaaaag aaaagagaga aactttacaa ctaaaactcc tttcctcaat ttcaaaggaa   6300
tatcgggtat tgttggagaa gttaagaagg ttcagaagat gcgctcaggt gacctgcttg   6360
ttgaggccag catctgactc tcaagcagaa attctggcaa gcatgaaatc tctggcaaat   6420
attgaagtga ctgtctctcc tcatagcaac ctgaactttc cttgtggtgt aatctcagca   6480
agggatttat tatattcgcc gacgcaagag atttacagaa tcagaaggtc tgtggcgtta   6540
gacgcattac agtcagacga gatggtaatg ttttcgatac taagtcctga cttttgcgac   6600
accattatgt aaaatctgcg tacatgaatt tacccgacag gccttacatc ccaaatcctt   6660
tgtgatgttt ccaatgtcag cgctttggac actcgagaaa tgcttgcaga ggcaaaacta   6720
cttgcgcccg ctgcgcggtg gttggccacg atagttcgaa ctgtacagct aaggagaggt   6780
gtgtcaactg tcatagtgat caccgctctc attctcgaag ttgttgtccg tatatattgg   6840
agaaagagat aaccacggtt aagttcaatc aaaaatgttc ttatcctgag gtgagacgat   6900
tgctcgctgc ttgcaatatt cagtcaggag tcagttatac cactgctgcc agaaaagtca   6960
ccaaatcaag cagctcttaa actgaatcat tttcgttttc cccaataaga ttatcccaaa   7020
catctgaaaa gccaaatttc aaaaaatctc ttacatttgc tagaaaagct ccttttgcta   7080
aatcaaaagc ggagaaagct ttaaaattaa aaaaactaaa cagttttcca ttttcaacca   7140
aaatatttc tcttgcttgg agactgacac gacttcttta cttccctcgg atgatgatac   7200
gtcactcgag gatatgacag aaaacccacc ttccaatccc gagaaaggag cttttcaatt   7260
taaaaaatga cttcctttat ttcttggaac tgccatggtt tgcgatcaca tcttgatggc   7320
atcaagtttc taataacaga ttataatccc ccatgtgttg cacttcagga gacattcctg   7380
aagtctaata aaaactttac catgcgtggg ttaacatgtt ttagaaaaga ctgtggtgat   7440
gatggtgcag tgtctggtgg tgttactgta ttaacatcca ctaattttcc cagtactgtc   7500
caccatttgg atactactct aaaagctgta gctgtgaaaa tacacactac atgcttgatt   7560
acagtctgtt gtttatattt tccatcacac aatccaccaa gaggaactcg atgctttagt   7620
tgatcagctg cccacaccat ttttgttcat cggtgacttt aacggacatc attctttgtg   7680
gagaagtgat gatatcaatt ctcgtggacg acagatagaa cagtttattt ctgataattg   7740
tctctgtctg cttaataccg acgagaagac atatttccat gtacccacaa gaatatttca   7800
ttccctcgat ttagccatct gttccccatc tcttctgcca ttattaaatt taactgtagg   7860
```

aaatgatctg cgtaatagct atcattttcc tctcgtcatc tcccagactg gaagtagtag 7920
tataagacaa cgcttaccta cttacgtgta cagttgggca gattggacat tatttacaca 7980
aatggcagtt gttgattatg aaatggtttc aatcgataat attgatatcg cagtttgtaa 8040
agtcaaaaaa acaattgaca atatagctta tacatcaatt cgaagagttc gcctatacca 8100
aacaggcgta gcaaacctta gtggaataaa gaatatcaag aaacaattaa aaaacagagg 8160
aagttatggg ggttatttag gaggtacccc acaacagaga atcttatcgc ctttaagaga 8220
gcaaaagcat tagctcgcag agctcttcgt cgaagtcaga aggaatcttg gtctcgctat 8280
gtatcttcaa ttacatcttc catatccagt aagcagctgt ggagaaaagt gaaagcagcc 8340
aatggaatat ataaggaatt ctttattcct attttaaaat ccggagctgc tatatactct 8400
tctcctaagg agattgctaa cgtccttcgt gaaacctttg ctagcgtctc aagcatcgac 8460
tcttatagtc cttcgttctt aaggacaaag agtctggctg agcaaacagc aattcgtttc 8520
aaacatggat aagctttgct ttacaactgt gaatttccga tgttggaatt gaagagagca 8580
ttacagcaga ccaataatac cagtccagaa tcttatggaa tcagatatca aatgcttcgt 8640
catttatgtc cagattcctt atcgaacgaa ttgtttttgt tcaataggat atggattgaa 8700
aagaaatttc catcactttg gattgaagca acagtgattc cggtcctgaa ggctgataaa 8760
gatccttcat atacttcaca ttatcaacca atcgctctga agagttgctg atgtaagtaa 8820
gattctcgaa cgtattgcca acgcacgtct cgtatatgtc ctagaaaaaa attaatgtat 8880
acatattaat cagagtggct tccgaaagat ccacttttga taatatcact taattggaaa 8940
cccagatacg aaacgccttt gtgcgaagga atcatctggt ttctgttttt ttcgacatag 9000
agaaggcata cgaccgtaca tggcgatatg gaattcttcg ttcattatat aattttggct 9060
ttcggggtaa tcttccaata ttcctataaa aatttttaag ctcccgtgtt tttaaagtcc 9120
gtgttggaac agtttttttcc aatactttta ttcaagctaa gggtgttccc caaggctcca 9180
ttttaagtgt cactattttt aatcttttca tcattaacat ccttcatcaa ttaccgcctt 9240
caataaatgg tacactatat gttgacgacc tgtaaatatc atgtcagggg tctaatatgc 9300
gattgacaga caactgcaaa cagcagttaa caaacttcct gcatggtgtg tagaaatggc 9360
cataccttat caccaagcaa gagtaaatgt gtccactttc gttgaaagac tagcttacat 9420
aatgatccaa ttatttatat caacaacact ccaatacaag tagtcaatga aataaaattt 9480
ttgggaatta tctttgaccg aaaattaacc tttcttccgc atgttttata tttgcggaag 9540
aagtgtgagc aatcgcttaa tatcctcaaa gtgttgtcaa atacatcttg ggtgcagat 9600
cacacatcac ttcttcaagt ttatcagtct ttgattttat cccgcattga ttacgaatga 9660
gttgtttatg gattggctag atcttctgtt ttacgaagac tggacacagt acatcactct 9720
gctttaagga tatgttctgg agcattccac acatccccta tcctgagtct atacgtgatt 9780
tgtcaataat tacttttaaa ccggagacga atgcagcaaa ctctcaatta tttcgcaaag 9840
ataatatcga ccccacatca cccattacgt tccatgattc ctagtgcgtt tcttattaga 9900
ctgtttgatg ctcgcccatt gagcatttca ccttttctca caagagccaa atcacatctg 9960
cggctcatag atctatgtga tgttcggaca aaatctgttg acaaatttgc ttatctacct 10020
tggtatgacc caacaaatac tttcattaat atctttgctc agtatagaaa atcggataca 10080
acacctattg tttttcaaca gtaatactct tctcatcgct gtcagtatca atcatataaa 10140
cctgtattca tagatggttc taaaacagca ggacatgttg cctgtggagt tttatcaat 10200

```
aatacagatt ttaattacag cctacatcca tcctgctcca tctttactgc tgacgcaacc  10260
accttatact gcgagcttca gcatgtgaac acagataact atcatcaata ttgtgtttat  10320
actgacaaca tgagtatttt agaagcctta agaagcaata gtttcacctg tcaccctgtt  10380
gtctccaaac tttttagagc actgaattcc cttgctgaca aaggaaatga aattgtattt  10440
tcttggatac caagccacgt aggtcttgtt ggaaatgaga gagcggatac agctgcaaag  10500
actgcatcag gtacagtttt accatcagtt cctctctcag atgtgagaaa atgtgttaaa  10560
atatttatac attctctatg gcaggaatca tggaacttac aggtcggcaa caaactacat  10620
accatttttt catccctcat cccattatca gttttatcgt tacgaagtgc tgatgttaga  10680
tagactcgcc atgatatcgg acacgcacgt tttacacacc gacatttatt cttacatgaa  10740
ttaattcctt ggtgtgatac gtgtgaagaa ccatatactg tgtttcaaat tttaatctca  10800
tgtcctactt ttaacgttta ccgttttaaa tttttcaaaa taaacatttt aaccatgtct  10860
gatttgctgg ggcaaccccc ccacagaaat ctatttgctt atttgagagc aacaggtatt  10920
ttaaatttta tataatttaa attttaaatt tgaaaattat atttatgttt gatttatctt  10980
attttatatc ctataattag ggagccagtc ccaagagatt tgaaagatta gatttatatt  11040
gtaattcccg gaacaatggc ctagagtcta ttccgggaaa tagctatatt gagtgatagt  11100
tgattaatat tgtaattcaa atctcttctc actccggcct gcacctctac gttggtggct  11160
cctagtaaca ccaataacat cggtggctaa cgtaggcgga ggggacaccg cttttgttct  11220
aatttttcat aatttgctta attttttttg gttgcgtgtg ccaaatttct tgacttattt  11280
tcgtttaagt taattttgtc aggtgtgcta aggcttagca caagacacca ttatgacgga  11340
agtaccgttg aaccaaggtg gagatgccac agttttaagt ttggacttaa acgaaagact  11400
caatgctgtc ttctatctcg aaaaagatat tcagactatt ttagctaaca gtaagatatc  11460
attaacatct caagctaaaa tacgagatgg agtgagcgac ttgatgaaga tagttatgaa  11520
tcaaatgcaa gagatatctt atttaaaagc acagataaag acaactaagt catatgcaga  11580
agtagtacag aaggtgacgg ggattgaaca taacttgcaa acgcaattaa gggctaagga  11640
aactagagat aggtctcgtc agaggaaaaa taacatacta atagtttatc ccaatcaaga  11700
agggaataca tctgatgata ctaggaatgt agttaagaga attatagatc catcaaaagt  11760
gaaagtaaac aaaactagat ctattagaaa gggaggcata ataatagaaa tgaatacagt  11820
tgaggacata gacattctgc tgggtgaaat taaaaaccaa gataaagata atgagttggt  11880
ggctaccaaa ccaaacagga gaaaaccaag aattataata tacgatgtag acaaggaaat  11940
agataaagat gaaatagtac ataaacttag gcaacaaaac gatttagatg aagacttcgg  12000
tctagaaaaa ctatataaat ttagcggaaa atatggaaat aattggatat tgagtgtaga  12060
gtctaaaatt tgaaactatt aaaagaaata tagaaccacg attgaatttc aaaacagttg  12120
atcagtcaaa attcagacaa aaaatagcaa ctctaataga agaaattaat gacgaaatca  12180
tagaagaatt ggaaacaaat gaattagtag aactgattga aaagagtata catagg atct  12240
gtatagaaag caataagaaa tctaataaac aaataagaag tactaactat tggtggacaa  12300
aagaactaac tactcaaaga tcaaaaatca gagcattaag aaggagatat cagaaagaac  12360
cagacgcaga taacagattg aaatttatga agacatataa aaaagcagct gcaatctata  12420
ggaagaacat agttcatacc aaacaaaaag catttaaaga ttatctaagc tcaattacca  12480
atgaaagtgc atttggaaat tactataaat ccattaaaca agaaagatcc agtaataatc  12540
tatctaatat gattttgaaa gaagatggaa accttaccac aaatttcatg gaggcaacaa  12600
```

-continued acgaaatttt aaactataac tttccctatg aagatcaagt acaagttgtt gagaactacg 12660
tcgatttaga agataagaac attactgaat atgaaatcga agaagctatt aatgaaatga 12720
aattgggtaa agcccctggt tttaacaata tcgaacttga aatctataaa gaaatatttt 12780
acattcataa agcatggttt gccaaaatat taaacaaatg ttggaggaat tataccttttt 12840
caaagacgtg gaaaactact aaagtggtct taataccgaa agaaggcaaa gatttaacaa 12900
tggcagattc ttacaggcca atttgcctat taccaatatt tgggaaaatc ttagataaaa 12960
ttattacaga ctaaactata tattgaacca ggagaacttt ataagcagta aacagtatgg 13020
atttatccgt ggtaaaagta caaatgacgc aatacacgaa atagtcaaac aaataaatga 13080
aaataagaga aataaacaat atacatgtat aatctcattg gatatcaaga acgcatttaa 13140
ttctgtaaga acagctaaca ttctggaaat cttgaataaa tgtaaattga ataaaaattt 13200
atacaagata attaaatcgt tcttaactga cagaacatat ttggattatg acaaaaaagc 13260
caaaagatat aatattgggg ttccacaggg ttcctcctta ggtccaattt tttggaactt 13320
ggtcgtaaat gagttactag tagagaatat aaatgataat gtttatctgc aggcttatgc 13380
ggacgacata ataatactat taaaggacaa aacatattat aaatttacta atctatcaag 13440
tgaacctttg aaaattatag aaaaatggat tattaattat agagaaatgg aaagaagtat 13500
taataagagc tgttactcaa tattccccat taaaaaagat attacaagaa gaccaaaaat 13560
acagattatg gggcagaata ttaaatatac atctcatatt aaatatcttg gagttattat 13620
ggataccaaa ttaagttggg cagatcacct aaataaccta caggagaagg tatacaagtt 13680
catgaataaa atacatagga tctctagagt gacttggggc attaaacccg aagtcactaa 13740
gaccatttac aaagcagtca tagaaaaaat gattctatat gcagctccaa tatggtacaa 13800
gaatacagtt aagataaata ataagttaaa tcagatacaa agaataccac tattgaaaat 13860
atctaaagcc tataaaaccg tttcaacgga cgctcttcaa gtattaacgg gttgcccacc 13920
catagattta ttggcctaca ttgaaaaaca aaaatactta atattgaatc aaggcattaa 13980
agtcagaata ggcaatatag attttgacaa taataattct tggcatagat ggaaatcata 14040
tatccatcct ccatgggaca agaaagaaat taattggcct cgaactataa atactcaata 14100
tcactttgca tttatagatg ggtccaaaat aaataataaa gtaggagcag ccataataat 14160
tgggtataat aataaaatag aagacattaa aaggataaga ctcaacgatc aggccacggt 14220
ctacgaggca gaggccaaag caatattaaa aacattggaa tacataatta acaaaaatat 14280
caatagctgt aatattcaca cagattccag atccgtccta gaaactttaa agagctataa 14340
acaaggtaat aaaacaatag atagcatatt aagcctcata catcaaaatg ataaaagatt 14400
tacttttcat tgggtcaaag cccatcaagg aattgaattt aacgaattag cggatttgaa 14460
cgcaaaacat gctactaacg aaccaatcat atcgcatatt gcaccatatt cgaaacaaca 14520
aattaaaaca atagccaata aacacatact gagtctttgg caggacagat ggaaaacatc 14580
aactaaaact agaagactat gaaatttatc ctgcagtaat aactaagaga ctctcagcgg 14640
atttccttct taatcaagtc aagacaggcc atggggcctt tggctcatat cagaacagat 14700
ttttcaataa gactgaaatt tgtaaatacg acaataaatt acaagatgtt gaacacatta 14760
tttatgactg tacaaatttt aaagaaataa ggaataaaac attccctaaa aattataaat 14820
tattggaaat aaaacaattg ttaagtagta ttaaaactag aaaaggaata gtcgaaatga 14880
tgtatattct cttcatagac tccttaccat gtacatatta accgttaatt tattgtattt 14940

-continued

```
tataagtttg tagacaagat caggtctact catgttaaac ttaagttttt gatttgctaa  15000
acgggttgtt taattgttgt taaccttttg ttagattctt tagttttgaa ttttaataaa  15060
ggcaagttgc ccattcttcc gtcagagcga gtctgggtgg accgcagggt ggtggtcacc  15120
ggtctgcgtg tgaggcccag accgtaacat ggtgttatgg acctttttgga ctgcgccgat  15180
gttgttgcag tcttggatcg gaagctggtg taccggctac cgatcggcca tgggccgggt  15240
gctctcctgg cggattactg tccgcgaaca gtcatttttcg ctgccgtata ccttagggtg  15300
ggtcggcctt aacatctagc gttatatcct ataattatat atatagattt taaaataata  15360
tatacactga tttttttaaa gttttactgt tccttgggtt tccaaaaaaa aagtaataaa  15420
taaataaata aaatatcttc ttcaaaaact ttattcttgg cgcagcatgt ccattttgga  15480
ccttttgcca taaaatccaa ccaaccaatc ttttgatact gacggtgaat aataaaacaa  15540
gactttctga tatatttaaa acaagctgta ccgaataaat tatcagtcgg ttatagataa  15600
aatttagtga caaaaaatat tagcgagcgc ttgcatgaat gattagattt tttcttaaag  15660
cttttataga aatcaagagt aagtaatcta tgagagataa tttgctcaat cttatttgta  15720
caaaatggtg aagaatagct ttaatcgtca ttttaaaatg attttatagg ctcttcaatg  15780
tagagttgga atttataaaa aaagaaaata acatgagaca aaatttttatt aaataaaaat  15840
aatacagact ataaatttga tttatttgcc aaacttagca aaactatact cagaggctcc  15900
tgactacttt tccatctttc tgtctggtag agcgaggatt cagagtaatt ttgaatctta  15960
tgacacgaaa aaaaccgatt agaaattggt ttcggaggga aggagagttt cggttcggct  16020
gctgctcaaa agtattgagc cgggcataca cccataacat cttaagtgcg actaagtctc  16080
attaatttaa tttaattgta cttaaaacaa attcttcttt aagaaaatcc aactcatttg  16140
ttattttcat agtatgcatt tccactaaag attccatggg tcataaggtt tggaaaccac  16200
tgttctttgt ggtttgaagt tgaatcttta cagatatttt atatataaag aattatgtgt  16260
gtgagagtga tatatttctt attcaacaaa atttcagtct gtaaaccaaa tatttagcac  16320
ttattactta tttatattcc taaatataga aatatttata aatacagttg taaagaaata  16380
taaacatatt tacagattat aataaattta tttcaaacaa attctgcgta ttacggtttc  16440
aatttgacca ataaaaacga taaaagcata aatcttctca aacatgtttc tcaatttatt  16500
aacttttcga aatttcgaat taaagactca aatccttata acattttcga tgtatttaaa  16560
gaactccatt taaaaatatg ctgaaaaagt ttccgaaaat gtgttacata ctataatgtt  16620
aaaaagatta tatatttgag aactaaaata tatataacta tgttgaacat gaaatatttt  16680
taaaaaaaac actacaaaaa tatacataat aattttaaat taaaactgac ttaaattata  16740
actgacttat agtgtatttc tatacactat aagtcaattt aaataacaaa ataaatttta  16800
tcattttaag gaaatttatc attttagtat actaaaaaat aattaataga aattttcaaa  16860
cagtacatca ttttgagaaa gctaagcatt gatttttatg cagaaagttt ttaaacttat  16920
taaagaattt tagtaaaatt tcaataagta aaataaataa tataatcaaa ataaggttag  16980
acgtctgaat taaatttttg acaaaaaatt actacgcatt tcatttcgcc accaacagct  17040
gaatttgcca cgcagccaga tttagagcgt cacaaaataa cgtcgcgatg atatcattac  17100
ttgcacattt ccaggtggat ttgccaacct gctttttatc acgaaaacac atatagtata  17160
aaaaggatac gcatttttgg aacaatattc agtagggatt tcccaatgac tacaatgaat  17220
tggtctactc gacttgtgtt gtcaatactc gtagtgcttt gcactcagag cctctgtgct  17280
ctgggacaag caaacactcc gtggtccagt aaagaaaacg ctgacgcttt tataggcgca  17340
```

-continued

```
tttatgaatg ctgcttcaca aagtggagca ttttcatcgg atcagataga tgatatgtca  17400
gttattagta atacattgat ggctgcaatg gacaacatgg gtggaagaat cacacaatca  17460
aaattacagg ctttagatat ggcttttgca tcatccgtgg cagaaatagc tgtagctgat  17520
ggccaaaacg ttggagccgc tacgaatgcc atatcagacg cattacggtc agccttctat  17580
caaactaccg gagtggtaaa caatcaattt attactggga taagtagcct aattggcatg  17640
tttgcccaag tatcaggcaa tgaagtttct tattcatcag ctgggtcatc cagcgccgca  17700
gcttcagaag cagtctcagc aggacaagga ccagcagcac aaccagttta cgcaccaagc  17760
ggagcaagtg cagctgcagc agcggctagt ggagcagcac ctgcaataca acaagcatat  17820
gaacgaggag gttcaggatc agcagctgca gcagcaggct caggaccaag tggatacgga  17880
caaggagcag gaggaccagg aggagcaggt gctgcagcag gagcggctgc cgcaggagga  17940
tctggccctg gaggatacgg acaaggacca gctgcttatg gcccatcagg acctagtgga  18000
caacaaggtt acggaccagg tggatcagga gcagcagctg ccgcagccgc agcagcaggc  18060
tcaggaccta gtggatacgg accaggagca ggtggaccag gaggagcagg tgctgcagca  18120
gcagcggctg ccgcaggagg atctggccct ggaggatacg gacaaggaca agctagttat  18180
ggcccgtcag gacctagtgg acaacaaggt tacggaccag gtggatcagg agcagcagct  18240
gccgcagccg cagcagcagg atcaggacct agtggatacg gaccaggagc agctgcagca  18300
gctgcggcag gcagcgctgg acctggaaca caacaaggat atggaccagg aggatcaggt  18360
gcagccgctg ccgcaggttc aggacctaga ggatacggac caagaggacc aggaggagca  18420
ggtgcagcag caactgccgc aagaggatct ggccctggag gatacggaca aggaccagct  18480
ggttatggta catcaggacc tagtagacaa caaggttacg gaccaggagg atctggagca  18540
gcagccgcag cagctgcggc agcaggtgga gcaggacctg gtagacaaca aggatatgga  18600
ccaggaggtt ctggagcagc agctgcaaca gcagctggtg gaccaggata tgtaggtcaa  18660
caaaggtacg gaccaggagg agcaggtgca gcagcagcgg cagcagctgg tagtgcagga  18720
cctagtagac aacaagcata tggaccagga ggatcaggtc cagcagctgc aacagcagca  18780
gcaggctcag gacctagtgg atacggtcca ggagcaagtg gaccagtagg agcagatgca  18840
gctgcagcag ctgcgacagg cagcgctgga cctggaagac aacaagcata tggaccagga  18900
gaatctggag cagcagccgc ggcagcaagt ggagcaggac ctggtagaca actaggatat  18960
ggaccaggag gttctggagc agcagcggca gcagcagctg gtggaccagg atatggaggt  19020
caacaaggtt acggtccagg aggagcaggt gcagcagcag cggcggcagc tggtggtgca  19080
ggacctggta gacaacaaac atatggacca ggaggatccg gtgcagcagc aactgccgca  19140
ggaggatctg gacctggagg ttacggacaa ggaccatcag gttacggccc atcaggacct  19200
ggtggacaac aaggttacgg accaggagga tctggagcag cagcagccgc ggcagcaggt  19260
gaagcaggac ctggtagaca acaaggatat ggaccaagag gttctggagc agcagcggca  19320
gcagcagctg gtggaccagg atatggaggt caatcaggtt acggacctgg aggagcaggt  19380
gcagcagcag cggcggcagc tggtggtgca ggacctggta gacaacaaga atatggacca  19440
ggaggatcag gtgcagcagc tgcagcagcc gctgccgcag ggtcaggacc tagtggatac  19500
ggaccaggag cagcaggacc aattggacca ggaggagcag gtgcagctgc cgcaggagga  19560
tctggacctg taggttacgg acaaggacca tcaggttacg gcgcatcagg aactggtgga  19620
gaacaagatt atggaccagg aggatctgga gcagcagccg cagcagctgc ggcagcaggt  19680
```

ggagcaggac ctggtagaca acaaggatat ggaccaggag gttctggagc agcagcggca 19740
gcagcagctg gtggaccagg atatggaggt caacaaggtt acggaccagg aggagcaggt 19800
gcagcagcag cggcggcagc tggtggtgca ggacctggta gacaacaacc atatggacca 19860
ggaggagcag gtgcagcagc agctgccgca ggaggatctg gacctggagg ttacggacaa 19920
ggaccatcag gttacggcgc atcaggacct ggtggacaac aaggtttcgg accaggagga 19980
tctggagcag cagcagccgc ggcagcaggt ggagcaggac ctggtagaca acaaggatat 20040
ggaccaggag gttctggagc agcagcagca gctggtggaa caggatatgg aggtcaacaa 20100
ggttacggac caggaggagc aggtgcagca gcagcggcgg cagctgctgg tgcaggacct 20160
ggtagacaac aagaatatgg accaggagga acaggtgcag cagctgcagc agccgctgcc 20220
gcagggtcag gacctagtgg atacggacaa ggagcagccg gaccaagtgg accaggagga 20280
gaaggtacag cagcagcagc agctgctgca ggaggatctg gacctggagg ttacggacaa 20340
ggaccatcag gttacagcgc atcaggacct ggtggacaac aaggatacgg accaggggga 20400
tctggactag cagccgcagc agctgcggca gcaggtggag caggaactgg tagacaacaa 20460
ggatatggac ctggtggttc tggagcagca gcggcagcag cagctgttgg accaggatat 20520
ggaggtcaac aaggttacgg accaggagga gcaggtgcag cagcagctgc ggcagctggt 20580
ggtgcaggtc ctggtagaca acaggcatat ggaccaggag gatcaggtgc aacagccgct 20640
gcagcagtag cagggtcagg acctagtgga tacggaccag gaggagcagg tgcagcagca 20700
gcagctgcgg caggcggcgc tggtcctgga agacaacaag catatggacc aggaggatct 20760
ggagcagcag ccgcggcagc aagtggagca ggacctggta gacaacaagt atatggacca 20820
ggtggttctg gagcagcagc ggcagcagca gctggtggac caggatatgg aggtcaacaa 20880
ggttacggac caggaggagc aggtgcagca gctgcggcgg cagctggtgg tgcaggacaa 20940
ggtacaagac aagcatatgg accaggagga tcaggtgcag cagccgctgc cgcagggcca 21000
ggacctagtg gatacggacc aggagcagca ggaccaagtg gaccaggatt agcaggtgca 21060
gcagcagcag ctgccgcagg aggatctgga cctggaggta atggacaaag accatcaggt 21120
tacggccaat caggaactgg tggacaacaa ggttatggac caggaggatc tggagcagcc 21180
gctgcagcag ccgcggcagc aggtggagcc ggacctggta gacaacaagg atatggacca 21240
ggaagttctg gagcagcagc ggcagcagca gctggtggac caggatatgg aggtcaacaa 21300
ggttacggac caggaggagc aggtgcagca gctgcggcgg cagctggtgg tgcaggacct 21360
ggtacacaac aagcatatgg accaggagga tctggagcag cagctgcagc agccgcggca 21420
gcaggtggag ccggacctgg tagacaacaa ggatatggac caggaagttc tggagcagca 21480
gcggcagcag cagctggtgg accaggatat ggaggtcaac aaggttacgg accaggagga 21540
gcaggtgcag cagcagcggc ggcagctgga ggtgcaggag ctggtagaca acaagcatat 21600
ggaccaggag gatcaggtgc agcagcagca ggctcaggac ctagtggata cgaaccagga 21660
gcagctggac caggaggagc aggtgcagct gcagcagctg cggctgtcgg cgctggacct 21720
ggaagacaac aagcatatgg acaaggtggt tctggagcag tagcggcagc agcagctggt 21780
ggaccaggat atggaggtca acaaggttac gaacaaggag gagcaggtgc agcatcagcg 21840
gcggcagctg gaggtgaagg acctgctaga caacaagcat atggaccagg aggatcaggt 21900
gcagcagctg cagcagcagg tggagcagga cctggtagac aacaaggata tggaccagga 21960
agttctggag cagcagcggc agcagcagct ggtggaccag gatatggagg tcaacaaggt 22020
tacggaccag gaggagcagg tgcagcagca gcggcggcag ctggtggtgc aggaccaggt 22080
agacaacaag catatggacc aggaggatca ggtgcagcag ctgcagcagc agcaggcaca 22140
ggacctagtg gatacggacc aggagcagct ggaccgggag gagcaggtgc agctgcagca 22200
gctgcggcag gcagcgctgg acctggaaga caacaagcat atggaccagg tggttctgga 22260
gcagcagcgg cagcagctgc tggtggacca ggttatggag gtcaacaagg ttacggacca 22320
ggaggagcag gtgcagcagc tgcggcggca gctggtggtg caggacctgg tacacaacaa 22380
gcatatggac caggaggatc tggagcagca gctgcagcag ccgcggcagc aggtggagca 22440
ggacctgata gacaacaagg atatggacca ggaagttctg gagcagcagc ggcagcagca 22500
gctggtggac caggatatgg aggtcaacaa ggttatggac caggaggagc aggtgcagca 22560
gctgctgcag ccgctgccgc agggccagga cctagtggat acggaccagg aggagcaggt 22620
gcagcagcag cagcagctgc tgcaggagga tctggacctg gaggttacgg acaaggacca 22680
tcaggttaca gcgcatcagg acctggtgga caacaaggat acggaccagg gggatctgga 22740
ctagcagccg cagcagctgc ggcagcaggt ggagcaggaa ctggtagaca acaaggatat 22800
ggacctggtg gttctggagc agcagcggca gcagcagctg ttggaccagg atatggaggt 22860
caacaaggtt acggaccagg aggagcaggt gcagcagcag ctgcggcagc tggtggtgca 22920
ggtcctggta gacaacaggc atatggacca ggaggatcag gtgcaacagc cgctgcagca 22980
gcagcagggt caggacctag tggatacgga ccaggaggag caggtgcagc agcagcagct 23040
gcggcaggcg gcgctggtcc tggaagacaa caagcatatg gaccaggagg atctggagca 23100
gcagccgcgg cagcaagtgg agcaggacct ggtagacaac aagtatatgg accagttggt 23160
tctggagcag cagcggcagc agcagctggt ggaccaggat atggaggtca acaaggttac 23220
ggaccaggag gagcaggtgc agcagctgcg gcggcagctg gtggtgcagg acaaggtaca 23280
agacaagcat atggaccagg aggatcaggt gcagcagccg ctgccgcagg gccaggacct 23340
agtggatacg gaccaggagc agcaggacca agtggaccag gattagcagg tgcagcagca 23400
gcagctgccg caggaggatc tggacctgga ggtaatggac aaagaccatc aggttacggc 23460
caatcaggac ctggtggaca acaaggttat ggaccaggag gatctggagc agccgctgca 23520
gcagccgcgg cagcaggtgg agccggacct ggtagacaac aaggatatgg accaggaagt 23580
tctggagcag cagcggcagc agcagctggt ggaccaggat atggaggtca acaaggttac 23640
ggaccaggag gagcaggtgc agcagctgcg gcggcagctg gtggtgcagg acctggtaca 23700
caacaagcat atggaccagg aggatctgga gcagcagctg cagcagccgc ggcagcaggt 23760
ggagccggac ctggtagaca acaaggatat ggaccaggaa gttctggagc agcagcggca 23820
gcagcagctg gtggaccagg atatggaggt caacaaggtt acggaccagg aggagcaggt 23880
gcagcagcag cggcggcagc tggaggtgca ggagctggta gacaacaagc atatggacca 23940
ggaggatcag gtgcagcagc agcaggctca ggacctagtg gatacgaatc aggagcagct 24000
ggaccaggag gagcaggtgc agctgcagca gctgcggctg tcggcgctgg acctggaaga 24060
caacaagcat atggacaagg tggttctgga gcagtagcgg cagcagcagc tggtggacca 24120
ggatatggag gtcaacaagg ttacgaacaa ggaggagcag gtgcagcatc agcggcggca 24180
gctggaggtg aaggacctgc tagacaacaa gcatatggac caggaggatc aggtgcagca 24240
gctgcagcag caggtggagc aggacctggt agacaacaag gatatggacc aggaagttct 24300
ggagcagcag cggcagcagc agctggtgga ccaggatatg gaggtcaaca aggttacgga 24360
ccaggaggag caggtgcagc agcagcggcg gcagctggtg gtgcaggacc aggtagacaa 24420
caagcatatg gaccaggagg atcaggtgca gcagctgcag cagcagcagg cacaggacct 24480
agtggatacg gaccaggagc agctggaccg ggaggagcag gtgcagctgc agcagctgcg 24540
gcaggcggcg ctggacctgg aagacaacaa gcatatggac caggtggttc tggagcagca 24600
gcggcagcag ctgctggtgg accaggttat ggaggtcaac aaggttacgg accaggagga 24660
gcaggtgcag cagctgcggc ggcagctggt ggtgcaggac ctggtacaca acaagcatat 24720
ggaccaggag gatctggagc agcagctgca gcagccgcgg cagcaggtgg agcaggacct 24780
gatagacaac aaggatatgg accaggaagt tctggagcag cagcggcagc agcagctggt 24840
ggaccaggat atggaggtca acaaggttat ggaccaggag gagcaggtgc agcagctgct 24900
gcagccgctg ccgcagggcc aggacctagt ggatacggac caggaggagc aggtgcagca 24960
gcagcagcag ctgccgcagg aggatctgga cctggaggtt acggacaagg accatcaggt 25020
tacggcccat caggacctgg tggacaacaa ggtaacggac caggaggatc tggagcagca 25080
gctgcagcag ccgcggcagc aggtggagca ggacctggta gacaacaagg atatggacca 25140
ggaggagcag cagcggcagc cgcagctggt ggaccaggat atggaggtca acaaggttac 25200
ggaccaggag gagcaggtgc agcagcagcg gcggcagctg gtggtgcagg accaggtaga 25260
caacaagcat atggaccagg aggagcaggt gcagcagctg ctgcagccgc tgccgcaggt 25320
ccaggaccta gtggatacgg accaggagca tcaggaccaa gtggaacagg aggagcaggt 25380
gcagcagcag cagcagctgc cgcaggagga tctggacctg gaggttacgg acaaggagca 25440
tcaggttacg gcccatctgg acctggtgga caacaaggtt atggaccagg aggatctgga 25500
gcagcagctg cagcagccgc ggcagcaggt ggagcaggac ctggtagaca acaaggatat 25560
ggaccaggaa gttctggagc cgcagcggca gcagcagctg gtggaccagg atatggaggt 25620
ccacaaggat acggaccagg aggagcaggt gcagcagcag cggcggcagc tggtggtgca 25680
ggacctggta gacaacaagc atatggacca ggaggatcag gtgcagcagc tgcagcagca 25740
ggctcaggac ctagtggata cggaccagga gcagctggac caggaggaac aggtgcagca 25800
gcagtagctg cggcaggtgg tgctggtcct ggaagacaac aagcatatgg accaggtggt 25860
tctggagcag cagcggcagc agcagctggt ggaccaggat atggaggtca acaaggttac 25920
ggaccaggag gagcaggtgc agcagctgcg gcggcagctg gtggtgcagg acctggtaca 25980
caacaattat atggaccagg aggatctggt gcagcagctg cagcagccgc tgccgcaggg 26040
tcaggaccta gtggatacgg accaggagca gcaggaccaa gtggaccagg aggagcaggt 26100
gcagcagcag cagcagcttc cgcaggagga tctggacctg gaggttacgg acaaggacca 26160
tcaggttacg gcccaacagg acctgttgga caacaaggtt atggaccagg aggatctgga 26220
gcagcagctg cagcagccgc ggcagcaggt ggagcaggac ctggtagaca acaaggatat 26280
ggaccaggaa gttctggagc agcagcggca gcagcagctg gtggaccagg atatggaggt 26340
caacaaggtt acggaccagg aggagcaggt gcagcagcag cggtggcagc tggtggtgca 26400
ggacctggta gacaacaagg atatggacca ggaagttctg gagcagcagc ggcagcagca 26460
gctggtggac caggatatgg aggtcaacaa ggttacggac caggaggagc aggtgcagca 26520
gcagcggtgg cagctggtgg tgcaggacct ggtagacaac aaggatatgg accaggaagt 26580
tctggagcag cagcggcagc agcagctggt ggaccaggat atggaggtca acaaggttac 26640
ggattaggag tagcaggtgc agcagcagcg gtggcagctg gtggtgcagg acctggtaga 26700
caacaagcat atggaccagg aggatcaggt gcagcagctg ccgcagcagc aggctcagga 26760
cgtagtggat acggaccagg agcagctgga acaggaggag caggtgcagc agcagcagct 26820

-continued gcggcaggtg gcgctggttc tggaagacaa caagcatatg gaccaggtgg ttctggagca 26880
gcagcggcat cagcagctgg tggaccagga tatggaggtc aacaaggtta cggaccagga 26940
ggagcaggtg cagcagctgc ggcggcagct ggtggtgcag gacctggtac acaacaagca 27000
tatggaccag gaggatcagg tgcagcagct gcagcagccg ctgcctcagg gccaggacct 27060
agtggatacg aaccaggagc agcaggacca agtggaccag caggagcagg tgcagcagca 27120
gcagcagctg ccgcaggagg atctggacct ggaggttacg gacaaggacc atcaggttac 27180
ggcccatcag gacctggtgg acaacaaggt tacggaccag gaggatctgg agcagcagct 27240
gcagcagccg cggcagcagg tggagcagga cctggtagac aacaaggata tggacaagga 27300
agttctggag cagcagcggc cgcagcagct ggtggaccag gatatggagg tcaacaagtt 27360
tacggaccag gaggagcagg tgcagcagca gcggtggcag ctggtggtgc aggacctggt 27420
agacaacaag catatggacc aggaggatca ggtgcagcag caggctcagg acctagtgga 27480
tacggaccag gagcagctgc agcagctgcg gcaggcggcg ctggacctgg aagacaacaa 27540
gcatatggac caggtggttc tggagcagca gcggcagcag cagctggtgg accaggatat 27600
ggaggtcaac aaggttacgg accaggagga gcaggtgcag cagcagcagc tgccgcagga 27660
ggatctggac ctggaggtta cggacaagga ccatcaggtt acggcccatc aggatctggt 27720
ggacaaggtt acggacaagg aggatctgga gcagcagccg cggcagcagg tggagcagga 27780
cctggtagac aacaaggata tggaccagga agttctggag cagcagcggc agcagcagct 27840
ggtggaccag gatttggagg tcaacaaggt tacggaccag gaggatcagg tgcagcagca 27900
gcagcggcag ctggtggtgc aggacctggt aggcaacaag catatggacc aggaggatca 27960
ggagcagcag ctgcagcagc cgctgccgca ggctcaggac ccagtggata cggaccatca 28020
gcagcaggac caagtggacc aggaggatca ggtgccgcag gtggatctgg ccctggaggt 28080
tttggtcaag gaccagcagg ttatggtccc tcaggacctg gtggacaaca aggatacggg 28140
ccaggtgcat caggtgctgc agcggcagca gcagctagtg gatcaggtgg atatggtcct 28200
tcacaatatg ttcctagctc tgttgcttct agtgctgcat cagcagcctc agctttatct 28260
tcaccgacaa cgcatgctag aatttcttcc catgcatcaa ctctattatc aagtgggcca 28320
actaatgcgg cagctctttc taatgtcatt agtaatgccg tttcccaagt cagtgcaagt 28380
aatccaggat cttcctcttg tgatgtcctt gttcaagcac ttcttgaaat aattactgca 28440
ttaattagta tactagattc ctctagtgtt ggacaagtta attacggttc ttcaggacag 28500
tatgcacaaa ttgtagggca gtctatgcaa caggctatgg ggtgaagcct tatgttttga 28560
tttcttataa tgaatccgtg taatttgtag ttttaatttc agaataaatt ttcaaagcat 28620
tctttatttg tttgtcttct ctatggtttc agaagtaagg tcatttctga tgtattatat 28680
gtataattta agcgtttatt attctacatg atttctataa aaaattattt tctaaatata 28740
ttctaaatcc tggtacagtc aaaaaatgcga aaatgtattc ataatttaaa ttgtagatga 28800
attttttgtt gatagttgat atttttcata aatttttaaa ttatgtagat ataagacatg 28860
tcaatcatgt ttcctatcgt ttaaatttgt aaaatgaagt ggtcaatatc taactgttaa 28920
atactgaaat ttatcaggaa ttttgtttta cgtccatcat atttggcatt agtatttaaa 28980
ccagtaaatt ttcagtcata gtattttcaa taaaattcta aaaacagatt tagctgtcat 29040
tttaagaaaa agtttctgta aaaaaattga ttgatagatt attttaataa atttttagga 29100
aaaacctaat cttgaatttt tctcgattta aattcataaa taattattgg gagtttattt 29160
atctccttgg attctgtaag cgattcgttt ttatctatat tcagaataca attttatcaa 29220
aactgtcttt cttatcaatt catgcgaaca actgagtgag atcattgatc caggcatttt 29280
atttaaccgt taagtgaaaa agtaagtttc aatgatttca ttagaacact tttcaacagt 29340
taaataattt ttctcatgag tcgtaaagaa agttaaaaag gatatatcgt ttgcatttga 29400
atacgttttc cataatttgt catagtcata aatttactta ttttcaaaag aatgatagaa 29460
tgcatagttt tcatgttgtg ataaaatgat tgagtattat gtttacaaaa attgacagat 29520
caagtaaaat tgtttatgga tttaatggta atttcattct ttggtaattc tactccacgg 29580
aattagtcat tagaattaat aataaaaaat acatttggga gagtttctgg aaattcttta 29640
ggatgttcaa tgtttagcca aaacgcttcc tctttaaaga tattaatatg cattaaataa 29700
tattttcaat tccatttttt atagaaaata tgtcctggta atttctttaa aatagtccaa 29760
gttaatttta gagaaataat ttttctaata tatacctttc acatgataat agttaggcat 29820
aatatcaata ttaatttttc gcatagtgaa acccaatgtt tgccgaaaat cagtgaccat 29880
tgcttttatg aacgtaaact ttttcacgaa catttagatt ttattggtat tattttttcc 29940
tgggcagaaa ggaaacaatg atgcagtggt ttccttactg agaaaaactt aatcggacga 30000
cataccttgg gattatagac ataaatgcat tttcagatgt tcatggttca gtttgtcaaa 30060
tgatatgtcg aatagatacg aatagataaa aataacaaat taaatagaga ttgtgataga 30120
ataaaaaatt gttccaaaaa aagaaaccac ttagggagtt tgttgtactt attgtaatca 30180
aacgccgatg tatatacata cactactggc cattaaaatt gctacaccaa gaaggaatgc 30240
aaataacaaa aagatattta ttggacactt acattatagt ggaaagaaca agtgattaga 30300
tttacaggaa attaggatgt acagatcttc gacgccgcag gcggacagcc tactcgcgaa 30360
gcgagtgtaa ggctgttaat gtccgctgcg tagagaaaaa aacccatcac ggagaggcaa 30420
caagccaccc ccgccgggca tggaaatgag agctgatcca gtagccggtt tgaacagacg 30480
ggttattgct ctgactgacc gatgatctgg tctgtcatct aaagtctctg ggctcgattc 30540
cggaacaaac cagaaaagcc actccaccaa cccaacgtgt atgcatcatt ccccgtttat 30600
tgaaactttt tatcacatta ctaagcccga acgcgaggtg aggcccacgc agtgagcgtc 30660
acctttacat gtgcaggctg gggtttgaat gccttcatgg gggactttgt gggaaggtga 30720
gccgtattta cgctagtctg gagggaaacc atgaaaacct ctagaactca ccccgagctg 30780
acttgcaact ctactgcggt tacaggaaga gctgcagtac gctctatgac gctagtcttg 30840
ttacattgta gatttggtct ccggaataaa agttcaagtc gtcgacctct tcctttgtct 30900
aaatttgggt tggtggacgc ggttgaattt accttgctgt agcagtaaag ttcacttcag 30960
ttttgcaagg cgtcattctc gcgtgtcctg tgtgactgca ggtgatgccg ctatcctctg 31020
gatcaaagtt catcacattg aatgcgcaca cacacttgct tgtagttttc agaacatgtt 31080
gaacattgat cgtctgagaa accacagctg tggccgatca atgtcaactt tcactaatgt 31140
attggattgt ctctgaaagc acacatttgc attggtggca ctacacaaaa gtttgtaaga 31200
aactgccgct gtgagaaatc agtacccaga gcagccaact ctggctgcaa taacagcatt 31260
tatccgccca ggcatggagt caaacagaaa ttgtatggca tgtacgggga tctcagtcca 31320
tgcagcttca accctatgcc acagttcatc gacagtagta gatggtgagt gatggcgtgc 31380
caatcgttcg gcaaccattg accacacgtt ctcaattggt gacagatcag gagaacgtgc 31440
tagccaggtt aacaatcgaa tctgttctgt atcaaagaag ttcagaacag tacgaacata 31500
tggtcgtgca ttatcctgtt gaaacaaagc attagggagg cctcgaagat agggcagagc 31560

-continued

```
cacgggcctt aacacatcgg aaatgtaacg gttgctgttt aaagtacagg taatgcgaac  31620
aagaggttat cgagacgtgt atccaatggc accccatacc atcactccag cagatgggcc  31680
agtatggcga tgtctaatgc aagctggcaa tgcgcgttct ccacgatgcc tccaaacacg  31740
gatgcggccc tcatggtcct gtatacagga ccatgaggta taaaccgaga ttcatctgta  31800
aagatgacat gacgccaatc ccgcgtccag gttcgtcgcg gatcacacca ttgaaggcgc  31860
tcctgtctgt gacgcagcgt caatggtagc cgaagccatg gtcgccgtgc agaaaatcca  31920
tgctgctgca aacgtcttcg aactgttcga acagaaactt gttgccttgc aaatgactcc  31980
atttctcaac tcagggttcg tgacgtggct gtacgatccc ttgtgaccat gcgaataaga  32040
tgtctgtctt ctctgctatt agtgatgggg ggtcactgag atcctgcatg acgttccgta  32100
tgattgtcct gaacccatcg attccatatt ctgctaacag tcatggggtc tcgaccgacg  32160
cgagcagcaa tattgcggta cgataaaccg caatcccggt aggctataat ccttcctcga  32220
tcaaagtcag acacgtgctg ataggcattt ctttttctta ctcgaagcat tacaacaaat  32280
ttctttgccg aaaacaacat tgaaacggaa attgaatatt agaaaactgc tgtcaaatct  32340
ctggttttat acacattgta gatgtcacta ctatcgcctg ctttgtatga atgccctgaa  32400
aatctaatca tttgcatacc acagcaagtt ctacctatta tgcaaatttc acgtgtgtgg  32460
tgtgccgatt tcctggtgta gcaattataa tggccagtag tatatattat tgctattata  32520
ttgcattact ctcctaattt catacaaatt attttgctga aatctctttc tttcgaatct  32580
cataaatagt tgaagaacga acttgccctc aaaaaacttg tatatattaa caaaaatttt  32640
ctattacata aatattttta caattccttt tttatttgat tataaacagt aaaaacactg  32700
aatagaacaa ttatccaaaa tttctattat ttagtgacta gaccagtatt acagtaaact  32760
actgccaatt gaattacaaa gaaattggaa tttaataatg aaagttgaac acaaagttta  32820
agggcacttt ttcattttta tctttctaag ccaagaaata atgtctgaaa gtgaagccga  32880
aaaatcaatt tttttcatta aaatgtaaaa aatttcaaat actaatgata aagaatattc  32940
gcggcaacac ttgtcacact tcttcatcat tttatcaatg taaccatgaa tgaatcttcc  33000
acatggtagg aatagaggtt tttgcacttt aaaatgaaaa atatttcaga aaactaggta  33060
aaaataatgt acgattgttc tgtaataata tgatcgctta taatcttttt ccacaatcac  33120
tacttatgct tccgataagg aggactgtgt aaaatattac gctccccact tttaaaatat  33180
ccttccatta tttgaatgta gagggaagta agcaataagt gctaaatgtt tttaccagtg  33240
ttcattagat ggaatcattt gaatttctga atttagttac aggaaaggtt tctgaagtaa  33300
tatgtcaata gtagattagt attagtctgg attaccgctt ttatttgtta ttgcctctag  33360
tttaattagt ttcagcatta cctttttact tcattcaatt ttatggaaat attgacgata  33420
ccaaggtaat taatgtaact tgaaaggtcc aattatactg attcttttga gtaatagtgt  33480
cagaggcgag agtaattcat taattccgta atgttttttt cattgcaaag gttatgagtg  33540
gtttttaggc ttcaaacaac tgagaaaatt atatcttttg aatattcatc agttttgttc  33600
ccttaatttc aatttaacag ttctttaaca gagaaatatt ttgtgaagtt tccttacatt  33660
agcagtattt acatgatttg accatgagaa ttaaataaaa tattcagtac aagtttctga  33720
aaagtgaaag gggtaatatt tttctgcaaa aaattacttt ttgtgaaacg acgccactgt  33780
attgtatgac aatattgtag tcaacaaact taggttctac ttggaaggga attccttcga  33840
taaattaaga caattggaca gtattgaaat ttaggagtat acaaaaattt aatatagaaa  33900
```

-continued atcaaataaa atatttttaa atcatcaaag accaacgttg aattataact tcctgataat 33960
ctcatatttt taaatataaa aattatccca tagcaatata aaatattaaa tttatattca 34020
aatattttaa ttggctcaga aaaattgatt tggtatttag ttatattata taattaataa 34080
ttatatatag tttgccgcta tttatttgaa aattttcagt aaatttaaat atgctgccac 34140
aatccactgg taaactttaa taaatcaaag aatttagaat attatatttg gaacacgaag 34200
tgcataattt ctgaggactt tattatcttt ggacttttgc ttttaaagac atcaatttga 34260
tatgattagg aaaattaatt ttatttttcc atgtgttcta gttattaaaa tgaaagaaaa 34320
tattcataat ttttaattta taattaaaat attaatttaa atttatttat tttcaactat 34380
gatctctaat aatttctgaa aaataattaa actaaaattc taaccagtaa ataagtttaa 34440
aaaatttaat aaattcttca aaaaatctct acgttgttta atctcccaga aaaagtaatt 34500
ttaagtgtct gcatttatta ctatacactc aaattgcatg cattcttatg agtctccgaa 34560
tcataagaat cataattcga atcataagaa tccgaatcac acgcttacac aaatcactta 34620
tatataatga taaatttctc atgcaactac agcaacaaaa tgaagatttt atttatagtt 34680
acccataatc ttctcgcatt atgtgtttga ttaataaatc tttttgaaac tgattaaaaa 34740
cttctgaatt aatttaatat ataattgttt tatttttaaa gggtgtttgt ggaaatttta 34800
aatttaactt catatcatgc ttttaacttt taagtaaaat tttaatgtca cgtttccttg 34860
ggaaccctga tacctttttta ttaaaatatt cttacacaaa gactaaacat atataaagta 34920
aatacttcac gaaatgttga ttaatgtatc gttctgaata ttggaaggtt gtgctttcga 34980
gtcccgactt taccgnaaat ccgtggtcat cactaaaatc gactatggca cgtttaatat 35040
atcgtagttg caatgtcctc caagtgaaat tatgtcttta aattgcaggg catgtatagg 35100
gagtcttaat tggttcctgc ttccaaatta cgaagactcc cacacctctg attccaactg 35160
actgataggg ttaaactcag ggcaagtatt gcaaaacatg caacaaggaa ctaaaaccct 35220
aaagagtata ttttgattca ttttgataat acattccatt tagtcaaacg cataagttta 35280
ctgttcatat tcaaagaaat acttcttgaa aaagcataag tttactcatt gcatatttat 35340
cagtattaat tacttagtta agtcatcacg agcacgcgtc atatttcata atttttaaac 35400
ttacgaatat acctttagca tatttcattt ctgtttctta aatactgaaa catttccttc 35460
tctaatttta cttgagagca aagcttagct ttattttata aatccttata ttgaatgaaa 35520
tttacgaaaa gacacatttc tttttttta ttagagaaat tagttattat atgcttattt 35580
atttcaacac caaattagtt ttaaaagcgc aatgaattga taaaagctac aagctgagaa 35640
ttgcgctaag aatttttgtg attaattcat tattcatata tatattctaa ttttaggaat 35700
taggtgcgta aaagtcataa tacgtaacta gatagatatg aaatgagtta catgtaactg 35760
atatctgatg ctatagattt catgtctaag caatattata taacctattt tcatctatgt 35820
aaactagtaa actaggactt tcttttgaaa aaaaatcagc actgatttga atttttgact 35880
tctacatata tatatataat atatatatat atatatatat atatatatat atatatatat 35940
atatatatat atatatatat atattaataa attcatatga gaaatctact attcgataaa 36000
atatattaaa ttaaaattta aaatttcatt gtgttctttt attacctaat tgtaaaataa 36060
ttcataaatt tcctcacttt aatctcacag ggcagtataa agttttcact aagtatatat 36120
atagttttaa ataaattatt tgaagactat gctaggcttg atttatttac acattcttaa 36180
gaatcttcta ttgttgttcg tattttttac gttataaaat tcttttcaat actgaagttc 36240
attttaagct tgttatagta aaatagtcca tgcatatata ctgaaaaaaa ttacatttac 36300

-continued

```
tagactgatt ccttaattta tataaactgc tcaataatat aacattattt gaagcaacat  36360
tgcttataca gattactctg cataaatgat taattattgg ttgatgtgtg tgtttacatt  36420
aaaaaaacaa tctaagttta tttaatctac ttaatatata atgtacagta agaaactata  36480
tataccttaa aaaattatac atcactatat tgcatttcta attggttcac gttgatttgc  36540
ccatttccaa tttacacgtt gacacaagct acttaacttt ggttcattga tttcggatat  36600
gttatattca gtttaggtga tgaatcggca gattcagctc cttcgatttg aaattgtttg  36660
ggtcagtgtt cctggaaaat atcgtattca aacccgaatc ccataataat ttttcccaag  36720
tgatttggaa tggatttaag cacgttaagc ccagccgatc acatccattc atcatccaaa  36780
atgaagcatc acatccattt tggatgctga attcgtgtca tcgacaagtt cgatttaaag  36840
tccaaaagtt gttgagcaat attttgttct taaaacattg gtttttccac gaacaccaaa  36900
acaatagttc ctcaagacac ttaaaattga tttgagcccc gtgtatgttg atatacgcgg  36960
tttaatcaca gtcacatgac tttggataca ttacatttat tttaggtggt gaatccgtgg  37020
ttcacattcc ttcgatttaa agtacaaaag ttattgaaaa ataatttgtt cttaatacat  37080
tgattgttct g                                                       37091
```

```
<210> SEQ ID NO 60
<211> LENGTH: 34047
<212> TYPE: DNA
<213> ORGANISM: Latrodectus hesperus

<400> SEQUENCE: 60

ttcattcatc tatttatctg aacagaaaaa ttactatgaa acgaaaaatt ttacaccaaa     60
gaaggagttt taagaaacca tcaaaattaa gacgcacaat ttcactaaaa atataatcaa    120
ttgaggaacg aatctacttc cctgctgtgt ataaattata acaagtaaaa ataatatttc    180
acaactaaat taacttttta aaatgtttca ttggaaagtt tatttggaaa cgacaaatat    240
acctgcaata aaaatagcgc tttcaatagt ttaatataaa gatagttaaa aaaaaacatt    300
tgaaattttg gaatttaata tggagttatt tttcaatatt aaaataatta aataagtaaa    360
aataaatgca tactttaata acctaactat gaaaaaaata acaataaaat catgtatctt    420
gaaaatctat tgacaccata attttattaa cttttctcag aaacgttaaa tcacattgca    480
ctacaaaaaa ggtgaacgtc tatgcatcag ataactcttg tttcagaaag caatatatca    540
cttccagact aatactggac tgaggaattg gcttagcata cattttacac aacatagaaa    600
gtggtaatca cagccaagga tcacattccg ccaactaaac gtactttcta aggccaagct    660
cattaccaat ccattctacg tggctaggtt tatgatttca taaaagagaa taattgtagg    720
tgtaaacttg gaataaacaa taagtaatgc gcatgaaaat ctatcctatt caacaaatga    780
caccggaaat acgattggga caatgttgat gtacacatta cttcaatcag atagttcgat    840
gtccctgaac atttatggcc acaaaagatc aaaaatattt tcaggtggct gattgaatat    900
cattagattc tgctctggtg agatagcgta aatgctataa tttcttcttt aatttgtgtt    960
gctgaaacct attttcaacc aaccgatttc tcagagatta tgacataact gtttgcaaaa   1020
ttgtacaaaa gagtgttttg aaaatattta atagatttaa tcacaattag atacatttga   1080
tccatgttag aaaaatgata aacgacattt gaaatatggt aaaatttcgc ttgttgtaaa   1140
gaacagtgga atcgaatgtg aaagaaactg agaatttcat aaatttcaaa cgttgtaatg   1200
tatctaaagg aatattttta ttcggaggaa ggaataatta agcttatgaa aatttgcttg   1260
```

-continued

```
cactcttaaa gagaaaaaag actaagaaat atataatata aaattccaca cgctttaatc   1320
catacgttat gatgtaatat gtatattact tataacattc ttttcacatg taaatgccaa   1380
cgttataaaa cttctcaaac aatcgtaaat gtagtaaaaa ttatgtgcta tattcaatgc   1440
ctaattttct tgagtttaaa atttgatatt cgtggtaaat acttttgata agctatacct   1500
taaaattaaa ccttttatca ttttaaaata aaaatcatta acagacaaaa tgtgaaaatt   1560
cgatattctg tcttcgatat tcagaaacca taaaattgat agtatacttc tcttagatgt   1620
atcaaattca gtaattttat acaagaaaga tttaaaacat ttttggggta ttttataaaa   1680
aaaagtattt aaaatcggct ataagactag aaagttgcat gctaggaagt ttgttattca   1740
tgagtattag gtaatatatg cttttgctct tcaaaatgat ctactttatt ggaatgtata   1800
catgaatcaa aatctcatac gataatccat ttaagtaaaa attaaatatg aattttgatg   1860
aagattatgc actatttaat ttgtttatgt taacctttttt atgataaaag gaaaataaat   1920
ttaaaaaaac taaaagcttg aaattcactg tattaacaga tataaataat ataatcatgc   1980
gtcagtagat tttattaaaa ttagtttatc aactcaaatc tccattaaat aaaacttatt   2040
attgtgccat agaaatttta aaaagaaaat agttgactga tttgaaagaa atgctttaaa   2100
tgtctaatgt atgacgcgat gtctcaaaaa ttactattac attatttcct aaaatagcac   2160
aacttaagcg ctgtgccttt cagttataat tactcttaag gaaataagta taataaaagc   2220
gaaatttaat tgtagcattg aagcgtagtg tttaaatgta gtttatttgc gcattcggaa   2280
attgatattt ttttagtttc taacacttaa attatacata gcgaatatgc acactttcat   2340
acagcttggg atctatttga gttgaaaaca taaatcaaga aaaatgcaga aataaatgag   2400
agcataaatt aatgcagata agtaatgtaa gaacgaaaag tagaaaattt actagaccaa   2460
ataaaatgaa attaccaatc attttgtagt tttgctcttg aaaatagtgt ttcaaattta   2520
tataatttcc tcatatttta tcaaaaataa tttgtatggt agtatgtgca atttgttcta   2580
taaactcact gtgaatgtaa aagggggagc atataatgtt ttgcttttgt tactgtttta   2640
cttcttttca caattttata catacagtta atttgaaaaa aaagtattat gaaaatagaa   2700
tattaattgc ctgccccaat taaaataatt ttcgattatg gaacacatat attgtactgt   2760
caatggtaat aatgtctctt cgctgcgaag tatatttcaa agcatataaa tgtagataaa   2820
aaaattagaa attagaaact ttaaattaaa gaatattaat tcttcacaaa ttcttattta   2880
aatttgttaa atgaataagc attaagtatt tcttaagcat attttgtttg cagtattata   2940
ttttaaaata tacatacctc aggtattaaa aatattgaaa agtaatactt attttccacc   3000
tgtaaaaaga acaagcaaaa tatcctgcaa actaaatttt aaattaaatt aatttaagca   3060
aaacccgaca attctgcaga ttttttaaat attatatttt atttaacact tttagcaaaa   3120
taaagtgaaa agaaaactat ttttcttttt aattttaaga ggaaaaataa attgaaaaat   3180
aaacttccag atcagttttt atatttttga aaaatataca ttaatttttt aaaatgtttc   3240
tcctaggtag ttttttttaa agaaattgtt ttcttcatgg atctccaatg agcttttttt   3300
taacagacaa cataattgca tataaatcgc ctaaatatca ttgcttggct aaaacttaac   3360
aaaaaatatt agatagagca attcattagg ttacgaataa ataatttttt agacattttt   3420
gccctatttc ataaattaat tgacgaaaac ttgtatacgc tagaaagcag atcttaatac   3480
taattctatt ttataccgtt gagtatcctt gatttgtatg tacataaaat atttttccct   3540
gtaaactaaa actttttttaa aggttgataa aaattcaaga tttacgaaga ttttttttata   3600
taaaggaatt aagatgactt ttttttaaat taaagatttt atattttttt aaagattttt   3660
```

-continued

```
tctcacgata cccttgtata caaattacaa ggaaatttaa aaatttacgt aatataataa   3720
ttttatgaga aattattggg acatttatgt gatttaaaca agttttaaac attaataaat   3780
gctgtttttt catcaaaaat catttatata tcgattattt acgtaaattg taaaaaattt   3840
catggaatct cataaataat caaactattt tattccaaat atttgctaaa agtgtttgct   3900
tctaatatat tttaaatatg taaatctttc aagcgataaa cttaaaaaaa acctttctgt   3960
aattaataaa aaaataatat ttcatgtaaa tatatttgcg taaaattatt ctaaagtaag   4020
ccttctgagt ttaaagcaag ctcattcatc tgtttctttt gacattcatt caattaaata   4080
taaattaata cttagcatgc aaactttttt ttatttatca gaaattagat aaaaattatg   4140
ttggaaattt taaattagaa aatcacaaag aaaacaaaat aatcaagaaa aatgatgcag   4200
aatatttgtg catttcttaa acatttataa aaaaaaaagc ttttaggaca aacaaaacat   4260
ttttctatca tttaagtaaa gtaatttcga gataattaag tacaaataag cacaactttg   4320
atatttaaaa aaattaattt gtagttcctt ttcaacatta ttttaatttc ttttcattct   4380
acagaatatt ctgcagaatg tgtggtgatg aagtcaatga atattctatt ggaatatatt   4440
gtgatgaaaa aaatggaaag ttataattta tactttccgc atttttcatc gcaatacata   4500
ccctaaattg tattcatatt tactggataa gagcaactta aactcctttt ttttaaatga   4560
aataaaatgg ttcagaaaat agtattcaaa ataatatttc ttaatatatt cattgggaaa   4620
tgagaaattt atatttactt gacaaatgta taaaatattg cacgaaaaat atccaaagta   4680
attttattga atgaaaaatt agcttttgat gtctgaataa gctatattat ttttatttta   4740
attaacttcc tgcgatttca ttaaagttta ttcttgtaat ttagttttct cttccagatt   4800
caatacaaga cgtaaatacg caagtaacat ataaattaaa ttgtcaaata ttttataaaa   4860
atcttcaatt gtcctttatt gatgattaaa tcttgcttta gaaatctttc atctatcgta   4920
aagattatgg cattaaaatt aattctcaat gctattaatt cattttaatt cataaggaac   4980
aatttaatta gttacatcca tcaagcattt aagattaaca atttcattct gccgtaatta   5040
attatttgaa ataaatcgga aaatgcatgc gaaattttgc tcgactccga taaaaggtat   5100
gattgtgaca aataatcaca tttccttttt tacataaaac tgttccttaa ttgtttaatt   5160
tattcatgaa gaactttaac ataattttca gtaaaagaaa atatttattc atgatcataa   5220
taagcaagtg cttaaaattt cgtgtgaaaa catttaatac ttccaaaacg ttgtattgta   5280
ctcattttct tttactttct attactatct tctggagaag tcaacaaagt tttagtaaaa   5340
taattaacct tttacaattc caggattttt atattagttt ttactttggt tccgagaatt   5400
tgattactga ttatcatttc acaaaaaacc aaacagtttt taaatgcagt tcactattct   5460
tatttaatgg ttaacatgta acgcaaattt tgcgtgccaa caaatatcat tagcaaaaca   5520
tgtattgatt aaaaagggta aacgcaatat agagagacct aggtgaatta ttccattttg   5580
gcaaaattgt acaatttatt tttccttcat tacttatgtt tttacgtgat tattaacagc   5640
ttcttaattg attctttcag tctttctagg tgacatcttt caaatttcag aggaattcgt   5700
caaatgacaa taatgcaata ataatttgca tataaatatc gaacataatg aggattgtta   5760
aatatatttt tataactcga ctacaataca cttctaaaac tttccaccaa gagtgccttt   5820
gaatttcagt ttaaaagtat aaatacttaa tatatatgta cgatatcatc tcaattaaat   5880
ataaatttgc tgcaaagaat ttattttttc taagctttat ttaactaact aattgcaatc   5940
taaaatagtt aaatttttat ctaataaagt acttaagata gttaaatttt tcacaacaca   6000
```

-continued

```
tatcctaaaa tatattcata tttatgaaaa aaaaacaaca acttatattc actttcaaaa   6060
tgaataaagt gtttcagcaa agtattcgga atatattcat aggaaatgaa aaagaagaaa   6120
gcgaacactt tttaaccttt acgatggaat gtttaataaa aacattggct acacacactt   6180
acatttttat atttttctta ttttctcatt cttcaacatt atttttatcg aatttttttc   6240
aatgtttgtc ccaaaatttt tttttctaat tgtatcgtat aacatttctt taagatacta   6300
acctgaagta gttgctataa cggaggaaaa tagcatgtct caaaaagatt ggagtaaaaa   6360
agaatgcgca agatttggga tgaatagagt cagattcgat aaacaaaatg tttgtaaagc   6420
cctgaagtat tttcatattg aaatgcatta caaacattgg catcacgaat ctagaaattc   6480
tagaaaacac gttattgtct cagctttatt gctgacgcag ttaacaagcg ttgatgcaga   6540
ttccatggac aacattttta tgtatttatg cgattactgg cctagatttc caatacaatt   6600
tttgtgggaa gaagtgttta ttcagttgaa tttaattcgc aaaatcaaga tatattttaa   6660
aagcatgcct ctttaaaaat tttaaaattc agaaatcatt tacaaaaatt tattaacaac   6720
ttgtatcttg attacaagaa ttcagttttt tgtaatggaa tttaaaaaca ttaaaaaaga   6780
aagaaatatc tagcgaaatt aattaatttt aaggaaataa taatcattaa atattaaata   6840
gaatattcat taaatataga acttaaggaa tgctagtaaa ctttagattt caatacagca   6900
catttaagta tttttctcta aattacacaa aaatattttg aattacaaat acaaaattat   6960
atgaaccaaa aaacgtgaaa tatgtttatg aattgcaaca tactcataaa actcatatat   7020
ggtaataaaa tcagtaacac atttgaaatt atttgtttca aaataacgaa tgtttgcaaa   7080
ggtaaatttc taaaatttcc tttatacata ttaaattatc taggtgtata aatttccttt   7140
tttgtattgc aacaagtatt atgtttatgt attaaaacac atatttatga aacttatttc   7200
aactaataaa atcagtaaca catttaatac tattagtttc aaaataacga atgtttgcaa   7260
acgcaaattt ctgaaatttc ctatatatag atggaaatat cttggtatat aaatttatta   7320
tataaactta tttcgtgttt tttgttactt gatattaatt aggtacatac taataatagt   7380
taggtacata taagtatagt ggaaaatcaa aagatcgatc tttttcattg attacacaaa   7440
caatagatgt gtcctgcaca cacatcaatc ggaatcaata caacaatgtt tctgtttttt   7500
ttttacgtca cgttaataag actggtaaga aatgattaat tgaaatgcag tttgctgtat   7560
ctacccaaat attttgcaca atttaaaaaa aaactgttaa agcaacttaa aggctgacta   7620
tcaaaagtta attattaata ttttcaacaa ttagccttta aggagtctct atttcaaatg   7680
aatgtgtcat caaaaattta aaagtaaaaa tatgatagaa gataagcagt cagaaaatgt   7740
gatgtctgaa gaaaggagaa ctttttaatc ataatactag actttctgta aaaaggaata   7800
attttagaaa aaatttaata cataacttta atatataaca attttgaaaa ttatcttatt   7860
acgtatacct atatatcact taatattcaa aaattattaa tcttataagt aatgctttgt   7920
gtgcgttatc acaatttaag attaatatat cgtttaattc agtacaagta aaagtatttt   7980
agtgattact tttgtgtact gtgtaaatat atacatcatt agtaatatta tgcattaact   8040
ttaagaaggg atgaacaatc gatacatttg aatgtttaaa atgtactaaa acagaaattg   8100
caaactaata tacacgagga tttttgtcta aaataagaaa tttgagcaat atgttttatc   8160
agataacagg gtcacatttt ctactgacac atacataaca cgtagataga gcattgttaa   8220
aaaatcacga aaatcggagg acaatttatt gaatatttaa aaatcctaat ttgtgaagta   8280
atgtgatttc aattcataaa tcaacatttc aaaaacatta ataacctaca cactatacat   8340
gatagaaaat cttttttttac cagaaaaaga tcaatgattg caaaaaacac attttataag   8400
```

-continued

```
cactgaaata aatgaaaatt gattgtatta atcttttgga atactaaaac aaaagcacaa   8460
tgtgatgaaa ttctcgcaat tactgtataa ataaactgtt tacaacaaaa caaatgaaat   8520
tgagtcttga ctaacgaaga attatggtgt ttgtagttca gaacgataaa gatttatgta   8580
agaacaagta atagtaggaa tggtctatag gttgataatt gaattttgta atttaacaaa   8640
atgaaattaa atgacaccat tagaacaaaa atatccatag ataatatacc accttatcat   8700
ttttaaaata tacttgaatt gcaacttgaa tgcttaagtt tataaaagaa ggataaaaca   8760
ttttaaaaca aatggcgaag atatcatcgt agtggctaac agctgcggac ttccagcatt   8820
ttatatgaag tgattagaaa taagcgatgt tccagagaat aaaaatttgt gttgaggtag   8880
tgactaagaa atatatactc tcgacttttc tcataatttt tcattttatt ataaatattt   8940
ttcttatttt ttaaaaattt gcatttattt atacttataa tttattcttc gtaagcagtg   9000
attatgatag tttaaaactt tctaatgctt ttatttcaaa ccctaaaggt taaatattca   9060
aatgttaaat ctaaattagg gtattcgcga aaagaaatag tttaaattca cttcaatcag   9120
aaagtaccag ccgaattaac aaacgaatta cggtataatc tggaaacact taagtgcgga   9180
gtaattgtaa atgtagttct agcagattgt aattttttaa taataagcac tgaaaagtgt   9240
tttgtaattt cgggtaatat cttctataaa atgaatagat aataattagc ttagaaaaaa   9300
aaacattaac atttccaaag acttcaaaag ttcaactgta gaattaaaat tattggaaga   9360
atccaatcaa aaataatttg cgtcaatgga ttaaattgtc agattttcta atgatagtac   9420
acttacaatt aaatgagtgc taataaataa attaaaaaga aaaatggtgt gtaattatta   9480
tagatgaaat aagaatcaat ttgatatttt tatcatgaat ttaaaattta gaacgacgat   9540
gttattcgaa tcaatccaaa tttaatgaaa aattattcaa taaaatatct ctaaatttat   9600
cataaaattt ataaactaaa taaagcaatt atagttccaa taaaaggcaa agttattaag   9660
taaagtttaa tgcaaaatac caaaaatgat attaaacacg taagtattcg catgtaaaaa   9720
cataagaaaa cttgcatttc accttggaaa aaacaggtga ctaaattcaa acaagaagta   9780
cacacgtcat cttagcacgc ggacatgaca caattgtctg catatctcca ggtgtattga   9840
aaaacctgct gcacagcacg accaatcatt gtataaaaga ggcaatcaat cagcgtacag   9900
tattcagtcg ggattttcca actactacaa tgacttggtc aactcgactt gccttatcat   9960
ttcttttcgt gctctgcact cagagcctgt acgctttggc gcaagccaac acgccatggt  10020
caagtaaagc gaatgctgat gcttttatca attcctttat ttcggcagct tcgaatactg  10080
gatccttctc ccaagatcag atggaagata tgtcattgat tggtaataca ttaatggcag  10140
caatggataa tatgggtgga agaattacgc catccaaatt acaggcttta gatatggctt  10200
tcgcatcatc tgtagcagaa attgctgctt cggaaggagg agacttagga gtaacaacaa  10260
atgcaattgc agatgcttta acgtcagctt tctatcaaac aaccggagta gttaatagca  10320
gatttataag cgaaattaga agtttgattg gcatgtttgc acaggcatct gccaacgatg  10380
tatacgcctc agcaggttcc agcggtggag gagggtatgg agcatcttct gcaagtgcag  10440
catctgcaag cgcagcagca ccatcaggtg tcgcatatca agctccagca caagcacaaa  10500
tttccttcac tttgagagga caacagccag ttagttatgg tcaaggaggc gctggaccag  10560
gaggagctgg agcagcagcg gcagccgcag cagcagctgg aggagcgggt caaggaggac  10620
aaggagggta tggacaagga ggatacggtc aaggaggtgc cggacaaggt ggatctggag  10680
cagcagcagc ggcagcagca gcagctggag gcaccggtca aggaggtgct ggacaaggtg  10740
```

-continued

```
gagcaggagc agcagcggca gccgcagcag cagctggagg tgcaggtcaa ggaggacaag  10800
gtggctatgg acaaggagga tacggtcaag gaggtaccgg acaaggtgga gctggagcag  10860
cagcagcggc agcagcagcc ggaggtgcag gtcaaggagg acaaggtgga tatggacaag  10920
gaggatatgg acaaggagga tacggacaag gtggatctgg agcagcagca gcggcagcag  10980
cagcagccgg aggtgcaggt caaggtggac aaggtggcta tggacaagga ggttacggtc  11040
aaggaggtgc cggacaaggt ggagctggag ccgcagcggc agcagcagct gcagctggtg  11100
gagccggaca aggaggatat ggccgaggtg gagcaggaca agggggagca gcagcagccg  11160
ctgctgcagc cgcaggagct ggtcaaggtg gttatggagg acaaggtgcc ggacaaggtg  11220
gatctggagc tgcagccgca gcagcagctg ctggaggggc aggtcaagga ggacaaggtg  11280
gatatggaca aggaggatac ggacaaggtg gatctggagc agcggcagca gcagcagcag  11340
ccggaggtgc aggtcaagga ggacaaggtg gctatggaca aggaggttac ggtcaaggag  11400
gtgccggaca aggtggagct ggagcagcag cagcggcagc tgcagccgga ggtgccggtc  11460
aaggaggaca aggtggctat ggacaaggag gttacggtca aggaggtgcc ggacaaggtg  11520
gagctggagc agcagcagcg gcagctgcag ccggaggtgc aggtcaagga ggacaaggtg  11580
gctatggaca aggaggttac ggtcaaggag gtgccggaca aggtggagct ggagcggcag  11640
ccgcagcagc agcagccgga ggtgcaggtc aaggaggaca aggtggctat ggacaaggag  11700
gttacggtca aggaggtgca ggacaaggtg gagccgcagc ggcagcagca gcagcagctg  11760
gtggagcagg acaaggagga tatggcagag gtggagcagg acaaggtgga gcagcagccg  11820
ccgctggagc tggtcaaggt ggttatggag gtcaaggtgc cggacaaggt ggagctggag  11880
ctgcagccgc agcagcagca gccggaggtg caggtcaagg aggacaaggt ggctatggac  11940
gaggaggtta cggtcaagga ggtgccggac aaggtggagc tggagcagca gcagcggcag  12000
cagcagccgg aggtgcaggt caaggaggac aaggtggcta tggacaagga ggttacggtc  12060
aaggaggcgc aggacaaggt ggagccgcag cagcagcagc agcagctggt ggagcaggac  12120
aaggaggata tggcagaggt ggagcaggac aaggtggagc agcagcagcc gctgctgcag  12180
ccgctggagc tggtcaaggt ggttatggag gtcaaggtgc cggacaaggt ggagctggag  12240
ctgcagccgc agcagcagca gccggaggtg caggtcaagg aggacaaggt gactatggac  12300
gaggaggtta tggtcaagga ggtgccggac aaggcggagc tggagcagca gcagcggcag  12360
cagcagccgg aggtgcaggt caaggaggac aaggtggcta tggacaagga ggttacggtc  12420
aaggaggtgc aggacaaggt ggagccgcag cggcagcatc agcagcagca gctggtggag  12480
caggacaagg aggatatggc agaggtggag caggacaagg tggagcagca gcagccgctg  12540
gagctggtca aggtggttat ggaggtcaag gtgccggaca aggtggagct ggagctgcag  12600
ccgcagcagc agcagccgga ggtgcaggtc aaggaggaca aggtggctat ggacgaggag  12660
gttacggtca aggaggtgcc ggacaaggcg gagctggagc agcagcagcg gcaacagcag  12720
ccggaggtgc aggtcaagga ggacaaggtg gctatggaca aggaggttat ggtcaaggag  12780
gcgcaggaca aggtggagcc gcagcggcag cagcagcagc agctggtgga gcaggacaag  12840
gaggatatgg cagaggtgga gcaggacaag gtggagcagc agcagccgct gctgcagccg  12900
ctggagctgg tcaaggtggt tatggaggtc aaggtgccgg acaaggtgga gctggagctg  12960
cagcagcagc agcaggaggt gcaggtcaag gaggacaagg tggctatgga cgaggaggtt  13020
acggtcaagg aggtgccgga caaggcggag ctggagcagc agcagcggca gcagcagccg  13080
gaggtgcagg tcaaggagga caaggtggct atggacaagg aggttacggt caaggaggcg  13140
```

-continued

```
caggacaagg tggagccgca gcggcagcag cagcagcagc tggtggagca ggacaaggag  13200
gatatggcag aggtggagca ggacaaggtg gagcagcagc agccgctgga gctggtcaag  13260
gtggttatgg aggtcaaggt gctggacaag gtggagctgg agctgcagca gcagcatcca  13320
gaggtgcagg tcaaggaggt cagggtggct atggacgagg aggttacggt caaggaggtg  13380
ccggacaagg cggagctgga gcagcagcag cggccgcagc agccggaggt gcaggtcaag  13440
gaggacaagg tggctatgga caaggaggtt acggtcaagg aggtgcagga caaggtggag  13500
cggcagcagc agcagcagcc gctggtggag caggacaagg aggatatggc agaggtggag  13560
caggacaagg tggagcagca gcagccgctg gagctggtca aggtggttat ggaggtcaag  13620
gtgccggaca aggtggagct ggagctgcag ccgcagcagc agcagccgga ggtgcaggtc  13680
aaggaggaca aggtggctat ggacgaggag gttacggtca aggaggtgcc ggacaaggcg  13740
gagctggagc agcagcagcg gcagcagcag ccggaggtgc aggtcaagga ggacaaggtg  13800
gctatggaca aggaggttac ggtcaaggag gcgcaggaca aggtggagcc gcagcggcag  13860
cagcagcagc agctggtgga gcaggacaag gaggatatgg cagaggtgga gcaggacaag  13920
gtggagcagc agcagccgct gctgcagccg ctggatctgg tcaaggtggt tatggaggtc  13980
aaggtgccgg acaaggtgga gctggagctg cagccgcagc agcagcagcc ggaggtgcag  14040
gtcaaggagg acaaggtggc tatggacgag gaggttacgg tcaaggaggt gccggacaag  14100
gcggagctgg agcagcagca gcggcagcag cagccggagg tgcaggtcaa ggaggacaag  14160
gtggctatgg acaaggaggt tacggtcaag gaggtgcagg acaaggtgga gccgcagcgg  14220
cagcagcagc agcagccgct ggtggagcag gacaaggagg atatggcaga ggtggagcag  14280
gacaaggtgg agcagcagca gccgctggag ctggtcaagg tggttatgga ggtcaaggtg  14340
ccggacaagg tggagctgga gctgcagccg cagcagcagc agccggaggt gcaggtcaag  14400
gaggacaagg tggctatgga cgaggaggtt acggtcaagg aggtgccgga caaggcggag  14460
caggaacagc agcagcggca gcagcagccg gaggtgcagg tcaaggagga caaggtggct  14520
atggtcaagg aggttatggt caaggaggcg caggacaagg tggagccgca gcggcagcag  14580
cagcagcagc tggtggagca ggacaaggag gatatggcag aggtggagca ggtcaaggtg  14640
gagcagcagc agccgctgct gcagccgctg gagctggtca aggtggttat ggaggtcaag  14700
gtgccggaca aggtggagct ggagctgcag ctgcagcagc agcagccgga ggtgcaggtc  14760
aaggaggaca aggtggctat ggacgagggg gttacggtca aggaggtgcc ggacaaggcg  14820
gagctggagc agcagcagcg gcagcagcag ccggaggtgc aagtcaagga ggacaaggtg  14880
gctatggaca aggagattac ggtcaaggag gtgcaggaca aggtggagcc gcagcggcag  14940
cagcagcagc tggtggagca ggacaaggag gatatggcag aggtggagca ggacaaggtg  15000
gagcagcagc agccgctgga gctggtcaag gtggttatgg aggtcaaggt gccggacaag  15060
gtggagctgg agctgcagcc gcagcagcag cagccggagg tgcaggtaga ggaggacaag  15120
gtggctatgg acgaggaggt tacggtcaag gaggtgccgg acaaggcgga gctggagcag  15180
cagcagcggc agcagcagcc ggaggtgcag gtcaaggagg acaaggtggc tatggacaag  15240
gaggttacgg tcaaggaggc acaggacaag gtggagccgc agcggcagca gcagcagcag  15300
ctggtggagc aggacaagga ggatatggca gaggtggagc aggacaaggt ggagcagcag  15360
cagccgctgc tgcagccgct ggagctggtc aaggtggtta tggaggtcaa ggtgctggac  15420
aaggtggagc tggagctgca gccgcagcag cagcagccgg aggtgcaggt caaggaggtc  15480
```

agggtggcta tggacgagga ggttacggtc aaggaggtgc cggacaaggc ggagctggag 15540
cagcagcagc ggccgcagca gccggaggtg caggtcaagg aggacaaggt ggctatggac 15600
aaggaggtta cggtcaagga ggttacggtc aaggaggtgc aggacaaggt ggagcggcag 15660
cagcagcagc agccgctggt ggagcaggac aaggaggata tggcagaggt ggagcaggac 15720
aaggtggagc agcagcagcc gctggagctg gtcaaggtgg ttatggaggt caaggtgccg 15780
gacaaggtgg agctggagct gcagccgcag cagcagcagc cggaggtgca ggtcaaggag 15840
gacaaggtgg ctatggacga ggaggttacg gtcaaggagg tgccggacaa ggcggagctg 15900
gagcagcagc agcggcagca gcagccggag gtgcaggtca aggaggacaa ggtggctatg 15960
gacaaggagg ttacggtcaa ggaggcgcag gacaaggtgg agccgcagcg gcagcagcag 16020
cagcagctgg tggagcagga caaggaggat atggcagagg tggagcagga caaggtggag 16080
cagctgcagc cgctgctgca gccgctggat ctggtcaagg tggttatgga ggtcaaggtg 16140
ccggacaagg tggagctgga gctgcagccg cagcagcagc agccggaggt gcaggtcaag 16200
gaggacaagg tggctatgga cgaggaggtt acggtcaagg aggtgccgga caaggcggag 16260
ctggagcagc agcagcggca gcagcagccg gaggtgcagg tcaaggagga caaggtggct 16320
atggacaagg aggttacggt caaggaggtt acggtcaagg aggtgcagga caaggtggag 16380
ccgcagcggc agcagcagca gcagccgctg gtggagcagg acaaggagga tatggcagag 16440
gtggagcagg acaaggtgga gcagcagcag ccgctggagc tggtcaaggt ggttatggag 16500
gtcaaggtgc cggacaaggt ggagctggag ctgcagccgc agcagcagca gccggaggtg 16560
caggtcaagg aggacaaggt ggctatggac gaggaggtta cggtcaagga ggtgccggac 16620
aaggcggagc tggagcagca gcagcggcag cagcagccgg aggtgcaggt caaggaggac 16680
aaggtggcta tggacaagga ggtaatggtc aaggaggcgc aggacaaggt ggagccgcag 16740
cagcagcagc agcagctggt ggagcaggac aaggaggata tggcagaggt ggagcaggac 16800
aaggtggagc agcagcagcc gctgctgcag ccgctggagc tggtcaaggt ggttatggag 16860
gtcaaggtgc cggacaaggt ggagctggag ctgcagccgc agcagcagca gccggaggtg 16920
caggtcaagg aggacaaggt ggctatggac gaggaggtta cggtcaagga ggtgccggac 16980
aaggcggagc tggagcagca gcagcggcag cagcagccgg aggtgcaagt caaggaggac 17040
aaggtggcta tggacaagga gattacggtc aaggaggtgc aggacaaggt ggagccgcag 17100
cggcagcagc agcagctggt ggagcaggac aaggaggata tggcagaggt ggagcaggac 17160
aaggtggagc agcagcagcc gctggagctg gtcaaggtgg ttatggaggt caaggtgccg 17220
gacaaggtgg agctggagct gcagccgcag cagcagcagc cggaggtgca ggtagaggag 17280
gacaaggtgg ctatggacga ggaggttacg gtcaaggagg tgccggacaa ggtggagctg 17340
gagcagcagc agcggcagca gcagctggag gtgcaggtca aggaggacaa ggtggctatg 17400
gacaaggagg ttatggtcaa ggaggcgcag gacaaggtgg agccgcagcg gcagcagcag 17460
cagcagctgg tggagcagga caaggaggat atggcagagg tggagcagga caaggtggag 17520
cagcagcagc cgctggagct ggtcaaggtg gttatggagg tcaaggtgcc ggacaaggtg 17580
gagctggagc tgcagccgca gcagcagcag ccggaggtgc aggtagagga ggacaaggtg 17640
gctatggacg aggaggttac ggtcaaggag gtgccggaca aggcggagct ggagcagcag 17700
cagcggcagc agcagctgga ggtgcaggtc aaggaggaca aggtggctat ggacaaggag 17760
gttatggtca aggaggcgca ggacaaggtg gagccgcagc ggcagcagca gcagcagttg 17820
gtggagcagg acaaggagga tatggcagag gtggagcagg acaaggtgga gcagcagcag 17880

```
cagccgctgc tgcagccgct ggatctggtc aaggtggtta tggaggtcaa ggtgccggac  17940
aaggtggagc tggagctgca gccgcagcag cagcagctgg aggtgcaggt caaggaggac  18000
aaggtggcta tggaggagga ggttacggtc aaggaggtgc cggacaaggc ggagctggag  18060
cagcagcagc ggcagcagca gccggaggtg caggtcaagg aggacaaggt ggctatggac  18120
aaggaggtta cggtcaagga ggtgcaggac aaggtggagc cgcagcggca gcagcagcag  18180
cagctggtgg agcaggacaa ggaggatatg gcagaggtgg agcaggacaa gggggagcag  18240
cagcagccac tggagctggt caaggtggtt atggaggtca aggtgccgga caaggtggag  18300
ctggagctgc agccgcagca gcagcagccg gaggtgcagg tcaaggagga caaggtggct  18360
atggacgagg aggttacggt caaggaggtg ccggacaagg tggagctgga gcagcagcag  18420
cggcagcagc agccggaggt gcaggtcaag gaggacaagg tggctatgga caaggaggtt  18480
acggtcaagg aggtgcagga caaggtggag ccgcagcggc agcagcagca gctggtggag  18540
caggacaagg aggatatggc agaggtggag caggacaagg tggagcagca gcagccgctg  18600
ctgcagccgc tggagctggt caaggtggtt atggaggtca aggtgccgga caaggtggag  18660
ctggagctgc agccgcagca gcagcagccg gaggtgcagg tcaaggagga caaggtggct  18720
atggacgagg aggttacggt caaggaggtg ccggacaagg cggagctgga gcagcagcag  18780
ccggaggtgc aggtcaagga ggacaaggtg gctatggaca aggaggttac ggtcaaggag  18840
gtgccggaca aggtggagct gcagccgcag cggcagcagc tgcagctgga ggagcaggac  18900
aaggaggata tggtggatac ggtcaacaag gtggagcagg agccgcagca gcagctgcta  18960
gtggacctgg tcaaatttat tatggacccc aatctgttgc tgctccagca gcagcagcag  19020
cttctgcttt ggcagctcca gctacaagcg cgagaatttc ttcacacgcc tcagctcttc  19080
tttcaaatgg acctactaac cctgcttcta tttcaaacgt tattagtaat gctgtatccc  19140
aaattagttc cagcaatcca ggagcgtctg cgtgtgatgt tctcgttcaa gctcttcttg  19200
aacttgttac tgctttgctc accattattg gatcatcaaa tattggcagt gttaattatg  19260
attcttcagg ccaatatgcg caagttgtta ctcaatctgt tcaaaatgca ttcgcttgat  19320
tctaaaacgt tgcttaagca ttcattttat aaaatgtact aatataatat gcattgagta  19380
attctgatat tgaataaagc atttatcttc tctataatct catttgccta attatatttt  19440
tgttttttta cttctgtcct gagatcagtt tcttatatat ggtaattcag gcattttaac  19500
attgtaatat attattgaat tgtaacatct gcggaaaaaa tatttacaga atacaagttg  19560
tagaattcaa attaattaac ttttttaaat gaaaataaat tgaacttaat tttgaggact  19620
ttatgatatg gtttctaaat atttttattt tcacgctggt tttcctggag aaatcaataa  19680
tttccaacat aatatgtgtt tattataact gcgtagtccc attccttact tttcaggtat  19740
acgctttagt gtactgtact tctgcagtgt cttaatattg acctgaaacg tattagatga  19800
tttcgatctt tgaatgaaag aataatacta aaaacttttt aagttcttaa aataatttat  19860
tatatcacca gatttctttc aaaaggacag gtgtcatttt gtaattgaaa gaagaaattt  19920
tgaaattgaa taaagaattt tgagtggttt gctgcctaat cagctttgca cataagaatt  19980
attttttggc ctttatttgt tatatttctc aatgcacggt gtgaaattcc tttgcattta  20040
aaatcaaaaa tagttggttt tcaaacattt taaatgcaag tttcaataaa aggaaaataa  20100
ttatagtgtc tgttgcttat attaattttt atgtttttga aattattatt tctaattaat  20160
ttccaaaata tatcatggtg attgcaagag aaatagctaa cttttaaata aaaatttagt  20220
```

-continued

```
aaaaaaattt tttttggtcg ctttataaat tagaagtaaa tataacttct aaaccaaaat  20280
tttcctaatt ttgtctttct agaccaaatt gtctctgaaa gatgagagaa agtgataaga  20340
aactctcgta gactaaatcc ataacagatt tccaatacca aactaaagag gtttatgtat  20400
tcgtattagc taacaaaata agaaagaaat taaaattttt cagatttttt tttttacata  20460
ttcgttagta tacactagga tttaaataaa aaatgtatga gatatatatt ctgcatttac  20520
aatagaaatt cacaaaaatt acaaaatccg tttaaattgg cccaaaacat tggtgatttg  20580
aatatgatta taaaaaattc ttctgtacat aaaatgtcag gtgacaatat tttataagtc  20640
tacaaataaa atgtccttta atctgacaca ctggcgacag ccttttagta aggaaatgaa  20700
caaacttatt aaaaaaatat agttatattt tagataataa gaatgaaatt attaatctat  20760
ctttttaaaa ttgcacgctt tctgagggaa gacaaagctc atcatattaa aaccattatt  20820
tacattttaa taatatgttt gagaatatta aaattaagat tgactctgta ccgactccga  20880
aaaattgtaa ctgtttttca gaaaagagta tcccatttta aagattcaag taaccgttga  20940
tttaataaat gtgaaataat gaattgcagt agtaatatct ttaatttaat gtataaaatc  21000
caataaaaat atgaaatgga accctacaca tttcacagaa aaaattactt tattatctca  21060
tattttattt tgtaaaaact taagagaaca gaaaaaaacta tgaaattggc aacttattat  21120
aataaattaa tgtattcaag tgatgtgcat aatatttaaa tgtaaacttt acagaattat  21180
ttcatttata aaatattcat caattttaca aataataaaa cttttcaatt tatgaaaagt  21240
ataaattgaa aatatttaat atttcttctt cataaatctt actaacaata taaattttac  21300
aattctattt tattttttat gactgaatac aagcattatt ttgcataaat agttttcatt  21360
cattatcact gttacgcaaa ttaaaaacaa ggaattctat tttaatctta gtgaattcat  21420
taaatgaaag aaatagtaaa attcattaat aaatattaaa acaccaaagt acaagacata  21480
tatttttttg tcgtgtcatg tcgtatcaaa tatatatata atgtcgagaa tacttattat  21540
ggcttctgta atttcttcaa tgttttcgac atgtaagtca accaaggaaa atggaaaatt  21600
ccgattctcc ttatatcagt tcttattgct gggcagtcaa aaacgtagtc tggtgtcctt  21660
tgcgagtctg ggcatgtatt atagttccaa ataagttatt ttattaataa ttaaaatgaa  21720
atgcaatgca agtgtagtaa ttttaatctg atattatttg gtttttataa aatactgttg  21780
ttgttattac ttatgacact tgcacaagcc aattacgcaa tgctgttggc tatgcgaatt  21840
taagtcagta ggatgaatct ttttcgttta actagagcac cacgtaggtt gcagtgattt  21900
agatgccgta agtcagattt ttttttatca ccgacgaaaa tagtgaatag aataatactc  21960
caaaaaagtg aacaaacttt cataagcagt aggaggtgaa gtgcatgcta caagaacaac  22020
ggtacacgtt acaagattat ataatcagtt agttacaatt tagttacagt tttaagcaag  22080
gttgagtact ttacataagt gcataaagtt agtttttctg tgccgctagg ttggcacgtc  22140
aggtggggag atgcggtggt gtatggcatg gccaccgcag tacctccttc ccagcgtaac  22200
agttagttta gttgtgctgc aaagtgcaca tgacgagtcg aacgggtacg tcgatttctg  22260
ttcgatgctg tagtctacgg aggtaagtct tttgtggtga tctcgttgct tggttgtaaa  22320
ggagtccgtt ggttcctgtt cgcataagag ataggctggc ttcactctgt ccactgagat  22380
gaaaacctct ttgttgttct tcagtacctt gaacactttg tccgttttgt caaggaccgg  22440
gaacggccca tcgtaaggtg gatgttgtac ggcgtcaagc cgtatgaaga cgtgagtgca  22500
tttttgaga acctgtggaa tgaatattct gtccttacca tgattggtgg tttttggtgg  22560
tgaaaatgcg ctcattatgt ccctcaggtg gttaataaaa tctgcagcgt tgaaacctat  22620
```

```
tttgctagga acgaaaaact cacctggcaa cctcaaagag ctgccataca ctagctctgt  22680
ggttgaggct tagattgttt cacgaaatgc agaatgtaaa cccagctatg ccgttgatag  22740
gattattgtc caacgattgg tgagtcgggg gtcagatagc tgagatttaa gaacagattt  22800
caaggatcta taccaatttt ccactaagcc attagacttg gggtggtatg cagtggtatg  22860
gatatgcttg atacctaaaa gctgtgtgag agctcgaaac aagtaagatt caaactgtct  22920
gccctgatca gtaatcacta cactgggtac accaaaacga gttacccaac tggcgtagaa  22980
gtttttagca attgtctcag cagttatatt agaaattggt ctcgtttcca cccaacgggc  23040
atatctatca atcattattc aatcacattt aacagaccgt atatccgtac taaattgtcc  23100
gattaagtcc agatacctta actgacgagg agtgcacttg tctagctttt ctttgaacgc  23160
aaatattaag agtctgtggt ctgtatagat aaaaaagtgt tgaccctcta acatatgttt  23220
gaaattcttt atcgctgcgt atattgcgta aagcttccta tcaaaagttg accatttctg  23280
ctgagccgga gtaagcttag ccgagaagaa tacgagcggt tcatacttcg gtgaatctac  23340
atttttgctc tggtttaacg ttgctcctat cgccatatca ctggcataac aagaaagcat  23400
taattgcgct tcagaacaag gaggagctag catagcggcg ttcgccagtt gttgctgaca  23460
caattcaaat ggagcaattt gttcggtact ccatattaat gcgctgtttt ttattaactt  23520
taagtgtatt tcatttaatg atgcttgcat atgcgcagca tgtttgatat taccccctaca  23580
gtaatttagt aaacctaaaa atcgttgaag ttgttttact gtttgaggta atgggcaatc  23640
gagtataggt ttcactttgt cagagggagg tttaatacca tttttgctga cagaatatcc  23700
tacaaaacga tgcttggcaa ctccgaaaac acatttacct aaatttatac gaattccgta  23760
ctctgtcagg cgcttgagta ccatttctag atgtagtttg tgtttcgatt tggaattgct  23820
tgcgattaat atatcatcca ggtatgcgaa tacaaagtca aatccacgta agacttcatt  23880
aataaacctt tggaaagttt gaggtgcatt ggccaaaccg aatggagtaa atagaaattc  23940
aaataatcca aaaggtgtag tgattgcagc tttttggacg tcgtctgggt ggacaggaat  24000
ttgatggtaa gcttttacca aatctatttt tgaaaagatt actctattat gtaactgatt  24060
ctaaaagtct tgaatgtggg ggagcggata cccatcagga atagtaattc tgttaagggc  24120
tctgtagtca ccagtcggac gaaagtcggt acctgatgac ttgggtacta aatgcaaggg  24180
ggatgaccaa tttgacatac taggtctaca tatgccttgc tctaacatat attcaaactc  24240
tttcttggca attgccaatt ttgtgggatg taatcttcgc ggctttaaaa atacagactg  24300
cccgttagtt ataatactat aggttaaagt atgctttatt attcgctttg aagggtatgg  24360
gcgaattacc tcattgtatt tttccaagat ctgcctaaaa ggaaacgaca aagatggtgc  24420
accgacccac cctagggtat gcggtgaaag aacgcgtgca atagtagtca gtacttcaga  24480
actcggtgga cacaaggtca ggaaaaagtc caaactgtgc agaagagatg gcaccaaagc  24540
caagatctcc tggagtccaa aaagagggaa agttaacgtc tcaaaagaag ggcgttctat  24600
tctattactc tgatcggaag attgggcata acaggccttt attttctagt ttacaataca  24660
atatgatata ataatataag ataataatac aaagtggaaa agtatataca tgttttcagt  24720
agagagatta caacagttat gatttgtcaa agttaggtac agtttgtttg attaattgtt  24780
tggctgtctg tggaggtggt gtccctcatc tgatattgta gctcttgctg tatgatttcc  24840
ctgatgccaa tttgcaccct tgggatttgt agagctgaag ataacttatg gtcgtatgtt  24900
gtttcgggaa ccacttatct ctcatgtgtt gatactttgt gcatctcaag atgaggtgtt  24960
```

-continued cggagtcgca gggttcatcg tcatgtaggc aaagttccga tttgctatgg aatctatttc 25020
tgtaatatcc aaaaactccg tgtccagtga aagcttgatt cagaaagaaa tccccctaaa 25080
gtctggcttt ggaaactttg gagcagaaac tatagagcct tctggtcttt tcggagttat 25140
cccaaatgtg ttgccagcgc attaaaatgt ggtcctgaat taacttttta gtttgctgtt 25200
tgcttatcct gacttgtatt tcaattgact ctaaggtggt tgcttccttt gccgcagcgt 25260
ctgcttcctc attttgcttt atgccacagt gggcctcgac ccaatgaaat gtgaagctgt 25320
gtttgtgttg ttctagtaga ttctggatgt ccctaattgt gtggcttagg gtgtcgggtg 25380
tggaaagtgc ctggatgaca gagcaggaat ctgtatgaat gtggaatgtc taatctattt 25440
cgataatttg atttatggta cctaggatgg cttaggcttc cgcctcgaag acgttggcct 25500
catcattgag cctcatttgg tactttgaac ttgttcttga cctctaaaga ttagtgcagc 25560
acagcctgtt tgattattca tacgagaacc atttgtaaac gcaaatgtac cgttgtgatt 25620
ggtgaggaag tcccactcaa tgtgttggat ctgccatggg gggtttatcg tgctggaaaa 25680
agtccacgca ttgtttgggt tgaatgcgat cgtgtttaag ttaatttcct ttcctcttct 25740
ccaaagtatg tacctgagtt ggagtccctc agctttgagt tggatgggag ggcagcctga 25800
tagtacttgg agggcgtgag ttgatgtggt cttatatgat ttagcaatct ttaataaggc 25860
aattctttgg atttgttgaa gcttaatact ttgttttaca gtgctattgt accacgcagg 25920
ggatccatac agtatgatgc tctcgaaagc aatgttgtag atcaatttat tactgaggga 25980
tttaacccca agttcctctg gtgattctgg ctagtttgtt agttacatta ttgatcgaat 26040
ccttaacctt ggtaagatga ctattccaag ttagttttgg gtcacgcgtg attcctagat 26100
acttcatttt tctggtgtag gccaacttct ttcctcctat actaattccc tgtcttcttg 26160
tgatatccat tccgaattca aatgtagtat atttgcattt gttaatgctt aattggagac 26220
cgtgtttgag ggtccaactt tcgactatgt tgagaggttt tctagattgt atagtgaact 26280
taaagtagga ggagttggag agaagaagtg ctatatcgtc tgcgaaagct tggcaggaga 26340
cttgaggttc aaagtcctgg ataaataatt catttgcaat tagtaaccag agaaagggtc 26400
ctaggctgga tccttggggg actccgttca tgtattttac aggtttgaat tgtgcgttga 26460
aataggttct attatccaag aacgagcaga ttgttttgaa gatgttgttt ggaaatggga 26520
aattctataa tggtctcatg aggttcgtcc atctcgctga attaaagaca tttttgatgt 26580
ctaaggaaat caggcaattg tattgcttgt tttgctggtt agtcttgatg gtattggcaa 26640
tttgatagat cgcatctgag gtactcttcc gtttcctgaa cccaaattgg ttttgttgga 26700
ggagggagtt cgcctggaag aagtagctaa ctcttttatg tagaatctta tcgaggattt 26760
ttccccagat gggtaatagg caaataggac tatgtgaatc atatttagaa agatctttgc 26820
cgtctttgaa aaatagaata acagttgcct gtttccagat tcggggaaag atgccattcc 26880
gtatggataa attaagtatt cccgtgaacc atcccttgtc ttgtattaat tcctcataag 26940
tatctagact tatgtcgttg tatcctggtg cctttttgct gcccatggaa cttatgattt 27000
ccctaacttt atcaatggtg accggcgggt catcggacat cgccgtggag ttcaattgac 27060
tttgaattgg gttattggga aagtggaact tgagaatttc gtttgttgct tcttccgggg 27120
aattggggaa actgccgtcc atgaaaagaa tgcgatttat gtgtttcggt cttttaatat 27180
tatctctgac aattttatag gtgccgctga aggcattgcg ttcagttata gtccctaagt 27240
actgctcaaa gtgccggtaa tgcgaacaag aggtgatcga gatgtgtacc caatggcatc 27300
ccataccatc actccagcag atgggctagt atggtgatgt ccaatgcaag ctggcaatgc 27360

-continued

```
gcgttctcca cgatgcttcc aaacacggat gcgctcctgt ctgtgacgta gcgtcaatgg  27420
tagccgaagc catagtcgcc gtgcagacaa tccatactgc tgcaaacgtc gtcgaactgc  27480
tcgagcagaa acttgctgcc ttgaaaatga cgccatttct cgactcaggg ttcgtgacgt  27540
ggctgtacga tcccttgtga ccatgcggat aagatgtctg tcttctctgc tgttagtaat  27600
agggcggggg gtcgctgaga tcctgcatga ctttccgtat gattgtcgtg aaaccatcga  27660
ttccatattc tgctaacatt catggggtct cgaccgacac gagcagcaat attgcggtac  27720
gataaatcgg aatcccggta ggctataatc cttcctcgat caaagtcaga catatgctga  27780
taggcatttc ttcttcttac aagaggcatt acaatttctt tatcgaaaac aacgttgaaa  27840
cggaaattga gtatgaggaa actgctgtca aatctcgggt tttatacaca ttgtagatgt  27900
cgctactgtt gcctgttttg tatgaatgcg ctgaaaatct aattatttgc atatcacagc  27960
aagttctacc tgtcatgcaa atttcacgta tgtggtgtgc cgctttcctg gtgtagcaat  28020
tttcatggcc agtagcgtgt agggctgctg ccttttttaaa ttacgccttt cgtaaatcgc  28080
gtttaggatt gtccgtttct gcttgaaatc taccccctaag tgccctgact caacttcgtt  28140
cttcagttaa agctggggtc caccaatagt tggtgttagt cttatgtatt tgcttcctct  28200
tgtgtttttt acagagttct tgtatgttat gttcgactgt ttctatgtgt ccttttcaat  28260
attctctaat ttttagattg ggaattgtac tggtatgctc tttaattcat tcttgaattc  28320
tacccaattt aatgagtttg aattgtatct gaacttagtt ttaaaataag ctttaacatt  28380
agtgagatta aatgtcatga gctgaagatc gctggctgag aatttgtcat tgatagacca  28440
gttggagata ttgttgctat ttaaaatttt tgtgattagt aagtctatcc agctttctcc  28500
tagtgtacta aggtacgttg gtttgctgtt gggatcattt tcaaagatca gttagagttt  28560
agaggcgaat tcgattagtg tgtgtcgtct ttgatctgtg ttccttggac tccaaattgt  28620
ggaatttgcg ttgaaatcgc ctaagataat ccacttttgg ttatgataaa tcgctagaag  28680
ttcacctaac tctttaatgg attcattgat gttgcgagac ggtggacagt aaattgagca  28740
tatattgaaa gtgtctttat tatatttagt ttgaattaaa acaaggtctt ctgagacatg  28800
aatcggtgag acgagatatt gtttgttgct gatcacagcc gttttccggt agttactagc  28860
agtgatagtg aggctcagtg ggaagccgga aatttttcct tcaaaagtga acggatcatt  28920
aattgaaata aagtctaagt ttaattcctt gatatcttgg gagagagtta agttagctgc  28980
tcggcggtga ttaaggttga agtgggcaaa ttttattaga ttgttagaag acatgttagt  29040
catagttagt ttgaatgatt aatttgttga tctctttttt ataaatcggg cttttttttat  29100
cgtttgctag gtgattaatt ttgtatttag ttttatactt ataattgctc tcctcacaat  29160
ttttgcattt gatatcttta tcgcagtttt aatcaacatg cgctcctgag catcttctac  29220
aagagttctc tcctttgcag tctctggata tatgtccata acggagacat ttaaagcact  29280
ggcttattct tatgtattct ctaaattgga ccgtagtcca tcccacacaa aaatatctta  29340
ttccttttat ttaattcatt tagggctgct ccattgagtg tcattatcca gtttattcca  29400
tacctgcctt taaaactatg gacggcttca acacttaggg aattttggtt aataattctt  29460
tccacaattt tttcttttttt taacttcttt atctacattg taaagaatta ttctaggctc  29520
ctttagttcg ggcttcttaa cttctacaat ttctgtaagt ttatcattat ttttaatctc  29580
tgcgattaat tttttttattt ttttccatgg agctagtttc aagaactatt catcctttac  29640
ggactgggcg gattttctta acttttaatc ctagtttaat tgggtttata gcatttttta  29700
```

-continued

```
ttatttttgt agtgtcttcc gaggaagact ctttcttagg atacaccaaa acaacgttat  29760
cctttctttg acgacattta tctcgtctag acctgcttct acttctcatt cttaaagttt  29820
tgttgccttt cagcatacct ttcttaactg cctcagcaaa ggtttttgtc tgttttatcg  29880
gtaactcatc ttttgctttt aattgtcctt caagaaaagc attttttttt ctatctgctg  29940
caaggcaatg tgtagaatgt cagaaatgcc ttgtctaatt ttttgttgta tggtactgct  30000
cgccttactg gctgaaagag cctgttgtat ctctctttct gtctctaaca aatttagaat  30060
ttctgattta atcccattgt tcgctgtctc acaatcatac acagcgaact ccctttcggg  30120
agactgtttg tgttgccatg gggg aaagag ttaaagccgt gtccactcgt tataatttga  30180
gcttaaagca gtgtcagctc ttataagtcc ctctgctttc gttagccgcc agtaaactga  30240
cgtttccagg agccaccacg aggaagtgga ggtcagatgg tttcggagaa cagagaactt  30300
gacaagcaaa acccgaagga attgaaacgc caagacagag ttagcacttt ccggatagac  30360
tctaggccgt tgtccggaaa catattaatc tcaaaattac ttaagttctc gctgcggggc  30420
tggctccctg cctaaaagga aaagtatccg taattaaagt tacatgggat acatcgtgaa  30480
cggttttacc tgatgtaatt aaattagttt tactatccct aagacacgca tgcttcaaat  30540
caattagtaa accaaaatgc ttgagaaaat ctgcaccaat aataggttta tttacatcag  30600
caattataaa ataccaagga aactttctgc gaagattcaa acttacagta ataacttaat  30660
tccgtaagtt ttgattgtag agcaactagc tgaatataac ttaaatttgc tattactctg  30720
ctttgaaaat ttgcattttg agcgtggtaa aacacaagtc actaccactg tcgactagat  30780
aagttaaatt tgtaattggg tctgatacaa aaaggcggct tgtattgtcg aatttgaaat  30840
tgtattgtgc caggtcatac aattttgcta ttaaatttcc gatattgtaa atgaacaagg  30900
aaatttgcaa cgtttagcag ccgaaccgaa tttgaaatga taccagcact gatagtgagt  30960
ttttcttttg ggtgttcgag agcgttggcg gggaggagaa actcggtttt ccgggtcccg  31020
tgatttgtgc ctgcgacctt aagataaact tttaatttat tttctaagtt tcgcaatttg  31080
catttataat tcgcttaatt cacgagatga aattttgggg acttgaattt ctttaacaat  31140
cgcgtttgag gtatcatgga ttttatcacc attatagcaa gcttgtcgaa cttatcctcg  31200
gaaactgaaa gaatagcttg agactaagga gttagacgct gcaaccaaag cattttagga  31260
aatcttcact tacagtttta cccgctaatt gcctcatctt gcgtagtaag tgagaaggct  31320
tgtctcctag aattagttct gaaattagag ttttaatgcg tcgtcgctct gaatctgaga  31380
attcctcaac gagtcgagat tttaaagttt catatttatt tccctcaggt ggcgtgaaca  31440
caataccact aacgtaattt aaaatacccg acgttaaagc ggaaataaac gaataatatt  31500
tagtcgagtc ctgtgtaata ccagaaatta taaactgtgc ctctatattt gcaaactata  31560
gcacgggatg tttatccaag aaaagtggta attttaggct tactctagct atattagcct  31620
ccacccagtc gtttggcatg ataacagcga cataaataaa atgcctgtta caaaatttga  31680
aatagataat atgtgtgaat gatactgccg tttttagact tttcttctcc atagatactt  31740
gaagtaggaa attatcattg atattcttcc agcgagagac attattccaa cgtagtaaaa  31800
tcatccggtt caccagtgca gtgatttaga ggtcaaaagt cagatatttt atatcaccga  31860
cgaaattggc gattagaata ttactccata aaagtgaaca aatttttatt agcagtagga  31920
ggtgaagtgc gtgctacaag aataacagta cacgttaaaa gattatataa tcaattagtt  31980
acaatacaat tacagtttcc aagcaaggtt gagtaattta cataagtgca taaagttagt  32040
ttttccgtgc cgccaggttg gcatgccagg tcgggaattg cggtggtgta tggcatggcc  32100
```

-continued

```
accgcaaggt gaaagtacaa ctgtgcttta aacttcttcg atagatggca ccaccagcaa  32160
acccacttaa atcaattatg acattaatct ggagggggag gaaattttct ccagacaatt  32220
acacccatga taactgctca acgagcaacc acaggacttt caattccaca gatttaacga  32280
gcacgtatat cgcatgtact aggtggatct ttggtggcat tctgagtaga attctgctct  32340
tccggactga aggctgatgc tctaaccatt aggctaccac agcttatatg atcattgcat  32400
tcaacaacac catgagtagc taaattataa ggtaagtgcc cagatgttgt atttttcaa  32460
tctgcatgtt tgtcctgtac attttgatat ttaatttgta ttaatagtac aattggggcc  32520
aaagttgtta agcacttaat aactgtaaat ttttcatgtt ttttgtcgtc ttctctaaaa  32580
ttattaatgt actattgtaa ttaccattta ataactttgg agctgattgt cctatctcat  32640
tgaaattaat tttaacgtgg agtggataag ctaagctttt aaattacatc taatttatga  32700
ttgtagattt aatagtttc tctcaataat ttttcaaaat ttaacattgc tcaaaaattt  32760
ttatgtattt ttgccttatt tgtatacaat tttaatttca aaactgcctt aaaattttaa  32820
atattaatca atccactcca atatttctaa attaattcag agccgatttc tgtgattcag  32880
aatatattat tctttttatt aattttttaa ataattaata gttaaaaagt tatcaatttt  32940
atgtagaatg taattgtatc tttcactgtt ttttccccat ttcgaccaat gtaacttcag  33000
tgctcccctt tgtatatgta ttgcggctgt gatttcatct atgtccgacc attagcaggg  33060
tgatggtccc tctctttcat cctcctctta attccggcat taattaatta ctttaatcaa  33120
tttttaatta gcgaatttct cacctcctaa ttgtcccaga gacgcagaac taaattcatt  33180
gggttcattt ggcgttttct caactcccca ttagtctcag agactcggga ctaatctcta  33240
attttgttat ttaataatga gcttctaacg agaccactta gttgccatta ttacaaaatt  33300
atcccatttt ccttatattg atggattgga ttttttttaa ttattcattt ttatttttac  33360
ttatttattt atttatttat ttattttttg acgttcgtcg ctaagcctat ttccaagact  33420
ttaacttgtc tccattaaat tgccttgata ttcagtcaac tatcacacta ctattataac  33480
tattttaagt ttatcatcct ggccaattaa ttaaattaag ggctaactat atgcccaatt  33540
aatccttaaa tagtttaatt aacttaaata ttcatctttg gaaaggccta tcatgggggt  33600
ctgtggctcg atacagtatg cagggggagt agtgaacaca gattgtatcc cacaacttct  33660
aaactttcat taaaaccgtt tctaagacaa ttagcttgta aaggaataat tttattcaac  33720
tagcatttac tattaaccaa attacaaaaa cacattttaa gtaaattcga gtttttttaa  33780
atatttttta ttttatttat ttattttttt tatttattta ttttttttatt ttattttttta  33840
ttttttttat ttaatgggac cagatttaac ttagcttaat tcacccctct ttaaatttaa  33900
ctaccaagta tttaactgaa cgaaacaaat tttgcaatcg aatgggttgg tcacctcccc  33960
atagtaatat tgtatctcat ggcacaattt tttagagaga tggaactaag atcattcttc  34020
accctaacct cccactagca tatacaa                                      34047
```